(12) United States Patent
Tachdjian et al.

(10) Patent No.: US 11,129,397 B2
(45) Date of Patent: *Sep. 28, 2021

(54) METHOD OF IMPROVING STABILITY OF SWEET ENHANCER AND COMPOSITION CONTAINING STABILIZED SWEET ENHANCER

(71) Applicant: Firmenich Incorporated, Plainsboro, NJ (US)

(72) Inventors: Catherine Tachdjian, San Diego, CA (US); Donald Karanewsky, Escondido, CA (US); Xiao Qing Tang, San Diego, CA (US); Hanghui Liu, San Diego, CA (US)

(73) Assignee: FIREMENICH INCORPORATED, Plainsboro, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/352,430

(22) Filed: Mar. 13, 2019

(65) Prior Publication Data

US 2019/0208802 A1 Jul. 11, 2019

Related U.S. Application Data

(62) Division of application No. 14/670,331, filed on Mar. 26, 2015, now Pat. No. 10,244,779, which is a division of application No. 13/208,594, filed on Aug. 12, 2011, now Pat. No. 9,000,054.

(60) Provisional application No. 61/500,834, filed on Jun. 24, 2011, provisional application No. 61/373,083, filed on Aug. 12, 2010.

(51) Int. Cl.
*A23L 2/56* (2006.01)
*A23L 27/00* (2016.01)
*A23L 27/20* (2016.01)
*A61K 47/26* (2006.01)
*A61K 47/22* (2006.01)

(52) U.S. Cl.
CPC ............. *A23L 2/56* (2013.01); *A23L 27/2054* (2016.08); *A23L 27/88* (2016.08); *A61K 47/22* (2013.01); *A61K 47/26* (2013.01); *A23V 2002/00* (2013.01)

(58) Field of Classification Search
CPC ........ A23L 2/56; A23L 27/88; A23L 27/2054; A23L 2/60; A23L 2/62; A61K 47/22; A61K 47/26; A23V 2002/00
See application file for complete search history.

(56) References Cited

U.S. PATENT DOCUMENTS

| 3,278,532 | A | 10/1966 | Houlihan |
| 3,843,804 | A | 10/1974 | Evers et al. |
| 3,845,770 | A | 11/1974 | Theeuwes et al. |
| 3,857,972 | A | 12/1974 | Evers et al. |
| 3,916,899 | A | 11/1975 | Theeuwes et al. |
| 3,957,783 | A | 5/1976 | Hirohashi et al. |
| 3,960,860 | A | 6/1976 | Katz et al. |
| 4,146,716 | A | 3/1979 | Cox et al. |
| 4,196,207 | A | 4/1980 | Webber et al. |
| 4,377,580 | A | 3/1983 | Ueda et al. |
| 4,765,539 | A | 8/1988 | Noakes et al. |
| 4,960,870 | A | 10/1990 | Lehmann |
| 5,112,598 | A | 5/1992 | Biesalski |
| 5,380,541 | A | 1/1995 | Beyts et al. |
| 5,504,095 | A | 4/1996 | Nakane et al. |
| 5,556,611 | A | 9/1996 | Biesalski |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van der Linden et al. |
| 6,475,544 | B1 | 11/2002 | Hiramoto et al. |
| 6,852,862 | B2 | 2/2005 | Nishizawa et al. |
| 7,105,650 | B2 | 9/2006 | Adler |
| 7,928,111 | B2 | 4/2011 | Tachdjian et al. |
| 8,592,592 | B2 | 11/2013 | Tachdjian et al. |
| 2002/0025366 | A1 | 2/2002 | Jager |
| 2003/0008344 | A1 | 1/2003 | Adler et al. |
| 2003/0054448 | A1 | 3/2003 | Adler et al. |
| 2003/0232407 | A1 | 12/2003 | Zoller et al. |
| 2004/0091589 | A1 | 5/2004 | Roy et al. |
| 2004/0127435 | A1 | 7/2004 | Carson et al. |
| 2005/0032158 | A1 | 2/2005 | Adler et al. |
| 2005/0196503 | A1 | 9/2005 | Srivastava |
| 2006/0045953 | A1 | 3/2006 | Tachdjian et al. |
| 2006/0135552 | A1 | 6/2006 | Malherbe et al. |

(Continued)

FOREIGN PATENT DOCUMENTS

| CN | 1234691 | 1/2006 |
| CN | 101742925 | 6/2010 |

(Continued)

OTHER PUBLICATIONS

Eunok Choe and David B. Min, Mechanisms of Antioxidants in the Oxidation of Foods, Comprehensive Reviews in Food Science and Food Safety, vol. 8, Issue4, Oct. 2009, pp. 345-358 (Year: 2009).*
Alderman, "A Review of Cellulose Ethers in Hydrophilic Matrices for Oral Controlled-Release Dosage Forms," Int. J. Pharm. Tech. & Prod. Mfr. 5(3):1-9 (1984).
Bamba et al., "Release mechanisms in Gelforming Sustained Release Preparations," Int. J. Pharm. 2:307-315 (1979).
Berge et al., "Pharmaceutical Salts," J. Pharm. Sci. 66(1):1-19 (1977).

(Continued)

*Primary Examiner* — Sarah Pihonak
*Assistant Examiner* — Jason Deck
(74) *Attorney, Agent, or Firm* — Knobbe, Martens, Olson & Bear, LLP

(57) ABSTRACT

The present invention includes methods of stabilizing one or more sweet enhancers when they are exposed to a light source as well as liquid compositions containing one or more sweet enhancers and one or more photostabilizers.

6 Claims, 10 Drawing Sheets

(56) References Cited

U.S. PATENT DOCUMENTS

| | | | |
|---|---|---|---|
| 2006/0257543 | A1 | 11/2006 | Tachdjian et al. |
| 2007/0003680 | A1 | 1/2007 | Tachdjian et al. |
| 2007/0010480 | A1 | 1/2007 | Rusing et al. |
| 2007/0104709 | A1 | 5/2007 | Li et al. |
| 2008/0306053 | A1 | 12/2008 | Tachdjian et al. |
| 2008/0306093 | A1 | 12/2008 | Servant et al. |
| 2010/0075005 | A1 | 3/2010 | Roy |
| 2011/0195170 | A1 | 8/2011 | Shigemura et al. |
| 2011/0224155 | A1 | 9/2011 | Tachdjian et al. |
| 2011/0230502 | A1 | 9/2011 | Tachdjian et al. |
| 2014/0094453 | A1 | 4/2014 | Tachdjian et al. |
| 2015/0245642 | A1 | 9/2015 | Tachdjian et al. |

FOREIGN PATENT DOCUMENTS

| | | |
|---|---|---|
| EP | 0 530 994 | 3/1993 |
| WO | WO 93/013104 | 7/1993 |
| WO | WO 02/100192 | 6/2002 |
| WO | WO 03/001876 | 1/2003 |
| WO | WO 03/022214 | 3/2003 |
| WO | WO 07/004709 | 1/2007 |
| WO | WO 07/047988 | 4/2007 |
| WO | WO 08/154221 | 12/2008 |
| WO | WO 10/014666 | 2/2010 |
| WO | WO 10/014813 | 2/2010 |

OTHER PUBLICATIONS

Blackburn et al., "Identification and characterization of amino-piperidinequinolones and quinazolinones as MCHr1 antagonists," Bioorg. & Med. Chem. Lett. 16:2621-2627 (2006).
Boarland et al., "Monosubstituted Pyrimidines, and the Action of Thiourea on Chloropyrimidines," J. Chem. Soc. 1218-1221 (1951).
Brown, et al., "Evolution of a Series of Peptidoleukotriene Antagonists: Synthesis and Structure-Activity Relationships of 1,6-Disubstituted Indoles and Indazoles," J. Med. Chem. 33:1771-1781 (1990).
Buck et al., "A Novel Multigene Family May Encode Odorant Receptors: A Molecular Basis for Odor Recognition," Cell 65(1):175-187 (1991).
Calkins, May 2010, 2,1-Benzothiazines: Preparation and Reactivity, PhD thesis, University of Missouri-Columbia, https://mospace.umsystem.edu/xmlui/handle/10355/8309; 290 pp.
Campillo et al., "A study of peculiar tautomerism of pyrido[2,3-c][1,2,6]thiadiazine 2,2-dioxide system," J. Mol. Struct. 678:83-89 (2004).
Chandrashekar et al., "T2Rs Function as Bitter Taste Receptors," Cell 100:703-711 (2000).
Cheng et al., "Potential Purine Antagonists. XII. Synthesis of 1-Alkyl(aryl)-4,6-disubstituted Pyrazolo [3,4-d] pyrimidines", Journal of Organic Chemistry, American Chemical Society, Easton, US; 1958, 23:852-861.
Chien et al., "Nucleosides XI. Synthesis and Antiviral Evaluation of 5'-Alkylthio-5'-deoxy Quinazolinone Nucleoside Derivatives as S-Adenosyl-L-homocysteine Analogs," Chem. Pharm. Bull. 52(12):1422-1426 (2004).
Clauss et al., "Cycloadditionen von Halogensulfonylisocyanaten an Acetylene," Tetrahedron Lett. 2:119-122 (1970).
Corbett et al., "Novel 2,2-Dioxide-4,4-disubstituted-1,3-H-2,1,3-benzothiadiazines as Non-Nucleoside Reverse Transcriptase Inhibitors," Bioorg. Med. Chem. Lett. 10:193-195 (2000).
Dominguez et al., "Efficient synthesis of 4,4-disubstituted-3,4-dihydro-1H-2,1,3-benzothiadiazine 2,2-dioxides," Tetrahedron Lett. 41:9825-9828 (2000).
Dorwald, F. Zaragoza. Side Reactions in Organic Synthesis: A Guide to Successful Synthesis Design, Weinheim: WILEY-VCH Verlag GmbH & Co. KGaA, 2005, Preface.
Doucet-Personeni et al., 2001, A structure-based design approach to the development of novel reversible AChE Inhibitors, J. Med. Chem., 44:3203-3215.

During et al., "Controlled Release of Dopamine from a Polymeric Brain Implant: In Vivo Characterization," Ann. Neurol. 25:351-356 (1989).
Elmegeed et al., "Novel synthesizes aminosteroidal heterocycles intervention for inhibiting iron-induced oxidative stress," Eur. J. Med. Chem. 40:1283-1294 (2005).
El-Sherbeny et al., "Novel Pyridothienopyrimidine and Pyridothienothiazine Derivatives as Potential Antiviral and Antitumor Agents," Med. Chem. Res. 10:122-135 (2000).
Fan et al., 2004, Transient silylation of the guanosine O6 and amino groups facilitates n-acylation, Organic Letters, 6(15):2555-2557.
Francis et al., "Anxiolytic Properties of Certain Annelated [1,2,4]Triazolo[1,5-c]pyrimidin-5(6H)-ones," J. Med. Chem. 34:2899-2906 (1991).
Garcia-Munoz et al., "Synthesis of Purine-Like Ring Systems Derived From 1,2,6-Thiadiazine 1,1-Dioxide," J. Heterocyclic Chem. 13:793-796 (1976).
Goya and Martinez, "Synthesis and Cytostatic Screening of an $SO_2$ Analogue of Doridosine," Arch. Pharm. (Weinheim) 321:99-101 (1988).
Goya and Paez, "Pteridine Analogues; Synthesis and Physico-Chemical Properties of 7-Oxopyrazino [2,3-c][1,2,6] thiadiazine 2,2-Dioxides," Liebigs Ann. Chem., 121-124 (1988).
Goya et al., "Aminopyrido [2,3-c] [1,2,6] Thiadiazine 2,2-Dioxides: Synthesis and Physico-chemical Properties," Chemica Scripta, 26:607-611 (1986).
Goya et al., "Fused 1,2,6-Thiadiazines: Tetrahydrobenzo[b]thieno[2,3-c][1,2,6]thiadiazine 2,2-Dioxides," Arch. Pharm. (Weinheim) 317:777-781 (1984).
Goya et al., "Synthesis of 2S-Dioxo Isosteres of Purine and Pyrimidine Nucleosides IV. Selective Glycosylation of 4-Amino-5H-Imidazo [4,5-c]-1,2,6-Thiadiazine 2,2-Dioxide," Nucleosides & Nucleotides, 6(3), 631-642 (1987).
Goya et al., CAPLUS Accession No. 1987:18628, 2 pages, abstract of ES 531159 A1 (1985).
Harris et al., 1990, Antifolate and antibacterial activities of 5-substituted 2,4-diaminoquinazolines, Journal of Medicinal Chemistry, 33(1):434-444.
Hauser et al., "Synthesis of 5-Phenyl-4,6-Dimethyl-2-Pyrimidol and Derivatives from the Cyclization of Urea with 3-Phenyl-2,4-Pentanedione," J. Org. Chem. 18:588-593 (1953).
Hirohashi et al., "Nuclear magnetic resonance studies of bicyclic thiophene derivatives. I. Ring current effects of the benzene ring on the $H_\alpha$ and $H_\beta$ signals of the thiophene ring in benzoylthiophene, thienopyrimidine, and thienodiazepine derivatives", Bulletin of the Chemical Society of Japan, 1975, 48(I):147-156.
Hirota et al., "Synthesis and Biological Evaluation of 2,8-Disubstituted 9-Benzyladenines: Discovery of 8-Mercaptoadenines as Potent Interferon-Inducers," Bioorg. Med. Chem. 11:2715-2722 (2003).
Hoon et al., Putative Mammalian Taste Receptors: A Class of Taste-Specific GPCRs with Distinct Topographic Selectivity. Cell 96:541-551 (1991).
Howard et al., "Intracerebral drug delivery in rats with lesion-induced memory deficits," J. Neurosurg. 71:105-112 (1989).
Hu et al., "Organic Reactions in Ionic Liquids: Gewald Synthesis of 2-Aminothiophenes Catalyzed by Ethylenediammonium Diacetate," Synthetic Communication 34:3801-3806 (2004).
Jalil et al., Sep. 16, 2008, Polyphenols in cocoa and cocoa products: is there a link between antioxidant properties and health?, Molecules, 13(9):2190-2219.
Jordan, "Tamoxifen: A Most Unlikely Pioneering Medicine," Nature Reviews: Drug Discovery 2003, vol. 2, pp. 205-213.
Jung et al., "Discovery of Novel and Potent thiazoloquinazolines as Selective Aurora A and B Kinase Inhibitors," J. Med. Chem. 49:955-970 (2006).
Kamal et al., "Cyclization of 2-(Carbamoyloxy)- and 2-(Sulfamoyloxy)benzoates Mediated by Liver Microsomes," J. Org. Chem. 53:4112-4114 (1988).
Kanuma et al., "Lead optimization of 4-(dimethylamino)quinazolines, potent and selective antagonists for the melanin-concentrating hormone receptor 1," Bioorg. & Med. Chem. Lett. 15:3853-3856 (2005).

(56) References Cited

OTHER PUBLICATIONS

Keith, "Synthesis and Reduction of some 1H-2,1,3-Benzothiadiazin-4(3H)one 2,2-Dioxides," J. Heterocyclic Chem., 15:1521-1523 (1978).
Kim et al., 2004, Comprehensive study on vitamin c equivalent antioxidant capacity (VCEAC) of various polyphenolics in scavenging a free radical and its structural relationship, Critical Reviews in Food Science and Nutrition, 44:253-273.
Kyte et al., "A Simple Method for Displaying the Hydropathic Character of a Protein," J. Mol. Biol. 157:105-132 (1982).
Langer et al., "Chemical and Physical Structure of Polymers as Carriers for Controlled Release of Bioactive Agents: A Review," J. Macromol. Sci. Rev. Macromol Chem. 23:61-126 (1983).
Langer, "New Methods of Drug Delivery," Science 249:1527-1533 (1990).
Lee et al., "Acetonitrile-Mediated Synthesis of 2,4-Dichloroquinoline from 2-Ethynyl-aniline and 2,4-Dichloroquinazoline from Anthranilonitrile," Synlett, 2006 No. 1:65-68 (2006).
Leistner et al., "Eine einfache Synthese von 2-Alhylthio-4-aminothieno[2,3-d]pyrimidinen," Arch. Pharm. (Weinheim) 322(4):227-230 (1989).
Levy et al., "Inhibition of Calcification of Bioprosthetic Heart Valves by Local Controlled-Release Diphosphonate," Science 228:190-192 (1985).
Li et al., "Human receptors for sweet and umami taste," Proc. Natl. Acad. Sci. USA 99:4692-4696 (2002).
Linkies et al., "Ein neues Verfahren zur Herstellung von 6-Methyl-1,2,3-oxathiazin-4(3H)-on-2,2-dioxid Kaliumsalz (Acesulfam-K)," Synthesis 405-406 (1990).
Liu et al., "Discovery of a new class of 4-anilinopyrimidines as potent c-Jun N-terminal kinase inhibitors: Synthesis and SAR studies," Bioorg. & Med. Chem. Lett. 17:668-672 (2007).
Martinez et al., "Benzothiadiazine Dioxide Dibenzyl Derivatives as Potent Human Cytomegalovirus Inhibitors: Synthesis and Comparative Molecular Field Analysis," J. Med. Chem., 43:3218-3225 (2000).
Meyer et al., 1979, Synthesis of fused [1,2,6]thiadiazine 1,1-dioxides as potential transition-state analogue inhibitors of xanthine oxidase and guanase, J. Med. Chem. 22(8):944-948.
Nie et al., "Distinct Contributions of T1R2 and T1R3 Taste Receptor Subunits to the Detection of Sweet Stimuli," Curr. Biol. 15(21):1948-1952 (2005).
Pal et al., "Synthesis and Cyclooxygenase-2 (COX-2) Inhibiting Properties of 1,5-Diarylpyrazoles Possessing N-Substitution on the Sulfonamide (-$SO_2NH_2$) Moiety," Letters in Drug Design & Discovery 2:329-340 (2005).
PubChemCompound, datasheet [online compound summary], retrieved from the internet: <url: http://pubchem.ncbi.nlm.nih.gov/summary/summary.cgi?cid12715714&loc=ec_rcs> [5/11/2-12].
Rad-Moghadam et al., "One-pot Three-component Synthesis of 2-Substituted 4-Aminoquinazolines," J. Heterocyclic Chem. 43:913-916 (2006).
Rasmussen et al., "The Electrophilic Addition of Chlorosulfonyl Isocyanate to Ketones. A Convenient Synthesis of Oxazines, Oxathiazines, and Uracils," J. Org. Chem. 38:2114-2115 (1978).
Reddy et al., "An Efficient Synthesis of 3,4-Dihydro-4-Imino-2(1H)-Quinazolinones," Synthetic Commun. 18:525-530 (1988).
Rosowsky and Modest, "Quinazolines. III. Synthesis of 1,3-Diaminobenzo[f]quinazoline and Related Compounds," J. Org. Chem. 31:2607-2613 (1966).
Saudek et al., "A Preliminary Trial of the Programmable Implantable Medication System for Insulin Delivery," N. Engl. J Med. 321:574-579 (1989).
Seijas et al., "Microwave enhanced synthesis of 4-aminoquinazolines," Tetrahedron Lett. 41:2215-2217 (2000).
Sharma et al., "Synthesis and QSAR studies on 5-[2-(2-methylprop 1-enyl)-1H benzimidazol-lyl]-4,6-diphenyl-pyrimidin-2-(5H)-thione derivatives as antibacterial agents," Eur. J. Med. Chem. 41:833-840 (2006).
Silve et al., "Delineating a Ca2+ Binding Pocket within the Venus Flytrap Module of the Human Calcium Sensing Receptor," The Journal of Biological Chemistry, Nov. 2005, vol. 280, pp. 37917-37923.
Smith et al., 2001, March's Advanced Organic Chemistry. Reactions, Mechanisms, and Structure, Fifth Edition, John Wiley & Sons, Inc. pp. 479-480, 506-507, 510-511, 576-577, 862-865, 1179-1180 and 1552-1553.
Spatola, 1983, Chemistry and Biochemistry of Amino Acids, Peptides and Proteins, 7:267-357, Marcell Dekker, Peptide Backbone Modifications, NY.
Srivastava et al., "Solid Phase Synthesis of Structurally Diverse Pyrimido[4,5-d] Pyrimidines for the Potential Use in Combinatorial Chemistry," Bioorg. Med. Chem. Lett. 9:965-966 (1999).
Thurmond et al., 2008, Synthesis and biological evaluation of novel 2,4-diaminoquinazoline derivatives as SMN2 promoter activators for the potential treatment of spinal muscular atrophy, Journal of Medicinal Chemistry 51(3):449-469.
Tripathi et al., "Reaction of Flavanones with Chlorosulphonyl Isocyanate," Indian J. Chem. Sect. B 26B:1082-1083 (1987).
Trivedi et al., 1989, C2.$N^6$-distributed adenosines: synthesis and structure-activity relationships, Journal of Medicinal Chemistry, 32(8):1667-1673.
Uehling et al., "Biarylaniline Phenethanolamines as Potent and Selective $\beta_3$ Adrenergic Receptor Agonists," J. Med. Chem. 49:2758-2771 (2006).
Verma et al., "Osmotically Controlled Oral Drug Delivery," Drug Dev. Ind. Pharm. 26:695-708 (2000).
Verschoyle et al., "Pharmacokinetics of Isotretinoin (ISO) in Rats Following Oral Dosing or Aerosol Inhalation," British J. Cancer 80, Suppl. 2:96 Abstract No. P269 (1999).
Vippagunta et al., "Crystalline solids," Adv. Drug Deliv. Rev. 48:3-26 (2001).
Wilson, "Traceless Solid-Phase Synthesis of 2,4-Diaminoquinazolines," Org. Lett. 3:585-588 (2000).
Winkler et al., "Synthesis and microbial transformation of .beta.-amino nitriles," Tetrahedron 61:4249-4260 (2005).
Wright, "The Synthesis of 2,1,3-Benzothiadiazine 2,2-Dioxides and 1,2,3-Benzoxathiazine 2,2-Dioxides," Journal of Organic Chemistry 30(11):3960-3962 (1965).
Xu et al., "Purine and Pyrididine Nucleotides Inhibit a Noninactivating K1 Current and Depolarize Adrenal Cortical Cells through a G Protein-coupled Receptor," Molecular Pharmacology, 1999, vol. 55, pp. 364-376.
Yoshizawa et al., "Efficient solvent-free Thrope reaction," Green Chem. 4:68-70 (2002).
Zunszain et al., "Search for the pharmacophore in prazosin for Transport-P," Bioorg. & Med. Chem. 13:3681-3689 (2005).
Extended European Search Report dated Dec. 14, 2017 in patent application No. 11817131.3.
European Search Report for patent application No. 1217564.5, dated Feb. 22, 2013.
International Search Report and Written Opinion for applicatoin No. PCT/09/052258, dated Mar. 15, 2010.
International Search Report and Written Opinion for application No. PCT/11/047636, dated Apr. 9, 2012.

* cited by examiner

METHOD OF IMPROVING STABILITY OF SWEET ENHANCER AND COMPOSITION CONTAINING STABILIZED SWEET ENHANCER

CROSS-REFERENCE TO RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 14/670,331, filed Mar. 26, 2015, which is a divisional of U.S. patent application Ser. No. 13/208,594, filed Aug. 12, 2011 (now U.S. Pat. No. 9,000,054), which claims the benefit of priority to U.S. Provisional Application No. 61/500,834, filed on Jun. 24, 2011 and U.S. Provisional Application No. 61/373,083, filed on Aug. 12, 2010, the disclosures of which are incorporated herein by reference in their entireties.

FIELD OF THE INVENTION

The invention relates to stabilization of sweet enhancers in liquid compositions.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to have superior sweet taste enhancing properties and are described in the patent applications listed below.

(1) U.S. patent application Ser. No. 11/760,592, entitled "Modulation of Chemosensory Receptors and Ligands Associated Therewith", filed Jun. 8, 2007; (2) U.S. patent application Ser. No. 11/836,074, entitled "Modulation of Chemosensory Receptors and Ligands Associated Therewith", filed Aug. 8, 2007; (3) U.S. Patent Application Ser. No. 61/027,410, entitled "Modulation of Chemosensory Receptors and Ligands Associated Therewith", filed Feb. 8, 2008; and (4) International Application No. PCT/US2008/065650, entitled "Modulation of Chemosensory Receptors and Ligands Associated Therewith", filed Jun. 3, 2008; (5) U.S. Provisional Application Ser. No. 61/320,528, entitled "SWEET FLAVOR MODIFIER", filed Apr. 2, 2010; and (6) U.S. patent application Ser. No. 13/076,632, entitled "SWEET FLAVOR MODIFIER", filed Mar. 31, 2011. The content of these applications are herein incorporated by reference in their entirety for all purposes.

The present invention provides methods of stabilizing sweet enhancers and compositions containing stabilized sweet enhancers.

SUMMARY OF THE INVENTION

In one embodiment, the present invention provides a liquid composition comprising: a sweet enhancer having structural formula (I) or (II), or a salt or solvate thereof; and a photostabilizer, or a salt or solvate thereof;

wherein the sweet enhancer having structural formula (I):

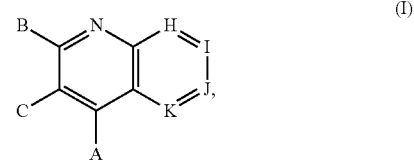

(I)

wherein:

A is —OR$^1$, —NR$^1$C(O)R$^2$, —NHOR$^1$, —NR$^1$R$_2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^4$, —S(O)$_a$R$^4$, —NR$^4$R$^5$, —C(O)NR$^4$R$^5$, —CO$_2$R$^4$, —NR$^4$CO$_2$R$^5$, —NR$^4$C(O)NR$^5$R$^6$, —NR$^4$C(S) NR$^5$R$^6$, —NR$^4$C(=NH)NR$^5$R$^6$, —SO$_2$NR$^4$R$^5$, —NR$^4$SO$_2$R$^5$, —NR$^4$SO$_2$NR$^5$R$^6$, —B(OR$^4$)(OR$^5$), —P(O)(OR$^4$)(OR$^5$), or —P(O)(R$^4$)(OR$^5$);

C is —OR$^7$, —S(O)$_b$R$^7$, SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR), —P(O)(R$^7$)(OR), or heteroaryl;

a and b are independently 0, 1 or 2; and

R$^1$, R$^2$, R$^3$, R$^4$, R$^5$, R$^6$, R$^7$, R$^8$, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, $R^1$ and $R^2$, $R^2$ and $R^3$, $R^4$ and $R^5$, $R^5$ and $R^6$, $R^7$ and $R^8$, or $R^8$ and $R^9$, together with the atoms to which they are bonded, form a cycloheteroalkyl or substituted cycloheteroalkyl ring;

H is —$C(R^{21})$— or —N—;
I is —$C(R^{22})$ or —N—;
J is —$C(R^{23})$— or —N—;
K is —$C(R^{24})$— or —N—;

$R^{21}$ is hydrogen, alkyl, substituted alkyl, halo, —CN, —$OR^{25}$;

$R^{22}$ is hydrogen, alkyl, substituted alkyl, halo, —CN, —$OR^{27}$;

$R^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —$OR^{29}$, —$S(O)_gR^{29}$, —$OC(O)R^{29}$, —$NR^{29}R^{30}$, —$C(O)NR^{29}R^{30}$, —$CO_2R^{29}$, —$SO_2NR^{29}R^{30}$, —$NR^{29}SO_2R^{30}$, —$B(OR^{29})(OR^{30})$, —$P(O)(OR^{29})(OR^{30})$ or —$P(O)(R^{29})(OR^{30})$;

$R^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —$OR^{31}$, —$S(O)_gR^{31}$, —$OC(O)R^{31}$, —$NR^{31}R^{32}$, —$C(O)NR^{31}R^{32}$, —$C(O)R^{31}$, —$CO_2R^{31}$, —$SO_2NR^{31}R^{32}$, —$NR^{31}SO_2R^{32}$, —$B(OR^{31})(OR^{32})$, —$P(O)(OR^{31})(OR^{32})$ or —$P(O)(R^{31})(OR^{32})$; or alternatively $R^{23}$ and $R^{24}$, taken together with the atom to which they are attached, form a cycloalkyl, substituted cycloalkyl, cycloheteroalkyl, or substituted cycloheteroalkyl ring;

f and g are independently 0, 1 or 2; and $R^{25}$, $R^{27}$, $R^{29}$, $R^{30}$, $R^{31}$, and $R^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively $R^{25}$ and $R^{27}$, $R^{27}$ and $R^{29}$, $R^{29}$ and $R^{30}$, $R^{29}$ and $R^{31}$, or $R^{31}$ and $R^{32}$, together with the atoms to which they are attached, form a cycloheteroalkyl or substituted cycloheteroalkyl ring;

with the proviso that at most, two of H, I, J and K are —N—;

the sweet enhancer having structural formula (II):

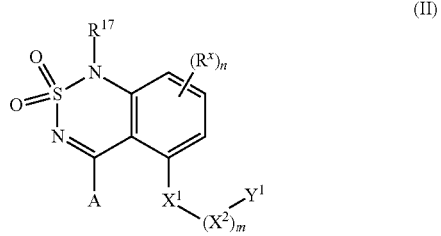

(II)

wherein,

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl,
—CN, —$OR^9$, —$NO_2$, —$S(O)_cR^9$, —$NOR^9$, —$NHOR^9$, —$NR^9COR^{10}$, —$NR^9R^{10}$, —$CONR^9R^{10}$, —$CO_2R^9$ or —$NR^9CO_2R^{10}$;

$R^{17}$ is hydrogen, alkyl, substituted alkyl, arylalkyl, or substituted arylalkyl;

$X^1$ is —$CH_2$—, —O—, —$NR^9$—, —S—, —S(O)—, or —$S(O)_2$—;

$X^2$ is alkylene, substituted alkylene, heteroalkylene, or substituted heteroalkylene;

m is 0 or 1;

$Y^1$ is heteroaryl, substituted heteroaryl, cycloheteroalkyl, substituted cycloheteroalkyl, or

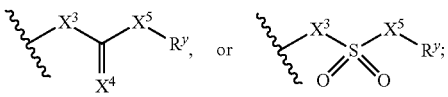

$X^3$ and $X^5$ are independently a covalent bond, —O— or —$NR^9$—;

$X^4$ is O, $NR^9$, N—$OR^9$, or S;

$R^x$ is halo, —$NO_2$, —CN, —OH, —$NH_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

n is 0, 1, 2, or 3;

$R^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —$NR^9R^{10}$; and each $R^9$ and $R^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

with the proviso that when $X^1$ is —O— or —S—, and m is zero; then $X^3$ is not —O—.

In another embodiment, the present invention provides a method of improving stability of a sweet enhancer having structural formula (I) or (II) in a liquid composition comprising: contacting a photostabilizer with the sweet enhancer in the liquid composition, wherein the photostabilizer is selected from the group consisting of a chromone derivative, a coumarine derivative, a phenylpropenioc carbonyl compound, and a combination thereof.

In another embodiment, the present invention provides a method of reducing degradation of a sweet enhancer having structural formula (I) or (II) in a liquid composition comprising: contacting a photostabilizer with the sweet enhancer in the liquid composition, wherein the photostabilizer is selected from the group consisting of a chromone derivative, a coumarine derivative, a phenylpropenioc carbonyl compound, and a combination thereof.

DETAILED DESCRIPTION OF THE INVENTION

Figure 1:
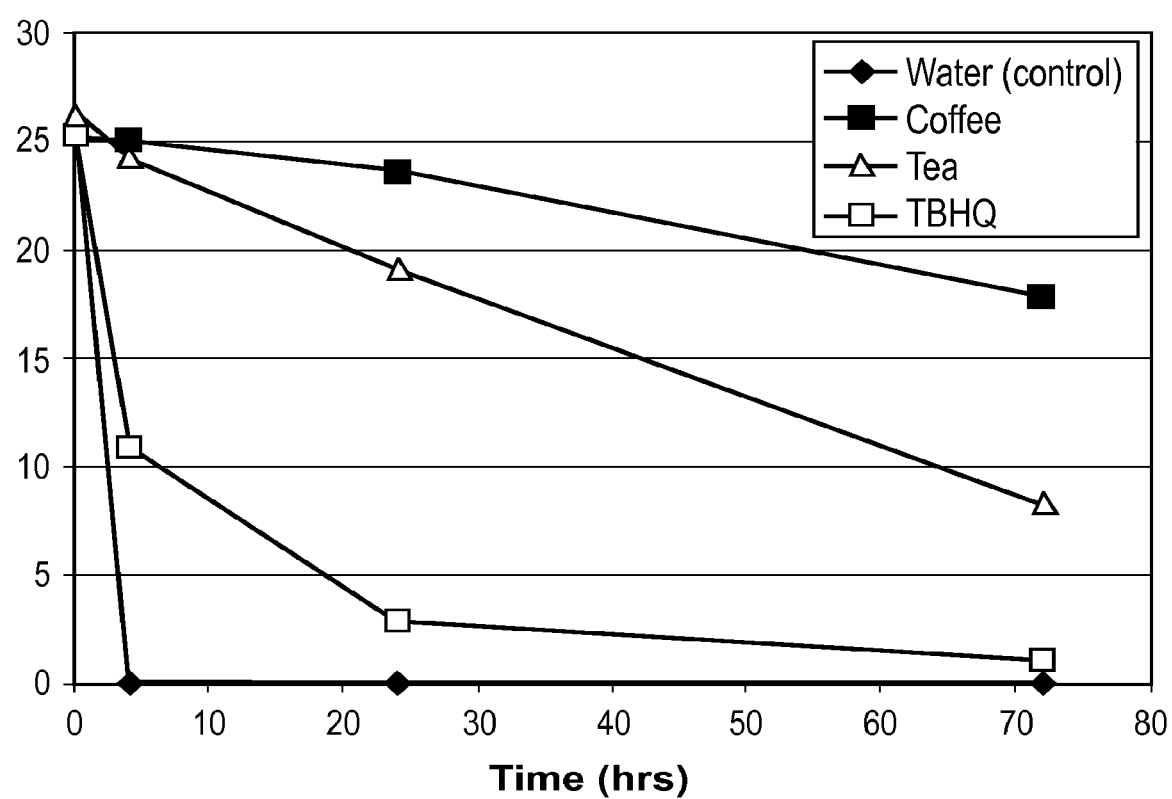
FIG. 1 is a graph showing the photostability of Compound A (25 ppm) in various mediums.

These and other embodiments, advantages, and features of the present invention are provided in the sections below. Unless defined otherwise, all technical and scientific terms used herein have the same meaning as commonly understood by one of ordinary skill in the art to which this invention belongs.

Definitions

The terms "a" and "an" do not denote a limitation of quantity, but rather denote the presence of at least one of the referenced item. The terms "a" and "an" are used interchangeably with "one or more" or "at least one". The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined hereinbelow. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined hereinbelow. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_2$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined hereinbelow. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined hereinbelow. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. "Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to, formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," by itself or as part of another substituent, refers to a saturated or unsaturated cyclic alkyl radical, as defined herein. Similarly, "Cycloalkylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynyenel" groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

The term "present compound(s)", "compound(s) of the present invention", or "sweet enhancer(s)" as used herein refers to compounds encompassed by structural formulae disclosed herein, e.g., formula (I), (Ia), and (II), and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, P3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —OS$(O)_2R^b$, —OS$(O)_2O$—, —OS$(O)_2OR^b$, —P(O)$(O^-)_2$, —P(O)$(OR^b)(O$—$)$, —P(O)$(OR^b)(OR^b)$, —C(O)$R^b$, —C(S)$R^b$, —C($NR^b$)$R^b$, —C(O)O—, —C(O)$O^-$, —C(O)$OR^b$, —C(S)$OR^b$, —C(O)$NR^cR^c$, —C($NR^b$)$NR^cR^c$, —OC(O)$R^b$, —OC(S)$R^b$, —OC(O)O—, —OC(O)$OR^b$, —OC(S)$OR^b$, —$NR^b$C(O)$R^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$, -alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —R$^a$, halo, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O—, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O—, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined. Substituent groups from the above lists useful for substituting other specified groups or atoms will be apparent to those of skill in the art.

The substituents used to substitute a specified group can be further substituted, typically with one or more of the same or different groups selected from the various groups specified above.

"Sugar ring" includes any ring structure formed by a monosaccharide, a disaccharide, an oligosaccharide, a polysaccharide, a sugar acid, a sugar alcohol, or a reducing sugar.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that use sucralose and or other sweeteners.

A "ingestibly acceptable carrier or excipient" is a solid or liquid medium and/or composition that is used to prepare a desired dispersed dosage form of the inventive compound, in order to administer the inventive compound in a dispersed/diluted form, so that the biological effectiveness of the inventive compound is maximized. Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

An "enhancer" herein refers to a compound that modulates (increases) the activation of a particular receptor, preferably the chemosensory, e.g., T1R2/T1R3 receptor but which by itself does not result in substantial activation of the particular receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto.

A "flavor" herein refers to the perception of taste in a subject, which include sweet, sour, salty, bitter and umami. The subject may be a human or an animal.

A "flavoring agent" herein refers to a compound or a biologically acceptable salt or solvate thereof that induces a flavor or taste in an animal or a human.

A "flavor modifier" herein refers to a compound or biologically acceptable salt or solvate thereof that modulates, including enhancing or potentiating, and inducing, the tastes of a natural or synthetic flavoring agent in an animal or a human.

A "flavor enhancer" herein refers to a compound or biologically acceptable salt thereof that enhances and/or multiplies the tastes of a natural or synthetic flavoring agent, or a comestible composition comprising the flavor enhancer.

A "sweet flavor" refers to the sweet taste typically induced by sugar, such as sucrose, in an animal or a human.

A "sweet flavoring agent", "sweet flavor entity", "sweetener", "sweet compound", or "sweet receptor activating compound" herein refers to a compound or biologically acceptable salt thereof that elicits a detectable sweet flavor in a subject, e.g., sucrose or a compound that activates a T1R2/T1R3 receptor in vitro. The subject may be a human or an animal.

A "sweet flavor modifier" herein refers to a compound or biologically acceptable salt or solvate thereof that modulates, including enhancing or potentiating, inducing, and blocking, the sweet taste of a natural or synthetic sweet flavoring agents in an animal or a human.

A "sweet flavor enhancer" herein refers to a compound or biologically acceptable salt thereof that enhances or potentiates the sweet taste of a natural or synthetic sweet flavoring agents in an animal or a human.

A "sweet receptor activating compound" herein refers to a compound that activates a sweet receptor, such as a T1R2/T1R3 receptor.

A "sweet receptor modulating compound" herein refers to a compound that modulates (activates, enhances or blocks) a sweet receptor such as a T1R2/T1R3 receptor.

A "sweet receptor enhancing compound" herein refers to a compound that enhances or potentiates the effect of a natural or synthetic sweet receptor activating compound, e.g., sucrose.

A "sweet flavor enhancing amount" herein refers to an amount of a compound that is sufficient to enhance the taste of a natural or synthetic flavoring agents, e.g., sucrose or sucralose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

A "photostabilizer" refers to a compound which can stabilize a sweet enhancer under light exposure. That is, the photostabilizer can improve, increase, or enhance the photostability of a sweet enhancer or decrease or reduce degradation of a sweet enhancer when exposed to a light source. The light source can be artificial, such as ultraviolet (UV) lamp, or natural, such as sunlight. The present photostabilizers may exert their photostabilizing capability via a wide range of mechanism. In other words, the present photostabilizers are not limited to any particular stabilization mechanism. In one embodiment, the degradation of the sweet enhancer is caused by photo-oxidation, then the photostabilizers may be antioxidants.

A "sweet enhancer stabilizing amount" refers to an amount or concentration of the photostabilizer that is sufficient to substantially reduce, decrease, lessen, or prevent the degradation of a sweet enhancer under light exposure. Depending on the amount and/or concentration of the sweet enhancer in a given composition, the sweet enhancer stabilizing amount may vary with a wide range. In one embodiment, the photostabilizer is present in a sweet enhancer-containing composition in an amount ranging from about 10 ppm to about 500 ppm. In one embodiment, the photostabilizer is present in a sweet enhancer-containing composition in an amount ranging from about 50 ppm to about 300 ppm. In another embodiment, the photostabilizer is present in a sweet enhancer-containing composition in an amount ranging from about 100 ppm to about 200 ppm.

A "liquid composition" refers to a composition that is not completely solid. The liquid composition can be a ingestible composition or a non-ingestible composition. For example, the liquid composition can be in form of a solution, suspension, oil, gel, paste, porridge, or mixture thereof. The liquid composition may also be a food or beverage product, a pharmaceutical composition, a nutritional product, a dietary supplement, over-the-counter medication, or oral care product.

Compounds of Formula (I)

In one embodiment, the sweet enhancers of the present invention have structural Formula (I) or (I'), or a tautomer, salt, and/or solvate thereof:

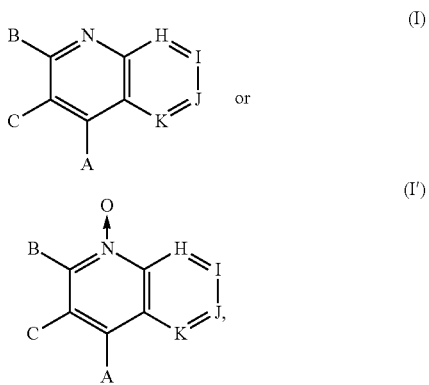

or a tautomer, salt, and/or solvate thereof, wherein:

A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^4$, —S(O)$_a$R$^4$, —NR$^4$R$^5$, —C(O)NR$^4$R$^5$, —CO$_2$R$^4$, —NR$^4$CO$_2$R$^5$, —NR$^4$C(O)NR$^5$R$^6$, —NR$^4$C(S)NR$^5$R$^6$, —NR$^4$C(=NH)NR$^5$R$^6$, —SO$_2$NR$^4$R$^5$, —NR$^4$SO$_2$R$^5$, —NR$^4$SO$_2$NR$^5$R$^6$, —B(OR$^4$)(OR$^5$), —P(O)(OR$^4$)(OR$^5$), or —P(O)(R$^4$)(OR$^5$);

C is —OR$^7$, —S(O)$_b$R$^7$, SO$_3$R$^7$, —C(O)NR$^7$R$^8$, —CO$_2$R$^7$, —NR$^7$CO$_2$R, —NR$^7$C(O)NR$^8$R$^9$, —NR$^7$C(=NH)NR$^8$R$^9$, —SO$_2$NR$^7$R, —NR$^7$SO$_2$R, —NR$^7$SO$_2$NR$^8$R$^9$, —B(OR$^7$)(OR$^8$), —P(O)(OR$^7$)(OR$^8$), —P(O)(R$^7$)(OR$^8$), or heteroaryl (for example, tetrazole);

D is an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl, or substituted cycloheteroalkyl ring;

a and b are independently 0, 1 or 2;

R$^1$, R$^2$, R$^3$, R$^4$, R$^5$, R$^6$, R$^7$, R, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^1$ and R$^2$, R$^2$ and R$^3$, R$^4$ and R$^5$, R$^5$ and R$^6$, R$^7$ and R$^8$, or R$^8$ and R$^9$, together with the atoms to which they are bonded, form a cycloheteroalkyl or substituted cycloheteroalkyl ring;

H is —C(R$^{21}$)— or —N—;
I is —C(R$^{22}$) or —N—;
J is —C(R$^{23}$)— or —N—;
K is —C(R$^{24}$)— or —N—;

R$^{21}$ is hydrogen, alkyl, substituted alkyl, halo, —CN, —OR$^{25}$;

R$^{22}$ is hydrogen, alkyl, substituted alkyl, halo, —CN, —OR$^{27}$;

R$^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{29}$, —S(O)$_c$R$^{29}$, —OC(O)R$^{29}$, —NR$^{29}$R$^{30}$, —C(O)NR$^{29}$R$^{30}$, —CO$_2$R$^{29}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{31}$, —S(O)$_g$R$^{31}$, —OC(O)R$^{31}$, —NR$^{31}$R$^{32}$, —C(O)NR$^{31}$R$^{32}$, —C(O)R$^{31}$, —CO$_2$R$^{31}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$); or alternatively R$^{23}$ and R$^{24}$, taken together with the atom to which they are attached, form a cycloalkyl, substituted cycloalkyl, cycloheteroalkyl, or substituted cycloheteroalkyl ring;

f and g are independently 0, 1 or 2; and

R$^{25}$, R$^{27}$, R$^{29}$, R$^{30}$, R$^{31}$, and R$^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively R$^{25}$ and R$^{27}$, R$^{27}$ and R$^{29}$, R$^{29}$ and R$^{30}$, R$^{29}$ and R$^{31}$, or R$^{31}$ and R$^{32}$, together with the atoms to which they are attached, form a cycloheteroalkyl or substituted cycloheteroalkyl ring;

with the proviso that at most, two of H, I, J and K are —N—.

In one embodiment of Formula (I) or (I'), one or two of H, I, J and K are —N—.

In one embodiment of Formula (I) or (I'), H is —N—, I is —C(R$^{22}$)—, J is —C(R$^{23}$)—, and K is —C(R$^{24}$)—.

In one embodiment of Formula (I) or (I'), H is —C(R$^{21}$)—, I is —N—, J is —C(R$^{23}$)—, and K is —C(R$^{24}$)—.

In one embodiment of Formula (I) or (I'), H is —C(R$^{21}$)—, I is —C(R$^{22}$)—, J is —N—, and K is —C(R$^{24}$)—.

In one embodiment of Formula (I) or (I'), H is —C(R$^{21}$)—, I is —C(R$^{22}$), J is —C(R$^{23}$)—, and K is —N—.

In one embodiment of Formula (I) or (I'), H and I are —N—.

In one embodiment of Formula (I) or (I'), H and J are —N—.

In one embodiment of Formula (I) or (I'), H and K are —N—.

In one embodiment of Formula (I) or (I'), I and J are —N—.

In one embodiment of Formula (I) or (I'), I and K are —N—.

In one embodiment of Formula (I) or (I'), J and K are —N—.

In one embodiment of the present invention, the compounds of Formula (I) have a structural Formula (Ia) or (I'a),

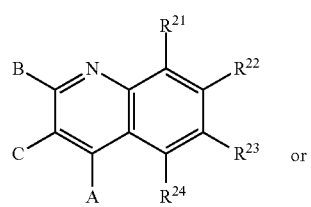

(Ia)

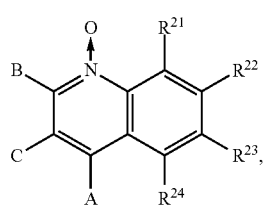

(I'a)

or a tautomer, salt, and/or solvate thereof.

In one embodiment of Formula (Ia) or (I'a), two or three of R$^{21}$, R$^{22}$, R$^{23}$, and R$^{24}$ are hydrogen.

In one embodiment of Formula (Ia) or (I'a), R$^{21}$ is hydrogen; R$^{22}$ is hydrogen, alkyl, substituted alkyl, halo, —CN, or —OR$^{27}$; R$^{23}$ is hydrogen, alkyl, substituted alkyl, —CN, —OR$^{29}$, —S(O)$_g$R$^{29}$, —OC(O)R$^{29}$, —NR$^{29}$R$^{30}$, —C(O)NR$^{29}$R$^{30}$, —C(O)R$^{29}$, —CO$_2$R$^{29}$, —SO$_2$NR$^{29}$R$^{30}$, or —NR$^{29}$SO$_2$R$^{30}$; R$^{24}$ is hydrogen, alkyl, substituted alkyl, —CN, —OR$^{31}$, —S(O)$_g$R$^{31}$, —OC(O)R$^{31}$, —NR$^{31}$R$^{32}$, —C(O)NR$^{31}$R$^{32}$, —C(O)R$^{31}$, —CO$_2$R$^{31}$, —SO$_2$NR$^{31}$R$^{32}$, or —NR$^{31}$SO$_2$R$^{32}$; or alternatively R$^{23}$ and R$^{24}$, taken together with the atoms to which they are attached, form a cycloalkyl, substituted cycloalkyl, cycloheteroalkyl, or substituted cycloheteroalkyl ring; and R$^{27}$, R$^{29}$, R$^{30}$, R$^{31}$, and R$^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively R$^{25}$ and R$^{27}$, R$^{27}$ and R$^{29}$, R$^{29}$ and R$^{30}$, R$^{29}$ and R$^{31}$, or R$^{31}$ and R$^{32}$, together with the atoms to which they are attached, form a cycloheteroalkyl or substituted cycloheteroalkyl ring.

In one embodiment of Formula (Ia) or (I'a), R$^{21}$ and R$^{22}$ are all hydrogen.

In one embodiment of Formula (Ia) or (I'a), R$^{23}$ and R$^{24}$, taken together with the atom to which they are attached, form a cycloalkyl, substituted cycloalkyl, cycloheteroalkyl, or substituted cycloheteroalkyl ring.

In one embodiment of Formula (Ia) or (I'a), R$^{23}$ and R$^{24}$, taken together with the atom to which they are attached, form a substituted cycloheteroalkyl ring containing one or more substituents selected from the group consisting of —R$^a$, halo, —O—, =O, —OR$^b$, —SR$^b$, —S—, =S, —NR$^c$R$^c$, =NR$^b$, =N—OR$^b$, trihalomethyl, —CF$_3$, —CN, —OCN, —SCN, —NO, —NO$_2$, =N$_2$, —N$_3$, —S(O)$_2$R$^b$, —S(O)$_2$NR$^b$, —S(O)$_2$O—, —S(O)$_2$OR$^b$, —OS(O)$_2$R$^b$, —OS(O)$_2$O—, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(O)OR$^b$, —C(S)R$^b$, —C(NR$^b$)R$^b$, —C(O)O—, —C(S)OR$^b$, —C(O)NR$^c$R$^c$, —C(NR$^b$)NR$^c$R$^c$, —OC(O)R$^b$, —OC(S)R$^b$, —OC(O)O—, —OC(O)OR$^b$, —OC(S)OR$^b$, —NR$^b$C(O)R$^b$, —NR$^b$C(S) R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S; or alternatively, two of the substituents on the cycloheteroalkyl ring, together with the atoms to which they are bonded, form a cycloalkyl, substituted cycloalkyl, cycloheteroalkyl, or substituted cycloheteroalkyl ring.

In one embodiment of Formula (Ia) or (I'a), R$^{21}$, R$^{22}$, R$^{23}$, and R$^{24}$ are all hydrogen.

In one embodiment of Formula (Ia) or (I'a), A is —OR$^1$, —NR$^1$C(O)R$^2$, —NHOR$^1$, —NR$^1$R$^2$, —NOR$^1$, —NR$^1$CO$_2$R$^2$, —NR$^1$C(O)NR$^2$R$^3$, —NR$^1$CSNR$^2$R$^3$, or —NR$^1$C(=NH)NR$^2$R$^3$.

In one embodiment of Formula (Ia) or (I'a), C is —S(O)$_b$R$^7$, SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(S)NR$^8$R$^9$, —NR⁷C(=NH)NR⁸R⁹, —SO₂NR⁷R⁸, —NR⁷SO₂R⁸, —NR⁷SO₂NR⁸R⁹, —B(OR⁷)(OR⁸), —P(O)(OR⁷)(OR⁸), or —P(O)(R⁷)(OR⁸).

In one embodiment of Formula (Ia) or (I'a), B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of Formula (Ia) or (I'a), three of R²¹, R²², R²³, and R²⁴ are hydrogen; A is —OR¹, —NR¹C(O)R², —NHOR¹, —NR¹R², —NR¹CO₂R², —NR¹C(O)NR²R³, —NR¹C(S)NR²R³, or —NR¹C(=NH)NR²R³; C is —S(O)ᵦR⁷, SO₃R⁷, —C(O)NR⁷R⁸, —CO₂R⁷, —NR⁷CO₂R⁸, —NR⁷C(O)NR⁸R⁹, —NR⁷C(S)NR⁸R⁹, —NR⁷C(=NH)NR⁸R⁹, —SO₂NR⁷R⁸, —NR⁷SO₂R⁸, —NR⁷SO₂NR⁸R⁹, —B(OR⁷)(OR⁸), —P(O)(OR⁷)(OR⁸), or —P(O)(R⁷)(OR⁸) or tetrazole; B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of the present invention, the compounds of Formula (Ia) or (I'a) have a structural Formula (Ib) or (I'b),

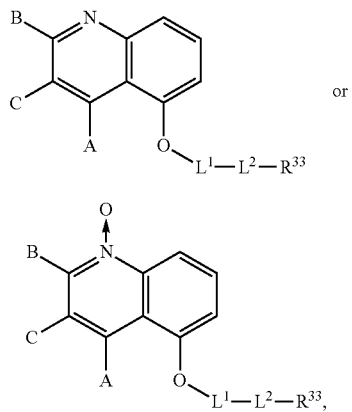

or a tautomer, salt, and/or solvate thereof; wherein

L¹ is alkylene or substituted alkylene;

L² is —NR³⁴—, —O—, —S—, —NR³⁴—C(O)—, —C(O)—NR³⁴—, —O—C(O)—, —C(O)—O—, —NR³⁴—C(O)—O—, —O—C(O)—NR³⁴—, —NR³⁴—C(O)—NR³⁵—, —O—C(O)—O—, -hetercyclylene-C(O)—, or -(substituted hetercyclylene)-C(O)—;

R³³ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and R³⁴ and R³⁵ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

In one embodiment of the present invention, the compounds of Formula (Ia) or (I'a) have a structural Formula (Ic), (I'c), (Id), or (I'd),

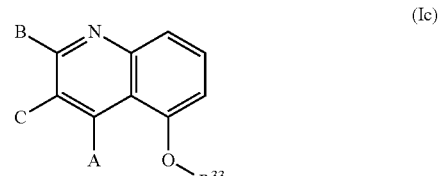

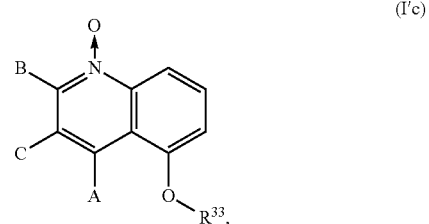

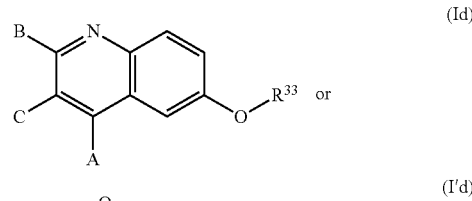

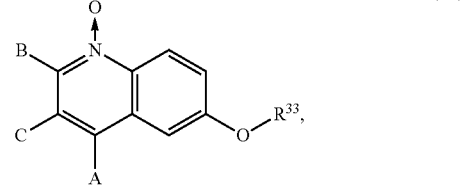

or a tautomer, salt, and/or solvate thereof; wherein R³³ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

In one embodiment of Formula (Ic), (I'c), (Id) or (I'd), R³³ is alkyl, substituted alkyl, carbocyclyl, substituted carbocyclyl; heterocyclyl, substituted heterocyclyl, heteroalkyl, or substituted heteroalkyl.

In one embodiment of Formula (Ib), (Ic), or (Id), A is —OR¹, —NR¹C(O)R², —NHOR¹, —NR¹R², —NR¹CO₂R², —NR¹C(O)NR²R³, —NR¹CSNR²R³, or —NR¹C(=NH)NR²R³.

In one embodiment of Formula (Ib), (Ic), or (Id), C is —S(O)ᵦR⁷, SO₃R⁷, —C(O)NR⁷R⁸, —CO₂R⁷, —NR⁷CO₂R, —NR⁷C(O)NR⁸R⁹, —NR⁷C(S)NR⁸R⁹, —NR⁷C(=NH)NR⁸R⁹, —SO₂NR⁷R, —NR⁷SO₂R, —NR⁷SO₂NR⁸R⁹, —B(OR⁷)(OR), —P(O)(OR⁷)(OR), or —P(O)(R⁷)(OR⁸).

In one embodiment of Formula (Ib), (Ic), or (Id), B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of Formula (Ib), A is —OR¹, —NHOR¹, or —NR¹R²; B is hydrogen, alkyl, substituted alkyl, aryl, or substituted aryl; C is —SO₃R⁷, —C(O)NR⁷R⁸, —CO₂R⁷, —SO₂NR⁷R⁸, —B(OR⁷)(OR⁸), —P(O)(OR⁷)(OR), or —P(O)(R⁷)(OR⁸); L¹ is alkylene or substituted alkylene; L² is —NR³⁴—, —O—, —NR³⁴—C(O)—, —C(O)—NR³⁴—, —O—C(O)—, —C(O)—O—, -hetercyclylene-C(O)—, or -(substituted heterocyclylene)-C(O)—;

$R^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and $R^{34}$ and $R^{35}$ are independently hydrogen, alkyl, or substituted alkyl.

In one embodiment of Formula (Ic) or (Id), A is —$OR^1$, —$NHOR^1$, or —$NR^1R^2$; B is hydrogen, alkyl, substituted alkyl, aryl, or substituted aryl; C is —$SO_3R^7$, —$C(O)NR^7R^8$, —$CO_2R^7$, —$SO_2NR^7R^8$, —$B(OR^7)(OR^8)$, —$P(O)(OR^7)(OR^8)$, or —$P(O)(R^7)(OR^8)$; $R^{33}$ is alkyl, substituted alkyl, carbocyclyl, substituted carbocyclyl; heterocyclyl, substituted heterocyclyl, heteroalkyl, or substituted heteroalkyl.

In one embodiment, the compound of Formula (Ia) can be represented by structural Formula (Ie):

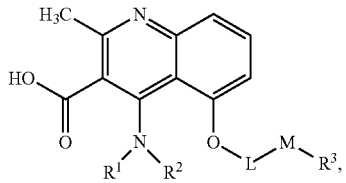

(Ie)

or a salt and/or solvate thereof; wherein $R^1$ and $R^2$ are independently hydrogen or $C_1$ to $C_6$ alkyl;
L is $C_1$ to $C_{12}$ alkylene or substituted $C_1$ to $C_{12}$ alkylene;
M is —$NR^4$—C(O)— or —C(O)—$NR^4$—;
$R^4$ is hydrogen or $C_1$ to $C_6$ alkyl; or alternatively, when M is —$NR^4$—C(O)—, $R^4$ and one or more atoms of L, together with the nitrogen to which they are attached, form a 5- to 8-membered heterocyclic ring which is optionally substituted and contains one to three heteroatoms selected from nitrogen, oxygen, and sulfur; and
$R^3$ is C1 to C12 alkyl, substituted C1 to C12 alkyl, 5- to 8-membered heterocyclyl, or substituted 5- to 8-membered heterocyclyl; or alternatively, when M is —C(O)—$NR^4$—, $R^4$ and one or more atoms of $R^3$, together with the nitrogen to which they are attached, form a 5- to 8-membered heterocyclic ring which is optionally substituted and contains one to three heteroatoms selected from nitrogen, oxygen, and sulfur.

In one embodiment of Formula (Ie), the substituent group(s) on the C1 to C12 alkylene, the heterocyclyl, the heterocyclic ring, and the C1 to C12 alkyl is selected from the group consisting of halo, amino, N-alkyl amino, N,N-dialkyl amino, hydroxyl, alkoxy, aryl, heteroaryl, heterocyclyl, carbocyclyl, =O, =S, =$NR^a$, =N—$OR^a$, —CN, —OCN, —SCN, —NO, —$NO_2$, =$N_2$, —$N_3$, —$C(O)R^b$, —$C(O)OR^a$, —$C(O)NR^aR^a$, —OC(O)OH, —$OC(O)OR^a$, —$NR^aC(O)R^b$, —$NR^aC(O)OR^a$, and —$NR^aC(O)NR^aR^a$, wherein each $R^a$ is independently hydrogen or alkyl including straight, branched, and cyclic alkyl; or alternatively, two $R^a$, taken together with the nitrogen to which they are attached, form a heterocyclic ring; and each $R^b$ is alkyl including straight, branched, and cyclic alkyl.

In one embodiment of Formula (Ie), $R^1$ and $R^2$ are both hydrogen.

In one embodiment of Formula (Ie), the alkylene is straight, branched, cyclic, or a combination thereof.

In one embodiment of Formula (Ie), the alkyl is straight, branched, cyclic, or a combination thereof.

In one embodiment of Formula (Ie), the compound can be represented by structural Formula (IeA):

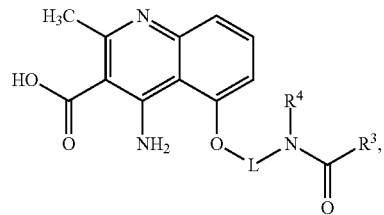

(IeA)

wherein,

L is C1 to C12 alkylene or substituted C1 to C12 alkylene;
$R^4$ is hydrogen or C1 to C6 alkyl; or alternatively, $R^4$ and one or more atoms of L, together with the nitrogen to which they are attached, form a 5- to 8-membered heterocyclic ring which is optionally substituted and contains one to three heteroatoms selected from nitrogen, oxygen, and sulfur; and
$R^3$ is C1 to C12 alkyl, substituted C1 to C12 alkyl, 5- to 8-membered heterocyclyl, or substituted 5- to 8-membered heterocyclyl.

In one embodiment of Formula (IeA), L is branched or cyclic C3 to C6 alkylene; $R^4$ is hydrogen; and $R^3$ is branched C3 to C6 alkyl or straight C1 to C6 alkyl.

In one embodiment of Formula (I), the compound can be represented by structural Formula (IeB):

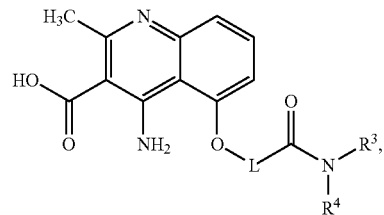

(IeB)

wherein:

L is C1 to C12 alkylene or substituted C1 to C12 alkylene;
$R^4$ is hydrogen or C1 to C6 alkyl; and
$R^3$ is C1 to C12 alkyl, substituted C1 to C12 alkyl, 5- to 8-membered heterocyclyl, substituted 5- to 8-membered heterocyclyl; or alternatively, $R^4$ and one or more atoms of $R^3$, together with the nitrogen to which they are attached, form a 5- to 8-membered heterocyclic ring which is optionally substituted and contains one to three heteroatoms selected from nitrogen, oxygen, and sulfur.

In one embodiment of Formula (IeB), L is straight C1 to C6 alkylene or branched C3 to C6 alkylene; $R^4$ is hydrogen; and $R^3$ is straight C1 to C6 alkyl or branched or cyclic C3 to C6 alkyl.

In some specific embodiments, the sweet enhancer having structural formula (I) or (I') is selected from the group consisting of

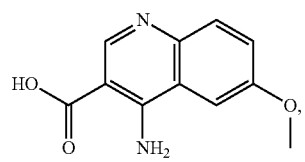

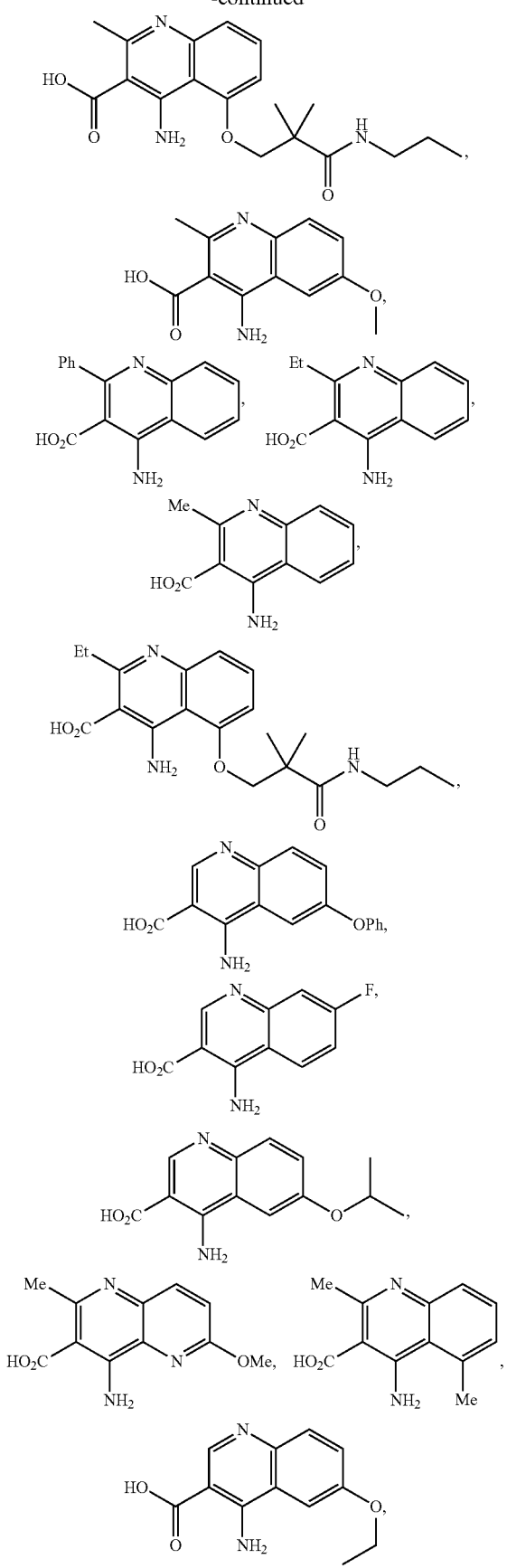
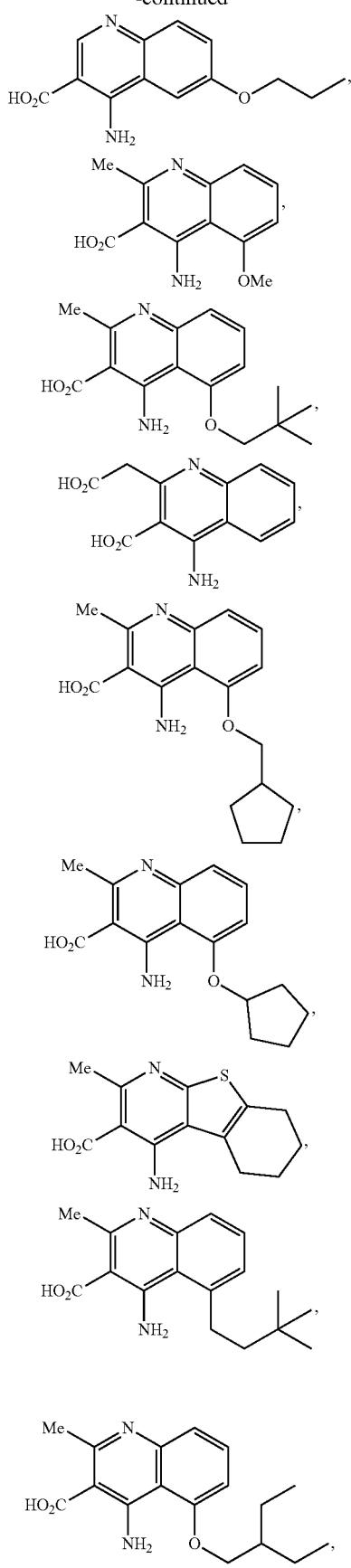

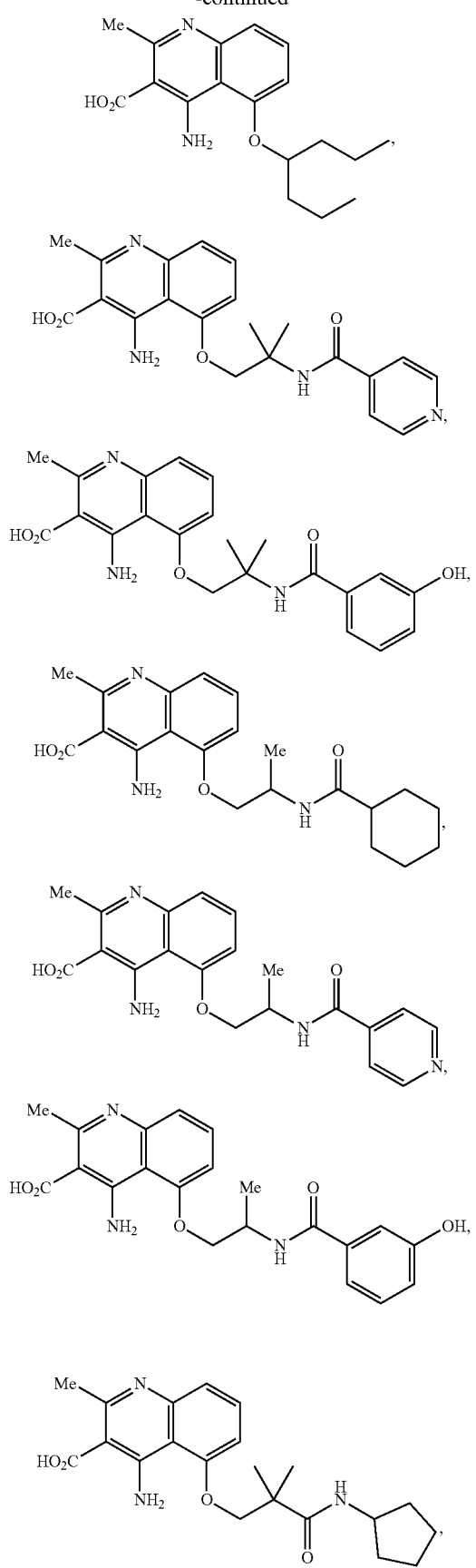
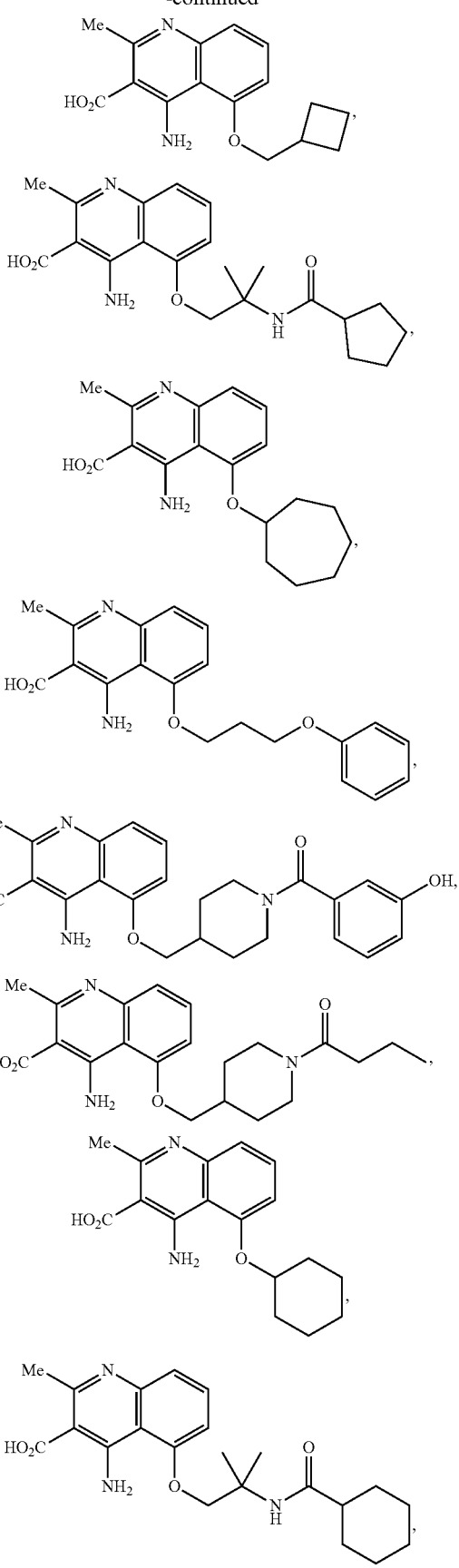

-continued
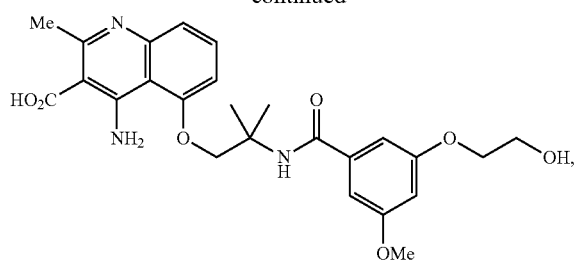
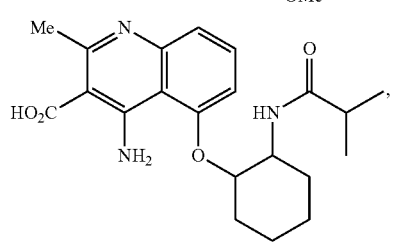
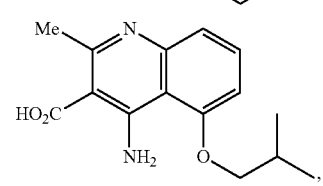
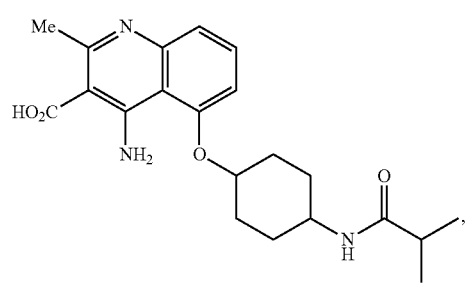
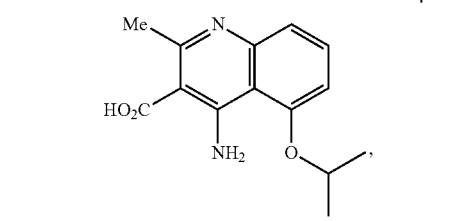
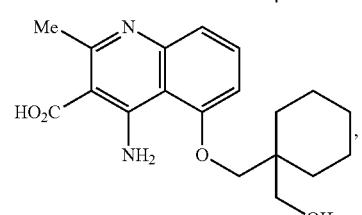
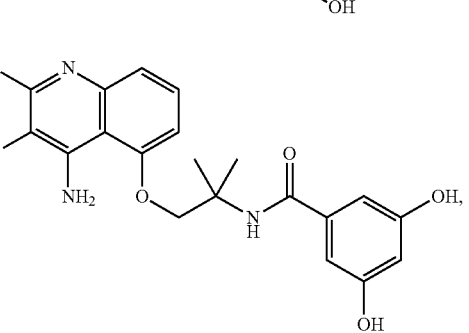
-continued
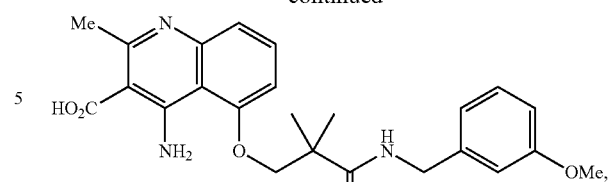
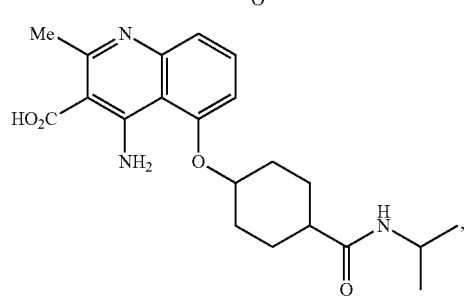
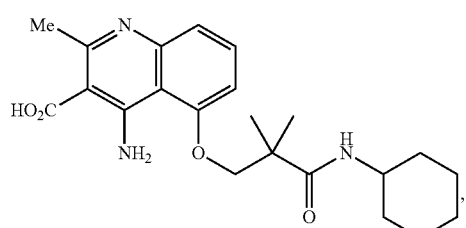
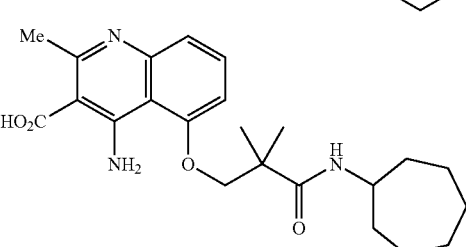
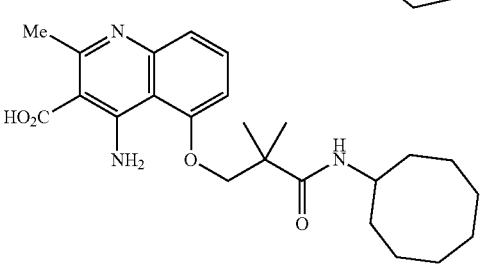
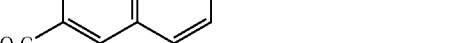
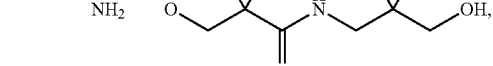

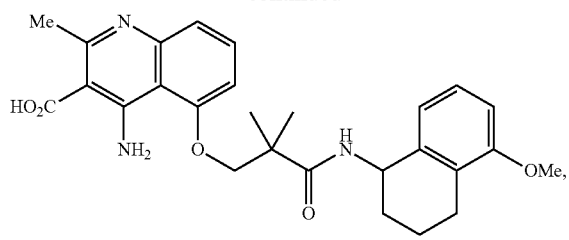
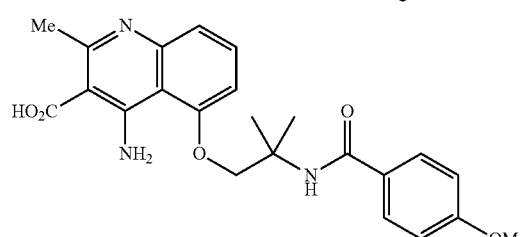
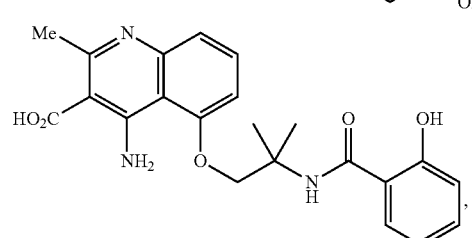
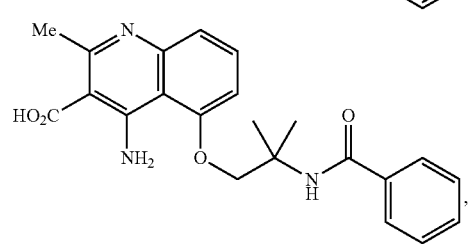
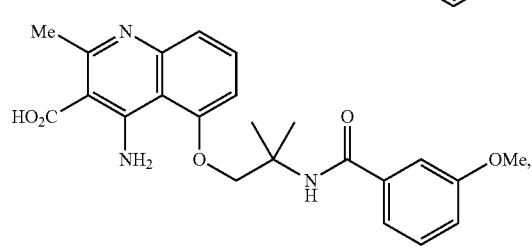
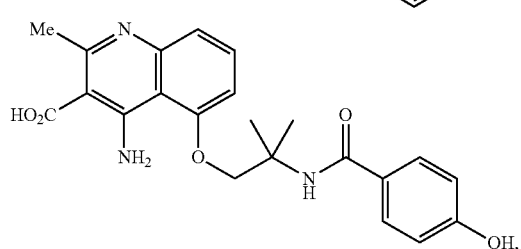
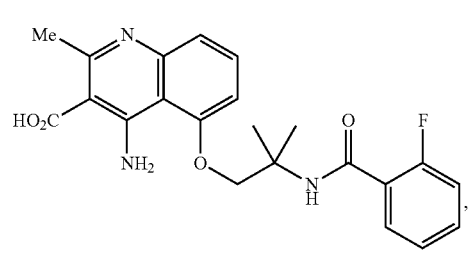
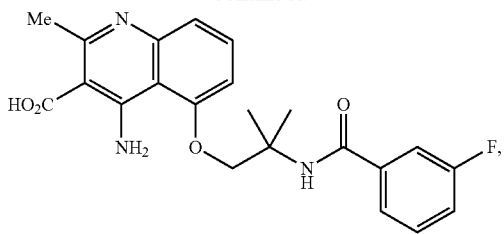
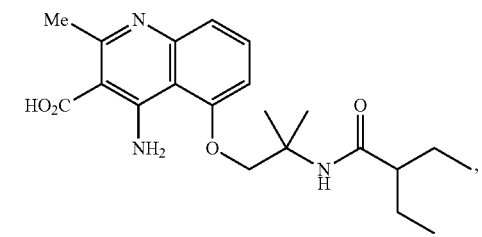
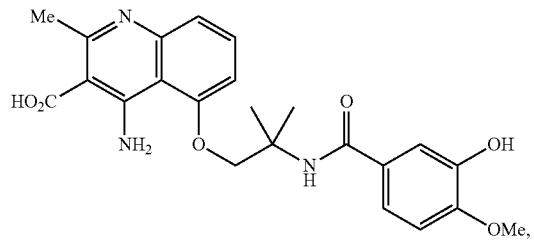
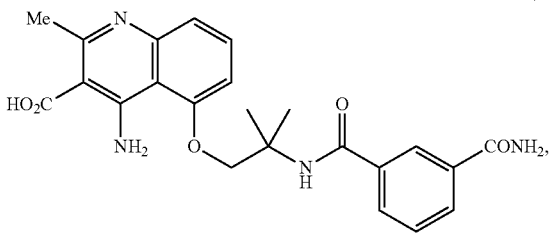
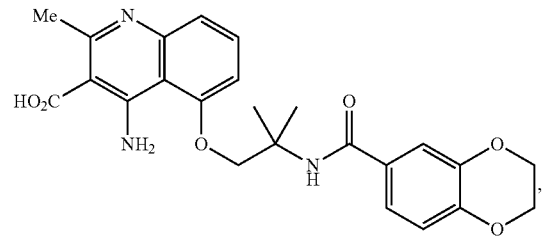
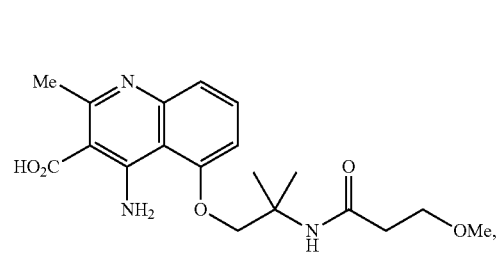
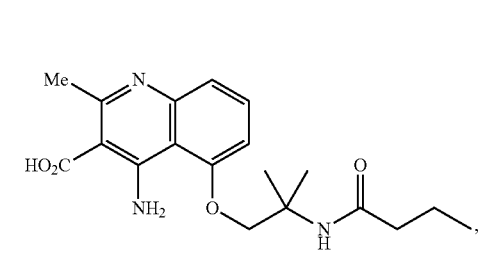

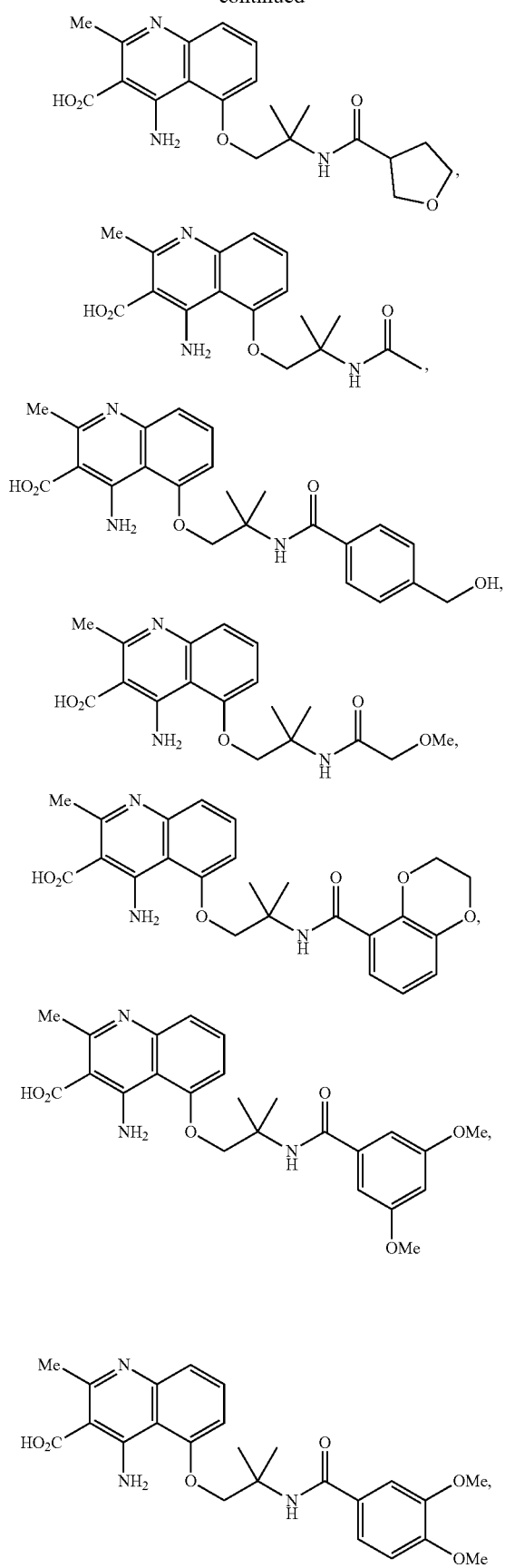
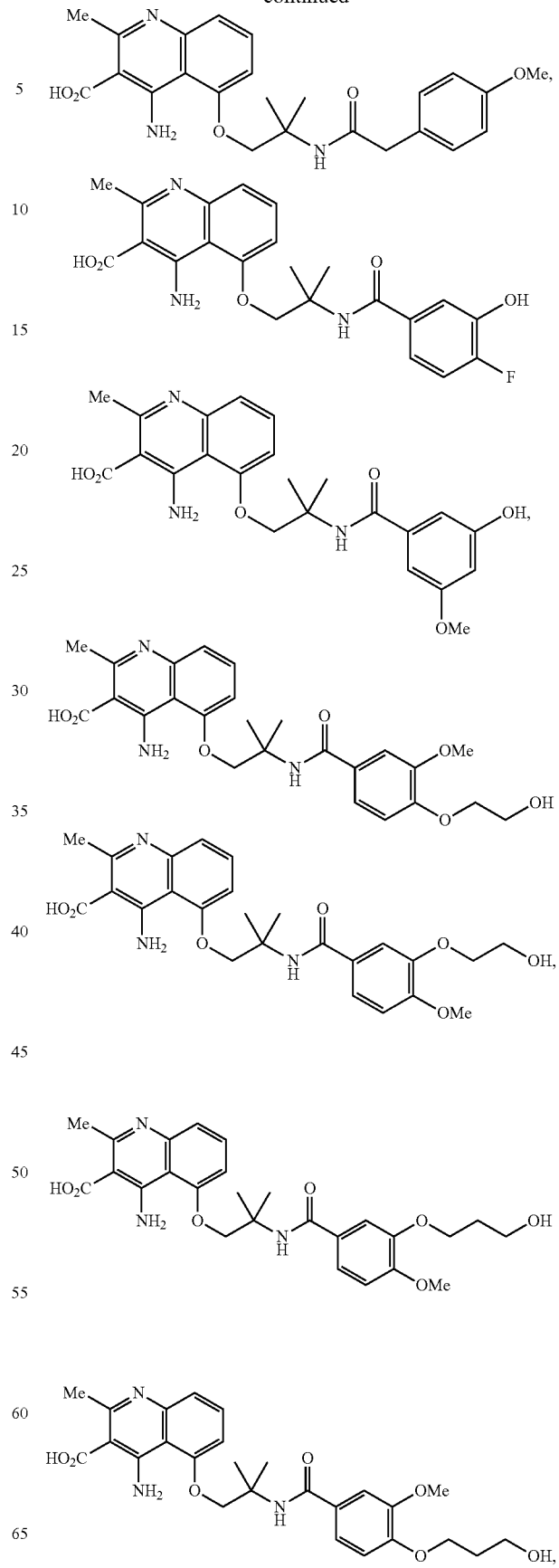

31
-continued
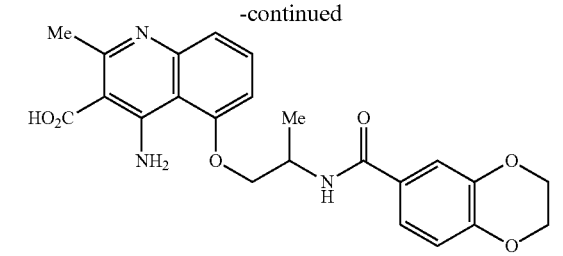
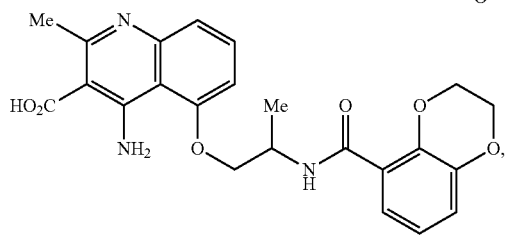
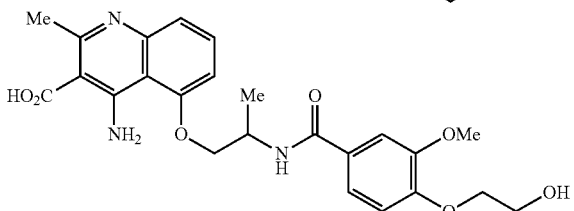
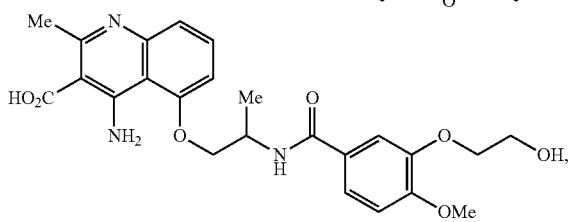
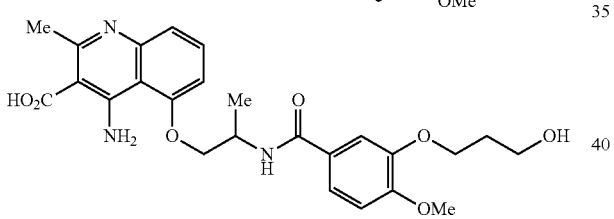
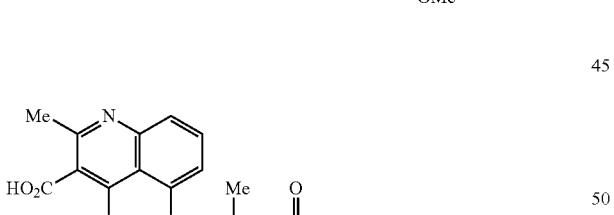
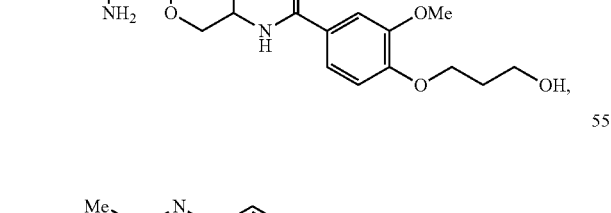
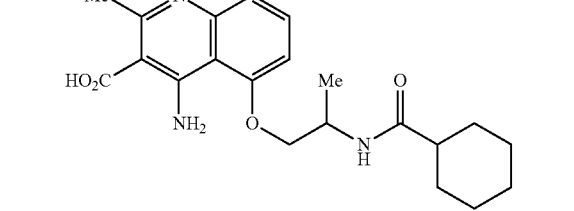
32
-continued
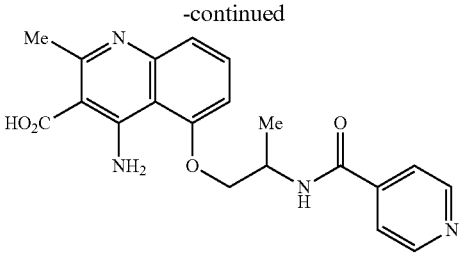
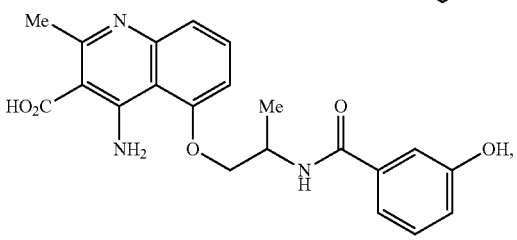
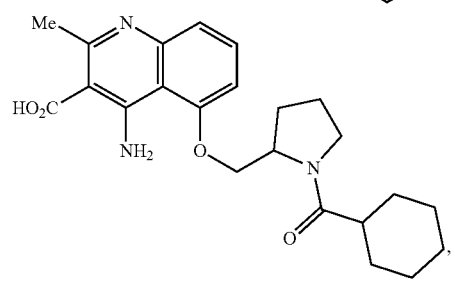
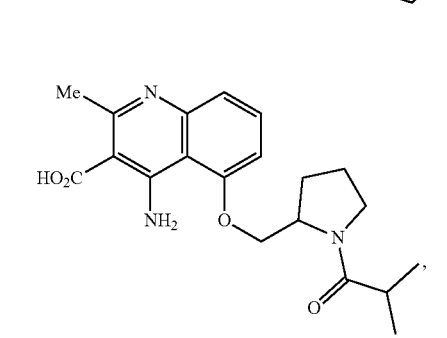
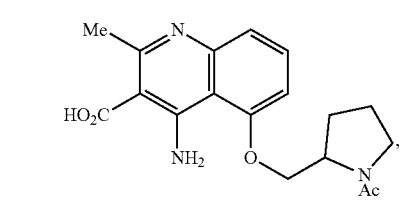
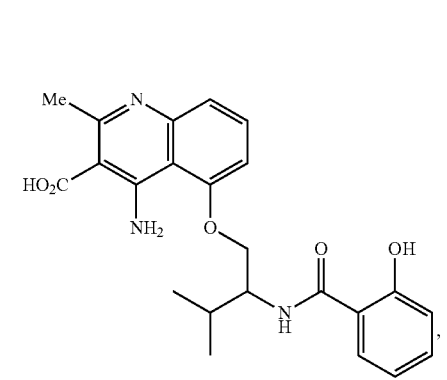

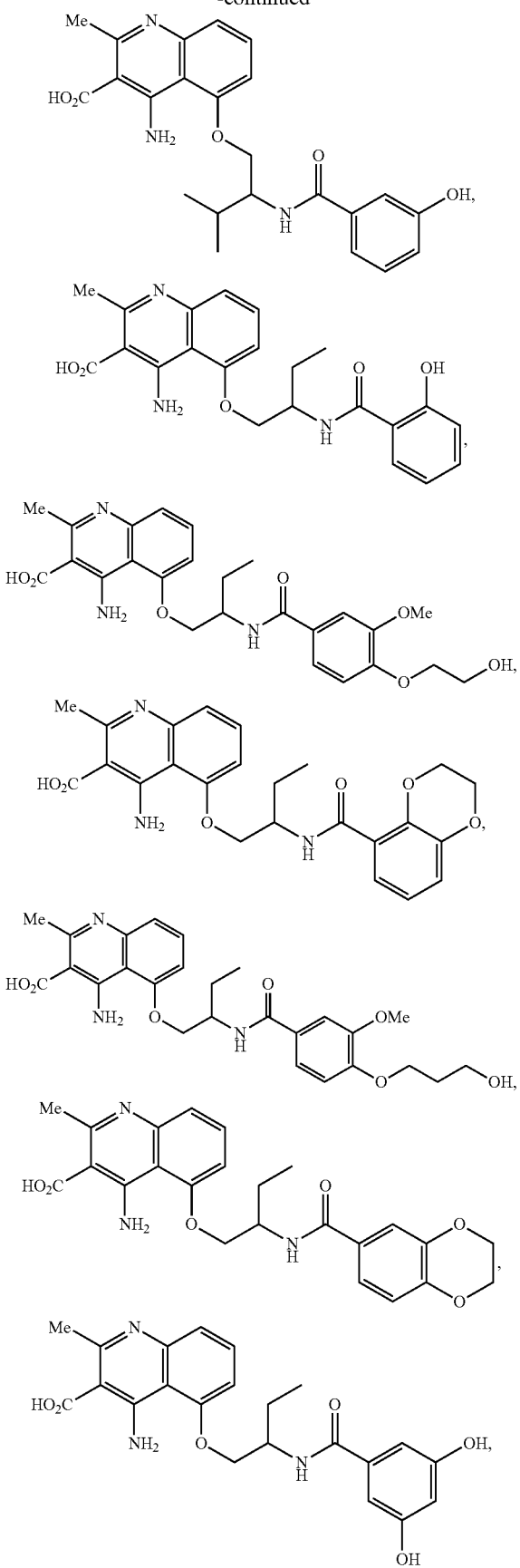
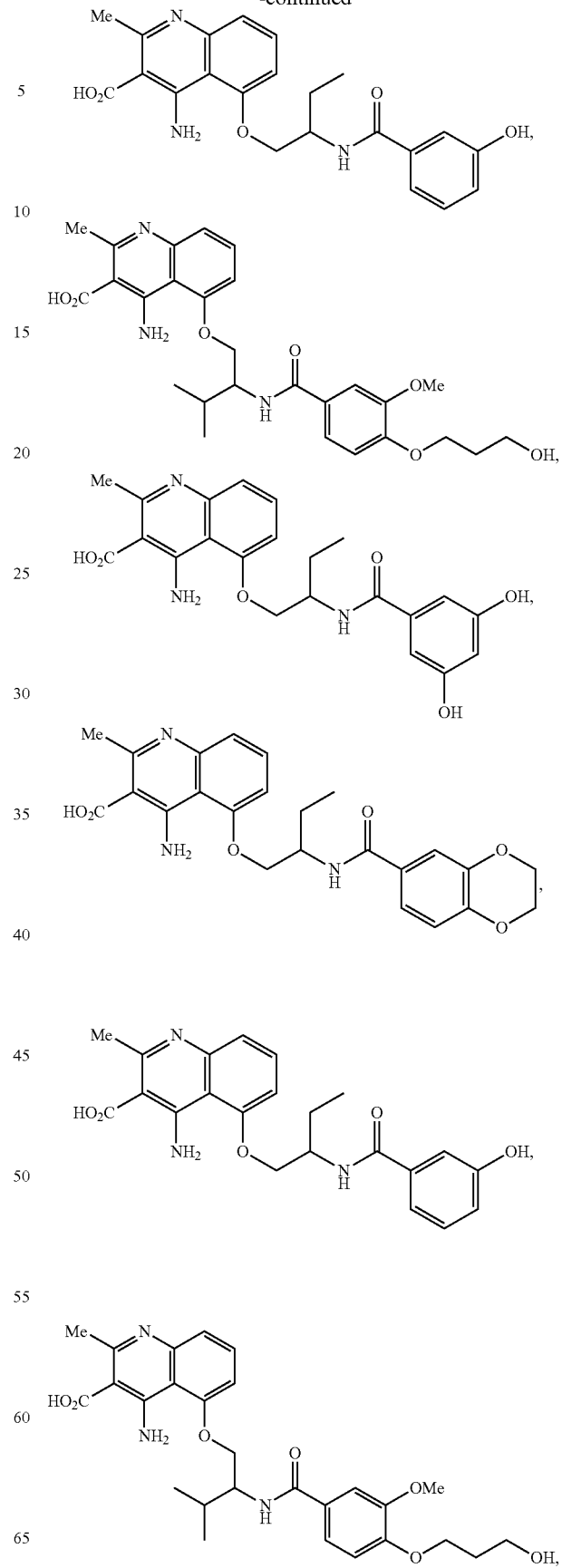

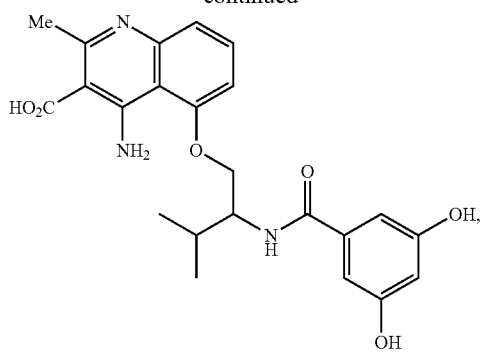
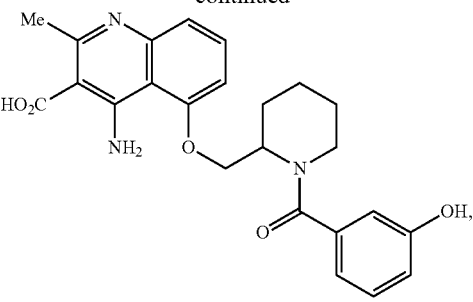
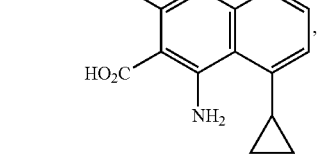
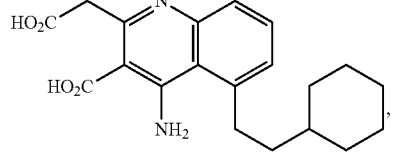
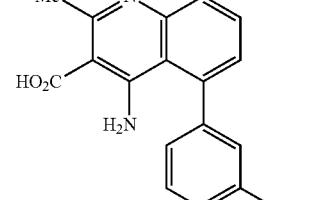
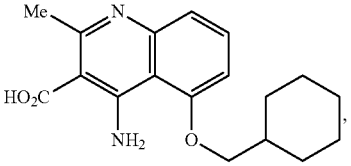
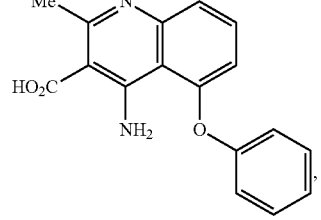
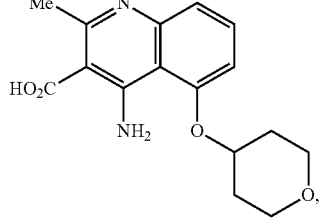
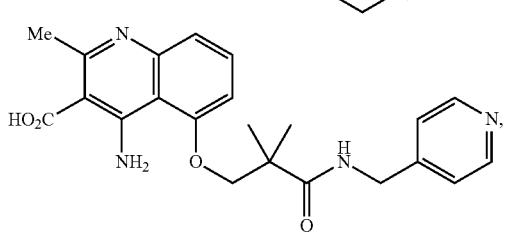

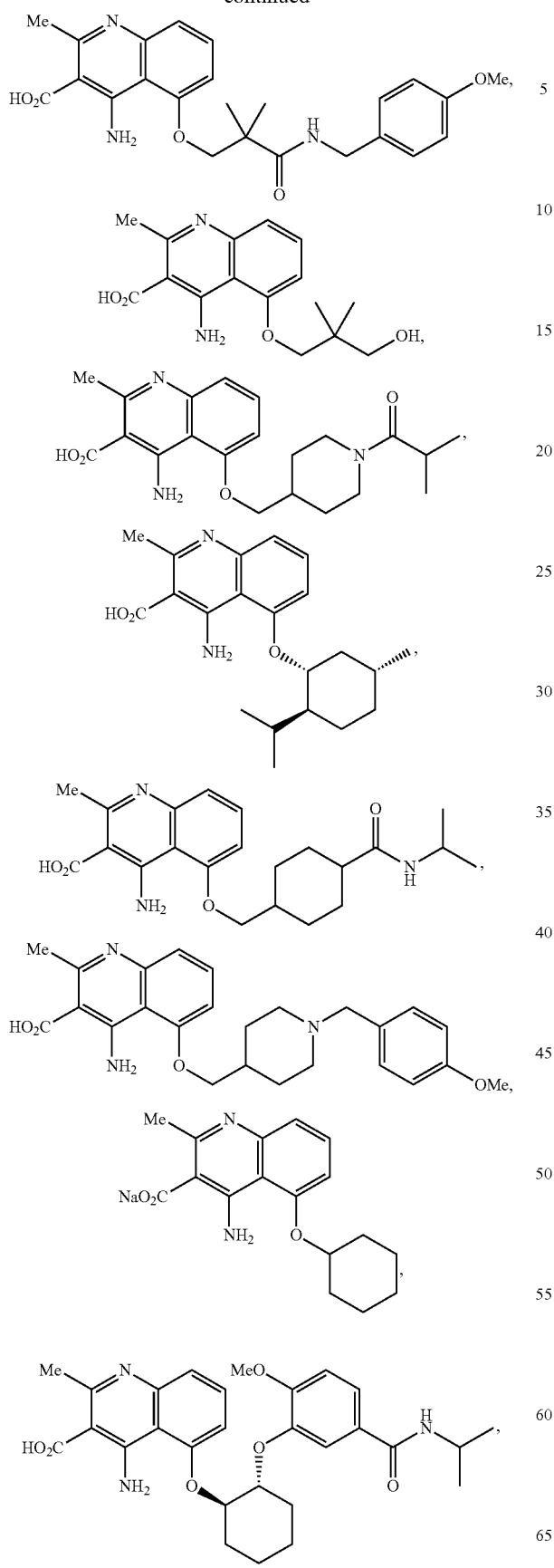
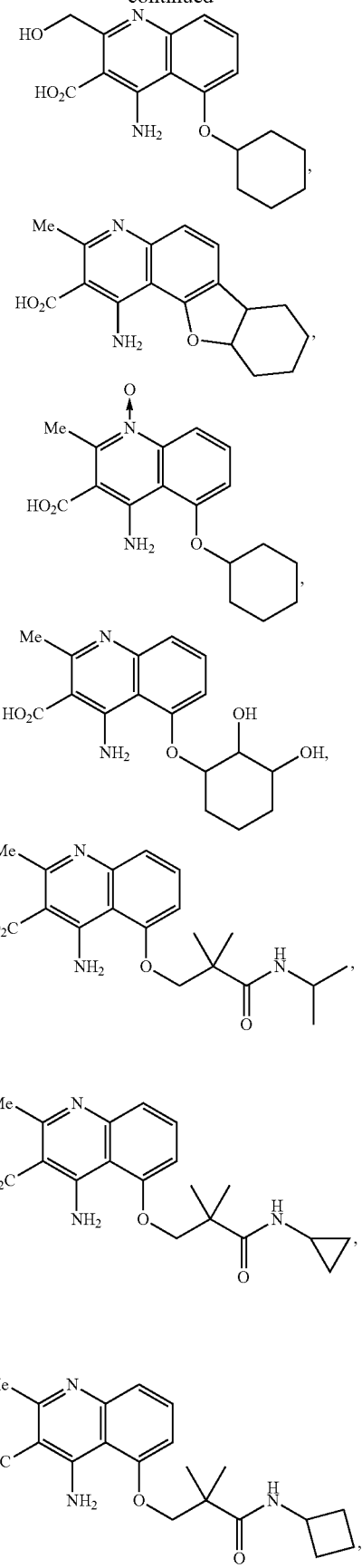

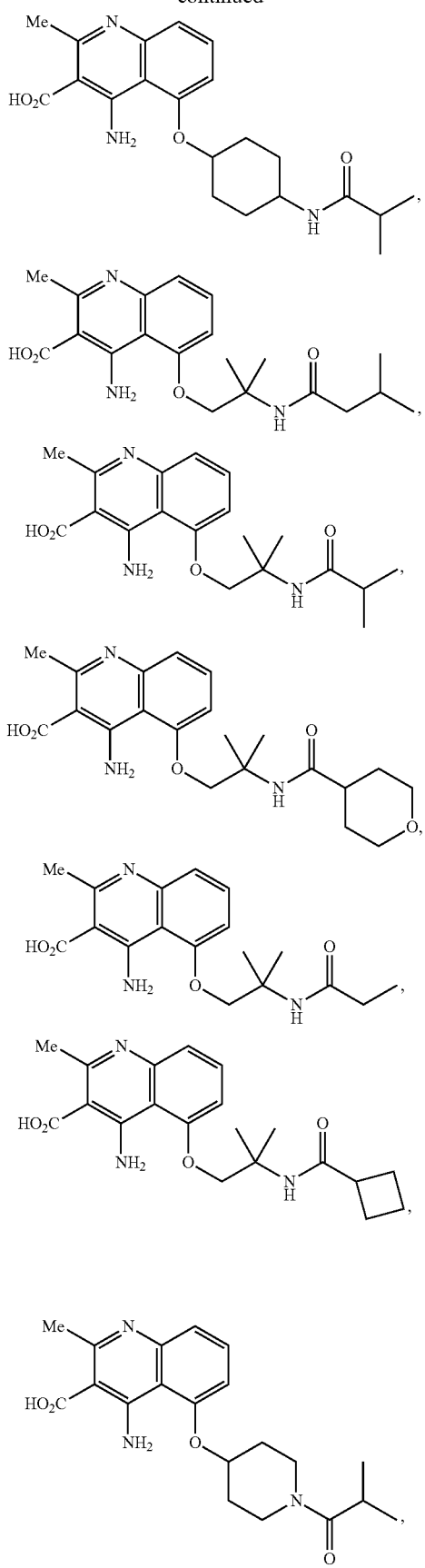
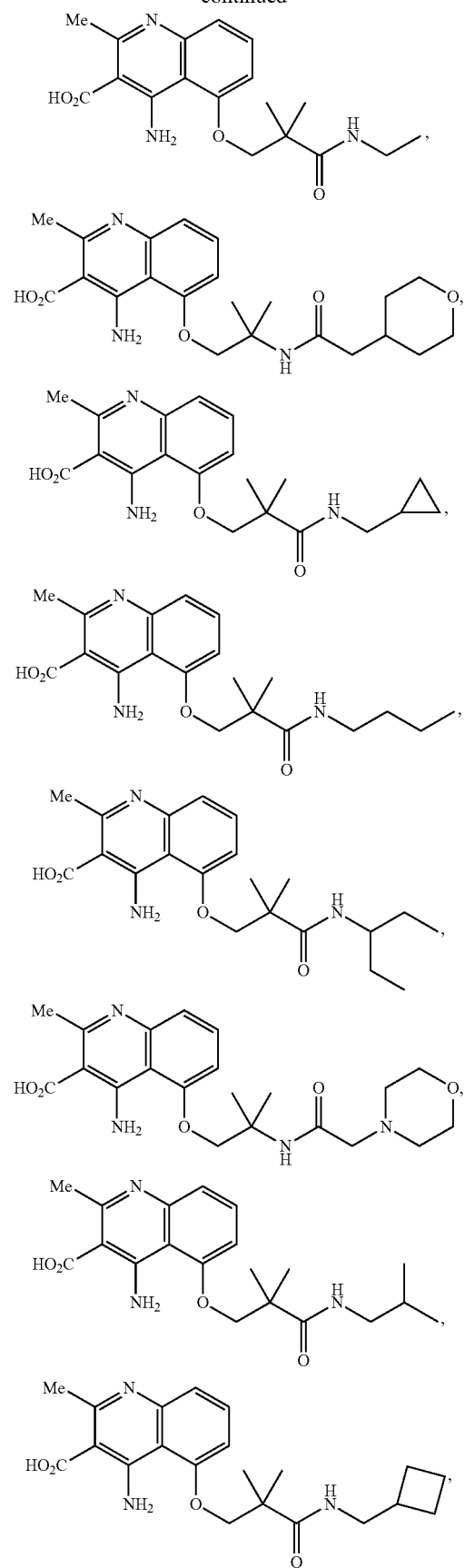

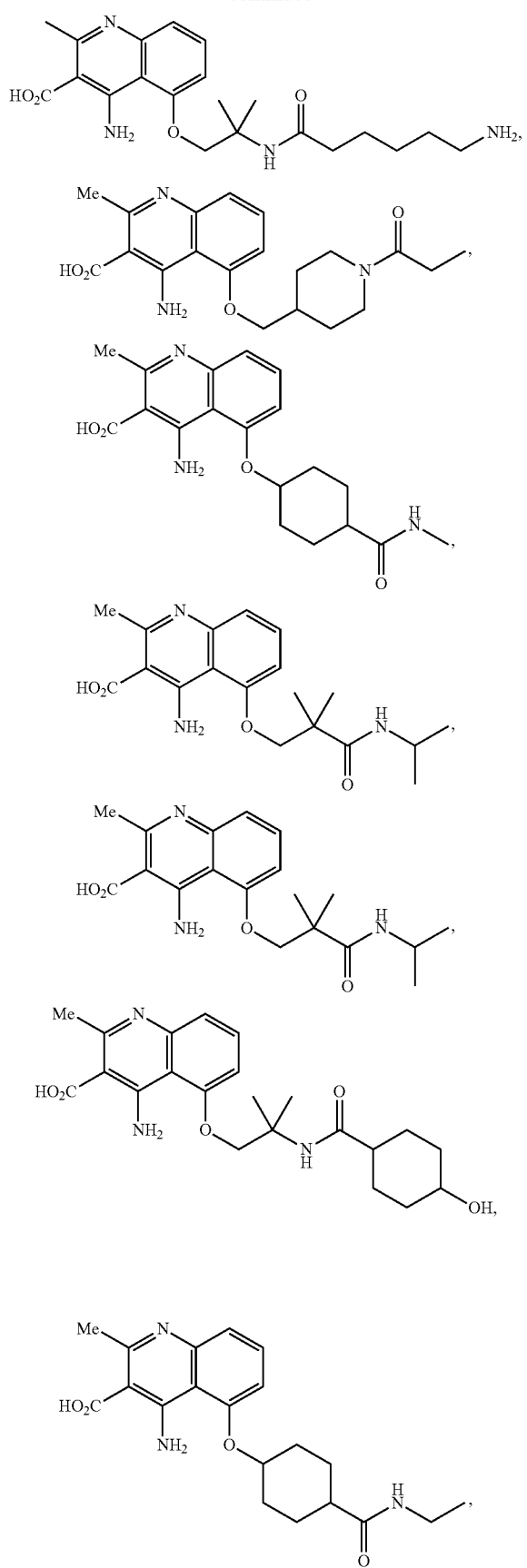
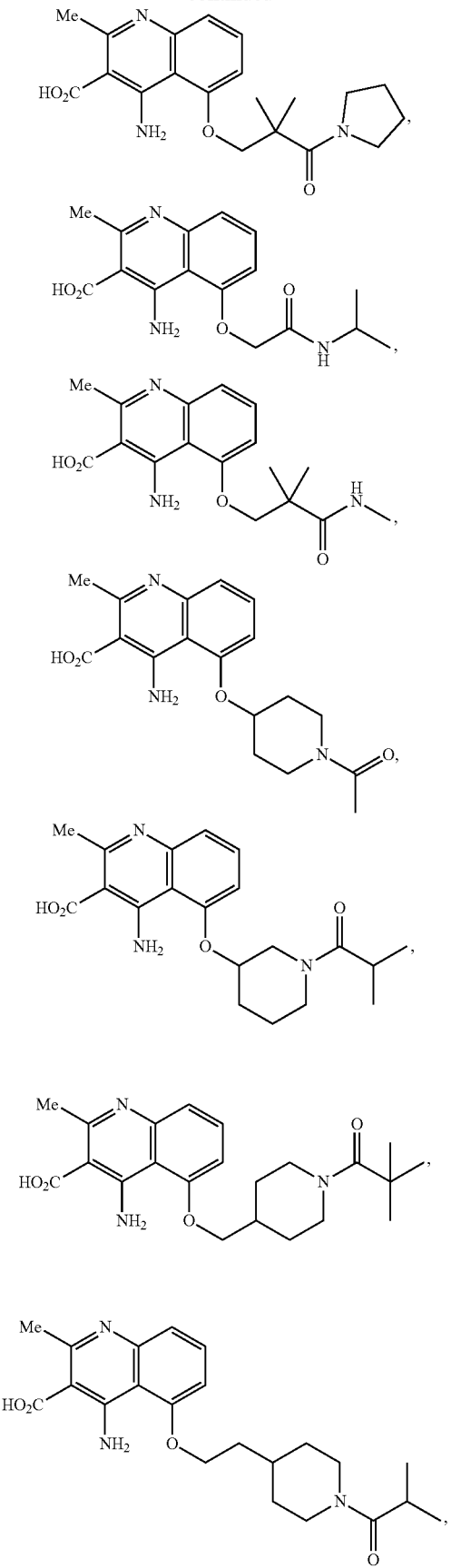

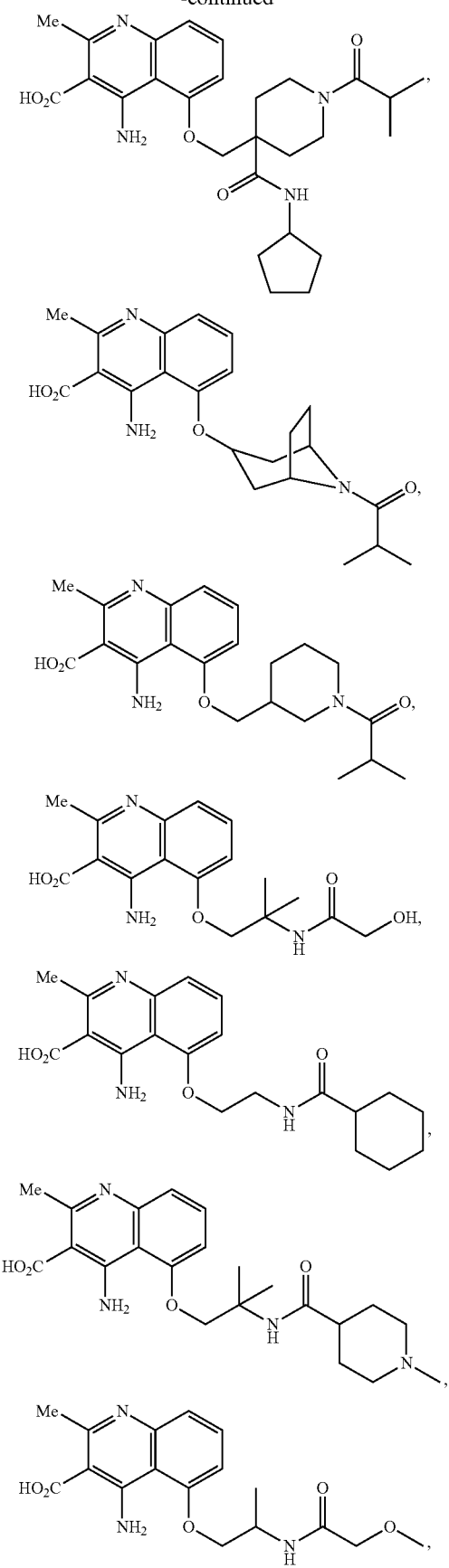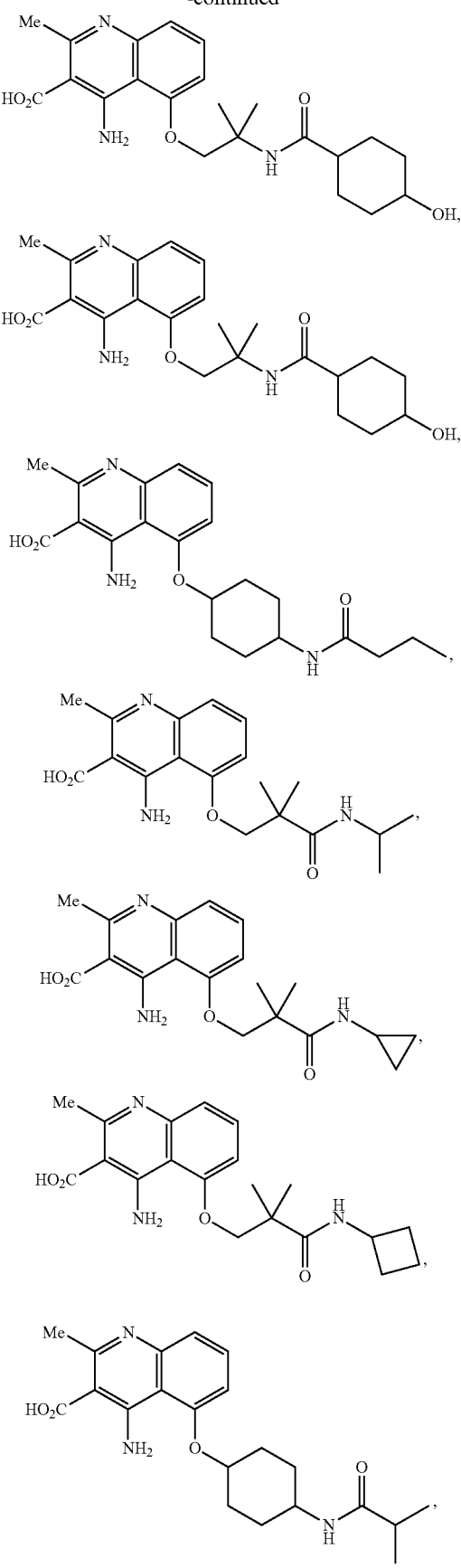

45
-continued
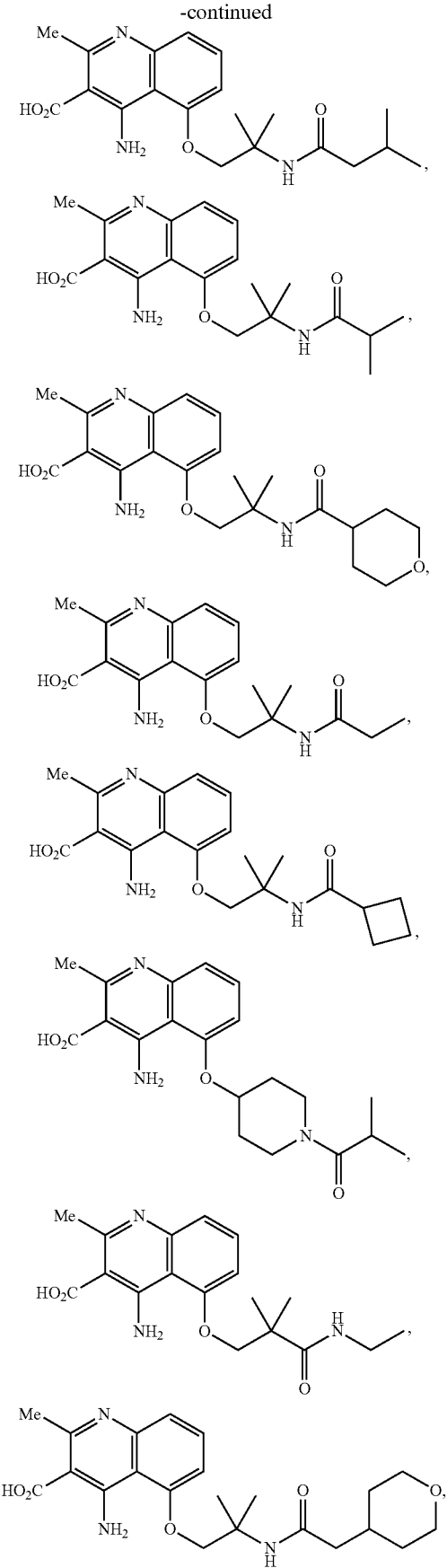
46
-continued
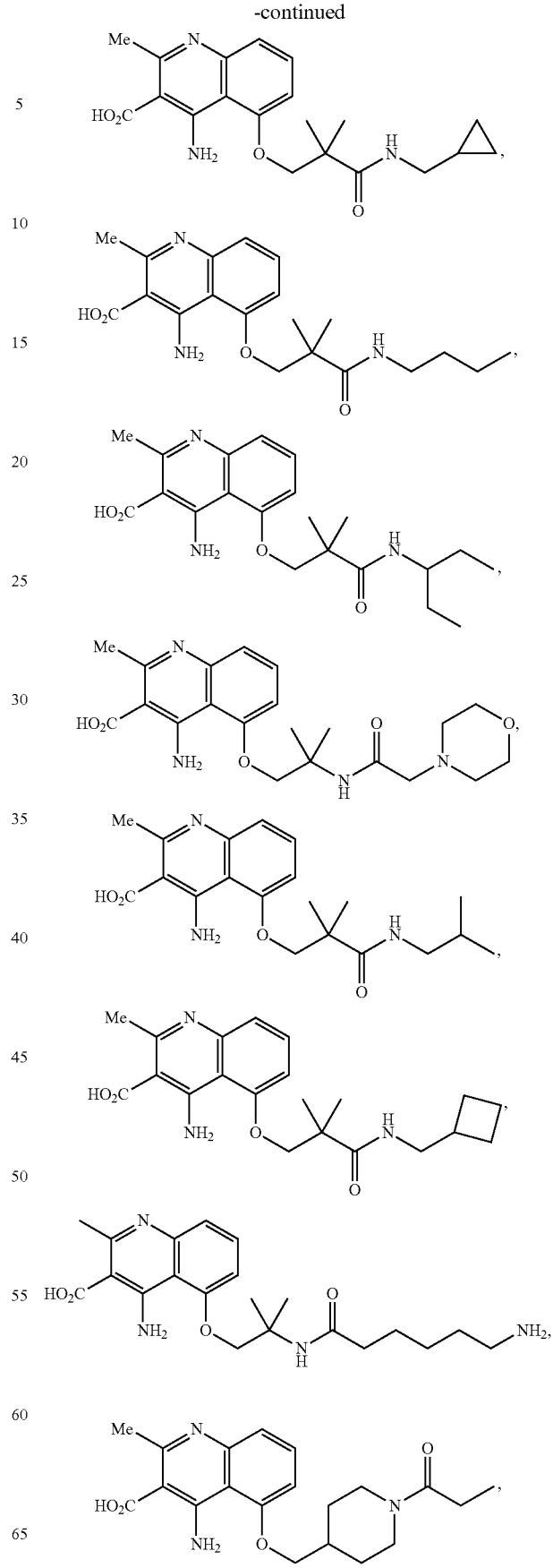

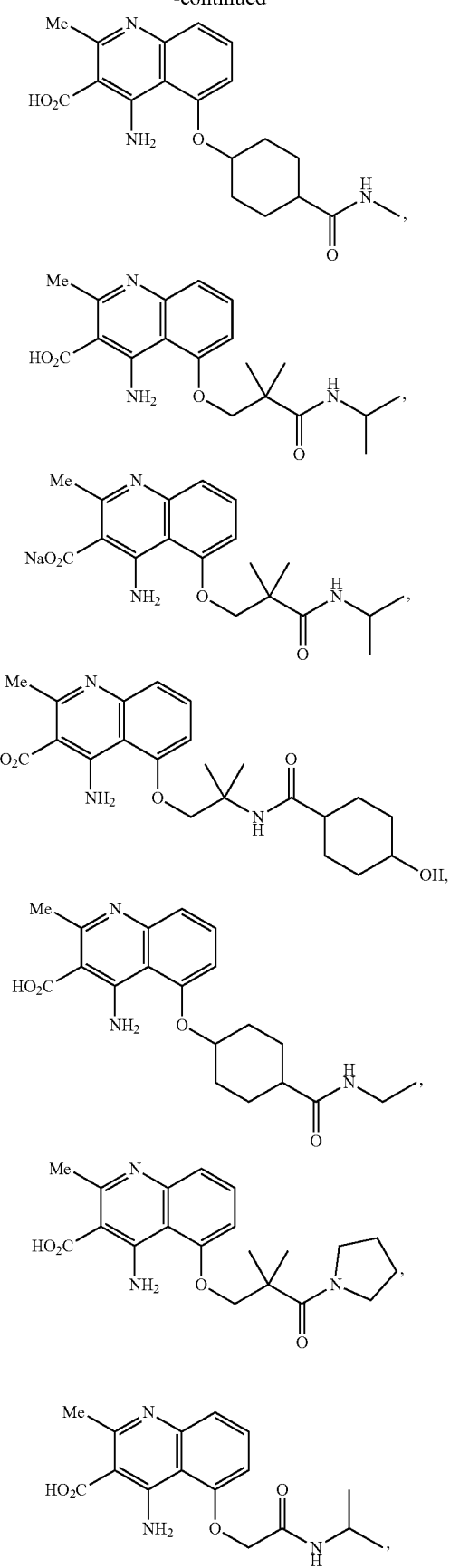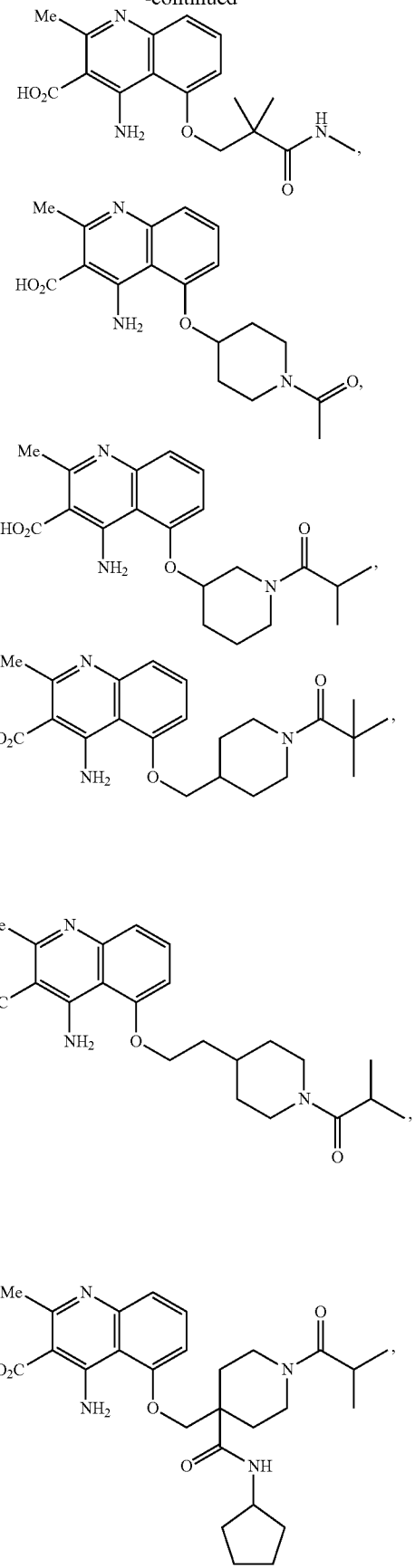

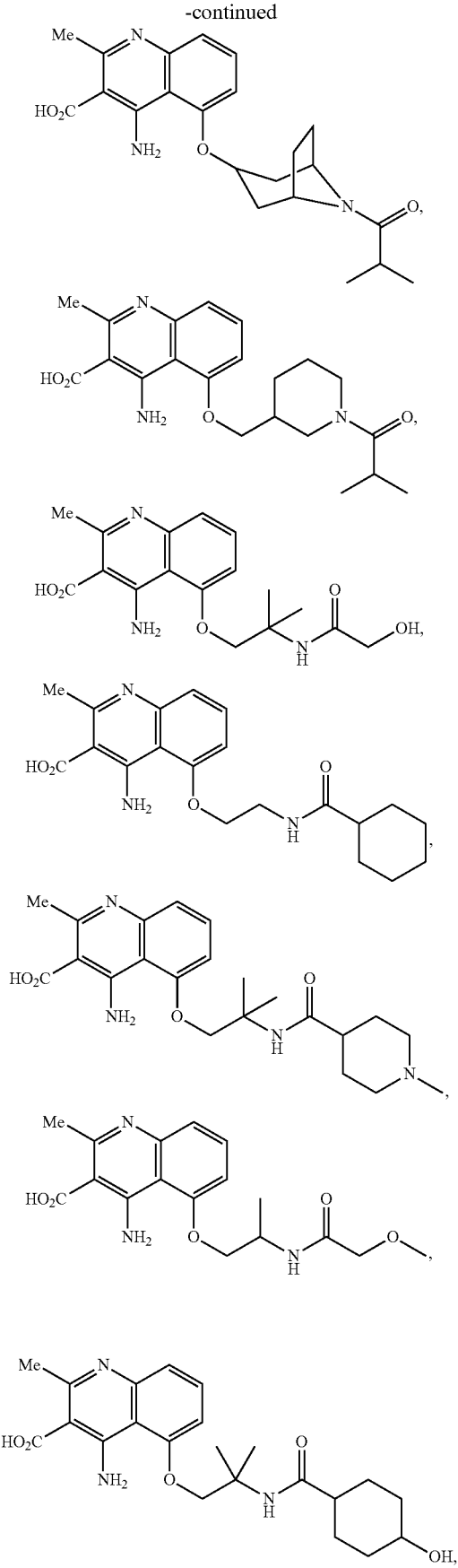

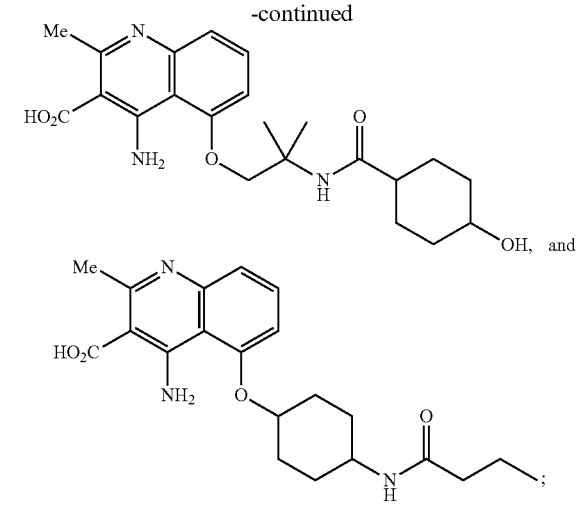

or a tautomer, salt, solvate, and/or ester thereof.

Compounds of Formula (II)

In one embodiment, the present invention provides a compound having structural Formula (II), or a tautomer, salt or solvate thereof:

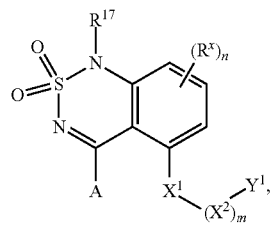

(II)

wherein,

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$;

R$^{17}$ is hydrogen, alkyl, substituted alkyl, arylalkyl, or substituted arylalkyl;

X$^1$ is —CH$_2$—, —O—, —NR$^9$—, —S—, —S(O)—, or —S(O)$_2$—;

X$^2$ is alkylene, substituted alkylene, heteroalkylene, or substituted heteroalkylene;

m is 0 or 1;

Y$^1$ is heteroaryl, substituted heteroaryl, cycloheteroalkyl, substituted cycloheteroalkyl, or

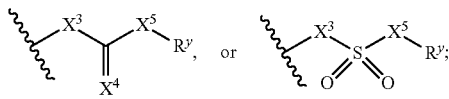

X$^3$ and X$^5$ are independently a covalent bond, —O— or —NR$^9$—;

X$^4$ is O, NR$^9$, N—OR$^9$, or S;

R$^x$ is halo, —NO$_2$, —CN, —OH, —NH$_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

n is 0, 1, 2, or 3;

$R^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —$NR^9R^{10}$; and each $R^9$ and $R^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

with the proviso that when $X^1$ is —O— or —S—, and m is zero; then $X^3$ is not —O—.

In one embodiment of Formula (II), $X^1$ is —$CH_2$—; and $Y^1$ is

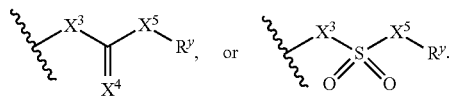

In one embodiment of Formula (II), $X^1$ is —O—, —$NR^9$—, or —S—; m is 0 or 1, and $Y^1$ is cycloheteroalkyl or substituted cycloheteroalkyl.

In one embodiment of Formula (II), $X^1$ is —O—, —$NR^9$—, or —S—; m is 1, and $Y^1$ is

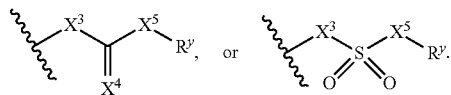

In some embodiments of Formula (II), $X^2$ is alkanylene, substituted alkanylene, heteroalkanylene, substituted heteroalkanylene, alkenylene, substituted alkenylene, heteroalkenylene, or substituted heteroalkenylene.

In some embodiments of Formula (II), $X^2$ is methylene, ethylene, propylene, iso-propylene, butylene, iso-butylene, sec-butylene, pentylene, hexylene, heptylene, dimethylethylene, methylcyclopropylene, cyclopropylmethylene, ethenylene, propenylene, or butenylene.

In one embodiment of Formula (II), A is hydrogen, alkyl, substituted alkyl, —CN, —$NO_2$, —$OR^9$, —$S(O)_cR^9$, —$NR^9COR^{10}$, —$NHOR^9$, —$NR^9R^{10}$, —$NOR^9$, —$CONR^9R^{10}$, —$CO_2R^9$, —$NR^9CO_2R^{10}$, —$NR^9CONR^{10}R^{11}$, —$NR^9CSNR^{10}R^{11}$, —$NR^9C(=NH)NR^{10}R^{11}$.

In one embodiment of Formula (II), $R^{17}$ is hydrogen, alkyl, or substituted alkyl.

In one embodiment of Formula (II), $Y^1$ is cycloheteroalkanyl, substituted cycloheteroalkanyl, cycloheteroalkenyl, or substituted cycloheteroalkenyl. It is preferable that $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, saccharide ring or its derivative, substituted saccharide ring or its derivative.

In one embodiment of Formula (II), $Y^1$ is heteroaryl or substituted heteroaryl. It is preferable that $Y^1$ is pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, and substituted oxazolyl. It is also preferable that the substituted cycloheteroalkanyl or the substituted cycloheteroalkenyl comprises one or more substituents selected from the group consisting of alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^9$, —$NO_2$, —$S(O)_cR^9$, —$NOR^9$, —$NHOR^9$, —$NR^9COR^{10}$, —$NR^9R^{10}$, —$CONR^9R^{10}$, —$CO_2R^9$, and —$NR^9CO_2R^{10}$.

In one embodiment of Formula (II), Y is

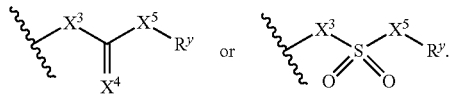

It is preferable that $X^4$ is O.

In one embodiment of Formula (II), —$X^3$—$C(X^4)$—$X^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —C(N—OH)—, or —C(S)—.

In one embodiment of Formula (II), A is hydrogen, alkyl, substituted alkyl, or —$NR^9R^{10}$; $R^{17}$ is hydrogen; and $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, monosaccharide ring, substituted monosaccharide ring, pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, or substituted oxazolyl.

In one embodiment of Formula (II), A is hydrogen, alkyl, substituted alkyl, or —$NR^9R^{10}$; $R^{17}$ is hydrogen; $Y^1$ is —$X^3$—$C(X^4)$—$X^5$—; and —$X^3$—$C(X^4)$—$X^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —$S(O)_2$—, —NH—$S(O)_2$—, —$S(O)_2$—NH—, —O—$S(O)_2$—, —$S(O)_2$—O—, —C(N—OH)— or —C(S)—.

In some specific embodiments of Formula (II), the compound has structural formula selected from the group consisting of

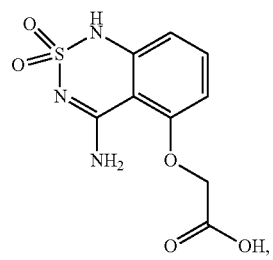

53
-continued
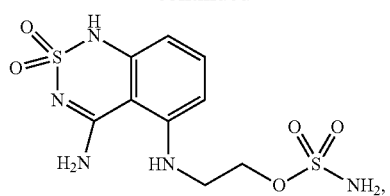
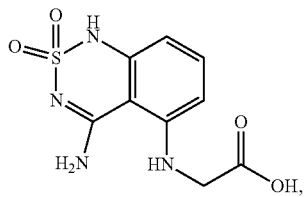
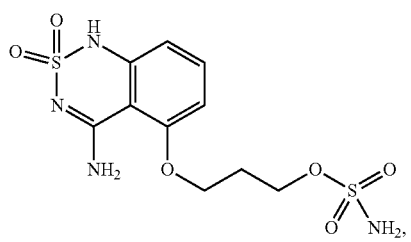
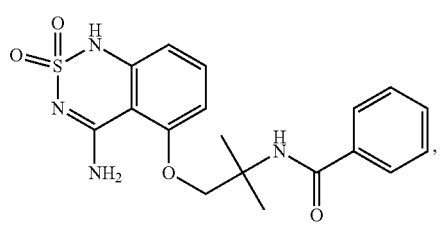
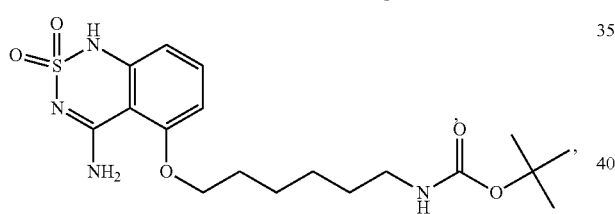
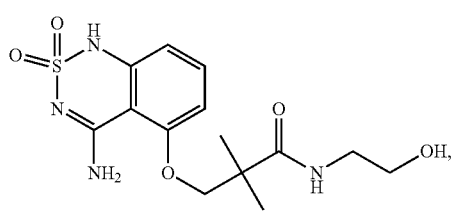
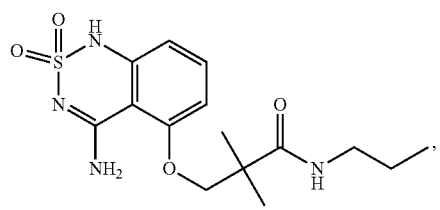
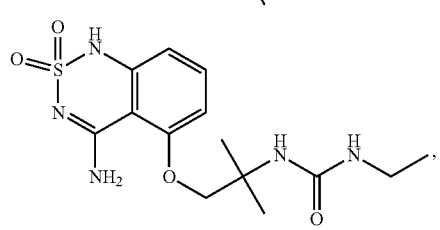
54
-continued
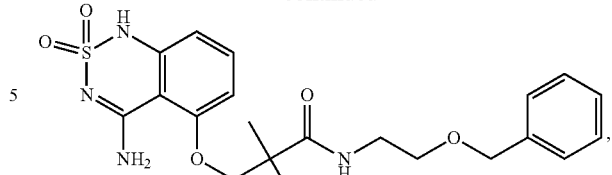
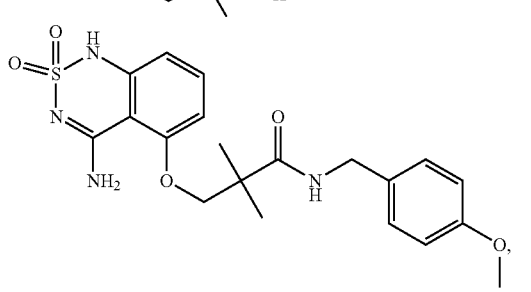
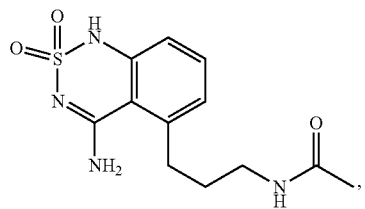
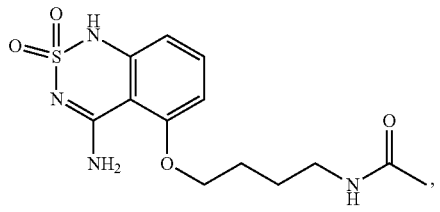
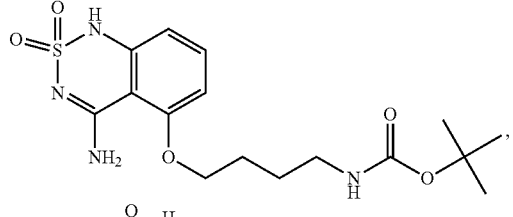
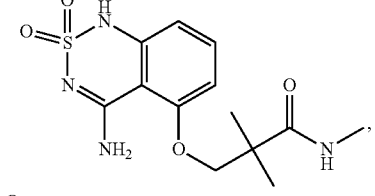
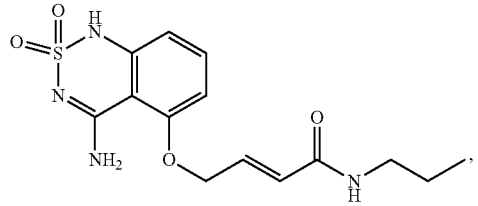
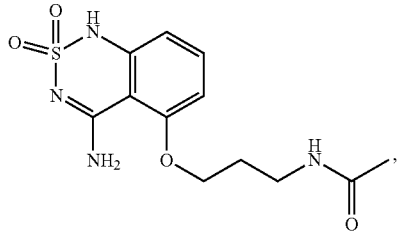

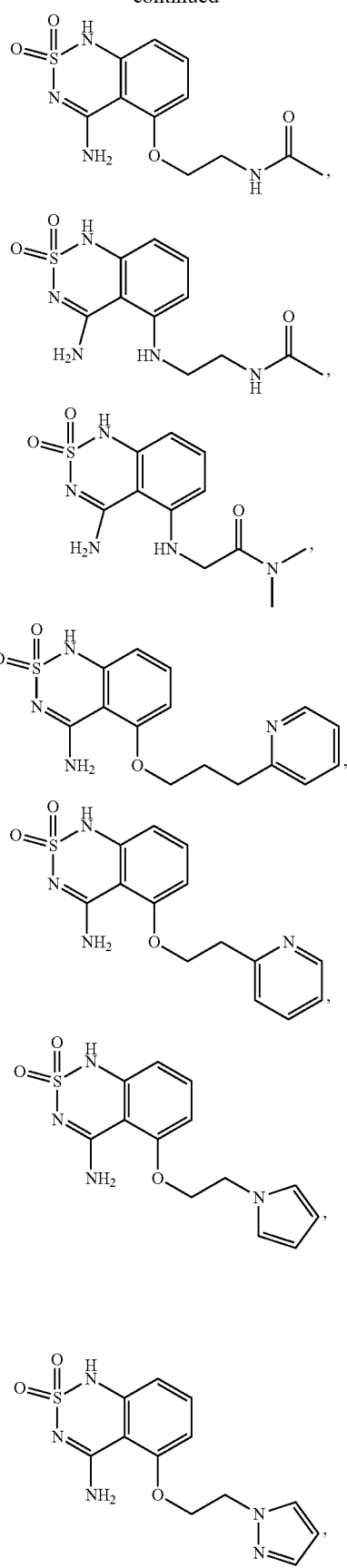
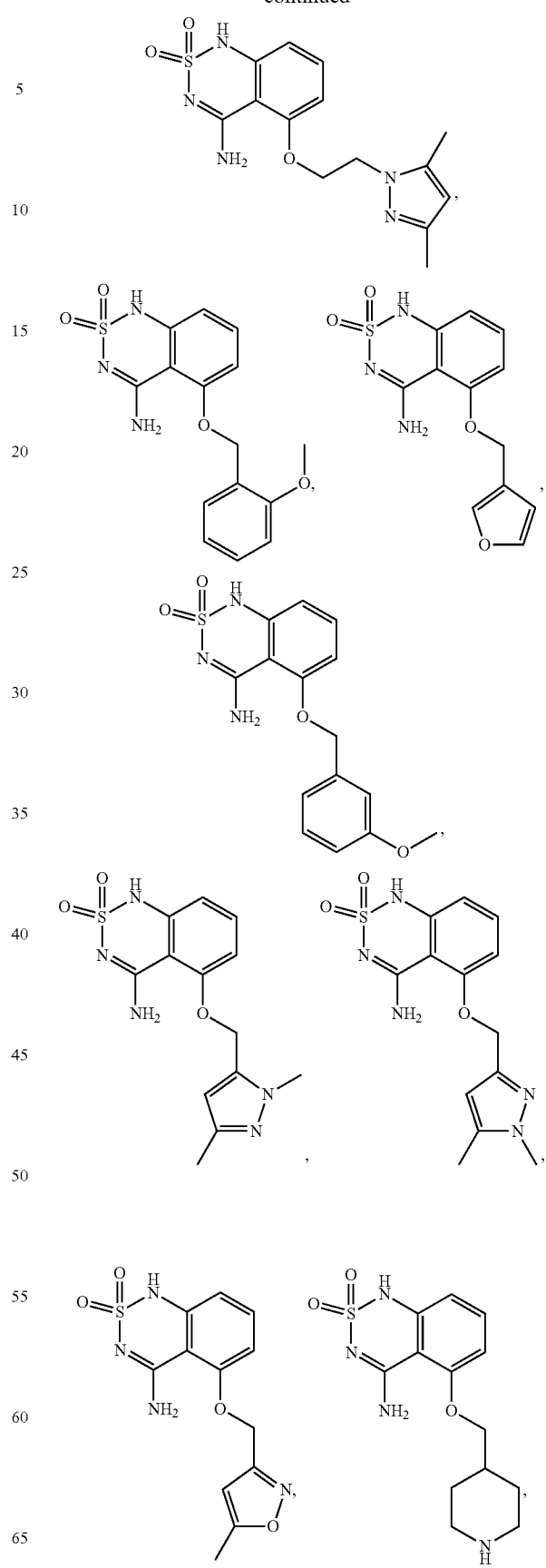

57
-continued
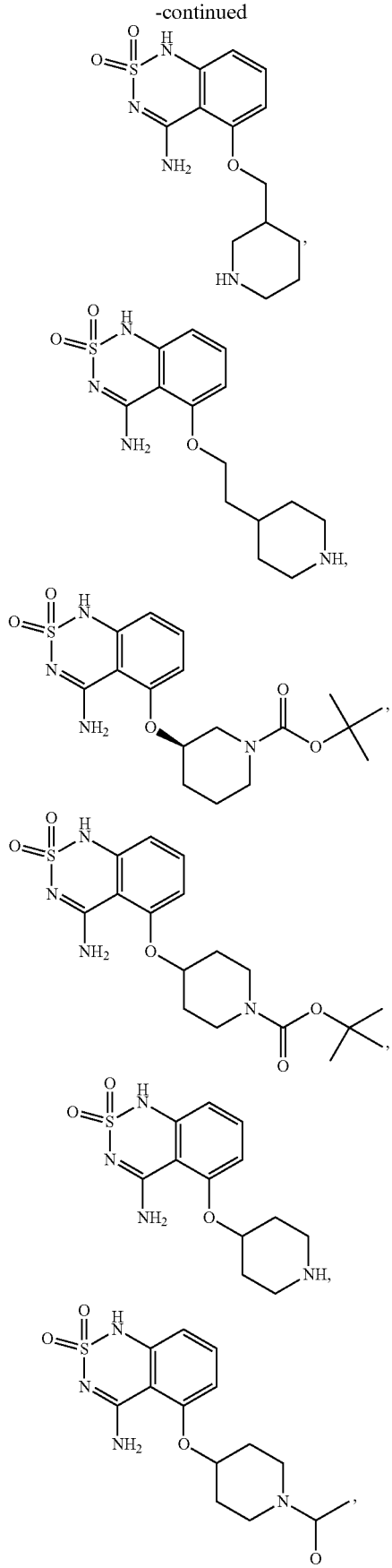
58
-continued
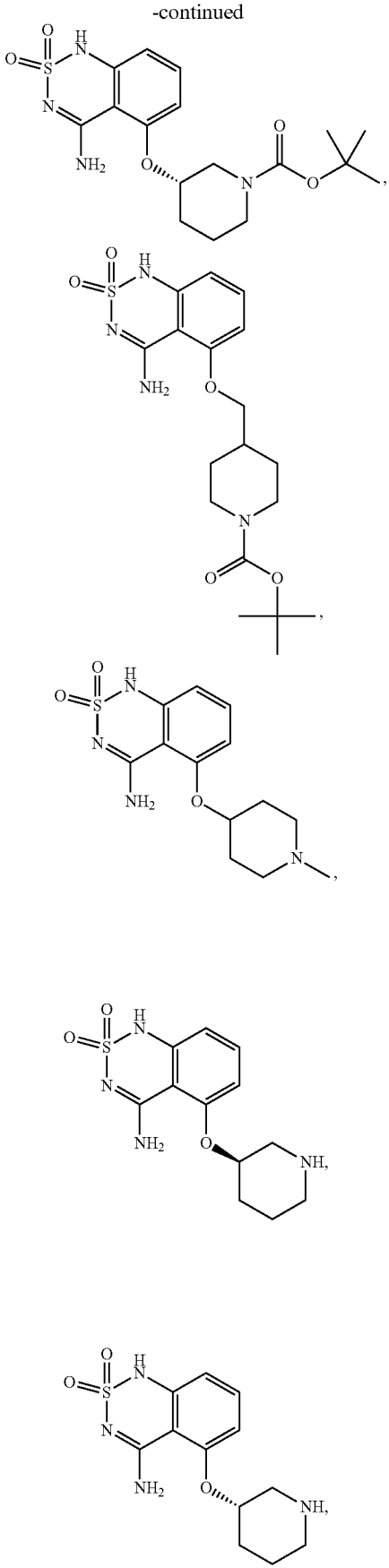

59
-continued
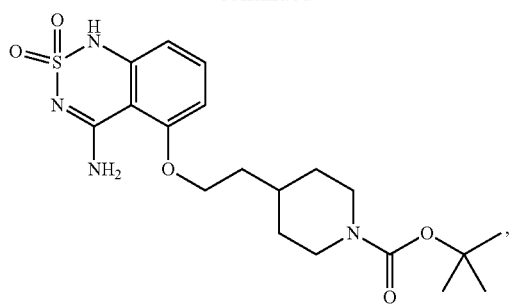
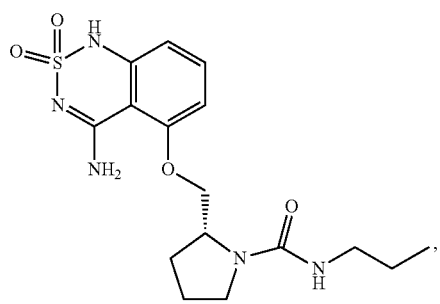
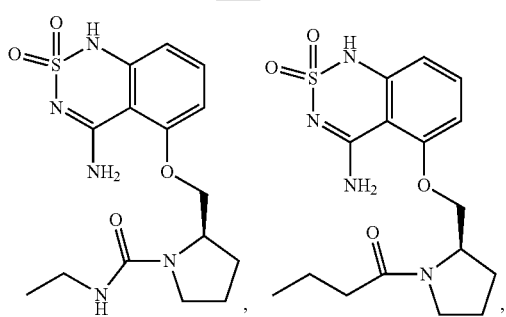
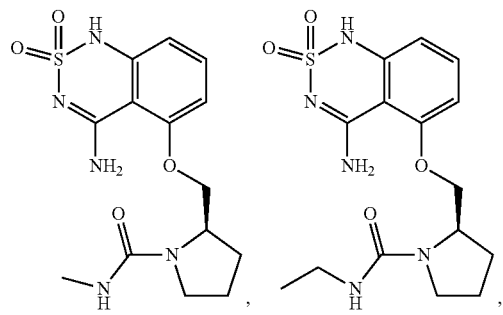
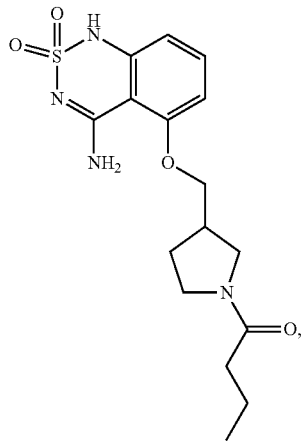
60
-continued
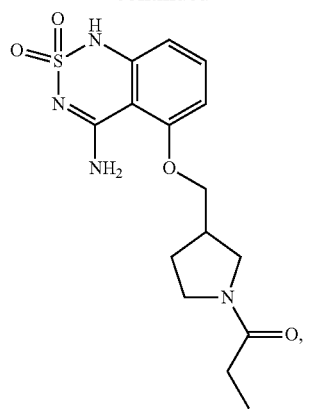
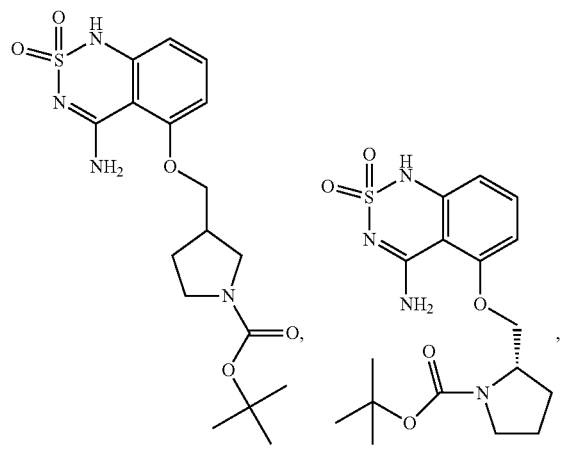
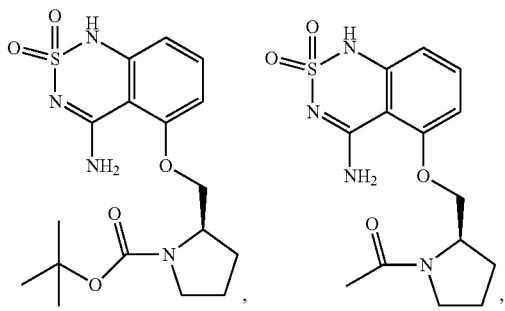
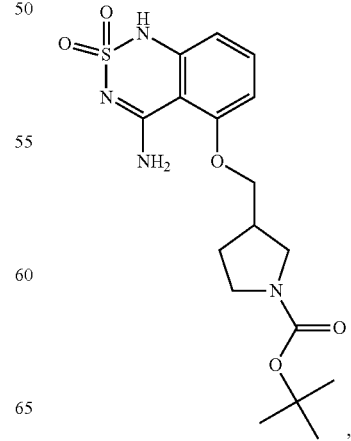

-continued
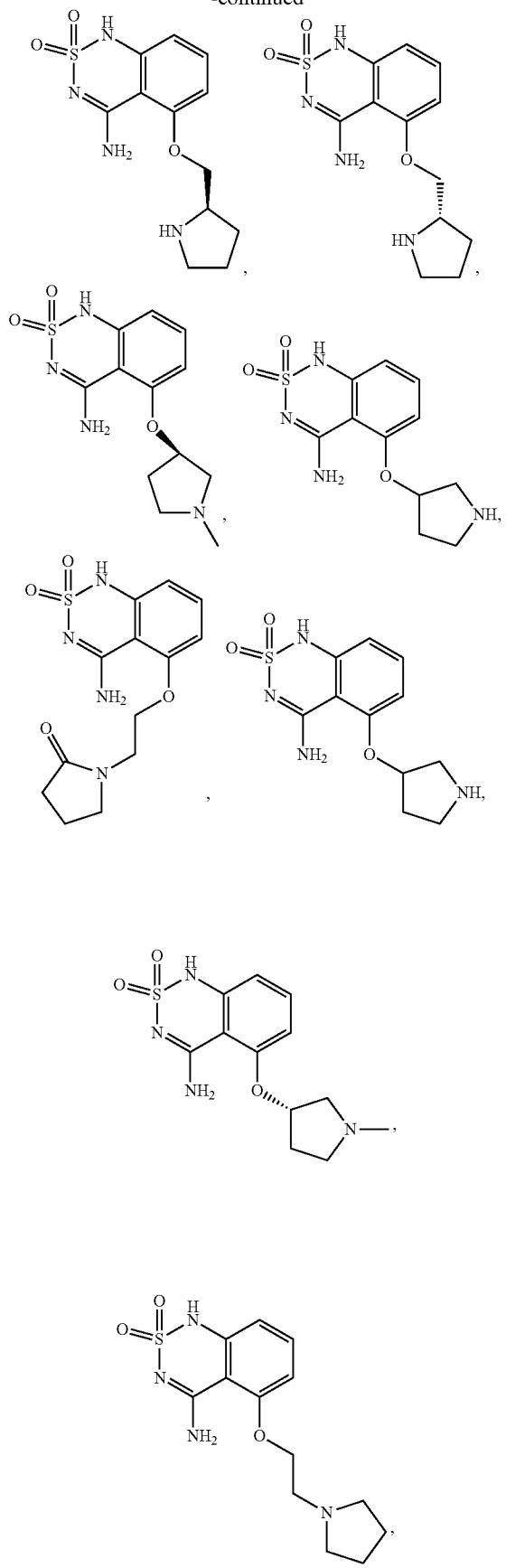
-continued
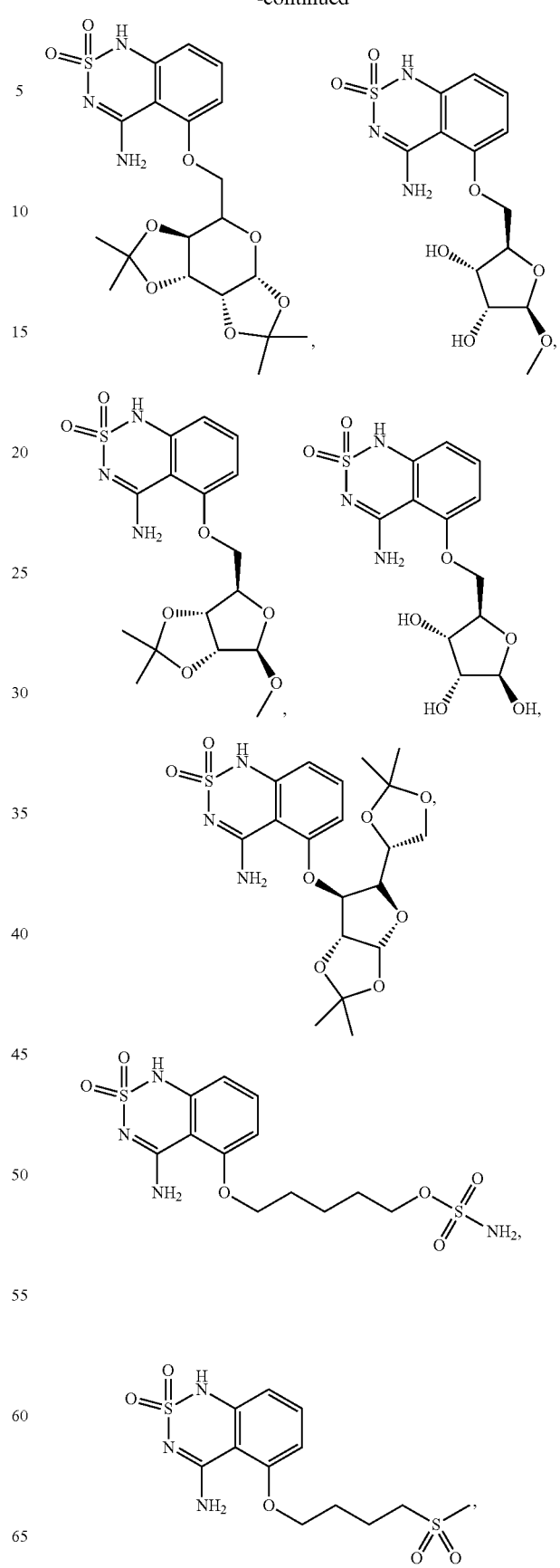

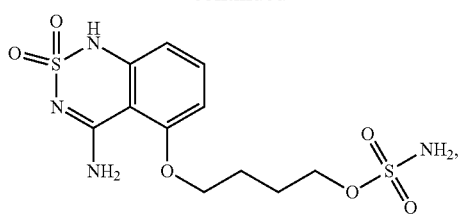
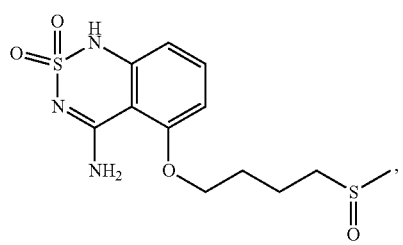
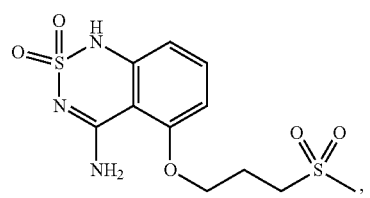
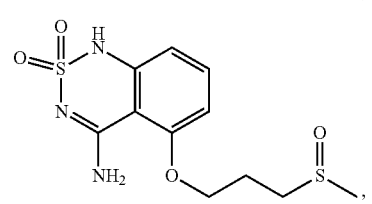
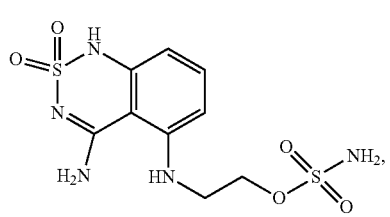
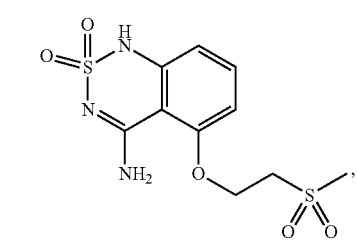
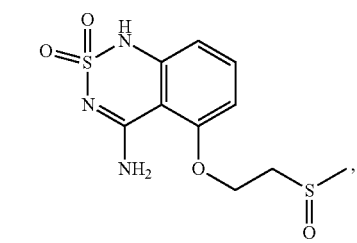
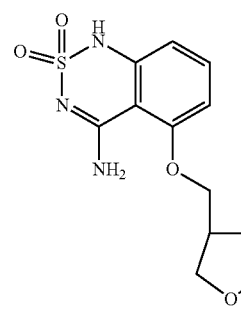
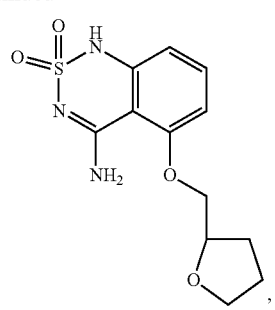
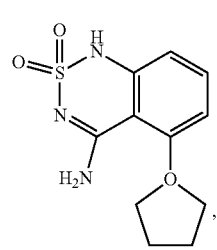
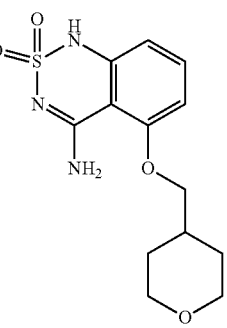
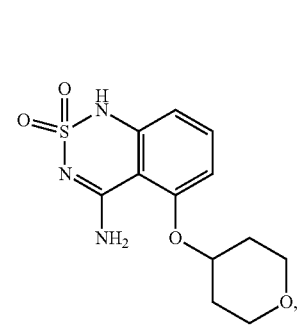
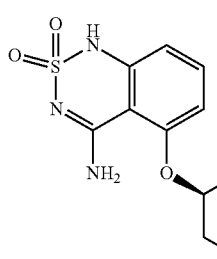
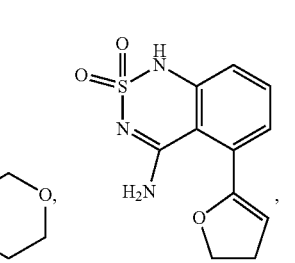
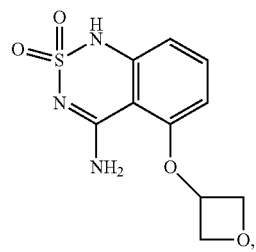
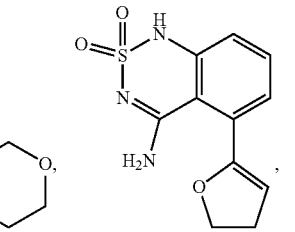
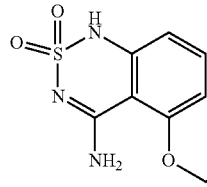
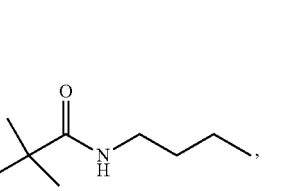

65
-continued
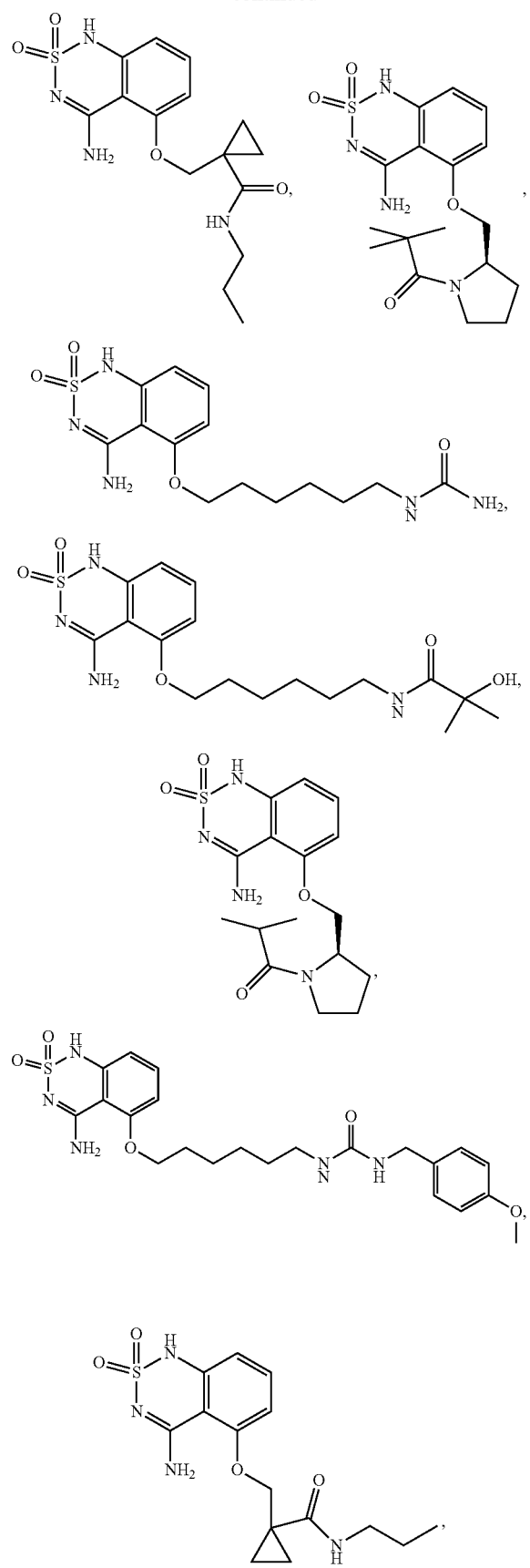
66
-continued
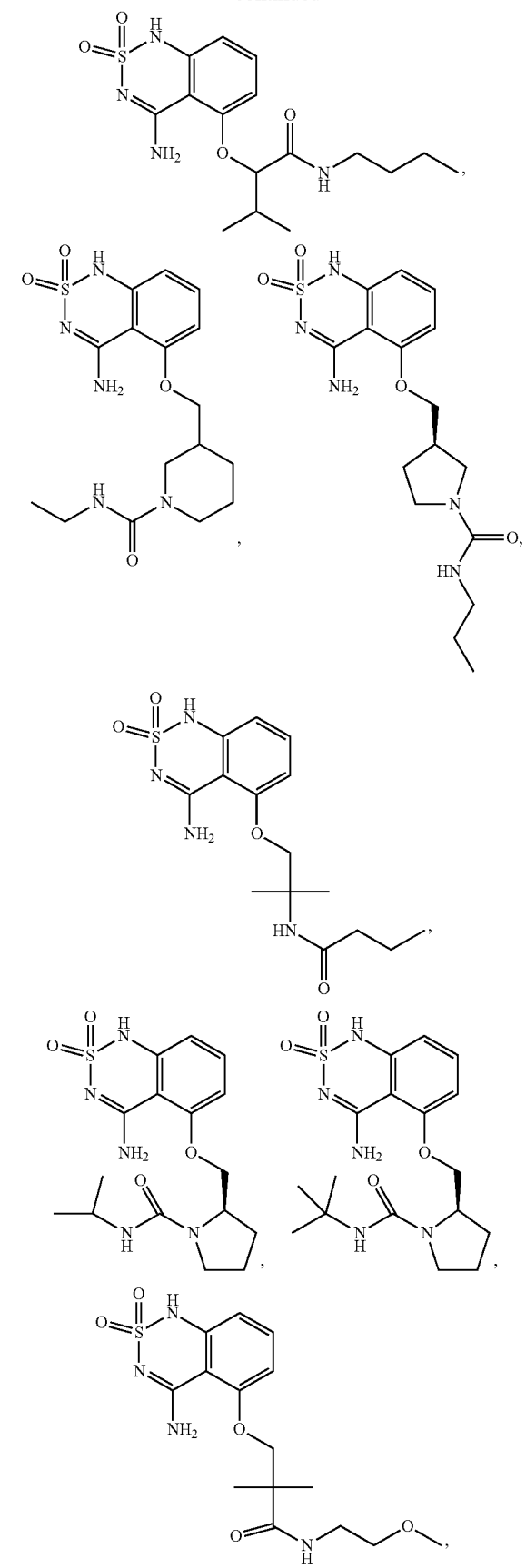

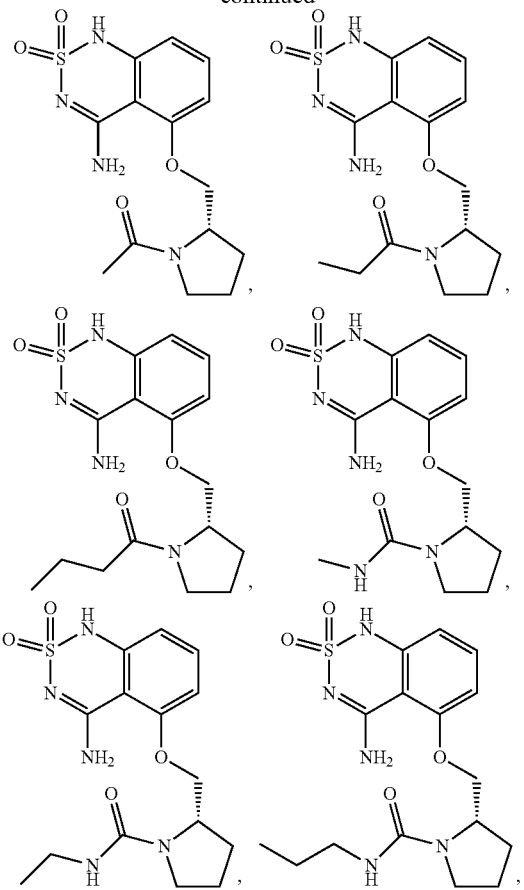
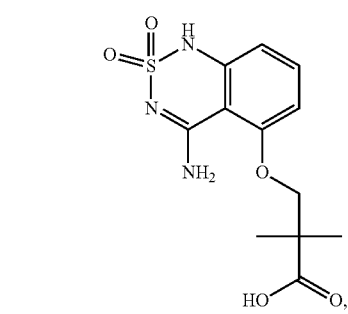
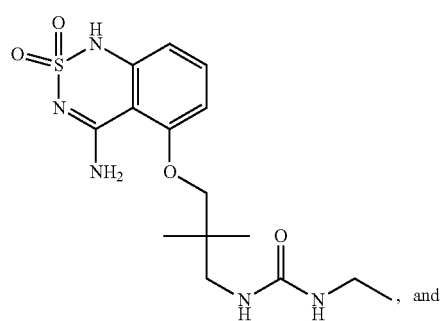

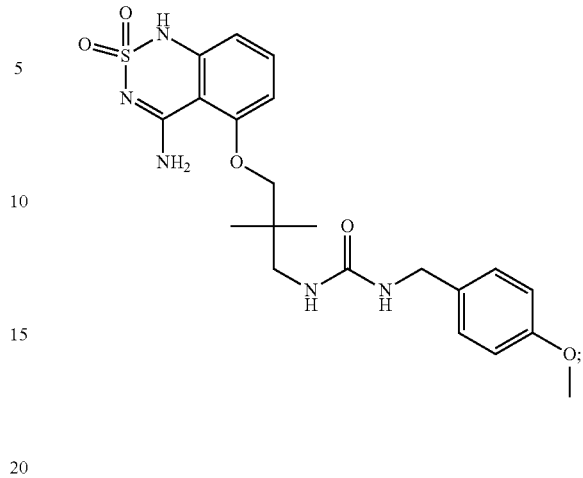

or a tautomer, salt, solvate, and/or ester thereof. In some preferred embodiments, the salt of these compounds is a hydrochloride or trifluoroacetate salt.

Photostabilizers

Sweet enhancers may degrade when exposed to a light source (artificial and/or natural), e.g., ultraviolet (UV) radiation and/or sunlight, and thereby decreases their sweet enhancing capability and may even produce other undesirable consequences. Photostabilizers can be used to stabilize the sweet enhancers that are under light exposure.

The photostability of the present sweet enhancers will be increased when those sweet enhancers are used together with photostabilizers. In other words, the degradation of the present sweet enhancers upon exposure to a light source will be reduced when those sweet enhancers are used together with photostabilizers. In one embodiment, the present invention provides a method of improving stability of one or more sweet enhancer in a liquid composition, wherein a photostabilizer is in contact with the sweet enhancer, for example, the photostabilizer and the sweet enhancer co-exist in the same liquid composition. In another embodiment, the present invention provides a method of reducing degradation of one or more sweet enhancer in a liquid composition when exposed to a light source, wherein a photostabilizer is in contact with the sweet enhancer, for example, the photostabilizer and the sweet enhancer co-exist in the same liquid composition.

The photostabilizers suitable for the present invention include, but are not limited to, antioxidants. In one embodiment, the antioxidant is a phenol-based compound, i.e., a phenol-based antioxidant. By "phenol-based compound", it is meant an organic compound containing a phenol moiety, i.e., —$C_6H_5$—OH. In one embodiment, the phenol-based antioxidant is selected from a group consisting of a dihydrochalcone derivative, a flavanone derivative, a chromone derivative, a coumarine derivative, a phenylpropenioc carbonyl compound, a phenylpropanioc carbonyl compound, and a combination thereof. In another embodiment, the phenol-based antioxidant is a naturally occurring compound and/or a FEMA GRAS compound.

In one embodiment, the chromone derivative has structural formula (III):

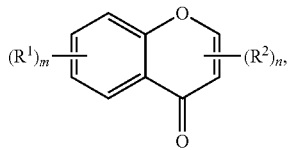

wherein,
m is 1, 2, 3, or 4;
n is 0, 1, or 2;
each $R^1$ and $R^2$ are independently —$R^a$, halo, —O—, =O, —$OR^b$, —$SR^b$, —S—, =S, —$NR^cR^c$, =$NR^b$, =N—$OR^b$, trihalomethyl, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —OC(O)$R^b$, —$OC(S)R^b$, —OC(O)O—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$; and at least one of $R^1$ is —OH;

$R^a$ is selected from the group consisting of a sugar ring, alkyl, substituted alkyl, cycloalkyl, substituted cycloalkyl, heteroalkyl, substituted heteroalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment, the coumarine derivative has structural formula (IV):

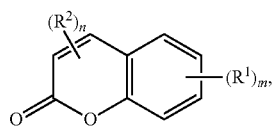

wherein,
m is 1, 2, 3, or 4;
n is 0, 1, or 2;
each $R^1$ and $R^2$ are independently —$R^a$, halo, —O—, =O, —$OR^b$, —$SR^b$, —S—, =S, —$NR^cR^c$, =$NR^b$, =N—$OR^b$, trihalomethyl, —CN, —OCN, —SCN, —NO, —$N_{02}$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —OC(O)$R^b$, —$OC(S)R^b$, —OC(O)O—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$; and at least one of $R^1$ is —OH;

$R^a$ is selected from the group consisting of a sugar ring, alkyl, substituted alkyl, cycloalkyl, substituted cycloalkyl, heteroalkyl, substituted heteroalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment, the phenylpropenioc carbonyl compound has structural formula (V):

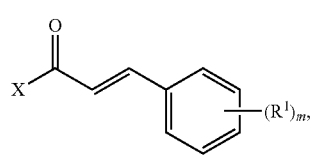

wherein,
m is 1, 2, 3, 4, or 5;
X is —$R^a$, —O—, —$OR^b$, —$SR^b$, —S—, —$NR^cR^c$, trihalomethyl, —OCN, —SCN, —$OS(O)_2R^b$, —$OS(O)_2O^-$, —$OS(O)_2OR^b$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —$OC(O)R^b$, —$OC(S)R^b$, —OC(O)O—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$, each $R^1$ is independently —$R^a$, halo, —O—, =O, —$OR^b$, —$SR^b$, —S—, =S, —$NR^cR^c$, =$NR^b$, =N—$OR^b$, trihalomethyl, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —$OC(O)R^b$, —$OC(S)R^b$, —OC(O)O—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$; and at least one of $R^1$ is —OH;

$R^a$ is selected from the group consisting of a sugar ring, alkyl, substituted alkyl, cycloalkyl, substituted cycloalkyl, heteroalkyl, substituted heteroalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment, the dihydrochalcone derivative has structural formula (VI):

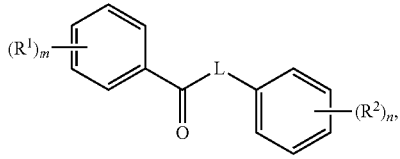

(VI)

wherein,
L is an optionally substituted $C_1$ to $C_4$ alkylene;
m is 1, 2, 3, 4, or 5;
n is 0, 1, 2, 3, 4, or 5;
each $R^1$ and $R^2$ are independently —$R^a$, halo, —O—, =O, —$OR^b$, —$SR^b$, —S—, =S, —$NR^cR^c$, =$NR^b$, =N—$OR^b$, trihalomethyl, —CN, —OCN, —SCN, —NO, —$NO_2$, =$N_2$, —$N_3$, —$S(O)_2R^b$, —$S(O)_2NR^b$, —S(O)$_2$O—, —$S(O)_2OR^b$, —$OS(O)_2R^b$, —OS(O)$_2$O—, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —OC(O)$R^b$, —OC(S)$R^b$, —OC(O)O—, —$OC(O)OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$; and at least one of $R^1$ and $R^2$ is —OH;

$R^a$ is selected from the group consisting of a sugar ring, alkyl, substituted alkyl, cycloalkyl, substituted cycloalkyl, heteroalkyl, substituted heteroalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

each $R^b$ is independently hydrogen or $R^a$; and
each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment, the chromone derivative has structural formula (VII):

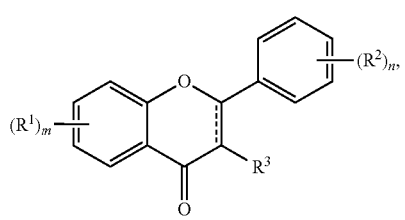

(VII)

wherein,
m is 1, 2, 3, or 4;
n is 0, 1, 2, 3, 4, or 5;
each $R^1$, $R^2$, and $R^3$ are independently —$R^a$, halo, —O—, =O, —$OR^b$, —$SR^b$, —S—, =S, —$NR^cR^c$, =$NR^b$, =N—$OR^b$, trihalomethyl, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —C(O)$OR^b$, —$C(S)OR^b$, —$C(O)NR^cR^c$, —$C(NR^b)NR^cR^c$, —OC(O)$R^b$, —OC(S)$R^b$, —OC(O)O—, —$OC(O)OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$, or —$NR^bC(NR^b)NR^cR^c$; and at least one of $R^1$ and $R^2$ is —OH;

$R^a$ is selected from the group consisting of a sugar ring, alkyl, substituted alkyl, cycloalkyl, substituted cycloalkyl, heteroalkyl, substituted heteroalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

each $R^b$ is independently hydrogen or $R^a$; and
each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment, the phenol-based antioxidant suitable for the present invention includes, but is not limited to, cinnamic acid derivatives; flavones; isoflavones; chromones; coumarins; chalcones; and combinations thereof.

In another embodiment, the phenol-based antioxidant suitable for the present invention includes, but is not limited to, caffeic acid, ferulic acid, sinapic acid, rosmarinic acid, chlorogenic acid, cichoric acid, caftaric acid, echinacoside, myricitrin, myricetin, apigenin, kaempferol, rhoifolin, luteolin, diosmin, apiin, morin, neodiosmin, quercetin, rutin, cupressuflavone, datiscetin, diosmetin, fisetin, galangin, gossypetin, geraldol, hinokiflavone, scutellarein, flavonol, primuletin, pratol, robinetin, quercetagetin, sinensetin, chrysoeriol, isorhamnetin, vitexin, isoquercitrin, daidzin, daidzein, biochamin A, prunetin, genistin, glycitein, glycitin, genistein, 6,7,4'-trihydroxyisoflavone, 7,3',4'-trihydroxyisoflavone, chromone, visnagin, sophorachromone A, volkensiachromone, sawarachromone, mycochromone, 2-carboxyethenyl-5,7-dihydroxychromone, 7-hydroxy-5-(4-hydroxy-2-oxopentyl)-2-methylchromone-7-O-beta-D-glucopyranoside, 8-glucosyl-5,7-dihydroxy-2-(1-methylpropyl)chromone, diacromone, hymecromone, 5-hydroxy-2-methylchromone, cassiachromone, coumarin, coumestrol, dalbergin, daphnetin, esculetin, citropten, umbelliferone, scopoletin, xanthotoxol, psoralen, bergapten, fraxetin, butein, phloridzin, echinatin, marein, isoliquiritigenin, phloretin, polyhydroxychalcones, pholoretin, trilobatin, naringin dihydrochalcone, neohesperidin dihydrochalcone, naringenin, homoeriodictyol, hesperetin, myricitrin, enzymatically modified isoquercitrin (EMIQ), and a combination thereof.

Compositions

The present sweet enhancer(s) and photostabilizer(s) can be formulated together in a liquid composition, which may be a ingestible composition or a non-ingestible composition. The sweet enhancer may be in a sweet flavor enhancing amount, while the photostabilizer may be in a sweet enhancer stabilizing amount. In the liquid composition, the sweet enhancer(s) and photostabilizer(s) may be completely dissolved or partially dissolved in the liquid.

In one embodiment of the present invention, the liquid composition comprises a sweet enhancer and a phenol-based antioxidant, wherein the sweet enhancer has a structural formula (II), or a tautomer, salt, or solvate thereof; and the phenol-based antioxidant is selected from the group consisting of a flavanone derivative having a structural formula (VII), a phenylpropenioc carbonyl compound having a structural formula (V), a coumarine derivative having structural formula (IV), and a combination thereof. In certain more specific embodiments of the liquid composition, the structural formula (II) includes any subgenus and species of formula (II) as described herein. In certain more specific embodiments of the liquid composition, the phenol-based antioxidant is selected from the group consisting of EMIQ, chlorogenic acid, caffeic acid, ferulic acid, sinapinic acid, scopoletin, daphnetin, and a combination thereof.

In one embodiment of the present invention, the liquid composition comprises a sweet enhancer and a phenol-based antioxidant, wherein the sweet enhancer has a structural formula (I), or a tautomer, salt, or solvate thereof; and the phenol-based antioxidant is selected from the group consisting of a chromone derivative having a structural formula (III), a flavanone derivative having a structural formula (VII), a coumarine derivative having structural formula (IV), and a combination thereof. In certain more specific embodiments of the liquid composition, the structural formula (I) includes any subgenus and species of formula (I) as described herein. In certain more specific embodiments of the liquid composition, the phenol-based antioxidant is selected from the group consisting of EMIQ, rutin, daphnetin, and a combination thereof.

In one embodiment of the present invention, the liquid composition comprises a sweet enhancer and a phenol-based antioxidant, wherein the sweet enhancer has a structural formula (Ie), or a tautomer, salt, or solvate thereof; and the phenol-based antioxidant is selected from the group consisting of a chromone derivative having a structural formula (III), a phenylpropenioc carbonyl compound having a structural formula (V), and a combination thereof. In certain more specific embodiments of the liquid composition, the structural formula (Ie) includes any subgenus and species of formula (Ie) as described herein. In certain more specific embodiments of the liquid composition, the phenol-based antioxidant is chlorogenic acid (CGA) or EMIQ.

The ingestible composition includes both "food or beverage products" and "non-edible products". The non-ingestible composition includes flavor concentrates in form of semi-solid or liquid. By "Food or beverage products", it is meant any edible product intended for consumption by humans or animals, including semi-solids or liquids (e.g., beverages). The term "non-edible products" or "noncomestible composition" includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products, and other personal care products that use sucrose and or other sweeteners.

In one embodiment, the compounds of the present invention can be used at very low concentrations on the order of a few parts per million, in combination with one or more known sweeteners, natural or artificial, so as to reduce the concentration of the known sweetener required to prepare an ingestible composition having the desired degree of sweetness.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corm syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

The present compounds can also be provided, individually or in combination, with any ingestible composition known or later discovered. For example, the ingestible composition can be a comestible composition or noncomestible composition. By "comestible composition", it is meant any composition that can be consumed as food by humans or animals, including gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical composition, which refers to a noncomestible composition intended to be used by humans or animals for therapeutic purposes. By "animal", it includes any non-human animal, such as, for example, farm animals and pets.

The liquid composition of the present invention can be either in form of a ready-to-be-consumed final product, such as the categories discussed herein below, or in form of a intermediate and/or precursor which will be further processed to become a ready-to-be-consumed final product.

Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, sucha as colas and non-cola carbonates; fruit juice, such as juice, nectars, juice drinks and fruit flavoured drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh, instant, and combined coffee; tea, such as black, green, white, oolong, and flavored tea; and other hot drinks including flavour-, malt- or plant-based powders, granules, blocks or tablets mixed with milk or water.

The Snack Food category generally refers to any food that can be a light informal meal including, but not limited to Sweet and savoury snacks and snack bars. Examples of snacke food include, but are not limited to fruit snacks, chips/crisps, extruded snacks, tortilla/corn chips, popcorn, pretzels, nuts and other sweet and savoury snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Typically at least a sweet flavor enhancing amount of one or more of the present compound will be added to the liquid composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and comestible compositions made therefrom. A broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

Photostability of the sweet enhancer can be measured via photostability test which is typically done under controlled conditions, often in a sealed chamber where exact exposure levels to the spectra of light a product is likely to encounter, can be delivered for precise analysis of the effects. The light levels used in photostability testing are generally high enough to accelerate hours, days, weeks, months, or even years worth of light exposure down to seconds, minutes, or hours in the testing chamber. Monitoring of the exposure levels is critical and is either done by built-in measurement equipment within the chamber or by external instrumentation. This type of exact, accelerated, laboratory-level photostability testing is typical for the pharmaceutical, paint, ink, and dye manufacturing industries among others. Visible light and UVA are the prime spectra of concern due to the abundance of both types in sunlight and typical indoor lighting which are the most likely light sources to be encountered by these photo-sensitive products when in use or in-situ.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions otMethoden der Organischen Chemie (Houben-Weyl), and the like. Many general methods for preparation of starting materials comprising variously substituted heterocyclic, hetereoaryl, and aryl rings (the precursors of Ar, hAr$^1$, and/or hAr$^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entirieties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3″ Ed., John Wiley & Sons (1999).

Some exemplary synthetic methods for preparing the present compounds are illustrated in the Schemes 1 to 6 below.

Scheme 1: Preparation of substituted 4-aminoquinoline-3-carboxylate derivatives (VI) from substituted anilines (I)

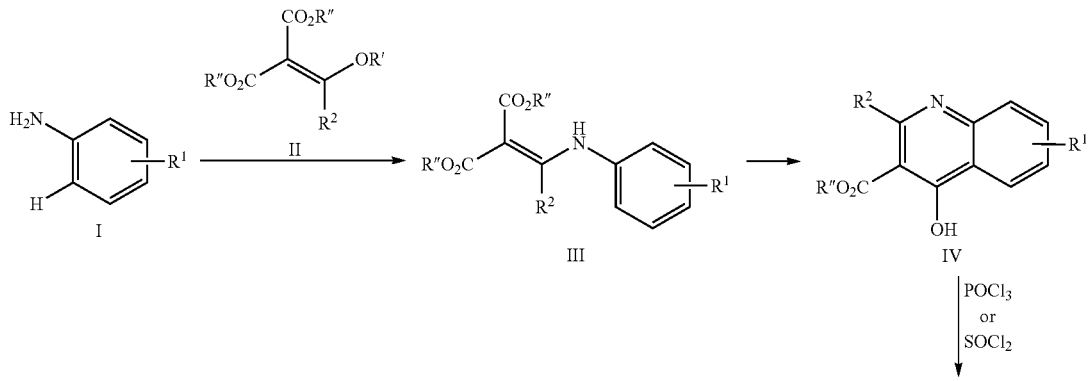

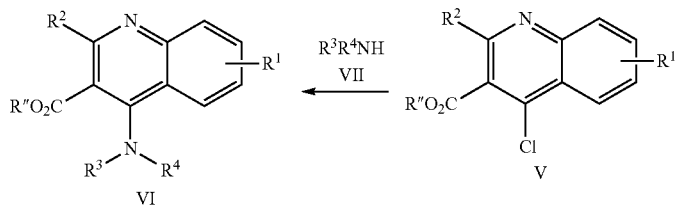

As shown in Scheme 1, substituted 4-aminoquinoline-3-carboxylate derivatives (VI) can be prepared by reacting the corresponding anilines I with 2-(alkoxymethylene)malonates II followed by cyclization of the intermediates III under elevated temperature to provide the hydroxyl intermediates IV that can be treated with $POCl_3$ or $SO_2Cl_2$ to provide the corresponding chloride derivatives V that can be further treated with ammonia or amines to give the desired amino-quinolines VI. (Kamal, A. et al. *Bioorg. Med. Chem.* 2005, 13, 2021-2029; Fryer, R. I. et al. *J. Med. Chem.* 1993, 36, 1669-1673; Bi, Y. et al. *Bioorg. Med. Chem. Lett.* 2004, 14, 1577-1580; Li, S. Y. et al. *Bioorg. Med. Chem.* 2006, 14, 7370-7376. Koga, H. et al. *J. Med. Chem.* 1980, 23, 1358-1363).

Scheme 2: Preparation of substituted 4-aminoquinoline-3-carboxylate derivatives (VI) from substituted 2-aminobenzoic acid derivatives (VIII)

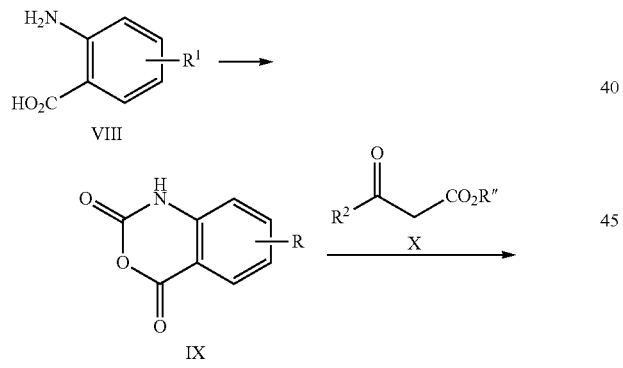

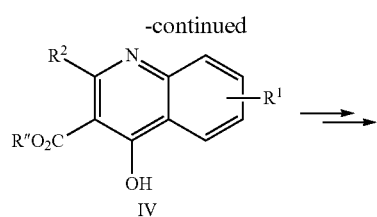

Substituted 4-aminoquinoline-3-carboxylate derivatives (VI) can also be prepared by reacting the corresponding 2-aminobenzoic acids VIII with phosgene or equivalent to provide the isatoic anhydrides IX that can be further reacted with X to give the derivatives IV (Mai, A. et al. *J. Med. Chem.* 2006, 49, 6897-6907. Beutner, G. L. et al. *J. Org. Chem.* 2007, 72, 7058-7061, and references cited therein), which can be converted to VI as described in Scheme 1.

Scheme 3: Preparation of substituted 4-aminoquinoline-3-carboxylate derivatives (VI) from substituted 2-amino benzonitrile derivatives (XI)

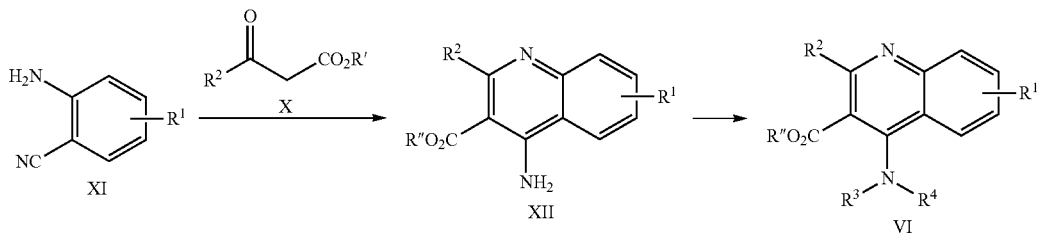

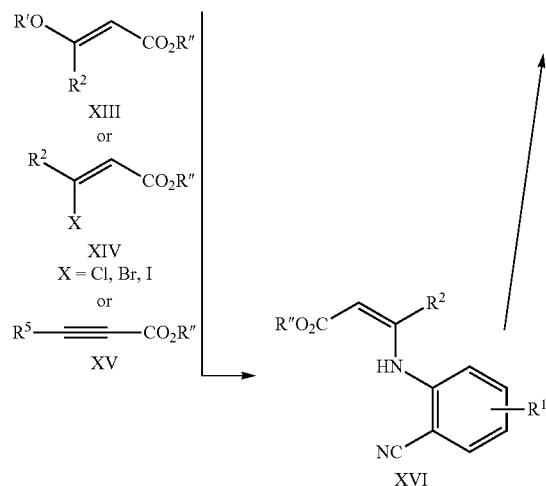

Alternatively, substituted 4-aminoquinoline-3-carboxylate derivatives (VI) can be prepared by reacting the corresponding amino benzonitriles XI with X to provide the amino derivatives XII (Sestili, I. et al. *Eur. J. Med. Chem.* 2004, 39, 1047-1057. Doucet-Personeni, C. et al. *J. Med. Chem.* 2001, 44, 3203-3215. Veronese, A. C. et al. *Tetrahedron* 1995, 51, 12277-12284, and the references cited therein) that can be further alkylated to give the substituted aminoquinolines VI as shown in Scheme 3. Amino quinolines XII can also be prepared via a Michael addition of the 2-amino benzonitriles XI to various α,β-unsaturated carboxylate derivatives XIII, XIV or XV to provide the adducts XVI (MacNab, H. et al. *Synthesis* 2009, 2171-2174. Vicario, J. L. *Synthesis* 2007, 2065-2092, and references cited therein) that can be further cyclized to give the amino quinolines XII (Han, G. F. et al. *Synth. Commun.* 2009, 39, 2492-2505. Tabarrini, O. et al. *Bioorg. Med. Chem.* 2001, 9, 2921-2928. Shutske, G. M. et al. *J. Med. Chem.* 1989, 32, 1805-1813, and references cited therein).

Scheme 4: Preparation of substituted 4-aminoquinoline-3-carboxylic acids (XVII, XX) and amides (XVIII and XXI)

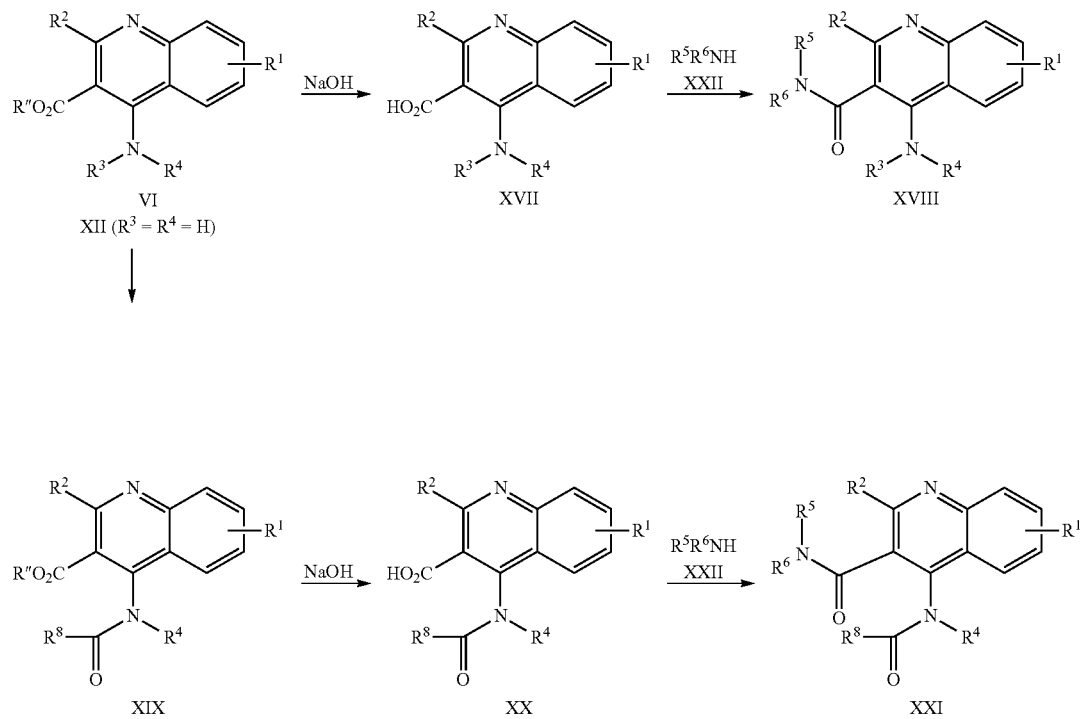

As described in Scheme 4, hydrolysis of 4-aminoquinoline-3-carboxylate derivatives VI or XII in the presence of NaOH provide 4-aminoquinoline-3-carboxylic acids XVII (Zhao, Y. L. et al. *Eur. J. Med. Chem.* 2005, 40, 792-797) which can be further coupled with amines XXII under standard conditions to give 4-aminoquinoline-3-carboxamide derivatives XVIII. When $R^3$ and/or $R^4$=H, 4-aminoquinoline-3-carboxylates VI or XII can be further functionalized by coupling with acids XXIII to give 4-carboxamidoquinoline-3-carboxylates XIX. Compound XIX can be further hydrolyzed to the acids XX that can be further coupled to the amines XXII to provide amide derivatives XXI.

Compound [1,2,6]thiadiazine-2,2-dioxides and fused [1,2,6]thiadiazine-2,2-dioxide derivatives such as, for example, 1H-benzo[c][1,2,6]thiadiazine-2,2-dioxides can be synthesized from 2-amino nitriles, 2-amino ketones, or 2-amino carboxyl derivatives A or C (Scheme 5), by reaction with $NH_2SO_2C_1$ (Hirayama et al., *Bioorg. & Med. Chem.* 2002, 10, 1509; Kanbe et al., *Bioorg. & Med. Chem. Lett.* 2006, 16, 4090 and references cited therein) or $NH_2SO_2NH_2$ (Maryanoff et al., *J. Med. Chem.* 2006, 49, 3496, and references cited therein) and followed by cyclization in the presence of NaOH (Goya et al., *Heterocycles*, 1986, 24, 3451; Albrecht et al., *J. Org. Chem.* 1979, 44, 4191; Goya et al., *Arch. Pharm.* (Weinheim) 1984, 317, 777). The condensation of the corresponding 1,3-dicarbonyl derivatives, α,β-unsaturated carbonyl derivatives with sulfamide derivatives (Scheme 4) also results in the formation of [1,2,6]thiadiazine-2,2-dioxide derivatives (Wright, *J. Org. Chem.* 1964, 29, 1905).

Scheme 5

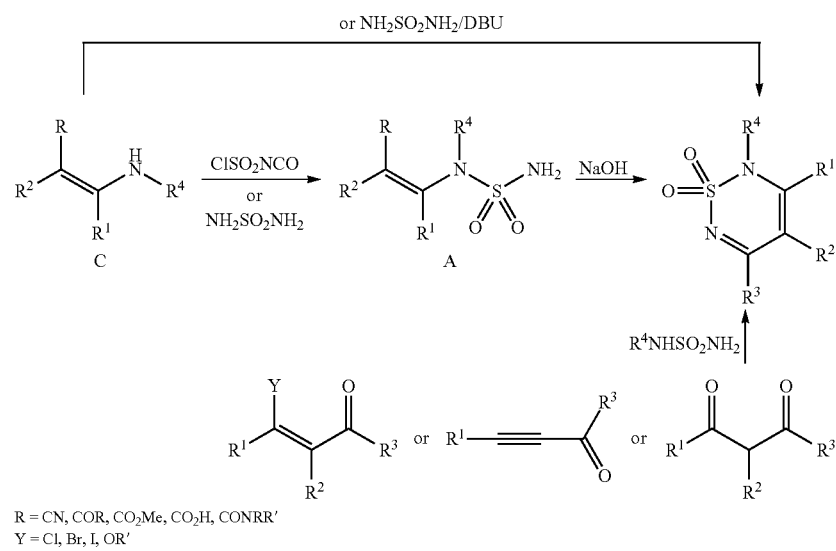

Compound 1H-benzo[c][1,2,6]thiadiazine-2,2-dioxide derivatives F are synthesized from the same starting materials D (Scheme 6) via their reactions with sulfamide or sulfamoyl chloride, followed by cyclization with NaOH. Direct reaction of compounds D with sulfamide in the presence of DBU at the elevated temperature also resulted in the formation of 1H-benzo[c][1,2,6]thiadiazine-2,2-dioxide derivatives F (Maryanoff et al., *J. Med. Chem.* 2006, 49, 3496, and references cited therein).

Scheme 6

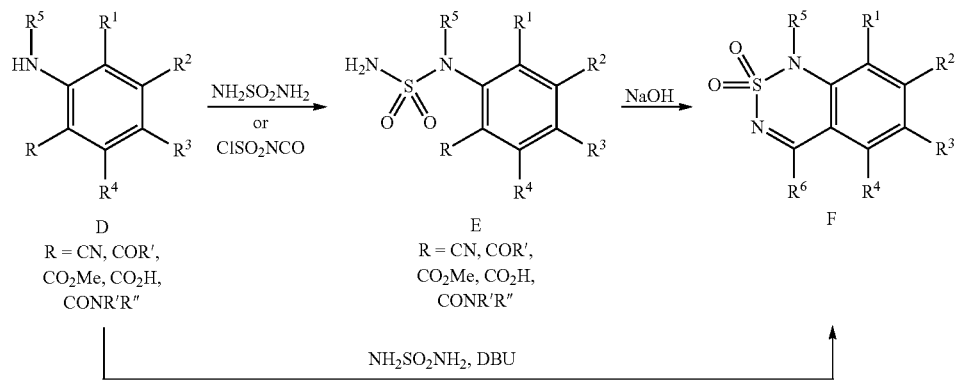

EXAMPLES

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

Example 1: 4-amino-6-methoxyquinoline-3-carboxylic Acid

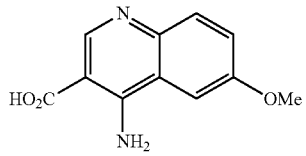 [SMILES: COc1ccc2ncc(C(=O)O)c(N)c2c1]

To a stirred solution of ethyl 4-amino-6-methoxyquinoline-3-carboxylate (Example 1a, 1.23 g, 5.0 mmol) in EtOH (20.0 mL) was added aqueous NaOH (2.0 N, 5.0 mL) at room temperature. The reaction mixture was then refluxed for 3 hr. The solution was then filtered and washed with water. The filtrate was cooled to 0° C. and neutralized carefully with 1 N HCl to pH 7. Most of the EtOH was removed under reduced pressure, and the precipitate was collected by filtration, washed with cold water, and dried under vacuum to give the title compound as an off-white solid (1.01 g, 93%). $^1$H NMR (400 MHz, DMSO-d$_6$) δ 3.89 (s, 3H), 7.40 (dd, J=2.8, 9.4 Hz, 1H), 7.73 (d, J=9.4 Hz, 1H), 7.77 (d, J=2.8 Hz, 1H), 8.77 (s, 1H). MS 219 (MH$^+$).

Example 1a: ethyl 4-amino-6-methoxyquinoline-3-carboxylate

A mixture of ethyl 4-chloro-6-methoxyquinoline-3-carboxylate (Example 1b, 796 mg, 3.0 mmol) and ammonia (25% aqueous solution, 10 mL) in isopropanol (40 mL) was stirred at 110° C. in a pressure reactor overnight. Most of the solvent was then removed under reduced pressure, and the reaction mixture was diluted with water. The precipitate was collected by filtration, washed with cold water, and dried under vacuum to give the title compound as an off-white solid (680 mg, 92%). $^1$H NMR (400 MHz, DMSO-d$_6$) δ 1.33 (t, J=7.0 Hz, 3H), 3.88 (s, 3H), 4.32 (q, J=7.0 Hz, 2H), 7.36 (dd, J=2.8, 8.8 Hz, 1H), 7.72 (d, J=8.8 Hz, 1H), 7.74 (d, J=2.8 Hz, 1H), 8.23 (bs, 2H), 8.77 (s, 1H). MS 247 (MH$^+$).

Example 1b: ethyl 4-chloro-6-methoxyquinoline-3-carboxylate

A solution of ethyl 4-hydroxy-6-methoxyquinoline-3-carboxylate (Example 1c, 1.24 g, 5.0 mmol) in POCl$_3$ was refluxed under nitrogen for 3 hrs. The solution was cooled to room temperature and evaporated under reduced pressure. The residue was carefully quenched with ice, and neutralized with 2.0 N NaOH to pH 7. The precipitate was collected by filtration, washed with cold water, and dried under vacuum to give the title compound as a pale-yellow solid (1.29 g, 97%). $^1$H NMR (400 MHz, DMSO-d$_6$) δ 1.36 (t, J=7.0 Hz, 3H), 3.96 (s, 3H), 4.41 (q, J=7.0 Hz, 2H), 7.57 (d, J=2.8 Hz, 1H), 7.61 (dd, J=2.8, 8.8 Hz, 1H), 8.05 (d, J=8.8 Hz, 1H), 8.97 (s, 1H). MS 266, 268 (MH$^+$).

Example 1c: ethyl 4-hydroxy-6-methoxyquinoline-3-carboxylate

A mixture of 4-methoxyaniline (12.3 g, 100 mmol) and diethyl 2-(ethoxymethylene)malonate (21.6 g, 100 mmol) was stirred at 120° C. under nitrogen for 4 hrs. The solution was cooled to room temperature and Ph$_2$O (100 mL) was added. The reaction mixture was refluxed at 260° C. under nitrogen for 8 hrs. The solution was cooled to room temperature and diluted with hexanes. The resultant precipitate was collected by filtration, washed with 25% ethyl acetate in hexanes, and dried under vacuum to give ethyl 4-hydroxy-6-methoxyquinoline-3-carboxylate as a pale-yellow solid (4.21 g, 17%). $^1$H NMR (400 MHz, DMSO-d$_6$) δ 1.26 (t, J=7.0 Hz, 3H), 3.83 (s, 3H), 4.19 (q, J=7.0 Hz, 2H), 7.32 (dd, J=3.2, 9.6 Hz, 1H), 7.55 (d, J=3.2 Hz, 1H), 7.56 (d, J=9.6 Hz, 1H), 8.47 (s, 1H), 12.27 (s, 1H). MS 248 (MH$^+$).

Example 2: 4-amino-5-(2,2-dimethyl-3-oxo-3-(propylamino)propoxy)-2-methyl-quinoline-3-carboxylic Acid

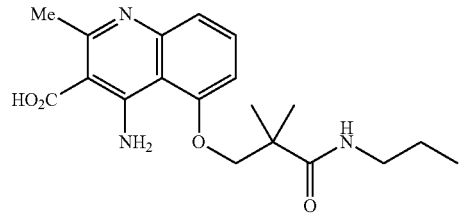 [SMILES: CCCNC(=O)C(C)(C)COc1cccc2nc(C)c(C(=O)O)c(N)c12]

Prepared as in Example 1 from ethyl 4-amino-5-(2,2-dimethyl-3-oxo-3-(propylamino)-propoxy)-2-methylquinoline-3-carboxylate (Example 2a) as an off-white solid (41%). $^1$H NMR (400 MHz, DMSO-d$_6$) δ 0.73 (t, J=7.6 Hz, 3H), 1.25 (s, 6H), 1.33-1.42 (m, 2H), 2.76 (s, 3H), 3.00-3.05 (m, 2H), 4.16 (s, 2H), 7.01 (d, J=8.0 Hz, 1H), 7.29 (d, J=8.0 Hz, 1H), 7.67 (t, J=8.0 Hz, 1H), 7.89 (t, J=5.8 Hz, 1H), 8.85 (bs, 1H), 12.28 (bs, 1H), 12.78 (bs, 1H). MS 360 (MH$^+$).

Example 2a: ethyl 4-amino-5-(2,2-dimethyl-3-oxo-3-(propylamino)propoxy)-2-methylquinoline-3-carboxylate To a solution of 3-(3-amino-2-cyanophenoxy)-2,2-dimethyl-N-propylpropan-amide (Tachdjian, C. et al. *PCT Int. Appl.* 2008, WO 2008154221, 1.38 g, 5.0 mmol) and ethyl acetoacetate (0.66 g, 5.0 mmol) in dry toluene (150 mL) was added SnCl$_4$ (2.61 g, 10.0 mmol) dropwise via syringe at room temperature under nitrogen. After 1 hr at room temperature, the reaction mixture was refluxed for an additional 5 hrs. The solution was cooled to room temperature and the solvent removed under reduced pressure. The residue was diluted with EtOAc, and aqueous NaOH (2N) was added at room temperature to pH >8. The solution was filtered and the organic layer separated. The aqueous layer was extracted with EtOAc (5×). The combined organic layers was washed with brine, and dried over Na$_2$SO$_4$. After evaporation of the solvent, the residue was purified by chromatography on silica gel (0.5% MeOH in EtOAc) to give the title compound as an off-white solid (1.63 g, 84%). $^1$H NMR (400 MHz, DMSO-d$_6$) δ 0.73 (t, J=7.6 Hz, 3H), 1.25 (s, 6H), 1.32 (t, J=7.4 Hz, 3H), 1.35-1.42 (m, 2H), 2.54 (s, 3H), 3.00-3.05 (m, 2H), 4.12 (s, 2H), 4.31 (q, J=7.4 Hz, 2H), 6.87 (d, J=8.0 Hz, 1H), 7.23 (d, J=8.0 Hz, 1H), 7.50 (t, J=8.0 Hz, 1H), 7.80 (t, J=5.6 Hz, 1H), 8.08 (s, 2H). MS 388 (MH$^+$).

Example 3: 4-amino-6-methoxy-2-methylquinoline-3-carboxylic Acid

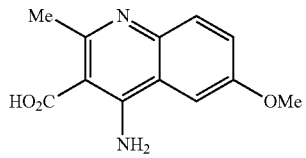

Prepared as in Example 1 from ethyl 4-amino-6-methoxy-2-methylquinoline-3-carboxylate (Example 3a) as a white solid (87%). $^1$H NMR (400 MHz, DMSO-d$_6$) δ 2.83 (s, 3H), 3.90 (s, 3H), 7.57 (dd, J=2.4, 8.2 Hz, 1H), 8.09 (d, J=8.2 Hz, 1H), 8.10 (d, J=2.4 Hz, 1H), 9.39 (s, 1H), 9.67 (s, 1H). MS 233 (MH$^+$).

Example 3a: ethyl 4-amino-6-methoxy-2-methylquinoline-3-carboxylate

Prepared as in Example 2a from 2-amino-5-methoxybenzonitrile (Campbell, J. B. et al. *Synth. Commun.* 1989, 19, 2255-2263) and ethyl acetoacetate as an off-white solid (92%). $^1$H NMR (400 MHz, DMSO-d$_6$) δ 1.33 (t, J=6.8 Hz, 3H), 2.57 (s, 3H), 3.86 (s, 3H), 4.33 (q, J=6.8 Hz, 2H), 7.28 (dd, J=2.8, 9.2 Hz, 1H), 7.59 (d, J=9.2 Hz, 1H), 7.60 (bs, 2H), 7.63 (d, J=2.8 Hz, 1H). MS 261 (MH$^+$).

Example 4: 4-amino-2-phenylquinoline-3-carboxylic Acid

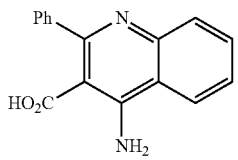 [SMILES: Nc1c(C(=O)O)c(-c2ccccc2)nc2ccccc12]

Prepared as in Example 1 from ethyl 4-amino-2-phenylquinoline-3-carboxylate (Example 4a) as an off-white solid (33%). $^1$H NMR (400 MHz, DMSO-d6) δ 7.39-7.52 (m, 7H), 7.79 (m, 3H), 8.33 (d, J=8.0 Hz, 1H), 12.63 (bs, 1H). MS 265 (MH$^+$).

Example 4a: ethyl 4-amino-2-phenylquinoline-3-carboxylate

Prepared as in Example 2a from 2-aminobenzonitrile and ethyl 3-oxo-3-phenylpropanoate as a yellow solid (45%). $^1$H NMR (400 MHz, DMSO-d$_6$) δ 0.72 (t, J=8.0 Hz, 3H), 3.92 (q, J=8.0 Hz, 2H), 7.44 (m, 5H), 7.50 (m, 1H), 7.61 (bs, 2H), 7.73 (m, 1H), 7.83 (d, J=8.0 Hz, 1H), 8.37 (d, J=8.0 Hz, 1H). MS 293 (MH$^+$).

Example 5: 4-amino-2-ethylquinoline-3-carboxylic Acid

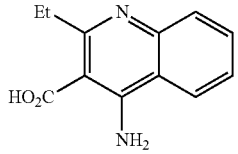

Prepared as in Example 2 from methyl 4-amino-2-ethylquinoline-3-carboxylate (Example 5a) as a white solid (26%). $^1$H NMR (400 MHz, DMSO-d$_6$+1 drop D$_2$O) δ 1.24 (t, J=8.0 Hz, 3H), 3.28 (q, J=8.0 Hz, 2H), 7.56 (t, J=8.0 Hz, 1H), 7.78 (d, J=8.0 Hz, 1H), 7.83 (t, J=8.0 Hz, 1H), 8.36 (d, J=8.0 Hz, 1H)). MS 217 (MH$^+$).

Example 5a: ethyl 4-amino-2-phenylquinoline-3-carboxylate

Prepared as in Example 2a from 2-aminobenzonitrile and methyl 3-oxopentanoate as a solid (27%). $^1$H NMR (400 MHz, DMSO-d$_6$) δ 1.18 (t, J=8.0 Hz, 3H), 2.88 (q, J=8.0 Hz, 2H), 3.86 (s, 3H), 7.40 (m, 1H), 7.44 (bs, 2H), 7.64 (m, 1H), 7.68 (m, 1H), 8.26 (d, J=8.0 Hz, 1H). MS 231 (MH$^+$).

Example 6: 4-amino-2-methylquinoline-3-carboxylic Acid

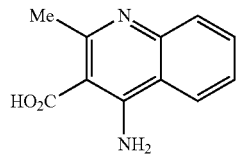

Prepared as in Example 1 from ethyl 4-amino-2-methylquinoline-3-carboxylate (Example 6a) as a off-white solid (41%). $^1$H NMR (400 MHz, DMSO-d$_6$) δ 1.05 (t, J=8.0 Hz, 3H), 2.84 (s, 3H), 7.56 (bs, 1H), 7.76 (m, 1H), 7.82 (bs, 1H), 8.39 (d, J=8.0 Hz, 1H), 8.99 (bs, 1H), 12.00 (bs, 1H), 12.98 (bs, 1H). MS 203 (MH$^+$).

Example 6a: ethyl 4-amino-2-methylquinoline-3-carboxylate

Prepared as in Example 2a from 2-aminobenzonitrile and ethyl 3-oxobutanoate as a yellow solid (32%). $^1$H NMR (400 MHz, DMSO-d$_6$) δ 1.33 (t, J=8.0 Hz, 3H), 2.61 (s, 3H), 4.34 (q, J=8.0 Hz, 2H), 7.41 (m, 1H), 7.66 (m, 2H), 7.74 (bs, 2H), 8.27 (d, J=8.0 Hz, 1H). MS 231 (MH$^+$).

Example 7: 4-amino-5-(2,2-dimethyl-3-oxo-3-(propylamino)propoxy)-2-ethyl-quinoline-3-carboxylic Acid

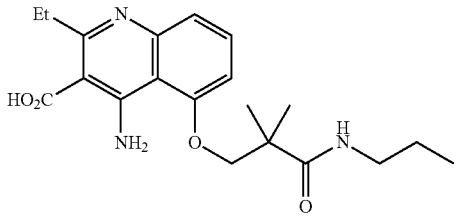

Prepared as in Example 1 from methyl 4-amino-5-(2,2-dimethyl-3-oxo-3-(propylamino)propoxy)-2-ethylquinoline-3-carboxylate (Example 7a) as a solid (75%). $^1$H NMR (400 MHz, DMSO-$d_6$) δ 0.75 (t, J=8.0 Hz, 3H), 1.03 (t, J=8.0 Hz, 3H), 1.27 (s, 6H), 1.39 (m, 2H), 3.04 (q, J=4.0 Hz, 2H), 3.45 (q, J=4.0 Hz, 2H), 4.17 (s, 2H), 7.04 (d, J=8.0 Hz, 1H), 7.32 (d, J=8.0 Hz, 1H), 7.69 (t, J=8.0 Hz, 1H), 7.90 (t, J=4.0 Hz, 1H), 8.89 (bs, 1H), 12.75 (bs, 1H). MS 374 (MH$^+$).

Example 7a: methyl 4-amino-5-(2,2-dimethyl-3-oxo-3-(propylamino)propoxy)-2-ethylquinoline-3-carboxylate Prepared as in Example 2a from 3-(3-amino-2-cyanophenoxy)-2,2-dimethyl-N-propylpropan-amide (Tachdjian, C. et al. *PCT Int. Appl.* 2008, WO 2008154221) and methyl 3-oxopentanoate as a yellow solid (17%). $^1$H NMR (400 MHz, DMSO-$d_6$) δ 0.75 (t, J=8.0 Hz, 3H), 1.17 (t, J=8.0 Hz, 3H), 1.26 (s, 6H), 1.40 (m, 2H), 2.84 (q, J=8.0 Hz, 2H), 3.04 (q, J=8.0 Hz, 2H), 3.85 (s, 3H), 4.13 (s, 2H), 6.88 (d, J=8.0 Hz, 1H), 7.27 (dd, J=8.0 Hz, 1H), 7.51 (t, J=8.0 Hz, 1H), 7.81 (m, 3H). MS 388 (MH$^+$).

Example 8: 4-amino-6-phenoxyquinoline-3-carboxylic Acid

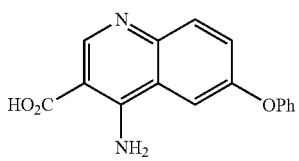 [SMILES: Nc1c(C(=O)O)cnc2ccc(Oc3ccccc3)cc12]

Prepared as in Example 1 from ethyl 4-amino-6-phenoxyquinoline-3-carboxylate (Example 8a) as a off-white solid (50%). $^1$H NMR (400 MHz, DMSO-$d_6$) δ 7.07 (d, J=8.0 Hz, 2H), 7.16 (t, J=8.0 Hz, 1H), 7.42 (m, 2H), 7.49 (dd, J=8.0 Hz, 1H), 7.87 (d, J=8.0 Hz, 1H), 8.13 (d, J=4.0 Hz, 1H), 8.86 (s, 1H). MS 281 (MH$^+$).

Example 8a: ethyl 4-amino-6-phenoxyquinoline-3-carboxylate

Prepared as in Example 1a from ethyl 4-chloro-6-phenoxyquinoline-3-carboxylate (Example 8b) and ammonia as a off-white solid (82%). $^1$H NMR (400 MHz, DMSO-$d_6$) δ 1.35 (t, J=8.0 Hz, 3H), 4.35 (q, J=8.0 Hz, 2H), 7.05 (d, J=8.0 Hz, 2H), 7.15 (t, J=8.0 Hz, 1H), 7.40 (m, d, 2H), 7.46 (dd, J=8.0 Hz, 1H), 7.87 (d, J=8.0 Hz, 1H), 8.13 (d, J=4.0 Hz, 1H), 8.27 (bs, 2H), 8.87 (s, 1H). MS 309 (MH$^+$).

Example 8b: ethyl 4-chloro-6-phenoxyquinoline-3-carboxylate

Prepared as in Example 1b from ethyl 4-hydroxy-6-phenoxyquinoline-3-carboxylate (Example 8c) and POCl$_3$ as a tan solid (96%). $^1$H NMR (400 MHz, DMSO-d6) δ 1.36 (t, J=8.0 Hz, 3H), 4.40 (q, J=8.0 Hz, 2H), 7.23 (d, J=8.0 Hz, 2H), 7.29 (t, J=8.0 Hz, 1H), 7.50 (t, J=8.0 Hz, 2H), 7.63 (d, J=4.0 Hz, 1H), 7.76 (dd, J=8.0 Hz, 1H), 8.21 (d, J=8.0 Hz, 1H), 9.06 (s, 1H). MS 328, 330 (MH$^+$).

Example 8c: ethyl 4-hydroxy-6-phenoxyquinoline-3-carboxylate

Prepared as in Example 1c from 4-phenoxyaniline and diethyl 2-(ethoxymethylene)malonate as a white solid (41%). $^1$H NMR (400 MHz, DMSO-$d_6$) δ 1.24 (t, J=8.0 Hz, 3H), 4.18 (q, J=8.0 Hz, 2H), 7.07 (d, J=8.0 Hz, 2H), 7.20 (t, J=8.0 Hz, 1H), 7.43 (t, J=8.0 Hz, 2H), 7.47 (m, 2H), 7.69 (d, J=12.0 Hz, 1H), 12.39 (bs, 1H). MS 310 (MH$^+$).

Example 9: 4-amino-7-fluoroquinoline-3-carboxylic Acid

Prepared as in Example 1 from ethyl 4-amino-7-fluoroquinoline-3-carboxylate (Example 9a) as an off white solid (66%). $^1$H NMR (CD$_3$OD, 400 MHz) δ ☐7.49 (m, 2H), 8.50 (dd, J=10.0, 5.2 Hz, 1H), 8.94 (s, 1H). MS 207 (MH$^+$).

Example 9a: ethyl 4-amino-7-fluoroquinoline-3-carboxylate

Prepared as in Example 1a from ethyl 4-chloro-7-fluoroquinoline-3-carboxylate (Example 9b) and ammonia as an off white solid (99%). MS 235 (MH$^+$).

Example 9b: ethyl 4-chloro-7-fluoroquinoline-3-carboxylate

Prepared as in Example 1b from ethyl 7-fluoro-4-hydroxyquinoline-3-carboxylate (Example 9c) and POCl$_3$ as an off white solid (96%). MS 254, 256 (MH$^+$).

Example 9c: ethyl 7-fluoro-4-hydroxyquinoline-3-carboxylate

Prepared as in Example 1c from 3-fluoroaniline and diethyl 2-(ethoxymethylene)malonate as a brown solid (51%). MS 236 (MH$^+$).

Example 10:
4-amino-6-isopropoxyquinoline-3-carboxylic Acid

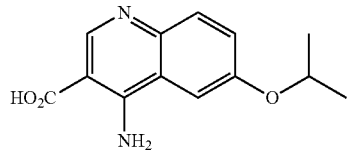 [SMILES: CC(C)Oc1ccc2ncc(C(=O)O)c(N)c2c1]

Prepared as in Example 1 from ethyl 4-amino-6-isopropoxyquinoline-3-carboxylate (Example 10a) as a an off white solid (94%). $^1$H NMR (400 MHz, DMSO-d6) δ 1.30 (s, 3H), 1.32 (s, 3H), 4.82 (m, 1H), 7.37 (d, J=9.2 Hz, 1H), 7.72 (d, J=9.2 Hz, 1H), 7.78 (s, 1H), 8.75 (s, 1H). MS 247 (MH$^+$).

Example 10a: ethyl 4-amino-6-isopropoxyquinoline-3-carboxylate

Prepared as in Example 1a from ethyl 4-chloro-6-isopropoxyquinoline-3-carboxylate (Example 10b) and ammonia as an off white solid (75%). MS 275 (MH$^+$).

Example 10b: 4-chloro-6-isopropoxyquinoline-3-carboxylate

Prepared as in Example 1b from ethyl 4-hydroxy-6-isopropoxyquinoline-3-carboxylate (Example 10c) and POCl$_3$ as a pale yellow solid (93%). MS 294, 296 (MH$^+$).

Example 10c: ethyl 4-hydroxy-6-isopropoxyquinoline-3-carboxylate

Prepared as in Example 1c from 4-isopropoxyaniline and diethyl 2-(ethoxymethylene)malonate as a yellow solid (20%). MS 276 (MH$^+$).

Example 11: 4-amino-6-methoxy-2-methyl-1,5-naphthyridine-3-carboxylic Acid

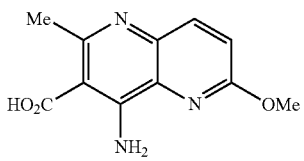

Prepared as in Example 1 from ethyl 4-amino-6-methoxy-2-methyl-1,5-naphthyridine-3-carboxylate (Example 11a) as an off white solid (56%). $^1$H NMR (400 MHz, DMSO-d$_6$) δ 2.68 (s, 3H), 4.02 (s, 3H), 7.21 (d, J=8.8 Hz, 1H), 7.99 (d, J=9.2 Hz, 1H). MS 234 (MH$^+$).

Example 11a: ethyl 4-amino-6-methoxy-2-methyl-1,5-naphthyridine-3-carboxylate

Prepared as in Example 2a from 3-amino-6-methoxypicolinonitrile (Example 11b) and ethyl 3-oxobutanoate as an off white solid (45%). MS 262 (MH$^+$).

Example 11b: 3-amino-6-methoxypicolinonitrile

To a solution of 6-methoxy-3-nitropicolinonitrile (Piersanti, G. et al. *Org. Biomolecular Chem.* 2007, 5, 2567-2571) (2.0 g, 11.1 mmol) in diglyme (52 mL) was added dropwise a solution of SnCl$_2$ (6.35 g, 33.5 mmol) in concentrated HCl solution (26 mL) at 0° C. The solution was stirred at 0° C. for 1 hr, then the reaction mixture was neutralized with concentrated NaOH solution, and extracted with EtOAc (2×). The combined organic layers were washed with brine, and dried over Na$_2$SO$_4$. After evaporation of the solvent, the residue was purified by chromatography on silica gel (50% EtOAc in hexanes) to give 3-amino-6-methoxypicolinonitrile (966 mg, 58%) as a brown solid. $^1$H NMR (400 MHz, CDCl$_3$) δ 3.81 (s, 3H), 4.10 (bs, 2H), 6.81 (d, J=8.0 Hz, 1H), 7.08 (d, J=8.0 Hz, 1H). MS 150 (MH$^+$).

Example 12: 4-amino-2,5-dimethylquinoline-3-carboxylic Acid

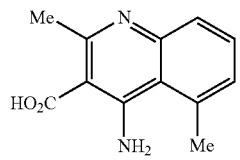

Ethyl 4-(4-methoxybenzylamino)-2,5-dimethylquinoline-3-carboxylate (Example 12a, 0.563 g, 1.54 mmol) was dissolved in TFA (8 mL) and the resultant solution was stirred at room temperature for 15 minutes, TFA was then removed under vacuum to give the crude ethyl 4-amino-2,5-dimethylquinoline-3-carboxylate product, which was dissolved in EtOH (4 mL). To this solution was added NaOH (4.0 N, 3.86 mL) and the reaction mixture was stirred at 100° C. for 1 hr. Water (25 mL) was added, and the solvent was decanted away from insoluble material then acidified with AcOH to pH 5.5. The precipitate was collected by filtration to give the title compound (300 mg, 90%) as a white solid. $^1$H NMR (400 MHz, DMSO-d$_6$) δ 2.78 (s, 3H), 2.88 (s, 3H), 7.30 (d, J=7.2 Hz, 1H), 7.58 (d, J=8.0 Hz, 1H), 7.65 (m, 1H), 7.8-8.0 (br, 1H), 12.2-12.9 (br, 2H). MS 217 (MH$^+$).

Example 12a: ethyl 4-(4-methoxybenzylamino)-2,5-dimethylquinoline-3-carboxylate

A solution of ethyl 4-chloro-2,5-dimethylquinoline-3-carboxylate (Example 12b, 0.518 g, 1.96 mmol) and (4-methoxyphenyl)methanamine (1.15 mL, 8.86 mmol) in toluene (10 mL) and DMF (5 mL) were stirred at 115° C. under nitrogen for 12 hrs. The solvent was removed under vacuum, and the residue was purified by chromatography on silica gel (0% to 50% EtOAc in hexanes) to give the title compound as an oil (563 mg, 79%). $^1$H NMR (400 MHz, DMSO-d$_6$) δ 1.24 (t, J=7.6 Hz, 3H), 2.45 (s, 3H), 2.78 (s, 3H), 3.73 (s, 3H), 4.2-4.3 (m, 4H), 6.27 (t, J=6.0 Hz, 1H), 6.88 (d, J=8.4 Hz, 2H), 7.19 (m, 3H), 7.48 (m, 1H), 7.58 (d, J=8.4 Hz, 1H). MS 365 (MH$^+$).

Example 12b: ethyl 4-chloro-2,5-dimethylquinoline-3-carboxylate

A solution of 5-methyl-1H-benzo[d][1,3]oxazine-2,4-dione (Example 12c) (1.36 g, 7.68 mmol), ethyl 3-oxobutanoate (1.46 mL, 11.5 mmol), and NaOH (0.046 g, 1.15 mmol) in anhydrous dioxane (10 mL) were refluxed under nitrogen for 15 hrs. The solvent was then removed under vacuum, and the residue was re-dissolved in DMF (15 mL). To this solution was added POCl$_3$ (1.41 mL, 15.4 mmol), and the reaction mixture was stirred at room temperature for 45 minutes. The reaction was carefully quenched with ice water (150 mL), and extracted with DCM (2×75 mL). The combined organic layers were washed with brine, and dried over $Na_2SO_4$. After evaporation of the solvent, the residue was purified by chromatography on silica gel eluting with 50% EtOAc in hexanes to give the title compound as red oil (520 mg, 26%). $^1$H NMR (400 MHz, DMSO-$d_6$) δ 1.36 (t, J=7.6 Hz, 3H), 2.58 (s, 3H), 2.97 (s, 3H), 4.46 (q, J=7.6 Hz, 2H), 7.51 (d, J=7.2 Hz, 1H), 7.71 (m, 1H), 7.87 (d, J=7.6 Hz, 1H). MS 264, 266 (MH$^+$)

Example 12c: 5-methyl-H-benzo[d][1,3]oxazine-2,4-dione

Trichloromethyl carbonochloridate (2.04 mL, 16.9 mmol) was added to 2-amino-6-methylbenzoic acid (2.13 g, 14.1 mmol) in anhydrous dioxane (32 mL) under nitrogen, then refluxed for 30 minutes. Diethyl ether (100 mL) was added, and the precipitated solid was collected by filtration to give 5-methyl-1H-benzo[d][1,3]oxazine-2,4-dione (1.4 g, 56%) which was used without further purification.

Example 13: 4-amino-6-ethoxyquinoline-3-carboxylic Acid

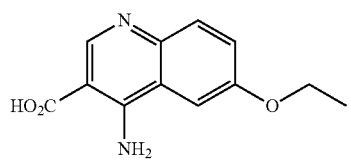

Prepared as in Example 1 from ethyl 4-amino-6-ethoxy-quinoline-3-carboxylate (Example 13a) as an off white solid (76%). $^1$H NMR (400 MHz, DMSO-$d_6$) δ 1.39 (t, J=7.2 Hz, 3H), 4.18 (q, J=7.2 Hz, 2H), 7.50-7.53 (m, 1H), 7.86 (d, J=8.8 Hz, 1H), 7.95 (d, J=2.0 Hz, 1H), 8.86 (s, 1H), 9.26 (bs, 1H), 9.86 (bs, 1H). MS 233 (MH$^+$).

Example 13a: ethyl 4-amino-6-ethoxyquinoline-3-carboxylate

Prepared as in Example 1a from ethyl 4-chloro-6-ethoxy-quinoline-3-carboxylate (Example 13b) and ammonia as an off white solid (77%). $^1$H NMR (400 MHz, DMSO-$d_6$) δ 1.31-1.40 (m, 6H), 4.15 (q, J=7.2 Hz, 2H), 4.31 (q, J=6.8 Hz, 2H), 7.34 (q, J=6.4 Hz, 1H), 7.69-7.74 (m, 2H), 8.21 (bs, 2H), 8.77 (s, 1H). MS 261 (MH$^+$).

Example 13b: ethyl 4-chloro-6-ethoxyquinoline-3-carboxylate

Prepared as in Example 1b from ethyl 6-ethoxy-4-hydroxyquinoline-3-carboxylate (Example 13c) and POCl$_3$ as pale yellow solid (100%). $^1$H NMR (400 MHz, DMSO-d6) δ 1.34-1.42 (m, 6H), 4.21 (q, J=7.2 Hz, 2H), 4.40 (q, J=7.2 Hz, 2H), 7.52 (d, J=2.8 Hz, 1H), 7.56-7.59 (m, 1H), 8.02 (d, J=8.8 Hz, 1H), 8.94 (s, 1H). MS 280, 282 (MH$^+$).

Example 13c: ethyl 6-ethoxy-4-hydroxyquinoline-3-carboxylate

Prepared as in Example 1c from 4-ethoxyaniline and diethyl 2-(ethoxymethylene)malonate as a white solid (26%). $^1$H NMR (400 MHz, DMSO-$d_6$) δ 1.24-1.37 (m, 6H), 4.09 (q, J=6.8 Hz, 2H), 4.19 (q, J=7.2 Hz, 2H), 7.29-7.32 (m, 1H), 7.52-7.56 (m, 2H), 8.47 (s, 1H), 12.27 (s, 1H). MS 262 (MH$^+$).

Example 14: 4-amino-6-propoxyquinoline-3-carboxylic Acid

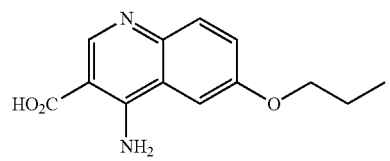 [SMILES: CCCOc1ccc2ncc(C(=O)O)c(N)c2c1]

Prepared as in Example 1 from ethyl 4-amino-6-propoxy-quinoline-3-carboxylate (Example 14a) as a white solid (56%). $^1$H NMR (400 MHz, DMSO-$d_6$) δ 1.01 (t, J=7.6 Hz, 3H), 1.77-1.82 (m, 2H), 4.06 (t, J=6.8 Hz, 2H), 7.43 (d, J=2.0 Hz, 1H), 7.71-7.78 (m, 2H), 8.77 (s, 1H). MS 247 (MH$^+$).

Example 14a: 4-amino-6-propoxyquinoline-3-carboxylate

Prepared as in Example 1a from ethyl 4-chloro-6-propoxyquinoline-3-carboxylate (Example 14b) and ammonia as a white solid. MS 275 (MH$^+$).

Example 14b: ethyl 4-chloro-6-propoxyquinoline-3-carboxylate

Prepared as in Example 1b from ethyl 4-hydroxy-6-propoxyquinoline-3-carboxylate (Example 14c) and POCl$_3$ as a pale yellow solid. MS 294, 296 (MH$^+$).

Example 14c: ethyl 4-hydroxy-6-propoxyquinoline-3-carboxylate

Prepared as in Example 1c from 4-propoxyaniline and diethyl 2-(ethoxymethylene)malonate as a white solid (65%). $^1$H NMR (400 MHz, DMSO-$d_6$) δ 0.98 (t, J=7.2 Hz, 3H), 1.25 (t, J=7.2 Hz, 3H), 1.72-1.77 (m, 2H), 3.98 (t, J=6.0 Hz, 2H), 4.16-4.21 (m, 2H), 6.97-6.99 (m, 1H), 7.53-7.56 (m, 2H), 8.47 (d, J=5.2 Hz, 1H), 12.27 (s, 1H). MS 276 (MH$^+$).

Example 15: 4-amino-5-methoxy-2-methylquinoline-3-carboxylic Acid

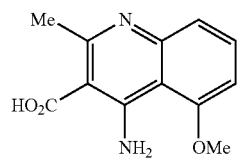 [SMILES: COc1cccc2nc(C)c(C(=O)O)c(N)c12]

Prepared as in Example 1 from ethyl 4-amino-5-methoxy-2-methylquinoline-3-carboxylate (Example 15a) as a off-white solid. $^1$H NMR (400 MHz, DMSO-$d_6$) δ 2.49 (s, 3H), 4.05 (s, 3H), 7.19 (d, J=7.6 Hz, 1H), 7.61 (d, J=8.0 Hz, 1H), 7.85 (t, J=8.0 Hz, 1H), 9.49 (s, 1H), 9.85 (s, 1H). MS 233 (MH+).

Example 15a: ethyl 4-amino-5-methoxy-2-methylquinoline-3-carboxylate

Prepared as in Example 2a from 2-amino-6-methoxybenzonitrile and ethyl 3-oxobutanoate as a pale yellow solid. $^1$H NMR (400 MHz, DMSO-d$_6$) δ 1.32 (t, J=7.2 Hz, 3H), 2.55 (s, 3H), 3.96 (s, 3H), 4.30 (q, J=7.2 Hz, 2H), 6.88 (d, J=8.4 Hz, 1H), 7.22 (d, J=7.6 Hz, 1H), 7.52 (t, J=8.0 Hz, 1H), 8.15 (s, 2H). MS 261 (MH+).

Example 16: 4-amino-2-methyl-5-(neopentyloxy)quinoline-3-carboxylic Acid

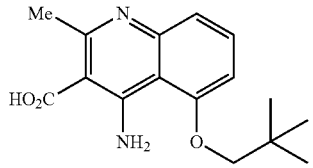 [SMILES: Cc1nc2cccc(OCC(C)(C)C)c2c(N)c1C(=O)O]

Prepared as in Example 1 from ethyl 4-amino-2-methyl-5-(neopentyloxy)quinoline-3-carboxylate (Example 16a) as a white solid. $^1$H NMR (400 MHz, DMSO-d6) δ 1.06 (s, 9H), 2.76 (s, 3H), 3.93 (s, 2H), 7.05 (d, J=8.4 Hz, 1H), 7.31 (d, J=8.0 Hz, 1H), 7.66 (t, J=8.0 Hz, 1H). MS 289 (MH+).

Example 16a: ethyl 4-amino-2-methyl-5-(neopentyloxy)quinoline-3-carboxylate

Prepared as in Example 2a from 2-amino-6-(neopentyloxy)benzonitrile (Tachdjian, C. et al. PCT Int. Appl. 2008, WO 2008154221) and ethyl 3-oxobutanoate as a white solid (64%). $^1$H NMR (400 MHz, DMSO-d$_6$) δ 1.06 (s, 9H), 1.32 (t, J=6.8 Hz, 3H), 2.54 (s, 3H), 3.86 (s, 2H), 4.31 (q, J=6.8 Hz, 2H). 6.88-6.91 (m, 1H), 7.22-7.25 (m, 1H), 7.50 (t, J=8.0 Hz, 1H), 8.06 (s, 2H). MS 317 (MH+).

Example 17: 4-amino-2-(carboxymethyl)quinoline-3-carboxylic Acid

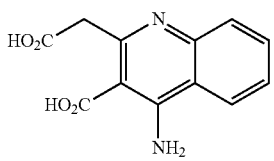

Prepared as in Example 1 from ethyl 4-amino-2-(2-ethoxy-2-oxoethyl)quinoline-3-carboxylate (Example 17a) as a white solid (26%). $^1$H NMR (400 MHz, DMSO-d6) δ 3.76 (s, 2H), 7.36 (t, J=8.0 Hz, 1H), 7.58 (t, J=8.0 Hz, 1H), 7.64 (d, J=12.0 Hz, 1H), 7.87 (bs, 2H), 8.17 (d, J=8.0 Hz, 1H). MS 188 (MH+—CH$_2$CO$_2$H).

Example 17a: ethyl 4-amino-2-(2-ethoxy-2-oxoethyl)quinoline-3-carboxylate

Prepared as in Example 2a from 2-aminobenzonitrile and diethyl 3-oxopentanedioate as a pale yellow solid (25%). $^1$H NMR (400 MHz, DMSO-d$_6$) δ 1.19 (t, J=8.0 Hz, 3H), 1.30 (t, J=8.0 Hz, 3H), 4.08 (m, 4H), 4.28 (q, J=8.0 Hz, 2H), 7.50 (m, 1H), 7.73 (m, 2H), 8.10 (bs, 2H), 8.53 (d, J=8.0 Hz, 1H). MS 303 (MH+).

Example 18: 4-amino-5-(cyclopentylmethoxy)-2-methylquinoline-3-carboxylic Acid

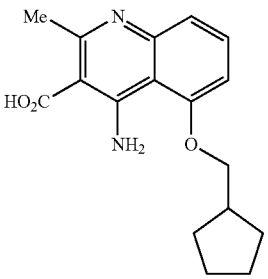 [SMILES: Cc1nc2cccc(OCC3CCCC3)c2c(N)c1C(=O)O]

Prepared as in Example 1 from ethyl 4-amino-5-(cyclopentylmethoxy)-2-methylquinoline-3-carboxylate (Example 18a) as a white solid (86%). $^1$H NMR (400 MHz, DMSO-d$_6$) δ 1.31-1.36 (m, 2H), 1.55-1.62 (m, 4H), 1.80-1.95 (m, 2H), 2.46-2.50 (m, 1H), 2.74 (s, 3H), 4.11 (d, J=7.6 Hz, 2H), 7.01 (d, J=8.0 Hz, 1H), 7.26 (d, J=8.0 Hz, 1H), 7.64 (t, J=8.0 Hz, 1H). MS 301 (MH+).

Example 18a: ethyl 4-amino-5-(cyclopentylmethoxy)-2-methylquinoline-3-carboxylate Prepared as in Example 2a from 2-amino-6-(cyclopentylmethoxy)benzonitrile (Tachdjian, C. et al. PCT Int. Appl. 2008, WO 2008154221) and ethyl 3-oxobutanoate as a pale yellow solid (75%). MS 329 (MH+).

Example 19: 4-amino-5-(cyclopentyloxy)-2-methylquinoline-3-carboxylic Acid

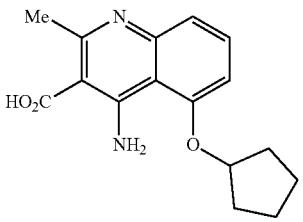 [SMILES: Cc1nc2cccc(OC3CCCC3)c2c(N)c1C(=O)O]

Prepared as in Example 1 from ethyl 4-amino-5-(cyclopentyloxy)-2-methylquinoline-3-carboxylate (Example 19a) as a off white solid (83%). $^1$H NMR (400 MHz, DMSO-d$_6$) δ 1.56-1.60 (m, 2H), 1.67-1.70 (m, 2H), 1.83-1.87 (m, 2H), 1.92-1.96 (m, 2H), 2.67 (s, 3H), 5.05-5.07 (m, 1H), 6.93 (d, J=8.4 Hz, 1H), 7.18 (d, J=8.4 Hz, 1H), 7.57 (t, J=8.4 Hz, 1H). MS 287 (MH+).

Example 19a: ethyl 4-amino-5-(cyclopentyloxy)-2-methylquinoline-3-carboxylate Prepared as in Example 2a from 2-amino-6-(cyclopentyloxy)benzonitrile (Tachdjian, C. et al. PCT Int. Appl. 2008, WO 2008154221) and ethyl 3-oxobutanoate as a yellow solid (40%). MS 315 (MH+).

Example 20: 4-amino-2,3-butylene-6-methylthieno[2,3-b]pyridine-5-carboxylic Acid

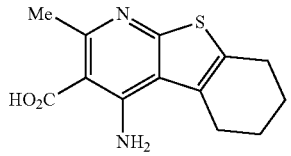 [SMILES: Cc1nc2sc3c(c2c(N)c1C(=O)O)CCCC3]

Prepared as in Example 1 from ethyl 4-amino-2,3-butylene-6-methylthieno[2,3-b]pyridine-5-carboxylate (Example 20a) as a solid. $^1$H NMR (400 MHz, DMSO-d6) δ 1.78-1.79 (m, 4H), 2.53 (s, 3H), 2.71-2.72 (m, 2H), 2.94-2.96 (m, 2H), 6.86 (s, 2H). MS 263 (MH$^+$).

Example 20a: ethyl 4-amino-2,3-butylene-6-methylthieno[2,3-b]pyridine-5-carboxylate Prepared as in Example 2a from 2-amino-4,5,6,7-tetrahydrobenzo[b]thiophene-3-carbonitrile (Tachdjian, C. et al. *PCT Int. Appl.* 2008, WO 2008154221) and ethyl 3-oxobutanoate as a yellow solid. MS 291 (MH$^+$).

Example 21: 4-amino-5-(3,3-dimethylbutyl)-2-methylquinoline-3-carboxylic Acid

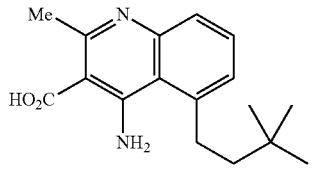 [SMILES: Cc1nc2cccc(CCC(C)(C)C)c2c(N)c1C(=O)O]

Prepared as in Example 1 from ethyl 4-amino-5-(3,3-dimethylbutyl)-2-methylquinoline-3-carboxylate (Example 21a) as a white solid (88%). $^1$H NMR (400 MHz, DMSO-d$_6$) δ 0.93 (s, 9H), 1.40 (t, J=8.8 Hz, 2H), 2.75 (s, 3H), 3.17 (t, J=8.4 Hz, 2H), 7.35 (d, J=7.2 Hz, 1H), 7.57 (d, J=8.4 Hz, 1H), 7.66 (t, J=8.0 Hz, 1H), 12.78 (s, 1H). MS 287 (MH$^+$).

Example 21a: ethyl 4-amino-5-(3,3-dimethylbutyl)-2-methylquinoline-3-carboxylate Prepared as in Example 2a from 2-amino-6-(3,3-dimethylbutyl)benzonitrile (Example 21b) and ethyl 3-oxobutanoate as a white solid (95%). $^1$H NMR (400 MHz, DMSO-d$_6$) δ 0.93 (s, 9H), 1.32 (t, J=7.2 Hz, 3H), 1.42-1.46 (m, 1H), 2.55 (s, 3H), 3.11-3.15 (m, 2H), 4.33 (q, J=7.2 Hz, 2H), 7.12 (s, 2H), 7.19-7.21 (m, 1H), 7.46-7.52 (m, 2H). MS 315 (MH$^+$).

Example 21b: 2-amino-6-(3,3-dimethylbutyl)benzonitrile

A suspension of 2-amino-6-(3,3-dimethylbut-1-ynyl)benzonitrile (Example 21c, 690 mg, 3.48 mmol) and 10% Pd/C (100 mg) in EtOAc/EtOH (1:1, 20 mL) was stirred under an atmosphere of H$_2$ with a balloon at room temperature overnight. The Pd/C was removed by filtration, the filtrate was concentrated, and purified by chromatography on silica gel eluting with 20% EtOAc in hexanes to give the title compound as a light yellow oil (620 mg, 88%). $^1$H NMR (400 MHz, DMSO-d$_6$) δ 0.92 (s, 9H), 1.36-1.40 (m, 2H), 2.52-2.56 (m, 2H), 5.88 (s, 2H), 6.45 (d, J=7.6 Hz, 1H), 6.57 (d, J=7.6 Hz, 1H), 7.15 (t, J=8.0 Hz, 1H). MS 203 (MH$^+$).

Example 21c: 2-amino-6-(3,3-dimethylbut-1-ynyl)benzonitrile

To a solution of 2-amino-6-bromobenzonitrile (1.97 g, 10.0 mmol), 3,3-dimethylbut-1-yne (2.46 g, 30 mmol), K$_2$CO$_3$ (2.76 g, 20.0 mmol), and CuI (191 mg, 0.1 mmol) in DME/H$_2$O (4:1, 50 mL) was added Pd(PPh$_3$)$_4$ (1.16 g, 0.1 mmol) at room temperature under nitrogen. The reaction mixture was refluxed under nitrogen overnight. After it was cooled down to room temperature, the reaction was quenched with brine, extracted with EtOAc. The organic layer was washed with brine, dried over Na$_2$SO$_4$, and concentrated. The residue was purified by chromatography on silica gel eluting with 20% EtOAc in hexanes to give the title compound as a light brown oil (1.84 g, 93%). $^1$H NMR (400 MHz, DMSO-d$_6$) δ 1.27 (s, 9H), 6.10 (s, 2H), 6.59 (d, J=7.2 Hz, 1H), 6.71 (d, J=8.0 Hz, 1H), 7.18-7.22 (m, 1H). MS 199 (MH$^+$).

Example 22: 4-amino-5-(2-ethylbutoxy)-2-methylquinoline-3-carboxylic Acid

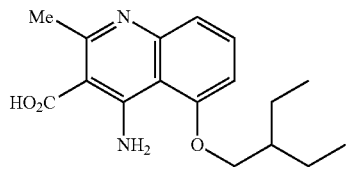 [SMILES: CCC(CC)COc1cccc2nc(C)c(C(=O)O)c(N)c12]

Prepared as in Example 1 from ethyl 4-amino-5-(2-ethylbutoxy)-2-methylquinoline-3-carboxylate (Example 22a) as a white solid (45%). M.p.: 145-151° C. $^1$H NMR (400 MHz, DMSO-d$_6$) δ 0.90 (t, J=8 Hz, 6H), 1.48-1.41, (m, 4H), 1.84-1.78 (m, 1H), 2.73 (s, 3H), 4.11 (d, J=8 Hz, 2H), 6.99 (d, J=8 Hz, 1H), 7.32 (d, J=8 Hz, 1H), 7.59 (t, J=8 Hz, 1H), 8.40 (brs, 1H), 11.09 (brs, 1H), 13.91 (brs, 1H). MS 303 (MH$^+$).

Example 22a: ethyl 4-amino-5-(2-ethylbutoxy)-2-methylquinoline-3-carboxylate Prepared as in Example 2a from 2-amino-6-(2-ethylbutoxy)benzonitrile (Example 22b) and ethyl 3-oxobutanoate as a white solid (89%). $^1$H NMR (400 MHz, DMSO-d$_6$) δ 0.90 (t, J=8 Hz, 6H), 1.32 (t, J=8 Hz, 3H), 1.48-1.41 (m, 4H), 1.79-1.73 (m, 1H), 2.54 (s, 3H), 4.08 (d, J=4 Hz, 2H), 4.31 (q, J=8 Hz, 2H), 6.92 (dd, J=2, 8 Hz, 1H), 7.23 (dd, J=2, 8 Hz, 1H), 7.50 (t, J=8 Hz, 1H), 8.04 (brs, 1H). MS 331 (MH$^+$).

Example 22b: 2-amino-6-(2-ethylbutoxy)benzonitrile

To a solution of 2-ethylbutan-1-ol (1.02 g, 10.0 mmol) in dry THF (60 mL) was carefully added NaH (60% in mineral oil, 480 mg, 12.0 mmol) in small portions at 0° C. under nitrogen. The reaction mixture was stirred at 0° C. under nitrogen for 2 hrs. To this solution was added 2-amino-6-fluorobenzonitrile (1.36 g, 10.0 mmol), and the reaction solution was stirred at 0° C.-RT for 2 hrs, and then at 65° C. overnight under nitrogen. The reaction was cooled down to room temperature then quenched with brine, and extracted with EtOAc (3×). The combined organic layers were washed with brine, dried over Na$_2$SO$_4$. Filtered and evaporated under reduced pressure. The residue was purified by chromatography on silica gel (eluent: 20% EtOAc in hexanes) to give the title compound as colorless oil (1.29 g, 59%). $^1$H NMR (400 MHz, CDCl$_3$) δ 0.93 (t, J=8 Hz, 6H), 1.55-1.43 (m, 4H), 1.73-1.65 (m, 1H), 3.90 (d, J=4 Hz, 2H), 4.10 (brs, 2H), 6.25 (d, J=8 Hz, 1H), 6.34 (d, J=8 Hz, 1H), 7.20 (t, J=8 Hz, 1H).

Example 23: 4-amino-5-(heptan-4-yloxy)-2-methylquinoline-3-carboxylic Acid

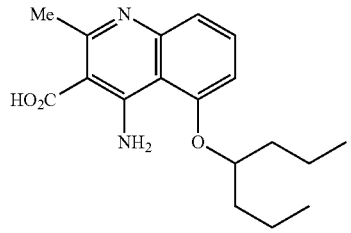 [SMILES: CCCC(CCC)Oc1cccc2nc(C)c(C(=O)O)c(N)c12]

Prepared as in Example 1 from ethyl 4-amino-5-(heptan-4-yloxy)-2-methylquinoline-3-carboxylate (Example 23a) as a white solid (59%). $^1$H NMR (400 MHz, DMSO-d$_6$) δ 0.87 (t, J=7.2 Hz, 6H), 1.49-1.25 (m, 4H), 1.84-1.60 (m 4H), 2.74 (s, 3H), 4.74-4.71 (m, 1H), 7.07 (d, J=8.4 Hz, 1H), 7.24 (d, J=8.0 Hz, 1H), 7.64 (t, J=8.4 Hz, 1H), 8.82 (brs, 1H). MS 317 (MH$^+$).

Example 23a: ethyl 4-amino-5-(heptan-4-yloxy)-2-methylquinoline-3-carboxylate Prepared as in Example 2a from 2-amino-6-(heptan-4-yloxy)benzonitrile (Example 23b) and ethyl 3-oxobutanoate as a pale yellow solid (65%). $^1$H NMR (400 MHz, DMSO-d$_6$) δ 0.87 (t, J=7.2 Hz, 6H), 1.31 (t, J=7.2 Hz, 3H), 1.47-1.33 (m, 4H), 1.77-1.59 (m, 4H), 2.54 (s, 3H), 4.30 (q, J=7.2 Hz, 2H), 4.67-4.64 (m, 1H), 6.92 (d, J=7.6 Hz, 1H), 7.19 (dd, J=0.8, 8.4 Hz, 1H), 7.49 (t, J=8.0 Hz, 1H), 8.13 (brs, 2H). MS 345 (MH$^+$).

Example 23b: 2-amino-6-(heptan-4-yloxy)benzonitrile

Prepared as in Example 22b from heptan-4-ol and 2-amino-6-fluorobenzonitrile as a white solid (24%). $^1$H NMR (400 MHz, CDCl$_3$) δ 0.92 (t, J=7.2 Hz, 6H), 1.55-1.31 (m, 8H), 3.88 (s, br, 1H), 4.33-4.27 (m, 1H), 6.26 (d, J=8.0 Hz, 1H), 6.35 (d, J=8.0 Hz, 1H), 7.20 (t, J=8.0 Hz, 1H).

Example 24: 4-amino-5-(2-(isonicotinamido)-2-methylpropoxy)-2-methylquinoline-3-carboxylic Acid

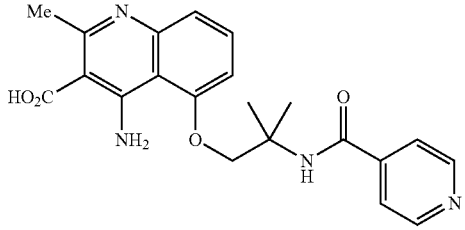 [SMILES: Cc1nc2cccc(OCC(C)(C)NC(=O)c3ccncc3)c2c(N)c1C(=O)O]

Prepared as in Example 1 from ethyl 4-amino-5-(2-(isonicotinamido)-2-methylpropoxy)-2-methylquinoline-3-carboxylate (Example 24a) as a white solid (67%). M.p.: 195-198° C. $^1$H NMR (400 MHz, DMSO-d$_6$) δ 1.51 (s, 6H), 2.75 (s, 3H), 4.48 (s, 2H), 7.07 (d, J=8 Hz, 1H), 7.31 (d, J=8 Hz, 1H), 7.67 (t, J=8 Hz, 1H), 7.70 (dd, J=1, 8 Hz, 2H), 8.50 (s, 1H), 8.67 (dd, J=1, 8 Hz, 2H), 8.76 (brs, 1H), 12.19 (brs, 1H), 12.85 (brs, 1H). MS 395 (MH$^+$).

Example 24a: ethyl 4-amino-5-(2-(isonicotinamido)-2-methylpropoxy)-2-methylquinoline-3-carboxylate To a solution of ethyl 4-amino-5-(2-amino-2-methylpropoxy)-2-methylquinoline-3-carboxylate (Example 24b, 1.0 g, 3.15 mmol) in dry DMF (20 mL) was added isonicotinic acid (504 mg, 4.10 mmol), followed by EDCI (783 mg, 4.10 mmol), HOBt (554 mg, 4.10 mmol), and triethylamine (414 mg, 4.10 mmol) at room temperature under nitrogen. After it was stirred at room temperature for 12 hrs, the reaction mixture was concentrated under reduced pressure. The residue was diluted with water, and extracted with EtOAc (3×). The aqueous layer was basified with 2N NaOH to pH 8 and extracted with EtOAc (3×). The combined organic layers were washed with brine, dried over MgSO$_4$, filtered, concentrated, and purified by chromatography on silica gel eluting with 10% MeOH in dichloromethane to give the title compound as a yellow solid (1.1 g, 83%). $^1$H NMR (400 MHz, DMSO-d$_6$) δ 1.29 (t, J=4 Hz, 3H), 1.51 (s, 6H), 2.94 (s, 3H), 4.28 (q, J=4 Hz, 2H), 4.42 (s, 2H), 6.93 (dd, J=1, 8 Hz, 1H), 7.24 (dd, J=1, 8 Hz, 2H), 7.52 (t, J=8 Hz, 1H), 7.69 (dd, J=2, 4 Hz, 2H), 8.14 (s, 2H), 8.37 (s, 1H), 8.67 (dd, J=2, 4 Hz, 2H). MS 423 (MH$^+$).

Example 24b: ethyl 4-amino-5-(2-amino-2-methylpropoxy)-2-methylquinoline-3-carboxylate Prepared as in Example 2a from benzyl 1-(3-amino-2-cyanophenoxy)-2-methylpropan-2-ylcarbamate (Example 24c) and ethyl 3-oxobutanoate as a yellow-brown solid (91%). $^1$H NMR (400 MHz, DMSO-d$_6$) δ 1.15 (s, 6H), 1.31 (t, J=4 Hz, 3H), 2.54 (s, 3H), 3.87 (s, 2H), 4.31 (q, J=4 Hz, 2H), 6.85 (d, J=4 Hz, 1H), 7.21 (d, J=4 Hz, 1H), 7.49 (t, J=8 Hz, 1H), 8.38 (brs, 2H). MS 318 (MH$^+$).

Example 24c: benzyl 1-(3-amino-2-cyanophenoxy)-2-methylpropan-2-ylcarbamate

To a solution of 2-amino-6-(2-amino-2-methylpropoxy) benzonitrile (Example 24d, 30.5 g, 148.6 mmol) in THF/H$_2$O (1:1, 400 mL) was added NaHCO$_3$ (24.7 g, 294 mmol), followed by benzyl (2,5-dioxopyrrolidin-1-yl) carbonate (44.0 g, 176 mmol) at room temperature. The reaction was stirred at room temperature for 4 h then the organic layer was separated and the aqueous layer was extracted with EtOAc (2×). The combined organic layers were washed with brine and dried over MgSO$_4$. After filtration, the solvent was evaporated and the crude oil was purified by chromatography on silica gel (eluent: 0-60% EtOAc in hexane) to give the title compound as yellow oil (44.8 g, 89%). $^1$H NMR (400 MHz, DMSO-d$_6$) δ 1.30 (s, 6H), 4.02 (s, 2H), 4.96 (s, 2H), 5.98 (s, 2H), 6.14 (d, J=8.0 Hz, 1H), 6.32 (dd, J=0.8, 8.4 Hz, 1H), 7.12 (t, J=8.4 Hz, 1H), 7.38-7.21 (m, 6H). MS 340 (MH$^+$).

Example 24d: 2-amino-6-(2-amino-2-methylpropoxy)benzonitrile

To a solution of 2-amino-2-methylpropan-1-ol (14.4 g, 161 mmol) in anhydrous THF (150 mL) was added NaH (6.8 g, 161 mmol, 60% in mineral oil) in small portions at 0° C. under nitrogen. The mixture was stirred at 0° C. for 30 minutes and then stirred at room temperature for another 30 minutes. The solution was cooled down to 0° C. again, and to this solution was added dropwise a solution of 2-amino-6-fluorobenzonitrile (20.0 g, 147 mmol) in anhydrous THF (50 mL). The reaction mixture was then refluxed overnight under nitrogen. The reaction mixture was cooled down to room temperature and carefully quenched with aqueous NH$_4$Cl solution and extracted with ethyl acetate (3×). The combined organic layers were washed with brine, dried over MgSO$_4$, filtered and concentrated. The crude mixture was purified by chromatography on silica gel eluting with 10% MeOH in DCM to give the title compound as yellow solid (23.4 g 71%). $^1$H NMR (400 MHz, DMSO-d$_6$) δ 1.08 (s, 6H), 3.15 (s, 2H), 3.64 (s, 2H), 5.98 (s, 2H), 6.13 (d, J=8.0 Hz, 1H), 6.31 (d, J=8.4 Hz, 1H), 7.15 (t, J=8.4 Hz, 1H). MS 236 (MH$^+$).

Example 25: 4-amino-5-(2-(3-hydroxybenzamido)-2-methylpropoxy)-2-methylquinoline-3-carboxylic Acid

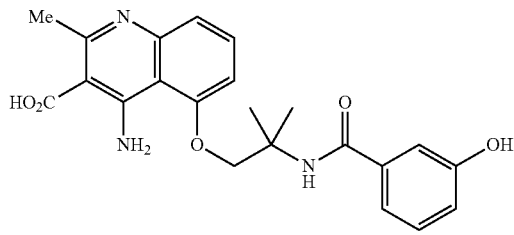 [SMILES: Cc1nc2cccc(OCC(C)(C)NC(=O)c3cccc(O)c3)c2c(N)c1C(=O)O]

Prepared as in Example 1 from ethyl 4-amino-5-(2-(3-hydroxybenzamido)-2-methylpropoxy)-2-methylquinoline-3-carboxylate (Example 25a) as a white solid (65%). M.p.: 195-198° C. $^1$H NMR (400 MHz, DMSO-d$_6$) δ 1.48 (s, 6H), 2.75 (s, 3H), 4.47 (s, 2H), 6.87 (dt, J=8, 4 Hz, 1H), 7.22-7.16 (m, 3H), 7.06 (d, J=8 Hz, 1H), 7.27 (d, J=8 Hz, 1H), 7.67 (t, J=8 Hz, 1H), 8.08 (s, 1H), 8.84 (brs, 1H), 9.69 (s, 1H), 12.12 (brs, 1H), 12.78 (brs, 1H). MS 410 (MH$^+$).

Example 25a: ethyl 4-amino-5-(2-(3-hydroxybenzamido)-2-methylpropoxy)-2-methyl-quinoline-3-carboxylate Prepared as in Example 24a from 4-amino-5-(2-amino-2-methylpropoxy)-2-methyl-quinoline-3-carboxylate (Example 24b) and 3-hydroxybenzoic acid as a yellow-brown solid (64%). $^1$H NMR (400 MHz, DMSO-d$_6$) δ 1.30 (t, J=4 Hz, 3H), 1.48 (s, 6H), 2.55 (s, 3H), 4.30 (q, J=4 Hz, 2H), 4.41 (s, 2H), 6.85-6.88 (m, 1H), 6.92 (d, J=8 Hz, 1H), 7.25-7.15 (m, 4H), 7.52 (t, J=8 Hz, 1H), 7.98 (s, 1H), 8.19 (s, 2H), 9.59 (s, 1H). MS 438 (MH$^+$).

Example 26: (S)-4-amino-5-(2-(cyclohexanecarboxamido)propoxy)-2-methylquinoline-3-carboxylic Acid

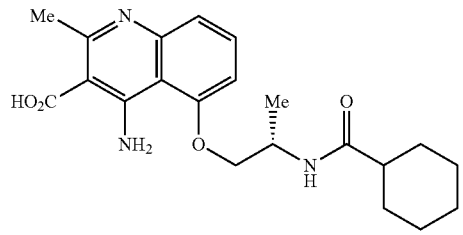 [SMILES: Cc1nc2cccc(OC[C@H](C)NC(=O)C3CCCCC3)c2c(N)c1C(=O)O]

Prepared as in Example 1 from (S)-ethyl 4-amino-5-(2-(cyclohexanecarboxamido)-propoxy)-2-methylquinoline-3-carboxylate (Example 26a) as a white solid (53%). $^1$H NMR (400 MHz, DMSO-d$_6$) δ 1.25-1.10 (m, 5H), 1.34-1.31 (m, 2H), 1.69-1.62 (m, 5H), 2.11-2.05 (m, 1H), 2.69 (s, 3H), 3.93 (t, J=9.2 Hz, 1H), 4.13 (dd, J=4, 9.6 Hz, 1H), 4.14-4.11 (m, 1H), 6.86 (d, J=8.0 Hz, 1H), 7.28 (d, J=8.4 Hz, 1H), 7.49 (t, J=8.0 Hz, 1H), 7.95 (d, J=8.4 Hz, 1H). MS 386 (MH$^+$).

Example 26a: (S)-ethyl 4-amino-5-(2-(cyclohexanecarboxamido)propoxy)-2-methyl-quinoline-3-carboxylate Prepared as in Example 24a from (S)-ethyl 4-amino-5-(2-aminopropoxy)-2-methyl-quinoline-3-carboxylate (Example 26b) and cyclohexanecarboxylic acid as brown solid (28%). MS 414 (MH$^+$).

Example 26b: (S)-ethyl 4-amino-5-(2-aminopropoxy)-2-methylquinoline-3-carboxylate Prepared as in Example 2a from (S)-benzyl (1-(3-amino-2-cyanophenoxy)propan-2-yl)-carbamate (Example 26c) and ethyl 3-oxobutanoate as brown solid. MS 304 (MH$^+$).

Example 26c: (S)-benzyl (1-(3-amino-2-cyanophenoxy)propan-2-yl)carbamate

Prepared as in Example 24c from (S)-2-amino-6-(2-aminopropoxy)benzonitrile (Example 26d) as brown solid (86%). $^1$H NMR (400 MHz, DMSO-d$_6$) δ 1.12 (d, J=6.4 Hz, 3H), 3.81 (d, J=8.4 Hz, 1H), 3.95-3.92 (m, 1H), 4.99 (s, 2H), 5.36 (s, 2H), 5.96 (s, 2H), 6.20 (d, J=8.0 Hz, 1H), 6.31 (d, J=8.4 Hz, 1H), 7.13 (t, J=8.4 Hz, 1H), 7.44-7.38 (m, 5H). MS 326 (MH$^+$).

Example 26d: (S)-2-amino-6-(2-aminopropoxy)benzonitrile

Prepared as in Example 24d from (S)-2-aminopropan-1-ol and 2-amino-6-fluoro-benzonitrile as brown solid (73%). $^1$H NMR (400 MHz, DMSO-d$_6$) δ 1.01 (d, J=6.5 Hz, 3H), 3.08

(m, 1H), 3.71 (d, J=6.1 Hz, 2H), 5.95 (s, 2H), 6.15 (d, J=8.3 Hz, 1H), 6.2 (d, J=8.3 Hz, 1H), 7.13 (t, J=8.3 Hz, 1H). MS 192 (MH+).

Example 27: (S)-4-amino-5-(2-(isonicotinamido) propoxy)-2-methylquinoline-3-carboxylic

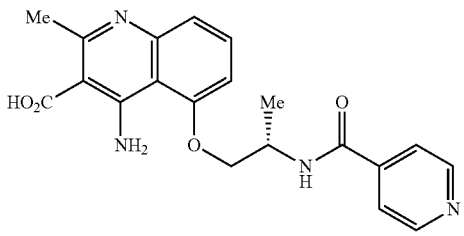 [SMILES: Cc1nc2cccc(OC[C@H](C)NC(=O)c3ccncc3)c2c(N)c1C(=O)O]

Prepared as in Example 1 from (S)-ethyl 4-amino-5-(2-(isonicotinamido)propoxy)-2-methylquinoline-3-carboxylate (Example 27a) as an off-white solid (42%). $^1$H NMR (400 MHz, DMSO-$d_6$) δ 1.31 (d, J=6.8 Hz, 3H), 2.66 (s, 3H), 4.14 (t, J=9.2 Hz, 1H), 4.28 (dd, J=3.6, 9.6 Hz, 1H), 4.70-4.55 (m, 1H), 6.92 (d, J=8.0 Hz, 1H), 7.26 (d, J=8.4 Hz, 1H), 7.51 (t, J=8.4 Hz, 1H), 7.75 (dd, J=1.2, 6.0 Hz, 2H), 8.71 (dd, J=1.2, 6.0 Hz, 2H), 8.95 (d, J=8.0 Hz, 1H). MS 409 (MH+).

Example 27a: (S)-ethyl 4-amino-5-(2-(isonicotinamido)propoxy)-2-methylquinoline-3-carboxylate Prepared as in Example 24a from (S)-ethyl 4-amino-5-(2-aminopropoxy)-2-methyl-quinoline-3-carboxylate (Example 26b) and isonicotinic acid as brown solid (36%). MS 409 (MH+).

Example 28: (S)-4-amino-5-(2-(3-hydroxybenzamido)propoxy)-2-methylquinoline-3-carboxylic Acid

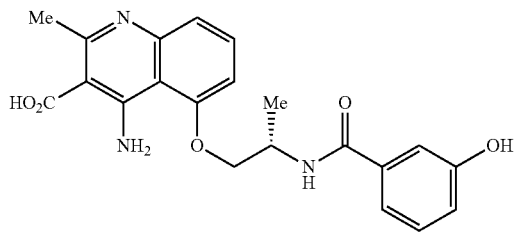 [SMILES: Cc1nc2cccc(OC[C@H](C)NC(=O)c3cccc(O)c3)c2c(N)c1C(=O)O]

Prepared as in Example 1 from (S)-ethyl 4-amino-5-(2-(3-hydroxybenzamido)propoxy)-2-methylquinoline-3-carboxylate (Example 28a) as a white solid (58%). $^1$H NMR (400 MHz, DMSO-$d_6$) δ 1.28 (d, J=7.2 Hz, 3H), 2.65 (s, 3H), 4.11 (t, J=8.8 Hz, 1H), 4.22 (dd, J=4.0, 10 Hz, 1H), 4.65-4.55 (m, 1H), 6.88 (d, J=8.0 Hz, 2H), 7.25-7.13 (m, 4H), 7.48 (t, J=8.0 Hz, 1H), 8.49 (d, J=8.0 Hz, 1H), 9.93 (brs, 1H). MS 396 (MH+).

Example 28a: (S)-ethyl 4-amino-5-(2-(3-hydroxybenzamido)propoxy)-2-methyl-quinoline-3-carboxylate Prepared as in Example 24a from (S)-ethyl 4-amino-5-(2-aminopropoxy)-2-methyl-quinoline-3-carboxylate (Example 26b) and 3-hydroxybenzoic acid as brown solid (41%). MS 424 (MH+).

Example 29: 4-amino-5-(3-(cyclopentylamino)-2,2-dimethyl-3-oxopropoxy)-2-methyl-quinoline-3-carboxylic Acid

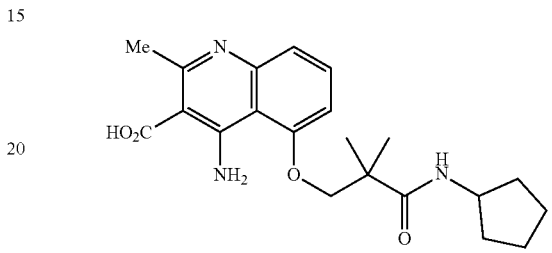

Prepared as in Example 1 from ethyl 4-amino-5-(3-(cyclopentylamino)-2,2-dimethyl-3-oxopropoxy)-2-methylquinoline-3-carboxylate (Example 29a) as a white powder (74%). $^1$H NMR (400 MHz, DMSO-$d_6$) δ 1.27 (s, 6H), 1.36-1.46 (m, 4H), 1.57-1.59 (m, 2H), 1.72-1.78 (m, 2H), 2.78 (s, 3H), 4.04 (m, 1H), 4.19 (s, 2H), 7.02 (d, J=8.0 Hz, 1H), 7.33 (d, J=8.0 Hz, 1H), 7.64-7.71 (m, 2H), 8.83 (brs, 1H), 12.25 (brs, 1H), 12.93 (brs, 1H). MS 386 (MH+).

Example 29a: ethyl 4-amino-5-(3-(cyclopentylamino)-2,2-dimethyl-3-oxopropoxy)-2-methylquinoline-3-carboxylate Prepared as in Example 2a from 3-(3-amino-2-cyanophenoxy)-N-cyclopentyl-2,2-dimethylpropanamide (Example 29b) and ethyl 3-oxobutanoate as a bright yellow solid (62%). $^1$H NMR (400 MHz, DMSO-$d_6$) δ 1.26 (s, 6H), 1.34 (t, J=8.0 Hz, 3H), 1.40-1.46 (m, 4H), 1.57-1.59 (m, 2H), 1.74-1.77 (m, 2H), 2.57 (s, 3H), 4.09 (q, J=4.0 Hz, 1H), 4.15 (s, 2H), 4.33 (q, J=8.0 Hz, 2H), 6.89 (d, J=4.0 Hz, 1H), 7.26 (dd, J=8.0 Hz, 1H), 7.53 (d, J=8.0 Hz, 1H), 7.56 (s, 1H), 8.09 (brs, 2H). MS 414 (MH+).

Example 29b: 3-(3-amino-2-cyanophenoxy)-N-cyclopentyl-2,2-dimethylpropanamide Prepared as in Example 22b from N-cyclopentyl-3-hydroxy-2,2-dimethylpropanamide (Example 29c) and 2-amino-6-fluorobenzonitrile as a white solid (45%). $^1$H NMR (400 MHz, DMSO-$d_6$) δ 1.19 (s, 6H), 1.40-1.49 (m, 4H), 1.61-1.63 (m, 2H), 1.74-1.79 (m, 2H), 3.95 (s, 2H), 4.03 (m, 1H), 5.98 (s, 2H), 6.19 (d, J=8.0 Hz, 1H), 6.33 (d, J=8.0 Hz, 1H), 7.17 (t, J=8.0 Hz, 1H), 7.23 (d, J=8.0 Hz, 1H). MS 302 (MH+).

Example 29c: N-cyclopentyl-3-hydroxy-2,2-dimethylpropanamide

Prepared as in Example 24a from hydroxypivalic acid and cyclopentyl amine as an orange oil (32%). $^1$H NMR (400 MHz, DMSO-$d_6$) δ 1.00 (s, 6H), 1.32-1.40 (m, 2H), 1.43-1.49 (m, 2H), 1.57-1.65 (m, 2H), 1.73-1.81 (m, 2H), 3.34 (d, J=4.0 Hz, 2H), 3.98 (m, 1H), 4.87 (t, J=4.0 Hz, 1H), 7.22 (d, J=4.0 Hz, 1H). MS 186 (MH+).

Example 30: 4-Amino-5-(cyclobutylmethoxy)-2-methylquinoline-3-carboxylic Acid

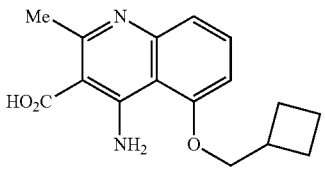 [SMILES: Cc1nc2cccc(OCC3CCC3)c2c(N)c1C(=O)O]

Prepared as in Example 1 from ethyl 4-amino-5-(cyclobutylmethoxy)-2-methylquinoline-3-carboxylate (Example 30a) as a white powder (51%). $^1$H NMR (400 MHz, DMSO-$d_6$) δ 1.84-1.99 (m, 4H), 2.10-2.15 (m, 2H), 2.77 (s, 3H), 2.92 (m, 1H), 4.23 (d, J=8.0 Hz, 2H), 7.05 (d, J=8.0 Hz, 1H), 7.29 (d, J=8.0 Hz, 1H), 7.68 (t, J=8.0 Hz, 1H), 8.71 (brs, 1H), 12.23 (brs, 1H), 12.81 (brs, 1H). MS 287 (MH+).

Example 30a: ethyl 4-amino-5-(cyclobutylmethoxy)-2-methylquinoline-3-carboxylate Prepared as in Example 2a from 2-amino-6-(cyclobutylmethoxy)benzonitrile (Tachdjian, C. et al. *PCT Int. Appl.* 2008, WO 2008154221) and ethyl 3-oxobutanoate as an orange solid (26%). $^1$H NMR (400 MHz, DMSO-$d_6$) δ 1.32 (t, J=8.0 Hz, 3H), 1.83-1.90 (m, 4H), 2.10-2.13 (m, 2H), 2.59 (s, 3H), 2.86 (m, 1H), 4.16 (d, J=4.0 Hz, 2H), 4.32 (q, J=8.0 Hz, 2H), 6.90 (d, J=8.0 Hz, 1H), 7.23 (d, J=8.0 Hz, 1H), 7.51 (t, J=8.0 Hz, 1H), 8.05 (brs, 2H). MS 315 (MH+).

Example 31: 4-amino-5-(2-(cyclopentanecarboxamido)-2-methylpropoxy)-2-methyl-quinoline-3-carboxylic Acid

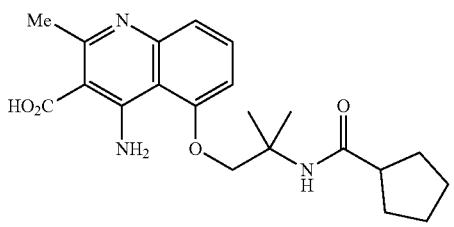 [SMILES: Cc1nc2cccc(OCC(C)(C)NC(=O)C3CCCC3)c2c(N)c1C(=O)O]

Prepared as in Example 1 from ethyl 4-amino-5-(2-(cyclopentanecarboxamido)-2-methylpropoxy)-2-methylquinoline-3-carboxylate (Example 31a) as an off-white solid (68%). $^1$H NMR (400 MHz, DMSO-$d_6$) δ 1.36 (s, 6H), 1.43-1.51 (m, 6H), 1.65-1.69 (m, 2H), 2.58 (m, 1H), 2.78 (m, 3H), 4.37 (s, 2H), 7.04 (m, 1H), 7.29 (d, J=8.0 Hz, 1H), 7.68 (m, 1H), 7.80 (s, 1H), 8.84 (brs, 1H), 12.42 (brs, 1H), 12.73 (brs, 1H). MS 386 (MH+).

Example 31a: ethyl 4-amino-5-(2-(cyclopentanecarboxamido)-2-methylpropoxy)-2-methylquinoline-3-carboxylate Prepared as in Example 24a from ethyl 4-amino-5-(2-amino-2-methylpropoxy)-2-methyl-quinoline-3-carboxylate (Example 24b) and cyclopentane carboxylic acid as a yellow solid (33%). $^1$H NMR (400 MHz, DMSO-$d_6$) δ 1.34 (t, J=4.0 Hz, 3H), 1.37 (s, 6H), 1.42-1.53 (m, 6H), 1.64-1.69 (m, 2H), 2.58 (m, 1H), 2.62 (s, 3H), 4.32 (s, 2H), 4.35 (m, 2H), 6.96 (m, 1H), 7.28 (d, J=8.0 Hz, 1H), 7.58 (m, 1H), 7.66 (s, 1H), 8.41 (d, 2H). MS 414 (MH+).

Example 32: 4-Amino-5-(cycloheptyloxy)-2-methylquinoline-3-carboxylic Acid

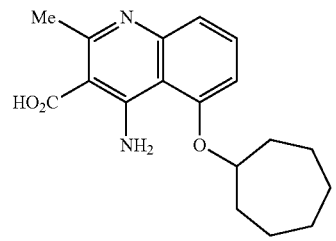 [SMILES: Cc1nc2cccc(OC3CCCCCC3)c2c(N)c1C(=O)O]

Prepared as in Example 1 from ethyl 4-amino-5-(cycloheptyloxy)-2-methylquinoline-3-carboxylate (Example 32a) as a light yellow solid (34%). $^1$H NMR (400 MHz, DMSO-$d_6$) δ 1.49-1.65 (m, 8H), 1.83-1.89 (m, 2H), 2.04-2.09 (m, 2H), 2.74 (s, 3H), 4.85 (m, 1H), 7.03 (d, J=8.0 Hz, 1H), 7.23 (d, J=8.0 Hz, 1H), 7.65 (t, J=8.0 Hz, 1H), 8.82 (brs, 1H), 12.24 (brs, 1H), 12.64 (brs, 1H). MS 315 (MH+).

Example 32a: ethyl 4-amino-5-(cycloheptyloxy)-2-methylquinoline-3-carboxylate Prepared as in Example 2a from 2-amino-6-(cycloheptyloxy)benzonitrile (Example 32b) and ethyl 3-oxobutanoate as a bright yellow solid (72%). $^1$H NMR (400 MHz, DMSO-$d_6$) δ 1.32 (t, J=8.0 Hz, 3H), 1.49-1.65 (m, 8H), 1.78-1.87 (m, 2H), 2.04-2.10 (m, 2H), 2.53 (s, 3H). 4.31 (q, J=8.0 Hz, 2H), 4.79 (m, 1H), 6.89 (d, J=8.0 Hz, 1H), 7.20 (d, J=8.0 Hz, 1H), 7.49 (t, J=8.0 Hz, 1H), 8.14 (brs, 2H). MS 343 (MH+).

Example 32b: 2-amino-6-(cycloheptyloxy)benzonitrile

Prepared as in Example 22b from cycloheptanol and 2-amino-6-fluorobenzonitrile as yellow oil (11%). $^1$H NMR (400 MHz, DMSO-$d_6$) δ 1.42-1.71 (m, 10H), 1.88-1.93 (m, 2H), 4.56 (m, 1H), 5.95 (s, 2H), 6.20 (d, J=8.0 Hz, 1H), 6.30 (d, J=8.0 Hz, 1H), 7.15 (t, J=8.0 Hz, 1H). MS 231 (MH+).

Example 33: 4-Amino-2-methyl-5-(3-phenoxypropoxy)quinoline-3-carboxylic Acid

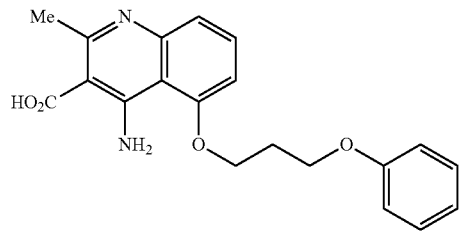 [SMILES: Cc1nc2cccc(OCCCOc3ccccc3)c2c(N)c1C(=O)O]

Prepared as in Example 1 from ethyl 4-amino-2-methyl-5-(3-phenoxypropoxy)quinoline-3-carboxylate (Example 33a) as a yellow solid (90%). $^1$H NMR (400 MHz, DMSO-d$_6$) δ 2.35 (m, 2H), 2.77 (s, 3H), 4.19 (t, J=4.0 Hz, 2H), 4.42 (t, J=4.0 Hz, 2H), 6.91-6.96 (m, 3H), 7.09 (d, J=8.0 Hz, 1H), 7.26-7.30 (m, 3H), 7.70 (t, J=8.0 Hz, 1H), 8.96 (brs, 1H), 12.24 (brs, 1H), 12.75 (brs, 1H). MS 353 (MH$^+$).

Example 33a: ethyl 4-amino-2-methyl-5-(3-phenoxypropoxy)quinoline-3-carboxylate

Prepared as in Example 2a from 2-amino-6-(3-phenoxypropoxy)benzonitrile (Example 33b) and ethyl 3-oxobutanoate as a yellow solid (47%). $^1$H NMR (400 MHz, DMSO-d$_6$) δ 1.33 (t, J=8.0 Hz, 3H), 2.34 (m, 2H), 2.57 (s, 3H), 4.19 (t, J=4.0 Hz, 2H), 4.33 (q, J=8.0 Hz, 2H), 4.37 (t, J=4.0 Hz, 2H), 6.91-6.97 (m, 4H), 7.24-7.29 (m, 3H), 7.53 (t, J=8.0 Hz, 1H), 8.17 (s, 2H). MS 381 (MH$^+$).

Example 33b: 2-amino-6-(3-phenoxypropoxy)benzonitrile

Prepared as in Example 22b from 3-phenoxy-1-propanol and 2-amino-6-fluorobenzonitrile as a yellow oil (93%). $^1$H NMR (400 MHz, DMSO-d$_6$) δ 2.14 (m, 2H), 4.10-4.16 (m, 4H), 5.98 (s, 2H), 6.23 (d, J=8.0 Hz, 1H), 6.33 (d, J=8.0 Hz, 1H), 6.89-6.94 (m, 5H), 7.16 (t, J=8.0 Hz, 1H).

Example 34: 44-Amino-5-((1-(3-hydroxybenzoyl)piperidin-4-yl)methoxy)-2-methyl-quinoline-3-carboxylic Acid

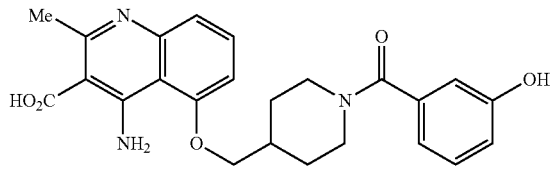 [SMILES: Cc1nc2cccc(OCC3CCN(C(=O)c4cccc(O)c4)CC3)c2c(N)c1C(=O)O]

Prepared as in Example 1 from ethyl 4-amino-5-((1-(3-hydroxybenzoyl)piperidin-4-yl)methoxy)-2-methylquinoline-3-carboxylate (Example 34a) as an orange powder (23%). $^1$H NMR (400 MHz, DMSO-d$_6$) δ 1.24 (brs, 2H), 1.79-1.88 (m, 2H), 2.29 (m, 1H), 2.77 (s, 3H), 3.07 (brs, 2H), 3.65 (brs, 1H), 4.17 (d, J=8.0 Hz, 2H), 4.50 (brs, 1H), 6.74-6.83 (m, 3H), 7.07 (d, J=8.0 Hz, 1H), 7.23 (t, J=8.0 Hz, 1H), 7.29 (d, J=8.0 Hz, 1H), 7.69 (t, J=8.0 Hz, 1H), 8.74 (brs, 1H), 9.75 (s, 1H), 12.25 (brs, 1H), 12.71 (brs, 1H). MS 436 (MH$^+$).

Example 34a: ethyl 4-amino-5-((1-(3-hydroxybenzoyl)piperidin-4-yl)methoxy)-2-methylquinoline-3-carboxylate Prepared as in Example 2a from 2-amino-6-((1-(3-hydroxybenzoyl)piperidin-4-yl)methoxy)benzonitrile (Example 34b) and ethyl 3-oxobutanoate as a yellow solid (49%). $^1$H NMR (400 MHz, DMSO-d$_6$) δ 1.24 (m, 2H), 1.31 (t, J=4.0 Hz, 3H), 1.77-1.89 (m, 2H), 2.22 (brs, 1H), 2.55 (s, 3H), 2.79 (brs, 1H), 3.04 (brs, 1H), 3.64 (brs, 1H), 4.10 (m, 2H), 4.32 (q, J=8.0 Hz, 2H), 4.49 (brs, 1H), 6.71-6.82 (m, 3H), 6.93 (d, J=8.0 Hz, 1H), 7.19-7.25 (m, 2H), 7.52 (t, J=8.0 Hz, 1H), 8.06 (brs, 2H), 9.64 (s, 1H). MS 464 (MH$^+$).

Example 34b: 2-amino-6-((1-(3-hydroxybenzoyl)piperidin-4-yl)methoxy)benzonitrile Prepared as in Example 24a from 2-amino-6-(piperidin-4-ylmethoxy)benzonitrile (Example 34c) and 3-hydroxy-benzoic acid as an orange glass (66%). $^1$H NMR (400 MHz, DMSO-d$_6$) δ 1.29 (m, 2H), 1.66-1.92 (m, 2H), 2.06 (m, 1H), 2.80 (brs, 1H), 3.05 (brs, 1H), 3.62 (brs, 1H), 3.91 (d, J=8.0 Hz, 2H), 4.49 (brs, 1H), 5.99 (s, 2H), 6.22 (d, J=8.0 Hz, 1H), 6.34 (d, J=8.0 Hz, 1H), 6.72-6.83 (m, 3H), 7.15-7.24 (m, 2H), 9.65 (s, 1H). MS 352 (MH$^+$).

Example 34c: 2-amino-6-(piperidin-4-ylmethoxy)benzonitrile

To a solution of tert-butyl 4-((3-amino-2-cyanophenoxy)methyl)piperidine-1-carboxylate (Example 34d, 1.33 g, 4.0 mmol) in EtOAc (20 mL) was added dropwise aqueous HCl solution (12 N, 6.6 mL) at 0° C. The reaction mixture was stirred at room temperature overnight. The solvent was removed under reduced pressure to give the title compound (100%) as a brown solid, which is pure enough and used directly in the next step without further purification. MS 232 (MH$^+$).

Example 34d: 2 tert-butyl 4-((3-amino-2-cyanophenoxy)methyl)piperidine-1-carboxylate Prepared as in Example 22b from N-Boc-4-piperidinemethanol and 2-amino-6-fluoro-benzonitrile as an off-white solid (37%). $^1$H NMR (400 MHz, DMSO-d$_6$) δ 1.15-1.21 (m, 2H), 1.40 (s, 9H), 1.74 (m, 2H), 1.99 (brs, 1H), 2.74 (brs, 2H), 3.87 (d, J=4.0 Hz, 2H), 3.96 (m, 2H), 5.99 (s, 2H), 6.21 (d, J=8.0 Hz, 1H), 6.33 (d, J=8.0 Hz, 1H), 7.17 (t, J=8.0 Hz, 1H). MS 232 (MH$^+$-Boc).

Example 35: 4-Amino-5-((1-butyrylpiperidin-4-yl)methoxy)-2-methylquinoline-3-carboxylic Acid

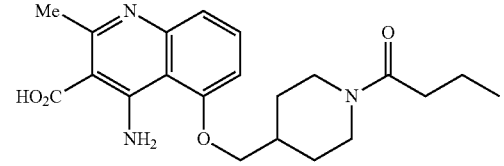 [SMILES: CCCC(=O)N1CCC(COc2cccc3nc(C)c(C(=O)O)c(N)c23)CC1]

Prepared as in Example 1 ethyl 4-amino-5-((1-butyrylpiperidin-4-yl)methoxy)-2-methylquinoline-3-carboxylate (Example 35a) as a white solid (61%). $^1$H NMR (400 MHz, DMSO-d$_6$) δ 0.87 (t, J=8.0 Hz, 3H), 1.05-1.22 (m, 2H), 1.50 (m, 2H), 1.80 (m, 2H), 2.24-2.31 (m, 3H), 2.65 (s, 3H), 3.02 (2H), 3.88-3.92 (m, 1H), 4.11 (m, 2H), 4.44 (m, 1H), 7.05 (m, 1H), 7.26 (d, J=8.0 Hz, 1H), 7.69 (m, 1H), 8.76 (brs, 1H), 12.33 (brs, 1H), 12.65 (brs, 1H). MS 386 (MH$^+$).

Example 35a: ethyl 4-amino-5-((1-butyrylpiperidin-4-yl)methoxy)-2-methylquinoline-3-carboxylate Prepared as in Example 24a from ethyl 4-amino-2-methyl-5-(piperidin-4-ylmethoxy)-quinoline-3-carboxylate (Example 35b) and butyric acid as a yellow oil (50%). MS 414 (MH$^+$).

Example 35b: ethyl 4-amino-2-methyl-5-(piperidin-4-ylmethoxy)quinoline-3-carboxylate Prepared as in Example 2a from benzyl 4-((3-amino-2-cyanophenoxy)methyl)piperidine-1-carboxylate (Example 35c) and ethyl 3-oxobutanoate as an orange solid (25%). $^1$H NMR (400 MHz, DMSO-d$_6$) δ 1.29-1.37 (m, 5H), 1.77-1.80

(m, 2H), 2.07 (brs, 1H), 2.53 (s, 3H), 2.55-2.65 (m, 3H), 3.06-3.09 (m, 2H), 4.06 (d, J=8.0 Hz, 2H), 4.32 (q, J=8.0 Hz, 2H), 6.92 (d, J=8.0 Hz, 1H), 7.24 (d, J=8.0 Hz, 1H), 7.51 (t, J=8.0 Hz, 1H), 8.08 (s, 2H). MS 344 (MH$^+$).

Example 35c: 4-((3-amino-2-cyanophenoxy)methyl)piperidine-1-carboxylate

Prepared as in Example 22b from 1-N-Cbz-4-(hydroxymethyl)piperidine and 2-amino-6-fluoro-benzonitrile as a yellow oil (18%). $^1$H NMR (400 MHz, DMSO-d$_6$) δ 1.20-1.25 (m, 2H), 1.75-1.78 (m, 2H), 1.96 (brs, 1H), 3.88 (d, J=8.0 Hz, 2H), 3.99-4.04 (m, 4H), 5.07 (s, 2H), 5.99 (s, 2H), 6.21 (d, J=8.0 Hz, 1H), 6.34 (d, J=8.0 Hz, 1H), 7.17 (t, J=8.0 Hz, 1H), 7.29-7.40 (m, 5H). MS 366 (MH$^+$).

Example 36: 4-amino-5-(cyclohexyloxy)-2-methylquinoline-3-carboxylic Acid

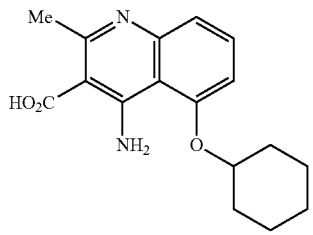 [SMILES: Cc1nc2cccc(OC3CCCCC3)c2c(N)c1C(=O)O]

To a solution of ethyl 4-amino-5-(cyclohexyloxy)-2-methylquinoline-3-carboxylate (Example 36a, 110 g, 0.335 mol) in EtOH (450 mL) was added a solution of NaOH (33.5 g, 0.837 mol) in water (200 mL) at room temperature. The reaction mixture was then refluxed overnight. The reaction solution was cooled down to 0° C. and carefully neutralized with 4N HCl to pH 7. The resultant solution was concentrated under reduced pressure to remove most of the EtOH. The precipitate was collected by filtration, and re-dissolved in EtOH (4 L) at 65° C. and treated with activated charcoal (5 g) for 0.5 h. The charcoal was removed by filtration over celite, and the filtrate was concentrated. The precipitate was collected by filtration, washed with cold water, and dried under vacuum at 60° C. overnight to give the title compound as a white solid (100 g, 99%). M.p.: 220.0-221.5° C. $^1$H NMR (400 MHz, DMSO-d$_6$) δ 1.28-1.72 (m, 8H), 2.00-2.04 (m, 2H), 2.75 (s, 3H), 4.69-4.71 (m, 1H), 7.10-7.12 (d, J=8.0 Hz, 1H), 7.24-7.26 (d, J=8.0 Hz, 1H), 7.65 (t, J=8.0 Hz, 1H), 12.80 (brs, 1H). MS 301 (MH$^+$). Elemental Analysis Calculated (Found) for C$_{17}$H$_{20}$N$_2$O$_3$: C, 67.98% (67.74%); H, 6.71% (7.01%); N, 9.33% (9.40%).

Example 36a: ethyl 4-amino-5-(cyclohexyloxy)-2-methylquinoline-3-carboxylate

A solution of ethyl 3-oxobutanoate (29.9 g, 0.230 mol) in anhydrous toluene (200 mL) was added to a solution of 2-amino-6-(cyclohexyloxy)benzonitrile (Example 36b, 49.8 g, 0.230 mol) in anhydrous toluene (1000 mL) under nitrogen in a 3 L round bottom flask sitting in an oil bath at room temperature. SnCl$_4$ (53.9 mL, 0.461 mol) was added slowly over a period of approximately 1 h. The oil bath temperature was then raised to 110° C. and the reaction mixture was stirred at that temperature for 2.5 h. It was then cooled down to 5° C., still under nitrogen, and the toluene was decanted away from the immiscible viscous oil at the bottom of the flask. The viscous oil was further concentrated under vacuum at 60° C., re-dissolved in boiling ethyl acetate (1 L), and transferred to a 4 liter Erlenmeyer flask. The solution was diluted with more EtOAc (1.5 L), cooled down to −15° C., and neutralized with NaOH (3 N, 500 mL). The organic layer was separated, and the aqueous emulsion was extracted once more with ethyl acetate. The insoluble tin salts were filtered out from the aqueous layer, then both the salts and aqueous filtrate were washed once more with ethyl acetate. The combined organic layers were dried over MgSO$_4$, concentrated, and passed through a silica column using 0% to 60% ethyl acetate in hexanes. The product was purified by recrystallization from EtOAc to give the title compound as an off-white solid (64.3 g, 85%). $^1$H NMR (400 MHz, DMSO-d$_6$) δ 1.28-1.34 (m, 1H), 1.32 (t, 3H), 1.37-1.45 (m, 2H), 1.51-1.63 (m, 3H), 1.67-1.71 (m, 2H), 1.99-2.03 (m, 2H), 2.54 (s, 3H), 4.28-4.33 (q, J=6.8 Hz, 2H), 4.64 (m, 1H), 6.95-6.97 (d, J=7.6 Hz, 1H), 7.19-7.21 (d, J=8.4 Hz, 1H), 7.65 (t, J=8.4 Hz, 1H), 8.15 (brs, 2H). MS 329 (MH$^+$).

Example 36b: 2-amino-6-(cyclohexyloxy)benzonitrile

To a solution of cyclohexanol (19.1 g, 0.191 mol) in anhydrous THF (500 mL) was added NaH (7.6 g, 40% in mineral oil, 0.191 mol) in small portions at 0° C. under nitrogen. The mixture was stirred at room temperature for 1 h and a solution of 2-amino-6-fluorobenzonitrile (20.0 g, 0.15 mol) in anhydrous THF (150 mL) was added drop-wise at room temperature. The reaction mixture was heated to reflux overnight then cooled to room temperature and most of the THF removed under reduced pressure. Ice water (100 mL) was added to the concentrated reaction mixture followed by EtOAc (500 mL). The organic layer was separated and successively washed with water and brine, dried over Na$_2$SO$_4$, filtered and evaporated under reduced pressure. The residue was purified by chromatography on silica gel eluting with 25-30% EtOAc in hexanes to give 2-amino-6-(cyclohexyloxy)benzonitrile as a light yellow oil (17.9 g, 56%). $^1$H NMR (400 MHz, CDCl$_3$) δ 1.32-1.43 (m, 3H), 1.51-1.55 (m, 1H), 1.62-1.69 (m, 2H), 1.79-1.95 (m, 4H), 4.31-4.36 (m, 3H), 6.23-6.27 (m, 2H), 7.18 (d, J=8.0 Hz, 1H). MS 329 (MH$^+$).

Example 36b: 2-amino-6-(cyclohexyloxy)benzonitrile

Alternative Method a):
To a solution of 2-(cyclohexyloxy)-6-nitrobenzonitrile (Example 36c, 50.0 g, 0.20 mol) in THF/AcOH (1:1 by volume, 500 mL) was added iron powder (34.0 g, 0.61 mol) in one portion at room temperature under nitrogen. The reaction mixture was refluxed for 40 min under nitrogen and cooled down to room temperature and EtOAc (2 L) was added. The precipitate that formed was filtered off and washed with EtOAc. The organic layer was separated and washed successively with water (2×300 mL), aqueous NaOH (1.0 N, 2×300 mL), saturated Na$_2$CO$_3$ solution (300 mL), brine (300 mL), dried over Na$_2$SO$_4$ filtered and evaporated under reduced pressure. The residue was purified by chromatography on silica gel eluting with 25% EtOAc in hexanes to give 2-amino-6-(cyclohexyloxy)benzonitrile as a pale yellow oil (45.0 g, 94%), which solidified after storage overnight at room temperature.

Alternative Method b):
A 3-L 3-neck round bottom flask was first purged with nitrogen. 10% Pd/C (2.81 g) was then added under nitrogen, followed successively by 2-(cyclohexyloxy)-6-nitrobenzonitrile (Example 36c, 43.2 g, 0.175 mol), anhydrous methanol (389 mL), and acetic acid (80.4 mL). A reflux condenser, a dropping funnel containing a solution of ammonium formate (49.8 g, 0.790 mol) in anhydrous methanol (498 mL), thermometer, nitrogen inlet and nitrogen outlet were attached. Ammonium formate solution (75 mL) was added at room temperature, then the reaction was slowly heated to a maximum of 42° C. The mixture was monitored carefully until initiation of the reaction was observed (an evolution of gas occurred with roughly a 10° C. exotherm). Initiation of the reaction often took up to 40 minutes before starting. The remaining of the ammonium formate solution was then added at a rate which maintained an internal reaction temperature of 40° C. to 48° C. After the addition was complete, the reaction mixture was stirred for another 10 minutes at 45° C., then cooled down to room temperature. The Pd/C was filtered out using a Teflon filter, and the solvent was evaporated. Ice water (1 L) was added to the residue, then the water was decanted and discarded. The residue was dissolved in diethyl ether, washed with water, then saturated sodium bicarbonate solution, then dried with magnesium sulfate and concentrated. The product was then purified on silica gel using isocratic DCM to give the product as a yellow oil (31.5 g, 83%).

Example 36c: 2-(cyclohexyloxy)-6-nitrobenzonitrile

To a solution of cyclohexanol (46.8 grams, 0.467 mol) in anhydrous THF (1 L) was added sodium hydride (20.3 grams, 0.508 mol) at −40° C. under nitrogen. The reaction mixture was allowed to warm slowly to room temperature and stir for another 1 hour. It was then cooled down to −55° C. and 2,6-dinitrobenzonitrile (78.4 g, 0.406 mol) was added. The reaction was stirred at room temperature overnight, then cooled down to −20° C., and citric acid (23.4 grams, 0.122 mol) was added. The mixture was then poured into ice water (5 L) which contained citric acid (7.8 g, 0.041 mol), stirred for 15 minutes, and the precipitated product was collected by filtration. The crude product was recrystallized from isopropanol (750 mL, heated to boiling, then cooled down to 0° C.), filtered, washed with isopropanol (300 mL), then air dried to give 84.4 g yellow solid. The solid was dissolved in dichloromethane (169 mL) and filtered through a plug of alumina to give the title compound as a pale yellow solid (83.2 g, 83.2%). $^1$H NMR (400 MHz, DMSO-$d_6$) δ 1.4 (m, 4H), 1.6 (m, 2H), 1.7 (m, 2H), 1.9 (m, 2H), 4.75 (m, 1H), 7.79 (dd, J=2.0, 8.0 Hz, 1H), 7.84-7.91 (m, 2H).

Example 37: 4-amino-5-(2-(cyclohexanecarboxamido)-2-methylpropoxy)-2-methyl-quinoline-3-carboxylic Acid

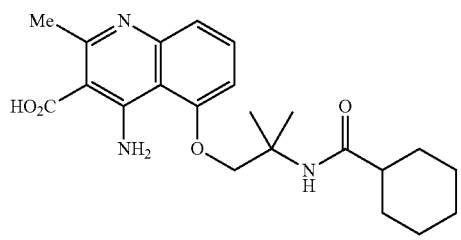 [SMILES: Cc1nc2cccc(OCC(C)(C)NC(=O)C3CCCCC3)c2c(N)c1C(=O)O]

Prepared as in Example 1 from ethyl 4-amino-5-(2-(cyclohexanecarboxamido)-2-methylpropoxy)-2-methylquinoline-3-carboxylate (Example 37a) as a white powder (78%). $^1$H NMR (400 MHz, DMSO-$d_6$) δ 1.11-1.22 (m, 5H), 1.33 (s, 6H), 1.56-1.62 (m, 5H), 2.14 (m, 1H), 2.78 (s, 3H), 4.34 (s, 2H), 7.01 (d, J=8.4 Hz, 1H), 7.30 (d, J=8.4 Hz, 1H), 7.66 (t, J=8.4 Hz, 1H), 7.74 (s, 1H). MS 400 (MH$^+$).

Example 37a: ethyl 4-amino-5-(2-(cyclohexanecarboxamido)-2-methylpropoxy)-2-methylquinoline-3-carboxylate Prepared as in Example 2a from N-(1-(3-amino-2-cyanophenoxy)-2-methylpropan-2-yl)cyclohexanecarboxamide (Example 37b) and ethyl 3-oxobutanoate as a bright yellow solid (55%). MS 428 (MH$^+$).

Example 37b: N-(1-(3-amino-2-cyanophenoxy)-2-methylpropan-2-yl)cyclohexanecarboxamide Prepared as in Example 22b from N-(1-hydroxy-2-methylpropan-2-yl)cyclohexanecarboxamide (Example 37c) and 2-amino-6-fluorobenzonitrile as an off-white solid (29%). MS 316 (MH$^+$).

Example 37c: N-(1-hydroxy-2-methylpropan-2-yl)cyclohexanecarboxamide

Prepared as in Example 24a from cyclohexanecarboxylic acid and 2-amino-2-methylpropan-1-ol as a colorless oil (15%). MS 200 (MH$^+$).

Example 38: 4-amino-5-(2-(3-(2-hydroxyethoxy)-5-methoxybenzamido)-2-methylpropoxy)-2-methylquinoline-3-carboxylic Acid

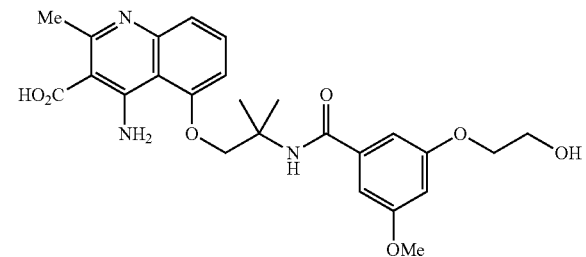 [SMILES: COc1cc(OCCO)cc(C(=O)NC(C)(C)COc2cccc3nc(C)c(C(=O)O)c(N)c23)c1]

To a solution of 4-amino-5-(2-(3-(2-(benzyloxy)ethoxy)-5-methoxybenzamido)-2-methy-propoxy)-2-methylquinoline-3-carboxylic acid (Example 38a, 237 mg, 0.5 mmol) in EtOH/EtOAc (1:1, 20 mL) was added 10% Pd/C (wet, 50 mg). The suspension was then stirred under an atmosphere of hydrogen at room temperature overnight. The Pd/C was filtered off, and the filtrate was concentrated. The residue was purified by HPLC (eluent: 10-100% MeOH in $H_2O$) to give the title compound as an off-white solid (152 mg, 63%). $^1$H NMR (400 MHz, DMSO-$d_6$) δ 1.49 (s, 6H), 2.75 (s, 3H), 3.68 (t, J=5.2 Hz, 2H), 3.73 (s, 3H), 3.99 (t, J=5.2 Hz, 1H), 4.47 (s, 2H), 6.57 (s, 1H), 6.88 (s, 1H), 6.96 (s, 1H), 7.06 (d, J=7.6 Hz, 1H), 7.28 (d, J=8 Hz, 1H), 7.67 (t, J=8 Hz, 1H), 8.14 (s, 1H). MS 484 (MH$^+$).

Example 38a: 4-amino-5-(2-(3-(2-(benzyloxy)ethoxy)-5-methoxybenzamido)-2-methylpropoxy)-2-methylquinoline-3-carboxylic Acid Prepared as in Example 1 from ethyl 4-amino-5-(2-(3-(2-hydroxyethoxy)-5-methoxy-benzamido)-2-methylpropoxy)-2-methylquinoline-3-carboxylate (Example 38b) as a white powder (95%). MS 574 (MH$^+$).

Example 38b: ethyl 4-amino-5-(2-(3-(2-hydroxy-ethoxy)-5-methoxy-benzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(2-(benzyloxy)ethoxy)-5-methoxybenzoic acid (Example 39c) as a pale-brown solid (90%). MS 602 (MH$^+$).

Example 38c: 3-(2-(benzyloxy)ethoxy)-5-methoxybenzoic

Prepared as in Example 1 from methyl 3-(2-(benzyloxy)ethoxy)-5-methoxybenzoate (Example 38d) as a white solid (64%). $^1$H NMR (400 MHz, DMSO-d$_6$) δ 3.83 (s, 3H), 3.84 (t, J=4.8 Hz, 2H), 4.18 (t, J=4.8 Hz, 2H), 4.65 (s, 2H), 6.74 (s, 1H), 7.25-7.37 (m, 7H).

Example 38d: methyl 3-(2-(benzyloxy)ethoxy)-5-methoxybenzoate

To a solution of methyl 3-hydroxy-5-methoxybenzoate (Chakraporty, T. K. and Reddy, G. V. *J. Org. Chem*, 57, 1992, 5462) (3.3 g, 18.1 mmol) in dry DMF (30 mL) was added K$_2$CO$_3$ (6.3 g, 45.3 mmol) at room temperature. The reaction was stirred at room temperature for 10 minutes then ((2-bromoethoxy)methyl)benzene (3.4 mL, 21.7 mmol) was added and the mixture stirred at 160° C. for 2 hrs. The reaction was cooled down to room temperature and diluted with EtOAc, washed with water and brine, and dried over MgSO$_4$, filtered and concentrated to give the crude product (90%) which was used in the next step without further purification.

Example 39: 4-amino-5-((2-isobutyramidocyclohexyl)oxy)-2-methylquinoline-3-carboxylic Acid

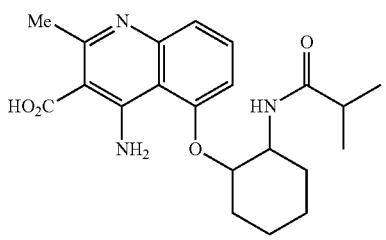 [SMILES: Cc1nc2cccc(OC3CCCCC3NC(=O)C(C)C)c2c(N)c1C(=O)O]

Prepared as in Example 1 from ethyl 4-amino-5-((2-isobutyramidocyclohexyl)oxy)-2-methylquinoline-3-carboxylate (Example 39a) as a white powder (90%). $^1$H NMR (400 MHz, DMSO-d$_6$) δ 0.83 (d, J=6.4 Hz, 3H), 0.93 (d, J=6.4 Hz, 3H), 1.42 (m, 3H), 1.65 (m, 4H), 1.96 (m, 1H), 2.40 (m, 1H), 2.76 (s, 3H), 4.13 (m, 1H), 4.99 (m, 1H), 7.07 (d, J=8.4 Hz, 1H), 7.25 (d, J=8.4 Hz, 1H), 7.63 (t, J=8 hz, 1H), 7.93 (d, J=7.6 Hz, 1H). MS 386 (MH$^+$).

Example 39a: ethyl 4-amino-5-((2-isobutyramidocyclohexyl)oxy)-2-methylquinoline-3-carboxylate Prepared as in Example 2a from N-(2-(3-amino-2-cyanophenoxy)cyclohexyl)isobutyramide (Example 39b) and ethyl 3-oxobutanoate as a yellow solid (63%). MS 414 (MH$^+$).

Example 39b: N-(2-(3-amino-2-cyanophenoxy)cyclohexyl)isobutyramide

Prepared as in Example 22b from N-(2-hydroxycyclohexyl)isobutyramide (Example 39c) and 2-amino-6-fluorobenzonitrile as a brown solid (70%). MS 302 (MH$^+$).

Example 39c: N-(2-hydroxycyclohexyl)isobutyramide

Prepared as in Example 24a from isobutyric acid and 2-aminocyclohexanol as a colorless oil (53%). MS 186 (MH$^+$).

Example 40: 4-amino-5-((4-isobutyramidocyclohexyl)oxy)-2-methylquinoline-3-carboxylic Acid

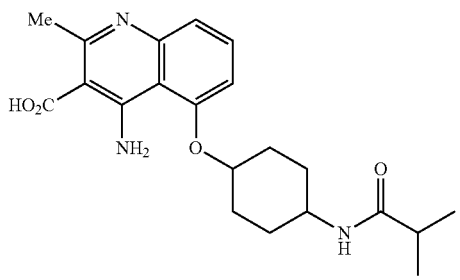 [SMILES: Cc1nc2cccc(OC3CCC(NC(=O)C(C)C)CC3)c2c(N)c1C(=O)O]

Prepared as in Example 1 from ethyl 4-amino-5-((4-isobutyramidocyclohexyl)oxy)-2-methylquinoline-3-carboxylate (Example 40a) as a white powder (87%). $^1$H NMR (400 MHz, DMSO-d$_6$) δ 0.97 (d, J=7.2 Hz, 6H), 1.34-1.37 (m, 2H), 1.65-1.68 (m, 2H), 1.81-1.84 (m, 2H), 2.13-2.16 (m, 2H), 2.33 (m, 1H), 2.75 (s, 3H), 3.58 (m, 1H), 4.84 (m, 1H), 7.15 (d, J=8.4 Hz, 1H), 7.23 (d, J=8 Hz, 1H), 7.65 (d, J=7.6 Hz, 2H). MS 386 (MH$^+$).

Example 40a: ethyl 4-amino-5-((4-isobutyramidocyclohexyl)oxy)-2-methylquinoline-3-carboxylate Prepared as in Example 2a from N-(4-(3-amino-2-cyanophenoxy)cyclohexyl)isobutyramide (Example 40b) and ethyl 3-oxobutanoate as a yellow solid (57%). MS 414 (MH$^+$).

Example 40b: N-(4-(3-amino-2-cyanophenoxy)cyclohexyl)isobutyramide

Prepared as in Example 22b from N-(4-hydroxycyclohexyl)isobutyramide (Example 40c) and 2-amino-6-fluorobenzonitrile as an off-white solid (99%). MS 302 (MH$^+$).

Example 40c: N-(4-hydroxycyclohexyl)isobutyramide

Prepared as in Example 24a from isobutyric acid and 4-aminocyclohexanol as a colorless oil (44%). MS 186 (MH$^+$).

Example 41: 4-amino-5-isobutoxy-2-methylquinoline-3-carboxylic Acid

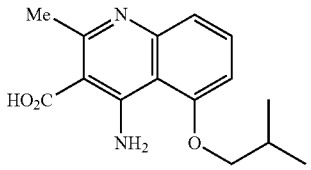 [SMILES: Cc1nc2cccc(OCC(C)C)c2c(N)c1C(=O)O]

To a solution of ethyl 4-amino-5-isobutoxy-2-methylquinoline-3-carboxylate (Example 41a, 18.0 g, 59.53 mmol) in EtOH (150 mL) was added aqueous NaOH solution (3 N, 50 mL) and the reaction mixture was refluxed overnight. It was then cooled down to room temperature and the solution was filtered to remove any possible solid residue. The filtrate was carefully neutralized with 6N HCl to pH 7 at 0° C. The resultant precipitate was collected by filtration, washed with water, re-dissolved in EtOH (700 mL) and water (20 mL), and treated with activated charcoal (650 mg) at 70° C. for 0.5 h. The charcoal was removed by filtration, and the filtrate was concentrated and stored at 4° C. overnight. The resulting precipitate was collected by filtration, washed with cold $H_2O$, and dried under vacuum at 60° C. overnight to give the title compound as a white solid (4.24 g, 26%). M.p.: 203.7° C. $^1$H NMR (400 MHz, DMSO-$d_6$) δ 1.01-1.02 (m, 6H), 2.19-2.24 (m, 1H), 2.77 (s, 3H), 4.05 (d, J=6.4 Hz, 2H), 7.08 (d, J=8.0 Hz, 1H), 7.33 (d, J=8.0 Hz, 1H), 7.71 (t, J=8.0 Hz, 1H), 8.9 (brs, 1H), 11.45 (brs, 1H), 13.2 (brs, 1H). MS 275 (MH$^+$). Elemental Analysis Calculated (Found) for $C_{15}H_{18}N_2O_3 \cdot 0.75H_2O$: C, 62.59% (62.23%); H, 6.83% (7.25%); N, 9.76% (9.73%).

Example 41a: ethyl 4-amino-5-isobutoxy-2-methylquinoline-3-carboxylate

To a solution of 2-amino-6-isobutoxybenzonitrile (Example 41b, 16.4 g, 86.32 mmol) and ethyl acetoacetate (10.9 mL, 86.32 mmol) in anhydrous toluene (200 mL) was added SnCl$_4$ (19.9 mL, 172.63 mmol) over a period of 15 minutes at room temperature under nitrogen. The stirred reaction mixture was then refluxed for 3.5 h under nitrogen. After it was cooled down to room temperature, the reaction solution was concentrated to remove most of the solvent under reduced pressure. The residue was re-dissolved in EtOAc (3 L) and carefully neutralized to pH 8 with aqueous NaOH solution (6.0 N, ~110 mL) at 0° C. The resultant mixture was stirred at room temperature overnight. The precipitate was filtered off, and the organic layer was separated and washed with brine (400 mL), dried over Na$_2$SO$_4$ and concentrated under reduced pressure. The residue was purified by column chromatography on silica gel eluting with 50% EtOAc in hexanes to give the title compound as a white solid (18.0 g, 69%). MS 303 (MH$^+$).

Example 41b: 2-amino-6-isobutoxybenzonitrile

To a solution of 2-isobutoxy-6-nitrobenzonitrile (Example 41c, 34.3 g, 0.156 mol) in AcOH/THF (1:1 by volume, 250 mL) was added iron powder (17.36 g, 0.311 mol) in one portion. The stirred suspension was heated to reflux for 30 minutes. After it was cooled down to room temperature, the reaction solution was diluted with EtOAc (1 L). The solid was removed by filtration, and the filtrate was washed subsequently with water (300 mL×2), 1N NaOH (300 mL), saturated Na$_2$CO$_3$ aqueous solution (300 mL), brine (300 mL), and dried over Na$_2$SO$_4$. After evaporation of the solvent, the residue was purified by chromatography on silica gel eluting with 20% EtOAc in hexanes to give the title compound as a yellow oil (16.4 g, 83%). $^1$H NMR (400 MHz, DMSO-$d_6$) δ 0.96 (d, J=6.8 Hz, 6H), 1.96-2.02 (m, 1H), 3.75 (d, J=6.4 Hz, 2H), 5.96 (s, 2H), 6.17 (d, J=8.4 Hz, 1H), 6.30 (d, J=8.4 Hz, 1H), 7.15 (t, J=8.8 Hz, 1H). MS 191 (MH$^+$).

Example 41b Alternative Procedure: 2-amino-6-isobutoxybenzonitrile

Sodium hydride (60% suspension in oil, 25.0 g, 0.625 mol) was suspended in anhydrous THF (1000 mL) under nitrogen and heated to an internal temperature of 40° C. to 45° C. 2-methylpropan-1-ol (61.2 mL, 0.661 mol) was then added slowly and portionwise. The mixture was heated at 40° C. to 45° C. for 1 hour, then cooled to 35° C. 2-amino-6-fluorobenzonitrile (50.0 g, 0.367 mol) was added and refluxed for 21 hours. The mixture was cooled to r.t., then ice (250 g), ice water (750 mL), and hexanes (1000 mL) was added. Insoluble solids were filtered out and the organic layer was separated. The aqueous layer was extracted once more with a mixture of diethyl ether (250 mL) and hexanes (250 mL). The combined organic layer was washed twice with a solution of citric acid (53 g) in water (500 mL), then washed with 80% brine (300 mL), then dried with magnesium sulfate, filtered and concentrated under reduced pressure. The residue was dissolved in methanol (500 mL), and the immiscible oil carried through from the sodium hydride suspension was separated off in a separatory funnel. The solvent was evaporated under vacuum, and the residue was washed with hexanes (250 mL), after which the product 2-amino-6-isobutoxybenzonitrile was obtained as a viscous oil (46 grams, yield: 66%). $^1$H NMR (400 MHz, DMSO-$d_6$) δ 7.16 (t, J=8.0 Hz, 1H), 6.33 (d, J=8.0 Hz, 1H), 6.17 (d, J=8.0 Hz, 1H), 5.97 (s, 2H), 3.75 (d, J=7.2 Hz, 2H), 2.00 (m, 1H), 0.97 (d, J=6.8 Hz, 6H) ppm. MS 191 (MH$^+$).

Example 41c: 2-isobutoxy-6-nitrobenzonitrile

To a solution of 2-methylpropan-1-ol (9.6 mL, 0.104 mol) in anhydrous THF (200 mL) was added NaH (60% in mineral oil, 4.565 g, 0.114 mol) in small portions at 0° C. under N$_2$. After it was stirred at room temperature for 30 min, the reaction mixture was cooled down to −70° C. and 2,6-dinitrobenzonitrile (20.0 g, 0.104 mol) was added portionwise. After the addition was complete, the reaction mixture was stirred at −70° C.-RT overnight, then poured into ice water (600 mL). The resultant precipitate was collected by filtration and rinsed with water, hexane, and air dried to provide 2-isobutoxy-6-nitrobenzonitrile as a light yellow solid (34.3 g, 100%). $^1$H NMR (400 MHz, DMSO-$d_6$) δ 1.0 (d, J=6.8 Hz, 6H), 2.04-2.11 (m, 1H), 4.02 (d, J=6.8 Hz, 2H), 7.69-7.71 (m, 1H), 7.84-7.90 (m, 2H). MS 221 (MH$^+$).

Example 42: 4-amino-5-isopropoxy-2-methylquinoline-3-carboxylic Acid

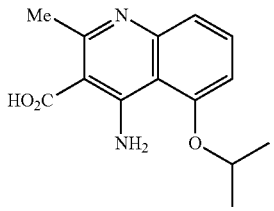 [SMILES: Cc1nc2cccc(OC(C)C)c2c(N)c1C(=O)O]

Prepared as in Example 1 from ethyl 4-amino-5-isopropoxy-2-methylquinoline-3-carboxylate (Example 42a) as a white solid (71%). $^1$H NMR (400 MHz, DMSO-$d_6$) δ 1.4 (d, J=6.4 Hz, 6H), 2.73 (s, 3H), 4.87-4.93 (m, 1H), 7.01 (d, J=8.0 Hz, 1H), 7.27 (d, J=8.0 Hz, 1H), 7.60 (t, J=8.4 Hz, 1H). MS 261 (MH$^+$).

Example 42a: ethyl 4-amino-5-isopropoxy-2-methylquinoline-3-carboxylate

Prepared as in Example 2a from 2-amino-6-isopropoxybenzonitrile (Tachdjian, C. et al. *PCT Int. Appl.* 2008, WO 2008154221) and ethyl 3-oxobutanoate as an off-white solid (32%). $^1$H NMR (400 MHz, DMSO-$d_6$) δ 1.32 (t, J=7.6 Hz, 3H), 1.38 (d, J=6.0 Hz, 6H), 2.54 (s, 3H), 4.3 (q, J=7.2 Hz, 2H), 4.83-4.89 (m, 1H), 6.93 (d, J=8.0 Hz, 1H), 7.20 (d, J=8.0 Hz, 1H), 7.50 (t, J=8.4 Hz, 1H), 8.14 (s, 2H). MS 289 (MH$^+$).

Example 43: 4-amino-5-((1-(hydroxymethyl)cyclohexyl)methoxy)-2-methylquinoline-3-carboxylic Acid

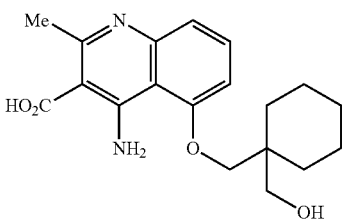 [SMILES: Cc1nc2cccc(OCC3(CO)CCCCC3)c2c(N)c1C(=O)O]

Prepared as in Example 1 from ethyl 4-amino-5-((1-(hydroxymethyl)cyclohexyl)-methoxy)-2-methylquinoline-3-carboxylate (Example 43a) as an off-white solid (49%). $^1$H NMR (400 MHz, DMSO-$d_6$) δ 1.37-1.48 (m, 10H), 2.75 (s, 3H), 3.50 (s, 2H), 4.03 (s, 2H), 5.08 (brs, 1H), 7.06 (d, J=8.4 Hz, 1H), 7.25 (d, J=8.8 Hz, 1H), 7.66 (t, J=8.4 Hz, 1H), 9.39 (brs, 1H), 12.17 (brs, 1H), 12.74 (brs, 1H). MS 345 (MH$^+$).

Example 43a: ethyl 4-amino-5-((1-(hydroxymethyl)cyclohexyl)methoxy)-2-methyl-quinoline-3-carboxylate Prepared as in Example 2a from (1-((3-amino-2-cyanophenoxy)methyl)cyclohexyl)-methyl acetate (Tachdjian, C. et al. *PCT Int. Appl.* 2008, WO 2008154221) and ethyl 3-oxobutanoate as an off-white solid (60%). MS 373 (MH$^+$).

Example 44: 4-amino-5-(2-(3,5-dihydroxybenzamido)-2-methylpropoxy)-2-methyl-quinoline-3-carboxylic Acid

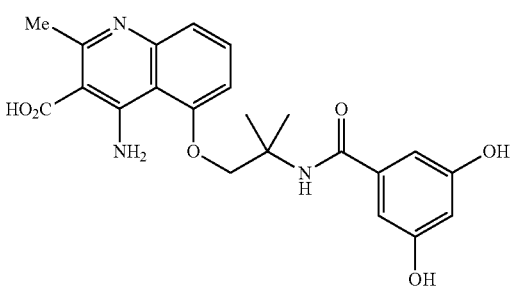 [SMILES: Cc1nc2cccc(OCC(C)(C)NC(=O)c3cc(O)cc(O)c3)c2c(N)c1C(=O)O]

Prepared as in Example 1 from ethyl 4-amino-5-(2-(3,5-dihydroxybenzamido)-2-methylpropoxy)-2-methylquinoline-3-carboxylate (Example 44a) as a white solid (73%). $^1$H NMR (400 MHz, DMSO-$d_6$) δ 1.46 (s, 6H), 2.75 (s, 3H), 4.44 (s, 2H), 6.3-6.31 (m, 1H), 6.61 (s, 2H), 7.04 (d, J=8.0 Hz, 1H), 7.27 (d, J=8.4 Hz, 1H), 7.66 (t, J=8.0 Hz, 1H), 7.98 (s, 1H), 8.79 (brs, 1H), 9.48 (s, 2H). MS 426 (MH$^+$).

Example 44a: ethyl 4-amino-5-(2-(3,5-dihydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,5-dihydroxybenzoic acid as a yellow-brown solid (15%). MS 454 (MH$^+$).

Example 45: 4-amino-5-((4-(isopropylcarbamoyl)cyclohexyl)oxy)-2-methylquinoline-3-carboxylic Acid

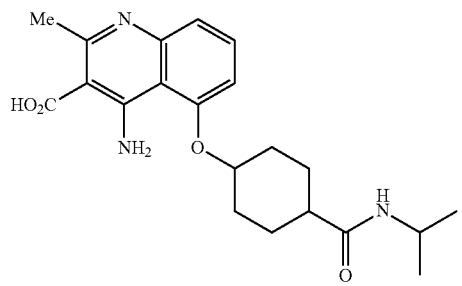 [SMILES: Cc1nc2cccc(OC3CCC(C(=O)NC(C)C)CC3)c2c(N)c1C(=O)O]

Prepared as in Example 1 from ethyl 4-amino-5-((4-(isopropylcarbamoyl)cyclohexyl)-oxy)-2-methylquinoline-3-carboxylate (Example 45a) as a white powder (71%). $^1$H NMR (400 MHz, DMSO-$d_6$) δ 1.01 (d, J=6.4 Hz, 6H), 1.59-1.68 (m, 6H), 2.06-2.09 (m, 2H), 2.2-2.22 (m, 1H), 2.76 (s, 3H), 3.77-3.83 (m, 1H), 4.96 (s, 1H), 7.06 (d, J=8.0 Hz, 1H), 7.26 (d, J=8.4 Hz, 1H), 7.58 (d, J=8.0 Hz, 1H), 7.65 (t, J=8.4 Hz, 1H), 8.79 (brs, 1H), 12.84 (brs, 2H). MS 386 (MH$^+$).

Example 45a: ethyl 4-amino-5-((4-(isopropylcarbamoyl)cyclohexyl)oxy)-2-methyl-quinoline-3-carboxylate Prepared as in Example 2a from 4-(3-amino-2-cyanophenoxy)-N-isopropylcyclohexanecarboxamide (Example 45b) and ethyl 3-oxobutanoate as a yellow solid (56%). MS 414 (MH+).

Example 45b: 4-(3-amino-2-cyanophenoxy)-N-isopropylcyclohexanecarboxamide

Prepared as in Example 22b from 4-hydroxy-N-isopropylcyclohexanecarboxamide (Example 45c) and 2-amino-6-fluorobenzonitrile as an off-white solid (17%). $^1$H NMR (400 MHz, DMSO-$d_6$) δ 1.01 (d, J=6.4 Hz, 6H), 1.47-1.57 (m, 4H), 1.67-1.77 (m, 2H), 1.89-1.93 (m, 2H), 2.08-2.15 (m, 1H), 3.75-3.84 (m, 1H), 4.57 (brs, 1H), 5.93 (s, 2H), 6.19 (d, J=8.0 Hz, 1H), 6.28 (d, J=8.0 Hz, 1H), 7.13 (t, J=8.0 Hz, 1H), 7.48 (d, J=8.0 Hz, 1H). MS 302 (MH+).

Example 45c: 4-hydroxy-N-isopropylcyclohexanecarboxamide

Prepared as in Example 24a from 4-hydroxycyclohexanecarboxylic acid and propan-2-amine as a colorless oil (68%). MS 186 (MH+).

Example 46: 4-amino-5-(3-((3-methoxybenzyl)amino)-2,2-dimethyl-3-oxopropoxy)-2-methylquinoline-3-carboxylic Acid

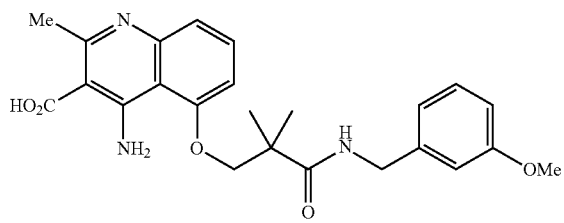 [SMILES: COc1cccc(CNC(=O)C(C)(C)COc2cccc3nc(C)c(C(=O)O)c(N)c23)c1]

Prepared as in Example 1 from ethyl 4-amino-5-(3-((3-methoxybenzyl)amino)-2,2-dimethyl-3-oxopropoxy)-2-methylquinoline-3-carboxylate (Example 46a) as a white powder (58%). M.p.: 172-174° C. $^1$H NMR (400 MHz, DMSO-$d_6$) δ 1.31 (s, 6H), 2.76 (s, 3H), 3.53 (s, 3H), 4.21 (s, 2H), 4.27 (d, J=5.6 Hz, 2H), 6.64 (dd, J=8.0, 2.4 Hz, 1H), 6.69 (m, 1H), 6.72 (d, J=8.0 Hz, 1H), 6.98-7.10 (m, 2H), 7.28 (d, J=8.0 Hz, 1H), 7.66 (t, J=8.0 Hz, 1H), 8.47 (t, J=5.6 Hz, 1H), 8.77 (brs, 1H), 12.26 (brs, 1H), 12.79 (brs, 1H). MS 438 (MH+).

Example 46a: ethyl 4-amino-5-(3-((3-methoxybenzyl)amino)-2,2-dimethyl-3-oxopropoxy)-2-methylquinoline-3-carboxylate Prepared as in Example 2a from 3-(3-amino-2-cyanophenoxy)-N-(3-methoxybenzyl)-2,2-dimethylpropanamide (Example 46b) and ethyl 3-oxobutanoate as a yellow solid (42%). MS 466 (MH+).

Example 46b: 3-(3-amino-2-cyanophenoxy)-N-(3-methoxybenzyl)-2,2-dimethylpropanamide Prepared as in Example 22b from 3-hydroxy-N-(3-methoxybenzyl)-2,2-dimethylpropanamide (Example 46c) and 2-amino-6-fluorobenzonitrile as a white solid (41%). MS 354 (MH+).

Example 46c: 3-hydroxy-N-(3-methoxybenzyl)-2,2-dimethylpropanamide

Prepared as in Example 24a from 3-hydroxy-2,2-dimethylpropanoic acid and (3-methoxyphenyl)methanamine as an orange oil (41%). MS 238 (MH+).

Example 47: 4-amino-5-(3-(cyclohexylamino)-2,2-dimethyl-3-oxopropoxy)-2-methyl-quinoline-3-carboxylic Acid

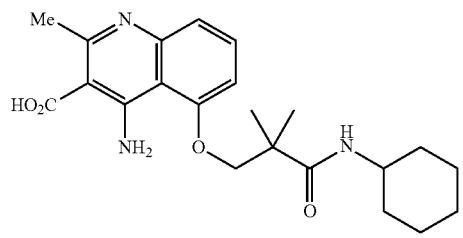 [SMILES: Cc1nc2cccc(OCC(C)(C)C(=O)NC3CCCCC3)c2c(N)c1C(=O)O]

Prepared as in Example 1 from ethyl 4-amino-5-(3-(cyclohexylamino)-2,2-dimethyl-3-oxopropoxy)-2-methylquinoline-3-carboxylate (Example 47a) as an off-white solid (13%). MS 400 (MH+).

Example 47a: ethyl 4-amino-5-(3-(cyclohexylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclohexanamine as a yellow-brown solid (46%). MS 428 (MH+).

Example 47b: 3-((4-amino-3-(ethoxycarbonyl)-2-methylquinolin-5-yl)oxy)-2,2-dimethylpropanoic Acid Prepared as in Example 2a from benzyl 3-(3-amino-2-cyanophenoxy)-2,2-dimethylpropanoate (Example 47c) and ethyl 3-oxobutanoate as a brown solid (80%). MS 192 (MH+).

Example 47c: 3-(3-amino-2-cyanophenoxy)-2,2-dimethylpropanoate

To a solution of benzyl 3-(2-cyano-3-nitrophenoxy)-2,2-dimethylpropanoate (Example 47d, 200 mg, 0.56 mmol) in AcOH (5 mL) was added iron powder (158 mg, 2.82 mmol) at room temperature. The reaction mixture was then stirred at 90° C. for 1 h. The reaction mixture was cooled to room temperature then diluted with AcOEt. The precipitate was filtered off and the filtrate was successively washed with 1 N NaOH and brine, then dried over $Na_2SO_4$, filtered and evaporated. The residue was purified by chromatography on silica gel (eluent: 40% EtOAc in hexanes) to give a title compound as a colorless oil (187 mg, 100%). MS 325 (MH+).

Example 47d: benzyl 3-(2-cyano-3-nitrophenoxy)-2,2-dimethylpropanoate

To a solution of benzyl 3-hydroxy-2,2-dimethylpropanoate (Yang, D. et al. *J. Am. Chem. Soc.* 2002, 124, 9966. 6.68 g, 32.1 mmol) in dry THF (200 mL) was carefully added NaH (60% in mineral oil, 3.5 g, 87.5 mmol) in small portions at 0° C. under nitrogen. The reaction mixture was stirred at 0° C. under nitrogen for 2 hrs. To this solution was added 2,6-dinitrobenzonitrile (6.19 g, 32.1 mmol), and the reaction solution was stirred at 0° C.-RT under nitrogen overnight. The reaction mixture was quenched with brine, and extracted with EtOAc (3×). The combined organic layers were washed with brine, dried over $Na_2SO_4$. After evaporation of the solvent, the residue was purified by chromatography on silica gel eluting (Elunet: 20% EtOAc in hexanes) to give the title compound as a brown solid (10.0 g, 87%). MS 355 (MH+).

Example 48: 4-amino-5-(3-(cycloheptylamino)-2,2-dimethyl-3-oxopropoxy)-2-methylquinoline-3-carboxylic Acid

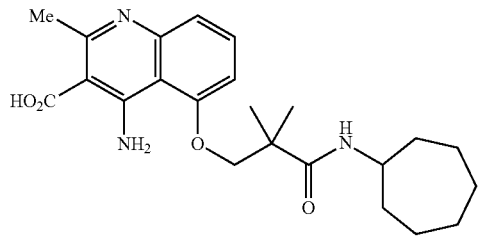 [SMILES: Cc1nc2cccc(OCC(C)(C)C(=O)NC3CCCCCC3)c2c(N)c1C(=O)O]

Prepared as in Example 1 from ethyl 4-amino-5-(3-(cycloheptylamino)-2,2-dimethyl-3-oxopropoxy)-2-methylquinoline-3-carboxylate (Example 48a) as an off-white solid (12%). MS 414 (MH+).

Example 48a: ethyl 4-amino-5-(3-(cycloheptylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cycloheptanamine as a brown solid (43%). MS 456 (MH+).

Example 49: 4-amino-5-(3-(cyclooctylamino)-2,2-dimethyl-3-oxopropoxy)-2-methylquinoline-3-carboxylic Acid

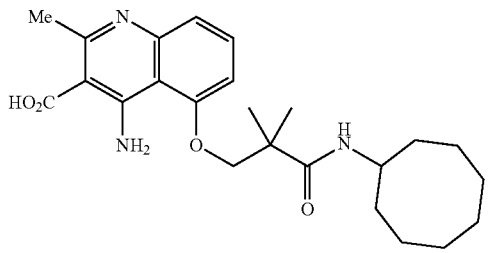 [SMILES: Cc1nc2cccc(OCC(C)(C)C(=O)NC3CCCCCCC3)c2c(N)c1C(=O)O]

Prepared as in Example 1 from ethyl 4-amino-5-(3-(cyclooctylamino)-2,2-dimethyl-3-oxopropoxy)-2-methylquinoline-3-carboxylate (Example 49a) as an off-white solid (11%). MS 428 (MH+).

Example 49a: ethyl 4-amino-5-(3-(cyclooctylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclooctanamine as a brown solid (46%). MS 456 (MH+).

Example 50: 4-amino-5-(3-((3-hydroxy-2,2-dimethylpropyl)amino)-2,2-dimethyl-3-oxopropoxy)-2-methylquinoline-3-carboxylic Acid

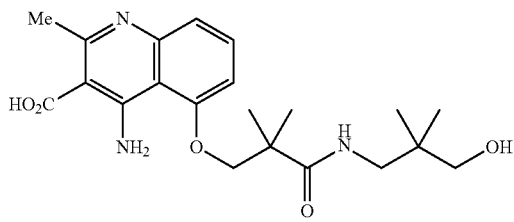 [SMILES: Cc1nc2cccc(OCC(C)(C)C(=O)NCC(C)(C)CO)c2c(N)c1C(=O)O]

Prepared as in Example 1 from ethyl 4-amino-5-(3-((3-hydroxy-2,2-dimethylpropyl)-amino)-2,2-dimethyl-3-oxopropoxy)-2-methylquinoline-3-carboxylate (Example 50a) as an off-white solid (87%). $^1$H NMR (400 MHz, DMSO-$d_6$) δ 0.71 (s, 6H), 1.28 (s, 6H), 2.74 (s, 3H), 2.97 (d, J=6.0 Hz, 2H), 3.0 (s, 2H), 4.57 (brs, 1H), 6.99 (d, J=8.4 Hz, 1H), 7.27 (d, J=8.0 Hz, 1H), 7.65 (t, J=8.4 Hz, 1H), 7.77 (t, J=6.4 Hz, 1H), 8.78 (brs, 1H), 12.04 (brs, 1H), 12.82 (brs, 1H). MS 404 (MH+).

Example 50a: ethyl 4-amino-5-(3-((3-hydroxy-2,2-dimethylpropyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and 3-amino-2,2-dimethylpropan-1-ol as a brown solid (40%). MS 432 (MH+).

Example 51: 4-amino-5-(3-(chroman-4-ylamino)-2,2-dimethyl-3-oxopropoxy)-2-methyl-quinoline-3-carboxylic Acid

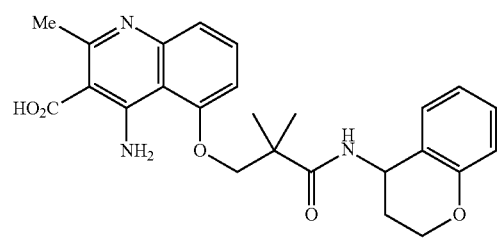 [SMILES: Cc1nc2cccc(OCC(C)(C)C(=O)NC3CCOc4ccccc43)c2c(N)c1C(=O)O]

Prepared as in Example 1 from ethyl 4-amino-5-(3-(chroman-4-ylamino)-2,2-dimethyl-3-oxopropoxy)-2-methylquinoline-3-carboxylate (Example 51a) as an off-white solid (80%). ¹H NMR (400 MHz, DMSO-$d_6$) δ 1.31 (d, J=4.0 Hz, 6H), 1.80-2.00 (m, 2H), 2.76 (s, 3H), 4.05-4.19 (m, 2H), 4.24 (s, 2H), 5.10 (q, J=6.8 Hz, 1H), 6.51 (t, J=7.6 Hz, 1H), 6.89 (d, J=8.4 Hz, 1H), 6.94 (d, J=8.0 Hz, 1H), 7.01 (dd, J=15.0, 8.4 Hz, 2H), 7.30 (d, J=8.8 Hz, 1H), 7.66 (t, J=8.4 Hz, 1H), 8.26 (d, J=8.8 Hz, 1H), 8.77 (brs, 1H), 12.31 (brs, 1H), 12.86 (brs, 1H). MS 450 (MH⁺).

Example 51a: ethyl 4-amino-5-(3-(chroman-4-ylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and chroman-4-amine (Lu, Y. et al. *PCT Int. Appl.* 2008, WO 2008043019) as a brown solid (37%). MS 478 (MH⁺).

Example 52: 4-amino-5-(3-((5-methoxy-1,2,3,4-tetrahydronaphthalen-1-yl)amino)-2,2-dimethyl-3-oxopropoxy)-2-methylquinoline-3-carboxylic Acid

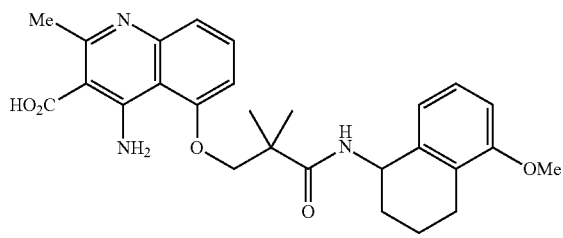 [SMILES: COc1cccc2c1CCCC2NC(=O)C(C)(C)COc1cccc2nc(C)c(C(=O)O)c(N)c12]

Prepared as in Example 1 from ethyl 4-amino-5-(3-((5-methoxy-1,2,3,4-tetrahydronaphthalen-1-yl)amino)-2,2-dimethyl-3-oxopropoxy)-2-methylquinoline-3-carboxylate (Example 52a) as an off-white solid (69%). ¹H NMR (400 MHz, DMSO-$d_6$) δ 1.30 (d, J=4.0 Hz, 6H), 1.52-1.87 (m, 4H), 2.75 (s, 3H), 4.22 (s, 2H), 4.95-5.05 (m, 1H), 6.59 (d, J=7.2 Hz, 1H), 6.67-6.75 (m, 2H), 6.97 (d, J=8.4 Hz, 1H), 7.28 (d, J=8.0 Hz, 2H), 7.64 (t, J=8.4 Hz, 1H), 8.13 (d, J=8.8 Hz, 1H), 8.74 (brs, 1H), 12.22 (brs, 1H), 12.80 (brs, 1H). MS 478 (MH⁺).

Example 52a: ethyl 4-amino-5-(3-((5-methoxy-1,2,3,4-tetrahydronaphthalen-1-yl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and 5-methoxy-1,2,3,4-tetrahydronaphthalen-1-amine as a brown solid (40%). MS 506 (MH⁺).

Example 53: 4-amino-5-(2-(4-methoxybenzamido)-2-methylpropoxy)-2-methylquinoline-3-carboxylic Acid

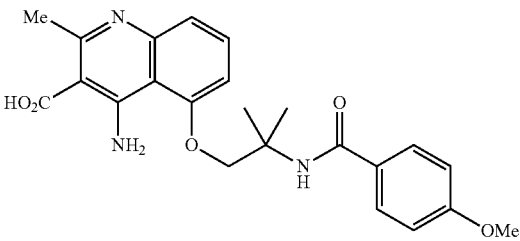 [SMILES: COc1ccc(C(=O)NC(C)(C)COc2cccc3nc(C)c(C(=O)O)c(N)c23)cc1]

Prepared as in Example 1 from ethyl 4-amino-5-(2-(4-methoxybenzamido)-2-methylpropoxy)-2-methylquinoline-3-carboxylate (Example 53a) as a white solid. MS 424 (MH⁺).

Example 53a: ethyl 4-amino-5-(2-(4-methoxybenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 4-methoxybenzoic acid as a brown solid. MS 452 (MH⁺).

Example 54: 4-amino-5-(2-(2-hydroxybenzamido)-2-methylpropoxy)-2-methylquinoline-3-carboxylic Acid

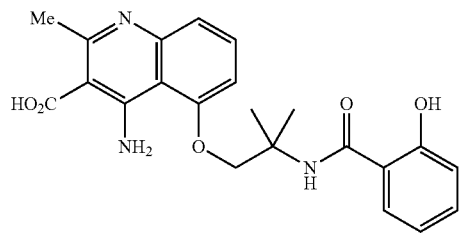 [SMILES: Cc1nc2cccc(OCC(C)(C)NC(=O)c3ccccc3O)c2c(N)c1C(=O)O]

Prepared as in Example 1 from ethyl 4-amino-5-(2-(2-hydroxybenzamido)-2-methylpropoxy)-2-methylquinoline-3-carboxylate (Example 54a) as an off-white solid. MS 410 (MH⁺).

Example 54a: ethyl 4-amino-5-(2-(2-hydroxybenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 2-hydroxybenzoic acid as a brown solid. MS 438 (MH⁺).

Example 55: 4-amino-5-(2-(3-methoxybenzamido)-2-methylpropoxy)-2-methylquinoline-3-carboxylic Acid

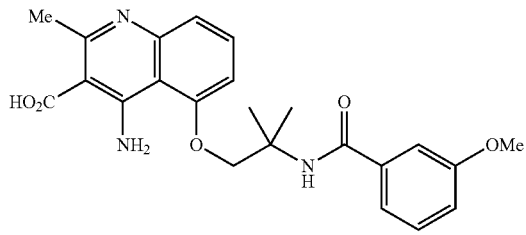 [SMILES: COc1cccc(C(=O)NC(C)(C)COc2cccc3nc(C)c(C(=O)O)c(N)c23)c1]

Prepared as in Example 1 from ethyl 4-amino-5-(2-(3-methoxybenzamido)-2-methylpropoxy)-2-methylquinoline-3-carboxylate (Example 55a) as a white solid. MS 424 (MH$^+$).

Example 55a: ethyl 4-amino-5-(2-(3-methoxybenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 3-methoxybenzoic acid as a brown solid. MS 452 (MH$^+$).

Example 56: 4-amino-5-(2-benzamido-2-methylpropoxy)-2-methylquinoline-3-carboxylic Acid

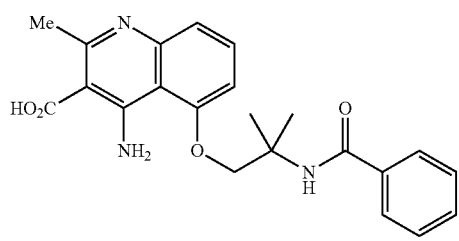 [SMILES: Cc1nc2cccc(OCC(C)(C)NC(=O)c3ccccc3)c2c(N)c1C(=O)O]

Prepared as in Example 1 from ethyl 4-amino-5-(2-benzamido-2-methylpropoxy)-2-methylquinoline-3-carboxylate (Example 56a) as a white solid. MS 394 (MH$^+$).

Example 56a: ethyl 4-amino-5-(2-benzamido-2-methylpropoxy)-2-methylquinoline-3-carboxylate Prepared as in Example 24a from 4-amino-5-(2-amino-2-methylpropoxy)-2-methylquinoline-3-carboxylate (Example 24b) and benzoic acid as a brown solid. MS 422 (MH$^+$).

Example 57: 4-amino-5-(2-(4-hydroxybenzamido)-2-methylpropoxy)-2-methylquinoline-3-carboxylic Acid

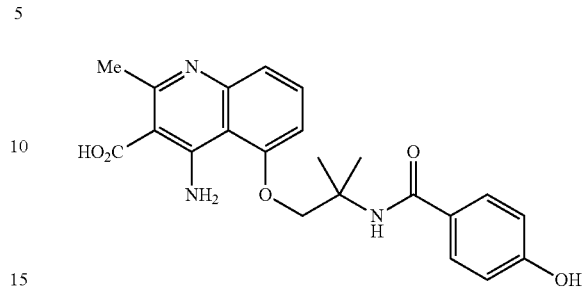

Prepared as in Example 1 from ethyl 4-amino-5-(2-(4-hydroxybenzamido)-2-methylpropoxy)-2-methylquinoline-3-carboxylate (Example 57a) as an off-white solid. MS 410 (MH$^+$).

Example 57a: ethyl 4-amino-5-(2-(4-hydroxybenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 4-hydroxybenzoic acid as a brown solid. MS 438 (MH$^+$).

Example 58: 4-amino-5-(2-(2-fluorobenzamido)-2-methylpropoxy)-2-methylquinoline-3-carboxylic Acid

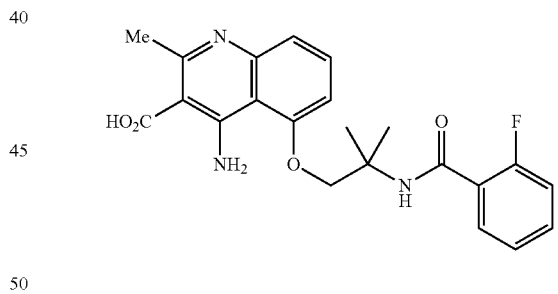

Prepared as in Example 1 from ethyl 4-amino-5-(2-(2-fluorobenzamido)-2-methylpropoxy)-2-methylquinoline-3-carboxylate (Example 58a) as an off-white solid. MS 412 (MH$^+$).

Example 58a: ethyl 4-amino-5-(2-(2-fluorobenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 2-fluorobenzoic acid as a brown solid. MS 440 (MH$^+$).

Example 59: 4-amino-5-(2-(3-fluorobenzamido)-2-methylpropoxy)-2-methylquinoline-3-carboxylic Acid

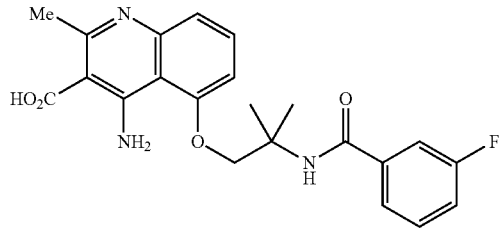 [SMILES: Cc1nc2cccc(OCC(C)(C)NC(=O)c3cccc(F)c3)c2c(N)c1C(=O)O]

Prepared as in Example 1 from ethyl 4-amino-5-(2-(3-fluorobenzamido)-2-methylpropoxy)-2-methylquinoline-3-carboxylate (Example 59a) as an off-white solid. MS 412 (MH+).

Example 59a: ethyl 4-amino-5-(2-(3-fluorobenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 3-fluorobenzoic acid as a brown solid. MS 440 (MH+).

Example 60: 4-amino-5-(2-(3-hydroxy-4-methoxybenzamido)-2-methylpropoxy)-2-methyl-quinoline-3-carboxylic Acid

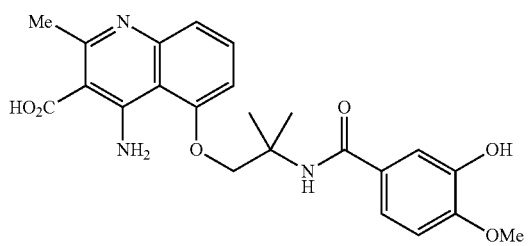 [SMILES: COc1ccc(C(=O)NC(C)(C)COc2cccc3nc(C)c(C(=O)O)c(N)c23)cc1O]

Prepared as in Example 1 from ethyl 4-amino-5-(2-(3-hydroxy-4-methoxybenzamido)-2-methylpropoxy)-2-methylquinoline-3-carboxylate (Example 60a) as an off-white solid. MS 440 (MH+).

Example 60a: ethyl 4-amino-5-(2-(3-hydroxy-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-hydroxy-4-methoxybenzoic acid as a brown solid. MS 468 (MH+).

Example 61: 4-amino-5-(2-(3-carbamoylbenzamido)-2-methylpropoxy)-2-methylquinoline-3-carboxylic Acid

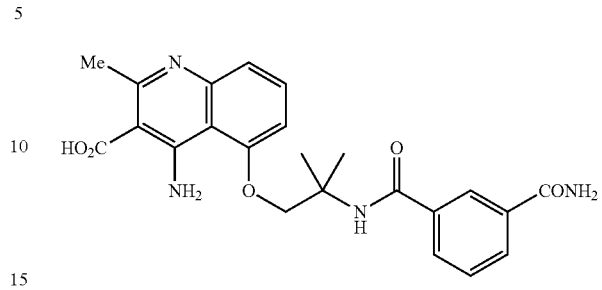

Prepared as in Example 1 from ethyl 4-amino-5-(2-(3-carbamoylbenzamido)-2-methylpropoxy)-2-methylquinoline-3-carboxylate (Example 61a) as an off-white solid. MS 437 (MH+).

Example 61a: ethyl 4-amino-5-(2-(3-carbamoylbenzamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 3-carbamoylbenzoic acid as a brown solid. MS 465 (MH+).

Example 62: 4-amino-5-(2-(2,3-dihydrobenzo[b][1,4]dioxine-6-carboxamido)-2-methylpropoxy)-2-methylquinoline-3-carboxylic Acid

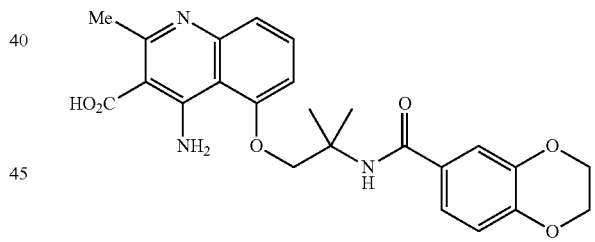

Prepared as in Example 1 from ethyl 4-amino-5-(2-(2,3-dihydrobenzo[b][1,4]dioxine-6-carboxamido)-2-methylpropoxy)-2-methylquinoline-3-carboxylate (Example 62a) as a pale-yellow solid (18%). $^1$H NMR (400 MHz, DMSO-$d_6$) δ 1.49 (s, 6H), 2.76 (s, 3H), 4.25 (m, 4H), 4.48 (s, 2H), 6.87 (d, J=8.8 Hz, 1H), 7.06 (d, J=7.6 Hz, 1H), 7.39-7.26 (m, 3H), 7.67 (t, J=7.2 Hz, 1H), 7.99 (s, 1H), 8.83 (brs, 1H), 12.31 (brs, 1H), 12.71 (brs, 1H). MS 452 (MH+).

Example 62a: ethyl 4-amino-5-(2-(2,3-dihydrobenzo[b][1,4]dioxine-6-carboxamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2,3-dihydrobenzo[b][1,4]dioxine-6-carboxylic acid as a brown solid (60%). MS 480 (MH+).

Example 63: 4-amino-5-(2-(2-ethylbutanamido)-2-methylpropoxy)-2-methylquinoline-3-carboxylic Acid

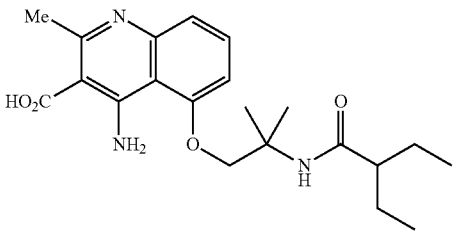 [SMILES: CCC(CC)C(=O)NC(C)(C)COc1cccc2nc(C)c(C(=O)O)c(N)c12]

Prepared as in Example 1 from ethyl 4-amino-5-(2-(2-ethylbutanamido)-2-methylpropoxy)-2-methylquinoline-3-carboxylate (Example 63a) as an off-white solid. MS 388 (MH⁺).

Example 63a: ethyl 4-amino-5-(2-(2-ethylbutanamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 2-ethylbutanoic acid as a brown solid. MS 416 (MH⁺).

Example 64: 4-amino-5-(2-(3-methoxypropanamido)-2-methylpropoxy)-2-methylquinoline-3-carboxylic Acid

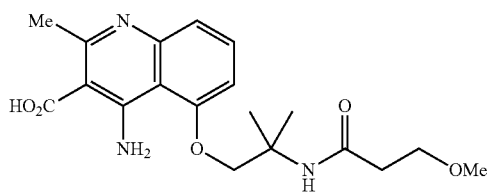 [SMILES: COCCC(=O)NC(C)(C)COc1cccc2nc(C)c(C(=O)O)c(N)c12]

Prepared as in Example 1 from ethyl 4-amino-5-(2-(3-methoxypropanamido)-2-methylpropoxy)-2-methylquinoline-3-carboxylate (Example 64a) as an off-white solid. MS 376 (MH⁺).

Example 64a: ethyl 4-amino-5-(2-(3-methoxypropanamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 3-methoxypropanoic acid as a brown solid. MS 404 (MH⁺).

Example 65: 4-amino-5-(2-butyramido-2-methylpropoxy)-2-methylquinoline-3-carboxylic

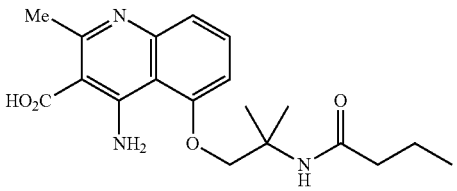 [SMILES: CCCC(=O)NC(C)(C)COc1cccc2nc(C)c(C(=O)O)c(N)c12]

Prepared as in Example 1 from ethyl 4-amino-5-(2-butyramido-2-methylpropoxy)-2-methylquinoline-3-carboxylate (Example 65a) as an off-white solid. MS 360 (MH⁺).

Example 65a: ethyl 4-amino-5-(2-butyramido-2-methylpropoxy)-2-methylquinoline-3-carboxylate Prepared as in Example 24a from 4-amino-5-(2-amino-2-methylpropoxy)-2-methylquinoline-3-carboxylate (Example 24b) and butyric acid as a brown solid. MS 388 (MH⁺).

Example 66: 4-amino-2-methyl-5-(2-methyl-2-(tetrahydrofuran-3-carboxamido)propoxy)-quinoline-3-carboxylic Acid

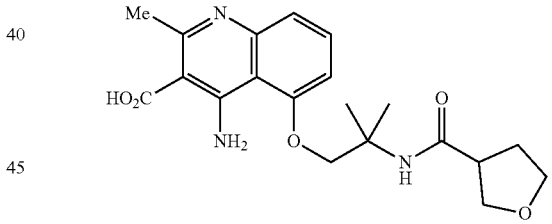

Prepared as in Example 1 from ethyl 4-amino-2-methyl-5-(2-methyl-2-(tetrahydrofuran-3-carboxamido)propoxy)quinoline-3-carboxylate (Example 66a) as an off-white solid. MS 388 (MH⁺).

Example 66a: ethyl 4-amino-2-methyl-5-(2-methyl-2-(tetrahydrofuran-3-carboxamido)-propoxy)quinoline-3-carboxylate Prepared as in Example 24a from 4-amino-5-(2-amino-2-methylpropoxy)-2-methylquinoline-3-carboxylate (Example 24b) and tetrahydrofuran-3-carboxylic acid as a brown solid. MS 416 (MH⁺).

Example 67: 4-amino-5-(2-(4-(hydroxymethyl)benzamido)-2-methylpropoxy)-2-methyl-quinoline-3-carboxylic Acid

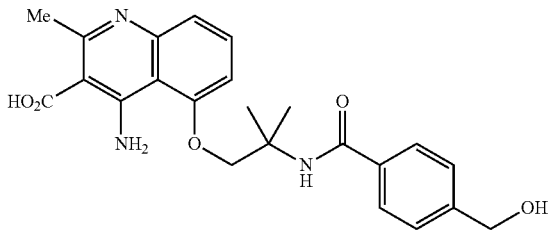 [SMILES: Cc1nc2cccc(OCC(C)(C)NC(=O)c3ccc(CO)cc3)c2c(N)c1C(=O)O]

Prepared as in Example 1 from ethyl 4-amino-5-(2-(4-(hydroxymethyl)benzamido)-2-methylpropoxy)-2-methylquinoline-3-carboxylate (Example 67a) as an off-white solid. MS 424 (MH$^+$).

Example 67a: ethyl 4-amino-5-(2-(4-(hydroxymethyl)benzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-(hydroxymethyl)benzoic acid as a brown solid. MS 452 (MH$^+$).

Example 68: 4-amino-5-(2-(2-methoxyacetamido)-2-methylpropoxy)-2-methylquinoline-3-carboxylic Acid

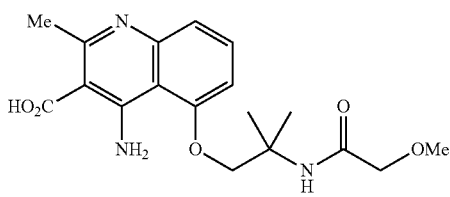 [SMILES: COCC(=O)NC(C)(C)COc1cccc2nc(C)c(C(=O)O)c(N)c12]

Prepared as in Example 1 from ethyl 4-amino-5-(2-(2-methoxyacetamido)-2-methylpropoxy)-2-methylquinoline-3-carboxylate (Example 68a) as an off-white solid. MS 362 (MH$^+$).

Example 68a: ethyl 4-amino-5-(2-(2-methoxyacetamido)-2-methylpropoxy)-2-methyl-quinoline-3-carboxylate Prepared as in Example 24a from 4-amino-5-(2-amino-2-methylpropoxy)-2-methylquinoline-3-carboxylate (Example 24b) and 2-methoxyacetic acid as a brown solid. MS 390 (MH$^+$).

Example 69: 5-(2-acetamido-2-methylpropoxy)-4-amino-2-methylquinoline-3-carboxylic Acid

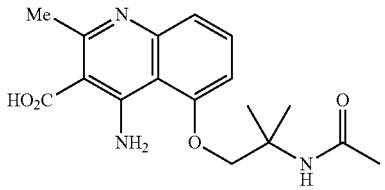 [SMILES: CC(=O)NC(C)(C)COc1cccc2nc(C)c(C(=O)O)c(N)c12]

Prepared as in Example 1 from ethyl 5-(2-acetamido-2-methylpropoxy)-4-amino-2-methylquinoline-3-carboxylate (Example 69a) as an off-white solid. MS 332 (MH$^+$).

Example 69a: ethyl 5-(2-acetamido-2-methylpropoxy)-4-amino-2-methylquinoline-3-carboxylate Prepared as in Example 24a from 4-amino-5-(2-amino-2-methylpropoxy)-2-methylquinoline-3-carboxylate (Example 24b) and acetic acid as a brown solid. MS 390 (MH$^+$).

Example 70: 4-amino-5-(2-(2,3-dihydrobenzo[b][1,4]dioxine-5-carboxamido)-2-methylpropoxy)-2-methylquinoline-3-carboxylic Acid

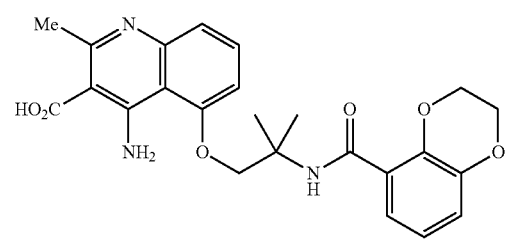

Prepared as in Example 1 from ethyl 4-amino-5-(2-(2,3-dihydrobenzo[b][1,4]dioxine-5-carboxamido)-2-methylpropoxy)-2-methylquinoline-3-carboxylate (Example 70a) as an off-white solid. MS 452 (MH$^+$).

Example 70a: ethyl 4-amino-5-(2-(2,3-dihydrobenzo[b][1,4]dioxine-5-carboxamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2,3-dihydrobenzo[b][1,4]dioxine-5-carboxylic acid as a brown solid. MS 480 (MH$^+$).

Example 71: 4-amino-5-(2-(3,5-dimethoxybenzamido)-2-methylpropoxy)-2-methylquinoline-3-carboxylic Acid

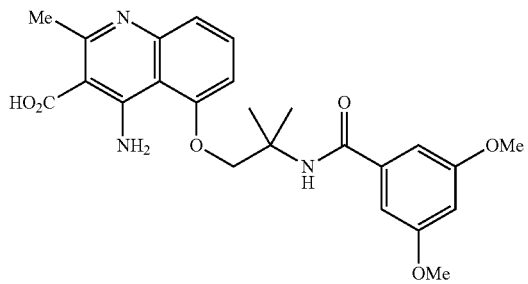 [SMILES: COc1cc(OC)cc(C(=O)NC(C)(C)COc2cccc3nc(C)c(C(=O)O)c(N)c23)c1]

Prepared as in Example 1 from ethyl 4-amino-5-(2-(3,5-dimethoxybenzamido)-2-methylpropoxy)-2-methylquinoline-3-carboxylate (Example 71a) as an off-white solid. MS 454 (MH+).

Example 71a: ethyl 4-amino-5-(2-(3,5-dimethoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,5-dimethoxybenzoic acid as a brown solid. MS 482 (MH+).

Example 72: 4-amino-5-(2-(3,4-dimethoxybenzamido)-2-methylpropoxy)-2-methylquinoline-3-carboxylic Acid

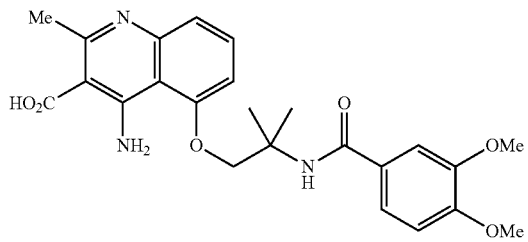 [SMILES: COc1ccc(C(=O)NC(C)(C)COc2cccc3nc(C)c(C(=O)O)c(N)c23)cc1OC]

Prepared as in Example 1 from ethyl 4-amino-5-(2-(3,4-dimethoxybenzamido)-2-methylpropoxy)-2-methylquinoline-3-carboxylate (Example 72a) as an off-white solid. MS 454 (MH+).

Example 72a: ethyl 4-amino-5-(2-(3,4-dimethoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,4-dimethoxybenzoic acid as a brown solid. MS 482 (MH+).

Example 73: 4-amino-5-(2-(2-(4-methoxyphenyl)acetamido)-2-methylpropoxy)-2-methyl-quinoline-3-carboxylic Acid

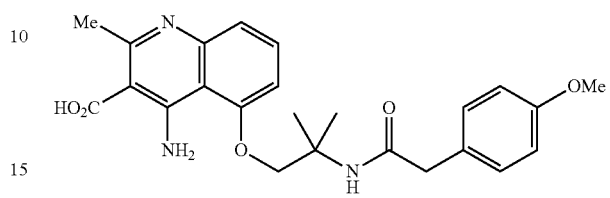

Prepared as in Example 1 from ethyl 4-amino-5-(2-(2-(4-methoxyphenyl)acetamido)-2-methylpropoxy)-2-methylquinoline-3-carboxylate (Example 73a) as an off-white solid. MS 438 (MH+).

Example 73a: ethyl 4-amino-5-(2-(2-(4-methoxyphenyl)acetamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-(3,4-dimethoxyphenyl)acetic acid as a brown solid. MS 466 (MH+).

Example 74: 4-amino-5-(2-(4-fluoro-3-hydroxybenzamido)-2-methylpropoxy)-2-methyl-quinoline-3-carboxylic Acid

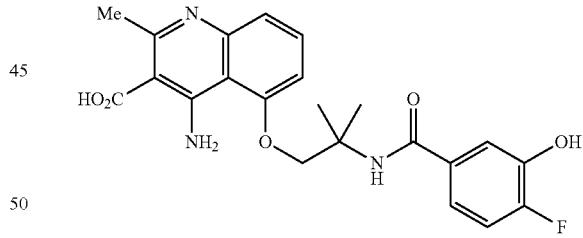

Prepared as in Example 1 from ethyl 4-amino-5-(2-(4-fluoro-3-hydroxybenzamido)-2-methylpropoxy)-2-methylquinoline-3-carboxylate (Example 74a) as an off-white solid. MS 428 (MH+).

Example 74a: ethyl 4-amino-5-(2-(4-fluoro-3-hydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-fluoro-3-hydroxybenzoic acid as a brown solid. MS 456 (MH+).

Example 75: 4-amino-5-(2-(3-hydroxy-5-methoxy-benzamido)-2-methylpropoxy)-2-methyl-quinoline-3-carboxylic Acid

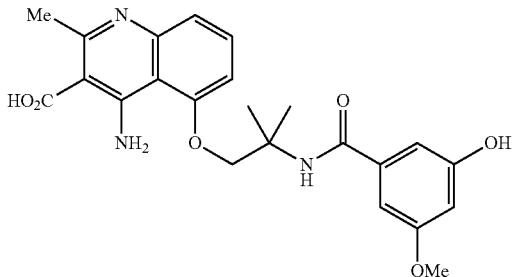 [SMILES: COc1cc(O)cc(C(=O)NC(C)(C)COc2cccc3nc(C)c(C(=O)O)c(N)c23)c1]

Prepared as in Example 1 from ethyl 4-amino-5-(2-(3-hydroxy-5-methoxybenzamido)-2-methylpropoxy)-2-methylquinoline-3-carboxylate (Example 75a) as an off-white solid. MS 440 (MH$^+$).

Example 75a: ethyl 4-amino-5-(2-(3-hydroxy-5-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-hydroxy-5-methoxybenzoic acid as a brown solid. MS 468 (MH$^+$).

Example 76: 4-amino-5-(2-(4-(2-hydroxyethoxy)-3-methoxybenzamido)-2-methylpropoxy)-2-methylquinoline-3-carboxylic Acid

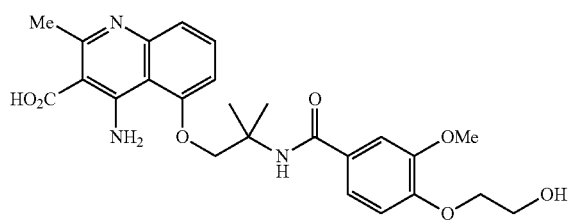 [SMILES: COc1cc(C(=O)NC(C)(C)COc2cccc3nc(C)c(C(=O)O)c(N)c23)ccc1OCCO]

Prepared as in Example 1 from ethyl 4-amino-5-(2-(4-(2-hydroxyethoxy)-3-methoxy-benzamido)-2-methyl-propoxy)-2-methylquinoline-3-carboxylate (Example 76a) as an off-white solid. MS 484 (MH$^+$).

Example 76a: ethyl 4-amino-5-(2-(4-(2-hydroxy-ethoxy)-3-methoxybenzamido)-2-methyl-propoxy)-2-methylquinoline-3-carboxylate Prepared as in Example 24a from 4-amino-5-(2-amino-2-methylpropoxy)-2-methylquinoline-3-carboxylate (Example 24b) and 4-(2-hydroxyethoxy)-3-methoxybenzoic acid (Uto, Y. et al. *Bioorg. Med. Chem. Lett.* 2009, 19, 4151) as a brown solid. MS 512 (MH$^+$).

Example 77: 4-amino-5-(2-(3-(2-hydroxyethoxy)-4-methoxybenzamido)-2-methylpropoxy)-2-methylquinoline-3-carboxylic Acid

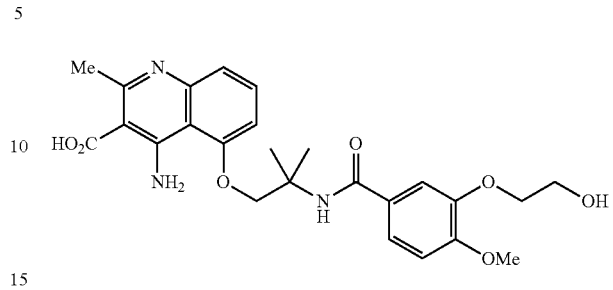

Prepared as in Example 1 from ethyl 4-amino-5-(2-(3-(2-hydroxyethoxy)-4-methoxy-benzamido)-2-methyl-propoxy)-2-methylquinoline-3-carboxylate (Example 77a) as an off-white solid. MS 484 (MH$^+$).

Example 77a: ethyl 4-amino-5-(2-(3-(2-hydroxy-ethoxy)-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(2-hydroxyethoxy)-4-methoxybenzoic acid as a brown solid. MS 512 (MH$^+$).

Example 78: 4-amino-5-(2-(3-(3-hydroxypropoxy)-4-methoxybenzamido)-2-methylpropoxy)-2-methylquinoline-3-carboxylic Acid

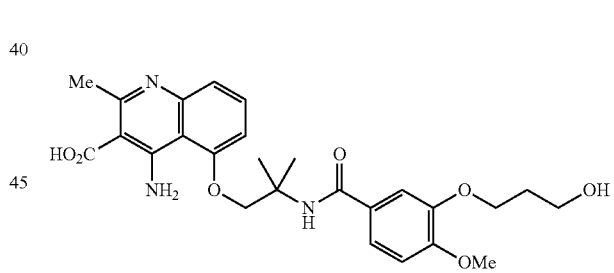

Prepared as in Example 1 from ethyl 4-amino-5-(2-(3-(3-hydroxypropoxy)-4-methoxy-benzamido)-2-methyl-propoxy)-2-methylquinoline-3-carboxylate (Example 78a) as an off-white solid. MS 498 (MH$^+$).

Example 78a: ethyl 4-amino-5-(2-(3-(3-hydroxy-propoxy)-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(3-hydroxypropoxy)-4-methoxybenzoic acid as a brown solid. MS 526 (MH$^+$).

Example 79: 4-amino-5-(2-(4-(3-hydroxypropoxy)-3-methoxybenzamido)-2-methylpropoxy)-2-methylquinoline-3-carboxylic Acid

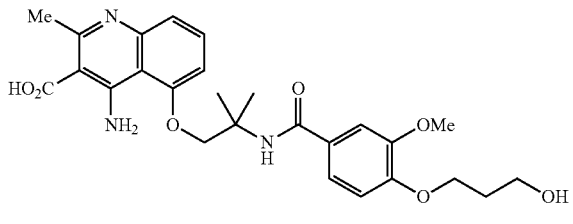 [SMILES: COc1cc(C(=O)NC(C)(C)COc2cccc3nc(C)c(C(=O)O)c(N)c23)ccc1OCCCO]

Prepared as in Example 1 from ethyl 4-amino-5-(2-(4-(3-hydroxypropoxy)-3-methoxy-benzamido)-2-methylpropoxy)-2-methylquinoline-3-carboxylate (Example 79a) as an off-white solid. MS 498 (MH+).

Example 79a: ethyl 4-amino-5-(2-(4-(3-hydroxypropoxy)-3-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-(3-hydroxypropoxy)-3-methoxybenzoic acid (Baraldi, P. G. et al. *J. Med. Chem.* 1999, 42, 5131) as a brown solid. MS 526 (MH+).

Example 80: (S)-4-amino-5-(2-(2,3-dihydrobenzo[b][1,4]dioxine-6-carboxamido)propoxy)-2-methylquinoline-3-carboxylic Acid

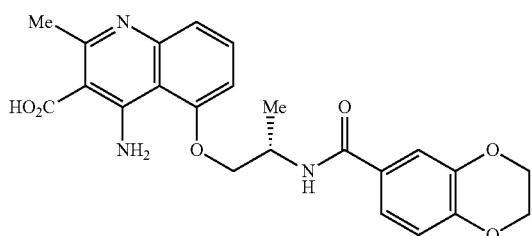

Prepared as in Example 1 from (S)-ethyl 4-amino-5-(2-(2,3-dihydrobenzo[b][1,4]dioxine-6-carboxamido)propoxy)-2-methylquinoline-3-carboxylate (Example 80a) as an off-white solid. MS 438 (MH+).

Example 80a: (S)-ethyl 4-amino-5-(2-(2,3-dihydrobenzo[b][1,4]dioxine-6-carboxamido)-propoxy)-2-methylquinoline-3-carboxylate Prepared as in Example 24a from (S)-ethyl 4-amino-5-(2-aminopropoxy)-2-methyl-quinoline-3-carboxylate (Example 26b) and 2,3-dihydrobenzo[b][1,4]dioxine-6-carboxylic acid as brown solid. MS 466 (MH+).

Example 81: (S)-4-amino-5-(2-(2,3-dihydrobenzo[b][1,4]dioxine-5-carboxamido)propoxy)-2-methylquinoline-3-carboxylic Acid

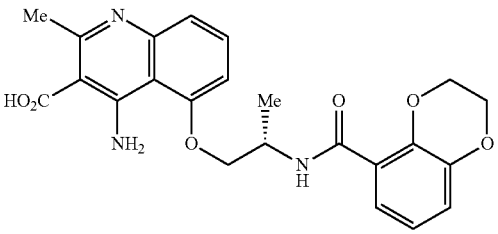 [SMILES: Cc1nc2cccc(OC[C@H](C)NC(=O)c3cccc4c3OCCO4)c2c(N)c1C(=O)O]

Prepared as in Example 1 from (S)-ethyl 4-amino-5-(2-(2,3-dihydrobenzo[b][1,4]dioxine-5-carboxamido)propoxy)-2-methylquinoline-3-carboxylate (Example 81a) as an off-white solid. MS 438 (MH+).

Example 81a: (S)-ethyl 4-amino-5-(2-(2,3-dihydrobenzo[b][1,4]dioxine-5-carboxamido)-propoxy)-2-methylquinoline-3-carboxylate Prepared as in Example 24a from (S)-ethyl 4-amino-5-(2-aminopropoxy)-2-methyl-quinoline-3-carboxylate (Example 26b) and 2,3-dihydrobenzo[b][1,4]dioxine-5-carboxylic acid as brown solid. MS 466 (MH+).

Example 82: (S)-4-amino-5-(2-(4-(2-hydroxyethoxy)-3-methoxybenzamido)propoxy)-2-methylquinoline-3-carboxylic Acid

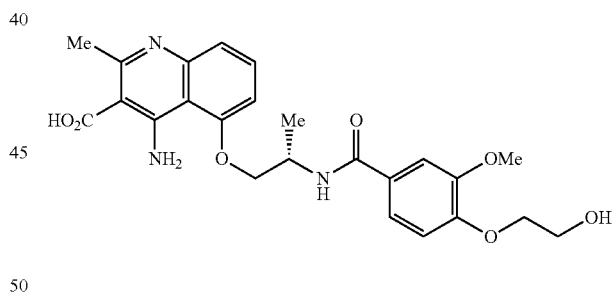

Prepared as in Example 1 from (S)-ethyl 4-amino-5-(2-(4-(2-hydroxyethoxy)-3-methoxybenzamido)propoxy)-2-methylquinoline-3-carboxylate (Example 82a) as an off-white solid. MS 470 (MH+).

Example 82a: (S)-ethyl 4-amino-5-(2-(4-(2-hydroxyethoxy)-3-methoxybenzamido)propoxy)-2-methylquinoline-3-carboxylate Prepared as in Example 24a from (S)-ethyl 4-amino-5-(2-aminopropoxy)-2-methyl-quinoline-3-carboxylate (Example 26b) and 4-(2-hydroxyethoxy)-3-methoxybenzoic acid (Uto, Y. et al. *Bioorg. Med. Chem. Lett.* 2009, 19, 4151) as a brown solid. MS 498 (MH+).

Example 83: (S)-4-amino-5-(2-(3-(2-hydroxyethoxy)-4-methoxybenzamido)propoxy)-2-methylquinoline-3-carboxylic Acid

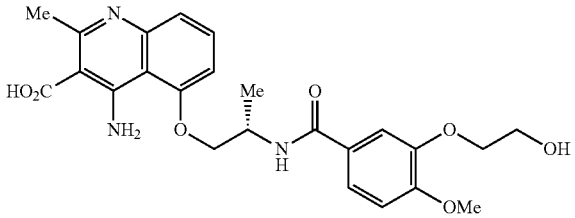 [SMILES: COc1ccc(C(=O)N[C@@H](C)COc2cccc3nc(C)c(C(=O)O)c(N)c23)cc1OCCO]

Prepared as in Example 1 from (S)-ethyl 4-amino-5-(2-(3-(2-hydroxyethoxy)-4-methoxybenzamido)propoxy)-2-methylquinoline-3-carboxylate (Example 83a) as an off-white solid. MS 470 (MH$^+$).

Example 83a: (S)-ethyl 4-amino-5-(2-(3-(2-hydroxyethoxy)-4-methoxybenzamido)propoxy)-2-methylquinoline-3-carboxylate Prepared as in Example 24a from (S)-ethyl 4-amino-5-(2-aminopropoxy)-2-methyl-quinoline-3-carboxylate (Example 26b) and 3-(2-hydroxyethoxy)-4-methoxybenzoic acid as a brown solid. MS 498 (MH$^+$).

Example 84: (S)-4-amino-5-(2-(3-(3-hydroxypropoxy)-4-methoxybenzamido)propoxy)-2-methylquinoline-3-carboxylic Acid

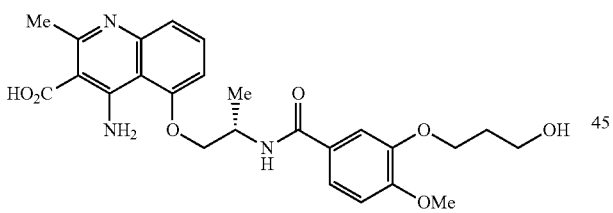

Prepared as in Example 1 from (S)-ethyl 4-amino-5-(2-(3-(3-hydroxypropoxy)-4-methoxybenzamido)propoxy)-2-methylquinoline-3-carboxylate (Example 84a) as an off-white solid. MS 484 (MH$^+$).

Example 84a: (S)-ethyl 4-amino-5-(2-(3-(3-hydroxypropoxy)-4-methoxybenzamido)propoxy)-2-methylquinoline-3-carboxylate Prepared as in Example 24a from (S)-ethyl 4-amino-5-(2-aminopropoxy)-2-methyl-quinoline-3-carboxylate (Example 26b) and 3-(3-hydroxypropoxy)-4-methoxybenzoic acid as a brown solid. MS 512 (MH$^+$).

Example 85: (S)-4-amino-5-(2-(4-(3-hydroxypropoxy)-3-methoxybenzamido)propoxy)-2-methylquinoline-3-carboxylic Acid

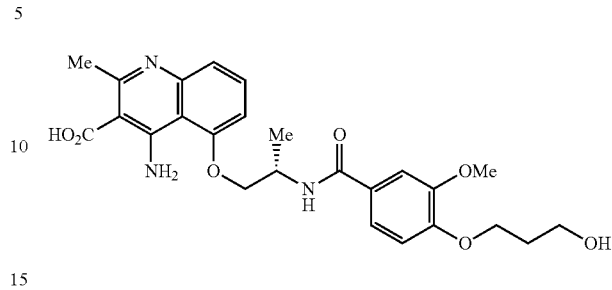

Prepared as in Example 1 from (S)-ethyl 4-amino-5-(2-(4-(3-hydroxypropoxy)-3-methoxybenzamido)propoxy)-2-methylquinoline-3-carboxylate (Example 85a) as an off-white solid. MS 484 (MH$^+$).

Example 85a: (S)-ethyl 4-amino-5-(2-(4-(3-hydroxypropoxy)-3-methoxybenzamido)propoxy)-2-methylquinoline-3-carboxylate Prepared as in Example 24a from (S)-ethyl 4-amino-5-(2-aminopropoxy)-2-methyl-quinoline-3-carboxylate (Example 26b) and 4-(3-hydroxypropoxy)-3-methoxybenzoic acid (Baraldi, P. G. et al. *J. Med. Chem.* 1999, 42, 5131) as a brown solid. MS 512 (MH$^+$).

Example 86: (R)-4-amino-5-(2-(cyclohexanecarboxamido)propoxy)-2-methylquinoline-3-carboxylic acid (SID 47687595)

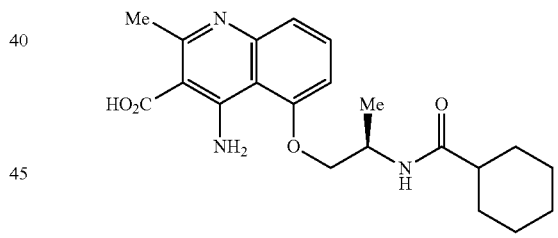

Prepared as in Example 1 from (R)-ethyl 4-amino-5-(2-(cyclohexanecarboxamido)-propoxy)-2-methylquinoline-3-carboxylate (Example 86a) as a white solid (43%). $^1$H NMR (400 MHz, DMSO-d$_6$) δ 1.25-1.10 (m, 5H), 1.34-1.31 (m, 2H), 1.69-1.62 (m, 5H), 2.11-2.05 (m, 1H), 2.69 (s, 3H), 3.93 (t, J=9.2 Hz, 1H), 4.13 (dd, J=4, 9.6 Hz, 1H), 4.14-4.11 (m, 1H), 6.86 (d, J=8.0 Hz, 1H), 7.28 (d, J=8.4 Hz, 1H), 7.49 (t, J=8.0 Hz, 1H), 7.95 (d, J=8.4 Hz, 1H). MS 386 (MH$^+$).

Example 86a: (R)-ethyl 4-amino-5-(2-(cyclohexanecarboxamido)propoxy)-2-methyl-quinoline-3-carboxylate Prepared as in Example 24a from (R)-ethyl 4-amino-5-(2-aminopropoxy)-2-methyl-quinoline-3-carboxylate (Example 86b) and cyclohexanecarboxylic acid as brown solid (31%). MS 414 (MH$^+$).

Example 86b: (R)-ethyl 4-amino-5-(2-aminopropoxy)-2-methylquinoline-3-carboxylate Prepared as in Example 2a from (R)-benzyl (1-(3-amino-2-cyanophenoxy)propan-2-yl)-carbamate (Example 86c) and ethyl 3-oxobutanoate as brown solid. MS 304 (MH$^+$).

Example 86c: (R)-benzyl (1-(3-amino-2-cyanophenoxy)propan-2-yl)carbamate

Prepared as in Example 24c from (R)-2-amino-6-(2-aminopropoxy)benzonitrile (Example 86d) as brown solid (79%). $^1$H NMR (400 MHz, DMSO-d$_6$) δ 1.12 (d, J=6.4 Hz, 3H), 3.81 (d, J=8.4 Hz, 1H), 3.95-3.92 (m, 1H), 4.99 (s, 2H), 5.36 (s, 2H), 5.96 (s, 2H), 6.20 (d, J=8.0 Hz, 1H), 6.31 (d, J=8.4 Hz, 1H), 7.13 (t, J=8.4 Hz, 1H), 7.44-7.38 (m, 5H). MS 326 (MH$^+$).

Example 86d: (R)-2-amino-6-(2-aminopropoxy)benzonitrile

Prepared as in Example 24d from (R)-2-aminopropan-1-ol and 2-amino-6-fluoro-benzonitrile as brown solid (81%). $^1$H NMR (400 MHz, DMSO-d$_6$) δ 1.01 (d, J=6.5 Hz, 3H), 3.08 (m, 1H), 3.71 (d, J=6.1 Hz, 2H), 5.95 (s, 2H), 6.15 (d, J=8.3 Hz, 1H), 6.2 (d, J=8.3 Hz, 1H), 7.13 (t, J=8.3 Hz, 1H). MS 192 (MH$^+$).

Example 87: (R)-4-amino-5-(2-(isonicotinamido)propoxy)-2-methylquinoline-3-carboxylic Acid

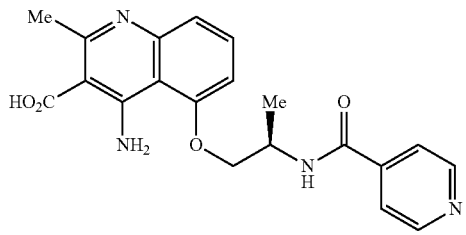 [SMILES: Cc1nc2cccc(OC[C@@H](C)NC(=O)c3ccncc3)c2c(N)c1C(=O)O]

Prepared as in Example 1 from (R)-ethyl 4-amino-5-(2-(isonicotinamido)propoxy)-2-methylquinoline-3-carboxylate (Example 87a) as an off-white solid (32%). $^1$H NMR (400 MHz, DMSO-d$_6$) δ 1.31 (d, J=6.8 Hz, 3H), 2.66 (s, 3H), 4.14 (t, J=9.2 Hz, 1H), 4.28 (dd, J=3.6, 9.6 Hz, 1H), 4.70-4.55 (m, 1H), 6.92 (d, J=8.0 Hz, 1H), 7.26 (d, J=8.4 Hz, 1H), 7.51 (t, J=8.4 Hz, 1H), 7.75 (dd, J=1.2, 6.0 Hz, 2H), 8.71 (dd, J=1.2, 6.0 Hz, 2H), 8.95 (d, J=8.0 Hz, 1H). MS 409 (MH$^+$).

Example 87a: (R)-ethyl 4-amino-5-(2-(isonicotinamido)propoxy)-2-methylquinoline-3-carboxylate Prepared as in Example 24a from (R)-ethyl 4-amino-5-(2-aminopropoxy)-2-methyl-quinoline-3-carboxylate (Example 86b) and isonicotinic acid as brown solid (41%). MS 409 (MH$^+$).

Example 88: (R)-4-amino-5-(2-(3-hydroxybenzamido)propoxy)-2-methylquinoline-3-carboxylic Acid

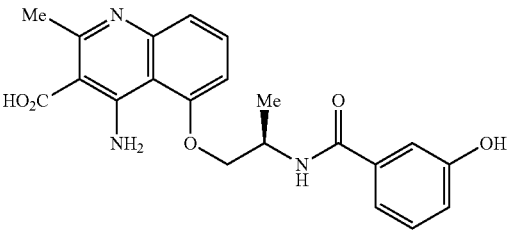 [SMILES: Cc1nc2cccc(OC[C@@H](C)NC(=O)c3cccc(O)c3)c2c(N)c1C(=O)O]

Prepared as in Example 1 from (R)-ethyl 4-amino-5-(2-(3-hydroxybenzamido)propoxy)-2-methylquinoline-3-carboxylate (Example 88a) as a white solid (51%). $^1$H NMR (400 MHz, DMSO-d$_6$) δ 1.28 (d, J=7.2 Hz, 3H), 2.65 (s, 3H), 4.11 (t, J=8.8 Hz, 1H), 4.22 (dd, J=4.0, 10 Hz, 1H), 4.65-4.55 (m, 1H), 6.88 (d, J=8.0 Hz, 2H), 7.25-7.13 (m, 4H), 7.48 (t, J=8.0 Hz, 1H), 8.49 (d, J=8.0 Hz, 1H), 9.93 (brs, 1H). MS 396 (MH$^+$).

Example 88a: (R)-ethyl 4-amino-5-(2-(3-hydroxybenzamido)propoxy)-2-methylquinoline-3-carboxylate Prepared as in Example 24a from (R)-ethyl 4-amino-5-(2-aminopropoxy)-2-methyl-quinoline-3-carboxylate (Example 86b) and 3-hydroxybenzoic acid as brown solid (36%). MS 424 (MH$^+$).

Example 89: (S)-4-amino-5-((1-(cyclohexanecarbonyl)pyrrolidin-2-yl)methoxy)-2-methyl-quinoline-3-carboxylic acid (SID 47039333)

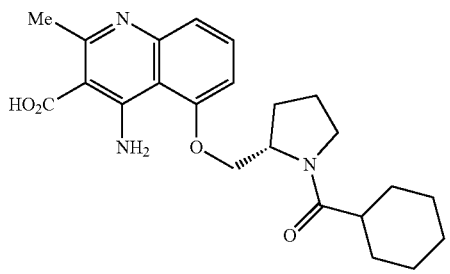 [SMILES: Cc1nc2cccc(OC[C@@H]3CCCN3C(=O)C3CCCCC3)c2c(N)c1C(=O)O]

Prepared as in Example 1 from (S)-ethyl 4-amino-5-((1-(cyclohexanecarbonyl)pyrrolidin-2-yl)methoxy)-2-methylquinoline-3-carboxylate (Example 89a) as an off-white solid (31%). $^1$H NMR (400 MHz, DMSO-d$_6$) δ 1.34-1.11 (m, 5H), 1.72-1.51 (m, 5H), 2.08-1.79 (m, 5H), 2.44-2.35 (m 1H), 2.52 (s, 3H), 3.55-3.45 (m, 2H), 4.02 (dd, J=6.8, 9.2 Hz, 1H), 4.17 (dd, J=4.8, 10.0 Hz, 1H), 4.45-4.38 (m, 1H), 6.75 (d, J=7.2 Hz), 7.11 (d, J=7.6 Hz, 1H), 7.27 (t, J=8.0 Hz, 1H). MS 412 (MH$^+$).

Example 89a: (S)-ethyl 4-amino-5-((1-(cyclohexan-ecarbonyl)pyrrolidin-2-yl)methoxy)-2-methylquinoline-3-carboxylate Prepared as in Example 24a from (S)-ethyl 4-amino-2-methyl-5-(pyrrolidin-2-ylmethoxy)-quinoline-3-carboxylate (Example 89b) and cyclohexanecarboxylic acid as brown solid (46%). MS 440 (MH+).

Example 89b: (S)-ethyl 4-amino-2-methyl-5-(pyrrolidin-2-ylmethoxy)quinoline-3-carboxylate Prepared as in Example 2a from (S)-benzyl 2-((3-amino-2-cyanophenoxy)methyl)pyrrolidine-1-carboxylate (Example 89c) and ethyl 3-oxobutanoate as brown solid. MS 330 (MH+).

Example 89c: (S)-benzyl 2-((3-amino-2-cyanophenoxy)methyl)pyrrolidine-1-carboxylate Prepared as in Example 24c from (S)-2-amino-6-(pyrrolidin-2-ylmethoxy)benzonitrile (Example 89d) as brown solid (79%). MS 351 (MH+).

Example 89d: (S)-2-amino-6-(pyrrolidin-2-ylmethoxy)benzonitrile

Prepared as in Example 24d from (S)-pyrrolidin-2-ylmethanol and 2-amino-6-fluoro-benzonitrile as brown solid (51%). MS 218 (MH+).

Example 90: (S)-4-amino-5-((1-isobutyrylpyrrolidin-2-yl)methoxy)-2-methylquinoline-3-carboxylic Acid

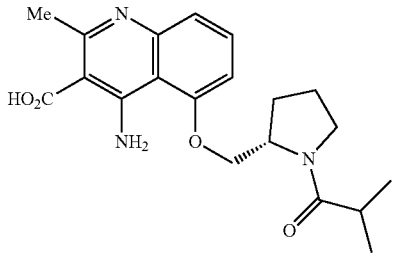 [SMILES: Cc1nc2cccc(OC[C@@H]3CCCN3C(=O)C(C)C)c2c(N)c1C(=O)O]

Prepared as in Example 1 from (S)-ethyl 4-amino-5-((1-isobutyrylpyrrolidin-2-yl)-methoxy)-2-methylquinoline-3-carboxylate (Example 90a) as an off-white solid (39%). 1H NMR (400 MHz, DMSO-d6) δ 0.99 (dd, J=2.0, 6.8 Hz, 6H), 2.05-1.83 (m, 4H), 2.65 (s, 3H), 3.53 (t, J=7.2 Hz, 2H), 4.08 (dd, J=6.8, 10.0 Hz, 1H), 4.20 (dd, J=6.0, 10.0 Hz, 1H), 4.54 (m, 1H), 6.99 (d, J=8.0 Hz, 1H), 7.21 (d, J=8.4 Hz, 1H), 7.50 (t, J=8.0 Hz, 1H). MS 344 (MH+).

Example 90a: (S)-ethyl 4-amino-5-((1-isobutyrylpyrrolidin-2-yl)-methoxy)-2-methyl-quinoline-3-carboxylate Prepared as in Example 24a from (S)-ethyl 4-amino-2-methyl-5-(pyrrolidin-2-ylmethoxy)-quinoline-3-carboxylate (Example 89b) and isobutyric acid as brown solid (46%). MS 400 (MH+).

Example 91: (S)-5-((1-acetylpyrrolidin-2-yl)methoxy)-4-amino-2-methylquinoline-3-carboxylic Acid

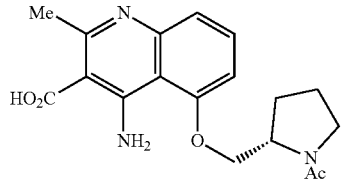

Prepared as in Example 1 from (S)-ethyl 5-((1-acetylpyrrolidin-2-yl)methoxy)-4-amino-2-methylquinoline-3-carboxylate (Example 91a) as an off-white solid (23%). 1H NMR (400 MHz, DMSO-d6) δ 1.98 (s, 3H), 2.03-1.82 (m, 4H), 2.71 (s, 3H), 3.48 (t, J=6.0 Hz, 2H), 4.05 (dd, J=6.4, 10.0 Hz, 1H), 4.22 (dd, J=6.8, 10.0 Hz, 1H), 4.54-4.46 (m, 1H), 6.99 (d, J=8.0 Hz, 1H), 7.34 (d, J=8.0 Hz, 1H), 7.54 (t, J=10.0 Hz, 1H). MS 344 (MH+).

Example 91a: (S)-ethyl 5-((1-acetylpyrrolidin-2-yl)methoxy)-4-amino-2-methylquinoline-3-carboxylate Prepared as in Example 24a from (S)-ethyl 4-amino-2-methyl-5-(pyrrolidin-2-ylmethoxy)-quinoline-3-carboxylate (Example 89b) and acetic anhydride as brown solid (31%). MS 372 (MH+).

Example 92: (R)-4-amino-5-((1-(cyclohexanecarbonyl)pyrrolidin-2-yl)methoxy)-2-methyl-quinoline-3-carboxylic Acid

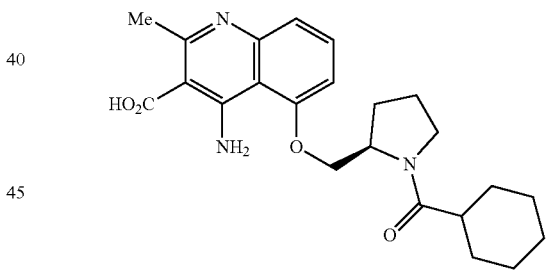

Prepared as in Example 1 from (R)-ethyl 4-amino-5-((1-(cyclohexanecarbonyl)pyrrolidin-2-yl)methoxy)-2-methylquinoline-3-carboxylate (Example 92a) as an off-white solid (37%). 1H NMR (400 MHz, DMSO-d6) δ 1.34-1.11 (m, 5H), 1.72-1.51 (m, 5H), 2.08-1.79 (m, 5H), 2.44-2.35 (m 1H), 2.52 (s, 3H), 3.55-3.45 (m, 2H), 4.02 (dd, J=6.8, 9.2 Hz, 1H), 4.17 (dd, J=4.8, 10.0 Hz, 1H), 4.45-4.38 (m, 1H), 6.75 (d, J=7.2 Hz), 7.11 (d, J=7.6 Hz, 1H), 7.27 (t, J=8.0 Hz, 1H). MS 412 (MH+).

Example 92a: (R)-ethyl 4-amino-5-((1-(cyclohexan-ecarbonyl)pyrrolidin-2-yl)methoxy)-2-methylquinoline-3-carboxylate Prepared as in Example 24a from (R)-ethyl 4-amino-2-methyl-5-(pyrrolidin-2-ylmethoxy)-quinoline-3-carboxylate (Example 92b) and cyclohexanecarboxylic acid as brown solid (39%). MS 440 (MH+).

Example 92b: (R)-ethyl 4-amino-2-methyl-5-(pyrrolidin-2-ylmethoxy)quinoline-3-carboxylate Prepared as in Example 2a from (R)-benzyl 2-((3-amino-2-cyanophenoxy)methyl)pyrrolidine-1-carboxylate (Example 92c) and ethyl 3-oxobutanoate as brown solid. MS 330 (MH+).

Example 92c: (R)-benzyl 2-((3-amino-2-cyanophenoxy)methyl)pyrrolidine-1-carboxylate Prepared as in Example 24c from (R)-2-amino-6-(pyrrolidin-2-ylmethoxy)benzonitrile (Example 92d) as brown solid (71%). MS 351 (MH+).

Example 92d: (R)-2-amino-6-(pyrrolidin-2-ylmethoxy)benzonitrile

Prepared as in Example 24d from (R)-pyrrolidin-2-ylmethanol and 2-amino-6-fluoro-benzonitrile as brown solid (57%). MS 218 (MH+).

Example 93: (R)-4-amino-5-((1-isobutyrylpyrrolidin-2-yl)methoxy)-2-methylquinoline-3-carboxylic Acid

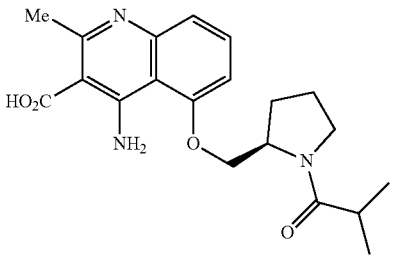 [SMILES: Cc1nc2cccc(OC[C@H]3CCCN3C(=O)C(C)C)c2c(N)c1C(=O)O]

Prepared as in Example 1 from (R)-ethyl 4-amino-5-((1-isobutyrylpyrrolidin-2-yl)-methoxy)-2-methylquinoline-3-carboxylate (Example 93a) as an off-white solid (44%). $^1$H NMR (400 MHz, DMSO-$d_6$) δ 0.99 (dd, J=2.0, 6.8 Hz, 6H), 2.05-1.83 (m, 4H), 2.65 (s, 3H), 3.53 (t, J=7.2 Hz, 2H), 4.08 (dd, J=6.8, 10.0 Hz, 1H), 4.20 (dd, J=6.0, 10.0 Hz, 1H), 4.54 (m, 1H), 6.99 (d, J=8.0 Hz, 1H), 7.21 (d, J=8.4 Hz, 1H), 7.50 (t, J=8.0 Hz, 1H). MS 344 (MH+).

Example 93a: (R)-ethyl 4-amino-5-((1-isobutyrylpyrrolidin-2-yl)-methoxy)-2-methyl-quinoline-3-carboxylate Prepared as in Example 24a from (R)-ethyl 4-amino-2-methyl-5-(pyrrolidin-2-ylmethoxy)quinoline-3-carboxylate (Example 92b) and isobutyric acid as brown solid (39%). MS 400 (MH+).

Example 94: (R)-5-((1-acetylpyrrolidin-2-yl)methoxy)-4-amino-2-methylquinoline-3-carboxylic Acid

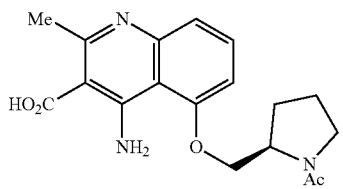

Prepared as in Example 1 from (R)-ethyl 5-((1-acetylpyrrolidin-2-yl)methoxy)-4-amino-2-methylquinoline-3-carboxylate (Example 94a) as an off-white solid (19%). $^1$H NMR (400 MHz, DMSO-$d_6$) δ 1.98 (s, 3H), 2.03-1.82 (m, 4H), 2.71 (s, 3H), 3.48 (t, J=6.0 Hz, 2H), 4.05 (dd, J=6.4, 10.0 Hz, 1H), 4.22 (dd, J=6.8, 10.0 Hz, 1H), 4.54-4.46 (m, 1H), 6.99 (d, J=8.0 Hz, 1H), 7.34 (d, J=8.0 Hz, 1H), 7.54 (t, J=10.0 Hz, 1H). MS 344 (MH+).

Example 94a: (R)-ethyl 5-((1-acetylpyrrolidin-2-yl)methoxy)-4-amino-2-methylquinoline-3-carboxylate Prepared as in Example 24a from (R)-ethyl 4-amino-2-methyl-5-(pyrrolidin-2-ylmethoxy)quinoline-3-carboxylate (Example 92b) and acetic anhydride as brown solid (28%). MS 372 (MH+).

Example 95: (S)-4-amino-5-(2-(2-hydroxybenzamido)-3-methylbutoxy)-2-methylquinoline-3-carboxylic Acid

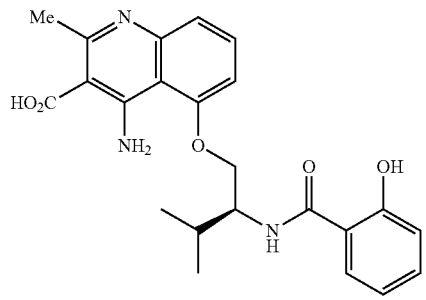 [SMILES: Cc1nc2cccc(OC[C@@H](NC(=O)c3ccccc3O)C(C)C)c2c(N)c1C(=O)O]

Prepared as in Example 1 from (S)-ethyl 4-amino-5-(2-(2-hydroxybenzamido)-3-methylbutoxy)-2-methylquinoline-3-carboxylate (Example 95a) as a white solid (82%). MS 424 (MH+).

Example 95a: (S)-ethyl 4-amino-5-(2-(2-hydroxybenzamido)-3-methylbutoxy)-2-methyl-quinoline-3-carboxylate Prepared as in Example 24a from (S)-ethyl 4-amino-5-(2-amino-3-methylbutoxy)-2-methylquinoline-3-carboxylate (Example 95b) and 2-hydroxybenzoic acid as brown solid (56%). MS 452 (MH+).

Example 95b: (S)-ethyl 4-amino-5-(2-amino-3-methylbutoxy)-2-methylquinoline-3-carboxylate Prepared as in Example 2a from (S)-benzyl 1-(3-amino-2-cyanophenoxy)-3-methylbutan-2-ylcarbamate (Example 95c) and ethyl 3-oxobutanoate as brown solid (79%). MS 332 (MH+).

Example 95c: (S)-benzyl 1-(3-amino-2-cyanophenoxy)-3-methylbutan-2-ylcarbamate

Prepared as in Example 24c from (S)-2-amino-6-(2-amino-3-methylbutoxy)benzonitrile (Example 95d) as brown solid (82%). MS 354 (MH+).

Example 95d: (S)-2-amino-6-(2-amino-3-methylbutoxy)benzonitrile

Prepared as in Example 24d from (S)-2-amino-3-methylbutan-1-ol and 2-amino-6-fluoro-benzonitrile as brown solid (71%). MS 220 (MH+).

Example 96: (S)-4-amino-5-(2-(3-hydroxybenzamido)-3-methylbutoxy)-2-methylquinoline-3-carboxylic Acid

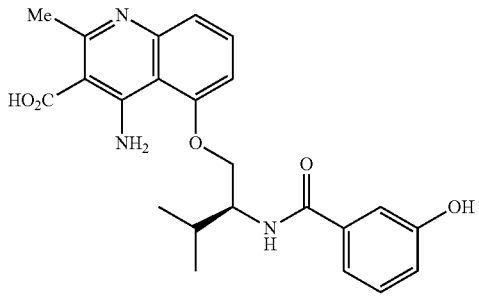 [SMILES: Cc1nc2cccc(OC[C@@H](NC(=O)c3cccc(O)c3)C(C)C)c2c(N)c1C(=O)O]

Prepared as in Example 1 from (S)-ethyl 4-amino-5-(2-(3-hydroxybenzamido)-3-methylbutoxy)-2-methylquinoline-3-carboxylate (Example 96a) as a white solid (83%). MS 424 (MH+).

Example 96a: (S)-ethyl 4-amino-5-(2-(3-hydroxybenzamido)-3-methylbutoxy)-2-methyl-quinoline-3-carboxylate Prepared as in Example 24a from (S)-ethyl 4-amino-5-(2-amino-3-methylbutoxy)-2-methylquinoline-3-carboxylate (Example 95b) and 3-hydroxybenzoic acid as brown solid (35%). MS 452 (MH+).

Example 97: (S)-4-amino-5-(2-(2-hydroxybenzamido)butoxy)-2-methylquinoline-3-carboxylic Acid

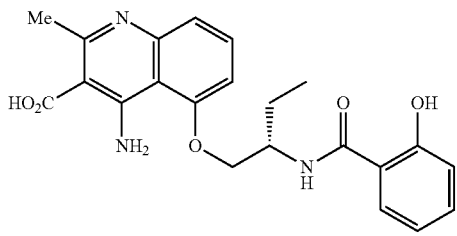 [SMILES: CC[C@@H](COc1cccc2nc(C)c(C(=O)O)c(N)c12)NC(=O)c1ccccc1O]

Prepared as in Example 1 from (S)-ethyl 4-amino-5-(2-(2-hydroxybenzamido)butoxy)-2-methylquinoline-3-carboxylate (Example 97a) as an off-white solid (78%). MS 410 (MH+).

Example 97a: (S)-ethyl 4-amino-5-(2-(2-hydroxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 2-hydroxybenzoic acid as brown solid (46%). MS 438 (MH+).

Example 97b: (S)-ethyl 4-amino-5-(2-aminobutoxy)-2-methylquinoline-3-carboxylate Prepared as in Example 2a from (S)-benzyl 1-(3-amino-2-cyanophenoxy)butan-2-ylcarbamate (Example 97c) and ethyl 3-oxobutanoate as brown solid (75%). MS 318 (MH+).

Example 97c: (S)-benzyl 1-(3-amino-2-cyanophenoxy)butan-2-ylcarbamate

Prepared as in Example 24c from (S)-2-amino-6-(2-aminobutoxy)benzonitrile (Example 97d) as brown solid (87%). MS 340 (MH+).

Example 97d: (S)-2-amino-6-(2-aminobutoxy)benzonitrile

Prepared as in Example 24d from (S)-2-aminobutan-1-ol and 2-amino-6-fluoro-benzonitrile as brown solid (73%). MS 206 (MH+).

Example 98: (S)-4-amino-5-(2-(4-(2-hydroxyethoxy)-3-methoxybenzamido)butoxy)-2-methylquinoline-3-carboxylic Acid

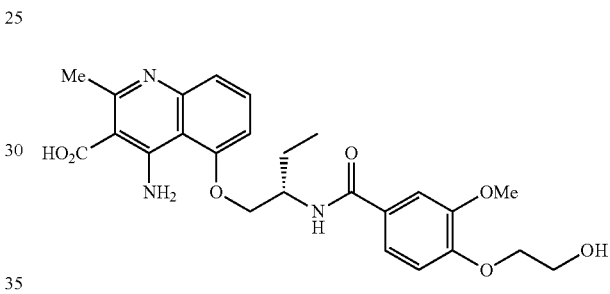

Prepared as in Example 1 from (S)-ethyl 4-amino-5-(2-(4-(2-hydroxyethoxy)-3-methoxy-benzamido)butoxy)-2-methylquinoline-3-carboxylate (Example 98a) as an off-white solid (83%). MS 484 (MH+).

Example 98a: (S)-ethyl 4-amino-5-(2-(4-(2-hydroxyethoxy)-3-methoxybenzamido)-butoxy)-2-methylquinoline-3-carboxylate Prepared as in Example 24a from (S)-ethyl 4-amino-5-(2-aminobutoxy)-2-methylquinoline-3-carboxylate (Example 97b) and 4-(2-hydroxyethoxy)-3-methoxybenzoic acid (Uto, Y. et al. Bioorg. Med. Chem. Lett. 2009, 19, 4151) as brown solid (38%). MS 512 (MH+).

Example 99: (S)-4-amino-5-(2-(2,3-dihydrobenzo[b][1,4]dioxine-5-carboxamido)butoxy)-2-methylquinoline-3-carboxylic Acid

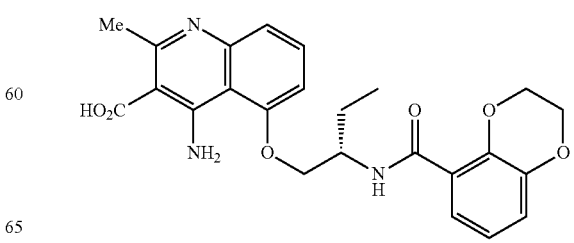

Prepared as in Example 1 from (S)-ethyl 4-amino-5-(2-(2,3-dihydrobenzo[b][1,4]dioxine-5-carboxamido)butoxy)-2-methylquinoline-3-carboxylate (Example 99a) as an off-white solid (78%). MS 452 (MH$^+$).

Example 99a: (S)-ethyl 4-amino-5-(2-(2,3-dihydrobenzo[b][1,4]dioxine-5-carboxamido)-butoxy)-2-methylquinoline-3-carboxylate Prepared as in Example 24a from (S)-ethyl 4-amino-5-(2-aminobutoxy)-2-methylquinoline-3-carboxylate (Example 97b) and 2,3-dihydrobenzo[b][1,4]dioxine-5-carboxylic acid as brown solid (40%). MS 480 (MH$^+$).

Example 100: (S)-4-amino-5-(2-(4-(3-hydroxypropoxy)-3-methoxybenzamido)butoxy)-2-methylquinoline-3-carboxylic Acid

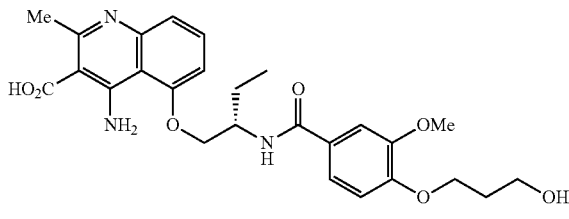 [SMILES: CC[C@@H](COc1cccc2nc(C)c(C(=O)O)c(N)c12)NC(=O)c1ccc(OCCCO)c(OC)c1]

Prepared as in Example 1 from (S)-ethyl 4-amino-5-(2-(4-(3-hydroxypropoxy)-3-methoxybenzamido)butoxy)-2-methylquinoline-3-carboxylate (Example 100a) as an off-white solid (79%). MS 498 (MH$^+$).

Example 100a: (S)-ethyl 4-amino-5-(2-(4-(3-hydroxypropoxy)-3-methoxybenzamido)-butoxy)-2-methylquinoline-3-carboxylate Prepared as in Example 24a from (S)-ethyl 4-amino-5-(2-aminobutoxy)-2-methylquinoline-3-carboxylate (Example 97b) and 4-(3-hydroxypropoxy)-3-methoxybenzoic acid (Baraldi, P. G. et al. *J. Med. Chem.* 1999, 42, 5131) as brown solid (41%). MS 526 (MH$^+$).

Example 101: (S)-4-amino-5-(2-(3,5-dihydroxybenzamido)butoxy)-2-methylquinoline-3-carboxylic Acid

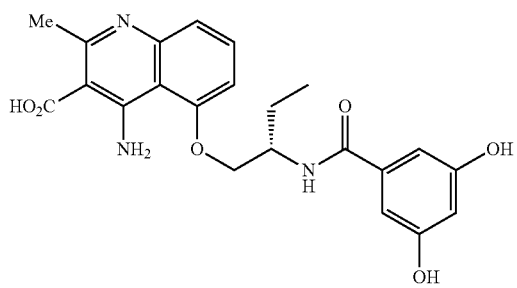 [SMILES: CC[C@@H](COc1cccc2nc(C)c(C(=O)O)c(N)c12)NC(=O)c1cc(O)cc(O)c1]

Prepared as in Example 1 from (S)-ethyl 4-amino-5-(2-(3,5-dihydroxybenzamido)butoxy)-2-methylquinoline-3-carboxylate (Example 101a) as an off-white solid (69%). MS 426 (MH$^+$).

Example 101a: (S)-ethyl 4-amino-5-(2-(3,5-dihydroxybenzamido)butoxy)-2-methyl-quinoline-3-carboxylate Prepared as in Example 24a from (S)-ethyl 4-amino-5-(2-aminobutoxy)-2-methylquinoline-3-carboxylate (Example 97b) and 3,5-dihydroxybenzoic acid as brown solid (37%). MS 454 (MH$^+$).

Example 102: (S)-4-amino-5-(2-(2,3-dihydrobenzo[b][1,4]dioxine-6-carboxamido)butoxy)-2-methylquinoline-3-carboxylic Acid

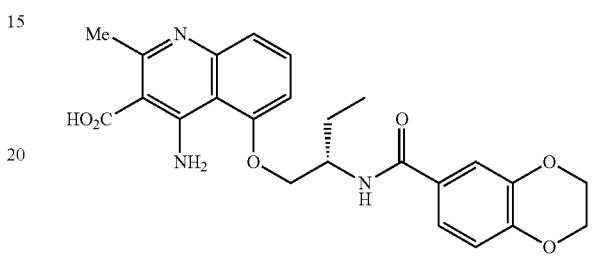

Prepared as in Example 1 from (S)-ethyl 4-amino-5-(2-(2,3-dihydrobenzo[b][1,4]dioxine-6-carboxamido)butoxy)-2-methylquinoline-3-carboxylate (Example 102a) as an off-white solid (71%). MS 452 (MH$^+$).

Example 102a: (S)-ethyl 4-amino-5-(2-(2,3-dihydrobenzo[b][1,4]dioxine-6-carboxamido) butoxy)-2-methylquinoline-3-carboxylate Prepared as in Example 24a from (S)-ethyl 4-amino-5-(2-aminobutoxy)-2-methylquinoline-3-carboxylate (Example 97b) and 2,3-dihydrobenzo[b][1,4]dioxine-6-carboxylic acid as brown solid (46%). MS 480 (MH$^+$).

Example 103: (S)-4-amino-5-(2-(3-hydroxybenzamido)butoxy)-2-methylquinoline-3-carboxylic Acid

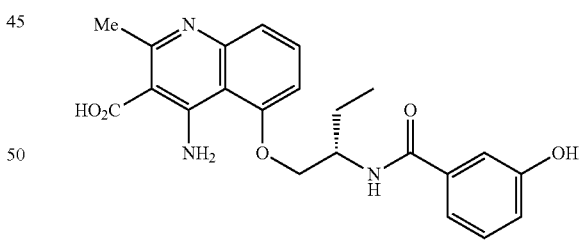

Prepared as in Example 1 from (S)-ethyl 4-amino-5-(2-(3-hydroxybenzamido)butoxy)-2-methylquinoline-3-carboxylate (Example 103a) as an off-white solid (72%). MS 410 (MH$^+$).

Example 103a: (S)-ethyl 4-amino-5-(2-(3-hydroxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 3-hydroxybenzoic acid as brown solid (49%). MS 438 (MH$^+$).

Example 104: (S)-4-amino-5-(2-(4-(3-hydroxypropoxy)-3-methoxybenzamido)-3-methylbutoxy)-2-methylquinoline-3-carboxylic Acid

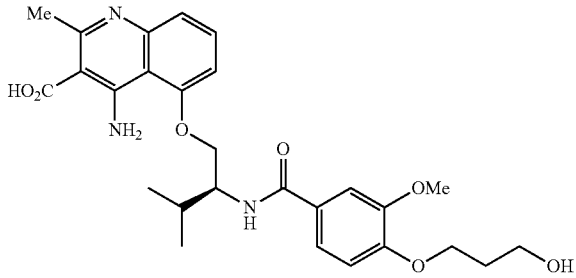 [SMILES: COc1cc(C(=O)N[C@H](COc2cccc3nc(C)c(C(=O)O)c(N)c23)C(C)C)ccc1OCCCO]

Prepared as in Example 1 from (S)-ethyl 4-amino-5-(2-(4-(3-hydroxypropoxy)-3-methoxybenzamido)-3-methylbutoxy)-2-methylquinoline-3-carboxylate (Example 104a) as an off-white solid (69%). MS 512 (MH$^+$).

Example 104a: (S)-ethyl 4-amino-5-(2-(4-(3-hydroxypropoxy)-3-methoxybenzamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 4-(3-hydroxypropoxy)-3-methoxybenzoic acid (Baraldi, P. G. et al. *J. Med. Chem.* 1999, 42, 5131) as brown solid (29%). MS 540 (MH$^+$).

Example 105: (S)-4-amino-5-(2-(3,5-dihydroxybenzamido)-3-methylbutoxy)-2-methyl-quinoline-3-carboxylic Acid

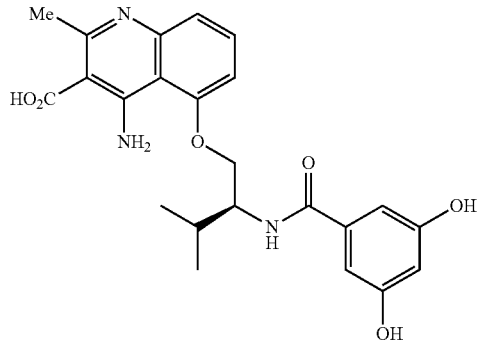 [SMILES: Cc1nc2cccc(OC[C@@H](NC(=O)c3cc(O)cc(O)c3)C(C)C)c2c(N)c1C(=O)O]

Prepared as in Example 1 from (S)-ethyl 4-amino-5-(2-(3,5-dihydroxybenzamido)-3-methylbutoxy)-2-methylquinoline-3-carboxylate (Example 105a) as a white solid (72%). MS 440 (MH$^+$).

Example 105a: (S)-ethyl 4-amino-5-(2-(3,5-dihydroxybenzamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 3,5-dhydroxybenzoic acid as brown solid (29%). MS 468 (MH$^+$).

Example 106: (S)-4-amino-5-(2-(2,3-dihydrobenzo[b][1,4]dioxine-5-carboxamido)-3-methylbutoxy)-2-methylquinoline-3-carboxylic Acid

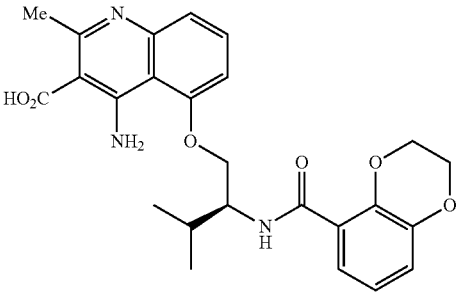 [SMILES: Cc1nc2cccc(OC[C@@H](NC(=O)c3cccc4c3OCCO4)C(C)C)c2c(N)c1C(=O)O]

Prepared as in Example 1 from (S)-ethyl 4-amino-5-(2-(2,3-dihydrobenzo[b][1,4]dioxine-5-carboxamido)-3-methylbutoxy)-2-methylquinoline-3-carboxylate (Example 106a) as a white solid (81%). MS 466 (MH$^+$).

Example 106a: (S)-ethyl 4-amino-5-(2-(2,3-dihydrobenzo[b][1,4]dioxine-5-carboxamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 2,3-dihydrobenzo[b][1,4]dioxine-5-carboxylic acid as brown solid (36%). MS 494 (MH$^+$).

Example 107: (S)-4-amino-5-(2-(2,3-dihydrobenzo[b][1,4]dioxine-6-carboxamido)-3-methylbutoxy)-2-methylquinoline-3-carboxylic Acid

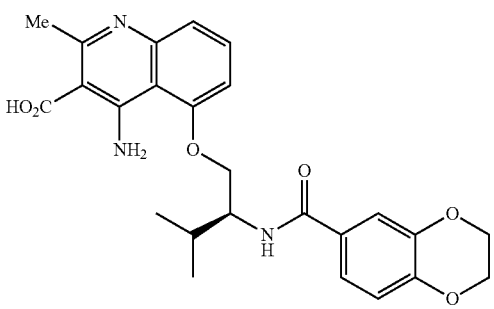 [SMILES: Cc1nc2cccc(OC[C@@H](NC(=O)c3ccc4c(c3)OCCO4)C(C)C)c2c(N)c1C(=O)O]

Prepared as in Example 1 from (S)-ethyl 4-amino-5-(2-(2,3-dihydrobenzo[b][1,4]dioxine-6-carboxamido)-3-methylbutoxy)-2-methylquinoline-3-carboxylate (Example 107a) as an off-white solid (76%). MS 466 (MH$^+$).

Example 107a: (S)-ethyl 4-amino-5-(2-(2,3-dihydrobenzo[b][1,4]dioxine-6-carboxamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 2,3-dihydrobenzo[b][1,4]dioxine-6-carboxylic acid as brown solid (29%). MS 494 (MH$^+$).

Example 108: 4-amino-5-((4-(isonicotinamido)cyclohexyl)methoxy)-2-methylquinoline-3-carboxylic Acid

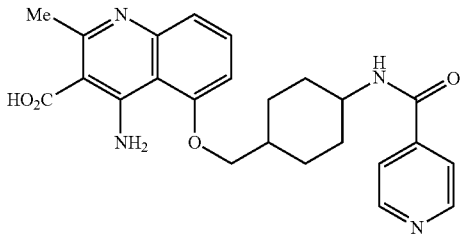 [SMILES: Cc1nc2cccc(OCC3CCC(NC(=O)c4ccncc4)CC3)c2c(N)c1C(=O)O]

Prepared as in Example 1 from ethyl 4-amino-5-((4-(isonicotinamido)cyclohexyl)-methoxy)-2-methylquinoline-3-carboxylate (Example 108a) as an off-white solid (43%). $^1$H NMR (400 MHz, DMSO-$d_6$) δ 1.52-2.01 (m, 8H), 2.13 (m, 1H), 2.74 (s, 3H), 3.99 (m, 1H), 4.18 (d, J=6.8 Hz, 2H), 7.05 (d, J=8.0 Hz, 1H), 7.26 (d, J=8.0 Hz, 1H), 7.66 (t, J=8.4 Hz, 1H), 7.71 (d, J=6.0 Hz, 2H), 8.40 (d, J=6.8 Hz, 1H), 8.71 (d, J=6.0 Hz, 2H), 12.70 (brs, 1H). MS 435 (MH$^+$).

Example 108a: ethyl 4-amino-5-((4-(isonicotinamido)cyclohexyl)-methoxy)-2-methyl-quinoline-3-carboxylate Prepared as in Example 2a from N-(4-((3-Amino-2-cyanophenoxy)methyl)cyclohexyl)-isonicotinamide (Example 108b) and ethyl 3-oxobutanoate as a yellow solid (25%). MS 463 (MH$^+$).

Example 108b: N-(4-((3-Amino-2-cyanophenoxy)methyl)cyclohexyl)isonicotinamide Prepared as in Example 22b from N-(4-(Hydroxymethyl)cyclohexyl)isonicotinamide (Example 108c) and 2-amino-6-fluorobenzonitrile as a colorless oil (6%). MS 351 (MH$^+$).

Example 108c: N-(4-(Hydroxymethyl)cyclohexyl)isonicotinamide

Prepared as in Example 24a from (4-Aminocyclohexyl)methanol and isonicotinic acid as a yellow oil (100%). MS 235 (MH$^+$).

Example 109: 4-amino-5-((2-methoxycyclohexyl)oxy)-2-methylquinoline-3-carboxylic Acid

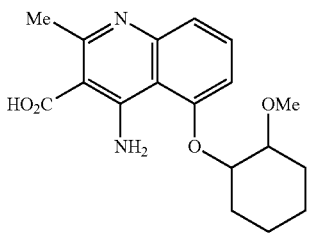 [SMILES: COC1CCCCC1Oc1cccc2nc(C)c(C(=O)O)c(N)c12]

Prepared as in Example 1 from ethyl 4-amino-5-((2-methoxycyclohexyl)oxy)-2-methylquinoline-3-carboxylate (Example 109a) as a white solid (79%). $^1$H NMR (400 MHz, DMSO-$d_6$) δ 1.20-1.68 (m, 6H), 2.16 (m, 2H), 2.78 (s, 3H), 3.34 (s, 3H), 3.58 (m, 1H), 4.50 (m, 1H), 7.17 (d, J=8.4 Hz, 1H), 7.29 (d, J=8.4 Hz, 1H), 7.67 (t, J=8.8 Hz, 1H), 8.92 (brs, 1H), 12.14 (brs, 1H), 12.86 (brs, 1H). MS 331 (MH$^+$).

Example 109a: ethyl 4-amino-5-((2-methoxycyclohexyl)oxy)-2-methylquinoline-3-carboxylate Prepared as in Example 2a from 2-Amino-6-(2-methoxycyclohexyloxy)benzonitrile (Example 109b) and ethyl 3-oxobutanoate as a pale yellow oil (16%). MS 359 (MH$^+$).

Example 109b: 2-Amino-6-(2-methoxycyclohexyloxy)benzonitrile

Prepared as in Example 22b from 2-methoxycyclohexanol and 2-amino-6-fluoro-benzonitrile as a yellow oil (34%). MS 247 (MH$^+$).

Example 110: 4-amino-5-((1-(3-hydroxybenzoyl)piperidin-3-yl)methoxy)-2-methylquinoline-3-carboxylic Acid

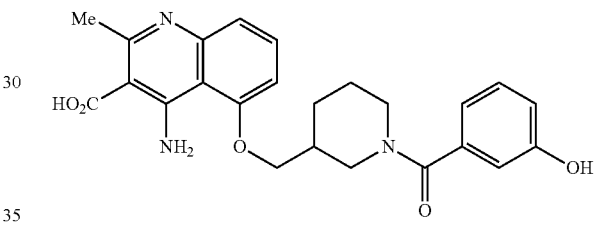

Prepared as in Example 1 from ethyl 4-amino-5-((1-(3-hydroxybenzoyl)piperidin-3-yl)methoxy)-2-methylquinoline-3-carboxylate (Example 110a) as a white solid (35%). MS 436 (MH$^+$).

Example 110a: ethyl 4-amino-5-((1-(3-hydroxybenzoyl)piperidin-3-yl)methoxy)-2-methylquinoline-3-carboxylate Prepared as in Example 24a from ethyl 4-amino-2-methyl-5-(piperidin-3-ylmethoxy)-quinoline-3-carboxylate (Example 110b) and 3-hydroxybenzoic acid as a white solid (34%). MS 464 (MH$^+$).

Example 110b: ethyl 4-amino-2-methyl-5-(piperidin-3-ylmethoxy)quinoline-3-carboxylate Prepared as in Example 2a from benzyl 3-((3-amino-2-cyanophenoxy)methyl)piperidine-1-carboxylate (Example 110c) and ethyl 3-oxobutanoate as a yellow oil (21%). MS 344 (MH$^+$).

Example 110c: benzyl 3-((3-amino-2-cyanophenoxy)methyl)piperidine-1-carboxylate Prepared as in Example 24c from 2-amino-6-(piperidin-3-ylmethoxy)benzonitrile (Example 110d) as a yellow solid (70%).

Example 110d: 2-amino-6-(piperidin-3-ylmethoxy)benzonitrile

Prepared as in Example 24d from 3-piperidinemethanol and 2-amino-6-fluoro-benzonitrile as a light yellow solid (27%). MS 232 (MH+).

Example 111: 4-amino-5-((1-(3-hydroxybenzoyl)piperidin-2-yl)methoxy)-2-methylquinoline-3-carboxylic Acid

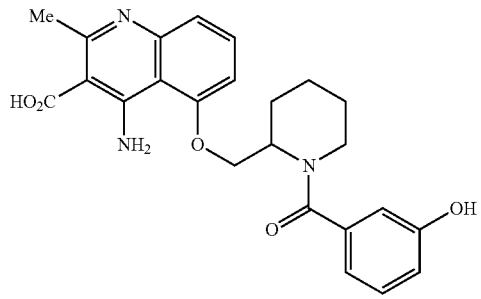 [SMILES: Cc1nc2cccc(OCC3CCCCN3C(=O)c3cccc(O)c3)c2c(N)c1C(=O)O]

Prepared as in Example 1 from ethyl 4-amino-5-((1-(3-hydroxybenzoyl)piperidin-2-yl)methoxy)-2-methylquinoline-3-carboxylate (Example 111a) as an off-white solid (35%). $^1$H NMR (400 MHz, DMSO-$d_6$) δ 1.25-1.89 (m, 6H), 2.74 (s, 3H), 3.44 (m, 2H), 4.27 (m, 1H), 4.75 (m, 2H), 5.29 (m, 1H), 6.64-6.73 (m, 2H), 6.78 (d, J=7.2 Hz, 1H), 7.18 (m, 2H), 7.26 (d, J=8.4 Hz, 1H), 7.68 (m, 1H), 8.87 (brs, 1H), 9.73 (brs, 1H), 11.96 (brs, 1H), 12.70 (brs, 1H). MS 436 (MH+).

Example 111a: ethyl 4-amino-5-((1-(3-hydroxybenzoyl)piperidin-2-yl)methoxy)-2-methylquinoline-3-carboxylate Prepared as in Example 24a from ethyl 4-amino-2-methyl-5-(piperidin-2-ylmethoxy)-quinoline-3-carboxylate (Example 111b) and 3-hydroxybenzoic acid as a white solid (28%). MS 464 (MH+).

Example 111b: ethyl 4-amino-2-methyl-5-(piperidin-2-ylmethoxy)quinoline-3-carboxylate Prepared as in Example 2a from benzyl 2-((3-amino-2-cyanophenoxy)methyl)piperidine-1-carboxylate (Example 111c) and ethyl 3-oxobutanoate as a colorless oil (13%). MS 344 (MH+).

Example 111c: benzyl 2-((3-amino-2-cyanophenoxy)methyl)piperidine-1-carboxylate Prepared as in Example 24c from 2-amino-6-(piperidin-2-ylmethoxy)benzonitrile (Example 111d) as a yellow solid (100%). MS 366 (MH+).

Example 111d: 2-Amino-6-(piperidin-2-ylmethoxy)benzonitrile

Prepared as in Example 24d from 2-piperidinemethanol and 2-amino-6-fluoro-benzonitrile as a light yellow solid (64%). MS 232 (MH+).

Example 112: 4-amino-5-cyclopropyl-2-methylquinoline-3-carboxylic Acid

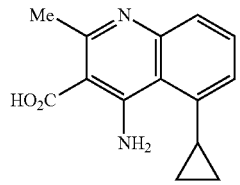 [SMILES: Cc1nc2cccc(C3CC3)c2c(N)c1C(=O)O]

Prepared as in Example 1 from ethyl 4-amino-5-cyclopropyl-2-methylquinoline-3-carboxylate (Example 112a) as a white solid (85%). $^1$H NMR (400 MHz, MeOH-d4) δ 1.03 (m, 2H), 1.31 (m, 2H), 2.53 (m, 1H), 2.81 (s, 3H), 7.50 (m, 1H), 7.58 (m, 1H), 7.73 (m, 1H). MS 243 (MH+).

Example 112a: ethyl 4-amino-5-cyclopropyl-2-methylquinoline-3-carboxylate

Prepared as in Example 2a from 2-amino-6-cyclopropylbenzonitrile (Tachdjian, C. et al. *PCT Int. Appl.* 2008, WO 2008154221) and ethyl 3-oxobutanoate as a pale yellow solid (80%). MS 271 (MH+).

Example 113: 4-amino-2-(carboxymethyl)-5-(2-cyclohexylethyl)quinoline-3-carboxylic Acid

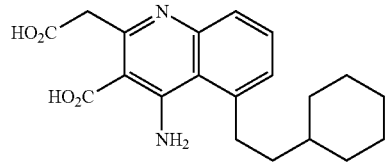 [SMILES: Nc1c(C(=O)O)c(CC(=O)O)nc2cccc(CCC3CCCCC3)c12]

Prepared as in Example 1 from ethyl 4-amino-5-(2-cyclohexylethyl)-2-(2-ethoxy-2-oxoethyl)quinoline-3-carboxylate (Example 113a) as an orange solid (69%). $^1$H NMR (400 MHz, DMSO-$d_6$) δ 0.89-0.92 (m, 2H), 1.14-1.29 (m, 4H), 1.44-1.49 (m, 2H), 1.56-1.66 (m, 4H), 1.73-1.76 (m, 1H), 3.15 (t, J=8.0 Hz, 2H), 3.70 (s, 2H), 7.09-7.11 (m, 1H), 7.38-7.42 (m, 1H), 7.46-7.51 (m, 2H). MS 338 (MH+—$H_2O$).

Example 113a: ethyl 4-amino-5-(2-cyclohexylethyl)-2-(2-ethoxy-2-oxoethyl)quinoline-3-carboxylate Prepared as in Example 2a from 2-amino-6-(2-cyclohexylethyl)benzonitrile (Example 113b) and diethyl 3-oxopentanedioate as an orange solid (33%). $^1$H NMR (400 MHz, DMSO-$d_6$) δ 0.87-0.96 (m, 2H), 1.14-1.22 (m, 7H), 1.27-1.32 (m, 4H), 1.47-1.52 (m, 2H), 1.61-1.68 (m, 4H), 1.74-1.77 (m, 2H), 3.21-3.25 (m, 2H), 4.03 (s, 2H), 4.09 (q, J=8.0 Hz, 2H), 4.27 (q, J=8.0 Hz, 2H), 7.27 (t, J=4.0 Hz, 1H), 7.57 (d, J=8.0 Hz, 2H), 7.63 (brs, 2H). MS 413 (MH+).

Example 113b: 2-amino-6-(2-cyclohexylethyl)benzonitrile

Prepared as in Example 21b from 2-amino-6-(cyclohexylethynyl)benzonitrile (Example 113c) as an orange solid (36%). ¹H NMR (400 MHz, DMSO-d₆) δ 0.90-0.95 (m, 2H), 1.16-1.24 (m, 4H), 1.41-1.46 (m, 2H), 1.60-1.75 (m, 5H), 2.58-2.62 (m, 2H), 5.90 (s, 2H), 6.48 (d, J=8.0 Hz, 1H), 6.61 (d, J=8.0 Hz, 1H), 7.18 (t, J=4.0 Hz, 1H). MS 229 (MH⁺).

Example 113c: 2-amino-6-(cyclohexylethynyl)benzonitrile

Prepared as in Example 21c from ethynylcyclohexane and 2-amino-6-bromobenzonitrile as a brown oil (100%). ¹H NMR (400 MHz, DMSO-d₆) δ 1.24-1.77 (m, 10H), 2.70 (m, 1H), 6.13 (s, 2H), 6.64 (d, J=8.0 Hz, 1H), 6.74 (d, J=8.0 Hz, 1H), 7.22 (t, J=8.0 Hz, 1H). MS 225 (MH⁺).

Example 114: 4-amino-5-(3-methoxyphenyl)-2-methylquinoline-3-carboxylic Acid

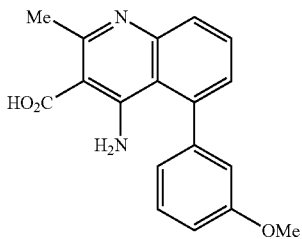 [SMILES: COc1cccc(-c2cccc3nc(C)c(C(=O)O)c(N)c23)c1]

Prepared as in Example 1 from ethyl 4-amino-5-(3-methoxyphenyl)-2-methylquinoline-3-carboxylate (Example 114a) as an off-white solid (38%). MS 309 (MH⁺).

Example 114a: ethyl 4-amino-5-(3-methoxyphenyl)-2-methylquinoline-3-carboxylate

Prepared as in Example 2a from 3-amino-3'-methoxy-[1,1'-biphenyl]-2-carbonitrile (Example 114b) and ethyl 3-oxobutanoate as a pale yellow solid (55%). MS 337 (MH⁺).

Example 114b: 3-amino-3'-methoxy-[1,1'-biphenyl]-2-carbonitrile

To a stirred solution of 2-amino-6-bromobenzonitrile (195 mg, 1.0 mmol) and (3-methoxyphenyl)boronic acid (300 mg, 2 mmol) in dioxane (2 mL) was added aqueous potassium carbonate (2.0 mmol, 0.7 mL). The reaction solution was degassed by bubbling N₂ for 2 minutes.

Palladium tetrakistriphenylphosphine (5% mol) was added to the reaction mixture and the reaction vessel was placed in a microwave reactor and irradiated at 165° C. for 20 minutes. The precipitate was removed by filtration and the filtrate concentrated. The residue was purified by HPLC (acetonitrile/water; 10-90% gradient, 25 minutes) to give the title compound as an off-white solid (180 mg, 80%). MS 225 (MH⁺).

Example 115: 4-amino-5-(cyclohexylmethoxy)-2-methylquinoline-3-carboxylic Acid

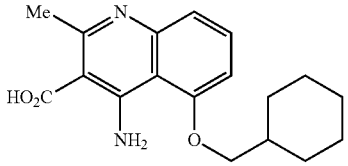 [SMILES: Cc1nc2cccc(OCC3CCCCC3)c2c(N)c1C(=O)O]

Prepared as in Example 1 from ethyl 4-amino-5-(cyclohexylmethoxy)-2-methylquinoline-3-carboxylate (Example 115a) as a white solid (84%). ¹H NMR (400 MHz, DMSO-d₆) δ 1.03-1.29 (m, 5H), 1.63-1.82 (m, 5H), 1.94 (m, 1H), 2.75 (s, 3H), 4.06 (d, J=6.4 Hz, 2H), 7.03 (d, J=8.0 Hz, 1H), 7.26 (d, J=8.4 Hz, 1H), 7.66 (t, J=8.4 Hz, 1H). MS 315 (MH⁺).

Example 115a: ethyl 4-amino-5-(cyclohexylmethoxy)-2-methylquinoline-3-carboxylate Prepared as in Example 2a from 2-amino-6-(cyclohexylmethoxy)benzonitrile (Example 115b) and ethyl 3-oxobutanoate as a pale yellow solid (47%). ¹H NMR (400 MHz, MeOD) δ 1.12-1.37 (m, 6H), 1.42 (t, J=4.0 Hz, 3H), 1.73-2.01 (m, 5H), 2.68 (s, 3H), 4.06 (d, J=4.0 Hz, 2H), 4.42 (q, J=8.0 Hz, 2H), 6.96 (d, J=8.0 Hz, 1H), 7.32 (d, J=8.0 Hz, 1H), 7.58 (t, J=8.0 Hz, 1H). MS 343 (MH⁺).

Example 115b: 2-amino-6-(cyclohexylmethoxy)benzonitrile

Prepared as in Example 22b from cyclohexylmethanol and 2-amino-6-fluorobenzonitrile as a colorless oil (50%). ¹H NMR (400 MHz, CDCl₃) δ 1.07-1.09 (m, 2H), 1.28-1.32 (m, 3H), 1.75-1.90 (m, 6H), 3.79 (d, J=6.4 Hz, 2H), 4.37 (s, 2H), 6.20 (d, J=8.4 Hz, 1H), 6.28 (d, J=8.4 Hz, 1H), 7.19 (t, J=8.4 Hz, 1H). MS 231 (MH⁺).

Example 116: 4-amino-5-(cyclohexylmethoxy)-2-methylquinoline-3-carboxylic Acid

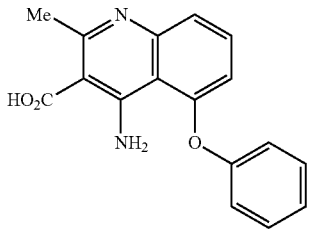 [SMILES: Cc1nc2cccc(Oc3ccccc3)c2c(N)c1C(=O)O]

Prepared as in Example 1 from ethyl 4-amino-2-methyl-5-phenoxyquinoline-3-carboxylate (Example 116a) as an off-white solid (47%). ¹H NMR (400 MHz, DMSO-d₆) δ 2.77 (s, 3H), 6.60 (d, J=4.0 Hz, 1H), 7.23 (d, J=8.0 Hz, 2H), 7.30 (t, J=8.0 Hz, 1H), 7.40 (dd, J=8.0 Hz, 1H), 7.49 (t, J=8.0 Hz, 2H), 7.60 (t, J=8.0 Hz, 1H), 8.81 (brs, 1H), 12.20 (brs, 1H), 12.81 (brs, 1H). MS 295 (MH⁺).

Example 116a: ethyl 4-amino-2-methyl-5-phenoxyquinoline-3-carboxylate

Prepared as in Example 2a from 2-amino-6-phenoxybenzonitrile and ethyl 3-oxobutanoate as a yellow oil (72%). ¹H NMR (400 MHz, DMSO-d$_6$) δ 1.32 (t, J=8.0 Hz, 3H), 2.59 (s, 3H), 4.33 (q, J=8.0 Hz, 2H), 6.61 (dd, J=8.0 Hz, 1H), 7.16 (d, J=4.0 Hz, 2H), 7.25 (t, J=8.0 Hz, 1H), 7.39-7.52 (m, 4H), 7.93 (brs, 2H). MS 323 (MH$^+$).

Example 117: 4-amino-5-(3-((4-methoxybenzyl) amino)-2,2-dimethyl-3-oxopropoxy)-2-methylquinoline-3-carboxylic Acid

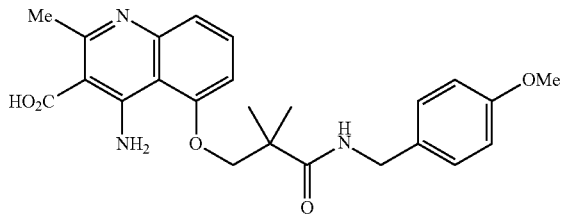 [SMILES: COc1ccc(CNC(=O)C(C)(C)COc2cccc3nc(C)c(C(=O)O)c(N)c23)cc1]

Prepared as in Example 1 from ethyl 4-amino-5-(3-((4-methoxybenzyl)amino)-2,2-dimethyl-3-oxopropoxy)-2-methylquinoline-3-carboxylate (Example 117a) as an off-white solid (38%). MS 438 (MH$^+$).

Example 117a: ethyl 4-amino-5-(3-((4-methoxybenzyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and (4-methoxyphenyl)methanamine as a yellow solid (100%). MS 466 (MH$^+$).

Example 118: 4-amino-2-methyl-5-((tetrahydro-2H-pyran-4-yl)oxy)quinoline-3-carboxylic Acid

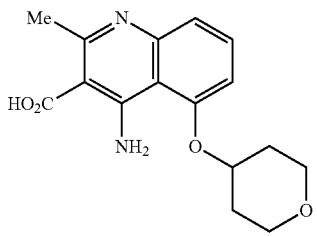 [SMILES: Cc1nc2cccc(OC3CCOCC3)c2c(N)c1C(=O)O]

Prepared as in Example 1 from ethyl 4-amino-2-methyl-5-((tetrahydro-2H-pyran-4-yl)oxy)quinoline-3-carboxylate (Example 118a) as an off-white solid (80%). $^1$H NMR (400 MHz, DMSO-d$_6$) δ 1.81 (m, 2H), 2.06 (m, 2H), 2.75 (s, 3H), 3.87 (m, 2H), 4.91 (m, 1H), 7.15 (d, J=8.0 Hz, 1H), 7.26 (d, J=8.0 Hz, 1H), 7.65 (t, J=8.0 Hz, 1H). MS 303 (MH$^+$).

Example 118a: ethyl 4-amino-2-methyl-5-((tetrahydro-2H-pyran-4-yl)oxy)quinoline-3-carboxylate Prepared as in Example 2a from 2-amino-6-((tetrahydro-2H-pyran-4-yl)oxy)benzonitrile (Example 118b) and ethyl 3-oxobutanoate as a pale yellow solid (51%). MS 331 (MH$^+$).

Example 118b: 2-amino-6-((tetrahydro-2H-pyran-4-yl)oxy)benzonitrile

Prepared as in Example 22b from tetrahydro-2H-pyran-4-ol and 2-amino-6-fluorobenzonitrile as a colorless oil (48%). $^1$H NMR (400 MHz, CDCl$_3$) δ 1.87 (m, 2H), 2.00 (m, 2H), 3.63 (m, 2H), 4.00 (m, 2H), 4.42 (s, 2H), 4.58 (m, 1H), 6.23 (d, J=8.4 Hz, 1H), 6.30 (d, J=8.4 Hz, 1H), 7.20 (t, J=8.4 Hz, 1H). MS 219 (MH$^+$).

Example 119: 4-amino-5-(2,2-dimethyl-3-oxo-3-((pyridin-4-ylmethyl)amino)propoxy)-2-methylquinoline-3-carboxylic Acid

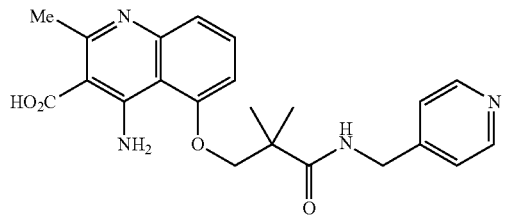 [SMILES: Cc1nc2cccc(OCC(C)(C)C(=O)NCc3ccncc3)c2c(N)c1C(=O)O]

Prepared as in Example 1 from ethyl 4-amino-5-(2,2-dimethyl-3-oxo-3-((pyridin-4-ylmethyl)amino)propoxy)-2-methylquinoline-3-carboxylate (Example 119a) as an off-white solid (44%). MS 409 (MH$^+$).

Example 119a: ethyl 4-amino-5-(2,2-dimethyl-3-oxo-3-((pyridin-4-ylmethyl)amino)propoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and pyridin-4-ylmethanamine as a brown solid (43%). MS 437 (MH$^+$).

Example 120: 4-amino-5-(3-hydroxy-2,2-dimethylpropoxy)-2-methylquinoline-3-carboxylic Acid

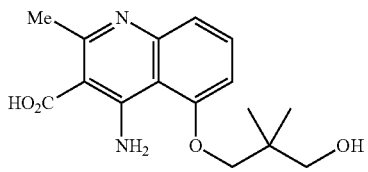 [SMILES: Cc1nc2cccc(OCC(C)(C)CO)c2c(N)c1C(=O)O]

Prepared as in Example 1 from ethyl 4-amino-5-(3-hydroxy-2,2-dimethylpropoxy)-2-methylquinoline-3-carboxylate (Example 120a) as an off-white solid (33%). $^1$H NMR (400 MHz, DMSO-d$_6$) δ 0.98 (s, 6H), 2.75 (s, 3H), 3.37 (s, 2H), 3.97 (s, 2H), 5.12 (brs, 1H), 7.01 (d, J=8.4 Hz, 1H), 7.25 (d, J=7.6 Hz, 1H), 7.66 (t, J=8.0 Hz, 1H), 9.27 (brs, 1H), 12.23 (brs, 1H), 12.73 (brs, 1H). MS 305 (MH$^+$).

Example 120a: ethyl 4-amino-5-(3-hydroxy-2,2-dimethylpropoxy)-2-methylquinoline-3-carboxylate Prepared as in Example 2a from 3-(3-amino-2-cyanophenoxy)-2,2-dimethylpropyl acetate (Tachdjian, C. et al. *PCT Int. Appl.* 2008, WO 2008154221) and ethyl 3-oxobutanoate as a pale yellow solid (26%). MS 333 (MH$^+$).

Example 121: 4-amino-5-((1-isobutyrylpiperidin-4-yl)methoxy)-2-methylquinoline-3-carboxylic Acid

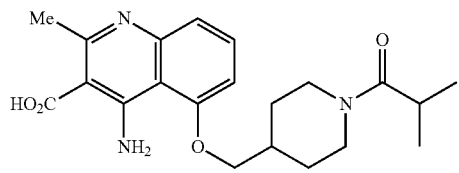 [SMILES: Cc1nc2cccc(OCC3CCN(C(=O)C(C)C)CC3)c2c(N)c1C(=O)O]

Prepared as in Example 1 from ethyl 4-amino-5-((1-isobutyrylpiperidin-4-yl)methoxy)-2-methylquinoline-3-carboxylate (Example 121a) as a white solid (38%). $^1$H NMR (400 MHz, DMSO-$d_6$) δ 0.99 (m, 6H), 1.13-1.23 (m, 2H), 1.78-1.89 (m, 2H), 2.26 (brs, 1H), 2.51 (m, 1H), 2.78 (brs, 3H), 2.88 (m, 1H), 3.06 (t, J=12.0 Hz, 1H), 4.02 (d, J=12.0 Hz, 1H), 4.41 (m, 2H), 4.44 (d, J=12.0 Hz, 1H), 7.07 (brs, 1H), 7.28 (d, J=8.0 Hz, 1H), 7.70 (brs, 1H), 8.76 (brs, 1H), 12.37 (brs, 1H), 12.67 (brs, 1H). MS 386 (MH$^+$).

Example 121a: ethyl 4-amino-5-((1-isobutyrylpiperidin-4-yl)methoxy)-2-methylquinoline-3-carboxylate Prepared as in Example 2a from 2-amino-6-((1-(4-methoxybenzyl)piperidin-4-yl)methoxy)benzonitrile (Example 121b) and ethyl 3-oxobutanoate as a yellow oil (36%). $^1$H NMR (400 MHz, DMSO-$d_6$) δ 0.97 (m, 6H), 1.32 (t, J=8.0 Hz, 3H), 1.79-1.88 (m, 3H), 2.15-2.18 (m, 2H), 2.55 (s, 3H), 2.86 (m, 1H), 3.04 (m, 1H), 4.00 (m, 2H), 4.07 (d, J=4.0 Hz, 2H), 4.32 (q, J=8.0 Hz, 2H), 4.46 (m, 1H), 6.91 (d, J=8.0 Hz, 1H), 7.24 (d, J=8.0 Hz, 1H), 7.51 (t, J=8.0 Hz, 1H), 8.07 (brs, 2H). MS 414 (MH$^+$).

Example 121b: 2-amino-6-((1-(4-methoxybenzyl)piperidin-4-yl)methoxy)benzonitrile Prepared as in Example 22b from 1-(4-(hydroxymethyl)piperidin-1-yl)-2-methylpropan-1-one (Example 121c) and 2-amino-6-fluorobenzonitrile as a pale yellow solid (21%). $^1$H NMR (400 MHz, DMSO-$d_6$) δ 0.99 (m, 6H), 1.13-1.24 (m, 2H), 1.74-1.81 (m, 2H), 1.99 (m, 1H), 2.55 (m, 1H), 2.84 (m, 1H), 3.01 (m, 1H), 3.88 (m, 2H), 4.02 (m, 1H), 4.46 (m, 1H), 5.99 (s, 2H), 6.22 (d, J=8.0 Hz, 1H), 6.34 (d, J=8.0 Hz, 1H), 7.17 (t, J=8.0 Hz, 1H). MS 302 (MH$^+$).

Example 121c: 1-(4-(hydroxymethyl)piperidin-1-yl)-2-methylpropan-1-one

Prepared as in Example 24a from isobutyric acid and piperidin-4-ylmethanol as a colorless oil (36%). MS 186 (MH$^+$).

Example 122: 4-amino-5-(((1R,2S,5R)-2-isopropyl-5-methylcyclohexyl)oxy)-2-methylquinoline-3-carboxylic Acid

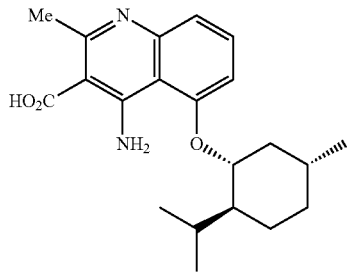 [SMILES: Cc1nc2cccc(O[C@@H]3C[C@H](C)CC[C@H]3C(C)C)c2c(N)c1C(=O)O]

Prepared as in Example 1 from ethyl 4-amino-5-(((1R,2S,5R)-2-isopropyl-5-methyl-cyclohexyl)oxy)-2-methylquinoline-3-carboxylate (Example 122a) as a white solid (64%). $^1$H NMR (400 MHz, DMSO-$d_6$) δ 0.70 (d, J=6.8 Hz, 3H), 0.89 (t, J=7.6 Hz, 6H), 0.9-1.0 (m, 2H), 1.04 (m, 2H), 1.50-1.82 (m, 5H), 1.95-2.05 (m, 1H), 2.05-2.20 (m, 1H), 2.72 (s, 3H), 4.52 (t-d, J=10.4, 4.4 Hz, 1H), 7.13 (d, J=8.0 Hz, 1H), 7.21 (d, J=8.0 Hz, 1H), 7.61 (t, J=8.0 Hz, 1H), 8.68 (brs, 1H), 11.72 (brs, 1H), 12.73 (brs, 1H). MS 357 (MH$^+$).

Example 122a: ethyl 4-amino-5-(((1R,2S,5R)-2-isopropyl-5-methylcyclohexyl)oxy)-2-methylquinoline-3-carboxylate Prepared as in Example 2a from 2-amino-6-(((1R,2S,5R)-2-isopropyl-5-methylcyclo-hexyl)oxy)benzonitrile (Example 122b) and ethyl 3-oxobutanoate as a pale yellow solid (43%). MS 385 (MH$^+$).

Example 122b: 2-amino-6-(((1R,2S,5R)-2-isopropyl-5-methylcyclohexyl)oxy)benzonitrile Prepared as in Example 22b from (1R,2S,5R)-2-isopropyl-5-methylcyclohexanol and 2-amino-6-fluorobenzonitrile as a white solid (51%). MS 273 (MH$^+$).

Example 123: 4-amino-5-(2-(3-(2-hydroxyethoxy)-5-methoxybenzamido)-2-methylpropoxy)-2-methylquinoline-3-carboxylic acid hydrochloride

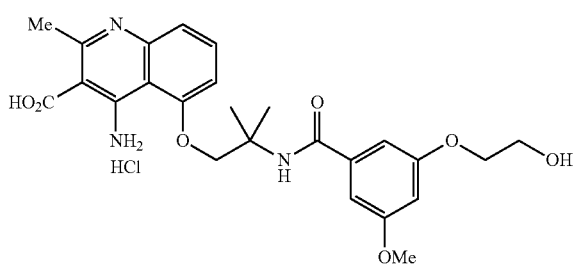 [SMILES: COc1cc(OCCO)cc(C(=O)NC(C)(C)COc2cccc3nc(C)c(C(=O)O)c(N)c23)c1 ; Cl]

To a stirred suspension of 4-amino-5-(2-(3-(2-hydroxyethoxy)-5-methoxybenzamido)-2-methylpropoxy)-2-methylquinoline-3-carboxylic acid (Example 38, 263 mg, 0.544 mmol) in EtOH (2 mL) was added HCl in EtOH (1.25 N, 479 uL, 1.1 equiv.). The mixture was stirred at room temperature until it became a clear solution (0.5 h). The solution was concentrated under reduced pressure to give the title compound as a white solid, which was further purified by re-crystallization from EtOH/H$_2$O and dried under vacuum overnight (248 mg, 87%). $^1$H NMR (400 MHz, DMSO-d$_6$) δ 1.51 (s, 6H), 2.80 (s, 3H), 3.68 (t, J=5.2 Hz, 2H), 3.74 (s, 3H), 3.97 (t, J=5.2 Hz, 1H), 4.53 (s, 2H), 6.59 (s, 1H), 6.92 (s, 1H), 6.94 (s, 1H), 7.27 (d, J=8.0 Hz, 1H), 7.57 (d, J=8.4 Hz, 1H), 7.86 (t, J=8.4 Hz, 1H), 8.03 (s, 1H), 9.40 (s, 1H), 9.98 (s, 1H). 484 (MH$^+$–HCl).

Example 124: 4-amino-5-(cyclopentylmethoxy)-2-methylquinoline-3-carboxylic acid Hydrochloride

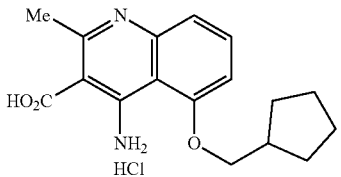 [SMILES: Cc1nc2cccc(OCC3CCCC3)c2c(N)c1C(=O)O ; Cl]

Prepared as in Example 123 from 4-amino-5-(cyclopentylmethoxy)-2-methylquinoline-3-carboxylic acid (Example 18) as a white solid (100%). $^1$H NMR (400 MHz, DMSO-d$_6$) δ 1.29-1.37 (m, 2H), 1.51-1.66 (m, 4H), 1.82-1.90 (m, 2H), 2.43-2.51 (m, 1H), 2.81 (s, 3H), 4.18 (d, J=7.2 Hz, 2H), 7.24 (d, J=8.4 Hz, 1H), 7.60 (d, J=8.4 Hz, 1H), 7.84 (t, J=8.4 Hz, 1H), 9.25 (brs, 1H), 9.86 (brs, 1H). MS 301 (MH$^+$—HCl).

Example 125: 4-amino-5-((1-(4-methoxybenzyl)piperidin-4-yl)methoxy)-2-methylquinoline-3-carboxylic Acid

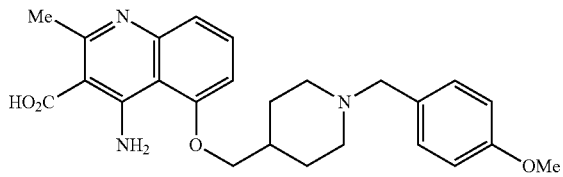 [SMILES: COc1ccc(CN2CCC(COc3cccc4nc(C)c(C(=O)O)c(N)c34)CC2)cc1]

Prepared as in Example 1 from ethyl 4-amino-5-((1-(4-methoxybenzyl)piperidin-4-yl)methoxy)-2-methylquinoline-3-carboxylate (Example 125a) as a white solid (23%). $^1$H NMR (400 MHz, DMSO-d$_6$) δ 1.67 (brs, 2H), 2.09 (m, 2H), 2.31 (brs, 1H), 2.92 (brs, 2H), 3.48 (brs, 2H), 3.82 (s, 3H), 4.15 (brs, 2H), 4.25 (d, J=8.0 Hz, 2H), 7.02 (d, J=8.0 Hz, 2H), 7.14 (d, J=8.0 Hz, 1H), 7.30 (d, J=8.0 Hz, 1H), 7.42 (d, J=8.0 Hz, 2H), 7.76 (t, J=8.0 Hz, 1H). MS 436 (MH$^+$).

Example 125a: ethyl 4-amino-5-((1-(4-methoxybenzyl)piperidin-4-yl)methoxy)-2-methylquinoline-3-carboxylate Prepared as in Example 2a from 2-amino-6-((1-(4-methoxybenzyl)piperidin-4-yl)methoxy)benzonitrile (Example 125b) and ethyl 3-oxobutanoate as an off-white solid (30%). $^1$H NMR (400 MHz, DMSO-d$_6$) δ 1.29-1.33 (m, 5H), 1.74 (m, 2H), 1.92 (m, 3H), 2.54 (s, 3H), 2.83 (m, 2H), 3.38 (s, 2H), 3.71 (s, 3H), 4.04 (d, J=8.0 Hz, 2H), 4.31 (q, J=8.0 Hz, 2H), 6.86 (d, J=8.0 Hz, 2H), 6.90 (d, J=8.0 Hz, 1H), 7.19 (d, J=8.0 Hz, 2H), 7.23 (d, J=8.0 Hz, 1H), 7.50 (t, J=8.0 Hz, 1H), 8.04 (brs, 2H). MS 464 (MH$^+$).

Example 125b: 2-amino-6-((1-(4-methoxybenzyl)piperidin-4-yl)methoxy)benzonitrile Prepared as in Example 22b from (1-(4-methoxybenzyl)piperidin-4-yl)methanol (Example 125c) and 2-amino-6-fluorobenzonitrile as an orange solid (19%). MS 352 (MH$^+$).

Example 125c: (1-(4-methoxybenzyl)piperidin-4-yl)methanol

To a solution of 4-piperidinemethanol (2.28 g, 19.78 mmol) and 4-methoxybenzaldehyde (2.30 mL, 19.77 mmol) in THF/DCE (1:1 by volume, 100 mL) was added acetic acid (1 mL), followed by NaBH(OAc)$_3$ (16.76 g, 79.08 mmol) in small portions. The reaction mixture was stirred at room temperature overnight under N$_2$. The reaction was diluted with DCM and basified to pH=10 with 2 N NaOH solution. The organic layer was separated, dried over Na$_2$SO$_4$, filtered and evaporated under reduced pressure. The residue was purified by chromatography on silica gel (Eluent: 60% EtOAc in hexanes) to give the title compound as a pale yellow oil (2.13 g, 46%). $^1$H NMR (400 MHz, DMSO-d$_6$) δ 1.04-1.13 (m, 2H), 1.28-1.32 (m, 1H), 1.58-1.61 (m, 2H), 1.79-1.86 (m, 2H), 2.75-2.77 (m, 2H), 3.22 (t, J=8.0 Hz, 2H), 3.34 (s, 2H), 3.72 (s, 3H), 4.38 (t, J=4.0 Hz, 1H), 6.85 (d, J=8.0 Hz, 2H), 7.16 (d, J=8.0 Hz, 2H). MS 236 (MH$^+$).

Example 126: 4-amino-5-((4-(isopropylcarbamoyl)cyclohexyl)methoxy)-2-methylquinoline-3-carboxylic Acid

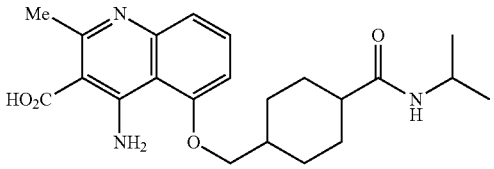 [SMILES: Cc1nc2cccc(OCC3CCC(C(=O)NC(C)C)CC3)c2c(N)c1C(=O)O]

Prepared as in Example 1 from ethyl 4-amino-5-((4-(isopropylcarbamoyl)cyclohexyl)-methoxy)-2-methylquinoline-3-carboxylate (Example 126a) as a yellow solid (76%). $^1$H NMR (400 MHz, DMSO-d$_6$) δ 1.00 (d, J=6.8 Hz, 6H), 1.15-2.32 (m, 10H), 2.75 (s, 3H), 3.82 (o, J=7.6 Hz, 1H), 4.16 (d, J=6.8 Hz, 2H), 7.07 (br d, J=7.2 Hz, 1H), 7.25 (d, J=8.0 Hz, 1H), 7.49 (d, J=7.6 Hz, 1H), 7.67 (br t, 1H), 8.77 (s, 1H), 12.23 (s, 1H), 12.66 (s, 1H). MS 400 (MH$^+$).

Example 126a: ethyl 4-amino-5-((4-(isopropylcarbamoyl)cyclohexyl)methoxy)-2-methylquinoline-3-carboxylate Prepared as in Example 2a from 4-((3-amino-2-cyanophenoxy)methyl)-N-isopropylcyclohexanecarboxamide (Example 126b) and ethyl 3-oxobutanoate as a pale yellow solid (37%). $^1$H NMR (400 MHz, DMSO-d$_6$) δ 1.01 (d, J=6.4 Hz, 6H), 1.32 (t, J=7.2 Hz, 3H), 1.38-1.81 (m, 8H), 1.88 (m, 1H), 2.25 (m, 1H), 2.55 (s, 3H), 3.82 (bro, J=7.6 Hz, 1H), 4.10 (d, J=6.4 Hz, 2H), 4.31 (q, J=7.6 Hz, 2H), 6.93 (d, J=7.6 Hz, 1H), 7.22 (d, J=8.8 Hz, 1H), 7.50 (m, 2H), 8.09 (s, 2H). MS 428 (MH$^+$).

Example 126b: 4-((3-amino-2-cyanophenoxy)methyl)-N-isopropylcyclohexanecarboxamide Prepared as in Example 21b from 4-((2-cyano-3-nitrophenoxy)methyl)-N-isoproplycyclo-hexanecarboxamide (Example 126c) as a yellow solid (81%). $^1$H NMR (400 MHz, DMSO-$d_6$) δ 0.99 (d, J=5.6 Hz, 6H), 1.22-1.99 (m, 9H), 2.17 (m, 1H), 3.80 (m, 1H), 3.88 (d, J=7.2 Hz, 2H), 5.94 (brs, 2H), 6.18 (t, J=8.0 Hz, 1H), 6.23 (d, J=8.0 Hz, 1H), 6.31 (d, J=8.8 Hz, 1H), 7.44 (s, 1H). MS 316 (H+).

Example 126c: 4-((2-cyano-3-nitrophenoxy)methyl-N-isopropylcyclohexancarboxamide To a solution of 4-(hydroxymethyl)-N-isopropylcyclohexanecarboxamide (Example 126d, 480 mg, 2.41 mmol) in dry THF (10 mL) was added NaH (60% in mineral oil, 116 mg, 4.82 mmol) in small portions at 0° C. under $N_2$. The reaction mixture was stirred at 0° C. under $N_2$ for 2 h. To this solution was added 2,6-dinitrobenzonitrile (465 mg, 2.41 mmol), and the reaction mixture was stirred at 0° C.-RT for another 2 h, and then at 60° C. overnight under $N_2$ and cooled down to room temperature. The reaction was quenched with brine, and extracted with EtOAc (3×). The combined organic layers were washed with brine, dried over $Na_2SO_4$, filtered, and evaporated under reduced pressure. The residue was purified by chromatography on silica gel (eluent: 50% EtOAc in hexanes) to give the title compound as yellow solid (594 mg, 71%). $^1$H NMR (400 MHz, DMSO-$d_6$) δ 1.00 (d, J=7.6 Hz, 6H), 1.22-2.08 (m, 9H), 2.19 (m, 1H), 3.79 (m, 1H), 4.15 (d, J=7.6 Hz, 2H), 7.45 (brs, 1H), 7.78 (d, J=7.2 Hz, 1H), 7.88 (m, 2H). MS 346 (H+).

Example 126d: 4-(hydroxymethyl)-N-isopropylcyclohexanecarboxamide

Prepared as in Example 24a from 4-(hydroxymethyl)cyclohexanecarboxylic acid and propan-2-amine as a colorless oil (57%). $^1$H NMR (400 MHz, DMSO-$d_6$) δ 1.00 (d, J=7.6 Hz, 6H), 1.22-2.08 (m, 9H), 2.12 (m, 1H), 3.28 (t, J=7.6 Hz, 2H), 3.79 (m, 1H), 4.34 (s, 1H), 7.43 (s, 1H). MS 200 (MH$^+$).

Example 127: 4-amino-5-(cyclohexyloxy)-2-methylquinoline-3-carboxylic acid Hydrochloride

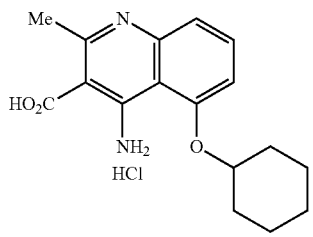 [SMILES: Cc1nc2cccc(OC3CCCCC3)c2c(N)c1C(=O)O ; Cl]

To a suspension of 4-amino-5-(cyclohexyloxy)-2-methylquinoline-3-carboxylic acid (Example 36, 1.0 g, 3.33 mmol) in ethanol (10 mL) was added 1.25 M solution of HCl in ethanol (2.93 mL, 3.66 mmol). The clear solution was stirred for 30 minutes and evaporated to dryness to provide 4-amino-5-(cyclohexyloxy)-2-methylquinoline-3-carboxylic acid hydrochloride (1.12 g, 100%) as a white solid. $^1$H NMR (400 MHz, DMSO-$d_6$) δ 1.30 (m, 1H), 1.39-1.47 (m, 2H), 1.53-1.72 (m, 5H), 2.01-2.05 (m, 2H), 2.82 (s, 3H), 4.78-4.82 (m, 1H), 7.29-7.31 (d, J=8.0 Hz, 1H), 7.61-7.63 (d, J=8.0 Hz, 1H), 7.82 (t, J=8.4 Hz, 1H), 9.30 (bs, 1H), 9.93 (bs, 1H). MS 301 (MH$^+$—HCl).

Example 128: sodium 4-amino-5-(cyclohexyloxy)-2-methylquinoline-3-carboxylate

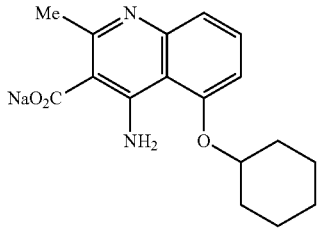

To a solution of 4-amino-5-(cyclohexyloxy)-2-methylquinoline-3-carboxylic acid (Example 36, 1.0 g, 3.33 mmol) in ethanol (20 mL) was added a solution of $NaHCO_3$ (294 mg, 3.50 mmol) in water (15 mL). The mixture was stirred and warmed up to 60° C. until the solution become clear then evaporated to dryness to provide sodium 4-amino-5-(cyclohexyloxy)-2-methylquinoline-3-carboxylate (1.07 g, 100%) as a white solid. $^1$H NMR (400 MHz, DMSO-$d_6$) δ 1.25-1.45 (m, 3H), 1.50-1.70 (m, 5H), 1.53-1.72 (m, 5H), 1.98-2.00 (m, 2H), 2.64 (s, 3H), 4.59-4.63 (m, 1H), 6.87-6.89 (d, J=7.6 Hz, 1H), 7.20-7.22 (d, J=8.0 Hz, 1H), 7.42 (t, J=8.0 Hz, 1H). MS 301 (MH$^+$+H-Na).

Example 129: (±)-4-amino-5-((2-(5-(isopropylcarbamoyl)-2-methoxyphenoxy)cyclohexyl)-oxy)-2-methylquinoline-3-carboxylic Acid

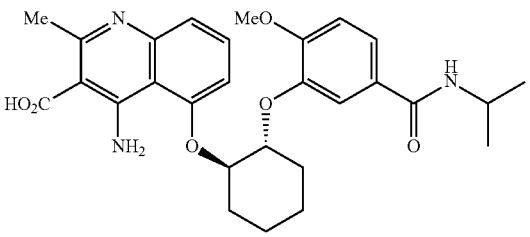 [SMILES: COc1ccc(C(=O)NC(C)C)cc1O[C@@H]1CCCC[C@H]1Oc1cccc2nc(C)c(C(=O)O)c(N)c12]

Prepared as in Example 1 from (±)-ethyl 4-amino-5-((2-(5-(isopropylcarbamoyl)-2-methoxyphenoxy)cyclohexyl)oxy)-2-methylquinoline-3-carboxylate (Example 129a) as a white solid (34%). $^1$H NMR (400 MHz, DMSO-$d_6$) δ 1.15 (d, J=8.0 Hz, 6H), 1.35-1.51 (m, 3H), 1.63-1.73 (m, 3H), 2.09 (d, J=12.0 Hz, 1H), 2.24 (d, J=12.0 Hz, 1H), 2.72 (s, 3H), 3.56 (s, 3H), 3.99-4.07 (m, 1H), 4.71-4.78 (m, 2H), 6.85 (d, J=8.0 Hz, 1H), 7.24 (d, J=12.0 Hz, 2H), 7.42 (dd, J=8.0 Hz, 1H), 7.46 (d, J=8.0 Hz, 1H), 7.66 (t, J=8.0 Hz, 1H), 8.03 (d, J=8.0 Hz, 1H), 8.64 (brs, 1H), 12.00 (brs, 1H), 12.61 (brs, 1H). MS 508 (MH$^+$).

Example 129a: (±)-ethyl 4-amino-5-((2-(5-(isopropylcarbamoyl)-2-methoxyphenoxy)-cyclohexyl)oxy)-2-methylquinoline-3-carboxylate Prepared as in Example 2a from (±)-3-((2-(3-amino-2-cyanophenoxy)cyclohexyl)oxy)-N-isopropyl-4-methoxybenzamide (Example 129b) and ethyl 3-oxobutanoate as a yellow solid (78%). MS 536 (MH$^+$).

Example 129b: (±)-3-((2-(3-amino-2-cyanophenoxy)cyclohexyl)oxy)-N-isopropyl-4-methoxybenzamide Prepared as in Example 21b from (±)-3-((2-(2-cyano-3-nitrophenoxy)cyclohexyl)oxy)-N-isopropyl-4-methoxybenzamide (Example 129c) as a brown oil (29%). $^1$H NMR (400 MHz, DMSO-$d_6$) δ 1.13-1.19 (m, 6H), 1.42-1.66 (m, 6H), 2.02-2.07 (m, 2H), 3.74 (s, 3H), 4.08 (m, 1H), 4.47 (m, 1H), 4.57 (m, 1H), 5.93 (brs, 2H), 6.32 (d, J=8.0 Hz, 1H), 6.38 (d, J=8.0 Hz, 1H), 7.00 (d, J=8.0 Hz, 1H), 7.17 (t, J=8.0 Hz, 1H), 7.48-7.50 (m, 2H), 7.98 (d, J=8.0 Hz, 1H). MS 424 (MH$^+$).

Example 129c: (±)-3-((2-(2-cyano-3-nitrophenoxy)cyclohexyl)oxy)-N-isopropyl-4-methoxybenzamide Prepared as in Example 126c from (±)-3-((2-hydroxycyclohexyl)oxy)-N-isopropyl-4-methoxybenzamide (Example 129d) and 2,6-dinitrobenzonitrile as a brown solid (100%). MS 454 (MH$^+$).

Example 129d: (±)-3-((2-hydroxycyclohexyl)oxy)-N-isopropyl-4-methoxybenzamide Prepared as in Example 24a from (±)-3-((2-hydroxycyclohexyl)oxy)-4-methoxybenzoic acid (Example 129e) and propan-2-amine as a white solid (80%). $^1$H NMR (400 MHz, DMSO-d6) δ 1.14 (d, J=8.0 Hz, 6H), 1.25-1.30 (m, 4H), 1.61 (m, 2H), 1.85 (m, 2H), 3.56 (m, 1H), 3.79 (s, 3H), 4.03-4.12 (m, 2H), 4.81 (d, J=4.0 Hz, 1H), 6.98 (d, J=8.0 Hz, 1H), 7.45-7.49 (m, 2H), 8.01 (d, J=8.0 Hz, 1H). MS 308 (MH$^+$).

Example 129e: (±)-3-((2-hydroxycyclohexyl)oxy)-4-methoxybenzoic Acid

Prepared as in Example 1 from (±)-ethyl 3-((2-hydroxycyclohexyl)oxy)-4-methoxy-benzoate (Example 129f) as a white solid (100%). $^1$H NMR (400 MHz, DMSO-$d_6$) δ 1.23-1.25 (m, 4H), 1.59 (brs, 2H), 1.88 (m, 2H), 3.53 (m, 1H), 3.72 (s, 3H), 3.92 (m, 1H), 4.73 (d, J=4.0 Hz, 1H), 6.82 (d, J=8.0 Hz, 1H), 7.39 (dd, J=4.0 Hz, 1H), 7.48 (d, J=4.0 Hz, 1H).

Example 129f: (±)-ethyl 3-((2-hydroxycyclohexyl)oxy)-4-methoxy-benzoate

To a solution of methyl 3-hydroxy-4-methoxybenzoate (210 mg, 1.15 mmol) and cyclohexane oxide (466 uL, 4.61 mmol) in ethanol (11 mL) was added K$_2$CO$_3$ (637 mg, 4.61 mmol) at room temperature. The reaction mixture was then refluxed overnight then cooled down to room temperature, and evaporated under reduced pressure until a small amount of ethanol remained. The solution was diluted with DCM and successively washed with 1N HCl and brine, dried over Na$_2$SO$_4$ filtered and evaporated under reduced pressure. The residue was purified by chromatography on silica gel (Eluent: 0-20% EtOAc/Hexanes) to afford (±)-ethyl 3-((2-hydroxycyclohexyl)oxy)-4-methoxy-benzoate as a colorless oil (307 mg, 91%). $^1$H NMR (400 MHz, DMSO-$d_6$) δ 1.16-1.34 (m, 7H), 1.61 (m, 2H), 1.84-1.94 (m, 2H), 3.55 (m, 1H), 3.83 (s, 3H), 4.03 (m, 1H), 4.28 (q, J=8.0 Hz, 2H), 4.85 (d, J=4.0 Hz, 1H), 7.05 (d, J=12.0 Hz, 1H), 7.55-7.58 (m, 2H).

Example 130: 4-amino-5-(cyclohexyloxy)-2-(hydroxymethyl)quinoline-3-carboxylic Acid

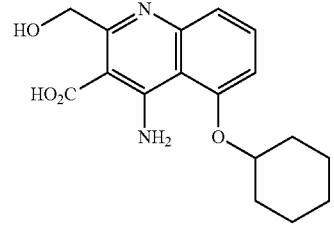 [SMILES: Nc1c(C(=O)O)c(CO)nc2cccc(OC3CCCCC3)c12]

Prepared as in Example 1 from 9-amino-8-(cyclohexyloxy)furo[3,4-b]quinolin-1 (3H)-one (Example 130a) as a tan powder (44%). $^1$H NMR (400 MHz, DMSO-$d_6$) δ 1.27-1.46 (m, 2H), 1.53-1.71 (m, 6H), 2.00-2.04 (m, 2H), 4.70 (m, 1H), 4.87 (s, 2H), 7.10 (d, J=8.0 Hz, 1H), 7.58 (d, J=8.0 Hz, 1H), 7.64 (t, J=8.0 Hz, 1H), 8.74 (brs, 1H), 11.90 (brs, 1H). MS 317 (MH$^+$).

Example 130a: 9-amino-8-(cyclohexyloxy)furo[3,4-b]quinolin-1 (3H)-one

Prepared as in Example 2a from 2-amino-6-(cyclohexyloxy)benzonitrile (Example 36b) and ethyl 4-chloro-3-oxobutanoate as an orange solid (29%). $^1$H NMR (400 MHz, DMSO-$d_6$) δ 1.30-1.72 (m, 8H), 2.04-2.08 (m, 2H), 4.70 (m, 1H), 5.26 (s, 2H), 7.09 (d, J=8.0 Hz, 1H), 7.36 (d, J=8.0 Hz, 1H), 7.64 (m, 2H), 8.14 (brs, 1H). MS 299 (MH$^+$).

Example 131: 1-amino-3-methyl-6b,7,8,9,10,10a-hexahydrobenzofuro[2,3-f]quinoline-2-carboxylic Acid

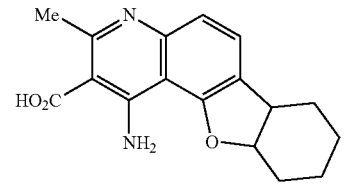 [SMILES: Cc1nc2ccc3c(c2c(N)c1C(=O)O)OC1CCCCC31]

Prepared as in Example 1 from ethyl 1-amino-3-methyl-6b,7,8,9,10,10a-hexahydrobenzofuro[2,3-f]quinoline-2-carboxylate (Example 131a) as an off-white solid (28%). $^1$H NMR (400 MHz, DMSO-$d_6$) δ 1.35-1.48 (m, 4H), 1.87-1.97 (m, 4H), 2.76 (s, 3H), 3.38 (m 1H), 5.03 (m 1H), 7.20 (d, J=8 Hz, 1H), 7.61 (d, J=8 Hz, 1H). MS 299 (MH$^+$).

Example 131a: ethyl 1-amino-3-methyl-6b,7,8,9,10,10a-hexahydrobenzofuro[2,3-f]quinoline-2-carboxylate Prepared as in Example 2a from 2-amino-6-(cyclohex-2-en-1-yloxy)benzonitrile (Example 131b) and ethyl 3-oxobutanoate as a pale yellow solid (11%). MS 327 (MH$^+$).

Example 131b: 2-amino-6-(cyclohex-2-en-1-yloxy)benzonitrile

Prepared as in Example 22b from cyclohex-2-enol and 2-amino-6-fluorobenzonitrile as a colorless oil (78%). $^1$H NMR (400 MHz, CDCl$_3$) δ 1.64 (m, 1H), 1.96 (m, 4H), 2.15 (m, 1H), 4.39 (s, 2H), 4.82 (m, 1H), 5.87 (m, 1H), 5.98 (m, 1H), 6.30 (d, 2H), 7.20 (t, 1H). MS 215 (MH$^+$).

Example 132: 4-amino-3-carboxy-5-(cyclohexyloxy)-2-methylquinoline 1-oxide

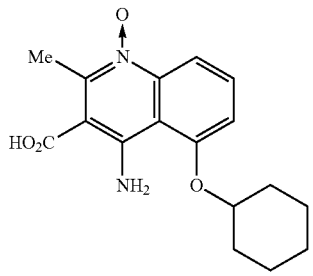 [SMILES: Cc1c(C(=O)O)c(N)c2c(OC3CCCCC3)cccc2[n+]1[O-]]

Prepared as in Example 1 from 4-(N-acetylacetamido)-5-(cyclohexyloxy)-3-(ethoxycarbonyl)-2-methylquinoline 1-oxide (Example 132a) as a white solid (38%). $^1$H NMR (400 MHz, DMSO-d$_6$) δ 1.31-1.68 (m, 8H), 1.98-2.04 (m, 2H), 2.69 (s, 3H), 4.71 (m, 1H), 7.20 (d, J=8.0 Hz, 1H), 7.67 (t, J=8.0 Hz, 1H), 7.87 (d, J=8.0 Hz, 1H), 8.75 (brs, 2H). MS 317 (MH$^+$).

Example 132a: 4-(N-acetylacetamido)-5-(cyclohexyloxy)-3-(ethoxycarbonyl)-2-methyl-quinoline 1-oxide To a solution of ethyl 4-(N-acetylacetamido)-5-(cyclohexyloxy)-2-methylquinoline-3-carboxylate (Example 132b, 100 mg, 0.24 mmol) in DCE (5 mL) was added mCPBA (163 mg, 0.73 mmol). The reaction mixture was stirred at room temperature overnight under N$_2$. The solvent was removed under reduce pressure, and the residue was purified by chromatography on silica gel eluting with 0-100% EtOAc/Hexanes gradient to give the title compound as an orange oil (100 mg, 97%). MS 429 (MH$^+$).

Example 132b: ethyl 4-(N-acetylacetamido)-5-(cyclohexyloxy)-2-methylquinoline-3-carboxylate To a solution of ethyl 4-amino-5-(cyclohexyloxy)-2-methylquinoline-3-carboxylate (Example 36a, 700 mg, 2.13 mmol) and Et$_3$N (891 uL, 6.39 mmol) in DCM (20 mL) was added acetyl chloride (455 uL, 6.39 mmol) at 0° C., and the reaction mixture was stirred at 0° C.-RT overnight. The reaction was diluted with DCM and washed successively with 10% citric acid, saturated NaHCO$_3$, H$_2$O, and brine, dried over Na$_2$SO$_4$, filtered and evaporated under reduced pressure. The residue was purified by chromatography on silica gel eluting with 0-40% EtOAc/Hexanes gradient to afford the title compound as a yellow oil (100 mg, 11%). MS 413 (MH$^+$).

Example 133: 4-amino-5-((2,3-dihydroxycyclohexyl)oxy)-2-methylquinoline-3-carboxylic Acid

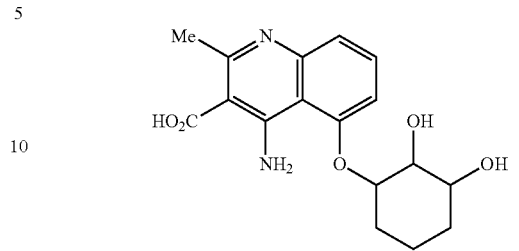

Prepared as in Example 1 from 3-((4-amino-3-(ethoxycarbonyl)-2-methylquinolin-5-yl)oxy)cyclohexane-1,2-diyl diacetate (Example 133a) as a white solid (74%). $^1$H NMR (400 MHz, DMSO-d$_6$) δ 1.42-1.50 (m, 3H), 1.66-1.70 (m, 2H), 2.12-2.15 (m, 1H), 2.74 (s, 3H), 3.71-3.73 (m, 1H), 3.90 (s, 1H), 4.60-4.62 (m, 1H), 4.71 (brs, 1H), 5.18 (brs, 1H), 7.06 (d, J=8 Hz, 1H), 7.24 (d, J=8 Hz, 1H), 7.60 (t, J=8.4 Hz, 1H). MS 333 (MH$^+$).

Example 133a: 3-((4-amino-3-(ethoxycarbonyl)-2-methylquinolin-5-yl)oxy)cyclohexane-1,2-diyl diacetate Prepared as in Example 2a from 3-(3-amino-2-cyanophenoxy)cyclohexane-1,2-diyl diacetate (Example 133b) and ethyl 3-oxobutanoate as a pale yellow solid (32%). MS 445 (MH$^+$).

Example 133b: 3-(3-amino-2-cyanophenoxy)cyclohexane-1,2-diyl diacetate

Prepared as in Example 21b from 3-(2-cyano-3-nitrophenoxy)cyclohexane-1,2-diyl diacetate (Example 133c) as a white solid (84%). MS 333 (MH$^+$).

Example 133c: 3-(2-cyano-3-nitrophenoxy)cyclohexane-1,2-diyl Diacetate

Prepared as in Example 132b from 2-((2,3-dihydroxycyclohexyl)oxy)-6-nitrobenzonitrile (Example 133d) and acetyl chloride as a white solid (19%). MS 363 (MH$^+$).

Example 133d: 2-((2,3-dihydroxycyclohexyl)oxy)-6-nitrobenzonitrile

To a solution of 2-(cyclohex-2-en-1-yloxy)-6-nitrobenzonitrile (Example 133e, 5.3 g, 21.7 mmol) in THF/H$_2$O (1:1 by volume, 110 mL) was added OsO$_4$ (110.3 mg, 0.434 mmol) at room temperature. After it was stirred for 30 minutes, NaClO$_3$ (2.71 g, 26.04 mmol) was added in small portions over a period of 1 h, and the reaction mixture was stirred at room temperature for 48 h. The reaction was carefully quenched with aqueous sodium bisulfite solution, and extracted with EtOAc (3×). The combined organic layers were washed with brine, dried over MgSO$_4$, filtered, and evaporated. The residue was purified by chromatography on silica gel eluting with 80-100% EtOAc in hexanes to give the title compound as a brown solid (3.88 g, 64%). MS 279 (MH$^+$).

Example 133e: 2-(cyclohex-2-en-1-yloxy)-6-nitrobenzonitrile

Prepared as in Example 126c from cyclohex-2-enol and 2,6-dinitrobenzonitrile as a brown solid (90%). MS 245 (MH$^+$).

Example 134: 4-amino-5-(3-(isopropylamino)-2,2-dimethyl-3-oxopropoxy)-2-methylquinoline-3-carboxylic Acid

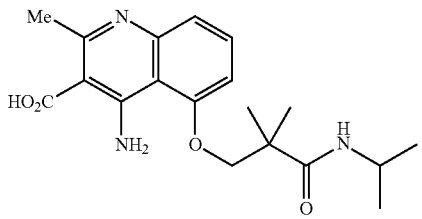 [SMILES: Cc1nc2cccc(OCC(C)(C)C(=O)NC(C)C)c2c(N)c1C(=O)O]

To a solution of ethyl 4-amino-5-(3-(isopropylamino)-2,2-dimethyl-3-oxopropoxy)-2-methylquinoline-3-carboxylate (Example 134a, 14.0 g, 36.2 mmol) in EtOH (140 mL) was added aqueous NaOH solution (2.0 N, 46 mL) at room temperature. The reaction mixture was stirred at 90° C. for 4 hrs. The resulting solution was neutralized at 0° C. to pH 7 with 6 N HCl, and concentrated under reduced pressure. The residue was re-dissolved in EtOH (400 mL) and water (25 mL), and treated with charcoal (200 mg) at 65° C. for 30 minutes. After removal of the charcoal by filtration, the filtrate was concentrated, and the resultant white solid was purified by re-crystallization from EtOH/H$_2$O and dried under vacuum at 70° C. to give the title compound as a white solid (11.5 g, 89%). M.p.: 216-218° C. $^1$H NMR (400 MHz, DMSO-d$_6$) δ 1.01 (d, J=6.4 Hz, 6H), 1.24 (s, 6H), 2.75 (s, 3H), 3.86-3.93 (m, 1H), 4.17 (s, 2H), 7.01 (d, J=8.0 Hz, 1H), 7.28 (d, J=8.4 Hz, 1H), 7.57 (d, J=7.6 Hz, 1H), 7.67 (t, J=8.0 Hz, 1H), 8.83 (brs, 1H), 12.34 (brs, 1H), 12.78 (brs, 1H). MS 360 (MH$^+$).

Example 134a: ethyl 4-amino-5-(3-(isopropylamino)-2,2-dimethyl-3-oxopropoxy)-2-methylquinoline-3-carboxylate Method A: to a solution of 3-(3-amino-2-cyanophenoxy)-N-isopropyl-2,2-dimethylpropanamide (Example 134b, 11.35 g, 41.27 mmol) and ethyl 3-oxobutanoate (5.2 mL, 41.27 mmol) in anhydrous 1,2-dichloroethane (110 mL) and toluene (110 mL) was added dropwise SnCl$_4$ (9.66 mL, 82.55 mmol) at room temperature under nitrogen. The reaction mixture was heated to reflux for 3 hrs. The solution was cooled to room temperature and the solvent removed under reduced pressure. The residue was dissolved in EtOAc (600 mL) and neutralized at 0° C. to pH 8 with 6 N NaOH. The organic layer was separated and the aqueous layer was further extracted with EtOAc (100 mL). The combined organic layers were washed with brine, dried over Na$_2$SO$_4$, filtered and evaporated. The residue was purified by chromatography on Biotage SP-1, 40S x4 column eluting with 0-5% MeOH in dichloromethane, and re-crystallized from EtOAc to give the title compound as a cream white solid (14.0 g, 88%). $^1$H NMR (400 MHz, DMSO-d$_6$) δ 1.01 (d, J=6.4 Hz, 6H), 1.24 (s, 6H), 1.32 (t, J=7.2 Hz, 3H), 2.55 (s, 3H), 3.87-3.93 (m, 1H), 4.12 (s, 2H), 4.31 (q, J=7.2 Hz, 2H), 6.87 (d, J=7.2 Hz, 1H), 7.23 (d, J=8.4 Hz, 1H), 7.49-7.53 (m, 3H), 8.09 (s, 2H). MS 388 (MH$^+$).

Method B: to a solution of 3-(3-amino-2-cyanophenoxy)-N-isopropyl-2,2-dimethylpropanamide (Example 134b, 10.0 g, 36.4 mmol) in ethyl 3-oxobutanoate (110 mL, 874 mmol, 24 eq.) was added anhydrous FeCl$_3$ (6.5 g, 40 mmol, 1.1 eq.) at room temperature under nitrogen. The black reaction mixture was stirred for 2 h at 110° C. Excess of ethyl 3-oxobutanoate was rotary evaporated at 80° C. The thick resulting mixture was dissolved in EtOAc (200 mL). An aqueous solution of NaOH (15%) (80 ml) was slowly added at 0° C. The mixture was stirred for 15 min. The organic layer was separated and the aqueous solution was extracted once more with EtOAc (100 mL). The combined organic layers were washed with brine, dried over Na$_2$SO$_4$. After evaporation of the solvent, the residue was purified by chromatography on silica gel eluting with 5-10% MeOH in DCM, and re-crystallized from EtOAc to give the title compound as an off-white solid (5.57 g, 40%).

Example 134b: 3-(3-amino-2-cyanophenoxy)-N-isopropyl-2,2-dimethylpropanamide To a solution of 3-hydroxy-N-isopropyl-2,2-dimethylpropanamide (Example 134c, 5.12 g, 32.15 mmol) in dry THF (100 mL) was added portion-wise NaH (60% in mineral oil, 1.41 g, 35.37 mmol) at 0° C. under nitrogen. The reaction mixture was stirred at 0° C. for about 30 minutes until bubbling ceased. 2-Amino-6-fluorobenzonitrile (4.38 g, 32.15 mmol) was added and the solution stirred at 80° C. overnight. The reaction mixture was quenched slowly with water at 0° C., and concentrated under reduced pressure. The residue was taken up in EtOAc and washed consecutively with brine and water, dried over Na$_2$SO$_4$ and concentrated. The residue was purified by re-crystallization from EtOAc/hexane to give the title compound as a white crystalline solid (4.4 g, 50%). $^1$H NMR (400 MHz, CDCl$_3$) δ 1.18 (d, J=6.8 Hz, 6H), 1.32 (s, 6H), 3.94 (s, 2H), 4.04-4.12 (m, 1H), 4.43 (s, 2H), 5.98 (d, J=6.8 Hz, 1H), 6.21 (d, J=8.0 Hz, 1H), 6.32 (d, J=8.0 Hz, 1H), 7.21 (t, J=8.0 Hz, 1H). MS 276 (MH$^+$).

Example 134c: 3-hydroxy-N-isopropyl-2,2-dimethylpropanamide

Method A: to a Parr Reactor was added methyl 3-hydroxy-2,2-dimethylpropanoate (66.0 g, 0.5 mol) and propan-2-amine (59.1 g, 1.0 mol) at room temperature. The reaction mixture was then stirred at 190° C. overnight. The reaction was cooled to room temperature and the solution concentrated under reduced pressure. The residue was dissolved in EtOAc and the solution successively washed with brine (5×), dried over Na$_2$SO$_4$, and evaporated under reduced pressure. The residue was co-evaporated with dry toluene (100 mL×2) to give the title compound as a colorless oil (38.76 g, 49%). $^1$H NMR (400 MHz, DMSO-d$_6$) δ 0.98 (s, 6H), 1.02 (d, J=6.4 Hz, 6H), 3.32 (d, J=5.2 Hz, 2H), 3.79-3.88 (m, 1H), 4.83 (t, J=5.2 Hz, 1H), 7.11 (d, J=7.2 Hz, 1H). MS 160 (MH$^+$).

Method B: to a solution of propan-2-amine (9.7 mL, 113.0 mmol) and 3-hydroxy-2,2-dimethylpropanoic acid (11.1 g, 94.2 mmol) in dichloromethane (500 mL) was added 1-(3-dimethylaminopropyl)-3-ethyl-carbodiimide hydrochloride (22.0 g, 113 mmol), 1-hydroxybenzotriazole monohydrate (17.3 g, 113 mmol), and triethylamine (16 mL, 113 mmol). The reaction was stirred at room temperature overnight. The crude mixture was concentrated on the rotovap. The residue was taken up in EtOAc and washed with saturated NaHCO$_3$, brine, and water. The organic layer was dried over Na₂SO₄, filtered and evaporated under reduced pressure to afford the tile compound as a clear oil (5.12 g, 34%). MS 160 (MH⁺).

Example 135: 4-amino-5-(3-(cyclopropylamino)-2,2-dimethyl-3-oxopropoxy)-2-methyl-quinoline-3-carboxylic Acid

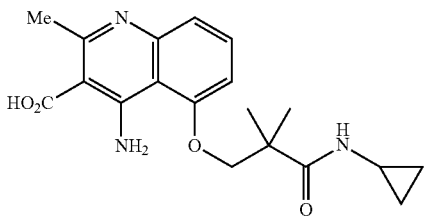 [SMILES: Cc1nc2cccc(OCC(C)(C)C(=O)NC3CC3)c2c(N)c1C(=O)O]

Prepared as in Example 1 from ethyl 4-amino-5-(3-(cyclopropylamino)-2,2-dimethyl-3-oxopropoxy)-2-methylquinoline-3-carboxylate (Example 135a) as a white solid (60%). M.p.: 227-229° C. ¹H NMR (400 MHz, DMSO-d₆) δ 0.40-0.44 (m, 2H), 0.58-0.62 (m, 2H), 1.24 (s, 6H), 2.62 (m, 1H), 2.77 (s, 3H), 4.15 (s, 2H), 7.01 (d, J=8.0 Hz, 1H), 7.30 (d, J=8.0 Hz, 1H), 7.67 (t, J=8.0 Hz, 1H), 7.86 (d, J=4.0 Hz, 1H), 8.75 (brs, 1H), 12.25 (brs, 1H), 12.77 (brs, 1H). MS 358 (MH⁺).

Example 135a: ethyl 4-amino-5-(3-(cyclopropylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclopropanamine as a pale yellow solid (64%). ¹H NMR (400 MHz, DMSO-d₆) δ 0.14-0.45 (m, 2H), 0.57-0.62 (m, 2H), 1.25 (s, 6H), 1.35 (t, J=8.0 Hz, 3H), 2.58 (s, 3H), 2.62-2.65 (m, 1H), 4.13 (s, 2H), 4.35 (q, J=8.0 Hz, 2H), 6.90 (d, 1H), 7.27 (d, 1H), 7.53 (t, J=8.0 Hz, 1H), 7.79 (d, J=4.0 Hz, 1H), 8.09 (s, 2H). MS 386 (MH⁺).

Example 136: 4-amino-5-(3-(cyclobutylamino)-2,2-dimethyl-3-oxopropoxy)-2-methylquinoline-3-carboxylic Acid

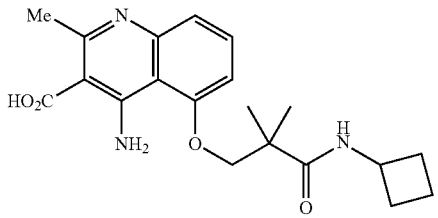 [SMILES: Cc1nc2cccc(OCC(C)(C)C(=O)NC3CCC3)c2c(N)c1C(=O)O]

Prepared as in Example 1 from ethyl 4-amino-5-(3-(cyclobutylamino)-2,2-dimethyl-3-oxopropoxy)-2-methylquinoline-3-carboxylate (Example 136a) as a white solid (45%). M.p.: 183-187° C. ¹H NMR (400 MHz, DMSO-d₆) δ 1.24 (s, 6H), 1.52-1.63 (m, 2H), 1.87-1.98 (m, 2H), 2.03-2.12 (m, 2H), 2.75 (s, 3H), 4.16 (s, 2H), 4.17-4.26 (m, 1H), 7.01 (d, J=8.0 Hz, 1H), 7.27 (d, J=8.0 Hz, 1H), 7.67 (t, J=8.0 Hz, 1H), 7.97 (d, J=8.0 Hz, 1H), 8.78 (brs, 1H), 12.35 (brs, 1H), 12.70 (brs, 1H). MS 372 (MH⁺).

Example 136a: ethyl 4-amino-5-(3-(cyclobutylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclobutanamine as an off-white solid (71%). MS 400 (MH⁺).

Example 137: 4-amino-5-(((1,4)-trans-4-isobutyramidocyclohexyl)oxy)-2-methylquinoline-3-carboxylic Acid

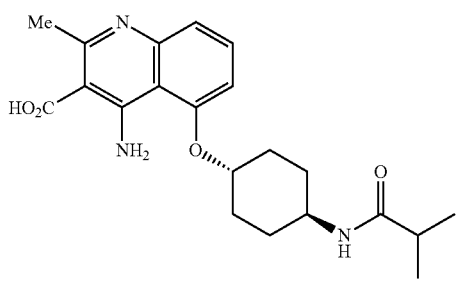 [SMILES: Cc1nc2cccc(O[C@H]3CC[C@H](NC(=O)C(C)C)CC3)c2c(N)c1C(=O)O]

Prepared as in Example 1 from ethyl 4-amino-5-(((1,4)-trans-4-isobutyramidocyclohexyl)oxy)-2-methylquinoline-3-carboxylate (Example 137a) as a white solid (86%). M.p.: 183-185° C. ¹H NMR (400 MHz, DMSO-d₆) δ 0.95 (s, 3H), 0.97 (s, 3H), 1.34-1.38 (m, 2H), 1.65-1.68 (m, 2H), 1.81-1.84 (m, 2H), 2.13-2.15 (m, 2H), 2.29-2.34 (m, 1H), 2.75 (s, 3H), 3.57-3.59 (m, 1H), 4.64 (m, 1H), 7.14 (d, J=8.4 Hz, 1H), 7.26 (d, J=8.4 Hz, 1H), 7.53 (s, 1H), 7.65 (m, 2H). MS 386 (MH⁺).

Example 137a: ethyl 4-amino-5-(((1,4)-trans-4-isobutyramidocyclohexyl)oxy)-2-methylquinoline-3-carboxylate Prepared as in Example 2a from N-((1,4)-trans-4-(3-amino-2-cyanophenoxy)cyclohexyl)isobutyramide (Example 137b) and ethyl acetoacetate as an off-white solid (88%). MS 414 (MH⁺).

Example 137b: N-((1,4)-trans-4-(3-amino-2-cyanophenoxy)cyclohexyl)isobutyramide

Prepared as in Example 22a from N-((1,4)-trans-4-hydroxycyclohexyl)isobutyramide (Example 137c) and 2-amino-6-fluorobenzonitrile as an off-white solid (91%). MS 302 (MH⁺).

Example 137c: N-((1,4)-trans-4-hydroxycyclohexyl)isobutyramide

Prepared as in Example 24a from isobutyric acid and (1,4)-trans-4-aminocyclohexanol as a colorless oil (51%). MS 186 (MH⁺).

Example 138: 4-amino-2-methyl-5-(2-methyl-2-(3-methylbutanamido)propoxy)quinoline-3-carboxylic Acid

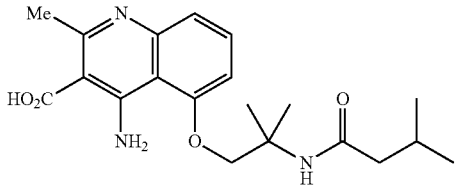 [SMILES: Cc1nc2cccc(OCC(C)(C)NC(=O)CC(C)C)c2c(N)c1C(=O)O]

Prepared as in Example 1 from ethyl 4-amino-2-methyl-5-(2-methyl-2-(3-methylbutan-amido)propoxy)quinoline-3-carboxylate (Example 138a) as a white solid (47%). M.p.: 195-198° C. $^1$H NMR (400 MHz, DMSO-$d_6$) δ 1.50 (d, J=4.0 Hz, 6H), 1.37 (s, 6H), 1.90-2.0 (m, 3H), 2.73 (s, 3H), 4.32 (s, 2H), 6.92 (d, J=8.0 Hz, 1H), 7.28 (d, J=8.0 Hz, 1H), 7.57 (t, J=8.0 Hz, 1H), 8.45 (s, 1H), 11.14 (brs, 1H), 12.94 (brs, 1H). MS 374 (MH$^+$).

Example 138a: ethyl 4-amino-2-methyl-5-(2-methyl-2-(3-methylbutanamido)propoxy)-quinoline-3-carboxylate Prepared as in Example 24a from ethyl 4-amino-5-(2-amino-2-methylpropoxy)-2-methylquinoline-3-carboxylate (Example 24b) and 3-methylbutanoic acid as an off-white solid (100%). MS 402 (MH$^+$).

Example 139: 4-amino-5-(2-isobutyramido-2-methylpropoxy)-2-methylquinoline-3-carboxylic Acid

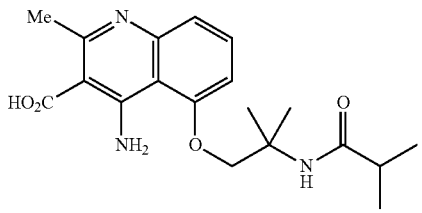 [SMILES: Cc1nc2cccc(OCC(C)(C)NC(=O)C(C)C)c2c(N)c1C(=O)O]

Prepared as in Example 1 from ethyl 4-amino-5-(2-isobutyramido-2-methylpropoxy)-2-methylquinoline-3-carboxylate (Example 139a) as a white solid (38%). M.p.: 184-186° C. $^1$H NMR (400 MHz, DMSO-$d_6$) δ 0.89 (d, J=8.0 Hz, 6H), 1.35 (s, 6H), 2.41 (m, 1H), 2.79 (s, 3H), 4.35 (s, 2H), 7.01 (d, J=8.0 Hz, 1H), 7.33 (d, J=8.0 Hz, 1H), 7.65 (t, J=8.0 Hz, 1H), 7.82 (s, 1H), 8.83 (brs, 1H), 12.10 (brs, 1H), 13.10 (brs, 1H). MS 360 (MH$^+$).

Example 139a: ethyl 4-amino-5-(2-isobutyramido-2-methylpropoxy)-2-methylquinoline-3-carboxylate Prepared as in Example 24a from ethyl 4-amino-5-(2-amino-2-methylpropoxy)-2-methylquinoline-3-carboxylate (Example 24b) and isobutyric acid as a white solid (58%). MS 388 (MH$^+$).

Example 140: 4-amino-2-methyl-5-(2-methyl-2-(tetrahydro-2H-pyran-4-carboxamido)-propoxy)quinoline-3-carboxylic Acid

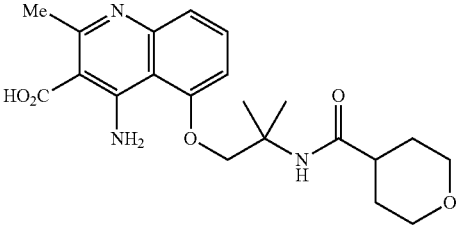 [SMILES: Cc1nc2cccc(OCC(C)(C)NC(=O)C3CCOCC3)c2c(N)c1C(=O)O]

Prepared as in Example 1 from ethyl 4-amino-2-methyl-5-(2-methyl-2-(tetrahydro-2H-pyran-4-carboxamido)propoxy)quinoline-3-carboxylate (Example 140a) as a white solid (65%). M.p.: 170-173° C. $^1$H NMR (400 MHz, DMSO-$d_6$) δ 1.35 (s, 6H), 1.44-1.49 (m, 4H), 2.40 (m, 1H), 2.76 (s, 3H), 3.19-3.25 (m, 2H), 3.75-3.79 (m, 2H), 4.34 (s, 2H), 6.99 (d, J=8.0 Hz, 1H), 7.27 (d, J=8.0 Hz, 1H), 7.65 (t, J=8.0 Hz, 1H), 7.84 (s, 1H). MS 402 (MH$^+$).

Example 140a: ethyl 4-amino-2-methyl-5-(2-methyl-2-(tetrahydro-2H-pyran-4-carboxamido)propoxy)quinoline-3-carboxylate Prepared as in Example 24a from ethyl 4-amino-5-(2-amino-2-methylpropoxy)-2-methylquinoline-3-carboxylate (Example 24b) and tetrahydro-2H-pyran-4-carboxylic acid as a pale-yellow solid (63%). MS 430 (MH$^+$).

Example 141: 4-amino-2-methyl-5-(2-methyl-2-propionamidopropoxy)quinoline-3-carboxylic Acid

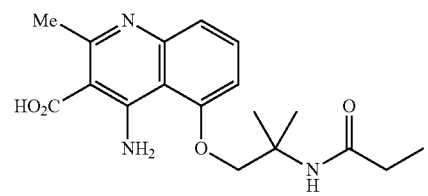 [SMILES: CCC(=O)NC(C)(C)COc1cccc2nc(C)c(C(=O)O)c(N)c12]

Prepared as in Example 1 from ethyl 4-amino-2-methyl-5-(2-methyl-2-propionamido-propoxy)quinoline-3-carboxylate (Example 141a) as a white solid (31%). M.p.: 189-193° C. $^1$H NMR (400 MHz, DMSO-$d_6$) δ 0.89 (t, J=8.0 Hz, 6H), 1.34 (s, 6H), 2.05 (q, J=8.0 Hz, 2H), 2.72 (s, 3H), 4.31 (s, 2H), 6.90 (d, J=8.0 Hz, 1H), 7.28 (d, J=8.0 Hz, 1H), 7.54 (t, J=8.0 Hz, 1H), 7.80 (s, 1H), 8.41 (brs, 1H), 11.02 (brs, 1H), 13.17 (brs, 1H). MS 346 (MH$^+$).

Example 141a: ethyl 4-amino-2-methyl-5-(2-methyl-2-propionamidopropoxy)quinoline-3-carboxylate Prepared as in Example 24a from ethyl 4-amino-5-(2-amino-2-methylpropoxy)-2-methylquinoline-3-carboxylate (Example 24b) and propionic acid as a pale-yellow solid (23%). MS 374 (MH$^+$).

Example 142: 4-amino-5-(2-(cyclobutanecarboxamido)-2-methylpropoxy)-2-methylquinoline-3-carboxylic Acid

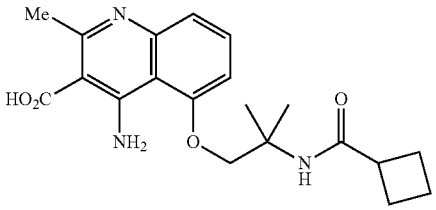 [SMILES: Cc1nc2cccc(OCC(C)(C)NC(=O)C3CCC3)c2c(N)c1C(=O)O]

Prepared as in Example 1 from ethyl 4-amino-5-(2-(cyclobutanecarboxamido)-2-methylpropoxy)-2-methylquinoline-3-carboxylate (Example 142a) as a white solid (65%). M.p.: 186-190° C. $^1$H NMR (400 MHz, DMSO-$d_6$) δ 1.34 (s, 6H), 1.56-1.66 (m, 1H), 1.73-1.84 (m, 1H), 1.87-2.03 (m, 4H), 2.78 (s, 3H), 3.00-3.08 (m, 1H), 4.36 (s, 2H), 7.01 (d, J=8.0 Hz, 1H), 7.32 (d, J=8.0 Hz, 1H), 7.66 (t, J=8.0 Hz, 1H), 7.73 (s, 1H), 8.76 (brs, 1H), 12.01 (brs, 1H), 13.05 (brs, 1H). MS 372 (MH$^+$).

Example 142a: ethyl 4-amino-5-(2-(cyclobutanecarboxamido)-2-methylpropoxy)-2-methylquinoline-3-carboxylate Prepared as in Example 24a from ethyl 4-amino-5-(2-amino-2-methylpropoxy)-2-methylquinoline-3-carboxylate (Example 24b) and cyclobutanecarboxylic acid as an off-white solid (61%). MS 400 (MH$^+$).

Example 143: 4-amino-5-((1-isobutyrylpiperidin-4-yl)oxy)-2-methylquinoline-3-carboxylic Acid

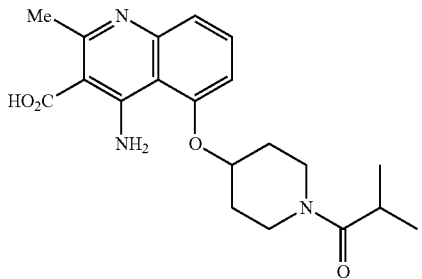 [SMILES: Cc1nc2cccc(OC3CCN(C(=O)C(C)C)CC3)c2c(N)c1C(=O)O]

Prepared as in Example 1 from ethyl 4-amino-5-((1-isobutyrylpiperidin-4-yl)oxy)-2-methylquinoline-3-carboxylate (Example 143a) as a white solid (88%). M.p.: 184-186° C. $^1$H NMR (400 MHz, DMSO-$d_6$) δ 0.95 (s, 3H), 0.99 (t, 6H), 1.68-1.82 (m, 2H), 2.02-2.11 (m, 2H), 2.74 (s, 3H), 2.89 (m, 1H), 3.01 (m, 1H), 3.35 (m, 1H), 3.84 (m, 1H), 4.04 (m, 1H), 4.94 (m, 1H), 7.16 (d, J=8.4 Hz, 1H), 7.26 (d, J=7.6 Hz, 1H), 7.67 (t, J=8.4 Hz, 1H). MS 372 (MH$^+$).

Example 143a: ethyl 4-amino-5-((1-isobutyrylpiperidin-4-yl)oxy)-2-methylquinoline-3-carboxylate Prepared as in Example 2a from 2-amino-6-((1-isobutyrylpiperidin-4-yl)oxy)benzonitrile (Example 143b) and ethyl acetoacetate as an off-white solid (82%). MS 400 (MH$^+$).

Example 143b: 2-amino-6-((1-isobutyrylpiperidin-4-yl)oxy)benzonitrile

Prepared as in Example 22a from 1-(4-hydroxypiperidin-1-yl)-2-methylpropan-1-one (Example 143c) and 2-amino-6-fluorobenzonitrile as an off-white solid (87%). MS 288 (MH$^+$).

Example 143c: 1-(4-hydroxypiperidin-1-yl)-2-methylpropan-1-one

Prepared as in Example 24a from isobutyric acid and piperidin-4-ol as a colorless oil (43%). MS 172 (MH$^+$).

Example 144: 4-amino-5-(3-(ethylamino)-2,2-dimethyl-3-oxopropoxy)-2-methylquinoline-3-carboxylic Acid

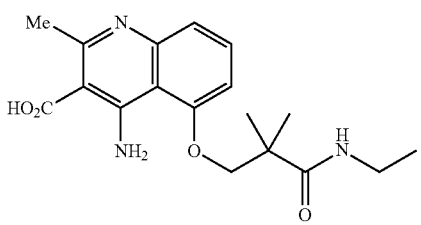

Prepared as in Example 1 from ethyl 4-amino-5-(3-(ethylamino)-2,2-dimethyl-3-oxopropoxy)-2-methylquinoline-3-carboxylate (Example 144a) as a white solid (75%). M.p.: 168-170° C. $^1$H NMR (400 MHz, DMSO-$d_6$) δ 0.96 (t, J=8 Hz, 3H), 1.24 (s, 6H), 3.06 (s, 3H), 3.09 (dq, J=1.6, 8.0 Hz, 2H), 4.14 (s, 2H), 7.00 (d, J=8.0 Hz, 1H), 7.26 (d, J=8.0 Hz, 1H), 7.66 (t, J=8.0 Hz, 1H), 7.90 (t, J=8.0 Hz, 1H), 8.85 (brs, 1H), 12.32 (brs, 1H), 12.70 (brs, 1H). MS 346 (MH$^+$).

Example 144a: ethyl 4-amino-5-(3-(ethylamino)-2,2-dimethyl-3-oxopropoxy)-2-methyl-quinoline-3-carboxylate Prepared as in Example 24a from 3-((4-amino-3-(ethoxycarbonyl)-2-methylquinolin-5-yl)oxy)-2,2-dimethylpropanoic acid (Example 47b) and ethylamine hydrochloride as an off-white solid (61%). MS 374 (MH$^+$).

Example 145: 4-amino-2-methyl-5-(2-methyl-2-(2-(tetrahydro-2H-pyran-4-yl)acetamido)-propoxy)quinoline-3-carboxylic Acid

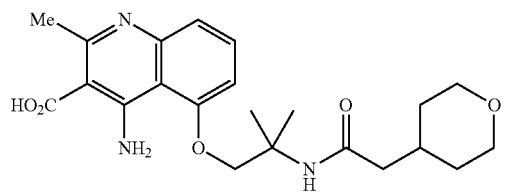

Prepared as in Example 1 from ethyl 4-amino-2-methyl-5-(2-methyl-2-(2-(tetrahydro-2H-pyran-4-yl)acetamido)propoxy)quinoline-3-carboxylate (Example 145a) as a white solid (28%). M.p.: 175-178° C. $^1$H NMR (400 MHz, DMSO-d$_6$) δ 1.06-1.13 (m, 2H), 1.35-1.38 (m, 8H), 1.79 (m, 1H), 1.98 (d, J=4.0 Hz, 2H), 2.77 (s, 3H), 3.10 (t, J=4.0 Hz, 2H), 3.60 (m, 2H), 4.34 (s, 2H), 7.01 (d, J=8.0 Hz, 1H), 7.27 (d, J=8.0 Hz, 1H), 7.65 (t, J=8.0 Hz, 1H), 7.88 (s, 1H), 8.76 (brs, 1H), 12.43 (brs, 1H), 12.71 (brs, 1H). MS 416 (MH$^+$).

Example 144a: ethyl 4-amino-2-methyl-5-(2-methyl-2-(2-(tetrahydro-2H-pyran-4-yl)acetamido)propoxy)quinoline-3-carboxylate Prepared as in Example 24a from ethyl 4-amino-5-(2-amino-2-methylpropoxy)-2-methylquinoline-3-carboxylate (Example 24b) and 2-(tetrahydro-2H-pyran-4-yl)acetic acid as a yellow solid (37%). $^1$H NMR (400 MHz, DMSO-d$_6$) δ 1.05-1.08 (m, 2H), 1.30-1.38 (m, 11H), 1.79 (m, 1H), 1.97 (d, J=4.0 Hz, 2H), 2.56 (s, 3H), 3.07 (t, J=8.0 Hz, 2H), 3.61 (d, J=8.0 Hz, 2H), 4.28-4.34 (m, 4H), 6.87 (d, J=8.0 Hz, 1H), 7.23 (d, J=8.0 Hz, 1H), 7.49 (t, J=8.0 Hz, 1H), 7.73 (s, 1H), 8.21 (s, 2H). MS 444 (MH$^+$).

Example 146: 4-amino-5-(3-((cyclopropylmethyl)amino)-2,2-dimethyl-3-oxopropoxy)-2-methylquinoline-3-carboxylic Acid

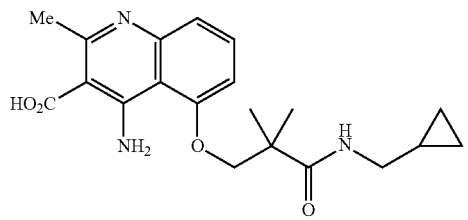 [SMILES: Cc1nc2cccc(OCC(C)(C)C(=O)NCC3CC3)c2c(N)c1C(=O)O]

Prepared as in Example 1 from ethyl 4-amino-5-(3-((cyclopropylmethyl)amino)-2,2-dimethyl-3-oxopropoxy)-2-methylquinoline-3-carboxylate (Example 146a) as a white solid (39%). M.p.: 177-179° C. $^1$H NMR (400 MHz, DMSO-d$_6$) δ 0.12-0.13 (m, 2H), 0.30-0.31 (m, 2H), 0.89 (m, 1H), 1.28 (s, 6H), 2.76 (s, 3H), 2.98 (t, J=4.0 Hz, 2H), 4.17 (s, 2H), 7.03 (d, J=8.0 Hz, 1H), 7.29 (d, J=8.0 Hz, 1H), 7.68 (t, J=8.0 Hz, 1H), 7.98 (t, J=8.0 Hz, 1H), 8.80 (brs, 1H), 12.26 (brs, 1H), 12.76 (brs, 1H). MS 372 (MH$^+$).

Example 146a: ethyl 4-amino-5-(3-((cyclopropylmethyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclopropylmethanamine as a pale-yellow solid (80%). $^1$H NMR (400 MHz, DMSO-d$_6$) δ 0.12-0.13 (m, 2H), 0.29-0.31 (m, 2H), 0.90 (m, 1H), 1.27 (s, 6H), 1.33 (t, J=8.0 Hz, 3H), 2.56 (s, 3H), 2.97 (t, J=8.0 Hz, 2H), 4.14 (s, 2H), 4.32 (q, J=8.0 Hz, 2H), 6.88 (d, J=8.0 Hz, 1H), 7.26 (d, J=4.0 Hz, 1H), 7.53 (t, J=8.0 Hz, 1H), 7.91 (t, J=4.0 Hz, 1H), 8.11 (s, 2H). MS 400 (MH$^+$).

Example 147: 4-amino-5-(3-(butylamino)-2,2-dimethyl-3-oxopropoxy)-2-methylquinoline-3-carboxylic Acid

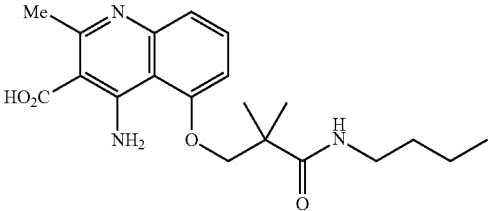 [SMILES: CCCCNC(=O)C(C)(C)COc1cccc2nc(C)c(C(=O)O)c(N)c12]

Prepared as in Example 1 from ethyl 4-amino-5-(3-(butylamino)-2,2-dimethyl-3-oxopropoxy)-2-methylquinoline-3-carboxylate (Example 147a) as an off-white solid (59%). M.p.: 195-199° C. $^1$H NMR (400 MHz, DMSO-d$_6$) δ 0.74 (t, J=8.0 Hz, 3H), 1.11-1.21 (m, 2H), 1.27 (s, 6H), 1.32-1.39 (m, 2H), 2.77 (s, 3H), 3.09 (q, J=8.0 Hz, 2H), 4.17 (s, 2H), 7.03 (d, J=8.0 Hz, 1H), 7.30 (d, J=8.0 Hz, 1H), 7.69 (t, J=8.0 Hz, 1H), 7.88 (t, J=8.0 Hz, 1H), 8.87 (brs, 1H), 12.41 (brs, 1H), 12.74 (brs, 1H). MS 374 (MH$^+$).

Example 147a: ethyl 4-amino-5-(3-(butylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and n-butylamine as a pale-yellow solid (91%). $^1$H NMR (400 MHz, DMSO-d$_6$) δ 0.74 (t, J=8.0 Hz, 3H), 1.15-1.20 (m, 2H), 1.27 (s, 6H), 1.32-1.38 (m, 5H), 2.57 (s, 3H), 3.06-3.11 (q, J=8.0 Hz, 2H), 4.14 (s, 2H), 4.35 (q, J=8.0 Hz, 2H), 6.90 (d, J=8.0 Hz, 1H), 7.26 (d, J=8.0 Hz, 1H), 7.53 (t, J=8.0 Hz, 1H), 7.81 (t, J=8.0 Hz, 1H), 8.10 (s, 2H). MS 402 (MH$^+$).

Example 148: 4-amino-5-(2,2-dimethyl-3-oxo-3-(pentan-3-ylamino)propoxy)-2-methyl-quinoline-3-carboxylic Acid

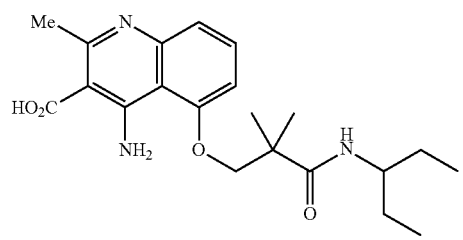 [SMILES: CCC(CC)NC(=O)C(C)(C)COc1cccc2nc(C)c(C(=O)O)c(N)c12]

Prepared as in Example 1 from ethyl 4-amino-5-(2,2-dimethyl-3-oxo-3-(pentan-3-ylamino)propoxy)-2-methylquinoline-3-carboxylate (Example 148a) as a white solid (72%). M.p.: 172-174° C. $^1$H NMR (400 MHz, DMSO-d$_6$) δ 0.69 (t, J=8.0 Hz, 6H), 1.29 (s, 6H), 1.32-1.42 (m, 4H), 2.76 (s, 3H), 3.59-3.64 (m, 1H), 4.21 (s, 2H), 7.03 (d, J=8.0 Hz, 1H), 7.29 (d, J=8.0 Hz, 1H), 7.43 (d, J=8.0 Hz, 1H), 7.69 (t, J=8.0 Hz, 1H), 8.79 (brs, 1H), 12.35 (brs, 1H), 12.73 (brs, 1H). MS 388 (MH$^+$).

Example 148a: ethyl 4-amino-5-(2,2-dimethyl-3-oxo-3-(pentan-3-ylamino)propoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and pentan-3-amine as a pale-yellow solid (78%). $^1$H NMR (400 MHz, DMSO-d$_6$) δ 0.68 (t, J=8.0 Hz, 6H), 1.27 (s, 6H), 1.31 (t, J=8.0 Hz, 3H), 1.37-1.42 (m, 4H), 2.54 (s, 3H), 3.56-3.61 (m, 1H), 4.16 (s, 2H), 4.30 (q, J=8.0 Hz, 2H), 6.87 (d, J=8.0 Hz, 1H), 7.23 (d, J=8.0 Hz, 1H), 7.32 (d, J=8.0 Hz, 1H), 7.51 (t, J=8.0 Hz, 1H), 8.06 (s, 2H). MS 416 (MH$^+$).

Example 149: 4-amino-2-methyl-5-(2-methyl-2-(2-morpholinoacetamido)propoxy)quinoline-3-carboxylic Acid

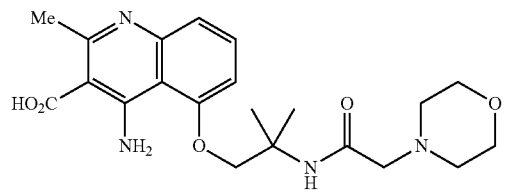 [SMILES: Cc1nc2cccc(OCC(C)(C)NC(=O)CN3CCOCC3)c2c(N)c1C(=O)O]

Prepared as in Example 1 from ethyl 4-amino-2-methyl-5-(2-methyl-2-(2-morpholino-acetamido)propoxy)quinoline-3-carboxylate (Example 149a) as a white solid (32%). M.p.: 173-175° C. $^1$H NMR (400 MHz, DMSO-d$_6$) δ 1.39 (s, 6H), 2.35 (t, J=4.8 Hz, 4H), 2.74 (s, 3H), 2.85 (s, 2H), 3.47 (t, J=4.8 Hz, 4H), 4.35 (s, 2H), 7.00 (d, J=8.0 Hz, 1H), 7.27 (d, J=8.4 Hz, 1H), 7.63 (t, J=8.0 Hz, 1H), 7.71 (s, 1H). MS 417 (MH$^+$).

Example 149a: ethyl 4-amino-2-methyl-5-(2-methyl-2-(2-morpholinoacetamido)propoxy)quinoline-3-carboxylate Prepared as in Example 24a from ethyl 4-amino-5-(2-amino-2-methylpropoxy)-2-methylquinoline-3-carboxylate (Example 24b) and 2-morpholinoacetic acid as a yellow solid (37%). MS 445 (MH$^+$).

Example 150: 4-amino-5-(3-(isobutylamino)-2,2-dimethyl-3-oxopropoxy)-2-methylquinoline-3-carboxylic Acid

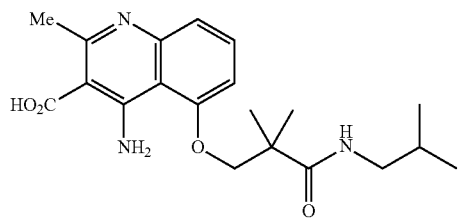 [SMILES: Cc1nc2cccc(OCC(C)(C)C(=O)NCC(C)C)c2c(N)c1C(=O)O]

Prepared as in Example 1 from ethyl 4-amino-5-(3-(isobutylamino)-2,2-dimethyl-3-oxopropoxy)-2-methylquinoline-3-carboxylate (Example 150a) as an off-white solid (60%). M.p.: 176-179° C. $^1$H NMR (400 MHz, DMSO-d$_6$) δ 0.73 (d, J=6.8 Hz, 6H), 1.27 (s, 6H), 1.65-1.75 (m, 1H), 2.77 (s, 3H), 2.89 (t, J=6.4 Hz, 2H), 4.17 (s, 2H), 7.01 (d, J=8.4 Hz, 1H), 7.31 (d, J=8.4 Hz, 1H), 7.67 (t, J=8.4 Hz, 1H), 7.90 (t, J=5.8 Hz, 1H), 8.84 (brs, 1H), 12.16 (brs, 1H), 12.91 (brs, 1H). MS 374 (MH$^+$).

Example 150a: ethyl 4-amino-5-(3-(isobutylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and isobutylamine as an off-white solid (82%). MS 402 (MH$^+$).

Example 151: 4-amino-5-(3-((cyclobutylmethyl)amino)-2,2-dimethyl-3-oxopropoxy)-2-methylquinoline-3-carboxylic Acid

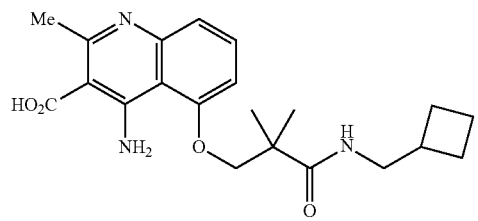 [SMILES: Cc1nc2cccc(OCC(C)(C)C(=O)NCC3CCC3)c2c(N)c1C(=O)O]

Prepared as in Example 1 from ethyl 4-amino-5-(3-((cyclobutylmethyl)amino)-2,2-dimethyl-3-oxopropoxy)-2-methylquinoline-3-carboxylate (Example 151a) as a white solid (54%). M.p.: 170-172° C. $^1$H NMR (400 MHz, DMSO-d$_6$) δ 1.26 (s, 6H), 1.54-1.71 (m, 4H), 1.76-1.84 (m, 2H), 2.35-2.42 (m, 1H), 2.76 (s, 3H), 3.10 (t, J=6.0 Hz, 2H), 4.18 (s, 2H), 7.13 (d, J=8.4 Hz, 1H), 7.33 (d, J=8.0 Hz, 1H), 7.77 (t, J=8.0 Hz, 1H), 7.87 (t, J=6.4 Hz, 1H), 9.21 (brs, 1H), 10.92 (brs, 1H). MS 386 (MH$^+$).

Example 151a: ethyl 4-amino-5-(3-((cyclobutylmethyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclobutylmethanamine as an off-white solid (67%). MS 414 (MH$^+$).

Example 152: 5-(2-(6-Ammoniohexanamido)-2-methylpropoxy)-3-carboxy-2-methylquinolin-4-aminium Trifluoroacetate

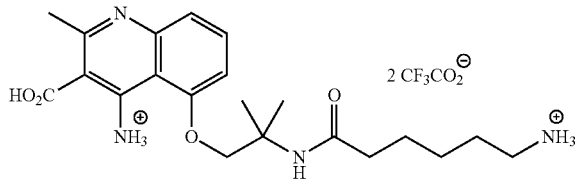 [SMILES: Cc1nc2cccc(OCC(C)(C)NC(=O)CCCCC[NH3+])c2c([NH3+])c1C(=O)O]

A solution of 4-amino-5-(2-(6-(tert-butoxycarbonylamino)hexanamido)-2-methylpropoxy)-2-methylquinoline-3-carboxylic acid (Example 152a) (59.6 mg, 0.12 mmol) in CH$_2$Cl$_2$ (9.0 mL) was treated with trifluoroacetic acid (1.0 mL) at room temperature. After being stirred at room temperature for 2 h the reaction mixture was evaporated to dryness. The residue was dissolved in H$_2$O (5.0 mL) and the product was isolated by preparative HPLC (RPC18, H$_2$O→CH$_3$CN gradient). The appropriate fractions were collected and evaporated under reduced pressure. The residue was dried in a dessicator over phosphorus pentoxide to give 43.6 mg (58%) of 5-(2-(6-ammoniohexanamido)-2-methylpropoxy)-3-carboxy-2-methylquinolin-4-aminium trifluoroacetate as a white solid. $^1$H NMR (400 MHz, DMSO-d$_6$) δ 13.56 (s, 1H), 9.98 (s, 1H), 9.40 (s, 1H), 7.88 (t, J=8.3 Hz, 1H), 7.75 (s, 1H), 7.72-7.56 (m, 3H), 7.42 (d, J=7.9 Hz, 1H), 7.25 (d, J=8.1 Hz, 1H), 4.42 (s, 2H), 2.81 (s, 3H), 2.72-2.60 (m, 2H), 2.08 (t, J=7.3 Hz, 2H), 1.50-1.39 (m, 4H), 1.38 (s, 6H), 1.26-1.14 (m, 2H). MS 404 (M+).

Example 152a: 4-Amino-5-(2-(6-(tert-butoxycarbonylamino)hexanamido)-2-methylpropoxy)-2-methylquinoline-3-carboxylic Acid A solution of 6-(tert-butoxycarbonylamino)hexanoic acid (0.21 g, 0.90 mmol) in dry DMF (10 mL) was treated with triethylamine (0.46 g, 4.51 mmol, 0.63 mL) and N,N,N',N'-tetramethyl-O—(N-succinimidyl)uronium tetrafluoroborate (TSTU) (0.30 g, 0.99 mmol) at room temperature under a nitrogen atmosphere. The reaction mixture was stirred at room temperature over 3 h and then a solution of 5-(2-ammonio-2-methylpropoxy)-3-carboxy-2-methylquinolin-4-aminium chloride (Example 152b) (0.33 g, 0.90 mmol) and triethylamine (0.46 g, 4.51 mmol, 0.63 mL) in dry DMF was added dropwise at room temperature. The obtained mixture was stirred at room temperature over 3 days and the solvent was evaporated. The residue was dissolved in a mixture of MeOH and H$_2$O (50 mL, 1:1) and the product was isolated by preparative HPLC (RPC18, H$_2$O→CH$_3$CN gradient). The appropriate fractions were collected and evaporated under reduced pressure. The residue was dried in a dessicator over phosphorus pentoxide to give 0.21 g (45%) of 4-amino-5-(2-(6-(tert-butoxycarbonylamino)hexanamido)-2-methylpropoxy)-2-methylquinoline-3-carboxylic acid as a white solid. $^1$H NMR (400 MHz, DMSO-d$_6$) δ 12.95-12.65 (m, 1H), 12.45-11.95 (m, 1H), 9.05-8.60 (m, 1H), 7.84 (s, 1H), 7.67 (t, J=8.0 Hz, 1H), 7.29 (d, J=8.2 Hz, 1H), 7.02 (d, J=8.1 Hz, 1H), 6.71 (t, J=5.6 Hz, 1H), 4.36 (s, 2H), 2.78 (s, 3H), 2.70 (q, J=6.4 Hz, 2H), 2.05 (t, J=7.3 Hz, 2H), 1.45-1.34 (m, 2H), 1.36 (s, 3H), 1.34 (s, 3H), 1.30-1.19 (m, 2H), 1.14-1.03 (m, 2H). MS 503 (MH$^+$).

Example 152b: 5-(2-Ammonio-2-methylpropoxy)-3-carboxy-2-methylquinolin-4-aminium Chloride To a solution of ethyl 4-amino-5-(2-amino-2-methylpropoxy)-2-methylquinoline-3-carboxylate (Example 24b) (0.65 g, 2.05 mmol) in EtOH (35 mL) was added a solution of NaOH in H$_2$O (2.0 M, 5.2 mL) at room temperature under a nitrogen atmosphere. The obtained reaction mixture was heated at 80° C. over 3 h and cooled to room temperature. The pH of the cold mixture was adjusted to 1 with a solution of HCl (1.5 M) and the acidified solution was evaporated to dryness. The residue was dissolved in a mixture of EtOH and H$_2$O (30 mL, 1:1) and the product was isolated by preparative HPLC (RPC18, H$_2$O→CH$_3$CN gradient). The appropriate fractions were collected and evaporated under reduced pressure. The residue was dried in a dessicator over phosphorus pentoxide to give 0.41 g (54%) 5-(2-ammonio-2-methylpropoxy)-3-carboxy-2-methylquinolin-4-aminium chloride as a white solid. $^1$H NMR (400 MHz, DMSO-d$_6$) δ 10.05-9.90 (m, 1H), 9.15-9.00 (m, 1H), 8.69-8.57 (m, 3H), 7.91 (t, J=8.3 Hz, 1H), 7.65 (d, J=8.0 Hz, 1H), 7.38 (d, J=8.3 Hz, 1H), 4.39 (s, 2H), 2.84 (s, 3H), 1.44 (s, 6H). MS 291 (M$^+$)

Example 153: 4-amino-2-methyl-5-((1-propionylpiperidin-4-yl)methoxy)quinoline-3-carboxylic Acid

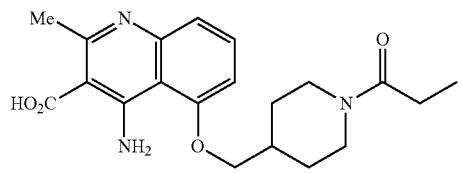 [SMILES: CCC(=O)N1CCC(COc2cccc3nc(C)c(C(=O)O)c(N)c23)CC1]

Prepared as in Example 1 from ethyl 4-amino-2-methyl-5-((1-propionylpiperidin-4-yl)methoxy)quinoline-3-carboxylate (Example 153a) as an off-white solid (55%). M.p.: 168-170° C. $^1$H NMR (400 MHz, DMSO-d$_6$) δ 0.96 (t, J=7.6 Hz, 3H), 1.08-1.25 (m, 2H), 1.81 (t, J=15.6 Hz, 2H), 2.19-2.26 (m, 1H), 2.30 (q, J=7.2 Hz, 2H), 2.55 (t, J=12 Hz, 1H), 2.75 (s, 3H), 3.01 (t, J=12 Hz, 1H), 3.88 (d, J=13.6 Hz, 1H), 4.1 (d, J=5.6 Hz 2H), 4.42 (d, J=13.2 Hz, 1H), 7.02 (d, J=8.4 Hz, 1H), 7.27 (d, J=7.6 Hz, 1H), 7.65 (t, J=8.4 Hz, 1H). MS 372 (MH$^+$).

Example 153a: ethyl 4-amino-2-methyl-5-((1-propionylpiperidin-4-yl)methoxy)quinoline-3-carboxylate Prepared as in Example 2a from 2-amino-6-((1-propionylpiperidin-4-yl)methoxy)benzonitrile (Example 153b) and ethyl acetoacetate as an off-white solid (41%). MS 400 (MH$^+$).

Example 153b: 2-amino-6-((1-propionylpiperidin-4-yl)methoxy)benzonitrile

Prepared as in Example 22a from 1-(4-(hydroxymethyl)piperidin-1-yl)propan-1-one (Example 153c) and 2-amino-6-fluorobenzonitrile as a pale-yellow solid (15%). MS 288 (MH$^+$).

Example 153c: 1-(4-(hydroxymethyl)piperidin-1-yl)propan-1-one

Prepared as in Example 24a from propionyl chloride and piperidin-4-ylmethanol as a colorless oil (40%). MS 172 (MH$^+$).

Example 154: 4-amino-2-methyl-5-(((1,4)-trans-4-(methylcarbamoyl)cyclohexyl)oxy)quinoline-3-carboxylic Acid

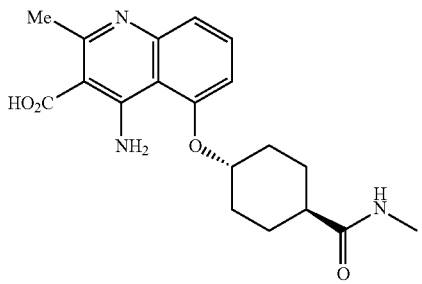 [SMILES: CNC(=O)[C@H]1CC[C@H](Oc2cccc3nc(C)c(C(=O)O)c(N)c23)CC1]

Prepared as in Example 1 from ethyl 4-amino-2-methyl-5-(((1,4)-trans-4-(methylcarbamoyl)cyclohexyl)oxy)quinoline-3-carboxylate (Example 154a) as a white solid (42%). M.p.: 195-198° C. $^1$H NMR (400 MHz, DMSO-d$_6$) δ 1.55-1.80 (m, 6H), 2.00-2.10 (m, 2H), 2.20-2.30 (m, 1H), 2.55 (d, J=8.0 Hz, 3H), 2.76 (s, 3H), 4.96 (s, 1H), 7.07 (d, J=8.0 Hz, 1H), 7.27 (d, J=8.0 Hz, 1H), 7.66-7.72 (m, 1H), 8.76 (brs, 1H), 12.00 (brs, 1H), 12.83 (brs, 1H). MS 358 (MH$^+$).

Example 154a: ethyl 4-amino-2-methyl-5-(((1,4)-trans-4-(methylcarbamoyl)cyclohexyl-)oxy)quinoline-3-carboxylate Prepared as in Example 2a from (1,4)-trans-4-(3-amino-2-cyanophenoxy)-N-methylcyclohexanecarboxamide (Example 154b) and ethyl acetoacetate as a yellow solid (43%). MS 386 (MH$^+$).

Example 154b: (1,4)-trans-4-(3-amino-2-cyanophenoxy)-N-methylcyclohexanecarboxamide Prepared as in Example 47c from 4-(2-cyano-3-nitrophenoxy)-N-methylcyclohexanecarboxamide (Example 154c) as pale-yellow solid (41%). MS 274 (MH$^+$).

Example 154c: 4-(2-cyano-3-nitrophenoxy)-N-methylcyclohexanecarboxamide

Prepared as in Example 24a from 4-(2-cyano-3-nitrophenoxy)cyclohexanecarboxylic acid (Example 154d) and methylamine hydrochloride as an orange solid (80%). MS 304 (MH$^+$).

Example 154d: 4-(2-cyano-3-nitrophenoxy)cyclohexanecarboxylic Acid

Prepared as in Example 47d from 4-hydroxycyclohexanecarboxylic acid and 2,6-dinitrobenzonitrile as a brown solid (50%). MS 291 (MH$^+$).

Example 155: 4-amino-5-(3-(isopropylamino)-2,2-dimethyl-3-oxopropoxy)-2-methylquinoline-3-carboxylic Acid Phosphate

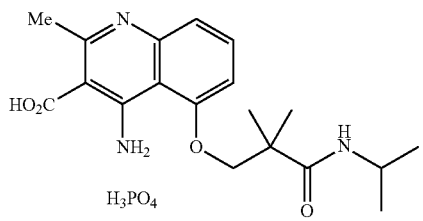

Prepared as in Example 127 from 4-amino-5-(3-(isopropylamino)-2,2-dimethyl-3-oxopropoxy)-2-methylquinoline-3-carboxylic acid (Example 134) and H$_3$PO$_4$ as a white solid (100%). $^1$H NMR (400 MHz, DMSO-d$_6$) δ 1.01 (d, J=6.4 Hz, 6H), 1.25 (s, 6H), 2.76 (s, 3H), 3.86-3.95 (m, 1H), 4.17 (s, 2H), 7.04 (d, J=8.0 Hz, 1H), 7.30 (dd, J=8.0 Hz, 0.8 Hz, 1H), 7.57 (d, J=8.0 Hz, 1H), 7.70 (t, J=8.0 Hz, 1H). MS 360 (MH$^+$+H—H$_3$PO$_4$).

Example 156: sodium 4-amino-5-(3-(isopropylamino)-2,2-dimethyl-3-oxopropoxy)-2-methylquinoline-3-carboxylate

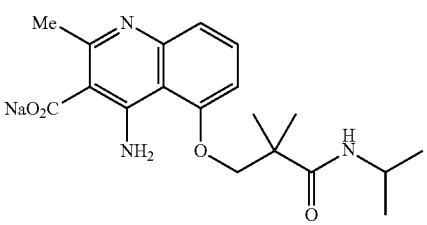

Prepared as in Example 128 from 4-amino-5-(3-(isopropylamino)-2,2-dimethyl-3-oxopropoxy)-2-methylquinoline-3-carboxylic acid (Example 134) and NaHCO$_3$ as a white solid (100%). $^1$H NMR (400 MHz, DMSO-d$_6$) δ 1.01 (d, J=6.4 Hz, 6H), 1.23 (s, 6H), 2.56 (s, 3H), 3.86-3.94 (m, 1H), 4.07 (s, 2H), 6.66 (d, J=8.0 Hz, 1H), 7.14 (d, J=8.0 Hz, 1H), 7.32 (t, J=8.0 Hz, 1H), 7.48 (d, J=8.0 Hz, 1H). MS 360 (MH$^+$+H-Na).

The following compounds in Table G were synthesized by following the procedures described above.

TABLE G

| Compound No. | Compound | MS (MH+) |
|---|---|---|
| G-1 | 4-amino-5-(2-(4-hydroxycyclohexanecarboxamido)-2-methylpropoxy)-2-methylquinoline-3-carboxylic acid | 416 |
| G-2 | 4-amino-5-((4-(ethylcarbamoyl)cyclohexyl)oxy)-2-methylquinoline-3-carboxylic acid | 372 |
| G-3 | 4-amino-5-(2,2-dimethyl-3-oxo-3-(pyrrolidin-1-yl)propoxy)-2-methylquinoline-3-carboxylic acid | 372 |
| G-4 | 4-amino-5-(2-(isopropylamino)-2-oxoethoxy)-2-methylquinoline-3-carboxylic acid | 318 |
| G-5 | 4-amino-5-(2,2-dimethyl-3-(methylamino)-3-oxopropoxy)-2-methylquinoline-3-carboxylic acid | 332 |

TABLE G-continued

| Compound No. | Compound | MS (MH+) |
|---|---|---|
| G-6 | 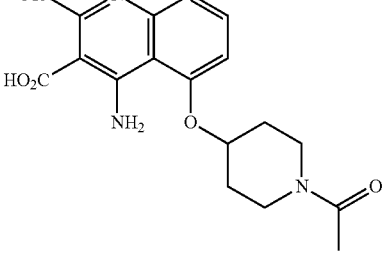<br>5-((1-acetylpiperidin-4-yl)oxy)-4-amino-2-methylquinoline-3-carboxylic acid | 344 |
| G-7 | 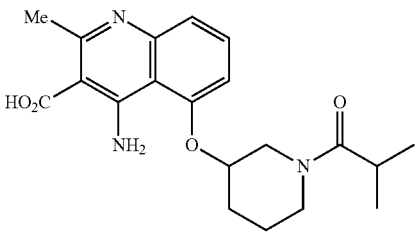<br>4-amino-5-((1-isobutyrylpiperidin-3-yl)oxy)-2-methylquinoline-3-carboxylic acid | 372 |
| G-8 | 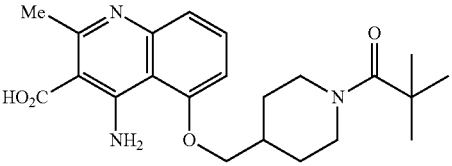<br>4-amino-2-methyl-5-((1-pivaloylpiperidin-4-yl)methoxy)quinoline-3-carboxylic acid | 400 |
| G-9 | 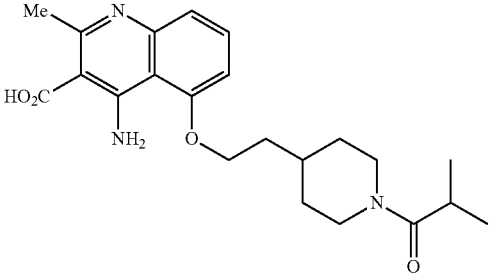<br>4-amino-5-(2-(1-isobutyrylpiperidin-4-yl)ethoxy)-2-methylquinoline-3-carboxylic acid | 400 |
| G-10 | 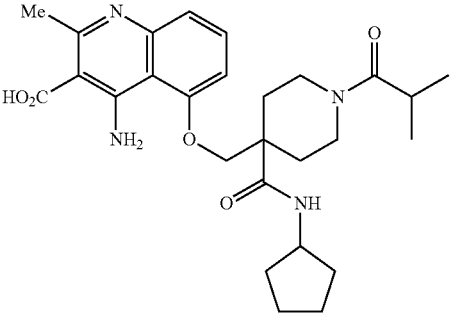<br>4-amino-5-((4-(cyclopentylcarbamoyl)-1-isobutyrylpiperidin-4-yl)methoxy)-2-methylquinoline-3-carboxylic acid | 497 |

TABLE G-continued

| Compound No. | Compound | MS (MH+) |
|---|---|---|
| G-11 | 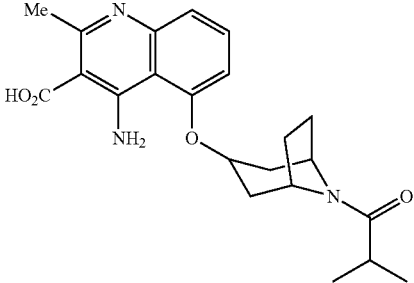  4-amino-5-(((1R,5S)-8-isobutyryl-8-azabicyclo[3.2.1]octan-3-yl)oxy)-2-methylquinoline-3-carboxylic acid | 398 |
| G-12 | 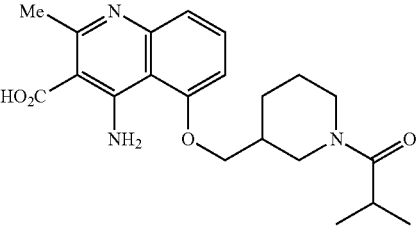  4-amino-5-((1-isobutyrylpiperidin-3-yl)methoxy)-2-methylquinoline-3-carboxylic acid | 386 |
| G-13 | 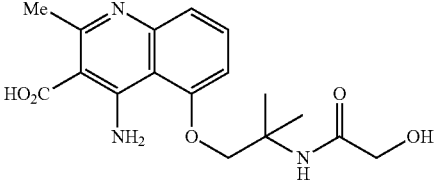  4-amino-5-(2-(2-hydroxyacetamido)-2-methylpropoxy)-2-methylquinoline-3-carboxylic acid | 348 |
| G-14 | 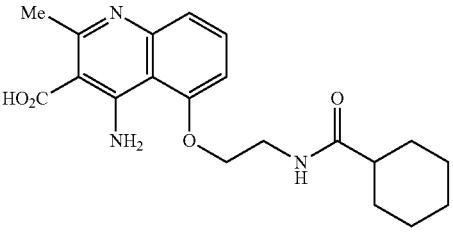  4-amino-5-(2-(cyclohexanecarboxamido)ethoxy)-2-methylquinoline-3-carboxylic acid | 372 |
| G-15 | 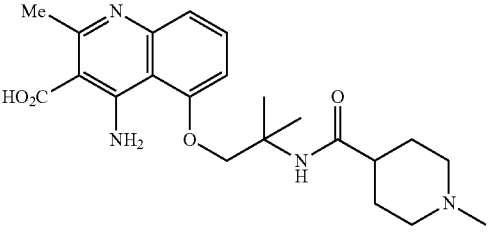  4-amino-2-methyl-5-(2-methyl-2-(1-methylpiperidine-4-carboxamido)propoxy)quinoline-3-carboxylic acid | 415 |

TABLE G-continued

| Compound No. | Compound | MS (MH+) |
|---|---|---|
| G-16 | (S)-4-amino-5-(2-(2-methoxyacetamido)propoxy)-2-methylquinoline-3-carboxylic acid | 348 |
| G-17 | 4-amino-5-(2-((1s,4s)-4-hydroxycyclohexanecarboxamido)-2-methylpropoxy)-2-methylquinoline-3-carboxylic acid | 416 |
| G-18 | 4-amino-5-(2-((1r,4r)-4-hydroxycyclohexanecarboxamido)-2-methylpropoxy)-2-methylquinoline-3-carboxylic acid | 416 |
| G-19 | 4-amino-5-(((1r,4r)-4-butyramidocyclohexyl)oxy)-2-methylquinoline-3-carboxylic acid | 386 |

Example 157: $N^5$-isopropyl-1H-benzo[c][1,2,6]thiadiazine-4,5-diamine-2,2-dioxide

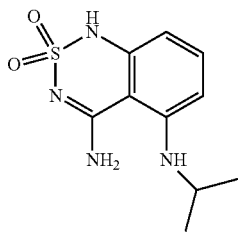

513

A solution of 2-amino-6-(isopropylamino)benzonitrile sulfamide (Example 157a) (0.14 g, 0.54 mmol) and NaOH (2 N, 0.54 mL) in EtOH (3 mL) was stirred at 90° C. under nitrogen for 0.5 hour. The reaction mixture was cooled to room temperature, and concentrated under vacuum. $H_2O$ (1 mL) was added and the reaction mixture was neutralized to pH ~3 with 10% AcOH. The resultant precipitate was extracted with EtOAc, and after evaporation of solvents the residue was purified by preparative thin layer chromatography using a DCM/EtOAc (4:1) solution as eluant, to give $N^5$-isopropyl-1H-benzo[c][1,2,6]thiadiazine-4,5-diamine-2,2-dioxide (0.02 g). $^1$H NMR (400 MHz, DMSO-$d_6$) δ 1.11 (d, J=6.4 Hz, 6H), 1.84 (bs, 1H), 5.24 (bs, NH), 6.22-6.19 (m, 2H, NH), 7.09 (t, J=8.0 Hz, 1H), 7.48 (bs, 2H). MS 255 (MH$^+$).

Example 157a: 2-amino-6-(isopropylamino)benzonitrile sulfamide

To a solution of 2-amino-6-(isopropylamino)benzonitrile (Example 157b) (0.09 g, 0.54 mmol) in DMA (3 mL) was added sulfamoyl chloride (0.19 g, 1.62 mmol). The reaction mixture was stirred at room temperature under nitrogen for 2 hours, diluted with $H_2O$ (5 mL) and extracted with EtOAc. Solvents of the combined organic phases were evaporated and the residue was purified by preparative thin layer chromatography using a Hexane/EtOAc (3:2) solution as eluant, to give 2-amino-6-(isopropylamino)benzonitrile sulfamide (0.14 g). MS 255 (MH$^+$).

Example 157b: 2-amino-6-(isopropylamino)benzonitrile

To a solution of 2-(isopropylamino)-6-nitrobenzonitrile (Example 157c) (0.21 g, 1.02 mmol) in MeOH (9 mL) was added concentrated HCl (2 mL). Then Fe (0.17 g, 3.07 mmol) was added portionwise, and the reaction mixture was refluxed at 90° C. for 15 minutes. After cooling to room temperature, dilution with $H_2O$ (50 mL) and extraction with DCM (3×50 mL), the combined organic phases were washed with brine, dried over $MgSO_4$ and the solvents were evaporated to give 2-amino-6-(isopropylamino)benzonitrile (0.19 g, 100%) as a brown oil which was used in the next step without any further purification. MS 176 (MH$^+$).

Example 157c: 2-(isopropylamino)-6-nitrobenzonitrile

To a solution of 2,6-dinitrobenzonitrile (0.58 g, 3.00 mmol) in DMF (6 mL) was added isopropylamine (0.71 g, 12.00 mmol) and the reaction mixture was stirred at 50° C. under nitrogen for ten minutes. After cooling to room temperature, dilution with $H_2O$ and extraction with EtOAc, solvents of the combined organic phases were evaporated and the residue was purified by flash chromatography (Biotage system, 80 g silicagel column) using a Hexane/EtOAc (3:2) solution as eluant, to give 2-(isopropylamino)-6-nitrobenzonitrile (0.22 g, 35%). $^1$H NMR (400 MHz, DMSO-$d_6$) δ 1.20 (d, J=6.4 Hz, 6H), 3.85-3.80 (m, 1H), 5.94 (d, J=8.0 Hz, NH), 7.26 (d, J=9.0 Hz, 1H), 7.42 (d, J=9.0 Hz, 1H), 7.60 (t, J=8.8 Hz, 1H).

Example 158: 4-Amino-5-(propyloxy)-1H-benzo[c][1,2,6]thiadiazine-2,2-dioxide

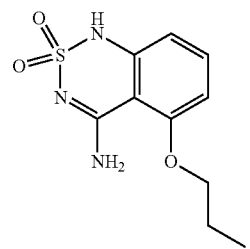

533

To a suspension of 2-sulfamoylamino-6-propoxybenzonitrile (Example 158a) (4.73 g, 18.53 mmol) in ethanol (65 mL), was added aqueous NaOH (2N, 18.6 ml, 37.06 mmol). The resulting clear solution was refluxed for 3 hours under nitrogen. After cooling to room temperature, the resulting solution was filtered, the filtrate was cooled to 0° C. and neutralized with 10% acetic acid. The resulting precipitate was collected by filtration, suspended in 50 ml of ethanol/water (1:1) and warmed to 40° C. for 20 min. The solid was collected by filtration to provide 4-Amino-5-(propyloxy)-1H-benzo[c][1,2,6]thiadiazine-2,2-dioxide (4 g, 85%) as a pale yellow powder. M.p.: 229-230° C. $^1$H NMR (400 MHz, DMSO-$d_6$) δ 0.96 (t, J=7.3 Hz, 3H), 1.81 (sext, J=7.3 Hz, 2H), 4.10 (t, J=6.7 Hz, 2H), 6.60 (d, J=8.6 Hz, 1H), 6.73 (d, J=8.6 Hz, 1H), 7.44 (t, J=8.6 Hz, 1H), 7.81 (br s, 1H), 8.35 (br s, 1H), 10.93 (br s, 1H). $^{13}$C NMR (400 MHz, DMSO-$d_6$) δ 11.07, 22.18, 71.41, 100.93, 105.64, 110.21, 135.53, 145.16, 158.47, 161.10. MS 256 (MH$^+$).

Example 158a: 2-Sulfamoylamino-6-propoxybenzonitrile

To a solution of 2-amino-6-propoxybenzonitrile (Example 158b) (4.23 g, 24.01 mmol) in dimethylacetamide (20 mL) under $N_2$ was added sulfamoyl chloride (5.56 g, 48.02 mmol). The reaction mixture was then stirred at room temperature under nitrogen for 4 hours. Upon completion, the reaction was quenched by addition of ice/water (250 mL). The resulting precipitate was collected by filtration, rinsed with water and dried to yield 2-sulfamoylamino-6-propoxybenzonitrile (4.73 g, 77%) as a pale yellow solid. $^1$H NMR (400 MHz, DMSO-$d_6$) δ 1.01 (d, J=7.2 Hz, 3H), 1.76 (sext, J=7.2 Hz, 2H), 4.08 (t, J=6.8 Hz, 2H), 6.96 (d, J=8.5 Hz, 1H), 7.15 (t, J=8.5 Hz, 1H), 7.28 (br s, 2H), 7.57 (d, J=8.5 Hz, 1H), 9.46 (s, 1H). MS 256 (MH$^+$).

Example 158b: 2-Amino-6-propoxybenzonitrile

2-Nitro-6-propoxybenzonitrile (Example 158c) (4.95 g, 24.01 mmol) was dissolved in EtOH (50 mL) and THF (15 mL). 10% Pd/C (255 mg, 2.4 mmol) was added, and the reaction was hydrogenated using a Parr apparatus for 12 hours at 40 psi. Upon completion, the reaction was filtered through celite and the filtrate concentrated to provide 2-nitro-6-propoxybenzonitrile (4.3 g, 100%) as a light brown gel. $^1$H NMR (400 MHz, CDCl$_3$) δ 1.05 (d, J=7.4 Hz, 3H), 1.83 (sext, J=7.0 Hz, 2H), 3.96 (t, J=7.0 Hz, 2H), 4.38 (br s, 2H), 6.20 (d, J=8.5 Hz, 1H), 6.28 (t, J=8.5 Hz, 1H), 7.19 (d, J=8.5 Hz, 1H).

Example 158c: 2-Nitro-6-propoxybenzonitrile

To a solution of 2,6-dinitrobenzonitrile (6 g, 31.07 mmol) in dry DMF (45 mL) at 0° C., was added a solution of sodium (815 mg, 35.42 mmol) in n-propanol (23.5 mL) dropwise over 30 minutes. After compete addition, the reaction mixture was warmed to room temperature and stirred for 2.5 hours. The reaction was poured into an ice/water mixture (250 mL), and the precipitate was collected by filtration and dried to yield 2-nitro-6-propoxybenzonitrile (4.95 g, 77%) as a light brown solid. $^1$H NMR (400 MHz, CDCl$_3$) δ 1.11 (d, J=7.5 Hz, 3H), 1.93 (sext, J=7.5 Hz, 2H), 4.14 (t, J=7.0 Hz, 2H), 7.31 (d, J=8.6 Hz, 1H), 7.69 (t, J=8.6 Hz, 1H), 7.82 (d, J=8.6 Hz, 1H).

Example 159: 4-Amino-5,6-(5',7'-dihydro-4'H-[2',3'-c]pyrano)thieno[2,3-d]-pyrimidine-2 (1H)-one

568

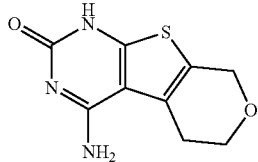

A solution of N-(3-cyano-5,7-dihydro-4H-thieno[2,3-c]pyran-2-ylcarbamoyl) benzamide (Example 159a) (500 mg, 1.53 mmol) and NaOH (2 N, 2.1 mL) in EtOH (40 mL) was stirred at 100° C. under nitrogen overnight. After cooling to room temperature, the clear reaction solution was filtered, and the filtrate was carefully neutralized with 10% AcOH with vigorous stirring at 0° C. The resultant precipitate was collected by filtration, washed with water and then 20% EtOH in water to give the final product (280 mg, 82%) as an off-white solid, which was dried under vacuum overnight. M.p.: >260° C. $^1$H NMR (400 MHz, DMSO-d$_6$) δ 2.83 (t, J=5.6 Hz, 2H), 3.86 (t, J=5.6 Hz, 2H), 4.58 (s, 2H), 7.23 (brs, 2H), 11.56 (brs, 1H). MS 224 (MH$^+$).

Example 159a: N-(3-cyano-5,7-dihydro-4H-thieno[2,3-c]pyran-2-ylcarbamoyl) benzamide To a solution of 2-amino-5,7-dihydro-4H-thieno[2,3-c]pyran-3-carbonitrile (Example 159b) (400 mg, 2.22 mmol) in 1.4-dioxane (30 mL) was added benzoyl isocyanate (327 mg, 2.22 mmol). The reaction mixture was then stirred at room temperature under nitrogen overnight. The precipitate was collected by filtration, washed with 1.4-dioxane, and dried in the air to give the title compound (577 mg, 80%) as a light yellow solid. $^1$H NMR (400 MHz, DMSO-d$_6$) δ 2.62 (t, J=5.2 Hz, 2H), 3.87 (t, J=5.2 Hz, 2H), 4.62 (s, 2H), 7.56-7.53 (m, 2H), 7.67-7.65 (m, 2H), 8.04-8.01 (m, 2H), 11.60 (brs, 1H), 12.13 (brs, 1H).

Example 159b: 2-amino-5,7-dihydro-4H-thieno[2,3-c]pyran-3-carbonitrile

To a mixture of dihydro-2H-pyran-4(3H)-one (820 mg, 8.19 mmol), malononitrile (541 mg, 8.19 mmol) and sulfur (263 mg, 8.19 mmol) in Ethanol (50 mL) was added triethylamine (1.14 mL, 8.19 mmol). The reaction mixture was then refluxed under nitrogen overnight. After cooling to room temperature, the precipitate was collected by filtration, washed with ethanol, and dried in the air to give the title compound (1.15 g, 78%) as a light brown solid. $^1$H NMR (400 MHz, DMSO-d$_6$) δ 2.43-2.40 (m, 2H), 3.80 (t, J=5.6 Hz, 2H), 4.40 (t, J=2.0 Hz, 2H), 7.09 (s, 2H). MS 181 (MH$^+$).

Example 160: 4-(2-(4-Amino-1H-benzo[c][1,2,6]thiadiazine-2,2-dioxide-5-yloxy)ethyl)piperidinium chloride

588

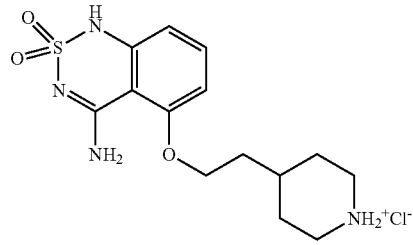

tert-Butyl-4-(2-(4-Amino-1H-benzo[c][1,2,6]thiadiazine-2,2-dioxide-5-yloxy)ethyl)piperidine-1-carboxylate (Example 160a) (20 mg, 0.047 mmol) was dissolved in a solution of HCl in EtOH (1 mL, 1.25 M). The reaction was stirred at reflux under N$_2$. Upon completion, the precipitate was collected by vacuum filtration to provide the desired product (17 mg, 100%) as a white solid. $^1$H NMR (400 MHz, DMSO-d$_6$) δ 1.38 (m, 2H), 1.73 (m, 1H), 1.81 (m, 2H), 1.87 (m, 2H), 2.84 (m, 2H), 3.24 (m, 2H), 4.21 (t, J=6.4 Hz, 2H), 6.64 (d, J=8.1 Hz, 1H), 6.78 (d, J=8.3 Hz, 1H), 7.47 (t, J=8.3 Hz, 1H), 7.81 (br s, 1H), 8.35 (br s, 1H), 8.59 (m, 1H), 8.85 (m, 1H), 10.99 (br s, 1H). MS 325 (MH$^+$).

Example 160a: tert-Butyl 4-(2-(4-amino-1H-benzo[c][1,2,6]thiadiazine-2,2-dioxide-5-yloxy)ethyl)piperidine-1-carboxylate Prepared as in Example 158 from tert-butyl 4-(2-(2-cyano-3-(sulfamoylamino)phenoxy)ethyl)piperidine-1-carboxylate (Example 160b) in 15% yield as a white solid. $^1$H NMR (400 MHz, DMSO-d$_6$) δ 1.07 (qd, J=12.8, 4.6 Hz, 2H), 1.40 (s, 9H), 1.60 (m, 1H), 1.70 (m, 2H), 1.79 (q, J=6.7 Hz, 2H), 2.70 (m, 2H), 3.93 (m, 2H), 4.21 (t, J=6.7 Hz, 2H), 6.62 (d, J=8.1 Hz, 1H), 6.78 (d, J=8.3 Hz, 1H), 7.46 (t, J=8.3 Hz, 1H), 7.82 (br s, 1H), 8.34 (br s, 1H), 10.96 (br s, 1H).

Example 160b: tert-Butyl-4-(2-(2-cyano-3-(sulfamoylamino)phenoxy) ethyl) piperidine-1-carboxylate Prepared as in Example 158a from tert-butyl 4-(2-(3-amino-2-cyanophenoxy)ethyl)piperidine-1-carboxylate (Example 160c) in 72% yield as a clear syrup. $^1$H NMR (400 MHz, DMSO-d$_6$) δ 1.08 (m, 2H), 1.40 (s, 9H), 1.71 (m, 5H), 2.70 (m, 2H), 3.93 (m, 2H), 4.17 (t, J=6.3 Hz, 2H), 6.98 (d, J=8.6 Hz, 1H), 7.16 (d, J=8.3 Hz, 1H), 7.28 (br s, 2H), 7.57 (t, J=8.3 Hz, 1H), 9.45 (br s, 1H).

Example 160c: tert-Butyl 4-(2-(3-amino-2-cyanophenoxy)ethyl)piperidine-1-carboxylate Prepared as in Example 158b from tert-butyl 4-(2-(2-cyano-3-nitrophenoxy)ethyl)piperidine-1-carboxylate (Example 160d) in 36% as a white foam. $^1$H NMR (400 MHz, CDCl$_3$) δ 1.06 (m, 2H), 1.40 (s, 9H), 1.68 (m, 5H), 2.70 (m, 2H), 3.93 (m, 2H), 4.05 (t, J=6.0 Hz, 2H), 5.98 (br s, 2H), 6.23 (d, J=8.4 Hz, 1H), 6.34 (d, J=8.4 Hz, 1H), 7.18 (t, J=8.2 Hz, 1H).

Example 160d: tert-Butyl-4-(2-(2-cyano-3-nitrophenoxy)ethyl)piperidine-1-carboxylate To a suspension of tert-butyl-4-(2-hydroxyethyl)piperidine-1-carboxylate (769 µL, 3.50 mmol) and NaH (118 mg, 3.50 mmol, 60% dispersion in mineral oil) in dry DMF (5 mL) at 0° C., was added a solution of 2,6-dinitrobenzonitrile (614 mg, 3.18 mmol) in dry DMF (4 mL). The reaction was stirred under N$_2$, warming to rt. Upon completion, the reaction was quenched with H$_2$O (50 mL), and the precipitate was collected by vacuum filtration to provide tert-butyl-4-(2-(2-cyano-3-nitrophenoxy)ethyl)piperidine-1-carboxylate (955 mg, 80%) as a tan solid $^1$H NMR (400 MHz, CDCl$_3$) δ 1.09 (m, 2H), 1.40 (s, 9H), 1.73 (m, 5H), 2.70 (m, 2H), 3.94 (m, 2H), 4.32 (t, J=6.8 Hz, 2H), 7.75 (m, 1H), 7.92 (m, 2H).

Example 161: 4-(2-(4-Amino-1H-benzo[c][1,2,6]thiadiazine-2,2-dioxide-5-yloxy)methyl)piperidinium Chloride

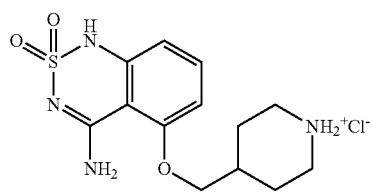

592

Prepared as in Example 166 of WO 2008/154221 from tert-butyl 4-(2-(4-amino-1H-benzo[c][1,2,6]thiadiazine-2,2-dioxide-5-yloxy)methyl)piperidine-1-carboxylate (Example 161a) in 89% yield as a white solid. $^1$H NMR (400 MHz, DMSO-d$_6$) δ 1.49 (m, 2H), 1.90 (d, J=13.1 Hz, 2H), 2.23 (m, 1H), 2.89 (q, J=11.6 Hz, 2H), 3.30 (d, J=12.3 Hz, 2H), 4.09 (br s, J=6.6 Hz, 2H), 6.65 (d, J=8.2 Hz, 1H), 6.82 (d, J=8.2 Hz, 1H), 7.48 (t, J=8.2 Hz, 1H), 7.74 (br s, 1H), 8.33 (br s, 1H), 8.69 (m, 1H), 8.92 (m, 1H), 11.01 (s, 1H). MS 272 (MH$^+$).

Example 161a: tert-Butyl 4-(2-(4-amino-1H-benzo[c][1,2,6]thiadiazine-2,2-dioxide-5-yloxy)methyl)piperidine-1-carboxylate Prepared as in Example 158 from tert-butyl 4-((2-cyano-3-(sulfamoylamino)phenoxy)methyl)piperidine-1-carboxylate (Example 161b) in 91% as a white solid. MS 355 (MH$^+$—C(CH$_3$)$_3$).

Example 161b: tert-Butyl 4-((2-cyano-3-(sulfamoylamino) phenoxy)methyl) piperidine-1-carboxylate Prepared as in Example 158a from tert-butyl 4-((3-amino-2-cyanophenoxy)methyl)piperidine-1-carboxylate (Example 161c) in 56% yield as a white solid. $^1$H NMR (400 MHz, DMSO-d$_6$) δ $^1$H NMR (400 MHz, DMSO-d$_6$) δ 1.20 (m, 2H), 1.41 (s, 9H), 1.76 (d, J=13.2 Hz, 2H), 1.97 (m, 2H), 4.00 (m, 4H), 6.96 (d, J=8.6 Hz, 1H), 7.16 (d, J=8.3 Hz, 1H), 7.28 (s, 2H), 7.57 (t, J=8.3 Hz, 1H), 9.47 (s, 1H).

Example 161c: tert-Butyl 4-((3-amino-2-cyanophenoxy)methyl)piperidine-1-carboxylate Prepared as in Example 158b from tert-butyl 4-((2-cyano-3-nitrophenoxy)methyl)piperidine-1-carboxylate (Example 161d) in 74% yield as a white solid. $^1$H NMR (400 MHz, DMSO-d$_6$) δ 1.18 (qd, J=12.6, 3.8 Hz, 2H), 1.41 (s, 9H), 1.74 (d, J=12.6 Hz, 2H), 1.93 (m, 2H), 2.75 (m, 2H), 3.88 (d, J=6.6 Hz, 2H), 3.99 (br d, J=12.1 Hz, 2H), 6.00 (br s, 2H), 6.21 (d, J=8.2 Hz, 1H), 6.34 (d, J=8.3 Hz, 1H), 7.18 (t, J=8.2 Hz, 1H).

Example 161d: tert-Butyl 4-((2-cyano-3-nitrophenoxy)methyl)piperidine-1-carboxylate Prepared as in Example 158c from 2,6-dinitrobenzonitrile and tert-butyl 4-(hydroxymethyl)piperidine-1-carboxylate in 73% as a tan solid. $^1$H NMR (400 MHz, MeOD) δ 1.24 (qd, J=12.8, 4.4 Hz, 2H), 1.41 (s, 9H), 1.78 (br d, J=12.1 Hz, 2H), 2.02 (m, 2H), 2.77 (m, 2H), 4.00 (br d, J=13.1 Hz, 2H), 4.15 (d, J=6.3 Hz, 2H), 7.74 (dd, J=7.5, 1.5 Hz, 1H), 7.91 (m, 2H).

Example 162: 4-Amino-5-(tetrahydro-2H-pyran-4-yloxy)-1H-benzo[c][1,2,6]thiadiazine-2,2-dioxide

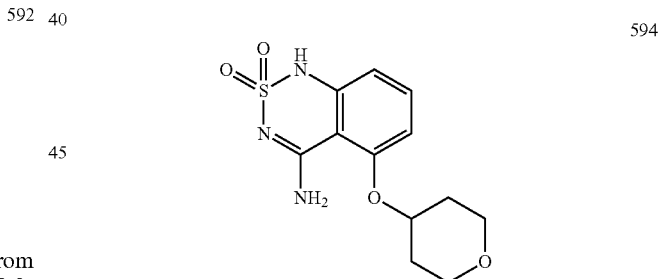

594

Prepared as in Example 158 from 2-sulfamoylamino-6-(tetrahydro-2H-pyran-4-yloxy)benzonitrile (Example 162a) in 69% yield as a white solid. $^1$H NMR (400 MHz, DMSO-d$_6$) δ 1.77 (m, 2H), 2.05 (m, 2H), 3.51 (td, J=11.6, 2.1 Hz, 2H), 3.85 (dt, J=11.4, 3.9 Hz, 2H), 4.83 (sept, J=4.1 Hz, 1H), 6.62 (d, J=8.0 Hz, 1H), 6.88 (d, J=8.4 Hz, 1H), 7.46 (t, J=8.2 Hz, 1H), 7.78 (br s, 1H), 8.39 (br s, 1H), 10.96 (br s, 1H). MS 298 (MH$^+$).

Example 162a: 2-Sulfamoylamino-6-(tetrahydro-2H-pyran-4-yloxy)benzonitrile

Prepared as in Example 158a from 2-amino-6-(tetrahydro-2H-pyran-4-yloxy)benzonitrile (Example 162b) in 58% as a light orange solid. $^1$H NMR (400 MHz, DMSO-d$_6$) δ 1.64 (m, 2H), 1.99 (m, 2H), 3.53 (ddd, J=11.6, 8.3, 3.1 Hz, 2H), 3.85 (m, 2H), 4.80 (sept, J=4.0 Hz, 1H), 7.07 (d, J=8.3 Hz, 1H), 7.16 (d, J=8.1 Hz, 1H), 7.28 (br s, 2H), 7.56 (t, J=8.5 Hz, 1H), 9.47 (br s, 1H).

Example 162b: 2-Amino-6-(tetrahydro-2H-pyran-4-yloxy)benzonitrile

Prepared as in Example 158b from 2-nitro-6-(tetrahydro-2H-pyran-4-yloxy)benzonitrile (Example 162c) in 49% as an orange syrup. MS 219 (MH+).

Example 162c: 2-Nitro-6-(tetrahydro-2H-pyran-4-yloxy)benzonitrile

Prepared as in Example 166d of WO 2008/154221 from 2,6-dinitrobenzonitrile and tetrahydro-2H-pyran-4-ol in 100% yield as a tan solid. $^1$H NMR (400 MHz, DMSO-$d_6$) δ 1.69 (m, 2H), 2.03 (m, 2H), 3.56 (m, 2H), 3.87 (m, 2H), 4.98 (sept, J=3.8 Hz, 1H), 7.90 (m, 3H).

Example 163: 4-Amino-5-(tetrahydrofuran-3-yloxy)-1H-benzo[c][1,2,6]thiadiazine-2,2-dioxide

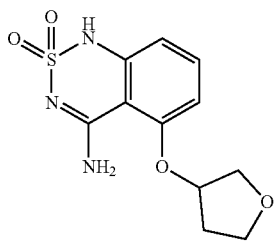

596

Prepared as in Example 158 from 2-sulfamoylamino-6-(tetrahydrofuran-3-yloxy)benzonitrile (Example 163a) in 33% yield as a white solid. $^1$H NMR (400 MHz, DMSO-$d_6$) δ 2.07 (m, 1H), 2.26 (m, 1H), 3.74 (td, J=8.4, 4.7 Hz, 1H), 3.84 (m, 2H), 3.95 (d, J=10.4 Hz, 1H), 5.23 (m, 1H), 6.61 (d, J=8.1 Hz, 1H), 6.73 (d, J=8.4 Hz, 1H), 7.45 (t, J=8.1 Hz, 1H), 7.64 (br s, 1H), 8.33 (br s, 1H), 10.97 (br s, 1H). MS 284 (MH+).

Example 163a: 2-Sulfamoylamino-6-(tetrahydrofuran-3-yloxy)benzonitrile

Prepared as in Example 158a from 2-amino-6-(tetrahydrofuran-3-yloxy)benzonitrile (Example 163b) in 40% yield as an off-white solid. $^1$H NMR (400 MHz, DMSO-$d_6$) δ 1.99 (m, 1H), 2.28 (m, 1H), 3.77 (td, J=8.3, 4.7 Hz, 1H), 3.83 (m, 1H), 3.87 (d, J=7.3 Hz, 1H), 3.92 (dd, J=10.2, 4.4 Hz, 1H), 5.19 (m, 1H), 6.96 (d, J=8.3 Hz, 1H), 7.18 (d, J=8.3 Hz, 1H), 7.29 (s, 2H), 7.58 (t, J=8.3 Hz, 1H), 9.49 (br s, 1H).

Example 163b: 2-Amino-6-(tetrahydrofuran-3-yloxy)benzonitrile

Prepared as in Example 158b from 2-nitro-6-(tetrahydrofuran-3-yloxy)benzonitrile (Example 163c) in 97% yield as a light brown syrup. MS 205 (MH+).

Example 163c: 2-Nitro-6-(tetrahydrofuran-3-yloxy)benzonitrile

Prepared as in Example 166d of WO 2008/154221 from 2,6-dinitrobenzonitrile and tetrahydrofuran-3-ol in 50% yield as a light yellow solid. $^1$H NMR (400 MHz, DMSO-$d_6$) δ 2.04 (m, 1H), 2.32 (m, 1H), 3.81 (td, J=8.3, 4.6 Hz, 1H), 3.89 (m, 2H), 3.98 (dd, J=10.8, 4.5 Hz, 1H), 5.36 (m, 1H), 7.75 (dd, J=8.1, 1.5 Hz, 1H), 7.91 (t, J=8.2 Hz, 1H), 7.95 (dd, J=8.2, 1.6 Hz, 1H).

Example 164: 4-Amino-5-(1-isopropylpiperidin-4-yloxy)-1H-benzo[c][1,2,6]thiadiazine-2,2-dioxide

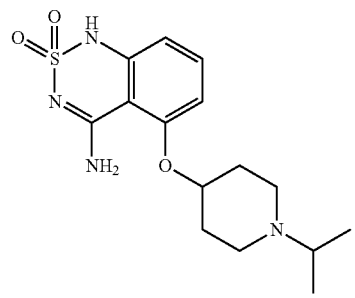

597

Prepared as in Example 111 of WO 2008/154221 from 2-sulfamoylamino-6-(1-isopropylpiperidin-4-yloxy)benzonitrile (Example 164a) in 12% yield as a white solid. $^1$H NMR (400 MHz, DMSO-$d_6$) δ 1.24 (d, J=6.7 Hz, 6H), 2.11 (m, 2H), 2.28 (m, 2H), 3.13 (m, 4H), 4.87 (m, 1H), 6.67 (d, J=8.0 Hz, 1H), 6.87 (d, J=8.6 Hz, 1H), 7.49 (t, J=8.3 Hz, 1H), 7.67 (br s, 1H), 8.43 (br s, 1H), 10.79 (br s, 1H). MS 339 (MH+).

Example 164a: 2-Sulfamoylamino-6-(1-isopropylpiperidin-4-yloxy)benzonitrile

Prepared as in Example 111a of WO 2008/154221 from 2-amino-6-(1-isopropylpiperidin-4-yloxy)benzonitrile (Example 164b). The product was carried onto the next step without further purification.

Example 164b: 2-Amino-6-(1-isopropylpiperidin-4-yloxy)benzonitrile

Prepared as in Example 111b of WO 2008/154221 from 2-nitro-6-(1-isopropylpiperidin-4-yloxy)benzonitrile (Example 164c) in 80% yield as a brown syrup. MS 260 (MH+).

Example 164c: 2-Nitro-(1-isopropylpiperidin-4-yloxy)-6-benzonitrile

Prepared as in Example 166d of WO 2008/154221 from 2,6-dinitrobenzonitrile and 1-isopropylpiperidin-4-ol in 90% yield as a tan solid. $^1$H NMR (400 MHz, DMSO-$d_6$) δ 0.99 (d, J=6.8 Hz, 6H), 1.72 (m, 2H), 1.95 (m, 2H), 2.41 (m, 2H), 2.71 (m, 3H), 4.80 (m, 1H), 7.81 (dd, J=8.2, 1.3 Hz, 1H), 7.89 (m, 2H).

Example 165: (R)-4-Amino-5-((1-butyrylpyrrolidin-2-yl)methoxy)-1H-benzo[c][1,2,6]thiadiazine-2,2-dioxide

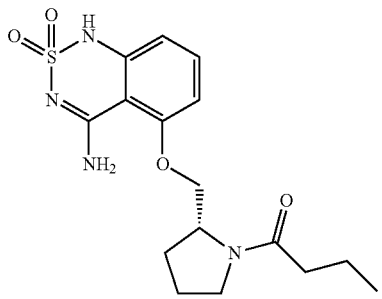

To a solution of (R)-2-amino-6-((1-butyrylpyrrolidin-2-yl)methoxy)benzonitrile (84 mg, 0.29 mmol) (Example 165a) in acetonitrile (9 mL), was added sulfamoyl chloride (70 mg, 0.60 mmol). The reaction was stirred at rt for 20 h, and upon completion was concentrated in vacuo. The resulting residue was dissolved in EtOH (1 mL), and 2N aqueous NaOH (4 mL) was added. The mixture was refluxed for 2 h, and upon completion was cooled to rt, neutralized with 1N HCl and stirred at 0° C. The resulting precipitate was collected by vacuum filtration to provide the desired product (38 mg, 35%) as a white solid. $^1$H NMR (400 MHz, DMSO-$d_6$) δ 0.89 (t, J=7.3 Hz, 3H), 1.54 (sext, J=7.3 Hz, 2H), 1.94 (m, 4H), 2.26 (t, J=7.3 Hz, 2H), 3.49 (m, 2H), 4.10 (m, 1H), 4.25 (m, 1H), 4.43 (m, 1H), 6.62 (d, J=8.2 Hz, 1H), 6.90 (d, J=8.2 Hz, 1H), 7.45 (t, J=8.2 Hz, 1H), 8.08 (br s, 1H), 8.34 (br s, 1H), 10.93 (br s, 1H). MS 367 (MH$^+$).

Example 165a: (R)-2-Amino-6-((1-butyrylpyrrolidin-2-yl)methoxy)benzonitrile

Prepared as in Example 111b of WO 2008/154221 from (R)-2-((1-butyrylpyrrolidin-2-yl)methoxy)-6-nitrobenzonitrile (Example 165b) in 77% yield. MS 274 (MH$^+$).

Example 165b: (R)-2-((1-Butyrylpyrrolidin-2-yl)methoxy)-6-nitrobenzonitrile

To a suspension of (R)-2-((2-cyano-3-nitrophenoxy)methyl)pyrrolidinium chloride (140 mg, 0.49 mmol) (Example 165c) in THF (3 mL) were added Et$_3$N (143 μL, 1.03 mmol) and butyryl chloride (56 μL, 0.54 mmol). The reaction was stirred for 72 h at rt under N$_2$. Upon completion, the reaction was filtered, and the filtrate was concentrated to provide (R)-2-((1-butyrylpyrrolidin-2-yl)methoxy)-6-nitrobenzonitrile (127 mg, 82%) as a yellow syrup. MS 318 (MH$^+$).

Example 165c: (R)-2-((2-Cyano-3-nitrophenoxy)methyl)pyrrolidinium Chloride

Prepared as in Example 166 of WO 2008/154221 from (R)-tert-butyl 2-((2-cyano-3-nitrophenoxy)methyl)pyrrolidine-1-carboxylate (Example 165d) in 71% yield as an off-white solid. $^1$H NMR (400 MHz, DMSO-$d_6$) δ 1.92 (m, 2H), 2.14 (m, 2H), 3.28 (m, 2H), 4.07 (m, 2H), 4.50 (dd, J=710.6, 6.4 Hz, 1H), 4.57 (dd, J=10.9, 3.5 Hz, 1H), 7.77 (d, J=8.0 Hz, 1H), 7.98 (m, 2H), 9.36 (br s, 1H), 9.74 (br s, 1H).

Example 165d: (R)-tert-Butyl 2-((2-cyano-3-nitrophenoxy)methyl)pyrrolidine-1-carboxylate Prepared as in Example 160d from 2,6-dinitrobenzonitrile and (R)-tert-butyl 2-(hydroxymethyl)pyrrolidine-1-carboxylate in 87% yield as a tan solid. $^1$H NMR (400 MHz, DMSO-$d_6$) δ 1.39 (s, 9H), 1.82 (m, 1H), 2.02 (m, 3H), 3.32 (m, 2H), 4.08 (m, 1H), 4.32 (m, 2H), 7.79 (d, J=8.0 Hz, 1H), 7.91 (m, 2H).

Example 161: (R)-2-((4-Amino-1H-benzo[c][1,2,6]thiadiazine-2,2-dioxide-5-yloxy)methyl)-N-propylpyrrolidine-1-carboxamide

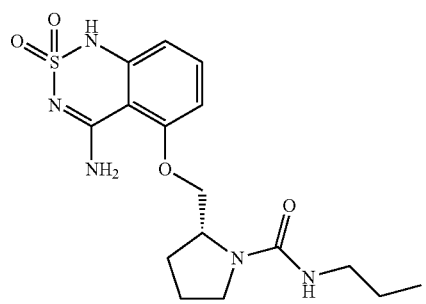

Prepared as in Example 165 from (R)-2-((3-amino-2-cyanophenoxy)methyl)-N-propylpyrrolidine-1-carboxamide (Example 166a) in 57% yield as a white solid. $^1$H NMR (400 MHz, DMSO-$d_6$) δ 0.83 (t, J=7.6 Hz, 3H), 1.42 (sext, J=7.3 Hz, 2H), 1.90 (m, 4H), 3.00 (m, 2H), 3.20 (m, 1H), 3.43 (m, 2H), 4.01 (m, 1H), 4.16 (m, 1H), 4.33 (m, 1H), 6.27 (m, 1H), 6.61 (d, J=8.4 Hz, 1H), 6.89 (d, J=8.3 Hz, 1H), 7.45 (t, J=8.2 Hz, 1H), 8.19 (br s, 1H), 8.27 (br s, 1H), 10.91 (s, 1H). MS 382 (MH$^+$).

Example 166a: (R)-2-((3-Amino-2-cyanophenoxy)methyl)-N-propylpyrrolidine-1-carboxamide Prepared as in Example 158b from (R)-2-((2-cyano-3-nitrophenoxy)methyl)-N-propylpyrrolidine-1-carboxamide (Example 166b) in 14% yield. MS 303 (MH$^+$).

Example 166b: (R)-2-((2-Cyano-3-nitrophenoxy)methyl)-N-propylpyrrolidine-1-carboxamide Prepared as in Example 165b from (R)-2-((2-cyano-3-nitrophenoxy)methyl)pyrrolidinium chloride (Example 165c) and propyl isocyanate in 100% yield as a light yellow solid. MS 333 (MH$^+$).

Example 162: (R)-2-((4-Amino-1H-benzo[c][1,2,6]thiadiazine-2,2-dioxide-5-yloxy)methyl)-N-ethylpyrrolidine-1-carboxamide

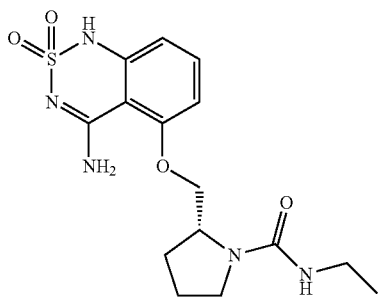

Prepared as in Example 165 from (R)-2-((3-amino-2-cyanophenoxy)methyl)-N-ethylpyrrolidine-1-carboxamide (Example 167a) in 60% yield as a white solid. ¹H NMR (400 MHz, DMSO-d₆) δ 1.02 (t, J=6.8 Hz, 3H), 1.90 (m, 4H), 3.08 (quint, J=6.8 Hz, 2H), 3.20 (m, 2H), 4.01 (m, 1H), 4.16 (m, 1H), 4.33 (m, 1H), 6.27 (m, 1H), 6.62 (d, J=8.4 Hz, 1H), 6.89 (d, J=8.4 Hz, 1H), 7.46 (t, J=8.4 Hz, 1H), 8.20 (br s, 1H), 8.27 (br s, 1H), 10.91 (s, 1H). MS 368 (MH⁺).

Example 167a: (R)-2-((3-Amino-2-cyanophenoxy)methyl)-N-ethylpyrrolidine-1-carboxamide Prepared as in Example 158b from (R)-2-((2-cyano-3-nitrophenoxy)methyl)-N-ethylpyrrolidine-1-carboxamide (Example 167b) in 62% yield. MS 289 (MH⁺).

Example 167b: (R)-2-((2-Cyano-3-nitrophenoxy)methyl)-N-ethylpyrrolidine-1-carboxamide Prepared as in Example 165b from (R)-2-((2-cyano-3-nitrophenoxy)methyl)pyrrolidinium chloride (Example 165c) and ethyl isocyanate in 95% yield as a light yellow solid. MS 319 (MH⁺).

Example 163: (R)-4-Amino-5-((1-isobutyrylpyrrolidin-2-yl)methoxy)-1H-benzo[c][1,2,6]thiadiazine-2,2-dioxide

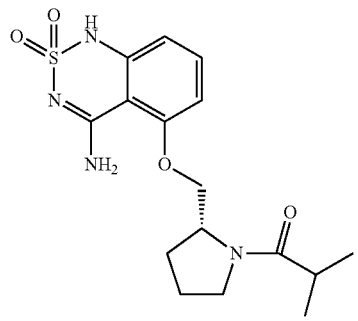

Prepared as in Example 165 from (R)-2-amino-6-((1-isobutyrylpyrrolidin-2-yl)methoxy)benzonitrile (Example 168a) in 100% yield as a white solid. ¹H NMR (400 MHz, DMSO-d₆) δ 1.02 (d, J=6.3 Hz, 6H), 1.94 (m, 4H), 2.70 (m, 1H), 3.55 (m, 2H), 4.12 (m, 1H), 4.24 (m, 1H), 4.43 (m, 1H), 6.62 (d, J=7.9 Hz, 1H), 6.91 (d, J=8.1 Hz, 1H), 7.47 (t, J=8.1 Hz, 1H), 8.04 (br s, 1H), 8.34 (br s, 1H), 10.93 (br s, 1H). MS 367 (MH⁺).

Example 168a: (R)-2-Amino-6-((1-isobutyrylpyrrolidin-2-yl) methoxy) benzonitrile Prepared as in Example 158b from (R)-2-((1-isobutyrylpyrrolidin-2-yl)methoxy)-6-nitrobenzonitrile (Example 168b) in 80% yield as a clear syrup. MS 288 (MH⁺).

Example 168b: (R)-2-((1-Isobutyrylpyrrolidin-2-yl)methoxy)-6-nitrobenzonitrile Prepared as in Example 165b from (R)-2-((2-cyano-3-nitrophenoxy)methyl)pyrrolidinium chloride and isobutyryl chloride in 100% yield as a yellow solid. ¹H NMR (400 MHz, DMSO-d₆) δ 0.96 (dd, J=6.6, 3.5 Hz, 6H), 1.93 (m, 4H), 2.14 (m, 1H), 2.66 (sept, J=6.6 Hz, 1H), 3.55 (m, 1H), 4.28 (m, 3H), 7.79 (dd, J=7.6, 1.8 Hz, 1H), 7.89 (m, 2H).

Example 164: (R)-4-Amino-5-((1-pivaloylpyrrolidin-2-yl)methoxy)-1H-benzo[c][1,2,6]thiadiazine-2,2-dioxide

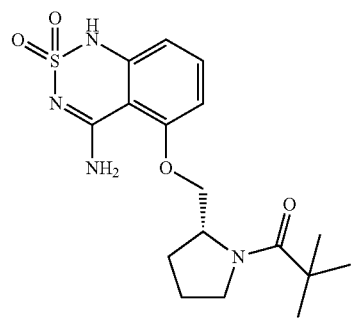

Prepared as in Example 176 of WO 2008/154221 from (R)-2-amino-6-((1-pivaloylpyrrolidin-2-yl)methoxy)benzonitrile (Example 169a) in 64% yield as a white solid. ¹H NMR (400 MHz, DMSO-d₆) δ 1.18 (s, 9H), 1.92 (m, 4H), 3.55 (m, 1H), 3.73 (m, 1H), 4.13 (m, 1H), 4.27 (m, 1H), 4.48 (m, 1H), 6.62 (d, J=8.2 Hz, 1H), 6.92 (d, J=8.2 Hz, 1H), 7.47 (t, J=8.2 Hz, 1H), 7.95 (br s, 1H), 8.37 (br s, 1H), 10.95 (br s, 1H). MS 381 (MH⁺).

Example 169a: (R)-2-Amino-6-((1-pivaloylpyrrolidin-2-yl)methoxy)benzonitrile Prepared as in Example 158b from (R)-2-((1-pivaloylpyrrolidin-2-yl)methoxy)-6-nitrobenzonitrile (Example 169b) in 91% yield as a clear syrup. MS 302 (MH⁺).

Example 169b: (R)-2-((1-Pivaloylpyrrolidin-2-yl)methoxy)-6-nitrobenzonitrile Prepared as in Example 165b from (R)-2-((2-cyano-3-nitrophenoxy)methyl)pyrrolidinium chloride and pivaloyl chloride in 99%. $^1$H NMR (400 MHz, DMSO-$d_6$) δ 1.16 (s, 9H), 1.91 (m, 3H), 2.13 (m, 1H), 3.70 (m, 2H), 4.35 (m, 3H), 7.81 (dd, J=7.5, 2.1 Hz, 1H), 7.92 (m, 2H).

Example 170: (R)-2-((4-Amino-1H-benzo[c][1,2,6]thiadiazine-2,2-dioxide-5-yloxy)methyl)-N-isopropylpyrrolidine-1-carboxamide

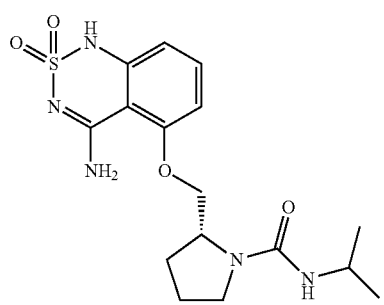

Prepared as in Example 165 from (R)-2-((3-amino-2-cyanophenoxy)methyl)-N-isopropylpyrrolidine-1-carboxamide (Example 170a) in 23% yield as an off-white solid. $^1$H NMR (400 MHz, DMSO-$d_6$) δ 1.05 (d, J=6.4 Hz, 6H), 1.87 (m, 4H), 3.17 (m, 1H), 3.79 (m, 1H), 3.98 (m, 1H), 4.15 (m, 1H), 4.31 (m, 1H), 5.88 (d, J=7.4 Hz, 1H), 6.59 (d, J=8.2 Hz, 1H), 6.86 (d, J=8.5 Hz, 1H), 7.43 (t, J=8.2 Hz, 1H), 8.18 (br s, 1H), 8.23 (br s, 1H), 10.88 (s, 1H). MS 382 (MH$^+$).

Example 170a: (R)-2-((3-Amino-2-cyanophenoxy)methyl)-N-isopropylpyrrolidine-1-carboxamide Prepared as in Example 158b from (R)-2-((2-cyano-3-nitrophenoxy)methyl)-N-isopropylpyrrolidine-1-carboxamide (Example 170b) in 86% yield as a clear syrup. 1H NMR (400 MHz, DMSO-$d_6$) δ 1.07 (d, J=5.9 Hz, 6H), 1.89 (m, 3H), 2.10 (m, 1H), 3.16 (m, 1H), 3.45 (m, 1H), 3.78 (m, 1H), 3.91 (m, 1H), 4.06 (m, 1H), 4.12 (m, 1H), 5.85 (d, J=7.7 Hz, 1H), 6.00 (br s, 2H), 6.31 (d, J=8.4 Hz, 1H), 6.34 (d, J=8.4 Hz, 1H), 7.18 (t, J=8.4 Hz, 1H).

Example 170b: (R)-2-((2-Cyano-3-nitrophenoxy)methyl)-N-isopropylpyrrolidine-1-carboxamide Prepared as in Example 165b from (R)-2-((2-cyano-3-nitrophenoxy)methyl)pyrrolidinium chloride (Example 165c) and isopropyl isocyanate in 100% yield as a yellow solid. $^1$H NMR (400 MHz, DMSO-$d_6$) δ 1.07 (d, J=6.5 Hz, 6H), 1.91 (m, 3H), 2.13 (m, 1H), 3.17 (m, 1H), 3.79 (m, 1H), 4.19 (m, 2H), 4.32 (d, J=8.8 Hz, 1H), 5.91 (d, J=8.1 Hz, 1H), 7.89 (m, 3H).

Example 171: (R)-2-((4-Amino-1H-benzo[c][1,2,6]thiadiazine-2,2-dioxide-5-yloxy)methyl)-N-tert-butylpyrrolidine-1-carboxamide

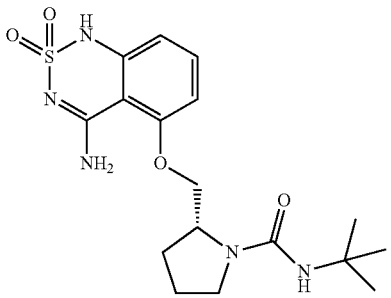

Prepared as in Example 165 from (R)-2-((3-amino-2-cyanophenoxy)methyl)-N-tert-butylpyrrolidine-1-carboxamide (Example 171a) in 56% yield as an off-white solid. $^1$H NMR (400 MHz, DMSO-$d_6$) δ 1.27 (s, 9H), 1.89 (m, 4H), 3.21 (m, 1H), 4.02 (m, 1H), 4.19 (m, 1H), 4.34 (m, 1H), 5.35 (s, 1H), 6.62 (m, 1H), 6.86 (m, 1H), 7.46 (m, 1H), 8.23 (br s, 1H), 8.25 (br s, 1H), 10.91 (s, 1H). MS 396 (MH$^+$).

Example 171a: (R)-2-((3-Amino-2-cyanophenoxy)methyl)-N-tert-butylpyrrolidin-1-carboxamide Prepared as in Example 158b from (R)-2-((2-cyano-3-nitrophenoxy)methyl)-N-tert-butylpyrrolidine-1-carboxamide (Example 171b) in 96% yield as a white solid. MS 317 (MH$^+$).

Example 171b: (R)-2-((2-Cyano-3-nitrophenoxy)methyl)-N-tert-butylpyrrolidine-1-carboxamide Prepared as in Example 165b from (R)-2-((2-cyano-3-nitrophenoxy)methyl)pyrrolidinium chloride (Example 176c) and tert-butyl isocyanate in 100% yield as an off-white solid. $^1$H NMR (400 MHz, DMSO-$d_6$) δ 1.s7 (s, 9H), 1.86 (m, 1H), 1.95 (m, 2H), 2.12 (m, 1H), 3.18 (m, 1H), 3.37 (m, 1H), 4.20 (m, 1H), 4.23 (dd, J=16.0, 6.3 Hz, 1H), 4.31 (dd, J=9.7, 2.7 Hz, 1H), 5.36 (s, 1H), 7.84 (dd, J=7.4, 0.9 Hz, 1H), 7.91 (m, 2H).

Example 172: 4-Amino-5-(methoxytetrahydro-2H-pyran-4-yl)-1H-benzo[c][1,2,6]thiadiazine-2,2-dioxide

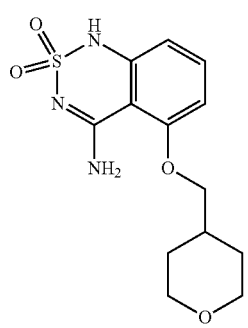

Prepared as in Example 158 from 2-sulfamoylamino-6-(tetrahydro-2H-pyran-4-yl)benzonitrile (Example 172a) in 92% yield as a cream colored solid. $^1$H NMR (400 MHz, DMSO-d$_6$) δ 1.31 (m, 4H), 1.63 (br m, 4H), 3.31 (br m, 2H), 3.86 (br m, 2H), 4.01 (d, J=6.8 Hz, 2H), 6.57 (d, J=8.4 Hz, 1H), 6.71 (d, J=8.0 Hz, 1H), 7.41 (t, J=8.0 Hz, 1H), 7.68 (br, 1H), 8.24 (s, 1H), 10.90 (br, 1H). MS 312 (MH$^+$).

Example 172a: 2-Sulfamoylamino-6-(tetrahydro-2H-pyran-4-yl)benzonitrile

Prepared as in Example 158a from 2-amino-6-((tetrahydro-2H-pyran-4-yl)methoxy)benzonitrile (Example 172b) in 51% yield as an orange solid. $^1$H NMR (400 MHz, DMSO-d$_6$) δ 1.35 (m, 2H), 1.66 (br, 2H), 2.01 (br, 1H), 3.32 (br, 2H), 3.87 (br m, 2H), 3.96 (d, J=6.4 Hz, 2H), 6.92 (d, J=8.4 Hz, 1H), 7.12 (d, J=8.4 Hz, 1H), 7.19 (br s, 2H), 7.52 (t, J=8.4 Hz, 1H), 9.44 (br s, 1H).

Example 172b: 2-Amino-6-((tetrahydro-2H-pyran-4-yl)methoxy)benzonitrile

Prepared as in Example 158b from 2-nitro-6-((tetrahydro-2H-pyran-4-yl)methoxy)benzonitrile (Example 172c) in 80% yield as a yellow solid. $^1$H NMR (400 MHz, DMSO-d$_6$) δ 1.32 (m, 2H), 1.64 (m, 2H), 1.97 (br, 1H), 3.31 (m, 2H), 3.86 (m, 4H), 5.97 (s, 2H), 6.19 (d, J=8.4 Hz, 1H), 6.31 (d, 1H), 7.15 (t, J=8.4 Hz, 1H).

Example 172c: 2-Nitro-6-((tetrahydro-2H-pyran-4-yl)methoxy)benzonitrile

To a solution of tetrahydropyran-4-methanol (782 mg, 6.73 mmol) in THF (25 mL), was added slowly 1.38M nBuLi (4.13 mL, 5.70 mmol) in hexane at −78° C. under nitrogen. At one hour a solution of 2,6-dinitrobenzonitrile (1.00 g, 5.18 mmol) in THF (25 mL) was added. The reaction was stirred under N$_2$ overnight at rt, then was quenched with water (100 mL). The precipitate was collected by filtration to provide 2-nitro-6-((tetrahydro-2H-pyran-4-yl)methoxy)benzonitrile (1.13 g, 83%) as a light brown solid. $^1$H NMR (400 MHz, DMSO-d$_6$) δ 1.68 (m, 2H), 2.06 (br, 1H), 3.33 (m, 2H), 3.88 (m, 2H), 4.11 (d, J=6.0 Hz, 2H), 7.72 (d, J=6.0 Hz, 1H), 7.89-7.85 (m, 2H).

Example 173: 4-Amino-5-(methoxytetrahydrofuran-3-yl)-1H-benzo[c][1,2,6]thiadiazine-2,2-dioxide

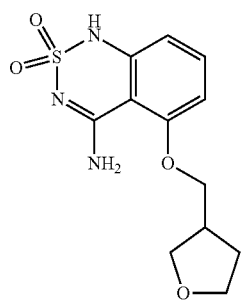

610

Prepared as in Example 158 from 2-sulfamoylamino-6-(methoxytetrahydrofuran-3-yl)benzonitrile (Example 173a) in 26% yield as a white solid. $^1$H NMR (400 MHz, DMSO-d$_6$) δ 1.64 (m, 1H), 1.99 (m, 1H), 2.73 (m, 1H), 3.56 (m, 2H), 3.67 (m, 1H), 3.75 (m, 1H), 4.04 (m, 2H), 6.51 (d, J=8.4 Hz, 1H), 6.62 (d, J=8.4 Hz, 1H), 7.34 (t, J=8.0 Hz, 1H), 7.70 (br s, 1H), 8.09 (br s, 1H), 10.92 (br s, 1H), MS 298 (M H+).

Example 173a: 2-Sulfamoylamino-6-(methoxytetrahydrofuran-3-yl)benzonitrile

Prepared as in Example 158a from 2-amino-6-((tetrahydrofuran-3-yl)methoxy)benzonitrile (Example 173b) in 14% yield as a white solid. $^1$H NMR (400 MHz, DMSO-d$_6$) δ 1.62 (m, 1H), 1.96 (m, 1H), 2.43 (m, 1H), 2.61 (m, 1H), 3.48 (m, 1H), 3.60 (m, 1H), 3.71 (m, 2H), 3.99 (m, 2H), 6.90 (d, J=8.8 Hz, 1H), 7.09 (d, J=8.0 Hz, 1H), 7.19 (s, 1H), 7.49 (t, J=8.4 Hz, 1H), 9.42 (s, 1H).

Example 173b: 2-Amino-6-((tetrahydrofuran-3-yl)methoxy)benzonitrile

Prepared as in Example 158b from 2-nitro-6-((tetrahydrofuran-3-yl)methoxy)benzonitrile (Example 173c) in 99% yield as a golden brown oil. MS 219 (MH$^+$).

Example 173c: 2-Nitro-6-((tetrahydrofuran-3-yl)methoxy)benzonitrile

Prepared as in Example 160d from 2,6-dinitrobenzonitrile and 3-hydroxymethyltetrahydrofuran in 48% yield as an orange-red solid. $^1$H NMR (400 MHz, DMSO-d$_6$) δ 1.68 (m, 1H), 2.00 (m, 1H), 2.70 (m, 1H), 3.54 (m, 1H), 3.66 (m, 1H), 3.76 (m, 2H), 4.03 (m, 1H), 4.19 (m, 1H), 7.73 (d, J=7.6 Hz, 1H), 7.90-7.95 (m, 2H).

Example 174: 4-Amino-5-((tetrahydrofuran-2-yl)methoxy)quinazolin-2(1H)-one

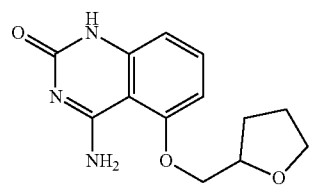

611

Prepared as in Example 158 from N-(2-cyano-3-((tetrahydrofuran-2-yl)methoxy)phenylcarbamoyl)benzamide (Example 174a) in 39% yield. $^1$H NMR (400 MHz, d-DMSO) δ 1.65 (br m, 1H), 1.85 (br m, 2H), 1.99 (br m, 1H), 3.71 (m, 2H), 3.78 (m, 1H), 3.98 (m, 1H), 6.70-6.67 (m, 2H), 7.42 (t, J=8.0 Hz, 1H), 7.62 (s, 1H), 7.88 (s, 1H), 10.62 (s, 1H).

Example 174a: N-(2-Cyano-3-((tetrahydrofuran-2-yl)methoxy) phenyl carbamoyl)benzamide Prepared as in Example 159a from 2-amino-6-((tetrahydrofuran-2-yl)methoxy)benzonitrile (Example 174b) in 45% yield as a white solid. $^1$H NMR (400 MHz, d-DMSO) δ 1.98-1.74 (m, 4H), 3.54 (m, 1H), 3.69 (m, 1H), 4.20-4.07 (m, 3H), 6.97 (d, J=8.8 Hz, 1H), 7.67-7.51 (m, 4H).

Example 174b: 2-Amino-6-((tetrahydrofuran-2-yl)methoxy)benzonitrile

Prepared as in Example 158b from 2-nitro-6-((tetrahydrofuran-2-yl)methoxy)benzonitrile (Example 174c) in 92% yield as a light blue clear oil. $^1$H NMR (400 MHz, MeOD) δ 1.97-1.68 (m, 4H), 3.75-3.64 (m, 1H), 3.80-3.75 (m, 1H), 3.98-3.90 (m, 2H), 4.15-4.12 (m, 1H), 5.96 (s, 1H), 6.18 (d, J=8.0 Hz, 1H), 6.31 (d, J=8.0 Hz, 1H), 7.14 (t, J=8.4 Hz, 1H).

Example 174c: 2-Nitro-6-((tetrahydrofuran-2-yl)methoxy)benzonitrile

Prepared as in Example 160d from 2,6-dinitrobenzonitrile and tetrafurfuryl alcohol in 68% yield. $^1$H NMR (400 MHz, MeOD) δ 2.10-1.70 (m, 7H), 3.68-3.66 (m, 1H), 3.80-3.78 (m, 1H), 4.29-4.20 (m, 3H), 7.72 (d, J=6.0 Hz, 1H), 7.90-7.84 (m, 2H).

Example 175: 4-Amino-5-(2-methoxybenzyloxy)-1H-benzo[c][1,2,6]thiadiazine-2,2-dioxide

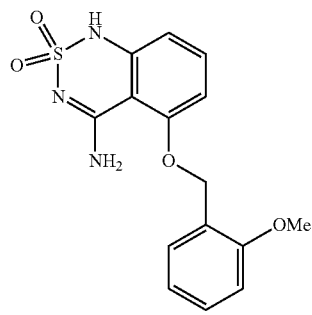

612

Prepared as in Example 158 from 2-sulfamoylamino-6-(4-methoxybenzyloxy) benzonitrile (Example 175a) in 85% yield. $^1$H NMR (400 MHz, DMSO-d$_6$) δ 3.81 (s, 3H), 5.25 (s, 2H), 6.59 (d, J=8.4 Hz, 1H), 6.86 (d, J=8.0 Hz, 1H), 6.96 (t, J=7.2 Hz, 1H), 7.09 (d, J=8.0 Hz, 1H), 7.37 (t, J=8.0 Hz, 1H), 7.46-7.42 (m, 2H), 7.91 (s, 1H), 8.31 (s, 1H), 10.96 (s, 1H). MS 334 (MH$^+$).

Example 175a: 2-Sulfamoylamino-6-(2-methoxybenzyloxy)benzonitrile

Prepared as in Example 158a from 2-amino-6-((tetrahydrofuran-2-yl)methoxy)benzonitrile (Example 175b) in 23% yield. $^1$H NMR (400 MHz, d-DMSO) δ 3.80 (s, 3H), 6.88 (d, J=8.4 Hz, 1H), 6.88 (d, J=8.1 Hz 1H), 6.96 (t, J=7.6 Hz, 1H), 7.06 (d, J=8.0 Hz, 2H), 7.16 (d, J=8.4 Hz, 1H), 7.39-7.33 (m, 5H), 7.45 (d, J=7.2 Hz, 1H), 11.20 (s, 1H).

Example 175b: 2-Amino-6-(2-methoxybenzyloxy)benzonitrile

Prepared as in Example 158b from 2-nitro-6-(2-methoxybenzyloxy) benzonitrile (example 175oc) in 56% yield. $^1$H NMR (400 MHz, MeOD) δ 3.79 (s, 3H), 5.04 (s, 2H), 6.30-6.26 (m, 2H), 7.06-6.94 (m, 3H), 7.33-7.28 (m, 3H), 7.54 (s, 1H).

Example 175c: 2-Nitro-6-(2-methoxybenzyloxy)benzonitrile

Prepared as in Example 158c from 2,6-dinitrobenzonitrile and 2-methoxybenzyl alcohol in 58% yield. $^1$H NMR (400 MHz, DMSO) δ 3.82 (s, 3H), 5.34 (s, 2H), 6.99 (t, J=7.6 Hz, 1H), 7.08 (d, J=8.4 Hz, 1H), 7.37 (t, J=8.4 Hz, 1H), 7.46 (d, J=6.0 Hz, 1H), 7.81 (d, J=7.6 Hz, 1H), 7.93-7.87 (m, 2H).

Example 176: 4-Amino-5-(methoxytetrahydrofuran-2-yl)-1H-benzo[c][1,2,6]thiadiazine-2,2-dioxide

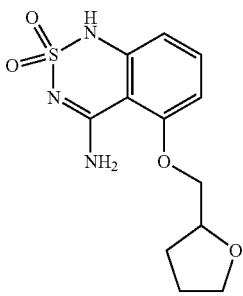

613

Prepared as in Example 158 from 2-sulfamoylamino-6-(methoxytetrahydrofuran-2-yl)benzonitrile (Example 176a) in 100% yield as a white solid. $^1$H NMR (400 MHz, DMSO-d$_6$) δ 1.65 (m, 1H), 1.86 (m, 1H), 1.98 (m, 1H), 3.69 (m, 1H), 3.78 (m, 1H), 3.98 (m, 1H) 4.25 (m, 1H), 6.61 (d, J=7.2 Hz, 1H), 6.74 (d, J=8.0 Hz, 1H).

Example 176a: 2-Sulfamoylamino-6-(methoxytetrahydrofuran-2-yl)benzonitrile

Prepared as in Example 158a from 2-amino-6-((tetrahydrofuran-2-yl)methoxy)benzonitrile (Example 39b) in 79% yield as a light yellow solid. $^1$H NMR (400 MHz, DMSO-d$_6$) δ 2.02-1.68 (m, 2H), 3.66 (m, 1H), 3.81-3.76 (m, 1H), 4.20-4.03 (m, 3H), 6.93 (d, J=8.4 Hz, 1H), 7.12 (d, J=8.4 Hz, 1H), 7.23 (s, 1H), 7.53 (t, J=8.4 Hz, 1H), 9.34 (br s, 1H).

Example 177: 4-Amino-5-(furan-3-ylmethoxy)-1H-benzo[c][1,2,6]thiadiazine-2,2-dioxide

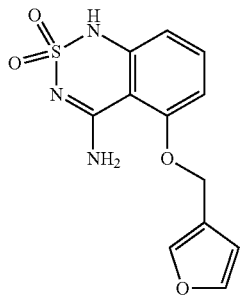

614

Prepared as in Example 158 from 2-sulfamoylamino-6-(furan-3-ylmethoxy)benzonitrile (Example 177a) in 45% yield as an off white solid. $^1$H NMR (400 MHz, DMSO-d$_6$) δ 5.11 (s, 2H), 6.54 (d, J=0.4 Hz, 1H), 6.56 (s, 1H), 6.80 (d, J=8.8 Hz, 1H), 7.39 (t, J=8.4 Hz, 1H), 7.64 (s, 1H), 7.74 (s, 1H), 7.81 (s, 1H), 8.23 (s, 1H), 10.90 (s, 1H). MS 294 (MH$^+$).

Example 177a: 2-Sulfamoylamino-6-(furan-3-ylmethoxy)benzonitrile

Prepared as in Example 158a from 2-amino-6-(furan-3-ylmethoxy)benzonitrile (Example 177b) in 57% yield as an off white solid. ¹H NMR (400 MHz, d-DMSO) δ 5.04 (s, 2H), 6.62 (s, 1H), 6.88 (d, J=8.8 Hz, 1H), 7.15 (d, J=8.1, 0.8 Hz, 1H), 7.35 (d, J=8.8 Hz, 1H), 7.39-7.32 (m, 2H), 7.67 (s, 1H), 7.79 (s, 1H), 7.86 (s. 1H), 7.93 (s, 1H), 10.91 (s, 1H).

Example 177b:
2-Amino-6-(furan-3-ylmethoxy)benzonitrile

Prepared as in Example 158b from 2-nitro-6-(furan-3-ylmethoxy)benzonitrile (Example 177c) in 21% yield as a light yellow oil. ¹H NMR (400 MHz, d-DMSO) δ 4.92 (s, 2H), 6.31-6.26 (m, 2H), 6.59 (s, 1H), 6.99 (t, J=8.4 Hz, 1H), 7.27 (s, 1H), 7.45 (s, 1H), 7.66 (s, 1H), 7.76 (s, 1H).

Example 177c:
2-Nitro-6-(furan-3-ylmethoxy)benzonitrile

Prepared as in Example 158c from 2,6-dinitrobenzonitrile and 3-furanmethanol in 100% yield. ¹H NMR (400 MHz, d-DMSO) δ 5.27 (s, 2H), 6.59 (s, 1H), 7.69 (s, 1H), 7.91-7.84 (m, 4H).

Example 178: 4-Amino-5-(3-methoxybenzyloxy)-1H-benzo[c][1,2,6]thiadiazine-2,2-dioxide

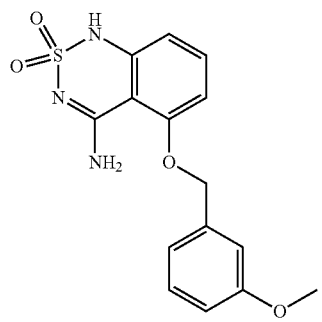

615

Prepared as in Example 158 from 2-sulfamoylamino-6-(3-methoxybenzyloxy)benzonitrile (Example 178a) in 54% yield. ¹H NMR (400 MHz, d-DMSO) δ 3.74 (s, 3H), 5.27 (s, 2H), 6.59 (d, J=8.0 Hz, 1H), 6.79 (d, J=8.0 Hz, 1H), 6.90 (d, J=8.0 Hz, 1H), 7.04 (d, J=7.2 Hz, 1H), 7.08 (s, 1H), 7.31 (t, J=8.4 Hz, 1H), 7.42 (t, J=8.0 Hz, 1H), 7.89 (br s, 1H), 8.32 (br s, 1H), 10.96 (br s, 1H). MS 334 (MH⁺).

Example 178a: 2-Sulfamoylamino-6-(3-methoxybenzyloxy)benzonitrile

Prepared as in Example 158a from 2-amino-6-(3-methoxybenzyloxy)benzonitrile (Example 178b) in 17% yield as a white solid. MS 334 (MH⁺).

Example 178b:
2-Amino-6-(3-methoxybenzyloxy)benzonitrile

To a mixture of 2-nitro-6-(3-methoxybenzyloxy)benzonitrile (Example 178c) (480 mg, 1.69 mmol) in 5:1 acetone:water (9 mL) was added zinc (552 mg, 8.44 mmol) and ammonium chloride (911 mg, 16.9 mmol). The reaction was stirred at room temperature for 30 minutes, then filtered and concentrated. The residue was purified by flash chromatography (55:45 EtOAc:Hexane) to provide 2-amino-6-(benzyloxy)benzonitrile (337 mg, 78%). ¹H NMR (400 MHz, d-DMSO) δ 3.73 (s, 3H), 5.04 (s, 1H), 6.27 (d, J=8.0 Hz, 1H), 6.31 (d, J=8.4 Hz, 1H), 7.06-6.97 (m, 3H), 7.27 (t, J=8.0 Hz, 1H), 7.36 (s, 1H), 7.55 (s, 1H).

Example 178c:
2-(3-Methoxybenzyloxy)-6-nitrobenzonitrile

Prepared as in Example 158c from 2,6-dinitrobenzonitrile and 3-methoxybenzylalcohol in 83% yield. ¹H NMR (400 MHz, d-DMSO) δ 3.75 (s, 3H), 5.38 (s, 2H), 6.91 (d, J=8.0 Hz, 1H), 7.04 (d, J=7.6 Hz, 1H), 7.07 (s, 1H), 7.33 (t, J=8.0 Hz, 1H), 7.78 (d, J=8.8 Hz, 4H), 7.93-7.87 (m, 2H).

Example 179: 4-(2-(4-Amino-1H-benzo[c][1,2,6]thiadiazine-2,2-dioxide-5-yloxy)methyl)pyrrolidinium Chloride

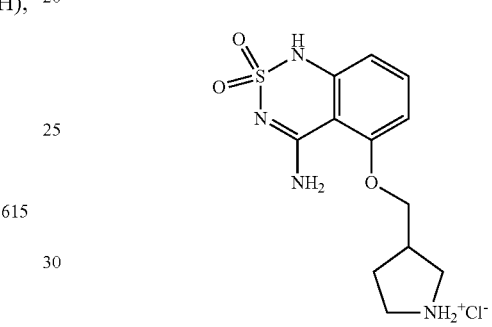

616

Prepared as in Example 160 from tert-Butyl 3-(2-(4-amino-1H-benzo[c][1,2,6]thiadiazine-2,2-dioxide-5-yloxy)methyl)pyrrolidine-1-carboxylate (Example 179a) in 27% yield as a white solid. ¹H NMR (400 MHz, DMSO-d₆) δ 1.72 (m, 1H), 2.07 (m, 1H), 2.52 (m, 1H), 2.64 (m, 1H), 2.94-2.74 (m, 3H), 3.79 (m, 2H), 6.26 (d, J=8.0 Hz, 1H), 6.37 (d, J=8.8 Hz, 1H), 7.09 (t, J=8.0 Hz, 1H), 7.31 (br s, 1H), 7.96 (br s, 1H), 9.03 (br s, 1H).

Example 179a: tert-Butyl 3-(2-(4-amino-1H-benzo[c][1,2,6]thiadiazine-2,2-dioxide-5-yloxy)methyl)pyrrolidine-1-carboxylate Prepared as in Example 158 from tert-butyl-3-((2-cyano-3-(sulfamoylmethyl)phenoxy)methyl) pyrrolidine-1-carboxylate (Example 179b) in 94% yield as a white solid. ¹H NMR (400 MHz, DMSO-d₆) δ 1.37 (s, 9H), 1.66 (br m, 1H), 1.97 (br m, 1H), 2.78 (br m, 1H), 3.48-3.20 (br m, 4H), 4.12 (br, m 2H), 6.60 (d, J=8.0 Hz, 1H), 6.74 (d, J=8.4 Hz, 1H), 7.44 (t, J=8.4 Hz, 1H), 7.70 (s, 1H), 8.33 (s, 1H), 10.95 (s, 1H).

Example 179b: tert-Butyl 3-((2-cyano-3-(sulfamoylamino)phenoxy)methyl) pyrrolidine-1-carboxylate Prepared as in Example 158a from tert-butyl 3-((3-amino-2-cyanophenoxy)methyl)pyrrolidine-1-carboxylate (Example 179c) in 47% yield as a white solid. ¹H NMR (400 MHz, DMSO-d₆) δ 1.37 (s, 9H), 1.70 (br, 1H), 1.97 (br, 1H), 2.63 (br, 1H), 3.47-2.98 (br m, 4H), 4.08 (br m, 2H), 6.94 (d, J=8.8 Hz, 1H), 7.14 (d, J=8.4 Hz, 1H), 7.24 (s, 1H), 7.48 (s, 1H), 7.54 (t, J=8.0, 1H), 9.48 (br s, 1H).

Example 179c: tert-Butyl 3-((3-amino-2-cyanophenoxy)methyl)pyrrolidine-1-carboxylate Prepared as in Example 158b from tert-butyl-((2-cyano-3-nitrophenoxy)methyl)pyrrolidine-1-carboxylate (Example 179d) in 100% yield as a clear oil. $^1$H NMR (400 MHz, DMSO-$d_6$) δ 1.37 (s, 9H), 1.69 (br, 1H), 1.96 (br, 1H), 2.59 (br, 1H), 3.07 (br, 1H), 3.23 (br, 1H), 3.35 (br, 1H), 3.40 (br, 1H), 3.96 (m, 2H), 5.98 (s, 2H), 6.20 (d, J=8.0 Hz, 1H), 6.32 (d, J=8.0 Hz, 1H), 7.15 (t, J=8.4 Hz, 1H).

Example 179d: tert-Butyl-((2-cyano-3-nitrophenoxy)methyl)pyrrolidine-1-carboxylate Prepared as in Example 160d from 2,6-dinitrobenzonitrile and tert-butyl 3-(hydroxymethyl)pyrrolidine-1-carboxylate in 69% yield as a yellow solid. MS 347 (MH$^+$).

Example 180: (R)-4-Amino-5-((1-acetylpyrrolidin-2-yl)methoxy)-1H-benzo[c][1,2,6]thiadiazine-2,2-dioxide

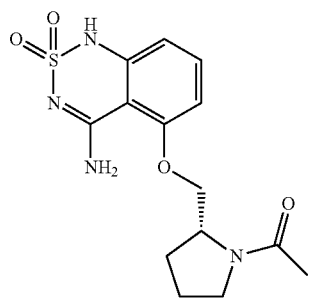

617

Prepared as in Example 165 from (R)-2-amino-6-((1-acetylpyrrolidin-2-yl)methoxy)benzonitrile (Example 180a) in 31% yield as a white solid. $^1$H NMR (400 MHz, DMSO-$d_6$) δ 1.90 (m, 4H), 2.00 (s, 3H), 3.49 (m, 2H), 4.09 (dd, J=9.7, 6.1 Hz, 1H), 4.24 (dd, J=9.8, 5.7 Hz, 1H), 4.41 (m, 1H), 6.62 (d, J=8.2 Hz, 1H), 6.87 (d, J=8.5 Hz, 1H), 7.46 (t, J=8.3 Hz, 1H), 8.12 (br s, 1H), 8.33 (br s, 1H), 10.93 (br s, 1H). MS 339 (MH$^+$).

Example 180a: (R)-2-Amino-6-((1-acetylpyrrolidin-2-yl)methoxy)benzonitrile

Prepared as in Example 158b from (R)-2-((1-acetylpyrrolidin-2-yl)methoxy)-6-nitrobenzonitrile (Example 180b) in 77% yield as a clear syrup. MS 260 (MH$^+$).

Example 180b: (R)-2-((1-Acetylpyrrolidin-2-yl)methoxy)-6-nitrobenzonitrile

Prepared as in Example 165b from (R)-2-((2-cyano-3-nitrophenoxy)methyl)pyrrolidinium chloride and acetyl chloride in 100% yield as a yellow syrup. MS 290 (MH$^+$).

Example 181: 4-Amino-5-(methoxy-3-pyrolidine-1-propionyl)-1H-benzo[c][1,2,6]thiadiazine-2,2-dioxide

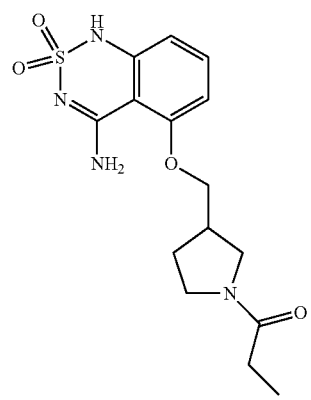

618

Prepared as in Example 158 from 2-sulfamoylamino-6-((1-propionylpyrrolidin-3-yl)methoxybenzonitrile (Example 181a) in 29% yield as an off-white solid. $^1$H NMR (400 MHz, DMSO-$d_6$) δ 0.95 (t, J=7.6 Hz, 3H), 1.66 (m, 1H), 1.77 (m, 1H), 1.97 (m, 1H), 2.05 (m, 1H), 2.21 (q, J=8.0 Hz, 2H), 2.74 (m, 1H), 2.86 (m, 1H), 3.63-3.23 (m, 4H), 4.13 (m, 2H), 6.60 (d, J=8.0 Hz, 1H), 6.75 (d, J=8.4 Hz, 1H), 7.44 (t, J=8.0 Hz, 1H), 7.72 (s, 1H), 8.37-8.32 (m, 1H), 10.94 (s, 1H).

Example 181a: 2-Sulfamoylamino-6-((1-propionylpyrrolidin-3-yl)methoxybenzonitrile Prepared as in Example 158a from 2-amino-6-((1-propionylpyrrolidin-3-yl)methoxy)benzonitrile (Example 181b) in 27% yield as a white solid. MS 353 (MH$^+$).

Example 181b: 2-Amino-6-((1-propionylpyrrolidin-3-yl)methoxy)benzonitrile

Prepared as in Example 158b from 2-nitro-6-((1-propionylpyrrolidin-3-yl)methoxy)benzonitrile (Example 181c) in 100% yield as a clear oil. MS 274 (MH$^+$).

Example 181c: 2-Nitro-6-((1-propionylpyrrolidin-3-yl)methoxy)benzonitrile

Prepared as in Example 165b from 2-nitro-6-(pyrrolidin-3-ylmethoxy)benzonitrile hydrochloride (Example 181d) and propionyl chloride in 51% as a yellow solid. MS 304 (MH$^+$).

Example 181d: 2-Nitro-6-(pyrrolidin-3-ylmethoxy)benzonitrile hydrochloride

Prepared as in Example 160 from tert-butyl-((2-cyano-3-nitrophenoxy)methyl)pyrrolidine-1-carboxylate (Example 44d) in 100% yield as a yellow solid. MS 248 (MH$^+$).

Example 182: 4-Amino-5-(methoxy-3-pyrolidine-1-butyryl)-1H-benzo[c][1,2,6]thiadiazine-2,2-dioxide

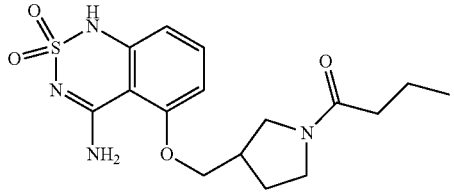

Prepared as in Example 158 from 2-sulfamoylamino-6-((1-butyrylpyrrolidin-3-yl)methoxybenzonitrile (Example 182a) in 73% yield as a white solid. $^1$H NMR (400 MHz, DMSO-d$_6$) δ 0.86 (t, J=7.6 Hz, 3H), 1.48 (q, J=7.6 Hz, 2H), 1.65 (m, 1H), 1.76 (m, 1H), 1.97 (m, 1H), 2.05 (m, 1H), 2.17 (t, J=7.2 Hz, 2H), 2.74 (m, 1H), 2.85 (m, 1H), 3.10 (m, 1H), 3.64-3.23 (m, 4H), 4.12 (m, 1H), 6.60 (d, J=8.0 Hz, 1H), 6.75 (d, J=8.8 Hz, 1H), 7.44 (t, J=8.4 Hz, 1H), 7.71 (s, 1H), 8.35-8.32 (m, 1H), 10.94 (s, 1H).

Example 182a: 2-Sulfamoylamino-6-((1-butyrylpyrrolidin-3-yl)methoxybenzonitrile Prepared as in Example 158a from 2-amino-6-((1-butyrylpyrrolidin-3-yl)methoxy)benzonitrile (Example 182b) in 19% yield as a white solid. $^1$H NMR (400 MHz, DMSO-d$_6$) δ 0.85 (t, J=7.6 Hz, 3H), 1.48 (q, J=7.6 Hz, 2H), 2.13-1.64 (m, 2H), 2.17 (m, 2H), 2.75-2.53 (m, 2H), 3.65-3.18 (m, 4H), 4.09 (m, 2H), 6.94 (m, 1H), 7.13 (m, 1H), 7.25 (s, 1H), 7.54 (m, 1H), 9.45 (m, 1H).

Example 182b: 2-Amino-6-((1-butyrylpyrrolidin-3-yl)methoxy)benzonitrile

Prepared as in Example 158b from 2-nitro-6-((1-butyrylpyrrolidin-3-yl)methoxy)benzonitrile (Example 182c) in 100% yield as a brown oil. MS 288 (MH$^+$).

Example 182c: 2-Nitro-6-((1-butyrylpyrrolidin-3-yl)methoxy)benzonitrile

Prepared as in Example 165b from 2-nitro-6-(pyrrolidin-3-ylmethoxy)benzonitrile hydrochloride (Example 181d) and butyryl chloride in 100% yield as an orange solid. MS 318 (MH$^+$).

Example 183: (E)-4-Amino-5-(1-(propylcarbamoyl)cyclopropylmethoxy)-1H-benzo[c][1,2,6]thiadiazine-2,2-dioxide

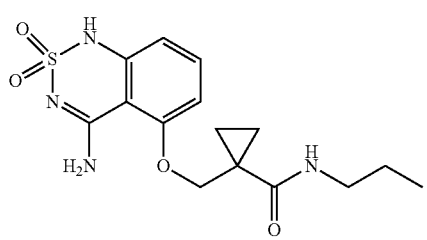

Prepared as in Example 158 from 1-((2-cyano-3-(sulfamoylamino)phenoxy)methyl)-N-propylcyclopropanecarboxamide (Example 183a) in 94% yield as a white solid. $^1$H-NMR (400 MHz, DMSO-d$_6$) δ10.95 (broad s, 1H), 8.35 (broad s, 1H), 7.95 (broad s, 1H), 7.76 (t, J=5.2 Hz, 1H), 7.45 (t, J=8.0 Hz, 1H), 6.69 (d, J=8.8 Hz, 1H), 6.61 (d, J=7.6 Hz, 1H), 4.22 (s, 2H), 3.01 (q, J=6.4 Hz, 2H), 1.40 (hex, J=6.8 Hz, 2H), 1.12-1.18 (m, 2H), 0.88-0.95 (m, 2H), 0.80 (t, J=7.6 Hz, 3H). MS 353 (MH$^+$).

Example 183a: 1-((2-Cyano-3-(sulfamoylamino)phenoxy)methyl)-N-propylcyclopropanecarboxamide Prepared as in Example 158a from 1-((3-amino-2-cyanophenoxy)methyl)-N-propylcyclopropanecarboxamide (Example 183b) and sulfamoyl chloride in 78% yield as a white solid. $^1$H-NMR (400 MHz, DMSO-d$_6$) δ9.45 (broad s, 1H), 7.51-7.61 (m, 2H), 7.26 (broad s, 2H), 7.16 (d, J=8.0 Hz, 1H), 6.91 (d, J=8.4 Hz, 1H), 4.24 (s, 2H), 3.04 (q, J=6.4 Hz, 2H), 1.43 (hex, J=7.6 Hz, 2H), 1.08-1.14 (m, 2H), 0.83-0.88 (m, 2H), 0.82 (t, J=7.2 Hz, 3H).

Example 183b: 1-((3-Amino-2-cyanophenoxy)methyl)-N-propylcyclopropanecarboxamide A solution of 1-(hydroxymethyl)-N-propylcyclopropanecarboxamide (Example 183c) (0.67 g, 4.25 mmol) in anhydrous THF (10 mL) was treated with NaH (0.17 g, 4.25 mmol, 60% suspension in mineral oil) at 0° C., under a nitrogen atmosphere. The obtained mixture was stirred at 0° C. for 10 min and at rt over 30 min. Then, a solution of 2-amino-6-fluorobenzonitrile (0.53 g, 3.86 mmol) in THF (5.0 mL) was added and the obtained mixture was heated at reflux overnight. The cold mixture was quenched with saturated aqueous solution of NH$_4$Cl (20 mL) and extracted with EtOAc (3×50 mL). The combined extract was washed with brine, dried over anhydrous MgSO$_4$, filtered and evaporated. The residue was purified by chromatography on silica gel using gradient hexanes-hexanes/EtOAc (4:6), to give 0.75 g (71%) of the title compound as a yellow solid. $^1$H-NMR (400 MHz, DMSO-d$_6$) δ7.51 (t, J=6.0 Hz, 1H), 7.17 (t, J=8.0 Hz, 1H), 6.34 (d, J=8.4 Hz, 1H), 6.19 (d, J=8.4 Hz, 1H), 5.97 (broad s, 2H), 4.13 (s, 2H), 3.04 (q, J=6.4 Hz, 2H), 1.43 (hex, J=6.8 Hz, 2H), 1.05-1.11 (m, 2H), 0.78-0.86 (m, 5H).

Example 183c: 1-(Hydroxymethyl)-N-propylcyclopropanecarboxamide

To a solution of ethyl 1-(propylcarbamoyl)cyclopropanecarboxylate (Example 183d) (1.65 g, 8.27 mmol) in EtOH (70 mL) was added NaBH$_4$ (0.97 g, 25.64 mmol) at rt. The obtained mixture was stirred at rt over 2 days, quenched with 1.5M HCl and concentrated under reduced pressure. The concentrated mixture was extracted with EtOAc (4×70 mL), the combined extract was washed with saturated NaHCO$_3$ and brine, and was dried over MgSO$_4$. The filtrate was evaporated and the residue was purified by chromatography on silica gel using the solvent gradient hexanes-hexanes/EtOAc (1:9), to furnish 1.14 g (88%) of the product as a white solid. $^1$H-NMR (400 MHz, DMSO-d$_6$) δ7.49 (broad s, 1H), 5.09 (broad s, 1H), 3.49 (s, 2H), 3.05 (q, J=6.4 Hz, 2H), 1.41 (hex, J=7.6 Hz, 2H), 0.86-0.91 (m, 2H), 0.83 (t, J=7.2 Hz, 3H), 0.55-0.60 (m, 2H).

Example 183d: Ethyl 1-(propylcarbamoyl)cyclopropanecarboxylate

To a solution of 1-(ethoxycarbonyl)cyclopropanecarboxylic acid (Wheeler, T. N.; Ray, J. A. *Synthetic Communications* 1988, 18(2), 141) (1.52 g, 9.62 mmol) and n-propylamine (0.63 g, 10.58 mmol) in anhydrous DMF (65 mL) at rt, were added NaHCO$_3$ (4.04 g, 48.11 mmol), N-(3-dimethylaminopropyl)-N'-ethylcarbodiimide hydrochloride (2.21 g, 11.54 mmol) and 1-hydroxybenzotriazole hydrate (1.77 g, 11.54 mmol) under a nitrogen atmosphere. After being stirred at rt overnight, the mixture was partitioned between water (100 mL) and EtOAc (300 mL). The organic phase was separated, washed with water and brine, and was dried over anhydrous MgSO$_4$. The filtrate was evaporated to give 1.65 g (86%) of the crude product which was used in the next step without purification. $^1$H-NMR (400 MHz, DMSO-d$_6$) δ8.33 (broad s, 1H), 4.08 (q, J=6.8 Hz, 2H), 3.07 (q, J=6.4 Hz, 2H), 1.43 (hex, J=6.4 Hz, 2H), 1.31 (s, 4H), 1.17 (t, J=6.4 Hz, 3H), 0.85 (t, J=7.2 Hz, 3H).

Example 184: (E)-4-Amino-5-(4-methoxybut-2-enyloxy)-1H-benzo[c][1,2,6]thiadiazine-2,2-dioxide

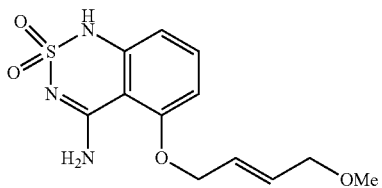

621

Prepared as in Example 158 from 2-sulfamoylamino-6-(4-methoxybut-2-enyloxy)benzonitrile (Example 184a) in 91% yield as a white solid. $^1$H-NMR (400 MHz, DMSO-d$_6$) δ10.94 (broad s, 1H), 8.34 (broad s, 1H), 7.90 (broad s, 1H), 7.45 (t, J=8.4 Hz, 1H), 6.75 (d, J=7.6 Hz, 1H), 6.61 (d, J=8.0 Hz, 1H), 5.88-6.02 (m, 2H), 4.75-4.81 (m, 2H), 3.88-3.93 (m, 2H), 3.22 (s, 3H). MS 298 (MH$^+$).

Example 184a: 2-Sulfamoylamino-6-(4-methoxybut-2-enyloxy)benzonitrile

Prepared as in Example 158a from (E)-2-amino-6-(4-methoxybut-2-enyloxy)benzonitrile (Example 184b) in 93% yield as a white solid. $^1$H-NMR (400 MHz, DMSO-d$_6$) δ9.46 (broad s, 1H), 7.56 (t, J=8.4 Hz, 1H), 7.26 (broad s, 2H), 7.15 (d, J=8.0 Hz, 1H), 6.96 (d, J=8.8 Hz, 1H), 5.84-6.00 (m, 2H), 4.68-4.76 (m, 2H), 3.89-3.95 (m, 2H), 3.23 (s, 3H).

Example 184b: (E)-2-Amino-6-(4-methoxybut-2-enyloxy)benzonitrile

To a solution of (E)-2-(4-methoxybut-2-enyloxy)-6-nitrobenzonitrile (Example 184c) (0.25 g, 1.00 mmol) in a mixture of AcOH, EtOH and water (33 mL, 1:1:1) was added iron powder (0.56 g, 10.00 mmol) at rt. The obtained mixture was stirred at rt for 20 min, then was heated to 50° C. for a further 15 min, and allowed to cool. The suspension was concentrated under reduced pressure; the residue was treated with water (50 mL) and extracted with EtOAc (4×50 mL). The combined extract was washed with saturated aqueous NaHCO$_3$ and brine, and was dried over anhydrous MgSO$_4$. The filtrate was evaporated and the residue was purified by silica gel flash chromatography using gradient hexanes-hexanes/EtOAc (1:1), to give 0.19 g (86%) of the title compound as a white solid. $^1$H-NMR (400 MHz, DMSO-d$_6$) 7.17 (t, J=8.4 Hz, 1H), 6.34 (d, J=8.8 Hz, 1H), 6.22 (d, J=8.4 Hz, 1H), 6.00 (broad s, 2H), 5.82-5.96 (m, 2H), 4.56-4.62 (m, 2H), 3.88-3.93 (m, 2H), 3.23 (s, 3H).

Example 184c: (E)-2-(4-Methoxybut-2-enyloxy)-6-nitrobenzonitrile

To a solution of (E)-2-(4-hydroxybut-2-enyloxy)-6-nitrobenzonitrile (Example 184d) (0.50 g, 2.13 mmol) and 2,6-di-tert-butyl-4-methylpyridine (2.18 g, 10.65 mmol) in CH$_2$Cl$_2$ (15.0 mL) at rt, was added trimethyloxonium tetrafluoroborate (1.58 g, 10.65 mmol) under a nitrogen atmosphere. After 1 h at rt, the reaction was quenched with water (50 mL) and extracted with EtOAc (4×50 mL). The combined extract was washed with water, 1.5M HCl, saturated aqueous NaHCO$_3$ and brine, and was dried over anhydrous MgSO$_4$. The filtrate was evaporated and the residue was purified by chromatography on silica gel using the solvent gradient hexanes→hexanes/EtOAc (3:7), to give 0.25 g (72%) of the title compound as a yellow solid. $^1$H-NMR (400 MHz, DMSO-d$_6$) δ7.84-7.92 (m, 2H), 7.68-7.73 (m, 1H), 5.82-6.03 (m, 2H), 4.82-4.88 (m, 2H), 3.87-3.93 (m, 2H), 3.21 (s, 3H).

Example 184d: (E)-2-(4-Hydroxybut-2-enyloxy)-6-nitrobenzonitrile

Prepared as in Example 160d from (E)-but-2-ene-1,4-diol (Miller, A. E. G.; Biss, J. W.; Schwartzman, L. H. *J. Org. Chem.* 1959, 24, 627 in 30% yield as a yellow solid. $^1$H-NMR (400 MHz, DMSO-d$_6$) δ7.83-7.94 (m, 2H), 7.67-7.74 (m, 1H), 5.97-6.07 (m, 1H), 5.78-5.89 (m, 1H), 4.80-89 (m, 3H), 3.94-4.02 (m, 2H).

Example 185: 4-Amino-5-(4,5-dihydrofuran-2-yl)-1H-benzo[c][1,2,6]thiadiazine-2,2-dioxide

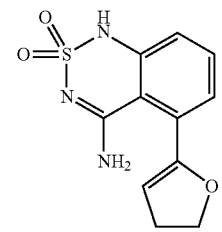

623

Prepared as in Example 158 from 2-sulfamoylamino-6-(4,5-dihydrofuran-2-yl)benzonitrile (Example 185a) in 31% yield as a white solid. $^1$H NMR (400 MHz, DMSO-d$_6$) δ 2.75-2.81 (m, 2H), 4.43 (t, J=9.2 Hz, 2H), 5.35-5.36 (m, 1H), 7.07 (dd, J=1.2, 8.0 Hz, 1H), 7.12 (dd, J=1.2, 7.2 Hz, 1H), 7.50-7.54 (m, 1H), 8.2-8.4 (broad s, 1H), 11.09 (s, 1H). MS 266 (MH$^+$).

Example 185a: 2-Sulfamoylamino-6-(4,5-dihydrofuran-2-yl)benzonitrile

Prepared as in Example 158a from 2-amino-6-(4,5-dihydrofuran-2-yl)benzonitrile (Example 185b) in 19% yield as a white solid. ¹H NMR (400 MHz, DMSO-d₆) δ 2.82-2.88 (m, 2H), 4.45 (t, J=9.6 Hz, 2H), 5.89 (t, J=3.2 Hz, 1H), 7.29 (s, 2H), 7.47 (d, J=7.2 Hz, 1H), 7.56 (d, J=7.6 Hz, 1H), 7.67 (t, J=8.0 Hz, 1H), 9.42 (s, 1H). MS 266 (MH⁺).

Example 185b:
2-amino-6-(4,5-dihydrofuran-2-yl)benzonitrile

2-Amino-6-bromobenzonitrile (0.75 g, 3.81 mmol), (4,5-dihydrofuran-2-yl)trimethylstannane (Menez, P.; Fargeas, V.; Poisson, J.; Ardisson, J.; Lallemand, J.-Y.; Pancrazi, A. Tetrahedron Letters 1994, 35(42), 7767) (1.02 g, 4.38 mmol), and palladium tetrakis(triphenylphosphine) (0.33 g, 0.28 mmol) were refluxed in toluene (10.0 mL) under nitrogen for 1.5 h. Saturated ammonium chloride (12 mL) and ammonium hydroxide (4 mL) were added, and the mixture was extracted with EtOAc. The organic layer was concentrated under vacuum and the residue was purified by chromatography on silica using 35% EtOAc/hexanes to give 0.48 g (68%) of the title compound as yellow oil. ¹H NMR (400 MHz, Acetone-d₆) δ 2.78-2.83 (m, 2H), 4.40 (t, J=9.2 Hz, 2H), 5.76 (t, J=3.2 Hz, 1H), 6.04 (s, 2H), 6.77-6.80 (m, 2H), 7.28 (t, J=8.0 Hz, 1H). MS 187 (MH⁺).

Example 186: 4-Amino-5-(tetrahydrofuran-2-yl)-1H-benzo[c][1,2,6]thiadiazine-2,2-dioxide

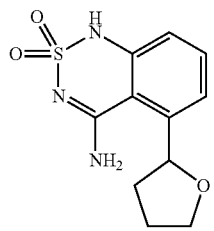

624

Prepared as in Example 158 from 2-sulfamoylamino-6-(tetrahydrofuran-2-yl)benzonitrile (Example 186a) in 52% yield as a white solid. ¹H NMR (400 MHz, DMSO-d₆) δ 1.94-2.05 (m, 3H), 2.21-2.28 (m, 1H), 3.81-3.87 (m, 1H), 3.92-3.97 (m, 1H), 5.23-5.27 (m, 1H), 7.02 (d, J=8.0 Hz, 1H), 7.30 (d, J=7.6 Hz, 1H), 7.51 (t, J=7.6 Hz, 1H), 7.9-8.5 (broad, 2H), 10.94 (s, 1H). MS 268 (MH⁺).

Example 186a: 2-Sulfamoylamino-6-(tetrahydrofuran-2-yl)benzonitrile

2-Amino-6-(4,5-dihydrofuran-2-yl)benzonitrile (Example 186b) (0.24 g, 1.28 mmol), 10% Pd/C (0.24 g), and ammonium formate (2.40 g, 38.1 mmol) were refluxed in MeOH (25 mL) under nitrogen for 1.5 h. The insoluble solids were filtered out and discarded, and the solvent was removed under vacuum. The resultant residue was dissolved in EtOAc, washed with saturated Na₂CO₃ and brine, dried over MgSO₄ and concentrated under vacuum. The residue was dissolved in anhydrous DMA (2.0 mL) and was treated with sulfamoyl chloride (0.11 g, 0.97 mmol). The reaction mixture was stirred under nitrogen for 30 minutes, quenched with water (5.0 mL) and extracted with EtOAc (3×50 mL). The combined extract was dried over MgSO₄, filtered and concentrated under vacuum. The crude product was purified by silica gel prep-TLC using 65% EtOAc/hexanes to give 45.0 mg (13%) of the title compound as a white solid. ¹H NMR (400 MHz, Acetone-d₆) δ 1.71-1.78 (m, 1H), 2.02-2.07 (m, 2H), 2.45-2.52 (m, 1H), 3.90-3.95 (m, 1H), 4.10-4.15 (m, 1H), 5.08 (t, J=6.8 Hz, 1H), 6.6-6.8 (broad, 2H), 7.36-7.39 (m, 1H), 7.62-7.63 (m, 2H), 8.22 (broad s, 1H). MS 268 (MH⁺).

Example 187: 4-Amino-5-(3-(pyridin-2-yl)propoxy)-1H-benzo[c][1,2,6]thiadiazine-2,2-dioxide

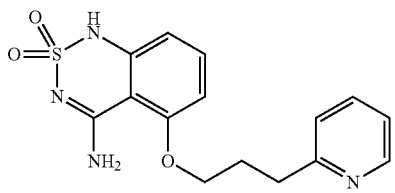

625

Prepared as in Example 158 from 2-sulfamoylamino-6-(3-(pyridin-2-yl)propoxy)benzonitrile (Example 187a) in 58% yield as a white solid. ¹H NMR (400 MHz, DMSO-d₆) δ 2.37 (quint, J=6.8 Hz, 2H), 2.89 (t, J=7.2 Hz, 2H), 4.19 (t, J=6.0 Hz, 2H), 6.60 (d, J=8.4 Hz, 1H), 6.73 (d, J=8.8 Hz, 1H), 7.19-7.22 (m, 1H), 7.29 (d, J=8.0 Hz, 1H), 7.44 (t, J=8.4 Hz, 1H), 7.68-7.72 (m, 1H), 7.92 (s, 1H), 8.36 (s, 1H), 8.49 (d, J=4.0 Hz, 1H), 10.94 (broad s, 1H). MS 333 (MH⁺).

Example 187a: 2-Sulfamoylamino-6-(3-(pyridin-2-yl)propoxy)benzonitrile

Prepared as in Example 158a from 2-amino-6-(3-(pyridin-2-yl)propoxy)benzonitrile (Example 187b) in 97% yield as a white solid. ¹H NMR (400 MHz, DMSO-d₆) δ 2.15 (quint, J=6.4 Hz, 2H), 2.92 (t, J=7.6 Hz, 2H), 4.15 (t, J=6.0 Hz, 2H), 6.93 (d, J=8.4 Hz, 1H), 7.14 (d, J=8.4 Hz, 1H), 7.20-7.29 (m, 4H), 7.55 (t, J=8.4 Hz, 1H), 7.68-7.72 (m, 1H), 8.48 (d, J=4.8 Hz, 1H), 9.49 (broad s, 1H). MS 333 (MH⁺).

Example 187b:
2-Amino-6-(3-(pyridin-2-yl)propoxy)benzonitrile

Prepared as in Example 49b from 2-nitro-6-(3-(pyridin-2-yl)propoxy)benzonitrile (Example 187c) in 85% yield as a white solid. ¹H NMR (400 MHz, DMSO-d₆) δ 2.12 (quint, J=6.8 Hz, 2H), 2.90 (t, J=7.2 Hz, 2H), 4.02 (t, J=6.4 Hz, 2H), 5.99 (s, 2H), 6.18 (d, J=8.0 Hz, 1H), 6.33 (d, J=8.8 Hz, 1H), 7.14-7.22 (m, 2H), 7.26 (d, J=8.0 Hz, 1H), 7.67-7.71 (m, 1H), 8.49 (d, J=3.6 Hz, 1H). MS 254 (MH⁺).

Example 187c:
2-Nitro-6-(3-(pyridin-2-yl)propoxy)benzonitrile

Prepared as in Example 37c from 3-(pyridin-2-yl)propan-1-ol 2,6-dinitrobenzonitrile in 86% yield as a white solid. ¹H NMR (400 MHz, DMSO-d₆) δ 2.21 (quint, J=6.4 Hz, 2H), 2.95 (t, J=7.2 Hz, 2H), 4.31 (t, J=6.4 Hz, 2H), 7.19-7.22 (m, 1H), 7.28 (d, J=7.6 Hz, 1H), 7.67-7.74 (m, 2H), 7.86-7.92 (m, 2H), 8.48 (d, J=4.8 Hz, 1H). MS 284 (MH⁺).

Example 188: 4-Amino-5-(2-(pyridin-2-yl)ethoxy)-1H-benzo[c][1,2,6]thiadiazine-2,2-dioxide

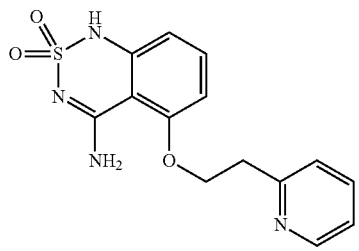

626

Prepared as in Example 158 from 2-sulfamoylamino-6-(2-(pyridin-2-yl)ethoxy)benzonitrile (Example 188a) in 22% yield as a white solid. $^1$H NMR (400 MHz, DMSO-$d_6$) δ 3.29 (t, J=5.6 Hz, 2H), 4.46 (t, J=5.6 Hz, 2H), 6.59 (d, J=8.0 Hz, 1H), 6.75 (d, J=8.8 Hz, 1H), 7.28-7.31 (m, 1H), 7.40-7.46 (m, 2H), 7.75-7.80 (m, 1H), 8.33-8.52 (m, 3H), 10.91 (s, 1H). MS 319 (MH$^+$).

Example 188a: 2-Sulfamoylamino-6-(2-(pyridin-2-yl)ethoxy)benzonitrile

Prepared as in Example 158a from 2-amino-6-(2-(pyridin-2-yl)ethoxy)benzonitrile (Example 188b) in 67% yield as a white solid. $^1$H NMR (400 MHz, DMSO-$d_6$) δ 3.22 (t, J=6.4 Hz, 2H), 4.48 (t, J=6.4 Hz, 2H), 7.00 (d, J=8.8 Hz, 1H), 7.14 (d, J=8.4 Hz, 1H), 7.23-7.26 (m, 3H), 7.39 (d, J=7.6 Hz, 1H), 7.55 (t, J=8.4 Hz, 1H), 7.73 (t, J=7.2 Hz, 1H), 8.51 (d, J=4.4 Hz, 1H), 9.42 (s, 1H). MS 319 (MH$^+$).

Example 188b: 2-Amino-6-(2-(pyridin-2-yl)ethoxy)benzonitrile

Prepared as in Example 197b from 2-nitro-6-(2-(pyridin-2-yl)propoxy)benzonitrile (Example 188c) in 60% yield as a white solid. $^1$H NMR (400 MHz, DMSO-$d_6$) δ 3.18 (t, J=6.8 Hz, 2H), 4.36 (t, J=6.8 Hz, 2H), 5.97 (s, 2H), 6.25 (d, J=8.4 Hz, 1H), 6.32 (d, J=8.4 Hz, 1H), 7.17 (t, J=8.0 Hz, 1H), 7.22-7.26 (m, 1H), 7.37 (d, J=8.0 Hz, 1H), 7.70-7.75 (m, 1H), 8.51 (d, J=4.4 Hz, 1H). MS 240 (MH$^+$).

Example 188c: 2-Nitro-6-(2-(pyridin-2-yl)ethoxy)benzonitrile

Prepared as in Example 172c from 2-(pyridin-2-yl)ethanol and 2,6-dinitrobenzonitrile in 82% yield as a yellow solid. $^1$H NMR (400 MHz, DMSO-$d_6$) δ 3.27 (t, J=6.4 Hz, 2H), 4.64 (t, J=6.4 Hz, 2H), 7.23-7.27 (m, 1H), 7.41 (d, J=8.0 Hz, 1H), 7.71-7.79 (m, 2H), 7.86-7.91 (m, 2H), 8.50-8.52 (m, 1H). MS 270 (MH$^+$).

Example 189: 4-Amino-5-((5-methylisoxazol-3-yl)methoxy)-1H-benzo[c][1,2,6]thiadiazine-2,2-dioxide

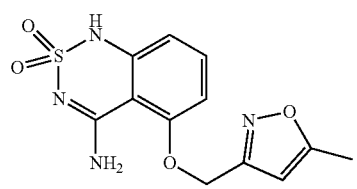

627

Prepared as in Example 158 from 2-sulfamoylamino-6-((5-methylisoxazol-3-yl)methoxy)benzonitrile (Example 189a) in 83% yield as a white solid. $^1$H NMR (400 MHz, DMSO-$d_6$) δ 2.42 (s, 3H), 5.40 (s, 2H), 6.36 (s, 1H), 6.65 (d, J=8.4 Hz, 1H), 6.81 (d, J=8.4 Hz, 1H), 7.48 (t, J=8.4 Hz, 1H), 8.06 (s, 1H), 8.40 (s, 1H), 11.02 (s, 1H). MS 309 (MH$^+$).

Example 189a: 2-Sulfamoylamino-6-((5-methylisoxazol-3-yl)methoxy)benzonitrile Prepared as in Example 158a from 2-amino-6-((5-methylisoxazol-3-yl)methoxy)benzonitrile (Example 189b) in 85% yield as a white solid. $^1$H NMR (400 MHz, DMSO-$d_6$) δ 2.42 (s, 3H), 5.32 (s, 2H), 6.34 (s, 1H), 7.07 (d, J=8.0 Hz, 1H), 7.19 (d, J=8.0 Hz, 1H), 7.30 (s, 2H), 7.59 (t, J=8.8 Hz, 1H), 9.53 (s, 1H). MS 309 (MH$^+$).

Example 189b: 2-Amino-6-((5-methylisoxazol-3-yl)methoxy)benzonitrile

Prepared as in Example 184184b from 2-((5-methylisoxazol-3-yl)methoxy)-6-nitrobenzonitrile (Example 189c) in 52% yield as a yellow solid. $^1$H NMR (400 MHz, DMSO-$d_6$) δ 2.42 (s, 3H), 5.19 (s, 2H), 6.07 (s, 2H), 6.31-6.33 (m, 2H), 6.37 (d, J=8.4 Hz, 1H), 7.20 (t, J=8.4 Hz, 1H). MS 230 (MH$^+$).

Example 189c: 2-((5-Methylisoxazol-3-yl)methoxy)-6-nitrobenzonitrile

Prepared as in Example 172172c from (5-methylisoxazol-3-yl)methanol and 2,6-dinitrobenzonitrile in 86% yield as a yellow solid. $^1$H NMR (400 MHz, DMSO-$d_6$) δ 2.43 (d, J=0.8 Hz, 3H), 5.50 (s, 2H), 6.38 (d, J=0.4 Hz, 1H), 7.83 (dd, J=1.2, 8.4 Hz, 1H), 7.91-7.98 (m, 2H). MS 260 (MH$^+$).

Example 190: (E)-4-Amino-5-(4-oxo-4-(propylamino)but-2-enyloxy)-1H-benzo[c][1,2,6]thiadiazine-2,2-dioxide

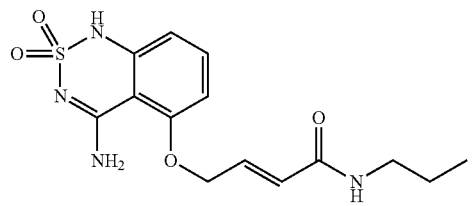

630

Prepared as in Example 158 from (E)-4-(2-cyano-3-(sulfamoylamino)phenoxy)-N-propylbut-2-enamide (Example 190a) in 19% yield as a white solid. $^1$H NMR (400 MHz, Acetone-$d_6$) δ 0.87 (t, J=7.2 Hz, 3H), 1.47 (hex, J=7.6 Hz, 2H), 3.11-3.17 (m, 4H), 5.35 (q, J=7.2 Hz, 1H), 6.70 (d, J=6.0 Hz, 1H), 6.77 (d, J=8.0 Hz, 1H), 6.87 (d, J=8.0 Hz, 1H), 7.2-7.5 (broad s, 2H), 7.51 (t, J=8.0 Hz, 1H), 8.19 (broad s, 1H), 9.5-10.5 (broad s, 1H). MS 339 (MH$^+$).

Example 190a: (E)-4-(2-Cyano-3-(sulfamoylamino)phenoxy)-N-propylbut-2-enamide Prepared as in Example 158a from (E)-4-(3-amino-2-cyanophenoxy)-N-propylbut-2-enamide (Example 190b) in 87% yield as a white solid. $^1$H NMR (400 MHz, DMSO-$d_6$) δ 0.84 (t, J=7.2 Hz, 3H), 1.43 (hex, J=6.8 Hz, 2H), 3.06 (q, J=6.8 Hz, 2H), 4.90 (d, J=2.8 Hz, 2H), 6.15 (d, J=15.6 Hz, 1H), 6.70-6.77 (m, 1H), 6.91 (d, J 8.8 Hz, 1H), 7.17 (d, J=8.4 Hz, 1H), 7.27 (broad s, 2H), 7.57 (t, J=8.8 Hz, 1H), 8.13-8.16 (m, 1H), 9.52 (broad s, 1H). MS 339 (MH$^+$).

Example 190b: (E)-4-(3-Amino-2-cyanophenoxy)-N-propylbut-2-enamide

Prepared as in Example 184b from (E)-4-(cyano-3-nitrophenoxy)-N-propylbut-2-enamide (Example 190c) in 73% yield as yellow solid. $^1$H NMR (400 MHz, DMSO-$d_6$) δ 0.84 (t, J=7.2 Hz, 3H), 1.42 (hex, J=7.2 Hz, 2H), 3.06 (q, J=6.8 Hz, 2H), 4.77-4.79 (m, 2H), 6.04 (s, 2H), 6.11-6.20 (m, 2H), 6.35 (d, J=8.4 Hz, 1H), 6.67-6.74 (m, 1H), 7.18 (t, J=8.0 Hz, 1H), 8.11-8.14 (m, 1H). MS 260 (MH$^+$).

Example 190c: (E)-4-(2-Cyano-3-nitrophenoxy)-N-propylbut-2-enamide (E)-4-Bromo-N-propylbut-2-enamide (Elliott, M.; Farnham, A. W.; Janes, N. F.; Johnson, D. M.; Pulman, D. A. *Pesticide Science* 1987 18(4) 229) (0.14 g, 0.70 mmol), 2-hydroxy-6-nitrobenzonitrile (0.14 g, 0.88 mmol), potassium carbonate (0.39 g, 2.81 mmol), and 18-crown-6 (0.11 g, 0.42 mmol) were refluxed in acetone (6 mL) for 2 h, and then poured into ice water (45 mL). The resultant precipitate was collected by filtration to give 0.16 g (79%) of the title compound as an off white solid. $^1$H NMR (400 MHz, DMSO-$d_6$) δ 0.84 (t, J=7.2 Hz, 3H), 1.42 (hex, J=7.2 Hz, 2H), 3.06 (q, J=6.8 Hz, 2H), 5.07 (d, J=2.8 Hz, 2H), 6.16 (d, J=16.0 Hz, 1H), 6.71-6.78 (m, 1H), 7.69 (d, J=8.0 Hz, 1H), 7.88-7.96 (m, 2H), 8.11-8.14 (m, 1H).

Example 191: (S)-4-Amino-5-((1-acetylpyrrolidin-2-yl)methoxy)-1H-benzo[c][1,2,6]thiadiazine-2,2-dioxide

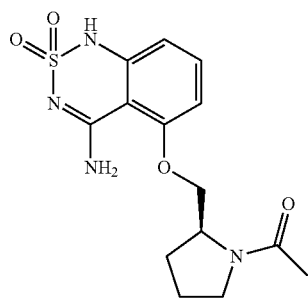

631

Prepared as in Example 165 from (S)-2-amino-6-((1-acetylpyrrolidin-2-yl)methoxy)benzonitrile (Example 191a) in 10% yield as a white solid. $^1$H NMR (400 MHz, DMSO-$d_6$) δ 1.93 (m, 4H), 2.00 (s, 3H), 3.50 (m, 2H), 4.09 (dd, J=10.0, 6.2 Hz, 1H), 4.24 (dd, J=10.0, 5.6 Hz, 1H), 4.41 (m, 1H), 6.62 (d, J=8.2 Hz, 1H), 6.87 (d, J=8.5 Hz, 1H), 7.46 (t, J=8.5 Hz, 1H), 8.12 (br s, 1H), 8.33 (br s, 1H), 10.93 (br s, 1H). MS 339 (MH$^+$).

Example 191a: (S)-2-Amino-6-((1-acetylpyrrolidin-2-yl)methoxy)benzonitrile

To a suspension of (S)-2-((2-cyano-3-nitrophenoxy)methyl)pyrrolidinium chloride (130 mg, 0.46 mmol) (Example 191b) in THF (5 mL) were added Et$_3$N (135 μL, 0.97 mmol) and acetyl chloride (36 μL, 0.50 mmol). The reaction was stirred at rt for 18 h, filtered and diluted with EtOH (20 mL). The resulting solution was hydrogenated (20 Bar) using 10% Pd/C as the catalyst. Upon completion, the reaction mixture was concentrated to provide the title compound (61 mg, 51%) as a clear syrup. MS 260 (MH$^+$).

Example 191b: (S)-2-((2-Cyano-3-nitrophenoxy)methyl)pyrrolidinium Chloride

Prepared as in Example 160 from (S)-tert-butyl-2-((2-cyano-3-nitrophenoxy)methyl)pyrrolidine-1-carboxylate (Example 191c) in 81% yield as an off-white solid. MS 248 (MH$^+$—HCl).

Example 191c: (S)-tert-Butyl 2-((2-cyano-3-nitrophenoxy)methyl)pyrrolidine-1-carboxylate Prepared as in Example 160d from 2,6-dinitrobenzonitrile and (S)-tert-butyl 2-(hydroxymethyl)pyrrolidine-1-carboxylate in 89% yield as a tan solid. $^1$H NMR (400 MHz, DMSO-$d_6$) δ 1.40 (s, 9H), 1.81 (m, 1H), 2.03 (m, 3H), 3.32 (m, 2H), 4.08 (m, 1H), 4.33 (m, 2H), 7.79 (d, J=7.8 Hz, 1H), 7.93 (m, 2H).

Example 192: (S)-4-Amino-5-((1-propionylpyrrolidin-2-yl)methoxy)-1H-benzo[c][1,2,6]thiadiazine-2,2-dioxide

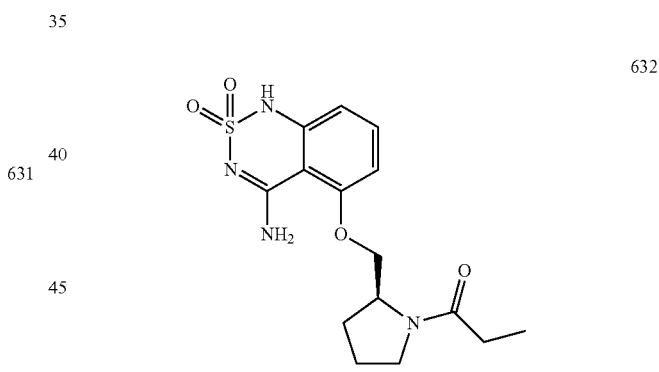

632

Prepared as in Example 165 from (S)-2-amino-6-((1-propionylpyrrolidin-2-yl)methoxy)benzonitrile (Example 192a) in 17% yield as an off-white solid. $^1$H NMR (400 MHz, DMSO-$d_6$) δ 1.01 (t, J=7.8 Hz, 3H), 1.95 (m, 4H), 2.31 (m, 2H), 3.48 (m, 2H), 4.11 (dd, J=10.0, 6.4 Hz, 1H), 4.27 (dd, J=9.8, 5.0 Hz, 1H), 4.43 (m, 1H), 6.64 (d, J=7.9 Hz, 1H), 6.92 (d, J=8.4 Hz, 1H), 7.48 (t, J=8.2 Hz, 1H), 8.09 (br s, 1H), 8.34 (br s, 1H), 10.95 (br s, 1H). MS 353 (MH$^+$).

Example 192a: (S)-2-Amino-6-((1-propionylpyrrolidin-2-yl)methoxy)benzonitrile

Prepared as in Example 191a from (S)-2-((2-cyano-3-nitrophenoxy)methyl)pyrrolidinium chloride (Example 191b) and propionyl chloride in 90% yield as a clear syrup. MS 274 (MH$^+$).

Example 193: (S)-4-Amino-5-((1-butyrylpyrrolidin-2-yl)methoxy)-1H-benzo[c][1,2,6]thiadiazine-2,2-dioxide

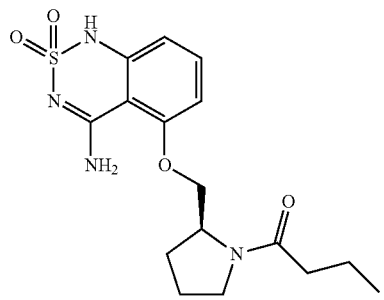

633

Prepared as in Example 165 from (S)-2-amino-6-((1-butyrylpyrrolidin-2-yl)methoxy)benzonitrile (Example 193a) in 78% yield as an off-white solid. $^1$H NMR (400 MHz, DMSO-d$_6$) δ 0.88 (t, J=7.5 Hz, 3H), 1.54 (q, J=7.5 Hz), 1.94 (m, 4H), 2.26 (t, J=7.5 Hz, 2H), 3.48 (m, 2H), 4.10 (m, 1H), 4.25 (m, 1H), 4.43 (m, 1H), 6.62 (d, J=8.1 Hz, 1H), 6.89 (d, J=8.6 Hz, 1H), 7.47 (t, J=8.3 Hz, 1H), 8.08 (br s, 1H), 8.32 (br s, 1H), 10.93 (br s, 1H). MS 367 (MH$^+$).

Example 193a: (S)-2-Amino-6-((1-butyrylpyrrolidin-2-yl)methoxy)benzonitrile

Prepared as in Example 191a from (S)-2-((2-cyano-3-nitrophenoxy)methyl)pyrrolidinium chloride (Example 191b) and butyryl chloride to in 90% yield as a white solid. MS 288 (MH$^+$).

Example 194: (S)-2-((4-Amino-1H-benzo[c][1,2,6]thiadiazine-2,2-dioxide-5-yloxy)methyl)-N-methylpyrrolidine-1-carboxamide

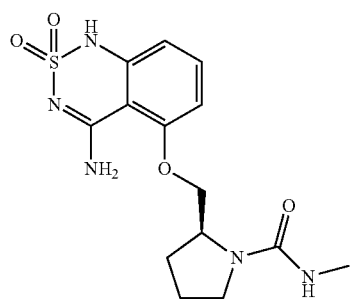

634

Prepared as in Example 165 from (S)-2-((3-amino-2-cyanophenoxy)methyl)-N-methylpyrrolidine-1-carboxamide (Example 194a) in 30% yield as an off-white solid. $^1$H NMR (400 MHz, DMSO-d$_6$) δ 1.89 (m, 4H), 2.60 (d, J=3.9 Hz, 3H), 3.20 (m, 2H), 4.01 (m, 1H), 4.16 (m, 1H), 4.32 (m, 1H), 6.23 (m, 1H), 6.62 (d, J=8.2 Hz, 1H), 6.89 (d, J=8.5 Hz, 1H), 7.46 (t, J=8.2 Hz, 1H), 8.19 (br s, 1H), 8.27 (br s, 1H), 10.92 (s, 1H). MS 354 (MH$^+$).

Example 194a: (S)-2-((3-Amino-2-cyanophenoxy)methyl)-N-methylpyrrolidine-1-carboxamide Prepared as in Example 191a from (S)-2-((2-cyano-3-nitrophenoxy)methyl)pyrrolidinium chloride (Example 191b) and methyl isocyanate in 53% yield as a white solid. MS 275 (MH$^+$).

Example 195: (S)-2-((4-Amino-1H-benzo[c][1,2,6]thiadiazine-2,2-dioxide-5-yloxy)methyl)-N-ethylpyrrolidine-1-carboxamide

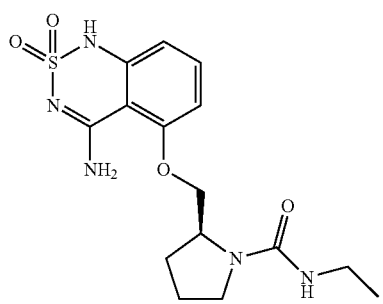

635

Prepared as in Example 237 from (S)-2-((3-amino-2-cyanophenoxy)methyl)-N-ethylpyrrolidine-1-carboxamide (Example 195a) in 68% yield as an off-white solid. $^1$H NMR (400 MHz, DMSO-d$_6$) δ 1.03 (t, J=6.9 Hz, 6H), 1.90 (m, 4H), 3.08 (quint, J=6.6 Hz, 2H), 3.20 (m, 1H), 3.31 (m, 1H), 4.00 (dd, J=9.7, 6.7 Hz, 1H), 4.17 (dd, J=9.7, 6.0 Hz, 1H), 4.33 (m, 1H), 6.27 (d, J=5.7 Hz, 1H), 6.62 (d, J=8.2 Hz, 1H), 6.89 (d, J=8.3 Hz, 1H), 7.46 (t, J=8.2 Hz, 1H), 8.20 (br s, 1H), 8.26 (br s, 1H), 10.91 (s, 1H). MS 368 (MH$^+$).

Example 195a: (S)-2-((3-Amino-2-cyanophenoxy)methyl)-N-ethylpyrrolidine-1-carboxamide Prepared as in Example 191a from (S)-2-((2-cyano-3-nitrophenoxy)methyl)pyrrolidinium chloride (Example 191b) and ethyl isocyanate in 100% yield as a white solid. MS 289 (MH$^+$).

Example 196: (S)-2-((4-Amino-1H-benzo[c][1,2,6]thiadiazine-2,2-dioxide-5-yloxy)methyl)-N-propylpyrrolidine-1-carboxamide

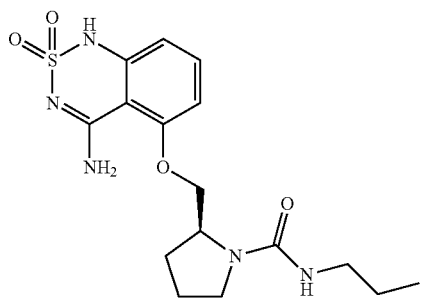

636

Prepared as in Example 237 from (S)-2-((3-amino-2-cyanophenoxy)methyl)-N-propylpyrrolidine-1-carboxamide (Example 196a) in 37% yield as an off-white solid. ¹H NMR (400 MHz, DMSO-d₆) δ 0.84 (t, J=7.6 Hz, 6H), 1.43 (sext, J=7.4 Hz, 2H), 1.92 (m, 4H), 3.01 (m, 2H), 3.21 (m, 1H), 3.33 (m, 1H), 4.02 (dd, J=9.7, 6.4 Hz, 1H), 4.18 (dd, J=9.7, 5.9 Hz, 1H), 4.34 (m, 1H), 6.27 (d, J=5.6 Hz, 1H), 6.62 (d, J=8.4 Hz, 1H), 6.89 (d, J=8.6 Hz, 1H), 7.46 (t, J=8.3 Hz, 1H), 8.20 (br s, 1H), 8.27 (br s, 1H), 10.91 (s, 1H). MS 382 (MH⁺).

Example 196a: (S)-2-((3-Amino-2-cyanophenoxy) methyl)-N-propylpyrrolidine-1-carboxamide Prepared as in Example 191a from (S)-2-((2-cyano-3-nitrophenoxy)methyl)pyrrolidinium chloride (Example 191b) and propyl isocyanate in 100% yield as a white solid. MS 303 (MH⁺).

Example 197: 3-(4-Amino-2,2-dioxide-1H-benzo[c][1,2,6]thiadiazin-5-yloxy)-2',2'-dimethyl-N-propyl-propanamide

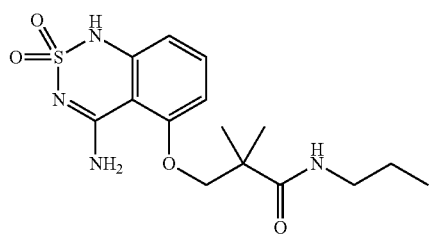

To a stirred solution of 3-(3-sulfamoylamino-2-cyanophenoxy)-2,2-dimethyl-N-propylpropanamide (18.52 g, 52.55 mmol) (Example 197a) in EtOH (150 mL) was added NaOH solution (2.0 N, 52.3 mL) at room temperature. The reaction mixture was then refluxed for 2 hrs until the reaction was complete by TLC. The solution was cooled to 0° C. and neutralized carefully with 10% acetic acid and the precipitate was collected by filtration and washed with water. The product was further purified by recrystallization from EtOH/H₂O (1:4), dried under vacuum to give the title compound as a white solid (13.5 g, 73%). M.p.: 225-226° C. ¹H NMR (400 MHz, DMSO-d₆) δ 0.75 (t, J=7.4 Hz, 3H), 1.22 (s, 6H), 1.38 (m, 2H), 3.01 (q, J=6.5 Hz, 2H), 4.07 (s, 2H), 6.59 (d, J=8.0 Hz, 1H), 6.71 (d, J=8.0 Hz, 1H), 7.44 (t, J=8.0 Hz, 1H), 7.82 (t, J=5.6 Hz, 1H), 7.92 (s, 1H), 8.33 (s, 1H), 10.93 (s, 1H). MS 355 (MH⁺).

Example 197a: 3-(3-sulfamoylamino-2-cyanophenoxy)-2,2-dimethyl-N-propylpropanamide To a solution of 3-(3-amino-2-cyanophenoxy)-2,2-dimethyl-N-propylpropanamide (16.5 g, 59.92 mmol) (Example 197b) in DMA (50 mL) was added sulfamoyl chloride (13.85 g, 119.84 mmol) at 0° C. under nitrogen. The reaction mixture was then stirred at room temperature under nitrogen for 3 hrs then diluted with EtOAc, washed successively with NaHCO₃, brine, dried over Na₂SO₄, filtered and evaporated to give the title compound as a off white solid (18.52 g, 87%). ¹H NMR (400 MHz, DMSO-d₆) δ 0.79 (t, J=7.6 Hz, 3H), 1.20 (s, 6H), 1.38 (m, 2H), 3.01 (q, J=6.5 Hz, 2H), 4.05 (s, 2H), 6.92 (d, J=8.4 Hz, 1H), 7.13 (d, J=8.4 Hz, 1H), 7.24 (s, 2H), 7.53 (t, J=8.4 Hz, 1H), 7.55 (t, J=5.6 Hz, 1H), 9.42 (s, 1H). MS 355 (MH⁺).

Example 197b: 3-(3-amino-2-cyanophenoxy)-2,2-dimethyl-N-propylpropanamide

Method A:
To a solution of 3-(2-cyano-3-nitrophenoxy)-2,2-dimethyl-N-propylpropanamide (305 mg, 1.0 mmol) (Example 197c) in EtOAc (20.0 mL) was added 10% Pd/C (50 mg). The suspension was stirred under an atmosphere of H₂ at room temperature overnight. The Pd/C was filtered off, and washed with EtOAc. The filtrate was concentrated under reduced pressure and the residue was purified by chromatography on silica gel eluting with 50% EtOAc in hexanes to give the title compound (267 mg, 97%) as a white solid. MS 276 (MH⁺).

Method B:
To a solution of 3-hydroxy-2,2-dimethyl-N-propylpropanamide (20.2 g, 0.127 mol) (Example 197d) in dry THF (500 mL) was carefully added NaH (60% in mineral oil, 7.64 g, 0.191 mol) in small portions at 0° C. under nitrogen. The reaction mixture was then warmed to room temperature and stirred under nitrogen for 1 hr. To this solution was slowly added at room temperature 2-amino-6-fluorobenzonitrile (17.3 g, 0.127 mol) in THF (100 mL) and the reaction mixture refluxed overnight under nitrogen then cooled down to room temperature, quenched with brine, and extracted with EtOAc (3×). The combined organic layers were washed with brine, dried over Na₂SO₄, evaporated and the residue was crystallized from EtOAc/Hexane to give the compound as a white solid (16.5 g, 48%). MS 276 (MH⁺).

Example 197c: 3-(2-cyano-3-nitrophenoxy)-2,2-dimethyl-N-propylpropanamide

To a solution of 3-hydroxy-2,2-dimethyl-N-propylpropanamide (1.59 g, 10.0 mmol) (Example 197d) in dry THF (30 mL) was carefully added NaH (60% in mineral oil, 400 mg, 10.0 mmol) in small portions at 0° C. under nitrogen. The reaction mixture was stirred at 0° C. under nitrogen for 2 hrs. To this solution was added 2,6-dinitrobenzonitrile (1.93, 10.0 mmol), and the reaction solution was stirred at 0° C.-RT under nitrogen overnight. The reaction mixture quenched with brine, and extracted with EtOAc (3×). The combined organic layers were washed with brine, dried over Na₂SO₄. After evaporation of the solvent, the residue was purified by chromatography on silica gel eluting with 60% EtOAc in hexanes to give the title compound as a pale yellow solid (2.21 g, 72%). MS 306 (MH⁺).

Example 197d: 3-hydroxy-2,2-dimethyl-N-propylpropanamide

Method A:
A solution of methyl 3-hydroxy-2,2-dimethylpropanoate (2.64 g, 20 mmol) and n-propylamine (1.81 g, 30 mmol) was heated at 190° C. under microwave for 10 hrs. The excessive amine was removed under vacuum to give the title compound as colorless oil (3.18 g, 100%). MS 160 (MH⁺).

Method B:
To a solution of 3-hydroxy-2,2-dimethylpropanoic acid (20.0 g, 0.169 mol), propylamine (15.3 mL, 0.186 mol), and HOBt (25.1 g, 0.186 mol) in dry dichloromethane (500 mL) was added EDCI (35.6 g, 0.186 mmol) at room temperature under nitrogen. The reaction mixture was then stirred at room temperature under nitrogen overnight. The reaction quenched with brine, and extracted EtOAc (8×). The combined organic layers were washed with saturated NaHCO₃ solution, dilute HCl, brine, and dried over Na₂SO₄. Evaporation of the solvent under reduced pressure gave the title compound as colorless oil (19.2 g, 71%). MS 160 (MH⁺).

Example 198: N-(1-(4-amino-2,2-dioxide-1H-benzo[c][1,2,6]thiadiazin-5-yloxy)-2'-methylpropan-2'-yl)benzamide

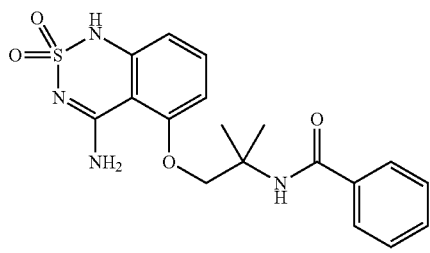

638

Prepared as in Example 197197 from N-(1-(3-sulfamoylamino-2-cyanophenoxy)-2-methylpropan-2-yl)benzamide (Example 198a) in 93% yield as a white solid. M.p.: 235-236° C. ¹H NMR (400 MHz, DMSO-d₆) δ 1.47 (s, 6H), 4.38 (s, 2H), 6.61 (d, J=8.4 Hz, 1H), 6.77 (d, J=8.0 Hz, 1H), 7.39-7.51 (m, 4H), 7.75 (d, J=7.6 Hz, 2H), 7.90 (s, 1H), 8.17 (s, 1H), 8.47 (s, 1H), 10.97 (s, 1H). MS 389 (MH⁺).

Example 198a: N-(1-(3-sulfamoylamino-2-cyanophenoxy)-2-methylpropan-2-yl)benzamide Prepared as in Example 197a from N-(1-(3-amino-2-cyanophenoxy)-2-methylpropan-2-yl)benzamide (Example 198b) in 98% yield as a white solid. MS 389 (MH⁺).

Example 198b: N-(1-(3-amino-2-cyanophenoxy)-2-methylpropan-2-yl)benzamide

Prepared as in Example 197b (Method A) from N-(1-(2-cyano-3-nitrophenoxy)-2-methylpropan-2-yl)benzamide (Example 198c) in 96% yield as a white solid. MS 310 (MH⁺).

Example 198c: N-(1-(2-cyano-3-nitrophenoxy)-2-methylpropan-2-yl)benzamide

Prepared as in Example 197c from N-(1-hydroxy-2-methylpropan-2-yl)benzamide (Boyd, R. N.; Hansen, R. H. *J. Am. Chem. Soc.* 1953, 75, 5896) and 2,6-dinitrobenzonitrile in 91% yield as a pale yellow solid. MS 340 (MH⁺).

Example 199: 3-(4-amino-2,2-dioxide-1H-benzo[c][1,2,6]thiadiazin-5-yloxy)-N-(2''-(benzyloxy)ethyl)-2',2'-dimethylpropanamide

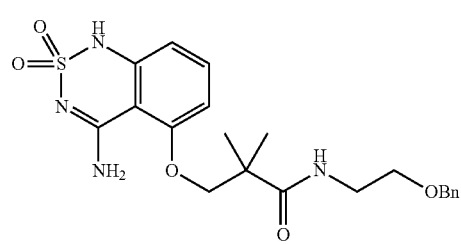

640

Prepared as in Example 197 from 3-(3-sulfamoylamino-2-cyanophenoxy)-N-(2-(benzyloxy)ethyl)-2,2-dimethylpropanamide (Example 199a) in 92% yield as a white solid. ¹H NMR (400 MHz, DMSO-d₆) δ 1.22 (s, 6H), 3.26 (q, J=5.8 Hz, 2H), 3.41 (t, J=5.8 Hz, 2H), 4.07 (s, 2H), 4.36 (s, 2H), 6.60 (d, J=7.6 Hz, 1H), 6.71 (d, J=7.6 Hz, 1H), 7.19-7.28 (m, 4H), 7.43 (t, J=8.0 Hz, 2H), 7.91 (s, 1H), 7.97 (t, J=5.8 Hz, 1H), 8.34 (s, 1H), 10.93 (s, 1H). MS 447 (MH⁺).

Example 199a: 3-(3-sulfamoylamino-2-cyanophenoxy)-N-(2-(benzyloxy)ethyl)-2,2-dimethylpropanamide Prepared as in Example 197a from 3-(3-amino-2-cyanophenoxy)-N-(2-(benzyloxy)ethyl)-2,2-dimethylpropanamide (Example 199b) in 100% yield. MS 447 (MH⁺).

Example 199b: 3-(3-amino-2-cyanophenoxy)-N-(2-(benzyloxy)ethyl)-2,2-dimethylpropanamide Prepared as in Example 197b (Method B) from N-(2-(benzyloxy)ethyl)-3-hydroxy-2,2-dimethylpropanamide (Example 199c) and 2-amino-6-fluorobenzonitrile in 82% yield. MS 368 (MH⁺).

Example 199c: N-(2-(benzyloxy)ethyl)-3-hydroxy-2,2-dimethylpropanamide

To a solution of 3-hydroxy-2,2-dimethylpropanoic acid (2.36 g, 20 mmol), 2-(benzyloxy)ethanamine (3.02 g, 20 mmol), and HOBt (2.71 g, 20 mmol) in dry dichloromethane (100 mL) was added EDCI (3.82 g, 20 mmol) at room temperature under nitrogen. The reaction mixture was then stirred at room temperature under nitrogen overnight. The reaction was quenched with brine, and extracted with EtOAc (3×). The combined organic layers were washed with saturated NaHCO₃ solution, dilute HCl, brine, and dried over Na₂SO₄. After evaporation of the solvent, the residue was purified by chromatography on silica gel eluting with 40% EtOAc in hexanes to give the title compound as colorless oil (4.89 g) in 97% yield. MS 252 (MH⁺).

Example 200: 3-(4-amino-2,2-dioxide-1H-benzo[c][1,2,6]thiadiazin-5-yloxy)-N-(2''-hydroxyethyl)-2',2'-dimethylpropanamide

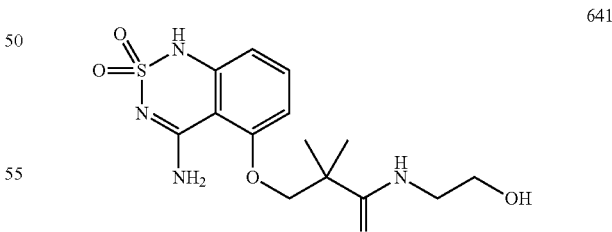

641

To a solution of 3-(4-amino-1H-benzo[c][1,2,6]thiadiazin-5-yloxy)-2,2-dioxide-N-(2'-(benzyloxy)ethyl)-2',2'-dimethylpropanamide (Example 199, 112 mg, 0.25 mmol) in EtOAc/EtOH/THF (1:1:1, 20.0 mL) was added 10% Pd/C (50 mg). And the suspension was stirred under an atmosphere of H₂ at room temperature for 2 hrs. The Pd/C was filtered off, and washed with MeOH. The filtration was concentrated under reduced pressure, and the residue was purified by recrystallization from EtOH to give the title compound as a white solid (81 mg) in 90% yield. $^1$H NMR (400 MHz, DMSO-$d_6$) δ 1.22 (s, 6H), 3.11 (q, J=6.0 Hz, 2H), 3.35 (q, J=6.0 Hz, 2H), 4.05 (s, 2H), 4.61 (t, J=6.0 Hz, 1H), 6.59 (d, J=8.0 Hz, 1H), 6.70 (d, J=8.0 Hz, 1H), 7.43 (t, J=8.0 Hz, 1H), 7.78 (t, J=6.0 Hz, 1H), 7.93 (s, 1H), 8.29 (s, 1H), 10.93 (s, 1H). MS 357 (MH$^+$).

Example 201: 3-(4-amino-2,2-dioxide-1H-benzo[c][1,2,6]thiadiazin-5-yloxy)-N-(4"-methoxybenzyl)-2',2'-dimethylpropanamide

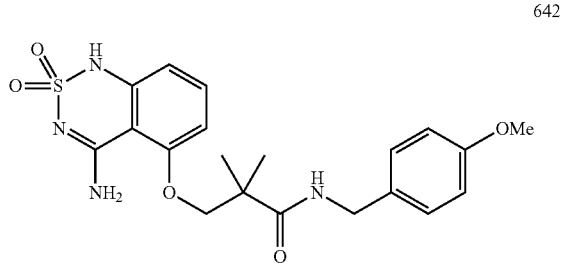 [SMILES: COc1ccc(CNC(=O)C(C)(C)COc2cccc3c2C(N)=NS(=O)(=O)N3)cc1]

Prepared as in Example 197 from 3-(3-sulfamoylamino-2-cyanophenoxy)-N-(4-methoxybenzyl)-2,2-dimethylpropanamide (Example 201a) in 92% yield as a white solid. $^1$H NMR (400 MHz, DMSO-$d_6$) δ 1.25 (s, 6H), 3.66 (s, 3H), 4.12 (s, 2H), 4.21 (d, J=5.6 Hz, 2H), 6.61 (d, J=8.4 Hz, 1H), 6.71 (d, J=8.4 Hz, 1H), 6.73 (d, J=8.0 Hz, 2H), 7.06 (d, J=8.0 Hz, 2H), 7.44 (t, J=8.4 Hz, 1H), 7.87 (s, 1H), 8.31 (s, 1H), 8.35 (t, J=5.6 Hz, 1H), 10.95 (s, 1H). MS 433 (MH$^+$).

Example 201a: 3-(3-sulfamoylamino-2-cyanophenoxy)-N-(4-methoxybenzyl)-2,2-dimethylpropanamide Prepared as in Example 197a from 3-(3-amino-2-cyanophenoxy)-N-(4-methoxybenzyl)-2,2-dimethylpropanamide (Example 201b) in 100% yield. MS 433 (MH$^+$).

Example 201b: 3-(3-amino-2-cyanophenoxy)-N-(4-methoxybenzyl)-2,2-dimethylpropanamide To a solution of 3-(2-cyano-3-nitrophenoxy)-N-(4-methoxybenzyl)-2,2-dimethylpropanamide (1.15 g, 3.0 mmol) (Example 201c) in diglyme (30 mL) was added dropwise a solution of SnCl$_2$.2H$_2$O (2.03 g, 9.0 mmol) in concentrated HCl (15 mL) at 0° C. The reaction mixture was then stirred at 0° C. for another 1 hr. The reaction solution was neutralized with 2 N NaOH at 0° C., and extracted with EtOAc (2×). The combined organic layers were washed with brine, dried over Na$_2$SO$_4$. After evaporation of the solvent, the residue was purified by chromatography on silica gel eluting with 50% EtOAc in hexanes to give the title compound as a white solid (0.91 g) in 86% yield. MS 354 (MH$^+$).

Example 201c: 3-(2-cyano-3-nitrophenoxy)-N-(4-methoxybenzyl)-2,2-dimethylpropanamide Prepared as in Example 197c from 3-hydroxy-N-(4-methoxybenzyl)-2,2-dimethylpropanamide (Example 201d) and 2,6-dinitrobenzonitrile in 95% yield as a pale yellow solid. MS 384 (MH$^+$).

Example 201d: 3-hydroxy-N-(4-methoxybenzyl)-2,2-dimethylpropanamide

Prepared as in Example 4c from 3-hydroxy-2,2-dimethylpropanoic acid and 4-methoxybenzylamine in 97% yield as a white solid. MS 238 (MH$^+$).

Example 202: 3-(4-amino-2,2-dioxide-1H-benzo[c][1,2,6]thiadiazin-5-yloxy)-N,2',2'-trimethylpropanamide

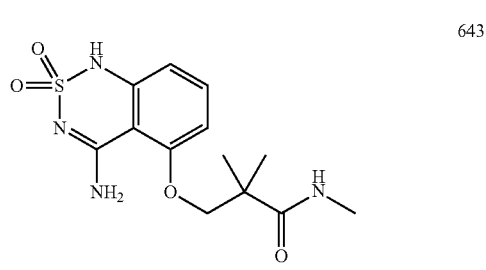 [SMILES: CNC(=O)C(C)(C)COc1cccc2c1C(N)=NS(=O)(=O)N2]

Prepared as in Example 197 from 3-(3-sulfamoylamino-2-cyanophenoxy)-N,2,2-trimethylpropanamide (Example 202a) in 62% yield as a white solid. $^1$H NMR (400 MHz, DMSO-$d_6$) δ 1.21 (s, 6H), 2.58 (d, J=1.2 Hz, 3H), 4.05 (s, 2H), 6.60 (d, J=8.0 Hz, 1H), 6.72 (d, J=8.0 Hz, 1H), 7.44 (t, J=8.0 Hz, 1H), 7.80 (q, J=1.2 Hz, 1H), 7.96 (s, 1H), 8.33 (s, 1H), 10.93 (s, 1H). MS 327 (MH$^+$).

Example 202a: 3-(3-sulfamoylamino-2-cyanophenoxy)-N,2,2-trimethylpropanamide

Prepared as in Example 197a from 3-(3-amino-2-cyanophenoxy)-N,2,2-trimethylpropanamide (Example 202b) in 69% yield. MS 327 (MH$^+$).

Example 202b: 3-(3-amino-2-cyanophenoxy)-N,2,2-trimethylpropanamide

Prepared as in Example 197b (Method A) from 3-(2-cyano-3-nitrophenoxy)-N,2,2-trimethylpropanamide (Example 202c) in 95% yield as a white solid. MS 248 (MH$^+$).

Example 202c: 3-(2-cyano-3-nitrophenoxy)-N,2,2-trimethylpropanamide

Prepared as in Example 197c from 3-hydroxy-N,2,2-trimethylpropanamide (Example 202d) and 2,6-dinitrobenzonitrile in 77% yield as a pale yellow solid. MS 378 (MH$^+$).

Example 202d: 3-hydroxy-N,2,2-trimethylpropanamide

Prepared as in Example 197d from methyl 3-hydroxy-2,2-dimethylpropanoate and methylamine in 51% yield. MS 132 (MH$^+$).

Example 203: 3-(4-amino-2-oxo-1,2-dihydroquinazolin-5-yloxy)-2,2-dimethyl-N-propylpropanamide

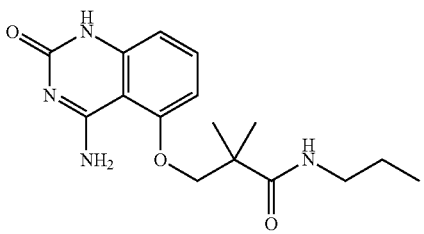

A solution of N-(2-cyano-3-(2,2-dimethyl-3-oxo-3-(propylamino)propoxy)-phenylcarbamoyl)benzamide (example 203a) (141 mg, 0.3 mmol) and NaOH (2 N, 0.3 mL) in EtOH (5 mL) was stirred at 100° C. under nitrogen for 2 hrs. After cooling to room temperature, the clear reaction solution was filtered, and the filtrate was carefully neutralized with 10% AcOH with vigorous stirring at 0° C. The resultant precipitate was collected by filtration, washed with water and then 20% EtOH in water to give the final product (81 mg) in 76% yield as an off-white solid. $^1$H NMR (400 MHz, DMSO-$d_6$) δ 0.73 (t, J=7.4 Hz, 3H), 1.21 (s, 6H), 1.33-1.41 (m, 2H), 3.01 (q, J=7.4 Hz, 2H), 4.08 (s, 2H), 6.64 (d, J=8.0 Hz, 1H), 6.69 (d, J=8.0 Hz, 1H), 7.42 (t, J=8.0 Hz, 1H), 7.47 (s, 1H), 7.79 (t, J=7.4 Hz, 1H), 7.84 (s, 1H), 10.60 (s, 1H). MS 319 (MH$^+$).

Example 203a: N-(2-cyano-3-(2,2-dimethyl-3-oxo-3-(propylamino)propoxy)phenyl-carbamoyl)benzamide Prepared as in Example 24a from 3-(3-amino-2-cyanophenoxy)-2,2-dimethyl-N-propylpropanamide (Example 197b, Method A) and benzoyl isocyanate in 85% yield as a white solid. MS 423 (MH$^+$).

Example 204: 3-(4-amino-2,2-dioxide-1H-benzo[c][1,2,6]thiadiazin-5-yloxy)-N-(2″-methoxyethyl)-2′,2′-dimethylpropanamide

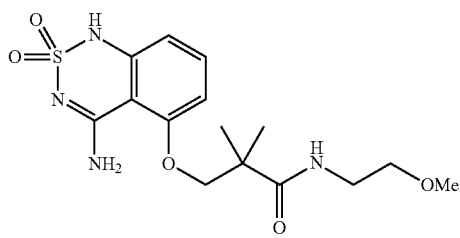

Prepared as in Example 197 from 3-(3-sulfamoylamino-2-cyanophenoxy)-N-(2-methoxyethyl)-2,2-dimethylpropanamide (Example 204a) in 12% yield as a white solid. $^1$H NMR (400 MHz, DMSO-$d_6$) δ 1.21 (s, 6H), 3.13 (s, 3H), 3.17-3.22 (m, 2H), 3.28 (t, J=6.0 Hz, 2H), 4.07 (s, 2H), 6.59 (d, J=8.0 Hz, 1H), 6.71 (d, J=8.0 Hz, 1H), 7.43 (t, J=8.0 Hz, 1H), 7.87 (s, 1H), 7.91 (t, J=5.6 Hz, 1H), 8.33 (s, 1H), 10.92 (s, 1H). MS 371 (MH$^+$).

Example 204a: 3-(3-sulfamoylamino-2-cyanophenoxy)-N-(2-methoxyethyl)-2,2-dimethylpropanamide Prepared as in Example 197a from 3-(3-amino-2-cyanophenoxy)-N-(2-methoxyethyl)-2,2-dimethylpropanamide (Example 204b) in 41% yield. MS 371 (MH$^+$).

Example 204b: 3-(3-amino-2-cyanophenoxy)-N-(2-methoxyethyl)-2,2-dimethylpropanamide Prepared as in Example 197b (Method A) from 3-(2-cyano-3-nitrophenoxy)-N-(2-methoxyethyl)-2,2-dimethylpropanamide (Example 204c) in 91% yield. MS 292 (MH$^+$).

Example 204c: 3-(2-cyano-3-nitrophenoxy)-N-(2-methoxyethyl)-2,2-dimethylpropanamide Prepared as in Example 197c from 3-hydroxy-N-(2-methoxyethyl)-2,2-dimethylpropanamide (Example 204d) and 2,6-dinitrobenzonitrile in 55% yield. MS 322 (MH$^+$).

Example 204d: 3-hydroxy-N-(2-methoxyethyl)-2,2-dimethylpropanamide

Prepared as in Example 197d (Method A) from methyl 3-hydroxy-2,2-dimethylpropanoate and 2-methoxyethanamine in 100% yield. MS 30 (MH$^+$).

Example 205: N-(3-(4-amino-)-2,2-dioxide-1H-benzo[c][1,2,6]thiadiazin-5-yloxy-2′,2′-dimethylpropyl)propionamide

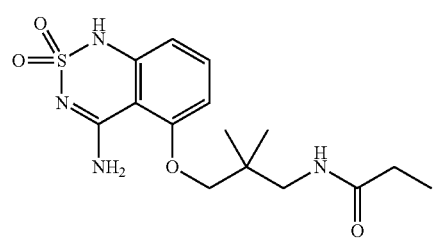

Prepared as in Example 197a from N-(3-(3-amino-2-cyanophenoxy)-2,2-dimethylpropyl)propionamide (Example 205a) and sulfamoyl chloride in 17% yield as a white solid. $^1$H NMR (400 MHz, DMSO-$d_6$) δ 0.93-0.96 (m, 9H), 2.06-2.11 (m, 2H), 3.07 (d, J=6.0 Hz, 2H), 3.74 (s, 2H), 6.58 (t, J=8.4 Hz, 1H), 6.69 (d, J=8.8 Hz, 1H), 7.41 (t, J=8.4 Hz, 1H), 7.93-7.98 (m, 2H), 8.35 (brs, 1H), 10.91 (brs, 1H). MS 355 (MH$^+$).

Example 205a: N-(3-(3-amino-2-cyanophenoxy)-2,2-dimethylpropyl)propionamide

Prepared as in Example 197b (Method A) from N-(3-(2-cyano-3-nitrophenoxy)-2,2-dimethylpropyl)propionamide (Example 205b) in 100% yield. MS 276 (MH$^+$).

Example 205b: N-(3-(2-cyano-3-nitrophenoxy)-2,2-dimethylpropyl)propionamide

Prepared as in Example 197c from N-(3-hydroxy-2,2-dimethylpropyl)propionamide (Example 205c) and 2,6-dinitrobenzonitrile in 68% yield. MS 306 (MH$^+$).

Example 205c: N-(3-hydroxy-2,2-dimethylpropyl)propionamide

Prepared according to the literature (Boyd, R. N.; Hansen, R. H. *J. Am. Chem. Soc.* 1953, 75, 5896) from 2-amino-2-methylpropan-1-ol and benzoyl chloride in 84% yield as a white solid. MS 160 (MH$^+$).

Example 206: 1-(3-(4-amino-2,2-dioxide-1H-benzo[c][1,2,6]thiadiazin-5-yloxy)-2',2'-dimethylpropyl)-3'-ethylurea

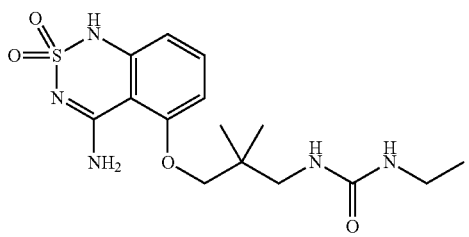

649

Prepared as in Example 197 from 1-(3-(3-sulfamoylamino-2-cyanophenoxy)-2,2-dimethylpropyl)-3-ethylurea (Example 206a) in 55% yield as a white solid. $^1$H NMR (400 MHz, DMSO-d$_6$) δ 0.88-0.96 (m, 9H), 2.90-2.97 (m, 2H), 3.01 (d, J=6.4 Hz, 2H), 3.72 (s, 2H), 5.75 (t, J=5.6 Hz, 1H), 6.07 (t, J=6.4 Hz, 1H), 6.56 (d, J=8.4 Hz, 1H), 6.67 (d, J=8.8 Hz, 1H), 7.39 (t, J=8.4 Hz, 1H), 8.05 (brs, 1H), 8.25 (brs, 1H), 10.89 (s, 1H). MS 370 (MH$^+$).

Example 206a: 1-(3-(3-sulfamoylamino-2-cyanophenoxy)-2,2-dimethylpropyl)-3-ethylurea Prepared as in Example 197a from 1-(3-(3-amino-2-cyanophenoxy)-2,2-dimethylpropyl)-3-ethylurea (Example 206b) in 100% yield. MS 370 (MH$^+$).

Example 206b: 1-(3-(3-amino-2-cyanophenoxy)-2,2-dimethylpropyl)-3-ethylurea

Prepared as in Example 197b (Method A) from 1-(3-(2-cyano-3-nitrophenoxy)-2,2-dimethylpropyl)-3-ethylurea (Example 206c) in 90% yield. MS 291 (MH$^+$).

Example 206c: 1-(3-(2-cyano-3-nitrophenoxy)-2,2-dimethylpropyl)-3-ethylurea

Prepared as in Example 197c from 1-ethyl-3-(3-hydroxy-2,2-dimethylpropyl)urea (Example 206d) and 2,6-dinitrobenzonitrile in 47% yield. MS 321 (MH$^+$).

Example 206d: 1-ethyl-3-(3-hydroxy-2,2-dimethylpropyl)urea

To a solution of 3-amino-2,2-dimethylpropan-1-ol (1.03 g, 10 mmol) in dry 1,4-dioxane (20 mL) was added dropwise ethyl isocyanate (0.71 g, 10 mmol) at room temperature under nitrogen. The reaction mixture was then stirred at room temperature under nitrogen overnight.

The solvent was removed under reduced pressure to give the title compound as colorless oil (1.74 g, 100%). MS 175 (MH$^+$).

Example 207: 3-(4-amino-2,2-dioxide-1H-benzo[c][1,2,6]thiadiazin-5-yloxy)-N-butyl-2',2'-dimethylpropanamide

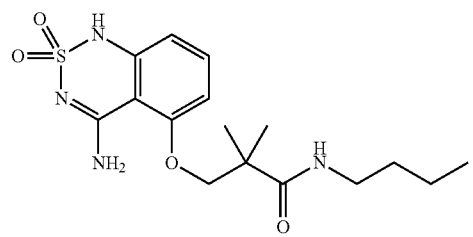

650

Prepared as in Example 197 and 1a from 3-(3-amino-2-cyanophenoxy)-N-butyl-2,2-dimethylpropanamide (Example 207a) and sulfamoyl chloride in 14% yield as a white solid. $^1$H NMR (400 MHz, DMSO-d$_6$) δ 0.78 (t, J=7.2 Hz, 3H), 1.14-1.22 (m, 8H), 1.33-1.37 (m, 2H), 3.02-3.07 (m, 2H), 4.07 (s, 2H), 6.60 (d, J=8.0 Hz, 1H), 6.71 (d, J=8.8 Hz, 1H), 7.44 (t, J=8.4 Hz, 1H), 7.80 (t, J=5.6 Hz, 1H), 7.91 (s, 1H), 8.33 (s, 1H), 10.92 (s, 1H). MS 369 (MH$^+$).

Example 207a: 3-(3-amino-2-cyanophenoxy)-N-butyl-2,2-dimethylpropanamide

Prepared as in Example 197b (Method A) from N-butyl-3-(2-cyano-3-nitrophenoxy)-2,2-dimethylpropanamide (Example 207b) in 89% yield. MS 290 (MH$^+$).

Example 207b: N-butyl-3-(2-cyano-3-nitrophenoxy)-2,2-dimethylpropanamide

Prepared as in Example 197c from N-butyl-3-hydroxy-2,2-dimethylpropanamide (Example 207c) and 2,6-dinitrobenzonitrile in 66% yield. MS 320 (MH$^+$).

Example 207c: N-butyl-3-hydroxy-2,2-dimethylpropanamide

Prepared as in Example 197d (Method A) from methyl 3-hydroxy-2,2-dimethylpropanoate and n-butyl amine in 100% yield. MS 174 (MH$^+$).

Example 208: N-(1-(4-amino-2,2-dioxide-1H-benzo[c][1,2,6]thiadiazin-5-yloxy)-2'-methylpropan-2'-yl)butyramide

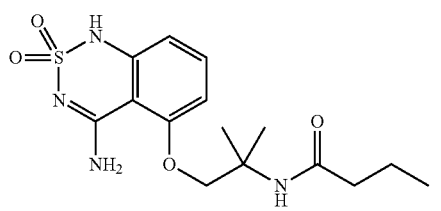

651

Prepared as in Example 197 from N-(1-(3-sulfamoylamino-2-cyanophenoxy)-2-methylpropan-2-yl)butyramide (Example 208a) and sodium hydroxide in 54% yield as a white solid. $^1$H NMR (400 MHz, DMSO-d$_6$) δ 0.78 (t, J=7.2

Hz, 3H), 1.32 (s, 6H), 1.43-1.44 (m, 2H), 2.00 (t, J=7.2 Hz, 2H), 4.24 (s, 2H), 6.60 (d, J=8.0 Hz, 1H), 6.73 (d, J=8.4 Hz, 1H), 7.44 (t, J=8.4 Hz, 1H), 7.77 (s, 1H), 7.82 (s, 1H), 8.42 (s, 1H), 10.97 (s, 1H). MS 355 (MH$^+$).

Example 208a: N-(1-(3-sulfamoylamino-2-cyanophenoxy)-2-methylpropan-2-yl)-butyramide Prepared as in Example 197a from N-(1-(3-amino-2-cyanophenoxy)-2-methylpropan-2-yl)butyramide (Example 208b) and sulfamoyl chloride in 100% yield. MS 355 (MH$^+$).

Example 208b: N-(1-(3-amino-2-cyanophenoxy)-2-methylpropan-2-yl)butyramide

Prepared as in Example 197b (Method A) from N-(1-(2-cyano-3-nitrophenoxy)-2-methylpropan-2-yl)butyramide (Example 208c) in 100% yield. MS 276 (MH$^+$).

Example 208c: N-(1-(2-cyano-3-nitrophenoxy)-2-methylpropan-2-yl)butyramide

Prepared as in Example 197c from N-(1-hydroxy-2-methylpropan-2-yl)butyramide (Example 208d) and 2,6-dinitrobenzonitrile in 72% yield. MS 306 (MH$^+$).

Example 208d: N-(1-hydroxy-2-methylpropan-2-yl)butyramide

Prepared according to the literature (Boyd, R. N.; Hansen, R. H. *J. Am. Chem. Soc.* 1953, 75, 5896) from 2-amino-2-methylpropan-1-ol and butyryl chloride in 32% yield. MS 160 (MH$^+$).

Example 209: 1-(1-(4-amino-2,2-dioxide-1H-benzo [c][1,2,6]thiadiazin-5-yloxy)-2'-methylpropan-2'-yl)-3'-ethylurea

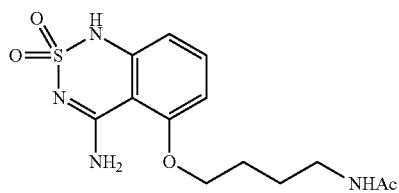

652

Prepared as in Example 197 from 1-(1-(3-sulfamoylamino-2-cyanophenoxy)-2-methylpropan-2-yl)-3-ethylurea (Example 209a) in 37% yield as a white solid. $^1$H NMR (400 MHz, DMSO-d$_6$) δ 0.92 (t, J=7.2 Hz, 3H), 1.27 (s, 6H), 2.90-2.93 (m, 2H), 4.21 (s, 2H), 5.63 (t, J=5.2 Hz, 1H), 5.95 (s, 1H), 6.59 (d, J=8.0 Hz, 1H), 6.72 (d, J=8.4 Hz, 1H), 7.42 (t, J=8.4 Hz, 1H), 7.94 (s, 1H), 8.34 (s, 1H), 10.94 (s, 1H). MS 356 (MH$^+$).

Example 209a: 1-(1-(3-sulfamoylamino-2-cyanophenoxy)-2-methylpropan-2-yl)-3-ethylurea Prepared as in Example 197a from 1-(1-(3-amino-2-cyanophenoxy)-2-methylpropan-2-yl)-3-ethylurea (Example 209b) and sulfamoyl chloride in 100% yield. MS 356 (MH$^+$).

Example 209b: 1-(1-(3-amino-2-cyanophenoxy)-2-methylpropan-2-yl)-3-ethylurea

Prepared as in Example 197b (Method A) from 1-(1-(2-cyano-3-nitrophenoxy)-2-methylpropan-2-yl)-3-ethylurea (Example 209c) in 86% yield. MS 277 (MH$^+$).

Example 209c: 1-(1-(2-cyano-3-nitrophenoxy)-2-methylpropan-2-yl)-3-ethylurea

Prepared as in Example 197c from 1-ethyl-3-(1-hydroxy-2-methylpropan-2-yl)urea (Example 209d) and 2,6-dinitrobenzonitrile in 65% yield. MS 307 (MH$^+$).

Example 209d: 1-ethyl-3-(1-hydroxy-2-methylpropan-2-yl)urea

Prepared as in Example 206d from 2-amino-2-methylpropan-1-ol and ethyl isocyanate in 94% yield. MS 161 (MH$^+$).

Example 210: N-(4-(4-amino-2,2-dioxide-1H-benzo [c][1,2,6]thiadiazin-5-yloxy)butyl)-acetamide

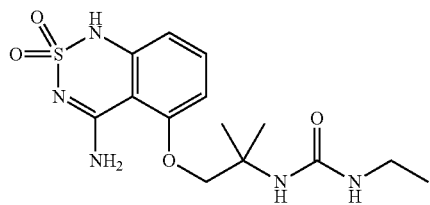

656

Prepared as in Example 197 from N-(4-(2-cyano-3-(sulfamoylamino)phenoxy)butyl)acetamide (Example 210a) in 30% yield. $^1$H NMR (400 MHz, DMSO-d$_6$) δ 1.48-1.51 (m, 2H), 1.77-1.81 (m, 5H), 3.03-3.08 (m, 2H), 4.14 (t, J=6.0 Hz, 2H), 6.59 (d, J=8.0 Hz, 1H), 6.73 (d, J=8.4 Hz, 1H), 7.43 (t, J=8.4 Hz, 1H), 7.78 (s, 1H). 7.84 (brs, 1H), 8.32 (s, 1H), 10.93 (s, 1H). MS 327 (MH$^+$).

Example 210a: N-(4-(2-cyano-3-(sulfamoylamino) phenoxy)butyl)acetamide

Prepared as in Example 197a from N-(4-(3-amino-2-cyanophenoxy)butyl)acetamide (Example 210b) and sulfamoyl chloride in 100% yield. $^1$H NMR (400 MHz, DMSO-d$_6$) δ 1.51-1.54 (m, 2H), 1.70-1.73 (m, 2H), 1.77 (s, 3H), 3.04-3.09 (m, 2H), 4.09 (t, J=6.4 Hz, 2H), 6.93 (d, J=8.4 Hz, 1H), 7.13 (d, J=8.0 Hz, 1H), 7.25 (s, 2H), 7.54 (t, J=8.0 Hz, 1H), 7.85 (brs, 1H), 9.42 (s, 1H).

Example 210b: N-(4-(3-amino-2-cyanophenoxy)butyl)acetamide

Prepared as in Example 197b (Method A) from N-(4-(2-cyano-3-nitrophenoxy)butyl)acetamide (Example 210c) in 85% yield. $^1$H NMR (400 MHz, DMSO-d$_6$) δ 1.49-1.54 (m, 2H), 1.66-1.70 (m, 2H), 1.77 (s, 3H), 3.03-3.08 (m, 2H), 3.97 (t, J=6.8 Hz, 2H), 5.95 (s, 2H), 6.18 (d, J=8.0 Hz, 1H), 6.31 (d, J=7.6 Hz, 1H), 7.15 (t, J=8.4 Hz, 1H), 7.83 (brs, 1H).

Example 210c: N-(4-(2-cyano-3-nitrophenoxy)butyl)acetamide

To a solution of 2-(4-aminobutoxy)-6-nitrobenzonitrile (Example 210d) (235 mg, 1.0 mmol), triethylamine (3 equiv.), and DMAP (0.1 equiv.) in dry dichloromethane (20 mL) was added dropwise acetyl chloride (1.5 equiv.) at 0° C. under nitrogen. The reaction mixture was then stirred at 0° C.-RT overnight. The reaction was diluted with EtOAc, washed with brine, and dried over $Na_2SO_4$. After evaporation of the solvent, the residue was purified by chromatography on silica gel eluting with 50% EtOAc in hexanes to give the title compound (158 mg, 57%). MS 278 ($MH^+$).

Example 210d: 2-(4-aminobutoxy)-6-nitrobenzonitrile

A solution of tert-butyl 4-(2-cyano-3-nitrophenoxy)butylcarbamate (Example 210e) (671 mg, 2 mmol) in DCM/TFA (1:1, 20 mL) was stirred at room temperature for 2 hrs. The solvent was removed under vacuum to give the title compound (698 mg, 100%). MS 236 ($MH^+$).

Example 210e: tert-butyl 4-(2-cyano-3-nitrophenoxy)butylcarbamate

Prepared as in Example 197c from tert-butyl 4-hydroxybutylcarbamate and 2,6-dinitrobenzonitrile in 7% yield as a pale yellow solid. $^1$H NMR (400 MHz, DMSO-$d_6$) δ 1.35 (s, 9H), 1.52-1.55 (m, 2H), 1.72-1.76 (m, 2H), 2.94-2.99 (m, 2H), 4.24 (t, J=6.8 Hz, 2H), 6.86 (brs, 1H), 7.69-7.72 (m, 1H), 7.85-7.90 (m, 2H).

Example 211: 4-(4-amino-2,2-dioxide-1H-benzo[c][1,2,6]thiadiazin-5-yloxy)butyl Sulfamate

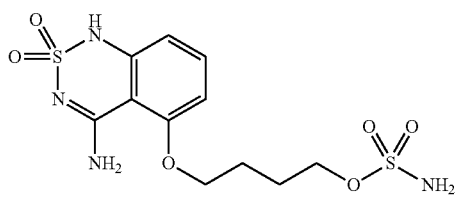

657

Prepared as in Example 197 from 4-(2-cyano-3-(sulfamoylamino)phenoxy)butyl sulfamate (Example 211a) in 31% yield. $^1$H NMR (400 MHz, DMSO-$d_6$) δ 1.74-1.79 (m, 2H), 1.85-1.91 (m, 2H), 4.07 (t, J=6.4 Hz, 2H), 4.18 (t, J=6.8 Hz, 2H), 6.58-6.60 (m, 1H), 6.74 (d, J=8.4 Hz, 1H), 7.42-7.46 (m, 3H), 7.79 (s, 1H), 8.32 (s, 1H), 10.93 (s, 1H). MS 365 ($MH^+$).

Example 211a: 4-(2-cyano-3-(sulfamoylamino)phenoxy)butyl sulfamate

Prepared as in Example 197a from 2-amino-6-(4-(tert-butyldimethylsilyloxy)butoxy)benzonitrile (Example 211b) and sulfamoyl chloride in 63% yield. MS 382 ($M+H_2O$).

Example 211b: 2-amino-6-(4-(tert-butyldimethylsilyloxy)butoxy)benzonitrile

Prepared as in Example 197b (Method A) from 2-(4-(tert-butyldimethylsilyloxy)butoxy)-6-nitrobenzonitrile (Example 211c) in 76% yield. MS 321 ($MH^+$).

Example 211c: 2-(4-(tert-butyldimethylsilyloxy)butoxy)-6-nitrobenzonitrile

Prepared as in Example 197c from 4-(tert-butyldimethylsilyloxy)butan-1-ol and 2,6-dinitrobenzonitrile in 25% yield as a pale yellow solid. $^1$H NMR (400 MHz, DMSO-$d_6$) δ 0.01 (s, 6H), 0.81-0.83 (m, 9H), 1.61-1.66 (m, 2H), 1.76-1.81 (m, 2H), 3.63 (t, J=6.8 Hz, 2H), 4.26 (t, J=6.4 Hz, 2H), 7.68-7.70 (m, 1H), 7.84-7.89 (m, 2H).

Example 212: 6-(4-amino-2,2-dioxide-1H-benzo[c][1,2,6]thiadiazin-5-yloxy)hexyl Sulfamate

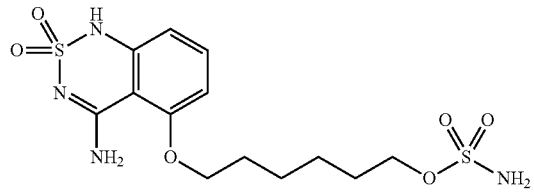

662

Prepared as in Example 197 from 6-(2-cyano-3-(sulfamoylamino)phenoxy)hexyl sulfamate (Example 212a) in 46% yield. $^1$H NMR (400 MHz, DMSO-$d_6$) δ 1.03-1.05 (m, 4H), 1.28 (m, 2H), 1.45 (m, 2H), 3.64 (t, J=6.4 Hz, 2H), 3.78 (t, J=6.4 Hz, 2H), 6.22 (d, J=7.6 Hz, 1H), 6.37 (d, J=7.6 Hz, 1H), 7.02 (s, 2H), 7.07 (t, J=7.6 Hz, 1H), 7.44 (s, 1H), 7.96 (s, 1H), 10.56 (s, 1H). MS 393 ($MH^+$).

Example 212a: 6-(2-cyano-3-(sulfamoylamino)phenoxy)hexyl sulfamate

Prepared as in Example 197a from 2-amino-6-(6-hydroxy-hexyloxy)benzonitrile (Example 212b) and sulfamoyl chloride in 20% yield. MS 393 ($MH^+$).

Example 212b: 2-amino-6-(6-hydroxyhexyloxy)benzonitrile

Prepared as in Example 197b (Method A) from 2-(6-hydroxyhexyloxy)-6-nitrobenzonitrile (Example 212c) in 99% yield. MS 235 ($MH^+$).

Example 212c: 2-(6-hydroxyhexyloxy)-6-nitrobenzonitrile

Prepared as in Example 197c from hexane-1,6-diol and 2,6-dinitrobenzonitrile in 88% yield as a pale yellow solid. MS 265 ($MH^+$).

Example 213: 5-(4-amino-2,2-dioxide-1H-benzo[c][1,2,6]thiadiazin-5-yloxy)pentyl sulfamate

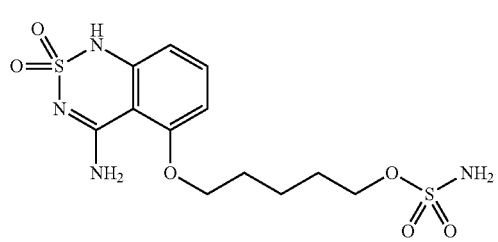

663

Prepared as in Example 197 from 5-(2-cyano-3-(sulfamoylamino)-phenoxy)pentyl sulfamate (Example 213a) in 44% yield. $^1$H NMR (400 MHz, DMSO-d$_6$) δ 1.09 (m, 2H), 1.33 (m, 2H), 1.47 (m, 2H), 3.66 (t, J=6.6 Hz, 2H), 3.79 (t, J=6.6 Hz, 2H), 6.22 (d, J=8.0 Hz, 1H), 6.37 (d, J=8.0 Hz, 1H), 7.03 (s, 2H), 7.07 (t, J=8.0 Hz, 1H), 7.43 (s, 1H), 7.95 (s, 1H), 10.57 (s, 1H). MS 379 (MH$^+$).

Example 213a: 5-(2-cyano-3-(sulfamoylamino)phenoxy)pentyl Sulfamate

Prepared as in Example 197a from 2-amino-6-(5-(tert-butyldimethylsilyloxy)pentyloxy)benzonitrile (Example 213b) and sulfamoyl chloride in 26% yield. MS 379 (MH$^+$).

Example 213b: 2-amino-6-(5-(tert-butyldimethylsilyloxy)pentyloxy)benzonitrile

Prepared as in Example 197b (Method A) from 2-(5-(tert-butyldimethyl-silyloxy)pentyloxy)-6-nitrobenzonitrile (Example 213c) in 93% yield. MS 335 (MH$^+$).

Example 213c: 2-(5-(tert-butyldimethylsilyloxy)pentyloxy)-6-nitrobenzonitrile

Prepared as in Example 197c from 5-(tert-butyldimethylsilyloxy)pentan-1-ol and 2,6-dinitrobenzonitrile as a pale yellow solid in 46% yield. MS 365 (MH$^+$).

Example 214: 5-(4-(methylsulfinyl)butoxy)-1H-benzo[c][1,2,6]thiadiazin-4-amine-2,2-dioxide

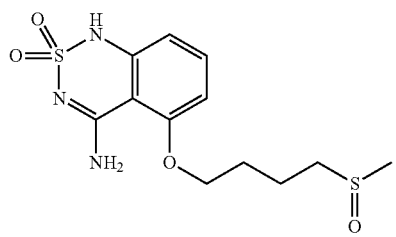

667

To a solution of 5-(4-(methylthio)butoxy)-1H-benzo[c][1,2,6]thiadiazin-4-amine-2,2-dioxide (Example 233) (79 mg, 0.25 mmol) in DCM/CH$_3$CO$_2$H (20:1, 20 mL) was added MCPBA (1.0 equiv.) at room temperature. The reaction mixture was then stirred at room temperature overnight. The solvent was evaporated under reduced pressure, and the residue was purified by chromatography on silica gel eluting with 15% MeOH in dichloromethane to give the title compound (74 mg, 90%) as a white solid. $^1$H NMR (400 MHz, DMSO-d$_6$) δ 1.74-1.77 (m, 2H), 1.88-1.95 (m, 2H), 2.50 (s, 3H), 2.68-2.73 (m, 1H), 2.77-2.83 (m, 1H), 4.19 (t, 2H), 6.58-6.60 (d, J=8.4 Hz, 1H), 6.73-6.75 (d, J=8.0 Hz, 1H), 7.44 (t, J=8.0 Hz, 1H), 7.79 (s, 1H), 8.33 (s, 1H), 10.92 (s, 1H). MS 332 (MH$^+$).

Example 215: 5-(4-(methylsulfonyl)butoxy)-1H-benzo[c][1,2,6]thiadiazin-4-amine-2,2-dioxide

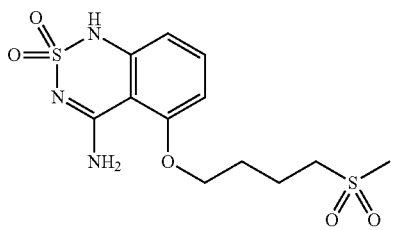

668

Prepared as in Example 214 from 5-(4-(methylthio)butoxy)-1H-benzo[c][1,2,6]thiadiazin-4-amine-2,2-dioxide (Example 98) by the reaction with 3 equivalent of MCPBA as a white solid in 88% yield. $^1$H NMR (400 MHz, DMSO-d$_6$) δ 1.80-1.82 (m, 2H), 1.91-1.95 (m, 2H), 2.93 (s, 3H), 3.18 (t, 2H), 4.18 (t, 2H), 6.58-6.60 (d, J=8.4 Hz, 1H), 6.73-6.75 (d, J=8.0 Hz, 1H), 7.44 (t, J=8.0 Hz, 1H), 7.79 (s, 1H), 8.34 (s, 1H), 10.92 (s, 1H). MS 348 (MH$^+$).

Example 216: 5-(3-(methylsulfinyl)propoxy)-1H-benzo[c][1,2,6]thiadiazin-4-amine-2,2-dioxide

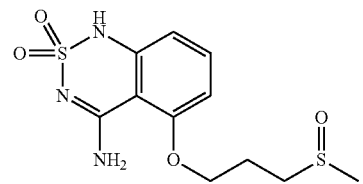

670

Prepared as in Example 214 from 5-(3-(methylthio)propoxy)-1H-benzo[c][1,2,6]thiadiazin-4-amine-2,2-dioxide (Example 99) by the reaction with 1.0 equivalent of MCPBA as a white solid in 90% yield. $^1$H NMR (400 MHz, DMSO-d$_6$) δ 2.18-2.22 (m, 2H), 2.54 (s, 3H), 2.75-2.78 (m, 1H), 2.89-2.93 (m, 1H), 4.26 (t, J=6.4 Hz, 2H), 6.60-6.61 (d, J=8.4 Hz, 1H), 6.73-6.75 (d, J=8.0 Hz, 1H), 7.44 (t, J=8.0 Hz, 1H), 7.83 (s, 1H), 8.30 (s, 1H), 10.92 (s, 1H). MS 318 (MH$^+$).

Example 217: 5-(3-(methylsulfonyl)propoxy)-1H-benzo[c][1,2,6]thiadiazin-4-amine-2,2-dioxide

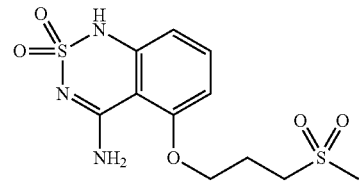

671

Prepared as in Example 214 from 5-(3-(methylthio)propoxy)-1H-benzo[c][1,2,6]thiadiazin-4-amine-2,2-dioxide (Example 99) by the reaction with 3.0 equivalent of MCPBA in 87% yield as a white solid. $^1$H NMR (400 MHz,

245

DMSO-d$_6$) δ 2.24-2.27 (m, 2H), 3.00 (s, 3H), 3.26 (t, J=7.6 Hz, 2H), 4.24 (t, J=6.4 Hz, 2H), 6.60-6.62 (d, J=8.0 Hz, 1H), 6.72-6.74 (d, J=8.0 Hz, 1H), 7.45 (t, J=8.0 Hz, 1H), 7.79 (s, 1H), 8.31 (s, 1H), 10.93 (s, 1H). MS 334 (MH$^+$).

Example 218: 1-(3-(4-amino-2,2-dioxide-1H-benzo [c][1,2,6]thiadiazin-5-yloxy)-2',2'-dimethylpropyl)-3'-(4''-methoxybenzyl)urea

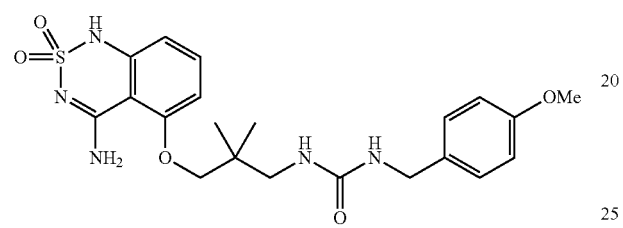

674

Prepared as in Example 197 from 1-(3-(3-sulfamoylamino-2-cyanophenoxy)-2,2-dimethylpropyl)-3-(4-methoxybenzyl)urea (Example 218a) in 77% yield as a white solid. $^1$H NMR (400 MHz, DMSO-d$_6$) δ 0.92 (s, 6H), 3.06 (d, J=6.4 Hz, 2H), 3.32 (s, 2H), 3.67 (s, 3H), 4.06 (d, J=6.0 Hz, 2H), 6.29 (t, J=6.0 Hz, 2H), 6.61 (d, J=8.0 Hz, 1H), 6.71 (d, J=8.0 Hz, 1H), 6.74 (d, J=8.8 Hz, 2H), 7.06 (d, J=8.8 Hz, 2H), 7.44 (t, J=8.0 Hz, 1H), 8.12 (s, 1H), 8.34 (s, 1H), 10.90 (s, 1H). MS 462 (MH$^+$).

Example 218a: 1-(3-(3-sulfamoylamino-2-cyanophenoxy)-2,2-dimethylpropyl)-3-(4-methoxybenzyl)urea Prepared as in Example 197a from 1-(3-(3-amino-2-cyanophenoxy)-2,2-dimethylpropyl)-3-(4-methoxybenzyl)urea (Example 218b) and sulfamoyl chloride in 100% yield. MS 462 (MH$^+$).

Example 218b: 1-(3-(3-amino-2-cyanophenoxy)-2,2-dimethylpropyl)-3-(4-methoxybenzyl)urea Prepared as in Example 197b (Method B) from 1-(3-hydroxy-2,2-dimethylpropyl)-3-(4-methoxybenzyl)urea (Example 218c) and 2-amino-6-fluorobenzonitrile in 60% yield. MS 383 (MH$^+$).

Example 218c: 1-(3-hydroxy-2,2-dimethylpropyl)-3-(4-methoxybenzyl)urea

Prepared as in Example 206d from 3-amino-2,2-dimethylpropan-1-ol and 4-methoxybenzyl isocyanate in 100% yield. MS 267 (MH$^+$).

246

Example 219: 1-(2-(4-amino-1H-benzo[c][1,2,6]thiadiazin-5-yloxy)ethyl)pyrrolidin-2-one-2,2-dioxide

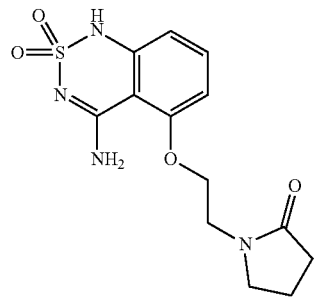

679

Prepared as in Example 158 from 2-amino-6-(2-(2-oxopyrrolidin-1-yl)ethoxy)benzonitrile sulfamide (Example 219a) in 45% yield. $^1$H NMR (400 MHz, DMSO-d$_6$) δ 1.94 (q, J=7.2 Hz, 2H), 2.26 (t, J=7.6 Hz, 2H), 3.43 (t, J=7.2 Hz, 2H), 3.68 (t, J=4.4 Hz, 2H), 4.23 (t, J=4.4 Hz, 2H), 6.59 (d, J=7.6 Hz, 1H), 6.70 (d, J=8.8 Hz, 1H), 7.43 (t, J=8.4 Hz, 1H), 7.82 (bs, NH), 8.21 (bs, NH), 10.98 (bs, NH). MS 325 (MH$^+$).

Example 219a: 2-amino-6-(2-(2-oxopyrrolidin-1-yl)ethoxy)benzonitrile sulfamide

Prepared as in Example 157a from 2-amino-6-(2-(2-oxopyrrolidin-1-yl)ethoxy)benzonitrile (Example 219b) in 100% yield. $^1$H NMR (400 MHz, DMSO-d$_6$) δ 1.94 (q, J=8.4 Hz, 2H), 2.22 (t, J=8.4 Hz, 2H), 3.50-3.58 (m, 4H), 4.21 (t, J=4.8 Hz, 2H), 6.94 (bs, 1H), 7.17 (d, J=7.6 Hz, 1H), 7.24 (bs, NH$_2$), 7.54 (t, J=7.2 Hz, 1H), 9.49 (bs, NH). MS 325 (MH$^+$).

Example 219b: 2-amino-6-(2-(2-oxopyrrolidin-1-yl)ethoxy)benzonitrile

Prepared as in example 235b from 2-nitro-6-(2-(2-oxopyrrolidin-1-yl)ethoxy)benzonitrile (Example 219c) using trifluoroethanol/hexafluoroisopropanol (1:1) as solvent in 100% yield MS 246 (MH$^+$).

Example 219c: 2-nitro-6-(2-(2-oxopyrrolidin-1-yl)ethoxy)benzonitrile

Prepared as in Example 160d from 1-(2-hydroxyethyl)pyrrolidin-2-one and 2,6-dinitrobenzonitrile in 74% yield. MS 276 (MH$^+$).

Example 220: 3-((4-Amino-1H-benzo[c][1,2,6]thiadiazin-5-yloxy)methyl)-N-propylpiperidine-1-carboxamide-2,2-dioxide

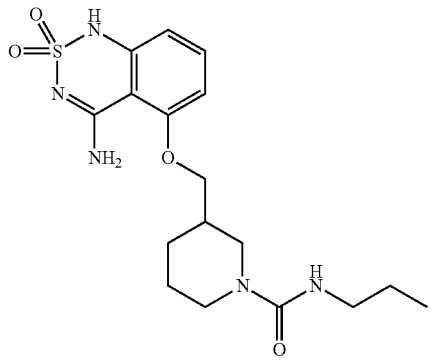

684

Prepared as in Example 158 from 3-((3-amino-2-cyanophenoxy)methyl)-N-propylpiperidine-1-carboxamide sulfamide (Example 220a) in 88% yield. $^1$H NMR (400 MHz, DMSO-d$_6$) δ 0.81 (t, J=6.8 Hz, 3H), 1.23-1.43 (m, 4H), 1.60-1.63 (bm, 1H), 1.81-1.84 (bm, 1H), 1.99-2.05 (bm, 1H), 2.67-2.75 (m, 1H), 2.80-2.85 (m, 1H), 2.93-2.98 (m, 2H), 3.71 (bd, J=12.8 Hz, 1H), 3.90 (bd, J=10.8 Hz, 1H), 3.98-4.08 (m, 2H), 6.44 (d, J=6.0 Hz, NH), 6.62 (d, J=8.0 Hz, 1H), 6.76 (d, J=8.4 Hz, 1H), 7.46 (t, J=8.4 Hz, 1H), 7.80 (s, NH), 8.37 (s, NH), 10.95 (s, NH). MS 396 (MH$^+$).

Example 220a: 3-((3-amino-2-cyanophenoxy)methyl)-N-propylpiperidine-1 carboxamide sulfamide Prepared as in Example 157a from 3-((3-amino-2-cyanophenoxy)methyl)-N-propylpiperidine-1-carboxamide (Example 220b) in 100% yield. $^1$H NMR (400 MHz, DMSO-d$_6$) δ 0.81 (t, J=7.2 Hz, 3H), 1.31-1.44 (m, 4H), 1.61-1.64 (bm, 1H), 1.85-1.87 (bm, 2H), 2.60-2.75 (m, 2H), 2.94-2.98 (m, 2H), 3.78 (bd, J=12.8 Hz, 1H), 3.93-3.97 (m, 1H), 4.01-4.10 (m, 2H), 6.38 (d, J=6.0 Hz, NH), 6.96 (d, J=8.8 Hz, 1H), 7.16 (d, J=8.4 Hz, 1H), 7.27 (s, NH), 7.41 (s, NH), 7.57 (t, J=8.4 Hz, 1H), 9.48 (s, NH). MS 396 (MH$^+$).

Example 220b: 3-((3-amino-2-cyanophenoxy)methyl)-N-propylpiperidine-1-carboxamide Prepared as in Example 235b from 3-((2-cyano-3-nitrophenoxy)methyl)-N-propylpiperidine-1-carboxamide (Example 220c) in 94% yield. MS 317 (MH$^+$).

Example 220c: 3-((2-cyano-3-nitrophenoxy)methyl)-N-propylpiperidine-1-carboxamide To a solution of 2-nitro-6-(piperidin-3-ylmethoxy)benzonitrile hydrochloride (Example 220d) (0.10 g, 0.34 mmol) in THF (6 mL) were added triethylamine (0.10 mL, 0.76 mmol) and propylisocyanate (0.05 mL, 0.52 mmol) and the reaction mixture was stirred at r.t. under nitrogen for 3 hour then filtered and evaporated, to give 3-((2-cyano-3-nitrophenoxy)methyl)-N-propylpiperidine-1-carboxamide (0.13 g, 100%). $^1$H NMR (400 MHz, DMSO-d$_6$) δ 0.81 (t, J=7.2 Hz, 3H), 1.34-1.41 (m, 4H), 1.62-1.64 (bm, 1H), 1.87-1.95 (bm, 2H), 2.64-2.77 (m, 2H), 2.93-2.98 (m, 2H), 3.77 (bd, J=12.8 Hz, 1H), 3.98 (bd, J=12.8 Hz, 1H), 4.09-4.13 (m, 1H), 4.17-4.20 (m, 1H), 6.38 (d, J=5.6 Hz, NH), 7.74 (bdd, J=1.6 Hz, J=8.0 Hz, 1H), 7.88-7.94 (m, 2H). MS 347 (MH$^+$).

Example 220d: 2-nitro-6-(piperidin-3-ylmethoxy)benzonitrile Hydrochloride

Prepared as in Example 160 from tert-butyl 3-((2-cyano-3-nitrophenoxy)methyl)piperidine-1-carboxylate (Example 220e) in 98% yield. MS 262 (MH$^+$).

Example 220e: tert-butyl 3-((2-cyano-3-nitrophenoxy)methyl)piperidine-1-carboxylate Prepared as in Example 197c from tert-butyl 3-(hydroxymethyl)piperidine-1-carboxylate and 2,6-dinitrobenzonitrile in 58% yield. MS 263 [M+H-Boc]$^+$.

Example 221: Tert-butyl 3-((4-amino-1H-benzo[c][1,2,6]thiadiazin-5-yloxy)methyl)piperidine-1-carboxylate-2,2-dioxide

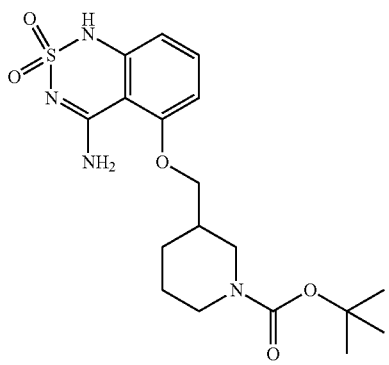

685

Prepared as in Example 158 from tert-butyl 3-((3-amino-2-cyanophenoxy)methyl)piperidine-1-carboxylate sulfamide (Example 221a), keeping the pH above 3 upon acidification, to give tert-butyl 3-((4-amino-1H-benzo[c][1,2,6]thiadiazin-5-yloxy)methyl)piperidine-1-carboxylate-2,2-dioxide (33 mg, 23%). $^1$H NMR (400 MHz, DMSO-d$_6$) δ 1.27-1.40 (bs, 11H), 1.62-1.66 (bm, 1H), 1.78-1.83 (bm, 1H), 2.05-2.12 (bm, 1H), 2.87-2.94 (m, 2H), 3.64-3.71 (bm, 1H), 3.83-3.86 (bm, 1H), 4.04 (bd, J=7.2 Hz, 2H), 6.62 (d, J=8.0 Hz, 1H), 6.77 (d, J=8.4 Hz, 1H), 7.46 (t, J=8.4 Hz, 1H), 7.76 (bs, NH), 8.37 (bs, NH), 10.95 (s, NH). MS 311 [M+H-Boc]$^+$.

Example 221a: tert-butyl 3-((3-amino-2-cyanophenoxy)methyl)piperidine-1-carboxylate Sulfamide Prepared as in Example 157a from tert-butyl 3-((3-amino-2-cyanophenoxy)methyl)piperidine-1-carboxylate (Example 221b). Upon extraction, NaOH 1M (1.56 mL, 1.56 mmol) was added to the ice-cooled reaction medium triggering formation of a sticky orangy material. Water was poured away and the residue diluted in EtOAc, and extracted, to give tert-butyl 3-((3-amino-2-cyanophenoxy)methyl)piperidine-1-carboxylate sulfamide (0.15 g, 84%). $^1$H NMR (400 MHz, DMSO-d$_6$) δ 1.35-1.40 (bs, 11H), 1.63-1.66 (bm, 1H), 1.79-1.83 (bm, 1H), 1.88-1.93 (bm, 1H), 2.78-2.85 (m, 2H), 3.74-3.78 (bm, 1H), 3.92-4.04 (m, 3H), 6.96 (d, J=8.4 Hz, 1H), 7.15 (d, J=8.4 Hz, 1H), 7.27 (s, NH$_2$), 7.56 (t, J=8.8 Hz, 1H), 9.47 (s, NH). MS 311 [M+H-Boc]$^+$.

Example 221b: tert-butyl 3-((3-amino-2-cyanophenoxy)methyl)piperidine-1-carboxylate Prepared as in example 100b from tert-butyl 3-((2-cyano-3-nitrophenoxy)methyl)piperidine-1-carboxylate (Example 220e) in 100% yield as an oil. MS 232 [M+H-Boc]$^+$.

Example 222: 4-Amino-5-(((2R,3S,4R)-3,4-dihydroxy-5-methoxytetrahydrofuran-2-yl)methoxy)-1H-benzo[c][1,2,6]thiadiazine-2,2-dioxide

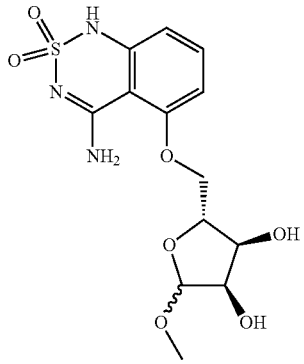

To a solution of 4-Amino-5-(((2R,3S,4R)-3,4,5-trihydroxytetrahydrofuran-2-yl)methoxy)-1H-benzo[c][1,2,6]thiadiazine-2,2-dioxide (Example 212a) (7 mg, 0.020 mmol) in dry methanol (1 mL) was added trifluoroacetic acid 0.2 mL) and the mixture was refluxed overnight. The resulting solution was evaporated to dryness to provide the title compound as a white powder (7.28 mg, 100%, mixture of diastereomers ~4/1). $^1$H NMR (400 MHz, DMSO-d$_6$): δ [3.17 (s, ¾H)], 3.22 (s, 3H), 3.81 (d, J=4.0 Hz, 1H), [3.93 (m, ½H)], 4.12 (m, 3H), 4.39 (m, 1H), 4.71 (s, 1H), [4.85 (d, J=4.0 Hz, H)], 5.44 (br s, 2H), 6.65 (d, J=8.0 Hz, 1H), 6.81 (d, J=8.0 Hz, 1H), 7.48 (t, J=8.0 Hz, 1H), 7.95 (s, 1H), 8.41 (s, 1H), 11.00 (s, 1H), [11.01 (s, 4H)].

Example 222a: 4-Amino-5-(((2R,3S,4R)-3,4,5-trihydroxytetrahydrofuran-2-yl)methoxy)-1H-benzo[c][1,2,6]thiadiazine-2,2-dioxide To a suspension of 4-Amino-5-(((3aR,4R,6R,6aR)-6-methoxy-2,2-dimethyltetrahydrofuro[3,4-d][1,3]dioxol-4-yl)methoxy)-1H-benzo[c][1,2,6]thiadiazine-2,2-dioxide (Example 212b) (15 mg, 0.038 mmol) in water (1 mL) was added trifluoroacetic acid (0.2 mL) and the mixture was heated overnight at 80° C. The reaction mixture was evaporated to dryness to furnish the title compound as a white solid in quantitative yield (mixture of diastereomers ~10/1).

$^1$H NMR (400 MHz, DMSO-d$_6$): δ 3.71 (m, 4H), 4.12 (m, 3H), 4.35 (m, 1H), 5.02 (s, 1H), 6.63 (d, J=8.0 Hz, 1H), 6.79 (d, J=8.0 Hz, 1H), 7.47 (t, J=8.0 Hz, 1H), 8.03 (br s, 1H), 8.31 (br s, 1H), 10.96 (br s, 1H), [11.00 (br s, 0.1H)].

Example 222b: 4-Amino-5-(((3aR,4R,6R,6aR)-6-methoxy-2,2-dimethyltetrahydrofuro[3,4-d][1,3]dioxol-4-yl)methoxy)-1H-benzo[c][1,2,6]thiadiazine-2,2-dioxide Prepared as in Example 158 from 2-sulfamoylamino-6-(((3aR,4R,6R,6aR)-6-methoxy-2,2-dimethyltetrahydrofuro[3,4-d][1,3]dioxol-4-yl)methoxy)benzonitrile (Example 212c) in 78% yield as a beige solid. $^1$H NMR (400 MHz, DMSO-d$_6$) δ 1.28 (s, 3H), 1.41 (s, 3H), 3.18 (s, 3H), 4.00 (t, J=9.2 Hz, 1H), 4.32 (dd, J=5.2, 10.0 Hz, 1H), 4.59 (dd, J=5.2, 8.8 Hz, 1H), 4.63 (d, J=6.0 Hz, 1H), 4.82 (d, J=6.0 Hz, 1H), 5.02 (s, 1H), 6.64 (d, J=8.4 Hz, 1H), 6.70 (d, J=8.4 Hz, 1H), 7.48 (t, J=8.4 Hz, 1H), 7.98 (br s, 1H), 8.43 (br s, 1H), 11.02 (br s, 1H).

Example 222c: 2-Sulfamoylamino-6-(((3aR,4R,6R,6aR)-6-methoxy-2,2-dimethyltetrahydrofuro[3,4-d][1,3]dioxol-4-yl)methoxy)benzonitrile Prepared as in Example 158a from 2-amino-6-(((3aR,4R,6R,6aR)-6-methoxy-2,2-dimethyltetrahydrofuro[3,4-d][1,3]dioxol-4-yl)methoxy)benzonitrile (Example 212d) in 77% yield as a white solid. $^1$H NMR (400 MHz, CDCl$_3$) δ 1.34 (s, 3H), 1.50 (s, 3H), 3.33 (s, 3H), 4.08 (m, 2H), 4.51 (dd, J=6.4, 7.6 Hz, 1H), 4.65 (d, J=6.0 Hz, 1H), 4.79 (d, J=6.0 Hz, 1H), 5.01 (s, 1H), 5.25 (br s, 2H), 6.70 (d, J=8.4 Hz, 1H), 7.28 (br s, 1H), 7.30 (d, J=8.0 Hz, 1H), 7.51 (t, J=8.4 Hz, 1H).

Example 222d: 2-Amino-6-(((3aR,4R,6R,6aR)-6-methoxy-2,2-dimethyltetrahydrofuro[3,4-d][1,3]dioxol-4-yl)methoxy)benzonitrile Prepared as in Example 158b from 2-(((3aR,4R,6R,6aR)-6-methoxy-2,2-dimethyltetrahydrofuro[3,4-d][1,3]dioxol-4-yl)methoxy)-6-nitrobenzonitrile (Example 212e) in 40% yield as colorless sticky material. $^1$H NMR (400 MHz, CDCl$_3$) δ 1.33 (s, 3H), 1.49 (s, 3H), 3.33 (s, 3H), 4.05 (m, 2H), 4.45 (br s, 2H), 4.56 (dd, J=6.0, 8.0 Hz, 1H), 4.65 (d, J=6.0 Hz, 1H), 4.82 (br d, J=6.0 Hz, 1H), 5.00 (s, 1H), 6.21 (dd, J=0.8, 8.4 Hz, 1H), 6.33 (dd, J=0.8, 8.4 Hz, 1H), 7.20 (t, J=8.4 Hz, 1H).

Example 222e: 2-(((3aR,4R,6R,6aR)-6-Methoxy-2,2-dimethyltetrahydrofuro[3,4-d][1,3]dioxol-4-yl)methoxy)-6-nitrobenzonitrile Prepared as in Example 158c from 2,6 dinitrobenzonitrile and ((3aR,4R,6R,6aR)-6-methoxy-2,2-dimethyltetrahydrofuro[3,4-d][1,3]dioxol-4-yl)methanol in 70% yield as white solid. $^1$H NMR (400 MHz, CDCl$_3$) δ 1.33 (s, 3H), 1.49 (s, 3H), 3.32 (s, 3H), 4.23 (d, J=2.0 Hz, 1H), 4.24 (s, 1H), 4.60 (br t, J=6.0 Hz, 1H), 4.67 (d, J=6.0 Hz, 1H), 4.86 (br d, J=6.0 Hz, 1H), 5.01 (s, 1H), 7.35 (d, J=8.4 Hz, 1H), 7.72 (t, J=8.4 Hz, 1H), 7.87 (dd, J=0.8, 8.4 Hz, 1H).

Example 223: 4-Amino-5-(((3aR,5aS,8aS,8bS)-2,2,7,7-tetramethyltetrahydro-3aH-bis[1,3]dioxolo[4,5-b:4',5'-d]pyran-5-yl)methoxy)-1H-benzo[c][1,2,6]thiadiazine-2,2-dioxide

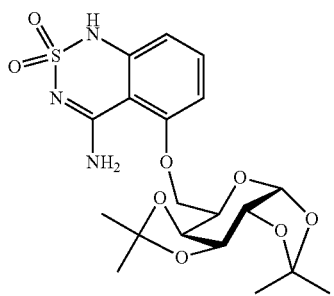

688

Prepared as in Example 236 from 2-amino-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile (Example 213a) in 72% yield as a white solid. $^1$H NMR (400 MHz, DMSO-$d_6$) δ 1.29 (s, 3H), 1.31 (s, 3H), 1.38 (s, 3H), 1.43 (s, 3H), 4.07 (m, 2H), 4.19 (br d, J=8.4 Hz, 1H), 4.36 (dd, J=1.2, 8.0 Hz, 1H), 4.41 (dd, J=2.4, 5.2 Hz, 1H), 4.44 (dd, J=2.4, 10.0 Hz, 1H), 4.67 (dd, J=2.4, 8.0 Hz, 1H), 5.51 (d, J=4.8 Hz, 1H), 6.63 (d, J=8.0 Hz, 1H), 6.77 (d, J=8.4 Hz, 1H), 7.45 (t, J=8.4 Hz, 1H), 7.86 (br s, 1H), 8.41 (br s, 1H), 10.98 (br s, 1H). MS 456 (MH$^+$).

Example 223a: 2-Amino-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile Prepared as in Example 158b from 2-nitro-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile (Example 213b) in quantitative yield. $^1$H NMR (400 MHz, DMSO-$d_6$) δ 1.28 (s, 3H), 1.31 (s, 3H), 1.37 (s, 3H), 1.39 (s, 3H), 4.05 (m, 2H), 4.16 (dd, J=4.0, 8.8 Hz, 1H), 4.37 (m, 2H), 4.67 (dd, J=2.4, 8.0 Hz, 1H), 5.47 (d, J=4.8 Hz, 1H), 6.01 (br s, 2H), 6.23 (d, J=8.0 Hz, 1H), 6.35 (d, J=8.4 Hz, 1H), 7.17 (t, J=8.4 Hz, 1H).

Example 223b: 2-Nitro-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile Prepared as in Example 158c from 2,6 dinitrobenzonitrile and ((3aR,5aS,8aS,8bS)-2,2,7,7-tetramethyltetrahydro-3aH-bis[1,3]dioxolo[4,5-b:4',5'-d]pyran-5-yl)methanol in 59% yield as white sticky material. MS 408 (MH$^+$), 424 (MH$_2$O$^+$).

Example 224: 8-(4-amino-2,2-dioxo-1H-benzo[c][1,2,6]thiadiazin-5-yloxy)octan-1-ol

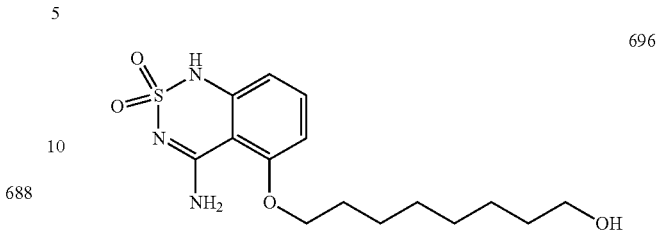

696

To a solution of 8-(3-amino-2-cyanophenoxy)octyl acetate (746 mol, 227 mg) in DMA (3 mL) was added sulfamoyl chloride (1.492 mmol, 172 mg) and pyridine (4.476 mmol, 362 µL). The reaction mixture was stirred at room temperature until completion, then quenched with sat. NaHCO$_3$ (15 mL) and solid NaCl added. The precipitate was collected and washed with water. The wet precipitate was suspended in EtOH (15 mL) and treated with NaOH (8.952 mmol, 1N, 8.95 mL). The reaction mixture was refluxed until completion then cooled to room temperature. Most of the EtOH and water were removed in vacuo, then the reaction mixture was dissolved in water (15 mL), extracted with ether (3×5 mL), filtered through a 0.45 m PTFE frit, then acidified with 10% citric acid/water solution to pH 4-5. The precipitate was filtered off, washed with water and dried to give the desired product 146 mg (57.3%) as an off-white solid. $^1$H NMR (400 MHz, DMSO-$d_6$) δ1.265 (m, 6H), 1.380 (m, 4H), 1.785 (pentet, J=7 Hz, 2H), 3.348 (q, J=6 Hz, 2H), 4.303 (t, J=5 Hz, 2H), 6.580 (d, J=8 Hz, 1H), 6.724 (d, J=8 Hz, 1H), 7.428 (t, J=8 Hz, 1H), 7.796 (br. s, 1H), 8.329 (br. s, 1H), 10.922 (s, 1H). MS 342 (MH$^+$).

Example 224a: 8-(3-amino-2-cyanophenoxy)octyl acetate

A solution of 8-(2-cyano-3-nitrophenoxy)octyl acetate (802 µmol, 268 mg) (Example 214b) in EtOH (15 mL) was hydrogenated in an H-cube apparatus using 10% Pd/C as catalyst. The solution was evaporated to give 8-(3-amino-2-cyanophenoxy)octyl acetate (244 mg, 244 mg). MS 305 (MH$^+$)

Example 224b: 8-(2-cyano-3-nitrophenoxy)octyl Acetate 2-(8-hydroxyoctyloxy)-6-nitrobenzonitrile (804 µmol, 235 mg) (Example 214c) was dissolved in dry DCM (10 mL), cooled to 0° C., and treated successively with pyridine (3.216 mmol, 260 µL) and acetyl chloride (1.608 mmol, 114 µL). The reaction mixture was stirred and allowed to warm slowly to room temperature. When the reaction was complete, the volatiles were removed in vacuo and the crude product purified on silica gel (10% to 50% EtOAc in hexanes) to give the desired product (268 mg, 100%). MS 335 (MH$^+$).

Example 224c: 2-(8-hydroxyoctyloxy)-6-nitrobenzonitrile

To a solution of 1,8-octanediol (3.87 mmol, 566 mg) in THF (dry, 10 mL) was added 2,6-dinitrobenzonitrile (1.29 mmol, 250 mg) and DBU (1.30 mmol, 194 µL). The reaction mixture was stirred for 24 hours at room temperature an evaporated. The oily residue was triturated with 10% citric acid/water and solid NaCl added. The precipitate was collected, washed with water, dried in vacuo and purified on silica gel (40% to 100% EtOAc in hexanes) to give the desired product (235 mg, 62.3%) as a pinkish solid. MS 293 (MH⁺).

Example 225: N-(6-(4-amino-2,2-dioxo-1H-benzo[c][1,2,6]thiadiazin-5-yloxy)hexyl)-2-hydroxy-2-methylpropanamide

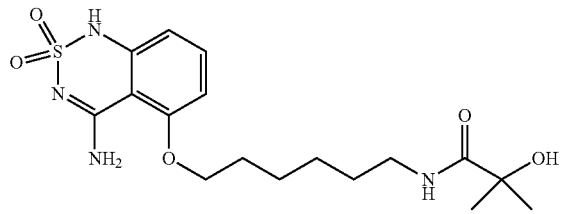

699

Prepared as in Example 224 from 1-(6-(3-amino-2-cyanophenoxy)hexylamino)-2-methyl-1-oxopropan-2-yl acetate (Example 225a) in 65.5% yield. $^1$H NMR (400 MHz, DMSO-$d_6$) δ 1.201 (s, 6H), 1.289 (m, 2H), 1.399 (m, 4H), 1.790 (pentet, J=7 Hz, 2H), 3.036 (q, J=6 Hz, 2H), 4.130 (t, J=6 Hz, 2H), 5.272 (s, 1H), 6.587 (d, J=8 Hz, 1H), 6.728 (d, J=8 Hz, 1H), 7.436 (t, J=8 Hz, 1H), 7.594 (br. t, 1H), 7.804 (br. s, 1H), 8.326 (br. s, 1H), 10.924 (s, 1H). MS 399 (MH⁺).

Example 225a: 1-(6-(3-amino-2-cyanophenoxy)hexylamino)-2-methyl-1-oxopropan-2-yl acetate Prepared as in Example 224a from 1-(6-(2-cyano-3-nitrophenoxy)hexylamino)-2-methyl-1-oxopropan-2-yl acetate (Example 225b) in 94.4% yield. MS 362 (MH⁺).

Example 225b: 1-(6-(2-cyano-3-nitrophenoxy)hexylamino)-2-methyl-1-oxopropan-2-yl acetate To a solution of tert-butyl 6-(2-cyano-3-nitrophenoxy)hexylcarbamate (333 μmol, 121 mg) (Example 225c) in dioxane (2 mL) was added con. HCl (1 mL). After 15 minutes, the solution was concentrated in vacuo and dried on high vacuum. The crude HCl salt was suspended in DCM (dry, 10 mL) and treated with pyridine (2.664 mmol, 62 μL) and 1-chloro-2-methyl-1-oxopropan-2-yl acetate (1.332 mmol, 193 μL). The reaction mixture was refluxed under a nitrogen atmosphere until clear (6 h), then cooled to room temperature and the volatiles removed in vacuo. The residue was purified on silica gel (40% to 100% EtOAc in hexanes) to give the product (117 mg, 90%) as a light yellow heavy oil. MS 392 (MH⁺).

Example 225c: tert-butyl 6-(2-cyano-3-nitrophenoxy)hexylcarbamate

Prepared as in Example 197c from tert-butyl 6-hydroxyhexylcarbamate in 53.8% yield as light yellow solid. MS 364 (MH⁺).

Example 226: 1-(6-(4-amino-2,2-dioxo-1H-benzo[c][1,2,6]thiadiazin-5-yloxy)hexyl)urea

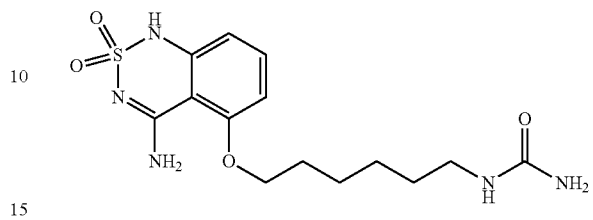

700

A solution of 1-(6-(4-amino-2,2-dioxo-1H-benzo[c][1,2,6]thiadiazin-5-yloxy)hexyl)-3-(4-methoxybenzyl)urea (122 μmol, 58 mg) (Example 227) in DCM (2.5 mL) was treated with TFA (2.5 mL). The reaction mixture was stirred at room temperature for 4 hours, then the volatiles were removed under a stream of nitrogen. The oily residue was triturated with ether, the precipitate collected, washed with ether, then dissolved in MeOH and evaporated to gives the desired product (44 mg, 100% yield). $^1$H NMR (400 MHz, DMSO-$d_6$) δ1.364 (m, 6H), 1.812 (pentet, J=7 Hz, 2H), 2.943 (br t, 2H), 4.154 (d, J=7 Hz, 2H), 4.131 (t, J=7 Hz, 2H), 5.349 (br. s, 2H), 5.894 (br. s, 1H), 6.607 (d, J=8 Hz, 1H), 6.752 (d, J=8 Hz, 1H), 7.456 (t, J=8 Hz, 1H), 7.824 (br. s, 1H), 8.351 (br. s, 1H), 10.945 (s, 1H). MS 356 (MH⁺).

Example 227: 1-(6-(4-amino-2,2-dioxo-1H-benzo[c][1,2,6]thiadiazin-5-yloxy)hexyl)-3-(4-methoxybenzyl)urea

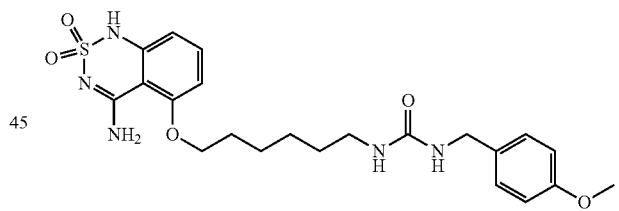

701

To a suspension of 6-(4-amino-2,2-dioxo-1H-benzo[c][1,2,6]thiadiazin-5-yloxy)hexan-1-aminium chloride (25 μmol, 52 mg) (Example 228) in dry DCM (6 mL) was successively added Et₃N (332 μmol, 46 μL) and 1-(isocyanatomethyl)-4-methoxybenzene (183 μmol, 26 μL). The reaction was stirred for 48 hours at room temperature then concentrated in vacuo. The residue was washed with water, dried, then purified on silica gel (20% to 100% EtOAc in hexanes) to give the desired product (64 mg, 81.0% yield). $^1$H NMR (400 MHz, DMSO-$d_6$) δ1.296 (m, 2H), 1.371 (m, 4H), 1.791 (pentet, J=8 Hz, 2H), 2.980 (q, J=6 Hz, 2H), 3.695 (s, 3H), 4.086 (d, J=6 Hz, 2H), 4.131 (t, J=6 Hz, 2H), 5.836 (br. t, J=5 Hz, 1H), 6.141 (br. t, J=6 Hz, 1H), 6.585 (d, J=8 Hz, 1H), 6.727 (d, J=8 Hz, 1H), 6.840 (d, J=9 Hz, 2H), 7.137 (d, J=9 Hz, 2H), 7.433 (t, J=8 Hz, 1H), 7.803 (br. s, 1H), 8.321 (br. s, 1H), 10.926 (s, 1H). MS 476 (MH⁺).

Example 228: 6-(4-amino-2,2-dioxo-1H-benzo[c][1,2,6]thiadiazin-5-yloxy)hexan-1-aminium Chloride

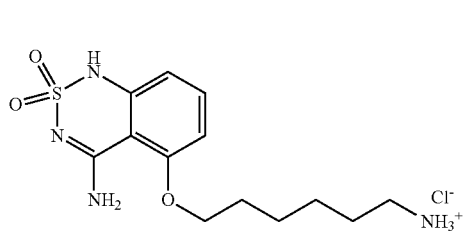

To a solution of tert-butyl 6-(4-amino-2,2-dioxo-1H-benzo[c][1,2,6]thiadiazin-5-yloxy)hexylcarbamate (118 mg, 286 umol) (Example 229) in dioxane (2 mL) was added con. HCl (1 mL) and the solution stirred at room temperature for 15 minutes. The solvents were removed in vacuo and the residue triturated with hot ethanol. After cooling to room temperature, the precipitated was collected, washed with hot ethanol, and dried in vacuo to give the desired product 56 mg (62.9%) as an off-white powder. $^1$H NMR (400 MHz, DMSO-$d_6$) δ1.367 (m, 4H), 1.529 (pentet, J=7 Hz, 2H), 1.795 (pentet, J=7 Hz, 2H), 2.741 (br m, 2H), 4.144 (t, J=7 Hz, 2H), 6.596 (d, J=8 Hz, 1H), 6.733 (d, J=8 Hz, 1H), 7.440 (t, J=8 Hz, 1H), 7.725 (br. s, 3H), 7.795 (br. s, 1H), 8.350 (br. s, 1H), 10.954 (s, 1H). MS 313 (MH$^+$).

Example 229: tert-butyl 6-(4-amino-2,2-dioxo-1H-benzo[c][1,2,6]thiadiazin-5-yloxy)hexylcarbamate

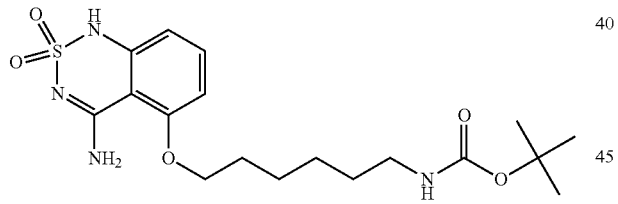

Prepared as in Example 224 from tert-butyl 6-(3-amino-2-cyanophenoxy)hexylcarbamate (Example 229a) and sulfamoyl chloride in 59.5% yield. $^1$H NMR (400 MHz, DMSO-$d_6$) δ1.274 (m, 2H), 1.339 (s, 9H), 1.361 (m, 4H), 1.779 (pentet, J=7 Hz, 2H), 2.878 (q, J=6 Hz, 2H), 4.122 (t, J=6 Hz, 2H), 6.580 (d, J=8 Hz, 1H), 6.722 (d, J=8 Hz, 1H), 6.75 (br t, J=6 Hz, 1H), 7.428 (t, J=8 Hz, 1H), 7.798 (br. s, 1H), 8.323 (br. s, 1H), 10.921 (s, 1H). MS 413 (MH$^+$).

Example 229a: tert-butyl 6-(3-amino-2-cyanophenoxy)hexylcarbamate

Prepared as in Example 224a from tert-butyl 6-(2-cyano-3-nitrophenoxy)hexylcarbamate (example 225c) in quantitative yield. MS 334 (MH$^+$).

Example 230: 5-(2-(1H-pyrrol-1-yl)ethoxy)-1H-benzo[c][1,2,6]thiadiazin-4-amine-2,2-dioxide

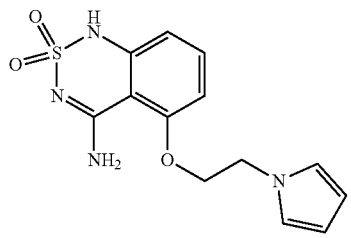

Prepared as in Example 224 from 2-(2-(1H-pyrrol-1-yl)ethoxy)-6-aminobenzonitrile (Example 230a) and sulfamoyl chloride in 66.6% yield. $^1$H NMR (400 MHz, DMSO-$d_6$) δ4.392 (m, 4H), 5.992 (t, J=2 Hz, 2H), 6.595 (d, J=8 Hz, 1H), 6.693 (d, J=8 Hz, 1H), 6.816 (t, J=2 Hz, 2H), 7.428 (t, J=8 Hz, 1H), 7.482 (br. s, 1H), 8.288 (br. s, 1H), 10.930 (s, 1H). MS 307 (MH$^+$).

Example 230a: 2-(2-(1H-pyrrol-1-yl)ethoxy)-6-aminobenzonitrile

Prepared as in Example 224a from 2-(2-(1H-pyrrol-1-yl)ethoxy)-6-nitrobenzonitrile (Example 230b) in 85.2% yield. MS 228 (MH$^+$).

Example 230b: 2-(2-(1H-pyrrol-1-yl)ethoxy)-6-nitrobenzonitrile

Prepared as in Example 160d from 2-(1H-pyrrol-1-yl)ethanol and 2,6-dinitrobenzonitrile, in 42.5% yield. MS 258 (MH$^+$).

Example 231: 5-(2-(1H-pyrazol-1-yl)ethoxy)-1H-benzo[c][1,2,6]thiadiazin-4-amine-2,2-dioxide

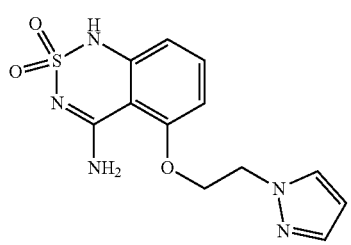

Prepared as in Example 224 from 2-(2-(1H-pyrazol-1-yl)ethoxy)-6-aminobenzonitrile (Example 231a) and sulfamoyl chloride in 54.5% yield. $^1$H NMR (400 MHz, DMSO-$d_6$) δ4.406 (t, J=5 Hz, 2H), 4.630 (t, J=5 Hz, 2H), 6.266 (t, J=2 Hz, 1H), 6.593 (d, J=8 Hz, 1H), 6.689 (d, J=8 Hz, 1H), 7.445 (br s, 1H), 7.425 (t, J=8 Hz, 1H), 7.805 (d, J=2 Hz, 1H), 8.224 (br. s, 1H), 8.301 (br. s, 1H), 10.904 (s, 1H). MS 308 (MH$^+$).

Example 231a: 2-(2-(1H-pyrazol-1-yl)ethoxy)-6-aminobenzonitrile

Prepared as in Example 224a from 2-(2-(1H-pyrazol-1-yl)ethoxy)-6-nitrobenzonitrile (Example 231b) in 46.2% yield. MS 229 (MH$^+$).

Example 231b: 2-(2-(1H-pyrazol-1-yl)ethoxy)-6-nitrobenzonitrile

Prepared as in Example 197197c from 2-(1H-pyrazol-1-yl)ethanol and 2,6-dinitrobenzonitrile in 89.2% yield. MS 259 (MH⁺).

Example 232: 5-(2-(3,5-dimethyl-1H-pyrazol-1-yl)ethoxy)-1H-benzo[c][1,2,6]thiadiazin-4-amine-2,2-dioxide

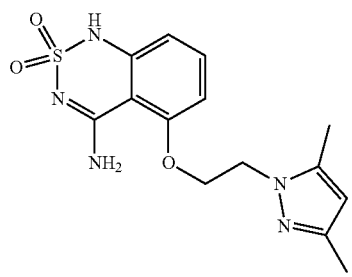

706

Prepared as in Example 224 from 2-(2-(3,5-dimethyl-1H-pyrazol-1-yl)ethoxy)-6-aminobenzonitrile (Example 232a) and sulfamoyl chloride in 18.2% yield. $^1$H NMR (400 MHz, DMSO-$d_6$) δ2.066 (s, 3H), 2.215 (s, 3H), 4.313 (t, J=4 Hz, 2H), 4.397 (t, J=4 Hz, 2H), 5.801 (s, 1H), 6.584 (d, J=8 Hz, 1H), 6.645 (d, J=8 Hz, 1H), 7.418 (t, J=8 Hz, 1H), 8.395 (br. s, 1H), 8.677 (br. s, 1H), 10.885 (s, 1H). MS 336 (MH⁺).

Example 232a: 2-(2-(3,5-dimethyl-1H-pyrazol-1-yl)ethoxy)-6-aminobenzonitrile

Prepared as in Example 224a from 2-(2-(3,5-dimethyl-1H-pyrazol-1-yl)ethoxy)-6-nitrobenzonitrile (example 232b) in 69.3% yield. MS 257 (MH⁺).

Example 232b: 2-(2-(3,5-dimethyl-1H-pyrazol-1-yl)ethoxy)-6-nitrobenzonitrile

Prepared as in Example 197c from 2-(3,5-dimethyl-1H-pyrazol-1-yl)ethanol and 2,6-dinitrobenzonitrile in 90.7% yield. MS 287 (MH⁺).

Example 233: 5-(4-(methylthio)butoxy)-1H-benzo[c][1,2,6]thiadiazin-4-amine-2,2-dioxide

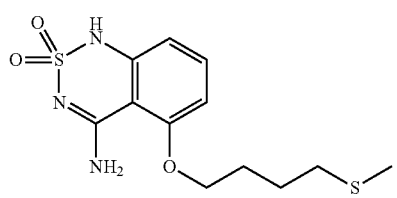

666

Prepared as in Example 197 from 2-sulfamoylamino-6-(4-(methylthio)butoxy)benzonitrile (Example 233a) in 79% yield. $^1$H NMR (400 MHz, DMSO-$d_6$) δ 1.63-1.67 (m, 2H), 1.86-1.90 (m, 2H), 2.02 (s, 3H), 2.48-2.53 (m, 2H), 4.16 (t, 2H), 6.57-6.60 (d, J=8.4 Hz, 1H), 6.72-6.74 (d, J=8.4 Hz, 1H), 7.43 (t, J=8 Hz, 1H), 7.80 (s, 1H), 8.35 (s, 1H), 10.92 (s, 1H). MS 316 (MH⁺).

Example 233a: 2-sulfamoylamino-6-(4-(methylthio)butoxy)benzonitrile

Prepared as in Example 197a from 2-amino-6-(4-(methylthio)-butoxy)benzonitrile (Example 233b) and sulfamoyl chloride in 66% yield. MS 316 (MH⁺).

Example 233b: 2-amino-6-(4-(methylthio)butoxy)benzonitrile

Prepared as in Example 197b (Method A) from 2-(4-(methylthio)butoxy)-6-nitrobenzonitrile (Example 233c) in 95% yield. MS 237 (MH⁺).

Example 233c: 2-(4-(methylthio)butoxy)-6-nitrobenzonitrile

Prepared as in Example 197c from 4-(methylthio)butan-1-ol and 2,6-dinitrobenzonitrile in 89% yield. MS 267 (MH⁺).

Example 234: 5-(3-(methylthio)propoxy)-1H-benzo[c][1,2,6]thiadiazin-4-amine-2,2-dioxide

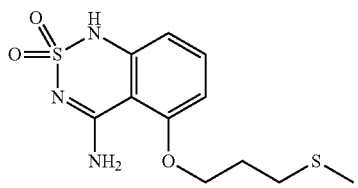

669

Prepared as in Example 197 from 2-sulfamoylamino-6-(3-(methylthio)propoxy)benzonitrile (Example 234a) in 69% yield. $^1$H NMR (400 MHz, DMSO-$d_6$) δ 2.05 (s, 3H), 2.08 (m, 2H), 2.59 (t, J=7.2 Hz, 2H), 4.21 (t, J=6.4 Hz, 2H), 6.59-6.61 (d, J=8.0 Hz, 1H), 673-6.75 (d, J=8.8 Hz, 1H), 7.44 (t, J=8.0 Hz, 1H), 7.79 (s, 1H), 8.33 (s, 1H), 10.93 (s, 1H). MS 302 (MH⁺).

Example 234a: 2-sulfamoylamino-6-(3-(methylthio)propoxy)benzonitrile

Prepared as in Example 197a from 2-amino-6-(3-(methylthio)propoxy)benzonitrile (Example 234b) and sulfamoyl chloride in 69% yield. MS 302 (MH⁺).

Example 234b: 2-amino-6-(3-(methylthio)propoxy)benzonitrile

Prepared as in Example 197b (Method A) from 2-(3-(methylthio)propoxy)-6-nitrobenzonitrile (Example 234c) in 98% yield. MS 223 (MH⁺).

Example 234c: 2-(3-(methylthio)propoxy)-6-nitrobenzonitrile

Prepared as in Example 197c from 4-(methylthio)butan-1-ol and 2,6-dinitrobenzonitrile in 89% yield. MS 253 (MH⁺).

259

Example 235: 5-((2-methylcyclopropyl)methoxy)-1H-benzo[c][1,2,6]thiadiazin-4-amine-2,2-dioxide

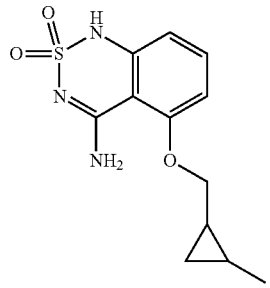

676

Prepared as in Example 157 from 2-amino-6-((2-methylcyclopropyl)methoxy)benzonitrile sulfamide (example 235a) in 68% yield (mixture of diastereoisomers). $^1$H NMR (400 MHz, DMSO-$d_6$) δ 0.17-0.40 (m, 1H), 0.54-0.58 (m, 1H), 0.76-0.85 (m, 1H), 0.99-1.12 (m, 4H), 3.96-4.33 (m, 2H), 6.58-6.61 (m, 1H), 6.67-6.77 (m, 1H), 7.41-7.47 (m, 1H), 7.97 (s, NH), 8.38 (s, NH), 10.97 (s, NH). MS 282 (MH$^+$).

Example 235a: 2-amino-6-((2-methylcyclopropyl)methoxy)benzonitrile Sulfamide

Prepared as in Example 157a from 2-amino-6-((2-methylcyclopropyl)methoxy)benzonitrile (Example 235b) in 100% yield. $^1$H NMR (400 MHz, DMSO-$d_6$) δ 0.34-0.36 (m, 1H), 0.51-0.53 (m, 1H), 0.77-0.79 (m, 1H), 0.95-0.97 (m, 1H), 1.04-1.09 (m, 3H), 3.92-4.03 (m, 2H), 6.86-6.88 (bm, 1H), 7.11-7.18 (bm, 3H), 7.48-7.52 (bm, 1H), 9.53 (bs, NH). MS 282 (MH$^+$).

Example 235b: 2-amino-6-((2-methylcyclopropyl)methoxy)benzonitrile

A solution of 2-((2-methylcyclopropyl)methoxy)-6-nitrobenzonitrile (example 235c) (0.29 g, 1.25 mmol) in EtOAc/EtOH 1:1 (30 mL) was hydrogenated in an H-cube apparatus using 10% Pd/C as catalyst. The solution was evaporated to give 2-amino-6-((2-methylcyclopropyl)methoxy)benzonitrile (0.20 g, 79%) as a yellow oil. MS 203 (MH$^+$).

Example 235c: 2-((2-methylcyclopropyl)methoxy)-6-nitrobenzonitrile

Example 236: 4-Amino-5-(trans-2-methylcyclopentyloxy)-1H-benzo[c][1,2,6]thiadiazine-2,2-dioxide

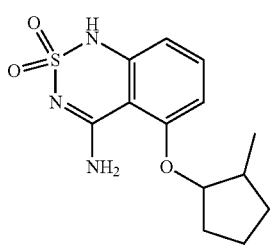

686

260

To a solution of 2-amino-6-(trans-2-methylcyclopentyloxy)benzonitrile (Example 236a) (150 mg, 0.694 mmol) in dimethylacetamide (3 mL) under $N_2$ was added sulfamoyl chloride (3 equiv.). The reaction mixture was stirred at room temperature under $N_2$ for 2 hours, diluted with ethyl acetate (50 mL) and quenched with water (20 mL). The layers were separated. The organic extract was evaporated. Ethanol (3 mL) and aqueous NaOH (2N, 2.5 equiv.) were consecutively added to the residue. The resulting mixture was heated at 90° C. for 16 hours. The workup was performed as in Example 158 to provide the desired product (160 mg, 78%) as a white powder. $^1$H NMR (400 MHz, DMSO-$d_6$) δ 1.02 (d, J=6.4 Hz, 3H), 1.26 (m, 1H), 1.71 (br s, 3H), 1.89 (m, 1H), 2.12 (m, 1H), 2.24 (m, 1H), 4.55 (br s, 1H), 6.60 (d, J=8.0 Hz, 1H), 6.71 (d, J=8.0 Hz, 1H), 7.45 (t, J=8.0 Hz, 1H), 7.73 (br s, 1H), 8.35 (br s, 1H), 10.96 (br s, 1H). MS 296 (MH$^+$).

Example 236a: 2-Amino-6-(trans-2-methylcyclopentyloxy)benzonitrile

Prepared as in Example 158b from 2-(trans-2-methylcyclopentyloxy)-6-nitrobenzonitrile (Example 236b) to give the title compound in quantitative yield as a colorless oil. $^1$H NMR (400 MHz, CDCl$_3$) δ 1.04 (d, J=7.2 Hz, 3H), 1.23 (m, 1H), 1.72 (m, 1H), 1.81 (m, 2H), 1.99 (m, 2H), 2.26 (m, 1H), 4.28 (m, 1H), 4.36 (br s, 2H), 6.18 (d, J=8.4 Hz, 1H), 6.18 (d, J=8.4 Hz, 1H), 7.18 (t, J=8.4 Hz, 1H). MS 296 (MH$^+$)

Example 236b: 2-(trans-2-Methylcyclopentyloxy)-6-nitrobenzonitrile

Prepared as in Example 158c from 2,6 dinitrobenzonitrile and trans-2-methylcyclopentanol in 65% as a yellow solid. MS 247 (MH$^+$).

Example 237: 9-(4-amino-2,2-dioxo-1H-benzo[c][1,2,6]thiadiazin-5-yloxy)nonan-1-ol

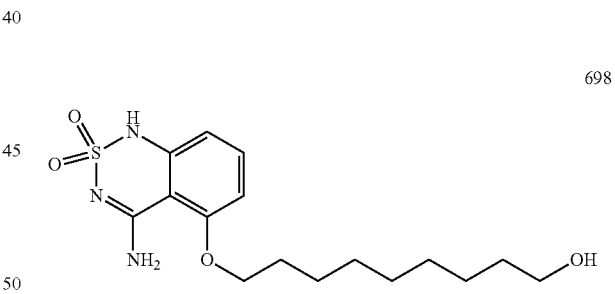

698

Prepared as in Example 224 from 9-(3-amino-2-cyanophenoxy)nonyl acetate (Example 237a) and sulfamoyl chloride in 62.3% yield. $^1$H NMR (400 MHz, DMSO-$d_6$) δ1.250 (m, 8H), 1.381 (m, 4H), 1.791 (pentet, J=7 Hz, 2H), 3.349 (q, J=6 Hz, 2H), 4.135 (t, J=6 Hz, 2H), 4.301 (t, J=5 Hz, 1H), 6.585 (d, J=8 Hz, 1H), 6.728 (d, J=8 Hz, 1H), 7.434 (t, J=8 Hz, 1H), 7.798 (br. s, 1H), 8.329 (br. s, 1H), 10.924 (s, 1H). MS 356 (MH$^+$).

Example 237a: 9-(3-amino-2-cyanophenoxy)nonyl Acetate

Prepared as in Example 224a from 9-(2-cyano-3-nitrophenoxy)nonyl acetate (Example 237b) in 99.3% yield. MS 319 (MH$^+$).

Example 237b: 9-(2-cyano-3-nitrophenoxy)nonyl Acetate

Prepared as in Example 224b from 2-(9-hydroxynonyloxy)-6-nitrobenzonitrile (Example 237c) in 100% yield. MS 349 (MH$^+$).

Example 237c: 2-(9-hydroxynonyloxy)-6-nitrobenzonitrile

Prepared as in Example 224c (except DBU was replaced with 1,1,3,3-tetramethylguanidine) from 1,9-nonanediol and 2,6-dinitrobenzonitrile in 30.7% yield. MS 307 (MH$^+$).

Photostability Tests

Buffer Preparation

Aqueous buffer solution at pH 7.1 contains 50 mM potassium dihydrogen phosphate and ~32 mM sodium hydroxide (solutions of 1.0 M hydrochloric acid and 1.0 M sodium hydroxide are used to adjust pH). Aqueous buffer solution at pH 4.0 contains 50 mM citric acid monosodium salt and ~7.4 mM sodium hydroxide (solutions of 1.0 M hydrochloric acid and 1.0 M sodium hydroxide are used to adjust pH). Aqueous buffer solution at pH 2.8 contains 50 mM citric acid and −16 mM sodium hydroxide (solutions of 1.0 M hydrochloric acid and 1.0 M sodium hydroxide are used to adjust pH).

Test Sample Preparation

The stock solutions of the test compounds at 25 mM are made by dissolving the compounds in dimethyl sulfoxide. The solutions of the stabilizers are made by dissolving the materials in the aqueous buffers. The stock solutions are then diluted to 25 µM with the stabilizer solutions to prepare the test solution and 4-mL aliquots of the solutions are transferred to 20-mL clear glass vial for testing.

Photostability Tester Settings

Accelerated photodegradation was studied using a Q-Sun Xenon Test Chamber (Q-Lab Model No. Xe-1-SC) at an irradiance setting of 350 mW/m$^2$ at 340 nm and temperature of 25 degrees Celsius. To put this in perspective, 24 hours of constant Q-Sun irradiation at these settings is approximately equivalent to 12.4 days of direct sunlight in the southwestern United States. At 0, 1, 2, 4, and 6 hours from the beginning of the radiation, a 0.4-mL aliquot from each vial is pippeted out to a 1-mL glass insert for analysis.

Sample Analysis and Data Analysis

The samples are analyzed using an Agilent 1100 LC/MSD equipped with a quaternary pump and a diode-array detector (DAD). The peak areas from the MSD chromatograms are used for quantitation, and the photostability is shown by plotting the percentages of the test compound which remains intact at all time points. The peak areas from the DAD chromatograms are used for quantitation for stabilizers with concentration at 250 uM or higher. The instrument conditions are listed below.

Column: YMC ODS AQ 3 um, 4.0×23 mm

Column Temperature: Room temperature

Auto-sampler Temperature: Room temperature

Mobile Phase A: Water

Mobile Phase B: Methanol

Mobile Phase C: 1% Formic Acid

Gradient: % C is constant at 5%; % B from 5% to 95% in 2 min, then back to 5% at 2.1 min, and then held at 5% until 3.25 min; flow rate is 2 mL/min Injection volume: 10 uL Data Collection time: 2.75 minutes MSD ion source: APCI MSD Signal settings: Positive, selected ion monitoring (SIM) at the mass of the expected molecular ions.

UV detection wavelength: 230 nm.

MSD detection start time: 0.5 min

Compounds A, B, C, D, and E are five Examples as described above, wherein Compound A is an exemplary species of structural formula (II), while Compounds B, C, D, and E are exemplary species of structural formula (I). More specifically, Compound E is an exemplary species of structural formula (Ie). For example, Compound B is Example 1.

A Q-Sun Xenon Test Chamber (Q-Lab Model No. Xe-1-SC), which reproduces the entire spectrum of natural sunlight, was used to study the photo-stability of Compounds A, B, C, and D in various mediums (with or without photostabilizers). The equivalent sunlight exposure time for 24 hours in the Q-Sun at a constant temperature of 25° C. and irradiance of 450 mW/m$^2$ @340 nm is estimated to be equivalent to approximately 15.9 days of direct sunlight in the Southwestern United States.

FIG. 1 illustrates the effect of coffee and tea on rate of photo-degradation of Compound A relative to water alone. Specifically, Compound A showed remarkably improved stability to photo-degradation in both brewed coffee and tea. By comparison, tert-butyl hydroquinone (TBHQ; 200 ppm in water) only has a marginal effect on the rate of photo-degradation of Compound A.

Figure 2:
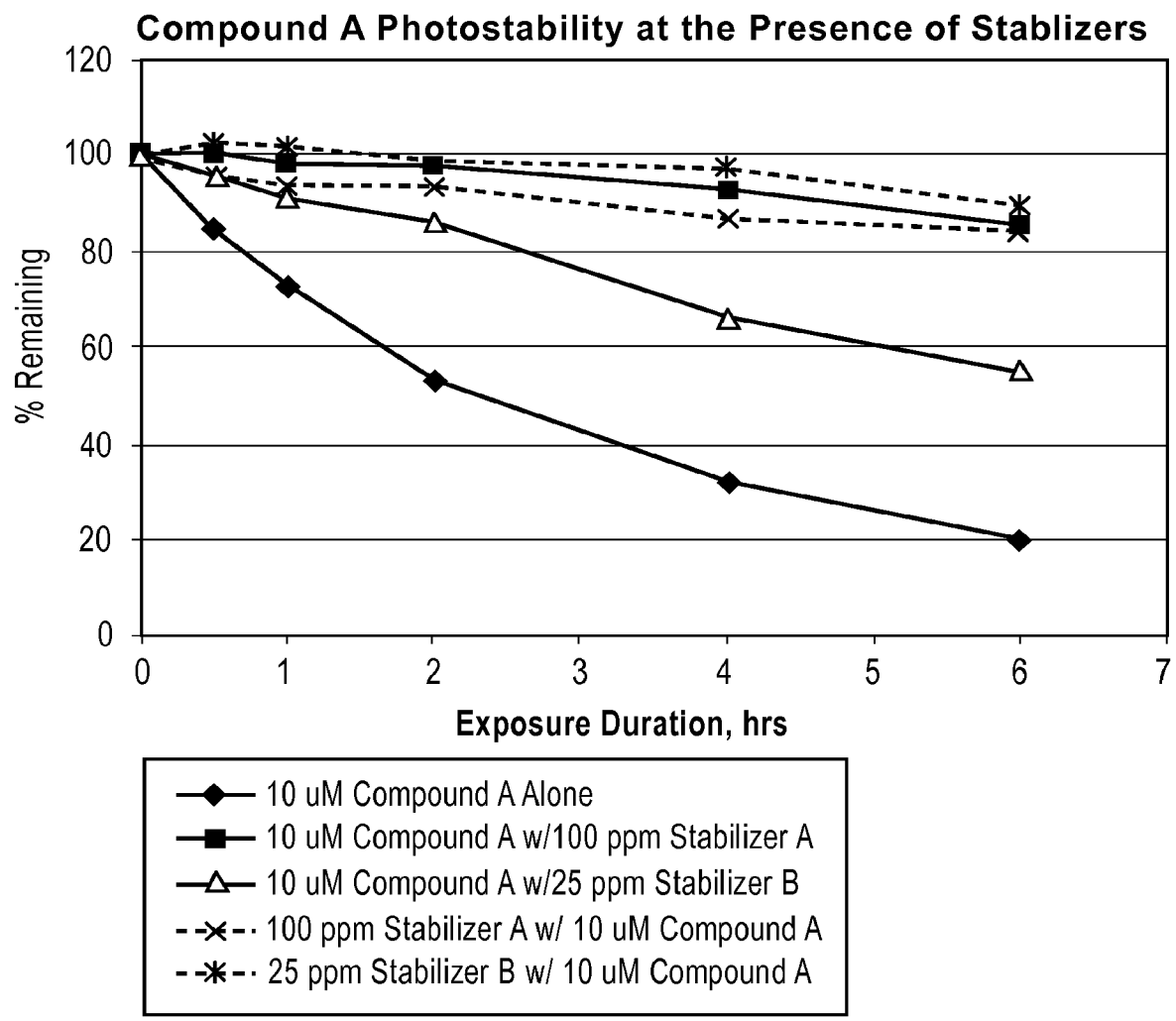
FIG. 2 is a graph showing the stabilization of Compound A by two photostabilizers, respectively.
Figure 3:
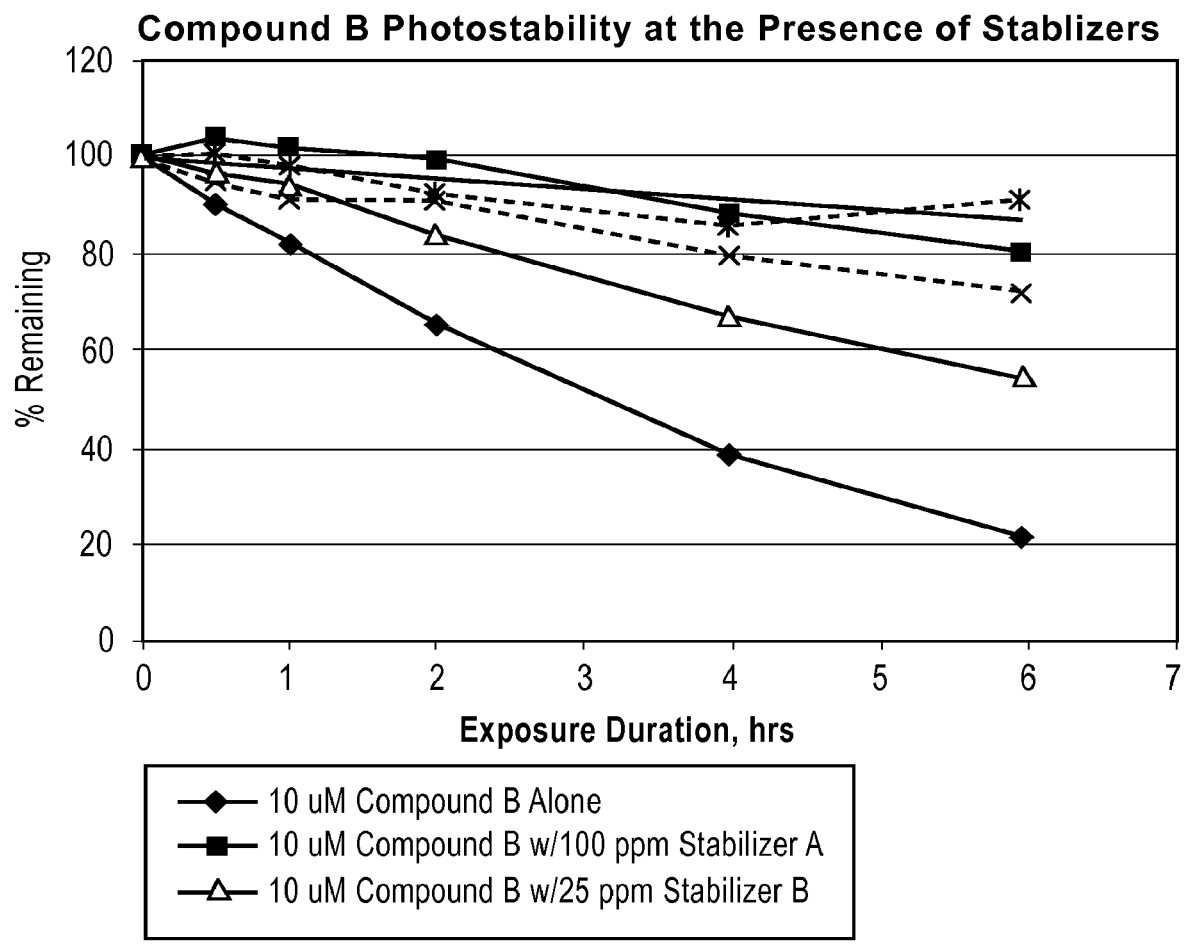
FIG. 3 is a graph showing the stabilization of Compound B by two photostabilizers, respectively.

FIGS. 2 and 3 illustrate the photostability study of Compounds A and B under these condition: Direct sunlight was modeled using a Q-Sun Xenon Test Chamber (Q-Lab Model No. Xe-1-SC) at an irradiance setting of 350 mW/m$^2$ @ 340 nm, 25° C. Test samples were irradiated in the Q-Sun at these settings in pH 2.8 buffer with/without Compounds A and B in the presence/absence of the photo-stabilizers A (chlorogenic acid) and B (rutin, a.k.a. quercetin-3-rutinoside).

As shown by FIG. 2, Compound A can be stabilized from photo-breakdown in the presence of either chlorogenic acid (i.e., Stabilizer A) or rutin (i.e., Stabilizer B). Chlorogenic acid and rutin are two representative photostabilizers of the specific photostabilizers recited in the Photostabilizer section herein above. In the absence of the photo-stabilizer, 80% of Compound A was degraded after 6 hr of irradiation (350 mW/m$^2$ @ 340 nm, 25° C.) in the Q-Sun system. By comparison, only 15% of Compound A was degraded in the presence of 100 ppm of chlorogenic acid, and 45% of Compound A was degraded in the presence of 25 ppm of rutin, under the same conditions.

As shown by FIG. 3, Compound B in solution can also be stabilized in the presence of photostabilizer A or B under UV exposure. Without the stabilizer, about 80% of Compound B was degraded after 6 hr exposure to ultraviolet (UV) radiation within the Q-Sun system. By comparison, only 20% of Compound B was degraded in the presence of 100 ppm of chlorogenic acid, and 47% of Compound B was degraded in the presence of 25 ppm of rutin, under the same conditions.

Figure 4:
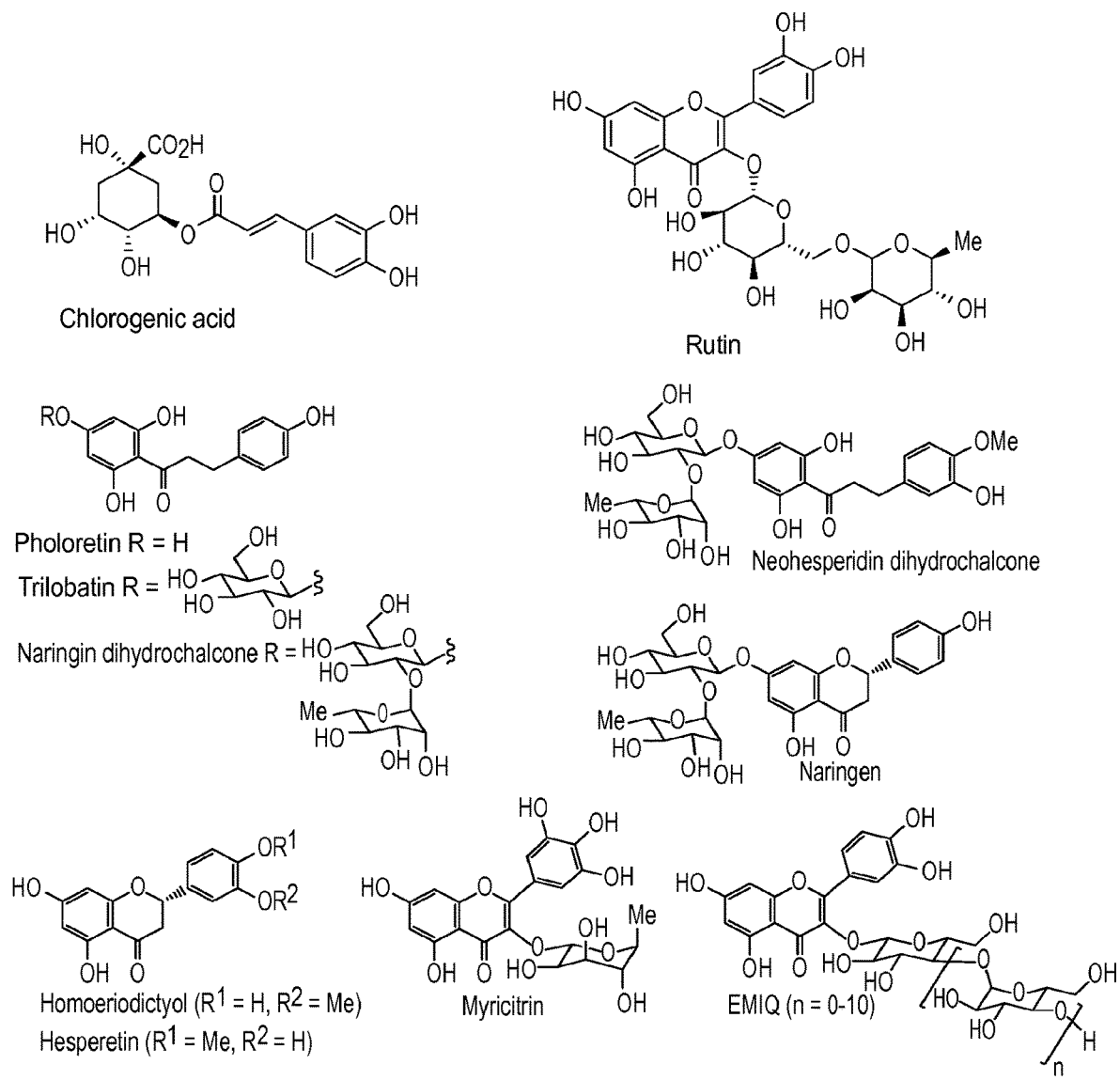
FIG. 4 shows the chemical structures of certain exemplary antioxidants that are suitable to be used as photostabilizers. Some of these antioxidants are FEMA GRAS compounds.

FIG. 4 shows some exemplary antioxidants that are suitable to be photostabilizers. Some of those antioxidants are FEMA GRAS compounds. Table 1 below indicates the approved use levels for those FEMA GRAS compounds in non-alcoholic beverages.

TABLE 1

| Compound | FEMA No. | Usual use level/ max use level (ppm) |
|---|---|---|
| Phloretin | 4390 | 30/300 ppm |
| Trilobatin | 4674 | 100/100 ppm |
| Naringin dihydrochalcone | 4495 | 50/60 ppm |
| Neohesperidin dihydrochalcone | 3811 | 5/10 ppm |
| Naringin | 2769 | NA |
| Homoeriodictyol | 4228 | 100/800 ppm |
| Hesperetin | 4313 | 100/800 ppm |
| Myricitrin | 4491 | 10/30 ppm |
| EMIQ | 4225 | 150/200 ppm |
| Grape seed extract | 4045 | 100/200 ppm |

Figure 5:
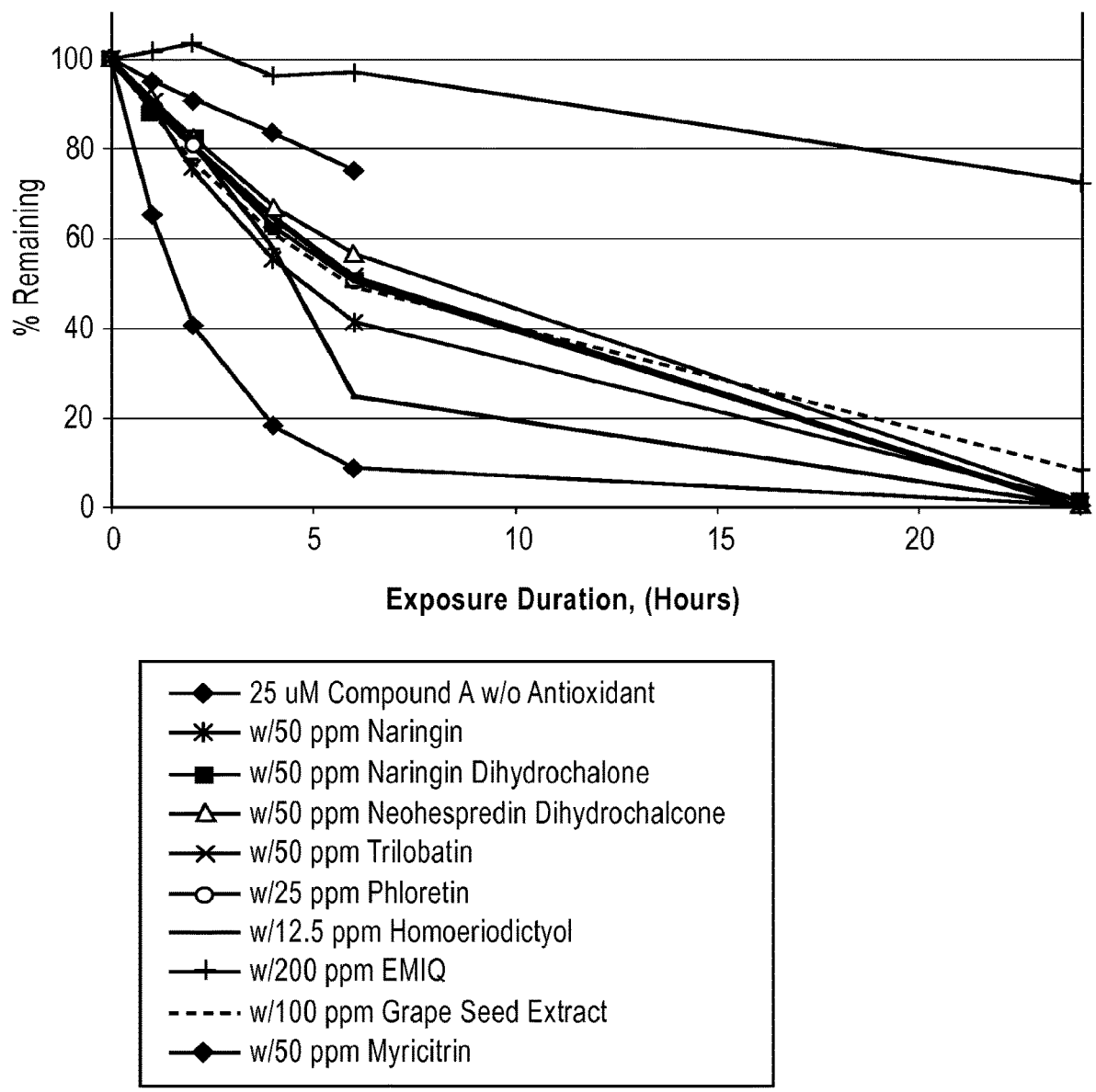
FIG. 5 is a graph showing the photostability of Compound A in the presence of various antioxidant photostabilizers.

FIG. 5 shows the time course of the photo-degradation of the sweet enhancer Compound A in the absence and the presence of several of the FEMA GRAS compounds with antioxidant properties. Direct sunlight was modeled using a Q-Sun Xenon Test Chamber (Q-Lab Model No. Xe-1-SC) at an irradiance setting of 350 mW/m² @ 340 nm, 25° C. Test samples were irradiated in the Q-Sun at these settings in pH 2.8 buffer with Compound A in the presence/absence of the photo-stabilizers. All of the antioxidants shown in FIG. 4 and Table 2 (below) are effective in stabilizing Compound A to photo-oxidation. In one embodiment, EMIQ (200 ppm) is particularly effective (72.64% remaining at 24 hrs).

TABLE 2

| Antioxidant | Conc (ppm) | % Remaining @ 1 hr | % Remaining @ 2 hrs | % Remaining @ 4 hrs | % Remaining @ 6 hrs |
|---|---|---|---|---|---|
| (none) | — | 65.43 | 40.68 | 18.39 | 8.95 |
| naringin | 50 ppm | 90.42 | 75.92 | 55.54 | 41.50 |
| naringin dihydro-chlacone | 50 ppm | 88.49 | 81.95 | 62.54 | 50.56 |
| neohesperidin dihydro-chalcone | 50 ppm | 91.42 | 82.53 | 66.95 | 56.72 |
| trilobatin | 50 ppm | 90.34 | 81.41 | 64.75 | 51.47 |
| phloretin | 25 ppm | 89.62 | 80.75 | 64.60 | 50.64 |
| homo-eriodictol | 12.5 ppm | 90.83 | 82.75 | 57.70 | 24.54 |
| EMIQ | 200 ppm | 101.92 | 103.71 | 96.24 | 97.26 |
| grape seed extract | 100 ppm | 89.43 | 77.83 | 61.29 | 49.64 |
| myricitrin | 50 ppm | 95.06 | 91.02 | 83.77 | 75.39 |

Figure 6A:
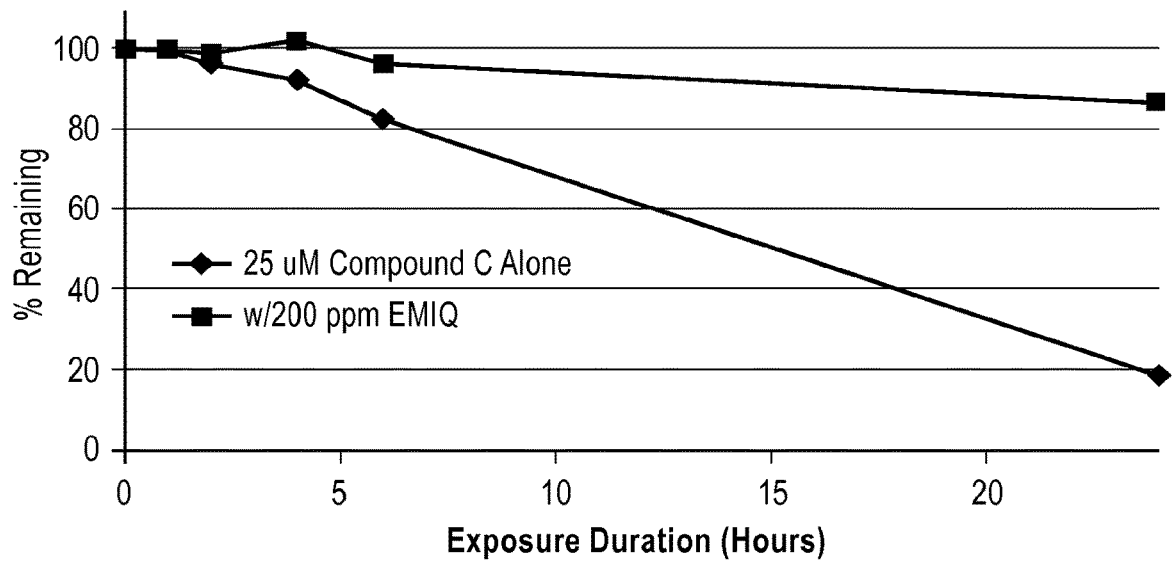
FIG. 6A is a graph showing the photostability of Compound C in the presence of EMIQ.
Figure 6B:
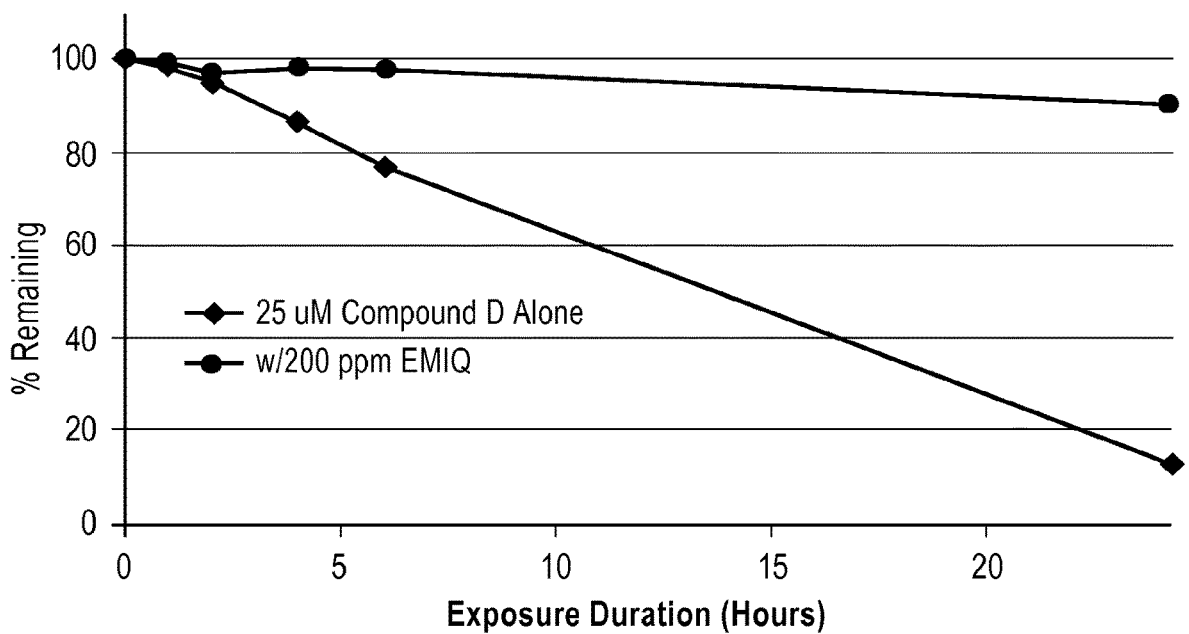
FIG. 6B is a graph showing the photostability of Compound D in the presence of EMIQ.

FIGS. 6A and 6B show the time course of photo-degradation of Compound C and Compound D in the presence and absence of EMIQ. Compounds C and D are analogs of Compound B. Similar to the photostability study of Compound A, EMIQ (200 ppm) is very effective in retarding the photo-degradation of both Compound C and Compound D out to at least 24 hrs under conditions of accelerated photo-oxidation. As indicated by FIGS. 6A and 6B and Table 3 below, 86-90% of the compound remained intact at 24 hrs in the presence of 200 ppm of EMIQ vs only 13-19% remaining in the absence of the antioxidant.

TABLE 3

| Sample | % Remaining @ 1 hr | % Remaining @ 2 hrs | % Remaining @ 4 hrs | % Remaining @ 6 hrs | % Remaining @ 24 hrs |
|---|---|---|---|---|---|
| 25 µM Compound C alone | 99.43 | 96.00 | 92.23 | 82.47 | 18.52 |
| 25 µM Compound C + 200 ppm EMIQ | 99.53 | 98.66 | 101.37 | 95.95 | 86.17 |
| 25 µM Compound D alone | 98.26 | 94.99 | 85.99 | 76.72 | 12.75 |
| 25 µM Compound D + 200 ppm EMIQ | 99.32 | 97.17 | 98.29 | 97.90 | 90.34 |

Figure 7:
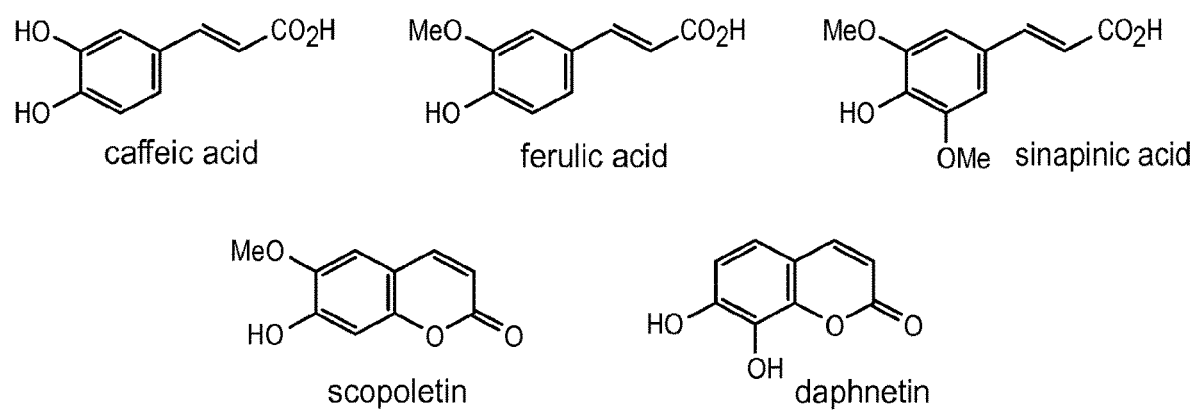
FIG. 7 shows the chemical structures of some naturally occurring cinnamic acid and coumarin derivatives.

FIG. 7 shows the chemical structures of some naturally occurring cinnamic acid and coumarin derivatives.

Figure 8:
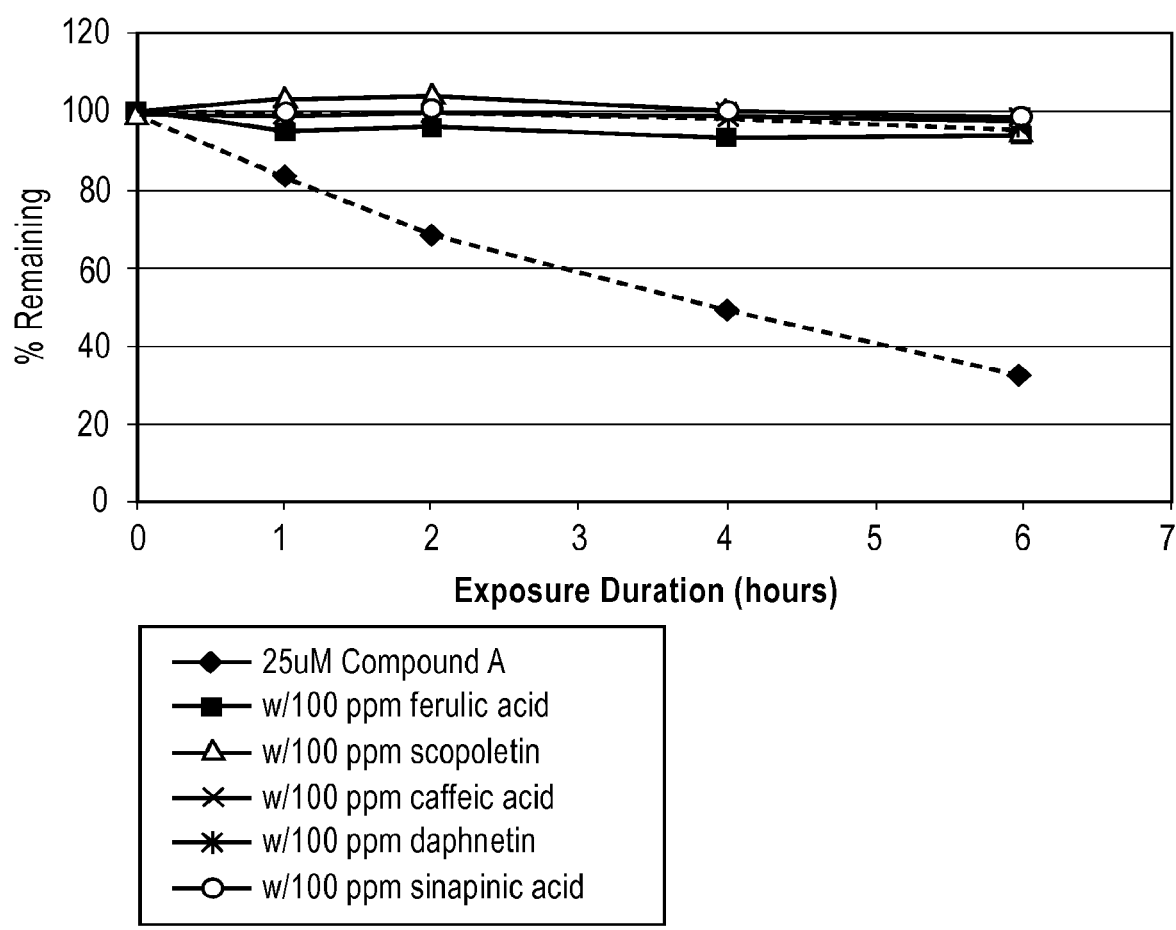
FIG. 8 is a graph showing the photostability of Compound A in the presence of certain antioxidant photostabilizers.

FIG. 8 shows the time course of the photo-degradation of Compound A in the absence and the presence of the cinnamic acid and coumarin derivatives shown in FIG. 7. Direct sunlight was modeled using a Q-Sun Xenon Test Chamber (Q-Lab Model No. Xe-1-SC) at an irradiance setting of 350 mW/m² @ 340 nm, 25° C. Test samples were irradiated in the Q-Sun at these settings in pH 2.8 buffer with 25 µM of Compound A in the presence/absence of the photo-stabilizers at a concentration of 100 ppm. All of the antioxidants shown in FIG. 8 and Table 4 are effective in stabilizing Compound A to photo-oxidation. Daphnetin and sinapinic acid are particularly effective (>98% remaining at 6 hrs).

TABLE 4

| Antioxidant | Conc. (ppm) | % Remaining @ 1 hr | % Remaining @ 2 hrs | % Remaining @ 4 hrs | % Remaining @ 6 hrs |
|---|---|---|---|---|---|
| (none) | — | 83.48 | 68.45 | 49.18 | 32.82 |
| ferulic acid | 100 ppm | 95.41 | 96.49 | 93.43 | 93.85 |
| scopoletin | 100 ppm | 103.59 | 104.11 | 100.07 | 95.72 |
| caffeic acid | 100 ppm | 98.02 | 99.54 | 98.74 | 95.55 |
| daphnetin | 100 ppm | 99.13 | 99.76 | 98.13 | 98.45 |
| sinapinic acid | 100 ppm | 100.00 | 99.98 | 100.12 | 98.52 |

Figure 9:
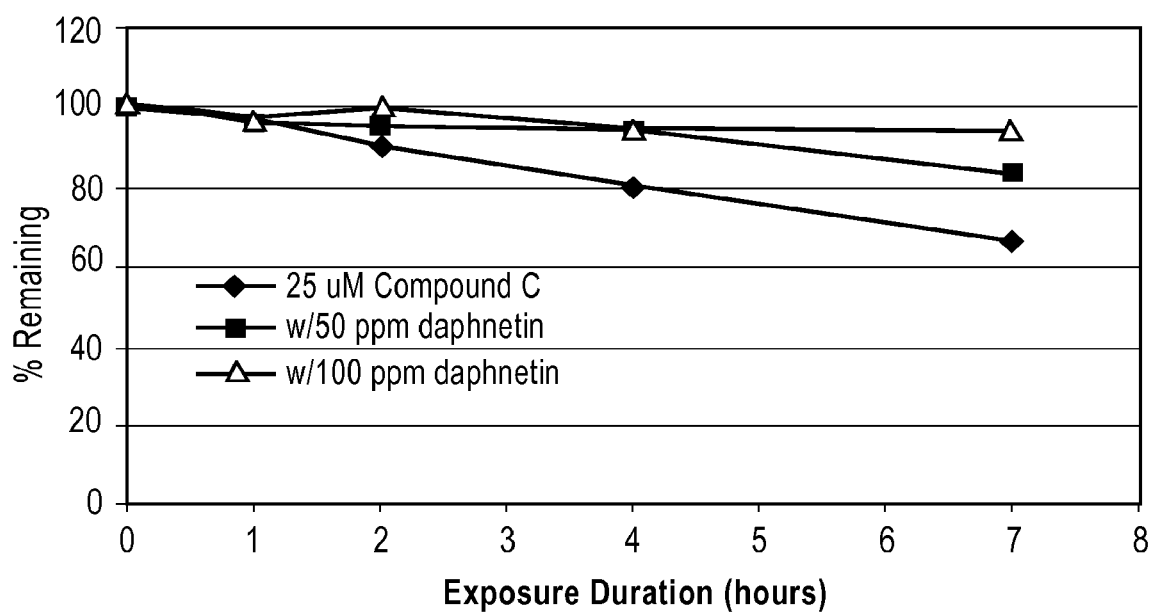
FIG. 9 is a graph showing the photostability of Compound C in the presence of Daphnetin.

FIG. 9 and Table 5 show the time course of photo-degradation of Compound C in the presence and absence of 50 and 100 ppm of daphnetin. Similar to the photostability study of Compound A, daphnetin is effective in retarding the photo-degradation of Compound C for at least 7 hrs under conditions of accelerated photo-oxidation. In the presence of 100 ppm of daphnetin, 93.8% of the compound remained intact at 7 hrs vs only 66.49% remaining in the absence of the antioxidant.

TABLE 5

| Sample | % Remaining @ 1 hr | % Remaining @ 2 hrs | % Remaining @ 4 hrs | % Remaining @ 7 hrs |
|---|---|---|---|---|
| 25 μM Cmpd C alone | 97.51 | 90.08 | 79.96 | 66.49 |
| 25 μM Cmpd C + 50 ppm daphnetin | 96.46 | 95.42 | 94.07 | 83.80 |
| 25 μM Cmpd C + 100 ppm daphnetin | 97.69 | 99.97 | 94.69 | 93.80 |

Figure 10:
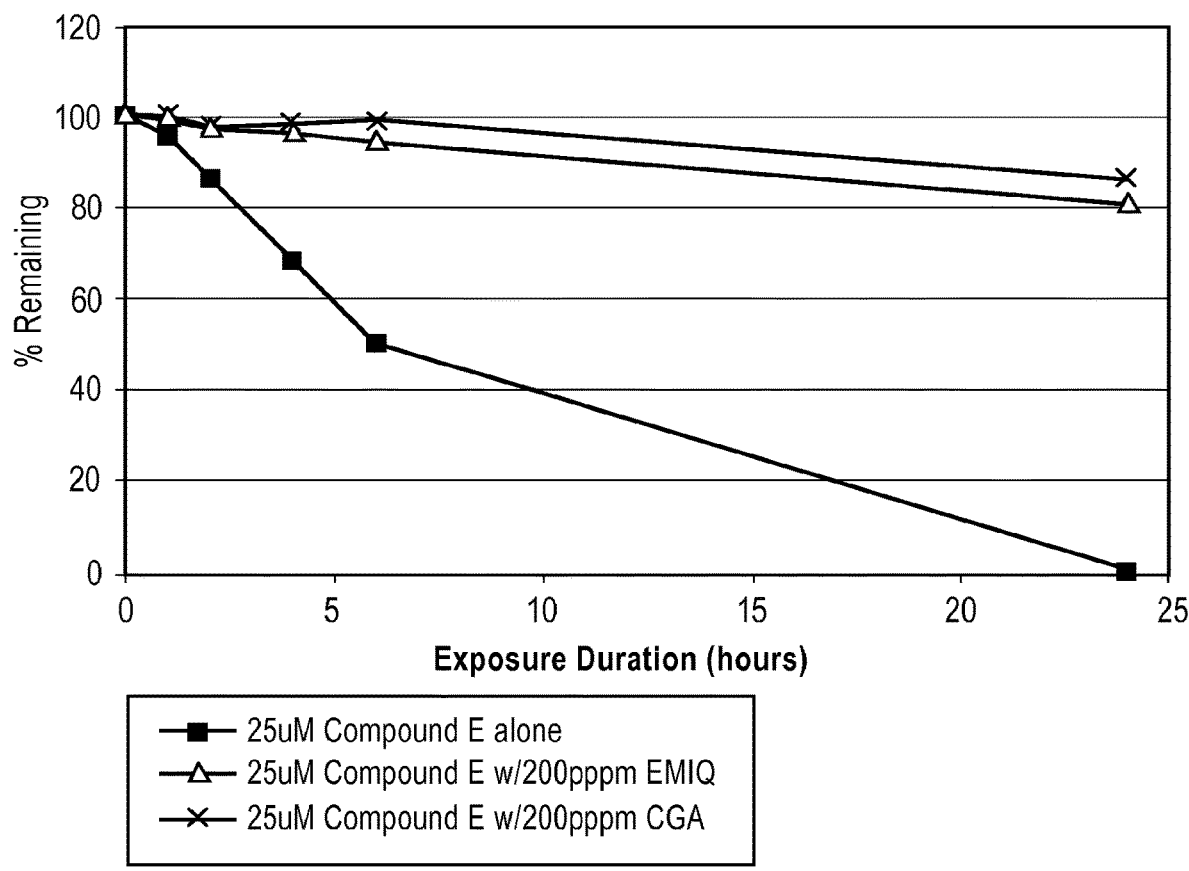
FIG. 10 is a graph showing the photostability of Compound E in the presence of EMIQ or Chlorogenic Acid.

Table 6 and FIG. 10 show the time course of the photodegradation of the sweet enhancer Compound E in the absence and the presence of either EMIQ or chlorogenic acid ("CGA"). Direct sunlight was modeled using a Q-Sun Xenon Test Chamber (Q-Lab Model No. Xe-1-SC) at an irradiance setting of 350 mW/m$^2$ @ 340 nm, 25° C. Test samples were irradiated in the Q-Sun at these settings in pH 2.8 buffer with sweet enhancer Compound E in the presence/absence of the photostabilizers. In the presence of 200 ppm of either EMIQ or chlorogenic acid (CGA), the photodegradation of Compound E is effectively retarded for at least 24 hrs under conditions of accelerated photo-oxidation. In both cases, 81-86% of the compound remained intact at 24 hrs in the presence of 200 ppm of the antioxidants vs <1% remaining in the absence of the antioxidant.

TABLE 6

| Sample | % Remaining @ 1 hr | % Remaining @ 2 hrs | % Remaining @ 4 hrs | % Remaining @ 6 hrs | % Remaining @ 24 hrs |
|---|---|---|---|---|---|
| 25 uM Cmpd E alone | 95.52 | 86.61 | 68.39 | 50.35 | 0.29 |
| 25 uM Cmpd E + 200 ppm EMIQ | 100.19 | 97.75 | 96.80 | 94.67 | 81.22 |
| 25 uM Cmpd E + 200 ppm CGA | 100.56 | 97.75 | 98.50 | 99.06 | 86.31 |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of improving stability or reducing degradation of a sweet enhancer in a liquid composition comprising contacting a photostabilizer with the sweet enhancer in the liquid composition, wherein:

the photostabilizer is selected from the group consisting of a chromone derivative, a coumarine derivative, a phenylpropenoic carbonyl compound, and a combination thereof; and the sweet enhancer having structural formula (Ia) or (I' a), or a salt or solvate thereof:

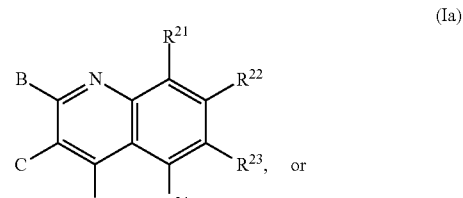

(Ia)

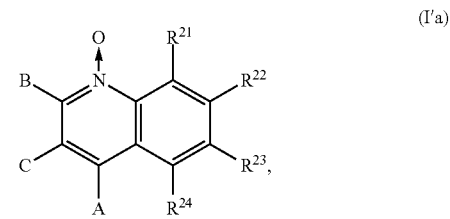

(I'a)

wherein:

A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;

C is —OR$^7$, —SR$^7$, —SOR$^7$, —SO$_2$R$^7$, —SO$_3$R$^7$, —C(O)NR$^7$R$^8$, —CO$_R$$^7$, —NR$^7$CO$_2$R$^8$, —NR$^7$C(O)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR$^8$), —P(O)(R$^7$)(OR$^8$), or heteroaryl;

R$^1$, R$^2$, R$^3$, R$^7$, R$^8$, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^1$ and R$^2$, R$^2$ and R$^3$, R$^7$ and R$^8$, or R$^8$ and R$^9$, together with the atoms to which they are bonded, form a cycloheteroalkyl or substituted cycloheteroalkyl ring;

R$^{21}$ is hydrogen, alkyl, substituted alkyl, halo, —CN, —OR$^{25}$;

R$^{22}$ is hydrogen, alkyl, substituted alkyl, halo, —CN, —OR$^{27}$;

R$^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{29}$, —SR$^{29}$, —SOR$^{29}$, —SO$_2$R$^{29}$, —OC(O)R$^{29}$, —NR$^{29}$R$^{30}$, —C(O)NR$^{29}$R$^{30}$, —C(O)R$^{29}$, —CO$_2$R$^{29}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{31}$, —SR$^{31}$, —SOR$^{31}$, —SO$_2$R$^{31}$, —OC(O)R$^{31}$, —NR$^{31}$R$^{32}$, —C(O)NR$^{31}$R$^{32}$, —C(O)R$^{31}$, —CO$_2$R$^{31}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$); or alternatively R$^{23}$ and R$^{24}$, taken together with the atoms to which they are attached, form a cycloalkyl, substituted cycloalkyl, cycloheteroalkyl, or substituted cycloheteroalkyl ring; and R$^{25}$, R$^{27}$, R$^{29}$, R$^{30}$, R$^{31}$, and R$^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively R$^{25}$ and R$^{27}$, R$^{27}$ and R$^{29}$, R$^{29}$ and R$^{30}$, R$^{29}$ and R$^{31}$, or R$^{31}$ and R$^{32}$, together with the atoms to which they are attached, form a cycloheteroalkyl or substituted cycloheteroalkyl ring.

2. A method of improving stability or reducing degradation of a sweet enhancer in a liquid composition comprising contacting a photostabilizer with the sweet enhancer in the liquid composition, wherein:

the photostabilizer is selected from the group consisting of a chromone derivative, a coumarine derivative, a phenylpropenoic carbonyl compound, and a combination thereof; and the sweet enhancer having structural formula (Ib) or (I'b), or a salt or solvate thereof:

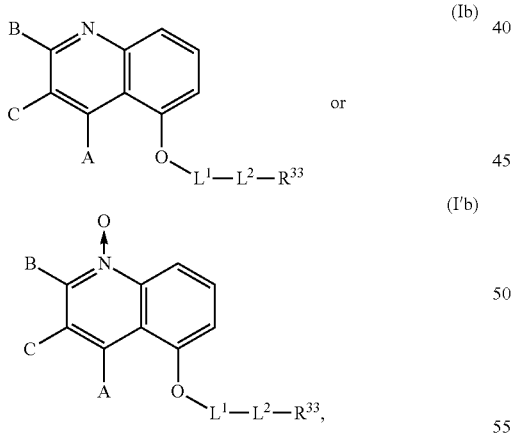

wherein:

A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;

C is —OR$^7$, —SR$^7$, —SOR$^7$, —SO$_2$R$^7$, —SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR$^8$), —P(O)(R$^7$)(OR$^8$), or heteroaryl;

R$^1$, R$^2$, R$^3$, R$^7$, R$^8$, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^1$ and R$^2$, R$^2$ and R$^3$, R$^7$ and R$^8$, or R$^8$ and R$^9$, together with the atoms to which they are bonded, form a cycloheteroalkyl or substituted cycloheteroalkyl ring;

L$^1$ is alkylene or substituted alkylene;

L$^2$ is —NR$^{34}$—, —O—, —S—, —NR$^{34}$—C(O)—, —C(O)—NR$^{34}$—, —O—C(O)—, —C(O)—O—, —NR$^{34}$—C(O)—O—, —O—C(O)—NR$^{34}$—, —NR$^{34}$—C(O)—NR$^{35}$—, —O—C(O)—O—, -heterocyclylene-C(O)—, or -(substituted heterocyclylene)-C(O)—;

R$^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and R$^{34}$ and R$^{35}$ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

3. A method of improving stability or reducing degradation of a sweet enhancer in a liquid composition comprising contacting a photostabilizer with the sweet enhancer in the liquid composition, wherein:

the photostabilizer is selected from the group consisting of a chromone derivative, a coumarine derivative, a phenylpropenoic carbonyl compound, and a combination thereof; and the sweet enhancer having structural formula (Ic), (I'c), (Id), or (I'd), or a salt or solvate thereof:

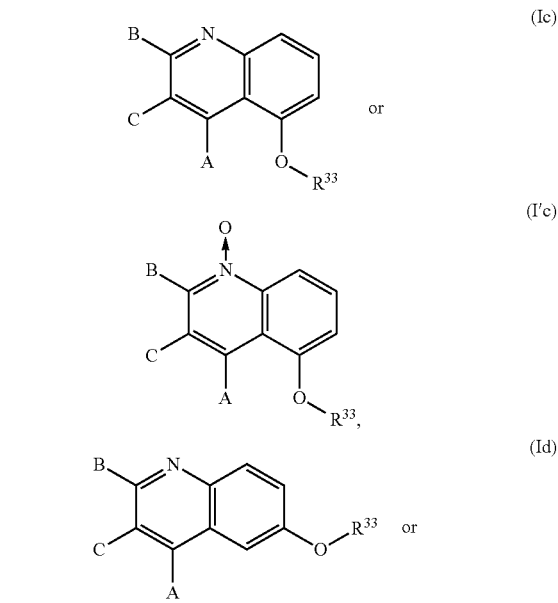

-continued

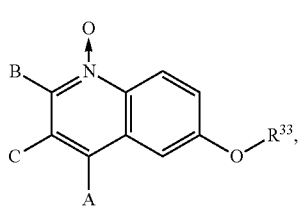

(I'd)

wherein:

A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;

C is —OR$^7$, —SR$^7$, —SOR$^7$, —SO$_2$R$^7$, —SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR$^8$), —P(O)(R$^7$)(OR$^8$), or heteroaryl;

R$^1$, R$^2$, R$^3$, R$^7$, R$^8$, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^1$ and R$^2$, R$^2$ and R$^3$, R$^7$ and R$^8$, or R$^8$ and R$^9$, together with the atoms to which they are bonded, form a cycloheteroalkyl or substituted cycloheteroalkyl ring; and R$^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

4. A method of improving stability or reducing degradation of a sweet enhancer in a liquid composition comprising contacting a photostabilizer with the sweet enhancer in the liquid composition, wherein:

the photostabilizer is selected from the group consisting of a chromone derivative, a coumarine derivative, a phenylpropenoic carbonyl compound, and a combination thereof; and the sweet enhancer having structural formula (Ie), or a salt or solvate thereof:

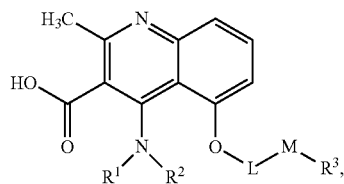

(Ie)

wherein:

R$^1$ and R$^2$ are independently hydrogen or C$_1$ to C$_6$ alkyl;

L is C$_1$ to C$_{12}$ alkylene or substituted C$_1$ to C$_{12}$ alkylene;

M is —NR$^4$—C(O)— or —C(O)—NR$^4$—;

R$^4$ is hydrogen or C$_1$ to C$_6$ alkyl; or alternatively, when M is —NR$^4$—C(O)—, R$^4$ and one or more atoms of L, together with the nitrogen to which they are attached, form a 5- to 8-membered heterocyclic ring which is optionally substituted and contains one to three heteroatoms selected from nitrogen, oxygen, and sulfur; and R$^3$ is C$_1$ to C$_{12}$ alkyl, substituted C$_1$ to C$_{12}$ alkyl, 5- to 8-membered heterocyclyl, or substituted 5- to 8-membered heterocyclyl; or alternatively, when M is —C(O)—NR$^4$—, R$^4$ and one or more atoms of R$^3$, together with the nitrogen to which they are attached, form a 5- to 8-membered heterocyclic ring which is optionally substituted and contains one to three heteroatoms selected from nitrogen, oxygen, and sulfur.

5. The method of claim 4, wherein the compound of formula (Ie) is represented by structural Formula (IeB):

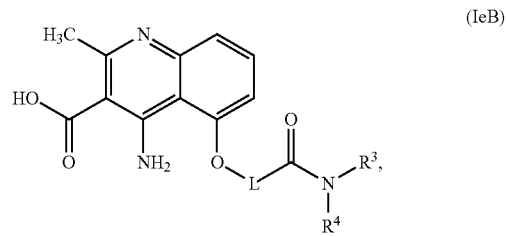

(IeB)

wherein:

L is C$_1$ to C$_{12}$ alkylene or substituted C$_1$ to C$_{12}$ alkylene;

R$^4$ is hydrogen or C$_1$ to C$_6$ alkyl; and

R$^3$ is C$_1$ to C$_{12}$ alkyl, substituted C$_1$ to C$_{12}$ alkyl, 5- to 8-membered heterocyclyl, substituted 5- to 8-membered heterocyclyl; or alternatively, R$^4$ and one or more atoms of R$^3$, together with the nitrogen to which they are attached, form a 5- to 8-membered heterocyclic ring which is optionally substituted and contains one to three heteroatoms selected from nitrogen, oxygen, and sulfur.

6. A method of improving stability or reducing degradation of a sweet enhancer in a liquid composition comprising contacting a photostabilizer with the sweet enhancer in the liquid composition, wherein:

the photostabilizer is selected from the group consisting of a chromone derivative, a coumarine derivative, a phenylpropenoic carbonyl compound, and a combination thereof; and the sweet enhancer having structural formula selected from the group consisting of

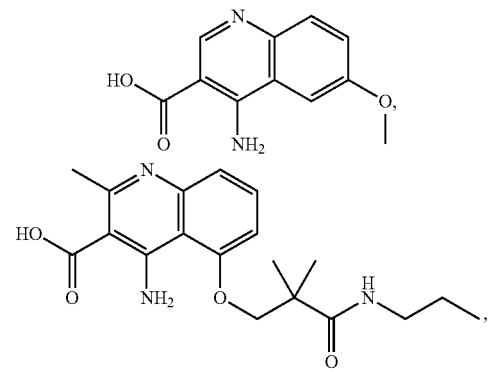

-continued
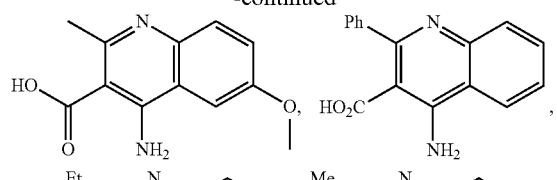
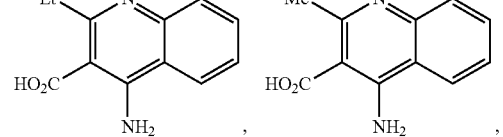
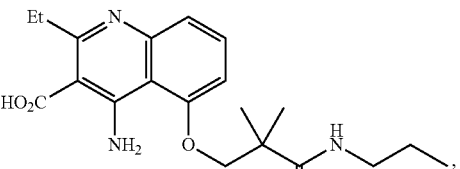
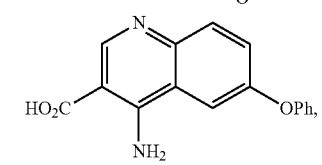
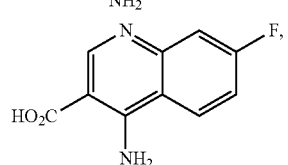
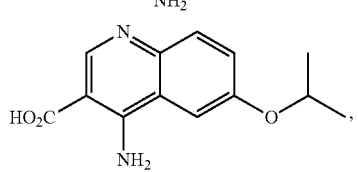
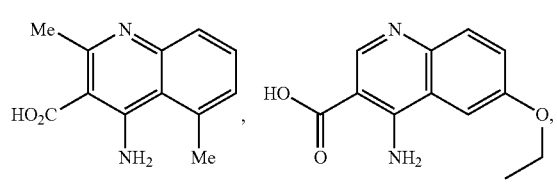
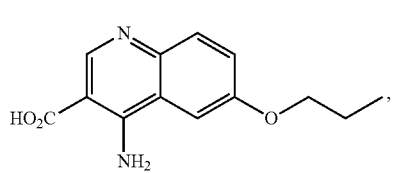
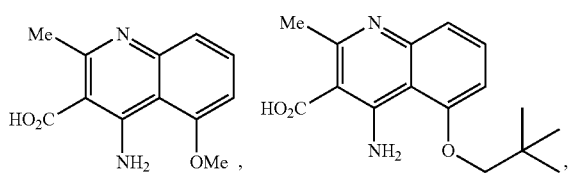
-continued
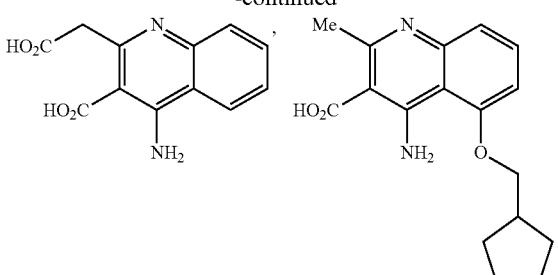
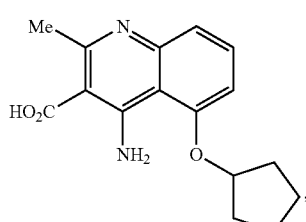
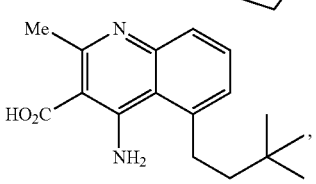
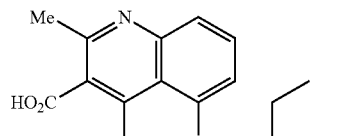
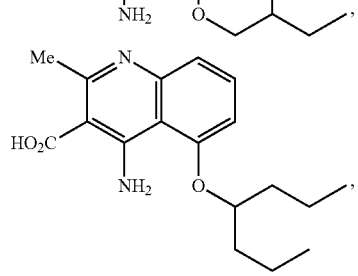
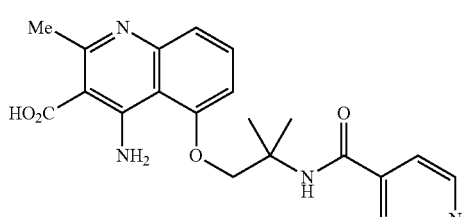
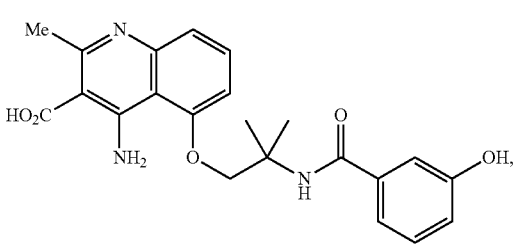

273
-continued
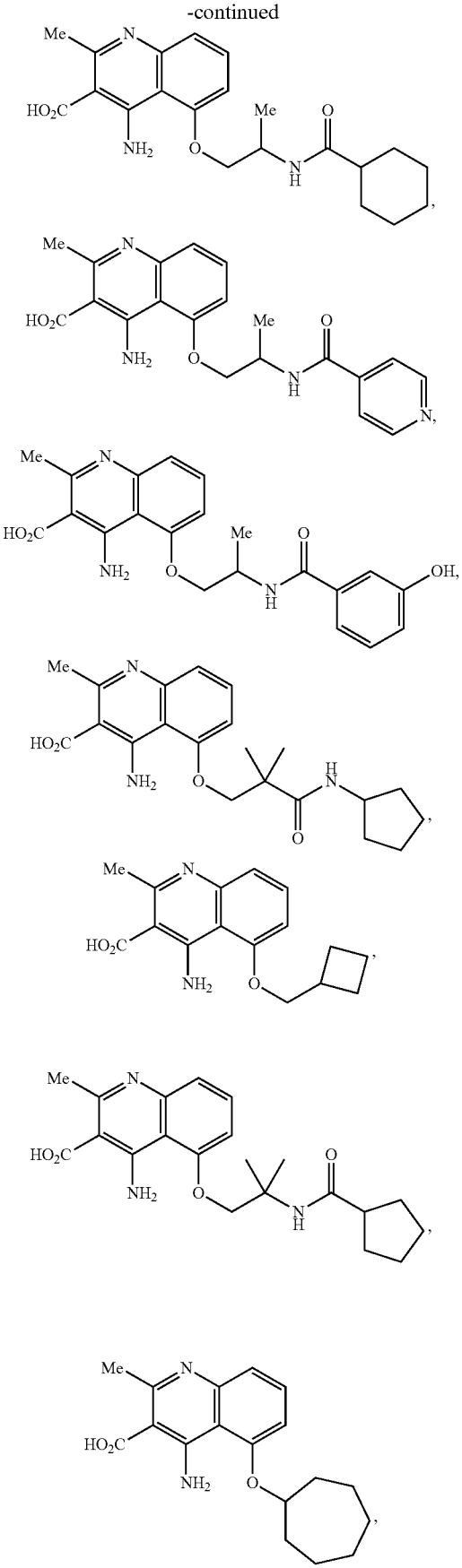
274
-continued
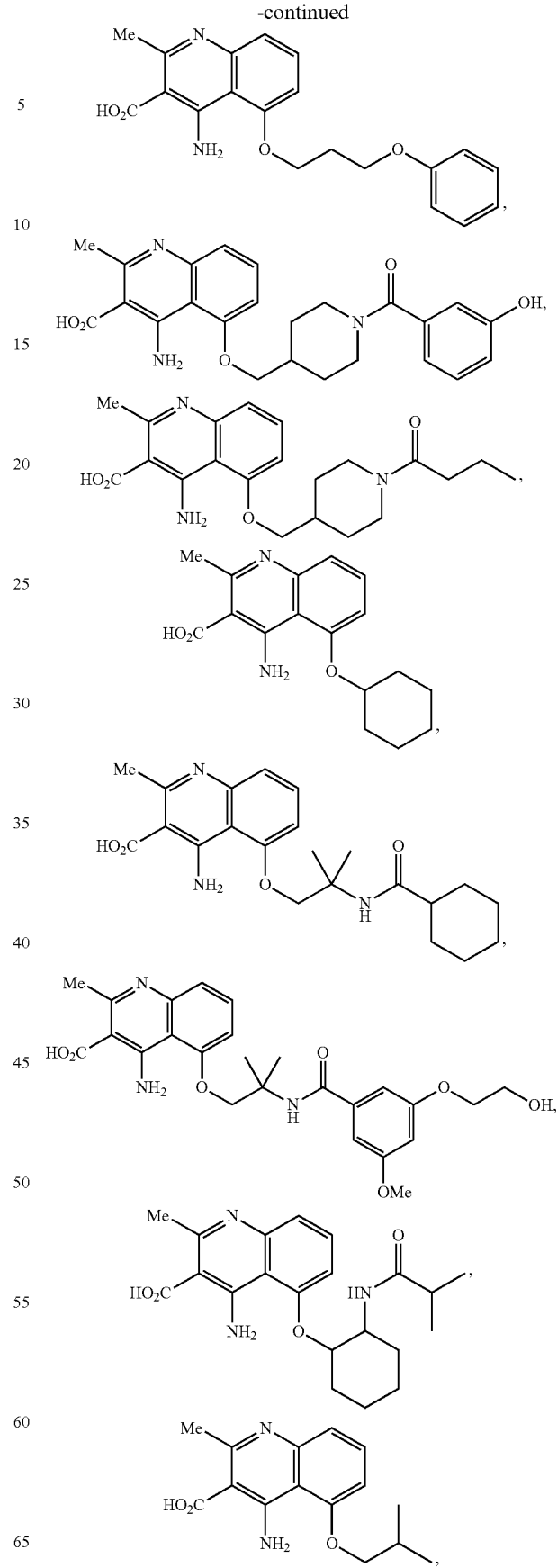

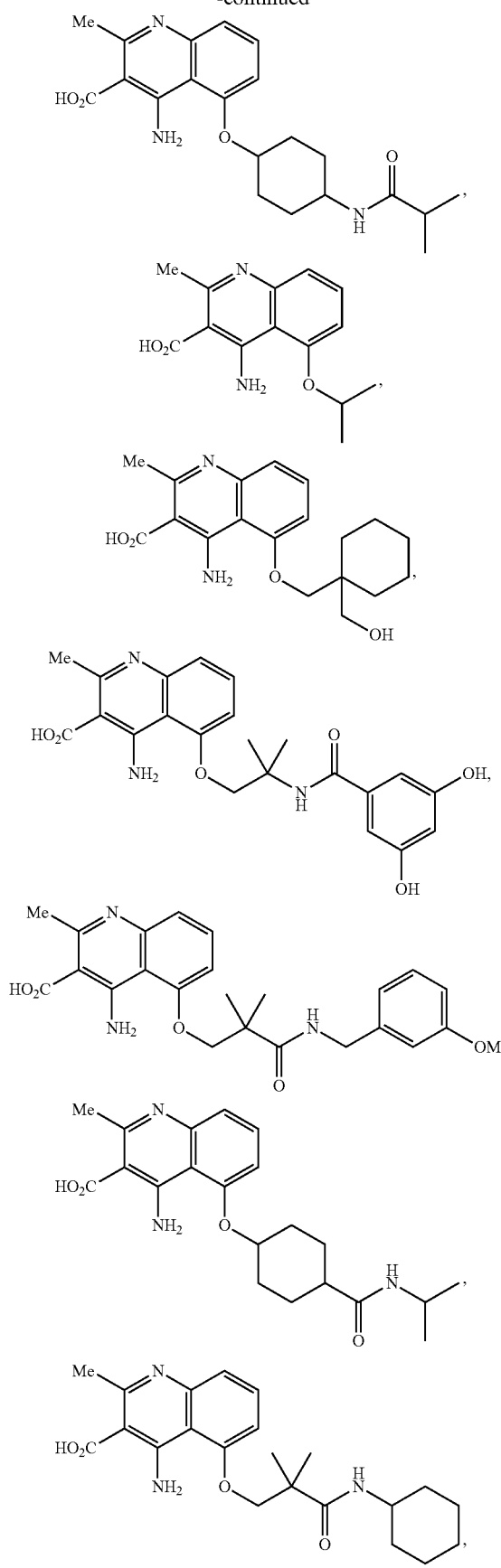
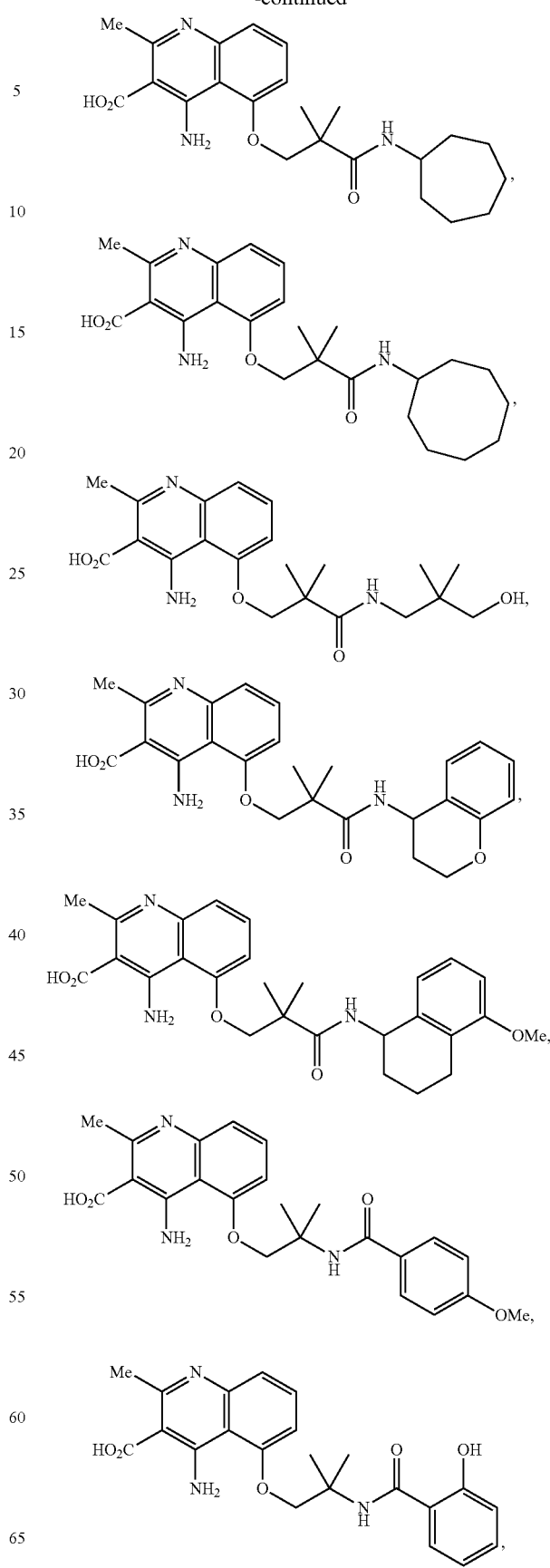

277
-continued
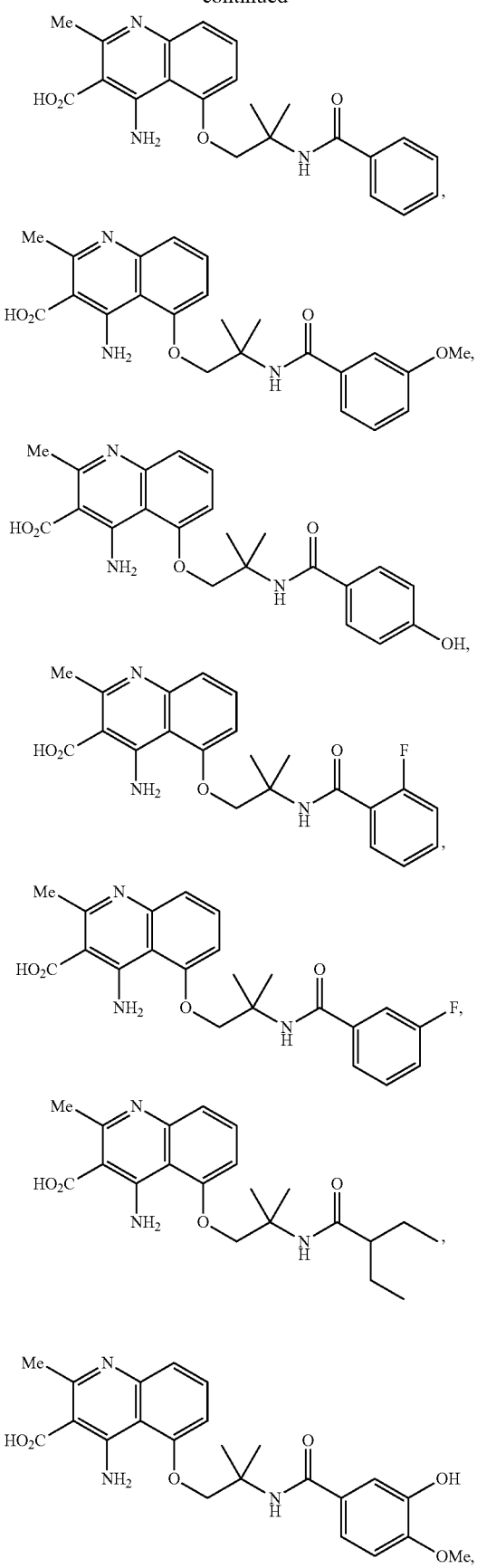
278
-continued
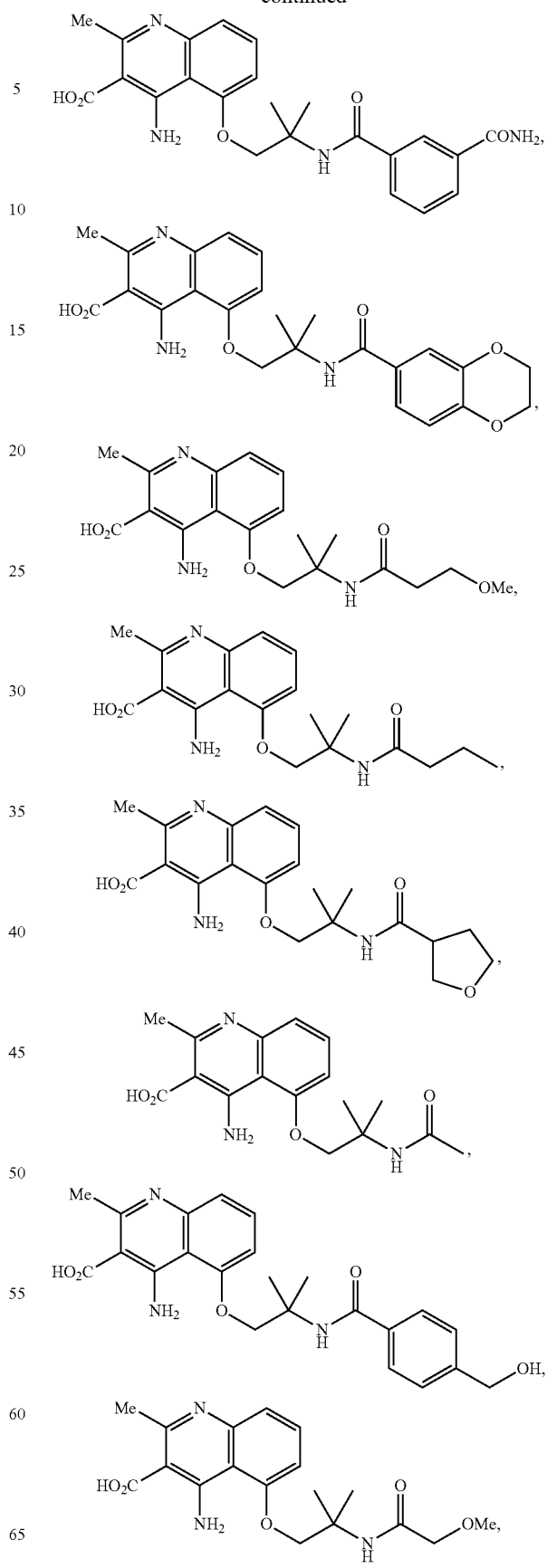

279
-continued
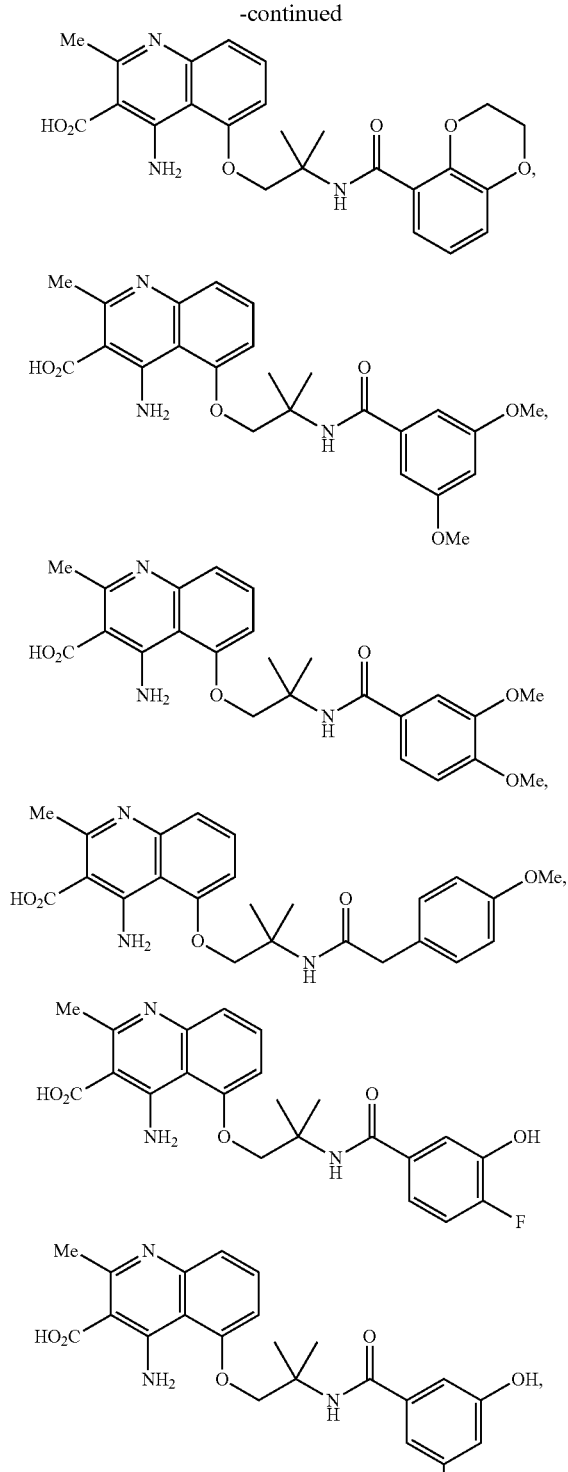
280
-continued
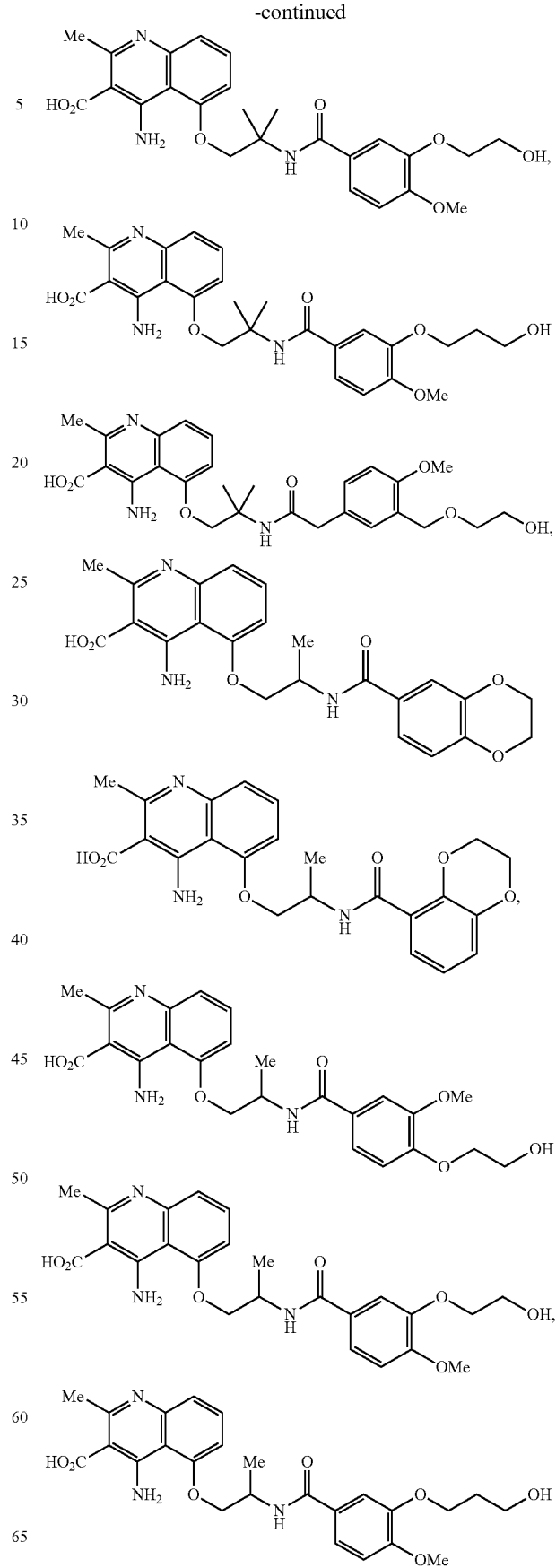

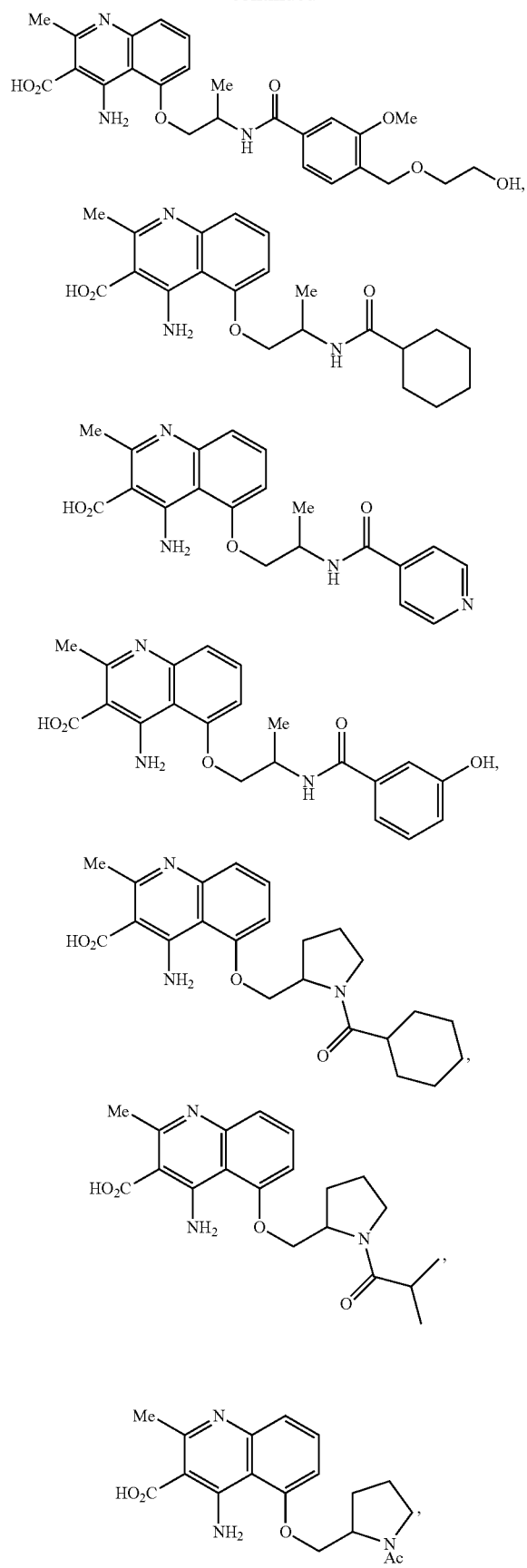
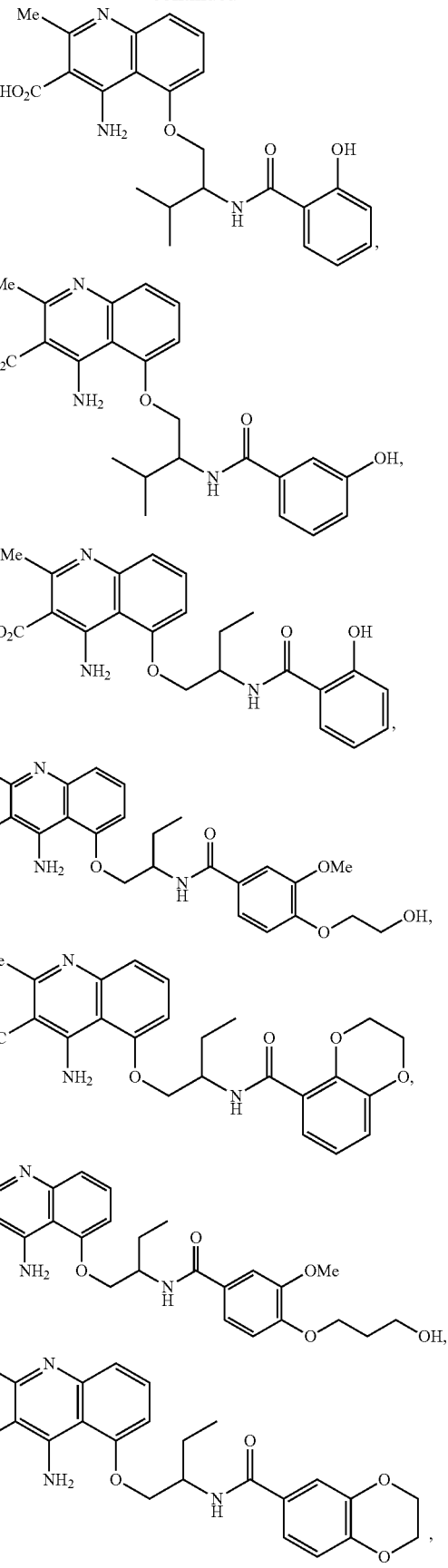

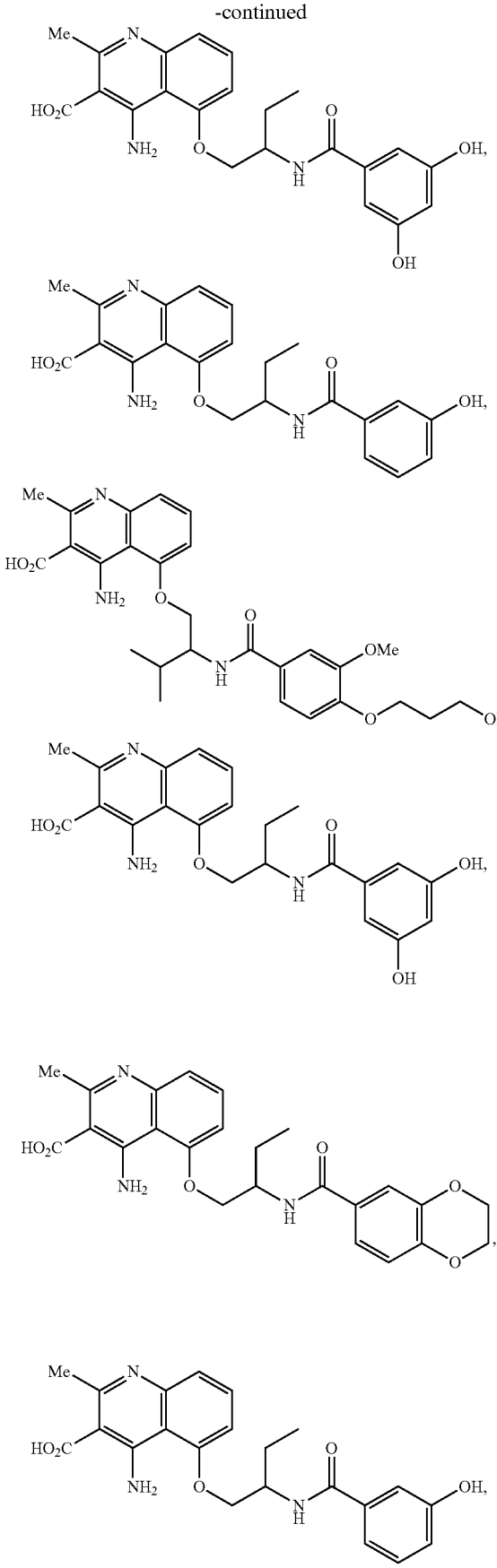
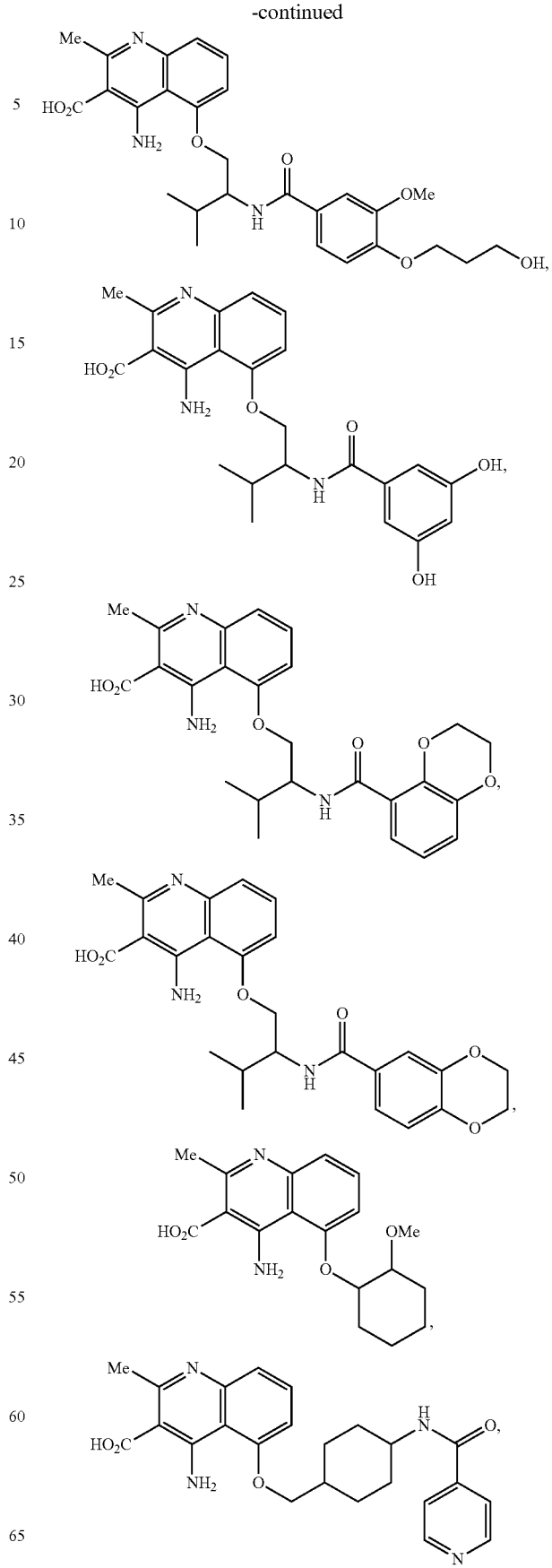

285
-continued
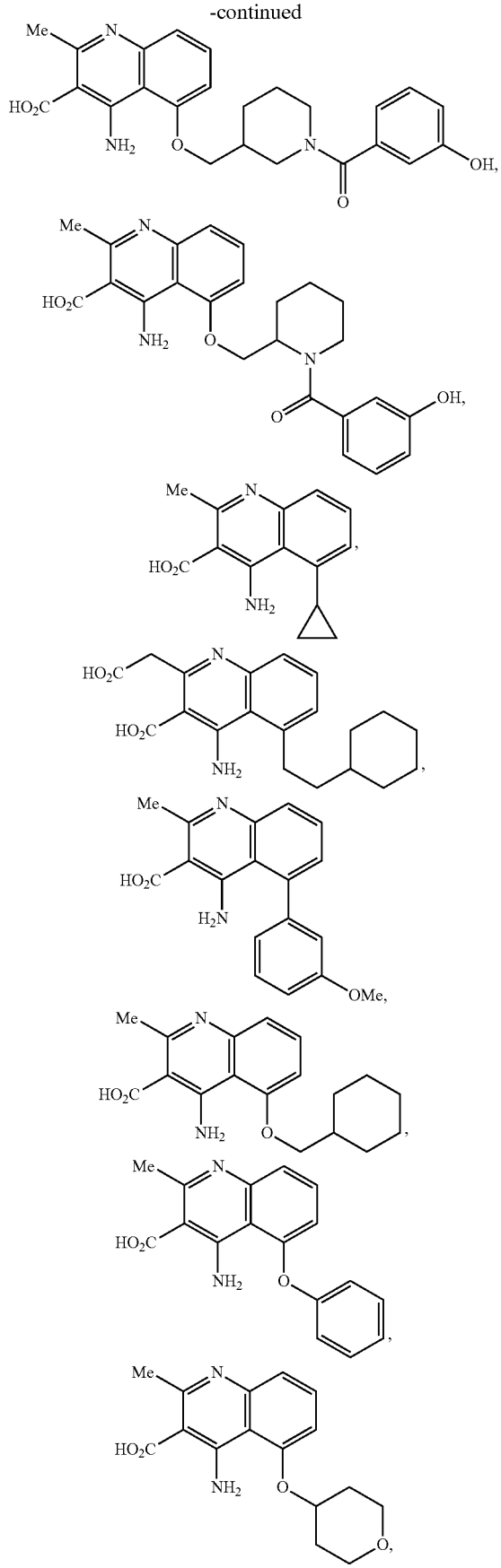
286
-continued
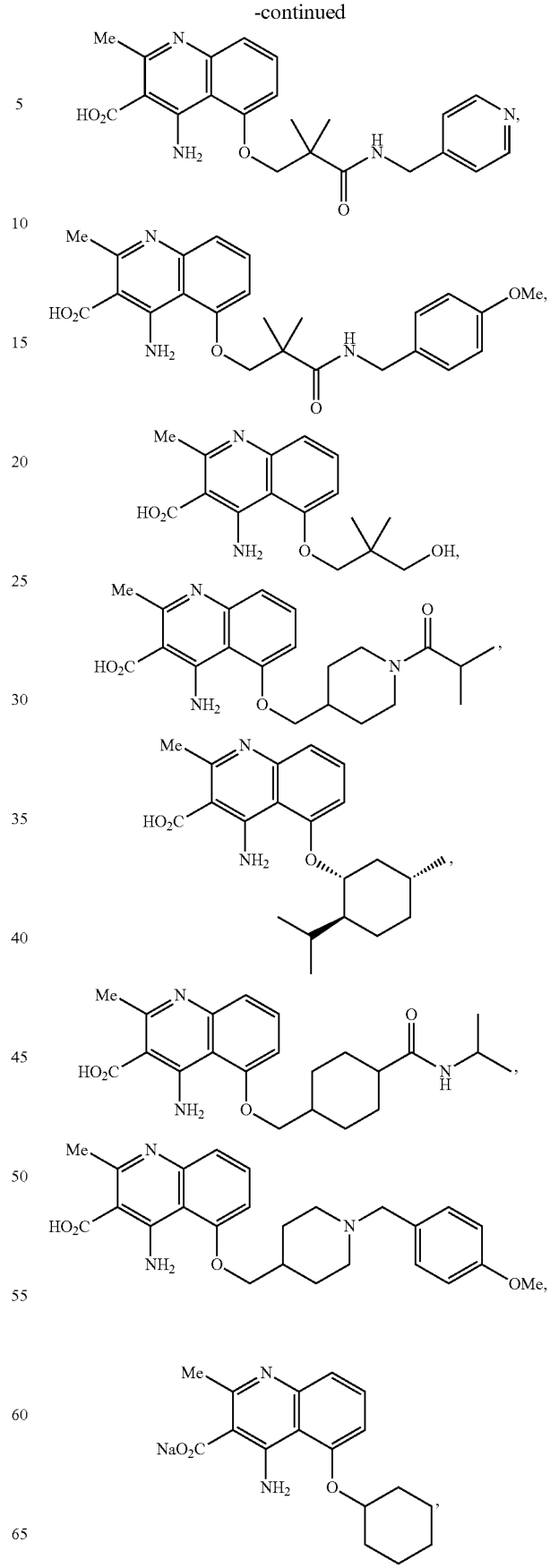

287
-continued
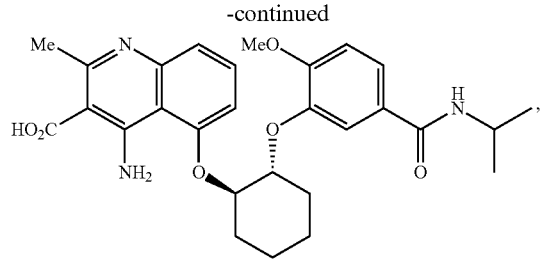
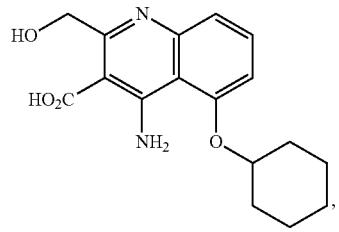
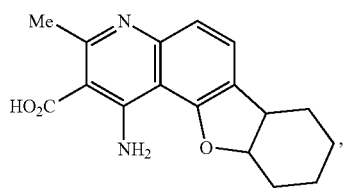
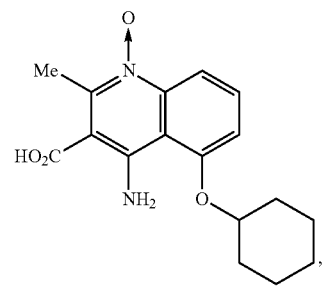
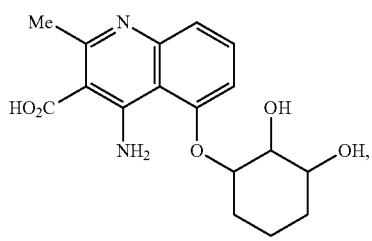
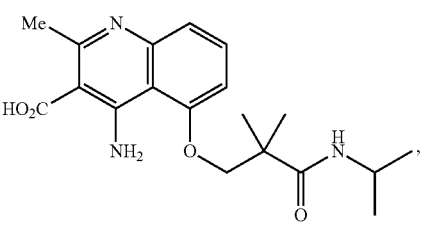
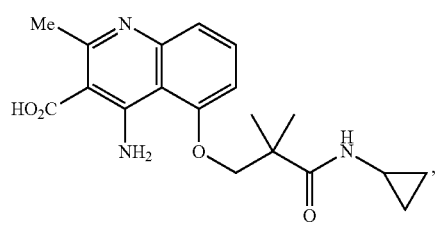
288
-continued
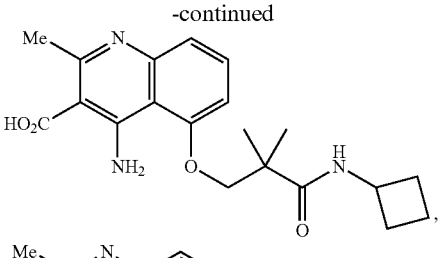
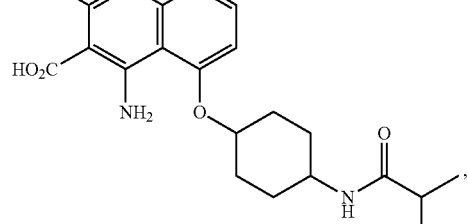
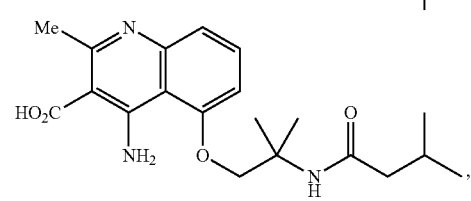
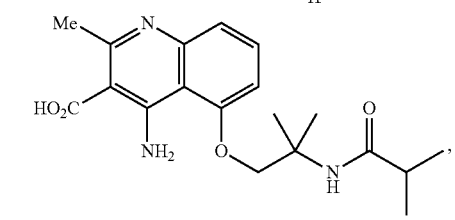
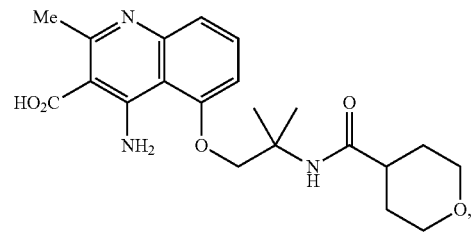
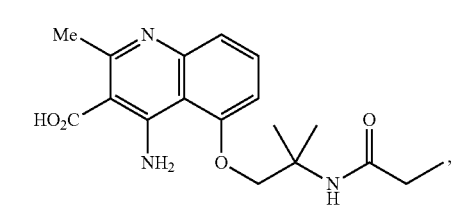
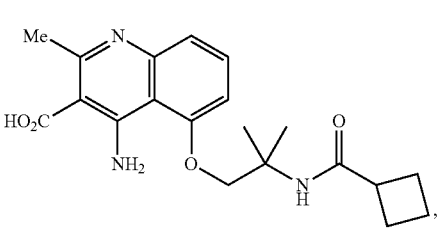

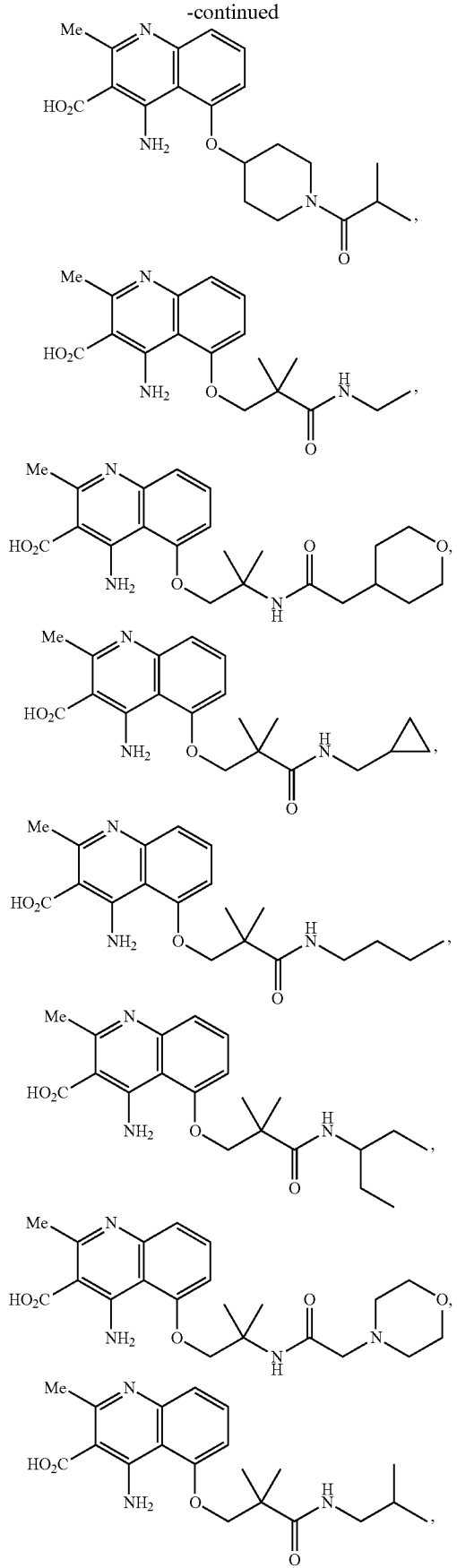
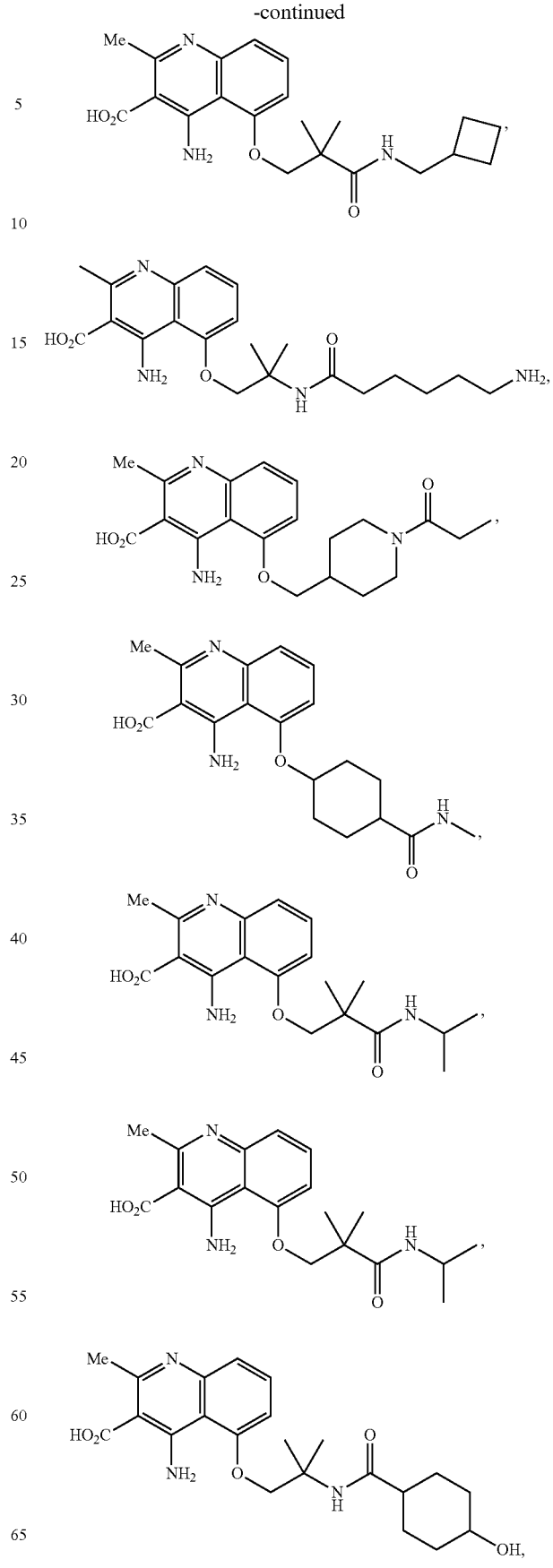

291
-continued
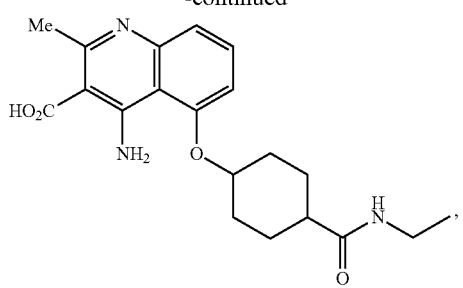
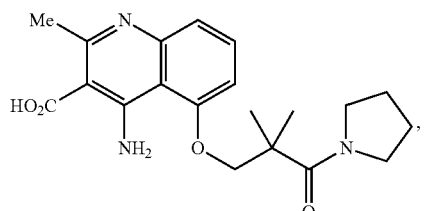
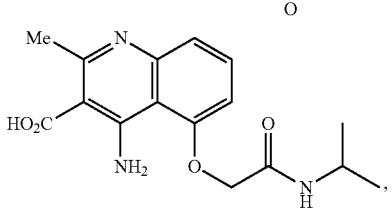
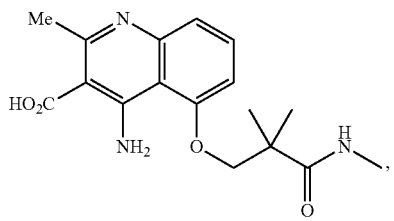
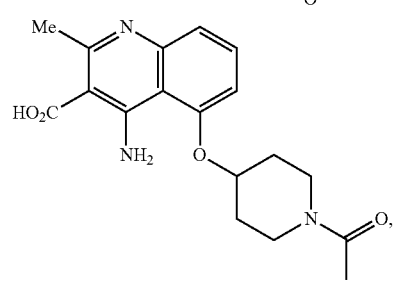
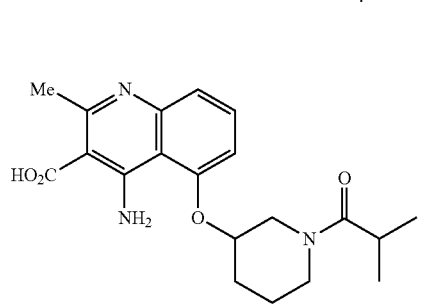
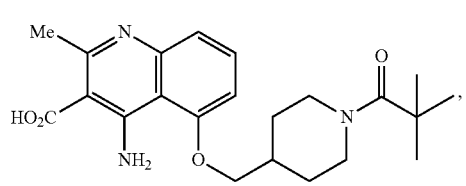
292
-continued
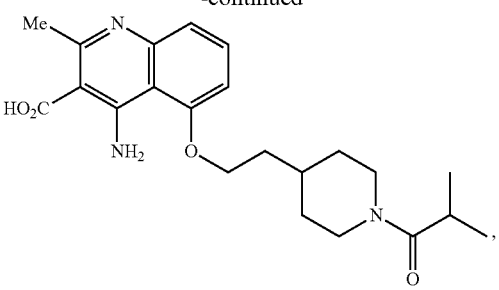
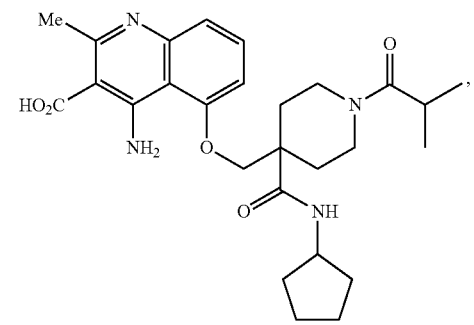
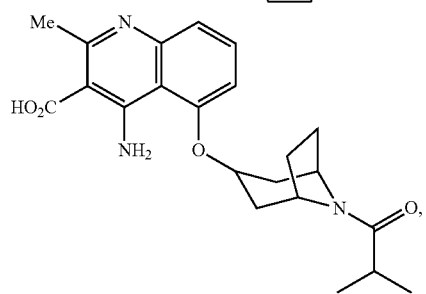
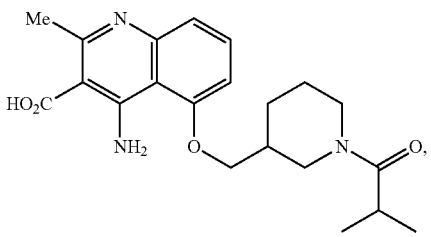
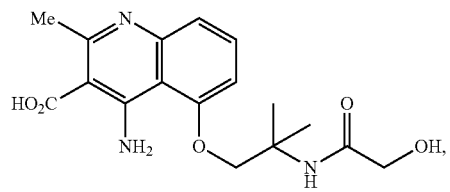
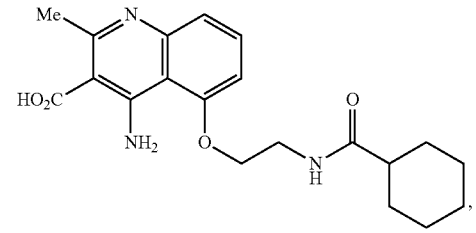

293
-continued
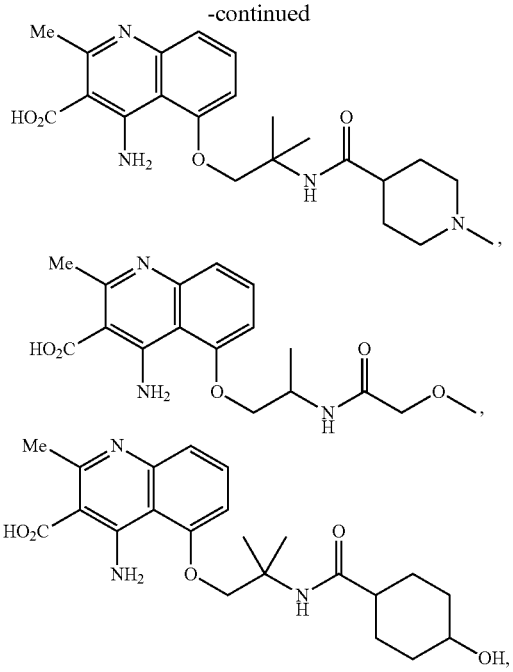
294
-continued
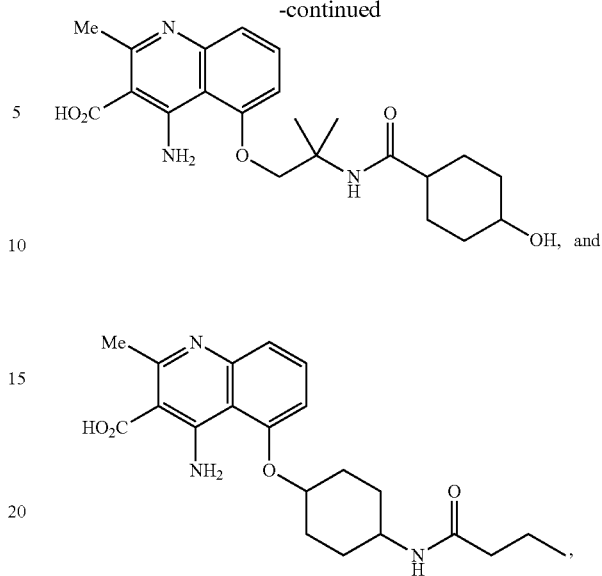
or a salt or solvate of any of the foregoing.
* * * * *

UNITED STATES PATENT AND TRADEMARK OFFICE
CERTIFICATE OF CORRECTION

PATENT NO. : 11,129,397 B2
APPLICATION NO. : 16/352430
DATED : September 28, 2021
INVENTOR(S) : Catherine Tachdjian Page 1 of 2

It is certified that error appears in the above-identified patent and that said Letters Patent is hereby corrected as shown below:

On the Title Page

Item [73], delete "FIREMENICH" and insert --FIRMENICH--.

In the Claims

Column 266, Claim 1, Line 7, delete "coumarine" and insert --coumarin--.

Column 266, Claim 1, Line 43, delete "$CO_R^7$," and insert --$CO_2R^7$--.

Column 267, Claim 2, Line 33, delete "coumarine" and insert --coumarin--.

Column 268, Claim 3, Line 37, delete "coumarine" and insert --coumarin--.

Column 269, Claim 4, Line 48, delete "coumarine" and insert --coumarin--.

Column 270, Claim 6, Line 47, delete "coumarine" and insert --coumarin--.

Column 279, Claim 6, Lines 40-45 (Approx.), after " 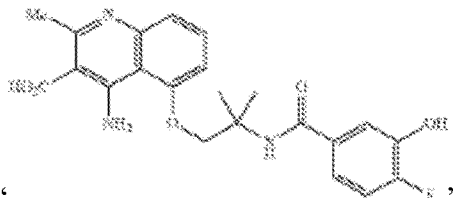 " insert --,--.

Signed and Sealed this
Thirty-first Day of May, 2022

Katherine Kelly Vidal
*Director of the United States Patent and Trademark Office*

CERTIFICATE OF CORRECTION (continued)
U.S. Pat. No. 11,129,397 B2

Column 279, Claim 6, Lines 60-65 (Approx.), after " 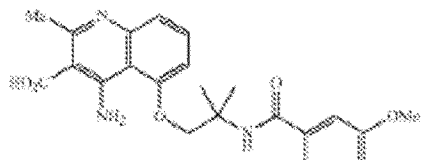 " insert --,--.

Column 280, Claim 6, Lines 10-15 (Approx.), after " 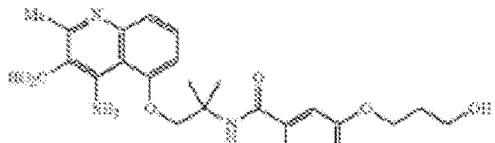 " insert --,--.